US012788400B2

(12) United States Patent
Swayze et al.

(10) Patent No.: US 12,788,400 B2
(45) Date of Patent: Nov. 10, 2026

(54) LOCAL DISPLAY OF TISSUE PARAMETER STABILIZATION

(71) Applicant: Cilag GmbH International, Zug (CH)

(72) Inventors: Jeffrey S. Swayze, West Chester, OH (US); Frederick E. Shelton, IV, Hillsboro, OH (US); Andrew T. Beckman, Cincinnati, OH (US)

(73) Assignee: Cliag GmbH International, Zug (CH)

(*) Notice: Subject to any disclaimer, the term of this patent is extended or adjusted under 35 U.S.C. 154(b) by 0 days.

(21) Appl. No.: 19/316,877

(22) Filed: Sep. 2, 2025

(65) Prior Publication Data

US 2026/0000403 A1 Jan. 1, 2026

Related U.S. Application Data

(63) Continuation of application No. 18/137,798, filed on Apr. 21, 2023, now Pat. No. 12,414,768, which is a (Continued)

(51) Int. Cl.

| | |
|---|---|
| ***A61B 17/072*** | (2006.01) |
| ***A61B 5/00*** | (2006.01) |

(Continued)

(52) U.S. Cl.

CPC ...... *A61B 17/07207* (2013.01); *A61B 5/6847* (2013.01); *A61B 17/00* (2013.01); *A61B 17/0644* (2013.01); *A61B 17/068* (2013.01); *A61B 17/072* (2013.01); *A61B 17/07292* (2013.01); *A61B 17/105* (2013.01); *A61B 17/1155* (2013.01); *A61B 17/32* (2013.01);

(Continued)

(58) Field of Classification Search

CPC ........ A61B 17/072; A61B 2017/07271; A61B 17/068

See application file for complete search history.

(56) References Cited

U.S. PATENT DOCUMENTS

| | | | |
|---|---|---|---|
| 4,423,456 | A | 12/1983 | Zaidenweber |
| 5,383,880 | A | 1/1995 | Hooven |

(Continued)

FOREIGN PATENT DOCUMENTS

| | | | |
|---|---|---|---|
| CN | 201001747 | Y | 1/2008 |
| CN | 201029899 | Y | 3/2008 |

(Continued)

OTHER PUBLICATIONS

Cuper et al., “The Use of Near-Infrared Light for Safe and Effective Visualization of Subsurface Blood Vessels to Facilitate Blood Withdrawal in Children,” Medical Engineering & Physics, vol. 35, No. 4, pp. 433-440 (2013).

(Continued)

*Primary Examiner* — Gloria R Weeks

(74) *Attorney, Agent, or Firm* — Lempia Summerfield Katz LLC

(57) ABSTRACT

A staple cartridge for use with a surgical stapler and surgical stapling systems are disclosed. The staple cartridge comprises a cartridge body having a tissue-contacting surface. One or more light emitting diodes (LEDs) are positioned at the edges of the tissue-contacting surface. A plurality of staple drivers is located within the cartridge body each supporting a staple.

18 Claims, 160 Drawing Sheets

Related U.S. Application Data continuation of application No. 16/580,493, filed on Sep. 24, 2019, now Pat. No. 11,653,918, which is a continuation of application No. 15/459,531, filed on Mar. 15, 2017, now Pat. No. 11,311,294, which is a continuation of application No. 14/479,108, filed on Sep. 5, 2014, now abandoned.

(51) Int. Cl.

| | |
|---|---|
| ***A61B 17/00*** | (2006.01) |
| ***A61B 17/064*** | (2006.01) |
| ***A61B 17/068*** | (2006.01) |
| ***A61B 17/10*** | (2006.01) |
| ***A61B 17/115*** | (2006.01) |
| ***A61B 17/32*** | (2006.01) |
| ***A61B 90/00*** | (2016.01) |
| ***A61B 90/70*** | (2016.01) |
| ***A61B 90/92*** | (2016.01) |
| ***A61B 90/98*** | (2016.01) |
| ***G01R 33/07*** | (2006.01) |
| ***G06F 1/26*** | (2006.01) |
| ***G06F 1/28*** | (2006.01) |
| ***G06F 1/30*** | (2006.01) |
| ***G06F 1/3215*** | (2019.01) |
| ***G06F 1/3287*** | (2019.01) |
| ***H02H 1/06*** | (2006.01) |
| ***H02H 3/06*** | (2006.01) |
| ***H02H 3/087*** | (2006.01) |
| ***H02H 3/18*** | (2006.01) |
| ***H02H 3/20*** | (2006.01) |
| ***H02H 3/24*** | (2006.01) |
| ***H02H 7/20*** | (2006.01) |
| ***H02H 11/00*** | (2006.01) |
| ***H02J 1/10*** | (2006.01) |
| ***H02J 7/00*** | (2006.01) |
| *A61B 5/06* | (2006.01) |
| *A61B 5/107* | (2006.01) |
| *A61B 8/00* | (2006.01) |
| *A61B 8/12* | (2006.01) |
| *A61B 17/29* | (2006.01) |
| *A61B 18/00* | (2006.01) |
| *A61B 90/30* | (2016.01) |
| *A61B 90/90* | (2016.01) |
| *A61B 90/94* | (2016.01) |
| *A61B 90/96* | (2016.01) |
| *H02H 3/02* | (2006.01) |
| *H02H 3/04* | (2006.01) |

(52) U.S. Cl.

CPC .............. *A61B 90/06* (2016.02); *A61B 90/70* (2016.02); *A61B 90/92* (2016.02); *A61B 90/98* (2016.02); *G01R 33/072* (2013.01); *G06F 1/266* (2013.01); *G06F 1/28* (2013.01); *G06F 1/30* (2013.01); *G06F 1/305* (2013.01); *G06F 1/3215* (2013.01); *G06F 1/3287* (2013.01); *H02H 1/06* (2013.01); *H02H 3/06* (2013.01); *H02H 3/087* (2013.01); *H02H 3/18* (2013.01); *H02H 3/202* (2013.01); *H02H 3/207* (2013.01); *H02H 3/243* (2013.01); *H02H 7/20* (2013.01); *H02H 11/002* (2013.01); *H02J 1/10* (2013.01); *H02J 7/865* (2026.01); *A61B 5/067* (2013.01); *A61B 5/1076* (2013.01); *A61B 5/6885* (2013.01); *A61B 8/12* (2013.01); *A61B 8/4483* (2013.01); *A61B 2017/00017* (2013.01); *A61B 2017/00022* (2013.01); *A61B 2017/00026* (2013.01); *A61B 2017/00039* (2013.01); *A61B 2017/00061* (2013.01); *A61B 2017/00066* (2013.01); *A61B 2017/00075* (2013.01); *A61B 2017/00106* (2013.01); *A61B 2017/00115* (2013.01); *A61B 2017/00119* (2013.01); *A61B 2017/00123* (2013.01); *A61B 2017/00199* (2013.01); *A61B 2017/00393* (2013.01); *A61B 2017/00398* (2013.01); *A61B 2017/0046* (2013.01); *A61B 2017/00477* (2013.01); *A61B 2017/00725* (2013.01); *A61B 2017/00734* (2013.01); *A61B 2017/00876* (2013.01); *A61B 2017/07214* (2013.01); *A61B 2017/07257* (2013.01); *A61B 2017/07271* (2013.01); *A61B 2017/07285* (2013.01); *A61B 2017/2927* (2013.01); *A61B 2018/00648* (2013.01); *A61B 2090/061* (2016.02); *A61B 2090/064* (2016.02); *A61B 2090/065* (2016.02); *A61B 2090/0803* (2016.02); *A61B 2090/0806* (2016.02); *A61B 2090/0807* (2016.02); *A61B 2090/0808* (2016.02); *A61B 2090/081* (2016.02); *A61B 2090/0811* (2016.02); *A61B 2090/0814* (2016.02); *A61B 2090/0818* (2016.02); *A61B 2090/304* (2016.02); *A61B 2090/309* (2016.02); *A61B 2090/702* (2016.02); *A61B 90/90* (2016.02); *A61B 90/94* (2016.02); *A61B 90/96* (2016.02); *A61B 2505/05* (2013.01); *A61B 2562/0223* (2013.01); *A61B 2562/0247* (2013.01); *A61B 2562/0257* (2013.01); *A61B 2562/0261* (2013.01); *A61B 2562/029* (2013.01); *A61B 2562/043* (2013.01); *A61B 2562/06* (2013.01); *A61B 2562/223* (2013.01); *H02H 3/02* (2013.01); *H02H 3/04* (2013.01)

(56) References Cited

U.S. PATENT DOCUMENTS

| | | | | |
|---|---|---|---|---|
| 5,413,268 | A | | 5/1995 | Green et al. |
| 5,431,322 | A | | 7/1995 | Green et al. |
| 5,433,721 | A | | 7/1995 | Hooven et al. |
| 5,465,896 | A | | 11/1995 | Allen et al. |
| 5,505,363 | A | | 4/1996 | Green et al. |
| 5,535,937 | A | | 7/1996 | Boiarski et al. |
| 5,628,446 | A | | 5/1997 | Geiste et al. |
| 5,632,432 | A | | 5/1997 | Schulze et al. |
| 5,664,404 | A | | 9/1997 | Ivanov et al. |
| 5,688,270 | A | * | 11/1997 | Yates ................. A61B 18/1447 606/49 |
| 5,693,051 | A | * | 12/1997 | Schulze ............. A61B 18/1206 606/41 |
| 5,709,680 | A | * | 1/1998 | Yates ............... A61B 17/07207 606/41 |
| 5,735,848 | A | * | 4/1998 | Yates ................... A61B 17/115 606/50 |
| 5,762,255 | A | | 6/1998 | Chrisman et al. |
| 5,792,165 | A | | 8/1998 | Klieman et al. |
| 5,817,119 | A | | 10/1998 | Klieman et al. |
| 5,954,259 | A | | 9/1999 | Viola et al. |
| 6,023,641 | A | | 2/2000 | Thompson |
| 6,315,184 | B1 | | 11/2001 | Whitman |
| 6,443,973 | B1 | | 9/2002 | Whitman |
| 6,516,073 | B1 | | 2/2003 | Schulz et al. |
| 6,716,233 | B1 | | 4/2004 | Whitman |
| 6,820,791 | B2 | | 11/2004 | Adams |
| 7,032,798 | B2 | | 4/2006 | Whitman et al. |
| 7,211,081 | B2 | | 5/2007 | Goble |
| 7,225,959 | B2 | | 6/2007 | Patton et al. |
| 7,272,002 | B2 | | 9/2007 | Drapeau |
| 7,464,847 | B2 | | 12/2008 | Viola et al. |
| 7,559,452 | B2 | | 7/2009 | Wales et al. |
| 7,559,453 | B2 | * | 7/2009 | Heinrich ............ A61B 18/1445 227/181.1 |

(56) References Cited

U.S. PATENT DOCUMENTS 7,568,603 B2 8/2009 Shelton, IV et al.
7,644,848 B2 1/2010 Swayze et al.
7,694,864 B2 4/2010 Okada et al.
7,717,312 B2 5/2010 Beetel
7,721,936 B2 5/2010 Shelton, IV et al.
7,819,299 B2 10/2010 Shelton, IV et al.
7,845,537 B2 12/2010 Shelton, IV et al.
7,900,805 B2 3/2011 Shelton, IV et al.
7,905,381 B2 3/2011 Baxter, III et al.
7,930,040 B1 4/2011 Kelsch et al.
7,950,560 B2 5/2011 Zemlok et al.
7,954,687 B2 6/2011 Zemlok et al.
7,959,050 B2 6/2011 Smith et al.
8,006,885 B2 8/2011 Marczyk
8,020,742 B2 9/2011 Marczyk
8,083,120 B2 12/2011 Shelton, IV et al.
8,161,977 B2 4/2012 Shelton, IV et al.
8,245,899 B2 8/2012 Swensgard et al.
8,348,129 B2 1/2013 Bedi et al.
8,369,056 B2 2/2013 Senriuchi et al.
8,414,577 B2 4/2013 Boudreaux et al.
8,439,830 B2 5/2013 McKinley et al.
8,444,036 B2 5/2013 Shelton, IV
8,453,906 B2 * 6/2013 Huang ............... A61B 17/1155 227/176.1
8,453,907 B2 6/2013 Laurent et al.
8,459,520 B2 6/2013 Giordano et al.
8,535,340 B2 9/2013 Allen
8,561,871 B2 10/2013 Rajappa et al.
8,608,045 B2 12/2013 Smith et al.
8,613,383 B2 12/2013 Beckman et al.
8,657,175 B2 2/2014 Sonnenschein et al.
8,708,213 B2 4/2014 Shelton, IV et al.
8,727,200 B2 5/2014 Roy
8,808,311 B2 8/2014 Heinrich et al.
8,851,354 B2 10/2014 Swensgard et al.
8,893,946 B2 11/2014 Boudreaux et al.
8,958,860 B2 2/2015 Banerjee et al.
8,960,519 B2 2/2015 Whitman et al.
8,960,520 B2 2/2015 McCuen
9,072,535 B2 7/2015 Shelton, IV et al.
9,124,097 B2 9/2015 Cruz
9,125,651 B2 9/2015 Mandakolathur Vasudevan et al.
9,204,830 B2 12/2015 Zand et al.
9,220,570 B2 12/2015 Kim et al.
9,295,468 B2 3/2016 Heinrich et al.
9,301,691 B2 4/2016 Hufnagel et al.
9,345,481 B2 5/2016 Hall et al.
9,364,279 B2 6/2016 Houser et al.
9,420,967 B2 8/2016 Zand et al.
9,421,014 B2 8/2016 Ingmanson et al.
9,439,651 B2 9/2016 Smith et al.
9,445,813 B2 9/2016 Shelton, IV et al.
9,483,095 B2 11/2016 Tran et al.
9,486,214 B2 11/2016 Shelton, IV
9,526,921 B2 12/2016 Kimball et al.
9,561,031 B2 2/2017 Heinrich et al.
9,724,094 B2 8/2017 Baber et al.
9,737,301 B2 8/2017 Baber et al.
9,757,128 B2 9/2017 Baber et al.
9,788,836 B2 10/2017 Overmyer et al.
9,808,244 B2 11/2017 Leimbach et al.
9,808,246 B2 11/2017 Shelton, IV et al.
9,844,368 B2 12/2017 Boudreaux et al.
9,861,359 B2 1/2018 Shelton, IV et al.
9,883,860 B2 2/2018 Leimbach et al.
9,888,919 B2 2/2018 Leimbach et al.
9,962,159 B2 5/2018 Heinrich et al.
10,016,199 B2 7/2018 Baber et al.
10,052,044 B2 * 8/2018 Shelton, IV ......... A61B 5/0538
10,085,751 B2 10/2018 Overmyer et al.
10,111,679 B2 10/2018 Baber et al.
10,135,242 B2 11/2018 Baber et al.
10,201,364 B2 2/2019 Leimbach et al.
10,231,634 B2 3/2019 Zand et al.
10,335,145 B2 * 7/2019 Harris .................. A61B 17/072
10,426,467 B2 * 10/2019 Miller .................. A61B 5/0053
10,492,814 B2 12/2019 Snow et al.
10,722,292 B2 7/2020 Arya et al.
10,722,293 B2 7/2020 Arya et al.
10,729,458 B2 8/2020 Stoddard et al.
10,779,818 B2 9/2020 Zemlok et al.
10,905,423 B2 2/2021 Baber et al.
10,932,781 B2 3/2021 Jones et al.
11,058,420 B2 7/2021 Shelton, IV et al.
11,076,854 B2 8/2021 Baber et al.
11,311,294 B2 4/2022 Swayze et al.
11,389,162 B2 7/2022 Baber et al.
11,612,395 B2 3/2023 Yates et al.
11,653,918 B2 5/2023 Swayze et al.
11,779,329 B2 * 10/2023 Shelton, IV ......... A61B 17/072 227/175.1
12,193,670 B1 1/2025 Shelton, IV et al.
12,376,917 B2 8/2025 Shelton, IV et al.
12,414,768 B2 9/2025 Swayze et al.
2005/0131390 A1 6/2005 Heinrich et al.
2009/0078736 A1 3/2009 Van Lue
2009/0090763 A1 4/2009 Zemlok et al.
2009/0192534 A1 7/2009 Ortiz et al.
2009/0296346 A1 12/2009 Shelton, IV et al.
2011/0022032 A1 1/2011 Zemlok et al.
2011/0024478 A1 2/2011 Shelton, IV
2011/0095064 A1 4/2011 Taylor et al.
2011/0218484 A1 * 9/2011 Zemlok ............ A61B 17/07207 604/26
2011/0278343 A1 * 11/2011 Knodel ............ A61B 17/07207 227/176.1
2012/0012638 A1 * 1/2012 Huang ................. A61B 17/115 227/176.1
2012/0211542 A1 8/2012 Racenet
2013/0006227 A1 1/2013 Takashino
2013/0023910 A1 1/2013 Solomon et al.
2013/0131476 A1 5/2013 Siu et al.
2013/0162198 A1 6/2013 Yokota et al.
2013/0334280 A1 12/2013 Krehel et al.
2014/0001231 A1 1/2014 Shelton, IV et al.
2014/0005653 A1 * 1/2014 Shelton, IV ........... A61B 17/29 606/205
2014/0263541 A1 9/2014 Leimbach et al.
2014/0263552 A1 9/2014 Hall et al.
2015/0011988 A1 * 1/2015 Whitman ............. A61B 5/4836 227/175.1
2015/0066000 A1 3/2015 An et al.
2016/0030042 A1 2/2016 Heinrich et al.
2016/0066913 A1 * 3/2016 Swayze ............ A61B 17/07207 227/176.1
2019/0201146 A1 * 7/2019 Shelton, IV ..... A61B 17/07207
2020/0046356 A1 * 2/2020 Baxter, III ............ A61L 31/022
2021/0196263 A1 * 7/2021 Shelton, IV ..... A61B 17/00234
2025/0120700 A1 * 4/2025 Fiebig .............. A61B 17/07207

FOREIGN PATENT DOCUMENTS

WO 2007137304 A2 11/2007
WO 2008061566 A1 5/2008

OTHER PUBLICATIONS

Mouser Electronics, "LM317 3-Terminal Adjustable Regulator with Overcurrent/Overtemperature Self Protection," Mar. 31, 2014 (Mar. 31, 2014), XP055246104, Retrieved from the Internet: URL: http://www.mouser.com/ds/2/405/lm317m-440423.pdf, pp. 1-9.

* cited by examiner

ANVIL CLOSED

RIGHT SIDE

4342

| TISSUE THICKNESS RANGES (T) ▽ | THRESHOLD FORCE (F) ▽ |
|---|---|
| T1-T2 | F1 |
| T2-T3 | F2 |
| T3-T4 | F3 |
| . | . |
| . | . |
| . | . |
| Tn-1 - Tn | Fn |
| | |
| | |

FIG. 90

LOCAL DISPLAY OF TISSUE PARAMETER STABILIZATION

CROSS-REFERENCE TO RELATED APPLICATIONS

The present application is a continuation application claiming priority under 35 U.S.C. § 120 to U.S. patent application Ser. No. 18/137,798, entitled LOCAL DISPLAY OF TISSUE PARAMETER STABILIZATION, filed Apr. 21, 2023, now U.S. Pat. No. 12,414,768, which is a continuation application claiming priority under 35 U.S.C. § 120 to U.S. patent application Ser. No. 16/580,493, entitled LOCAL DISPLAY OF TISSUE PARAMETER STABILIZATION, filed Sep. 24, 2019, which issued on May 23, 2023 as U.S. Pat. No. 11,653,918, which is a continuation application claiming priority under 35 U.S.C. § 120 to U.S. patent application Ser. No. 15/459,531, entitled POWERED MEDICAL DEVICE INCLUDING MEASUREMENT OF CLOSURE STATE OF JAWS, filed Mar. 15, 2017, which issued on Apr. 26, 2022 as U.S. Pat. No. 11,311,294, which is a continuation application claiming priority under 35 U.S.C. § 120 to U.S. patent application Ser. No. 14/479,108, entitled LOCAL DISPLAY OF TISSUE PARAMETER STABILIZATION, filed Sep. 5, 2014, now U.S. Patent Application Publication No. 2016/0066913, the entire disclosures of which are hereby incorporated by reference herein.

This application is also related to U.S. patent application Ser. No. 14/479,103 entitled CIRCUITRY AND SENSORS FOR POWERED MEDICAL DEVICE, now U.S. Pat. No. 10,111,679, Ser. No. 14/479,119 entitled ADJUNCT WITH INTEGRATED SENSORS TO QUANTIFY TISSUE COMPRESSION, now U.S. Pat. No. 9,724,094, Ser. No. 14/478,908 entitled MONITORING DEVICE DEGRADATION BASED ON COMPONENT EVALUATION, now U.S. Pat. No. 9,737,301, Ser. No. 14/478,895 entitled MULTIPLE SENSORS WITH ONE SENSOR AFFECTING A SECOND SENSOR'S OUTPUT OR INTERPRETATION, now U.S. Pat. No. 9,757,128, Ser. No. 14/479,110 entitled POLARITY OF HALL MAGNET TO DETECT MISLOADED CARTRIDGE, now U.S. Pat. No. 10,016,199, Ser. No. 14/479,098 entitled SMART CARTRIDGE WAKE UP OPERATION AND DATA RETENTION, now U.S. Pat. No. 10,135,242, and Ser. No. 14/479,115 entitled MULTIPLE MOTOR CONTROL FOR POWERED MEDICAL DEVICE, now U.S. Pat. No. 9,788,836, each of which is incorporated herein by reference in its entirety.

BACKGROUND

The present embodiments of the invention relate to surgical instruments and, in various circumstances, to surgical stapling and cutting instruments and staple cartridges therefor that are designed to staple and cut tissue.

SUMMARY

In one embodiment, a staple cartridge for use with a surgical stapler is provided. The staple cartridge comprises a cartridge body having a tissue-contacting surface; one or more LEDs positioned at the edges of the tissue-contacting surface; and a plurality of staple drivers within the cartridge body each supporting a staple. In one embodiment the one or more LEDs emit ultraviolet light or infrared light. In one embodiment, the staples are coated in a fluorescing dye.

In one embodiment, a surgical stapling system is provided. The surgical stapling system comprises an elongated shaft assembly configured to transmit actuation motions from an actuator; and an end effector for compressing and stapling tissue, the end effector operably coupled to the elongated shaft, the end effector comprising: an elongated channel; an anvil having a staple forming surface thereon, the anvil moveable relative to the elongated channel between an open position and a closed position; and a staple cartridge removably positioned within the elongated channel, the staple cartridge comprising: a cartridge body having a tissue-contacting surface in a confronting relationship with the anvil's staple forming surface when the anvil is in the closed position; one or more LEDs positioned to be visible when the anvil is in the closed position; and a plurality of staple drivers within the cartridge body each supporting a staple. In one embodiment, the one or more LEDs indicate that the compressed tissue is stable. In one embodiment, at least one LED is visible from either the left or the right side of the end effector, the at least one LED configured to flash at the rate of the tissue's stabilization and further configured to maintain a lit condition when the tissue is stable. In one embodiment, more than one LED is visible from either the left or the right side of the end effector. In one embodiment, the more than one LEDs light in sequence at the rate of the tissue's stabilization, such that when all the LEDs indicates that the tissue is stable. In one embodiment, the more than one LEDs light in sequence, the speed of the sequence indicating the rate of the tissue's stabilization, and wherein all the LEDs flash simultaneously when the tissue is stable. In one embodiment, the one or more LEDs indicate which portions of the end effector are in sufficient contact with the tissue.

In one embodiment, the system further comprises a processor, the processor configured to compare the tissue's parameters against the acceptable parameters for all staple cartridges. In one embodiment, the processor is further configured to compare the tissue's parameters against the acceptable parameters for the staple cartridge currently present in the elongated channel. In one embodiment, the LEDs indicate that the staple cartridge is appropriate for the tissue. In one embodiment, the one or more LEDs indicate that the staple cartridge is not compatible with the stapling system. In one embodiment, the one or more LEDs indicate that the end effector is enclosing more tissue than is suitable for the staple cartridge. In one embodiment, a surgical stapling system is provided. The surgical stapling system comprises: an elongated shaft assembly configured to transmit actuation motions from an actuator; and an end effector for compressing and stapling tissue, the end effector operably coupled to the elongated shaft, the end effector comprising: an elongated channel; an anvil having a staple forming surface thereon, the anvil moveable relative to the elongated channel between an open position and a closed position; and a staple cartridge removably positioned within the elongated channel, the staple cartridge comprising: a cartridge body having an upper surface in a confronting relationship with the anvil's staple forming surface when the anvil is in a closed position; one or more LEDs positioned to provide illumination to the area between the anvil and the staple cartridge when the anvil is in a closed position; and a plurality of staple drivers within the cartridge body each supporting a staple. In one embodiment, the one or more LEDs emit ultraviolet light or infrared light. In one embodiment, the staples are coated in a fluorescing dye.

BRIEF DESCRIPTION OF THE DRAWINGS

The features and advantages of the various embodiments of the invention, and the manner of attaining them, will become more apparent and the embodiment of the invention itself will be better understood by reference to the following description of embodiments of the embodiment of the invention taken in conjunction with the accompanying drawings, wherein:

FIG. 48A illustrates the circular stapler in an initial position with the anvil and the body in a closed configuration, FIG. 48B illustrates that the anvil is moved distally to disengage with the body and create a gap configured to receive a tissue section therein, once the circular stapler 3400 is positioned, FIG. 48C illustrates the tissue section compressed to a predetermined compression between the anvil and the body, and FIG. 48D illustrates the circular stapler in position corresponding to staple deployment;

FIG. 90 illustrates a table showing predefined tissue thicknesses and corresponding predefined threshold forces according to various embodiments described herein.

FIG. 115 is a partial view of the end effector shown in FIG. 114 showing sensors and/or electronic components located in an end effector.

FIG. 116 is a block diagram of a surgical instrument electronic subsystem comprising a short circuit protection circuit for the sensors and/or electronic components according to one embodiment.

FIG. 117 is a short circuit protection circuit comprising a supplementary power supply circuit 7014 coupled to a main power supply circuit, according to one embodiment.

FIG. 118 is a block diagram of a surgical instrument electronic subsystem comprising a sample rate monitor to provide power reduction by limiting sample rates and/or duty cycle of the sensor components when the surgical instrument is in a non-sensing state, according to one embodiment.

FIG. 119 is a block diagram of a surgical instrument electronic subsystem comprising an over current/voltage protection circuit for sensors and/or electronic components of a surgical instrument, according to one embodiment.

FIG. 120 is an over current/voltage protection circuit for sensors and electronic components for a surgical instrument, according to one embodiment.

FIG. 121 is a block diagram of a surgical instrument electronic subsystem with a reverse polarity protection circuit for sensors and/or electronic components according to one embodiment.

FIG. 122 is a reverse polarity protection circuit for sensors and/or electronic components for a surgical instrument according to one embodiment.

FIG. 123 is a block diagram of a surgical instrument electronic subsystem with power reduction utilizing a sleep mode monitor for sensors and/or electronic components according to one embodiment.

FIG. 124 is a block diagram of a surgical instrument electronic subsystem comprising a temporary power loss circuit to provide protection against intermittent power loss for sensors and/or electronic components in modular surgical instruments.

FIG. 125 illustrates one embodiment of a temporary power loss circuit implemented as a hardware circuit.

FIG. 126A illustrates a perspective view of one embodiment of an end effector comprising a magnet and a Hall effect sensor in communication with a processor;

Figure 126A:
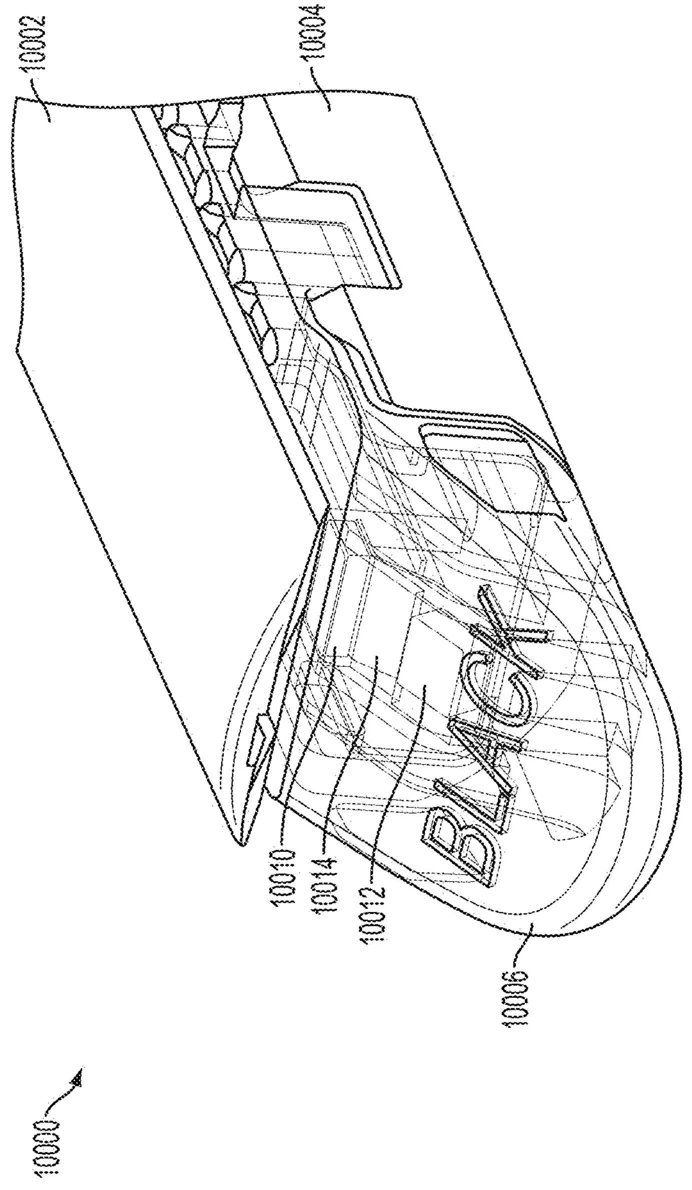
Figure 126B:
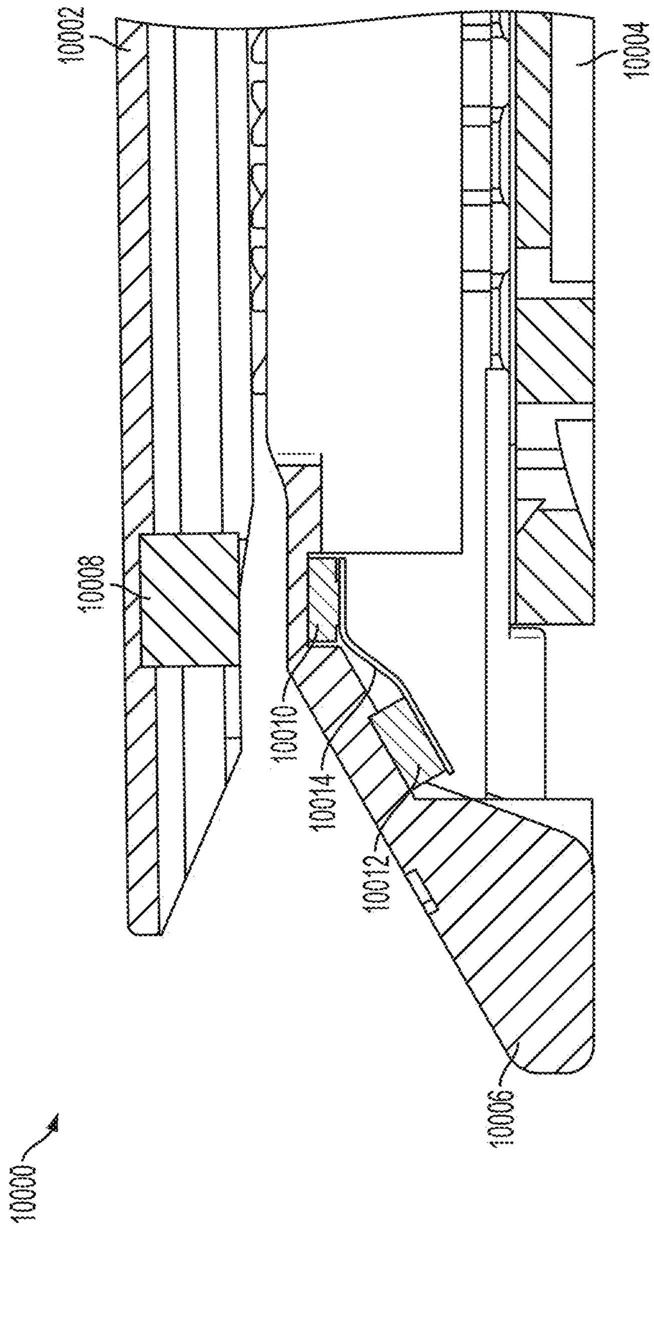
Figure 127:
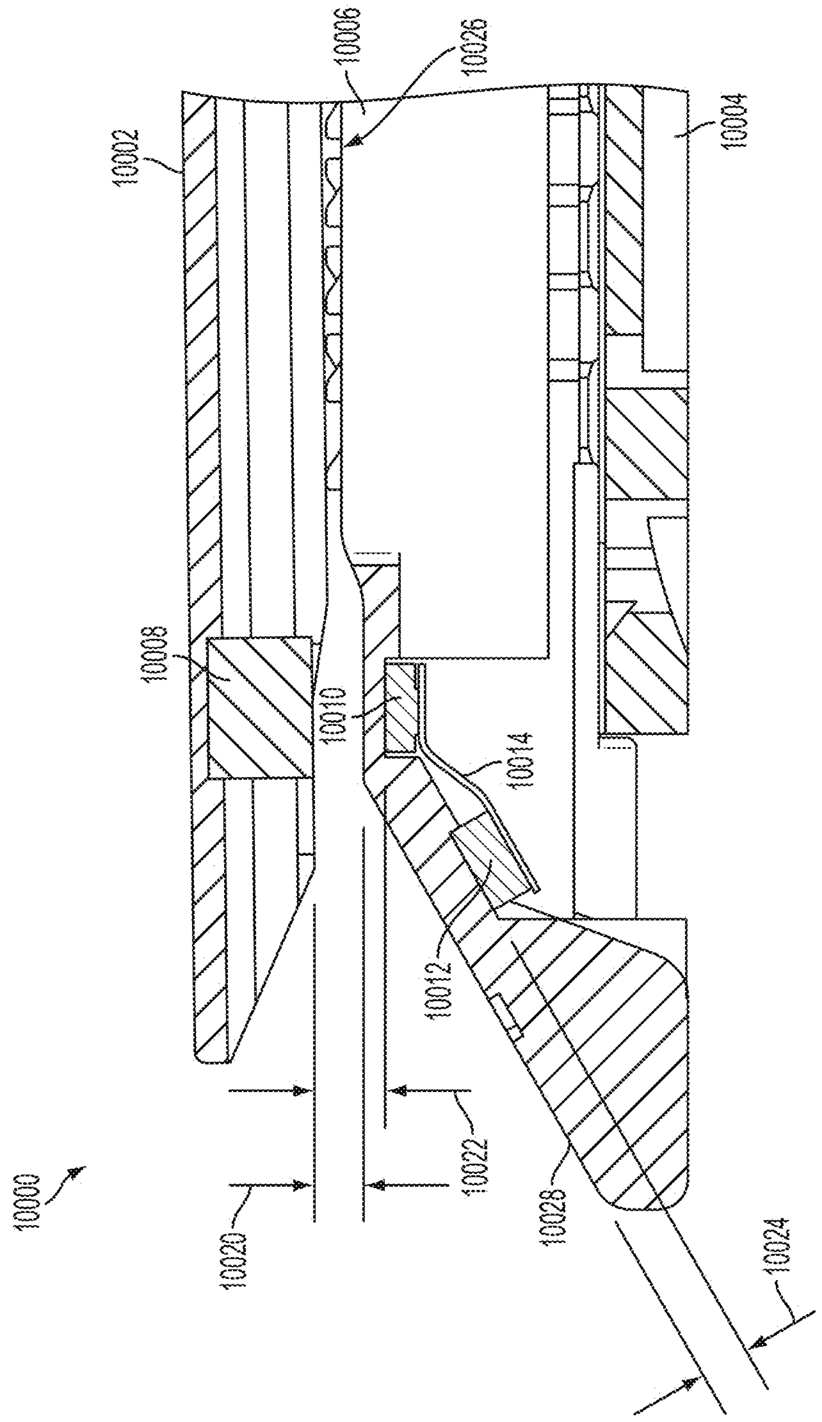
Figure 128A:
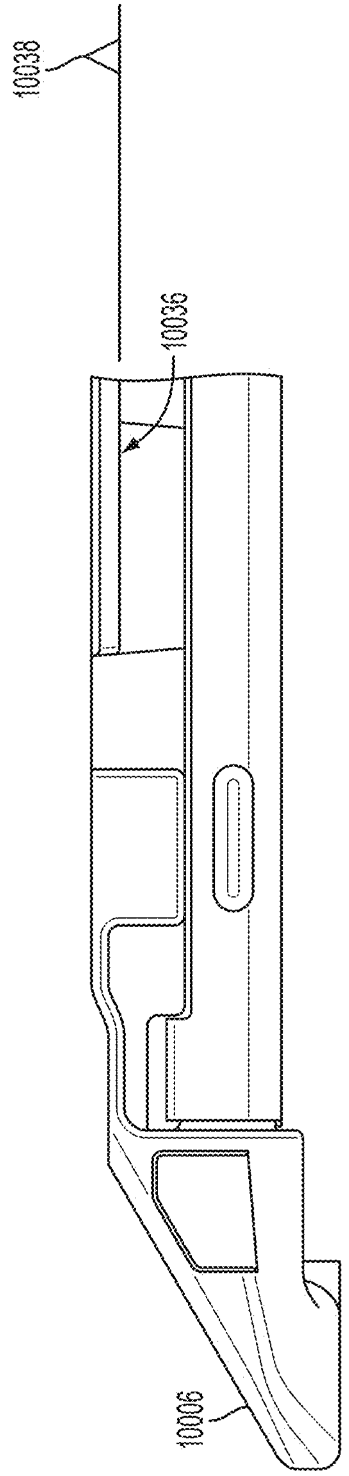
Figure 128B:
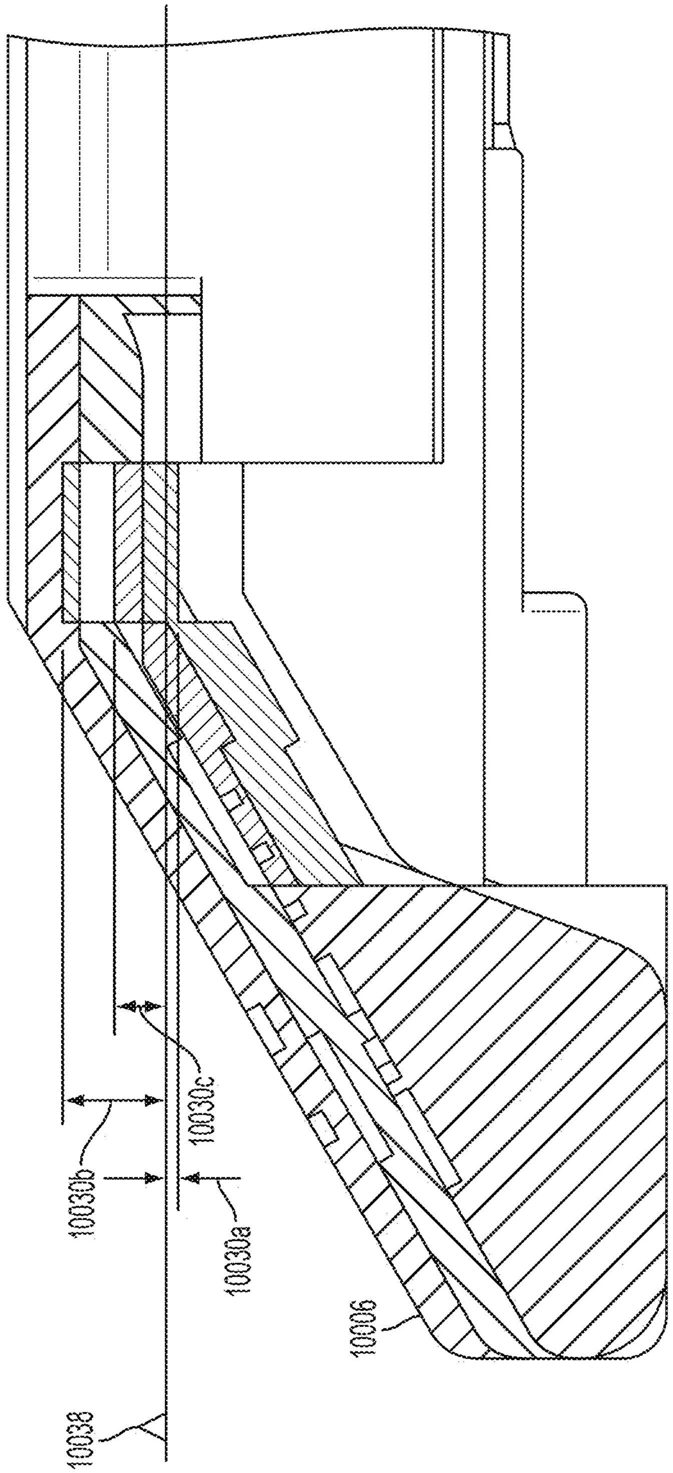
Figure 128C:
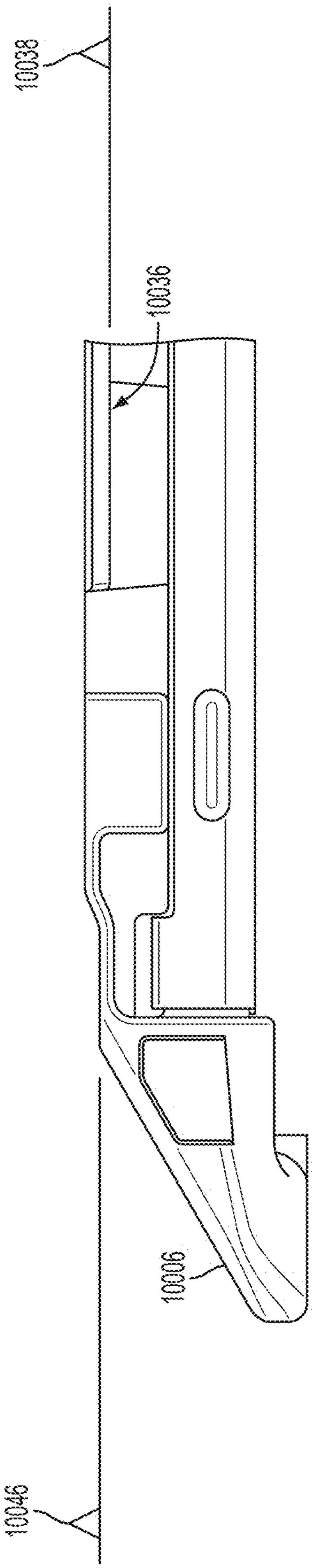
Figure 128D:
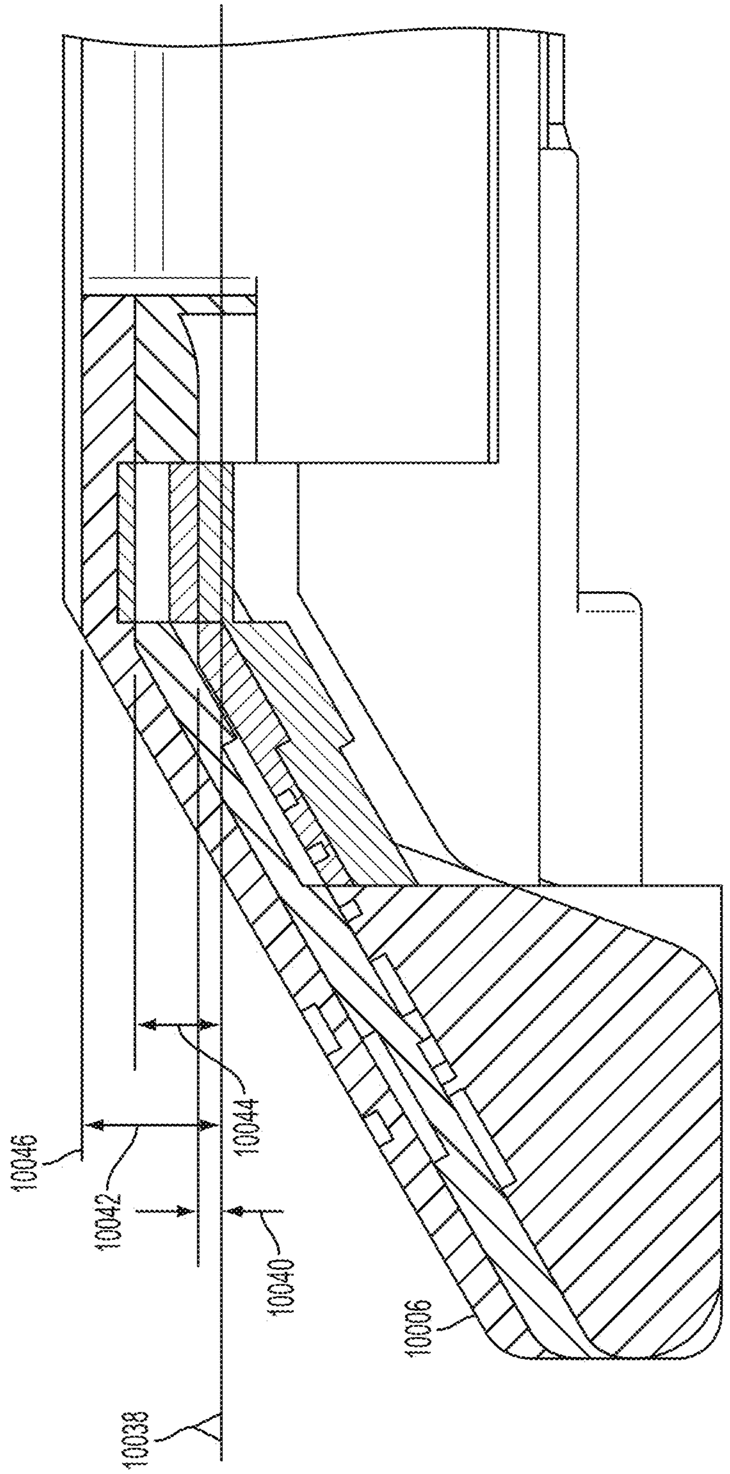
Figures 129A, 129B:
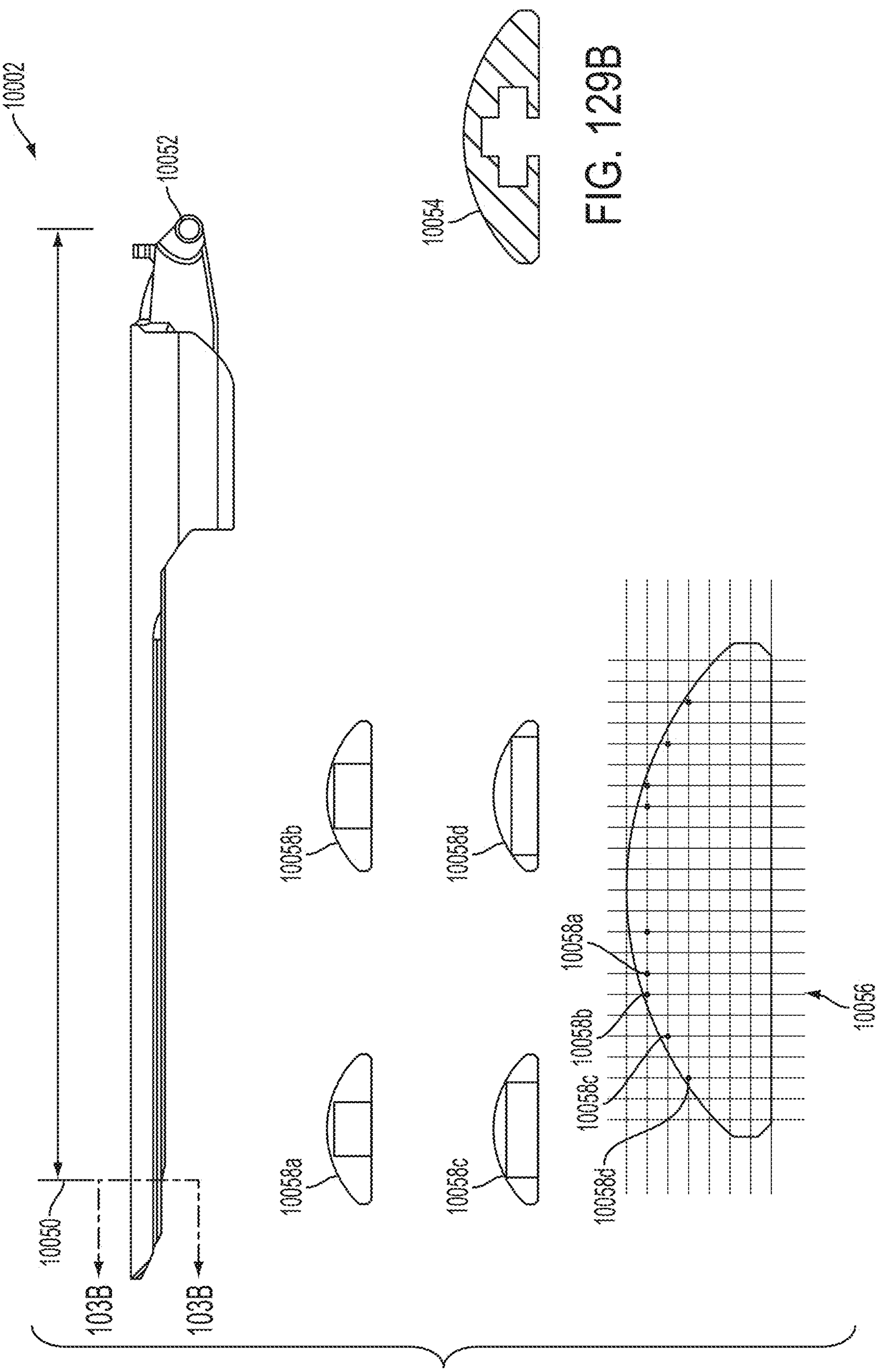
Figure 130B:
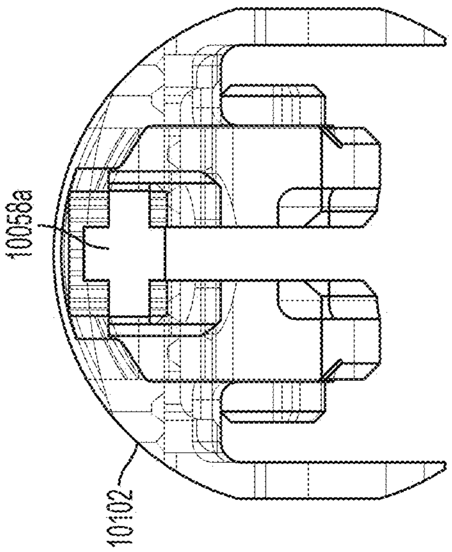
Figure 130A:
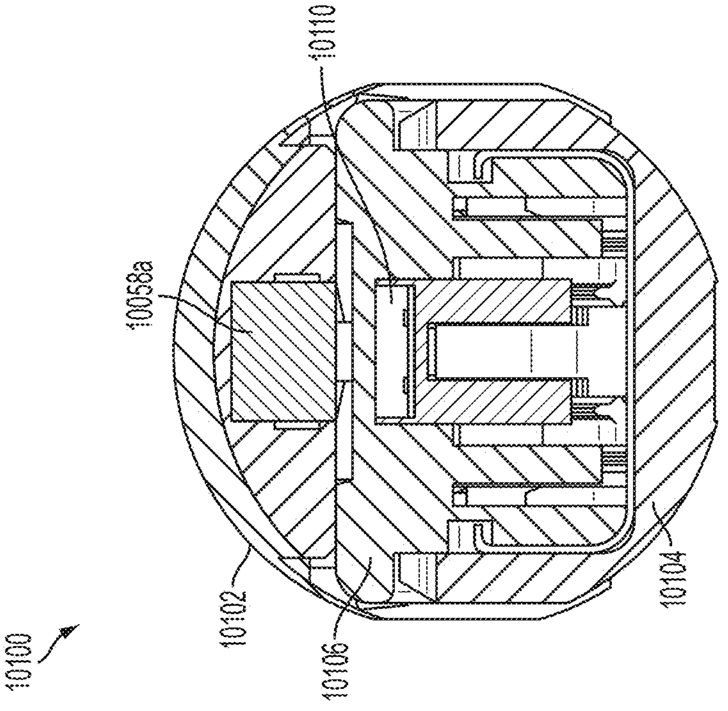
Figure 130D:
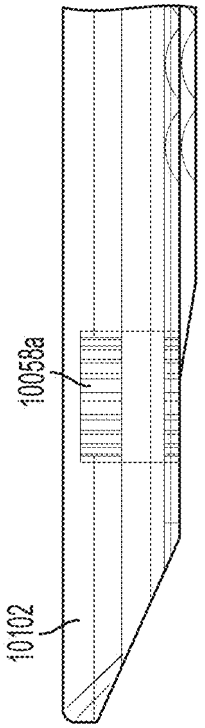
Figure 130E:
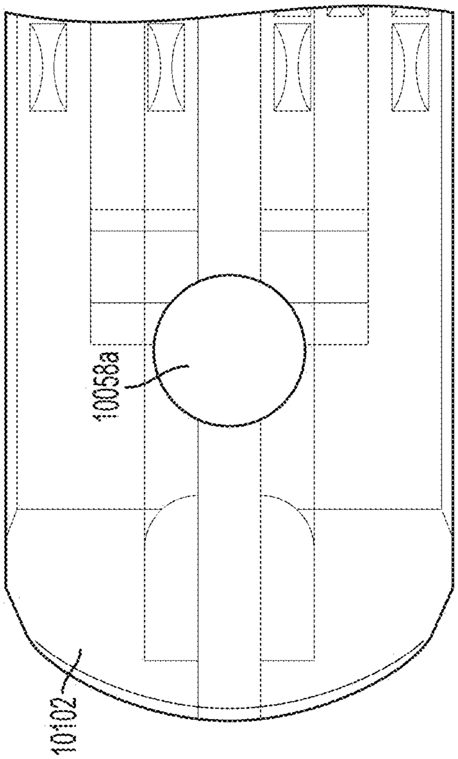
Figure 130C:
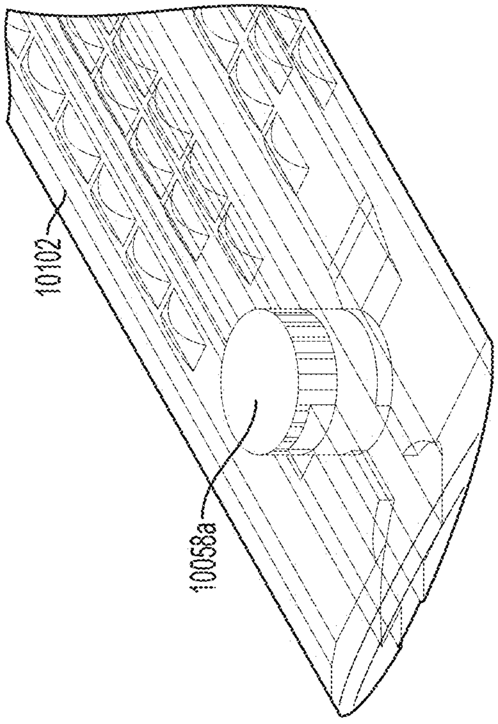
Figure 131B:
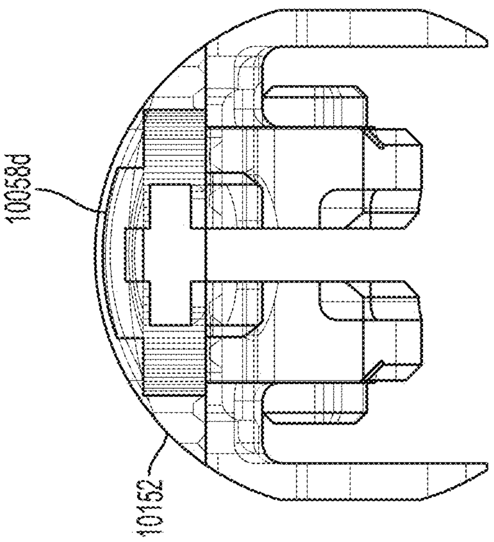
Figure 131A:
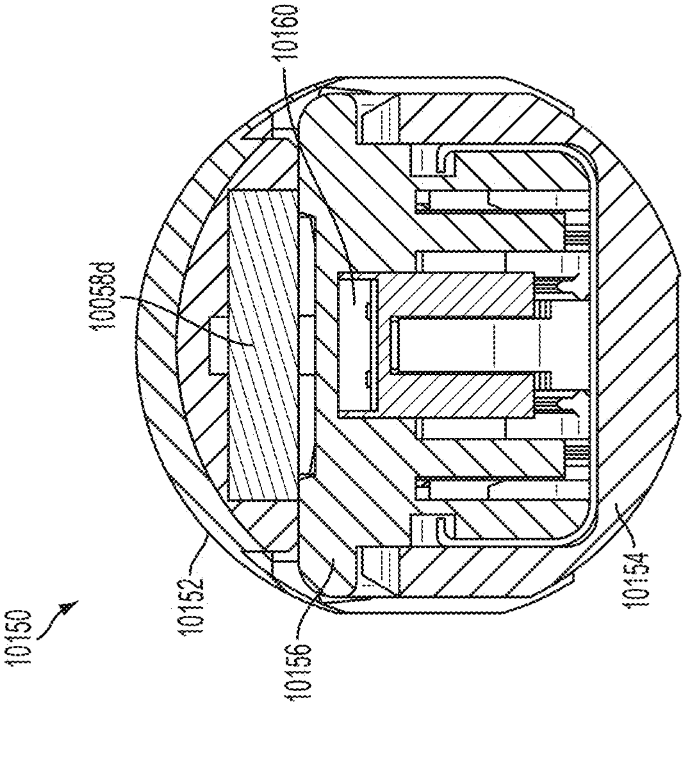
Figure 131D:
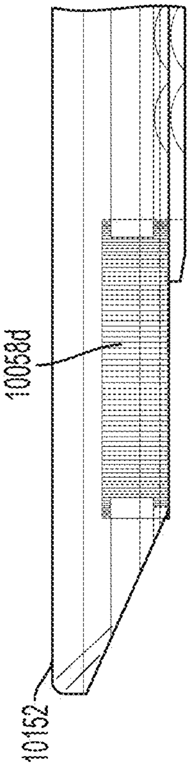
Figure 131E:
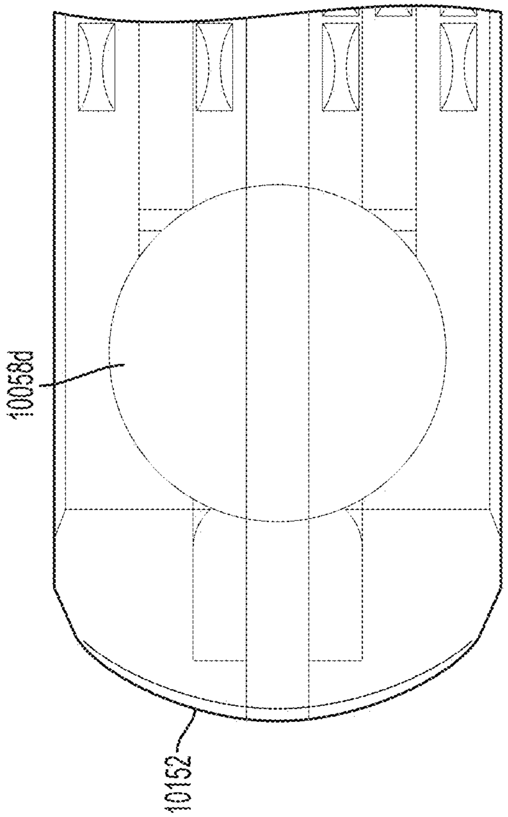
Figure 131C:
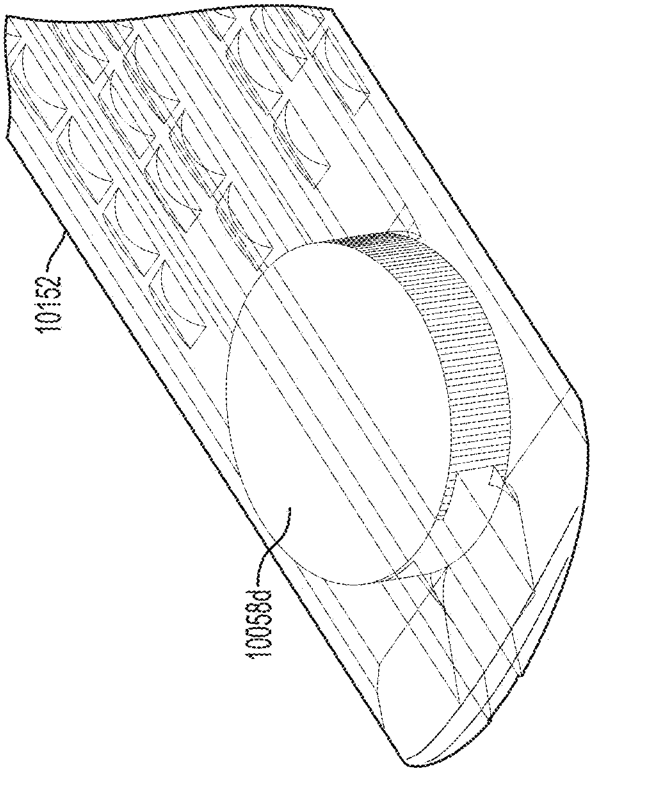
Figure 132:
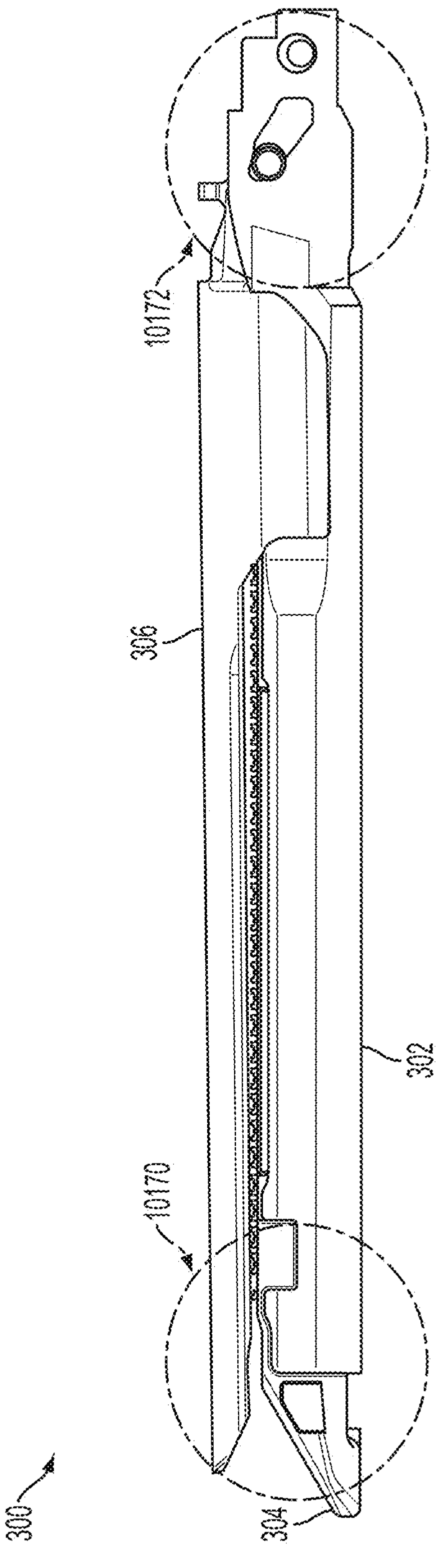
Figure 133A:
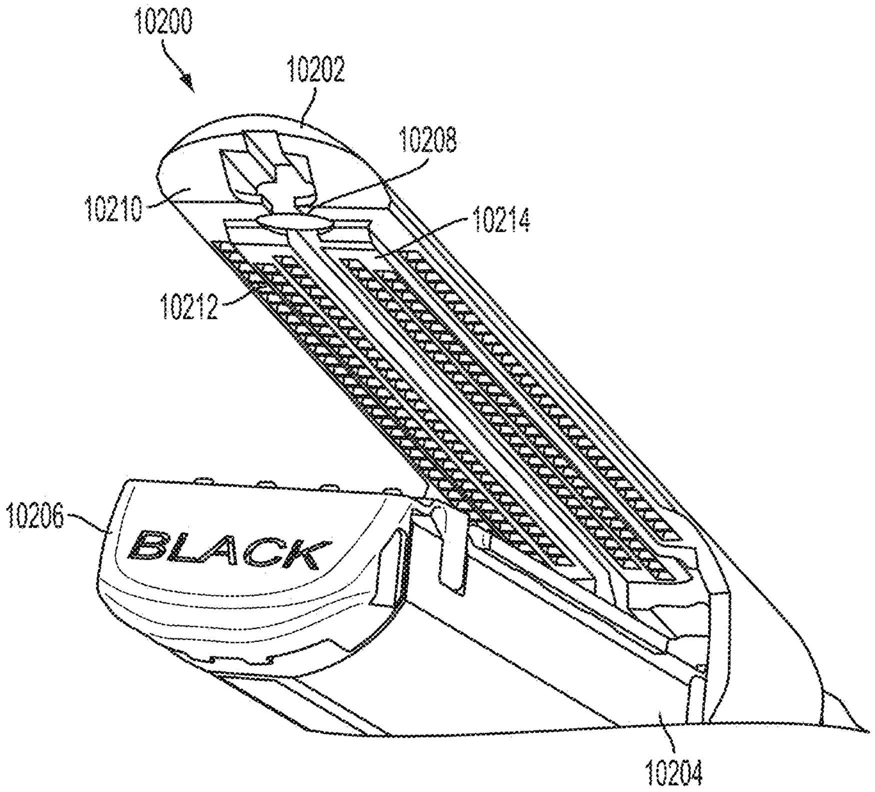
Figure 133B:
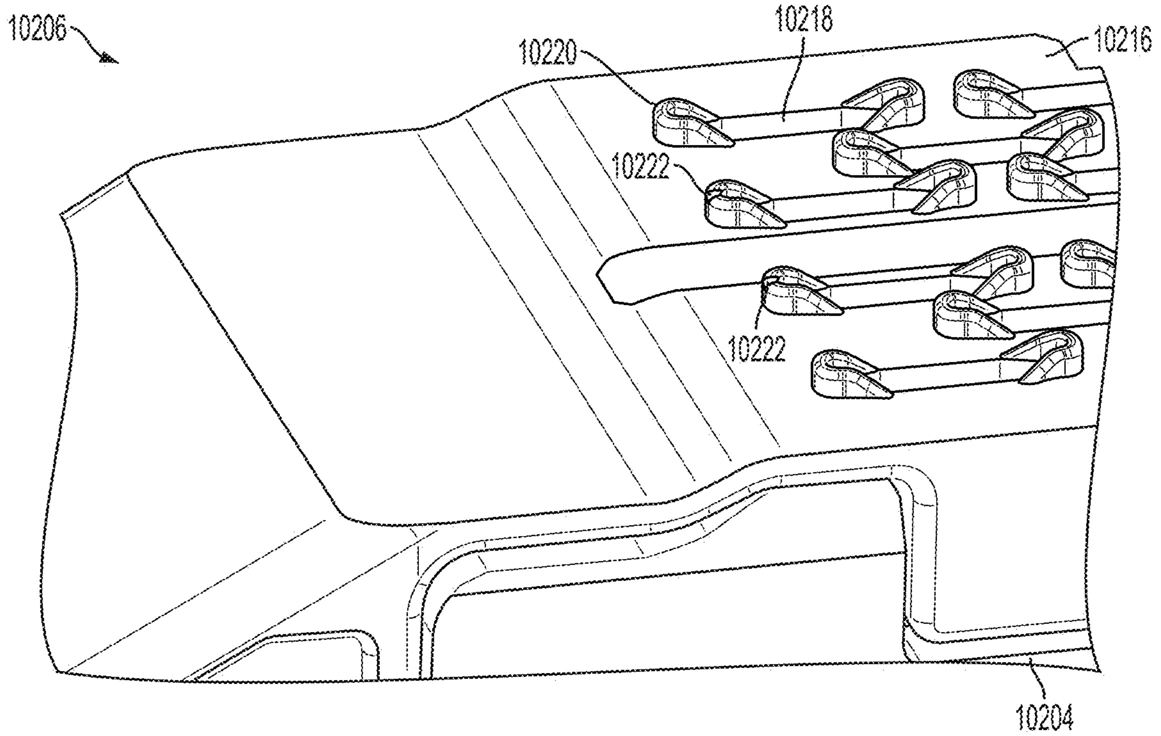
Figure 134B:
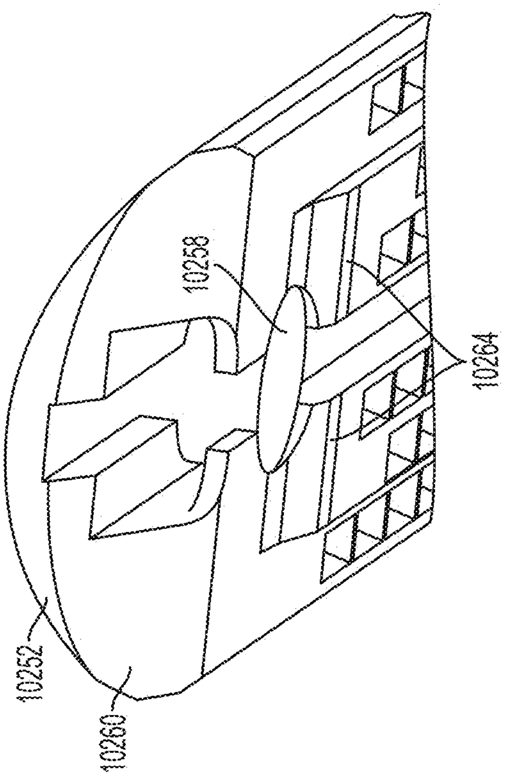
Figure 134C:
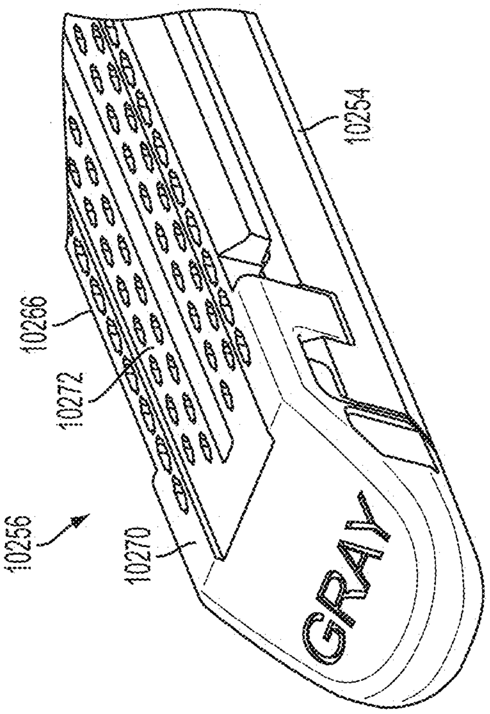
Figure 134A:
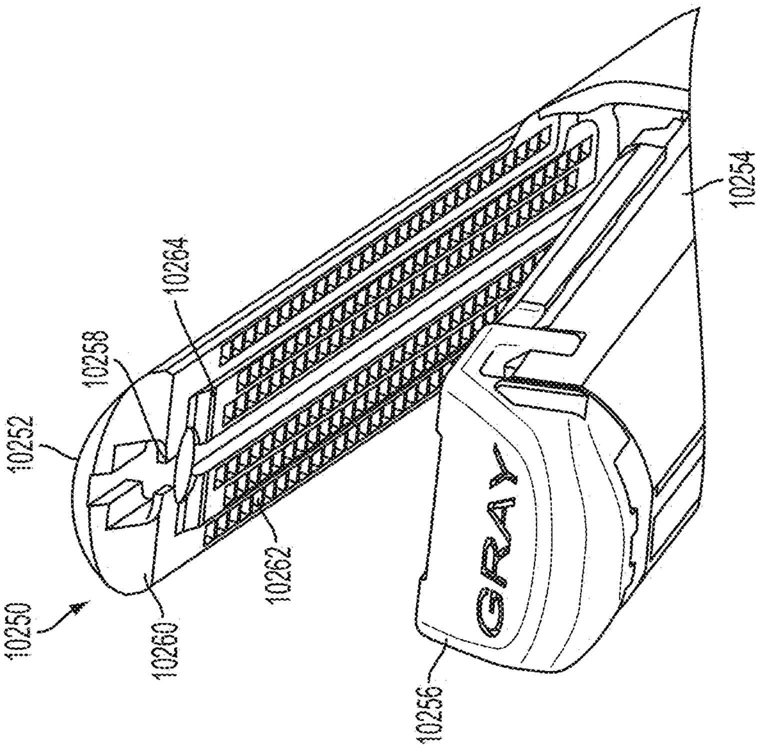
Figure 135A:
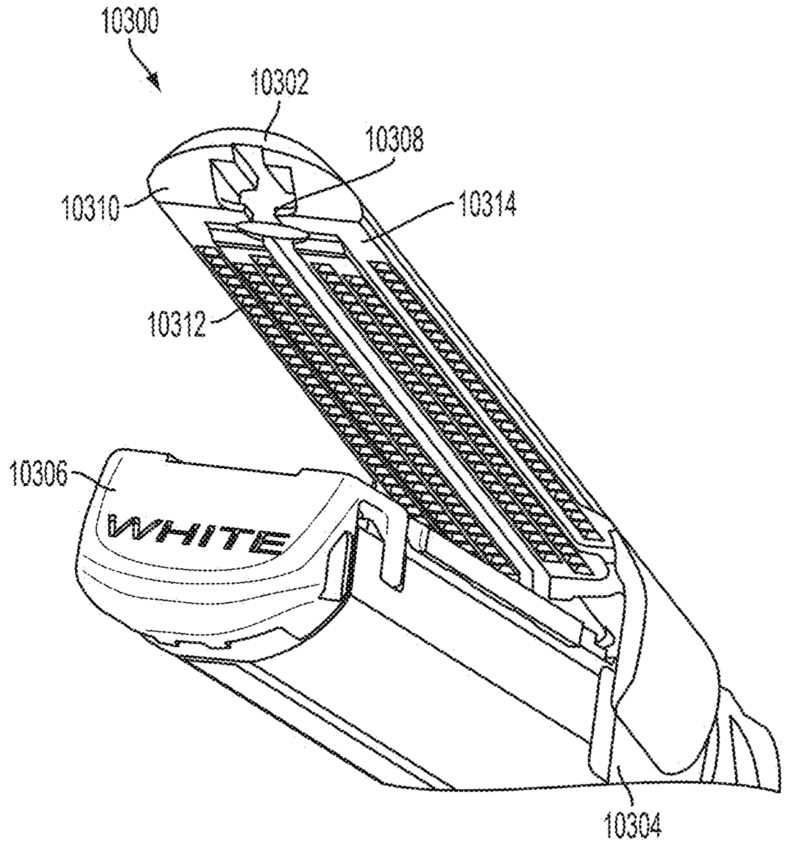
Figure 135B:
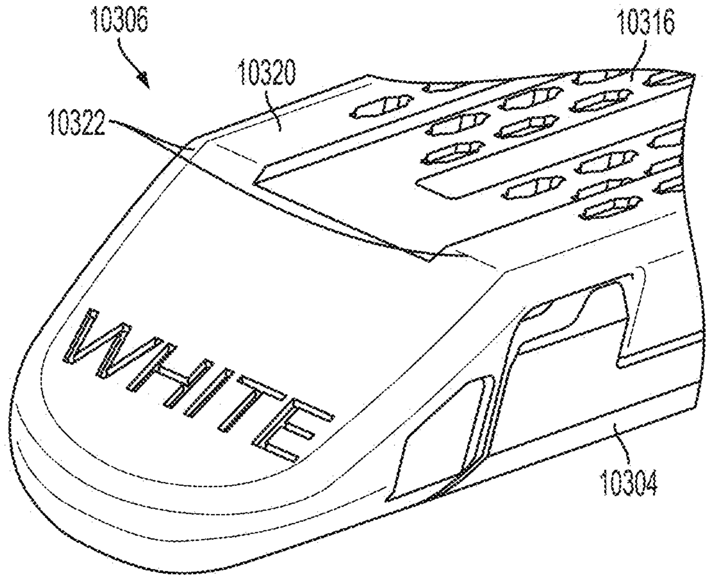
Figure 136A:
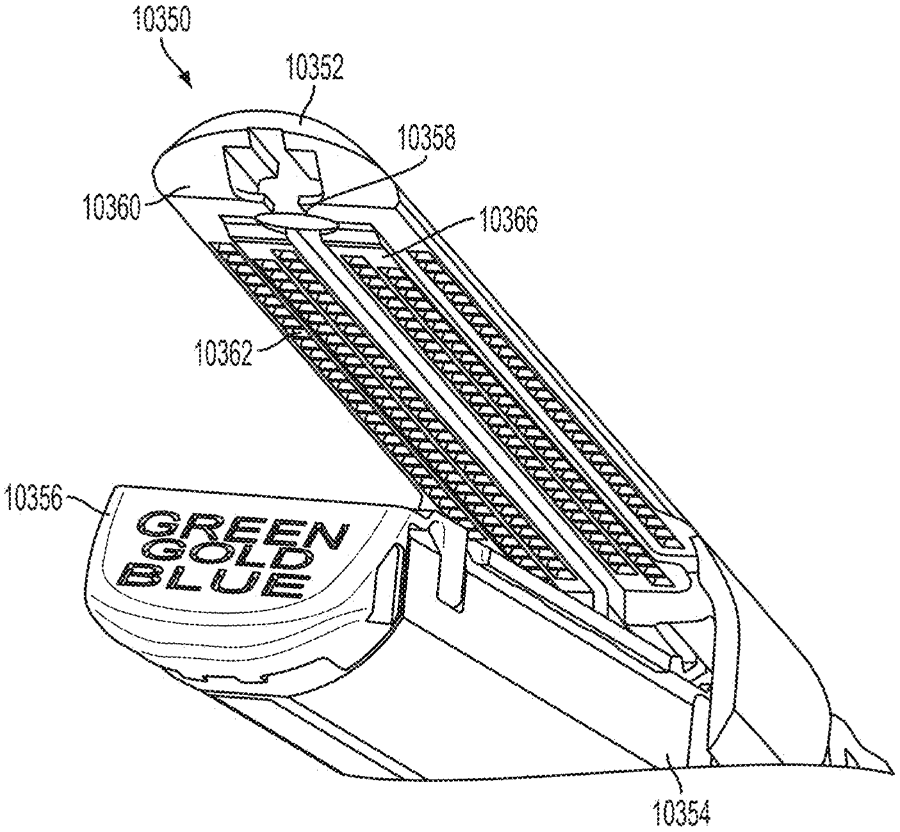
Figure 136B:
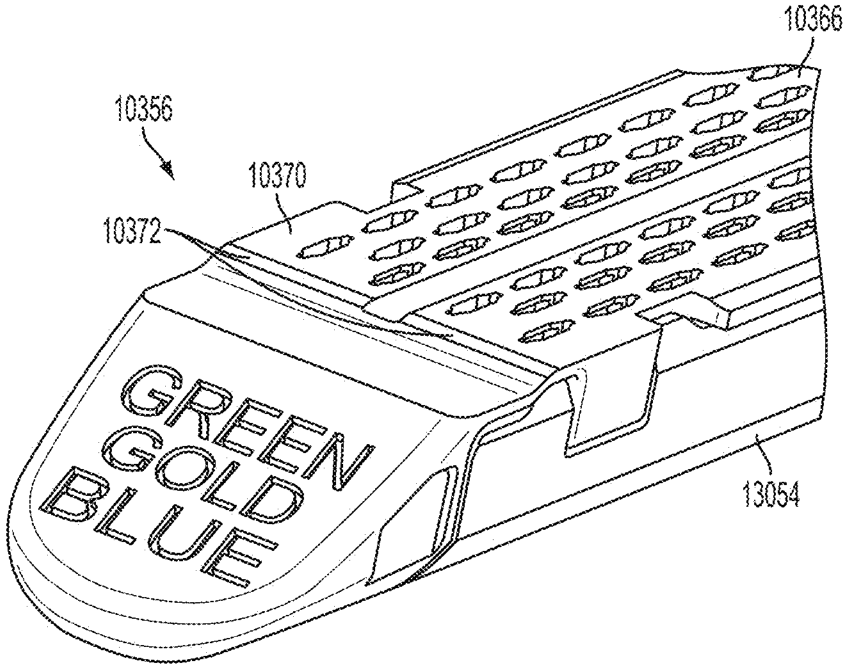
Figure 137C:
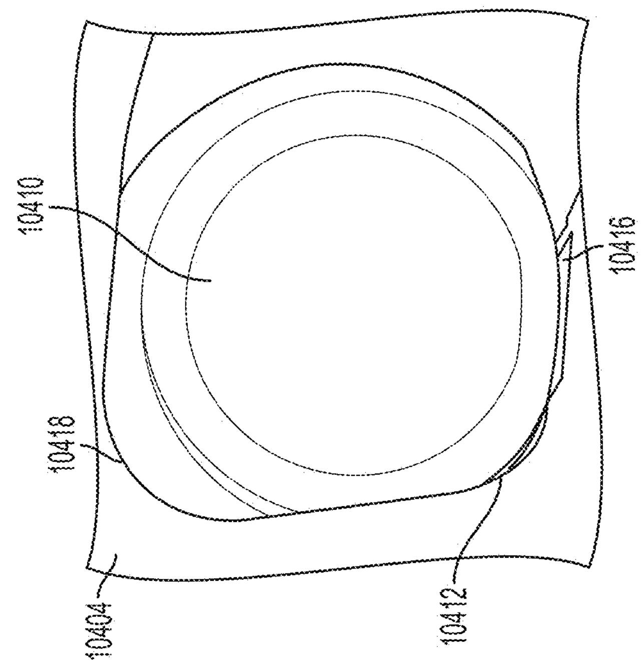
Figure 137A:
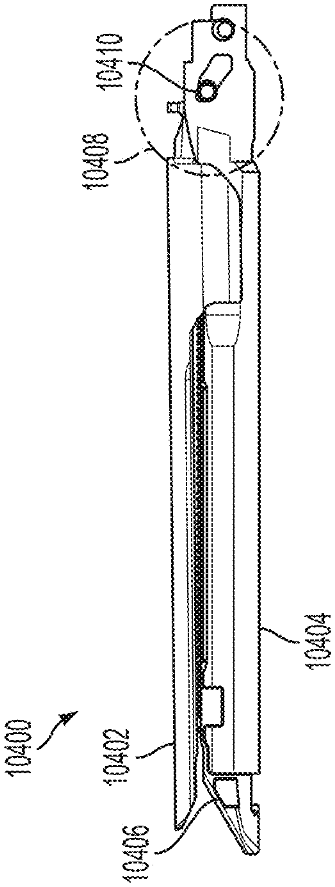
Figure 137B:
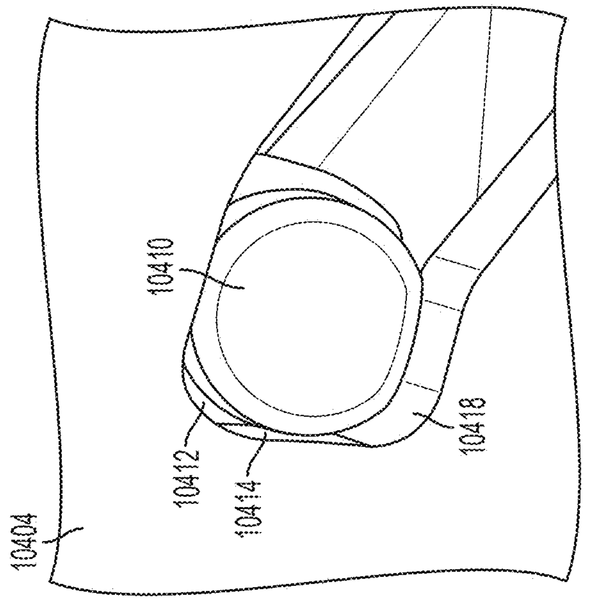
Figure 138:
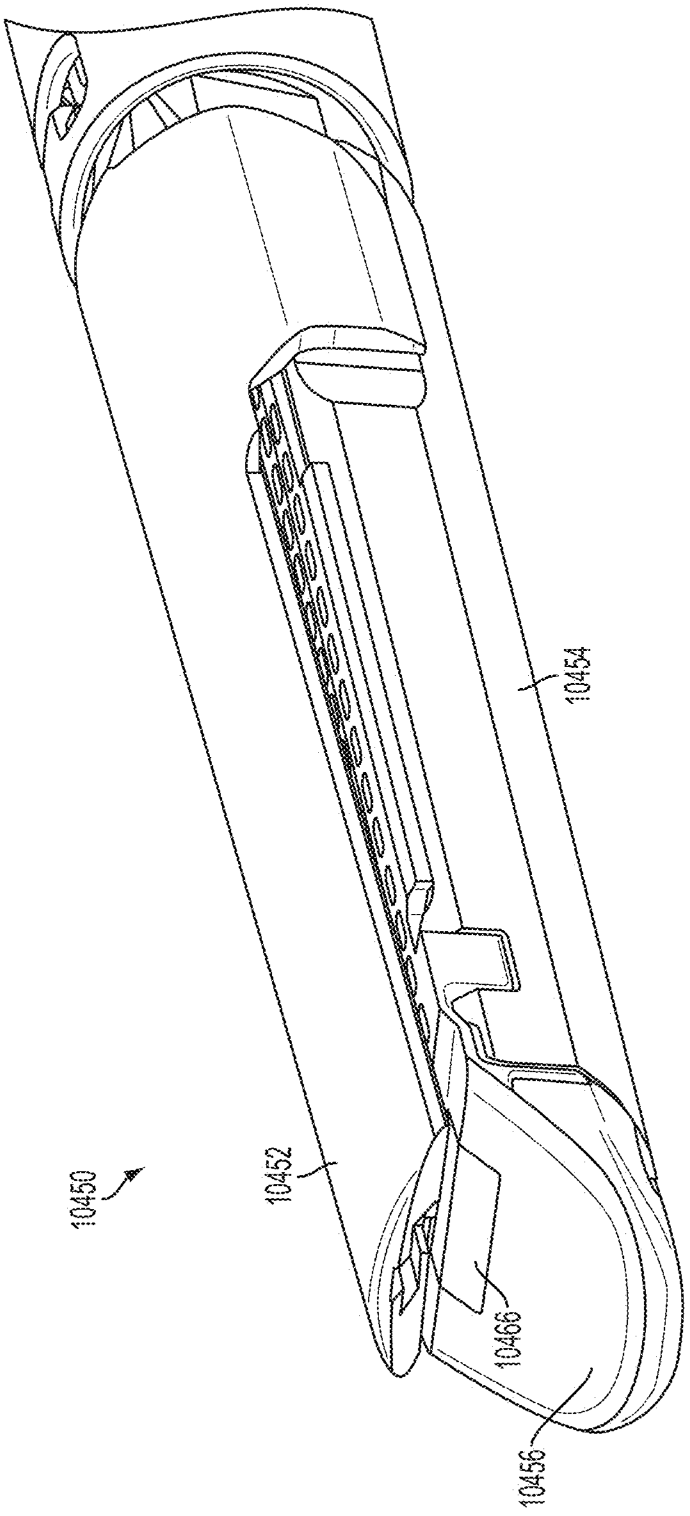
Figure 139A:
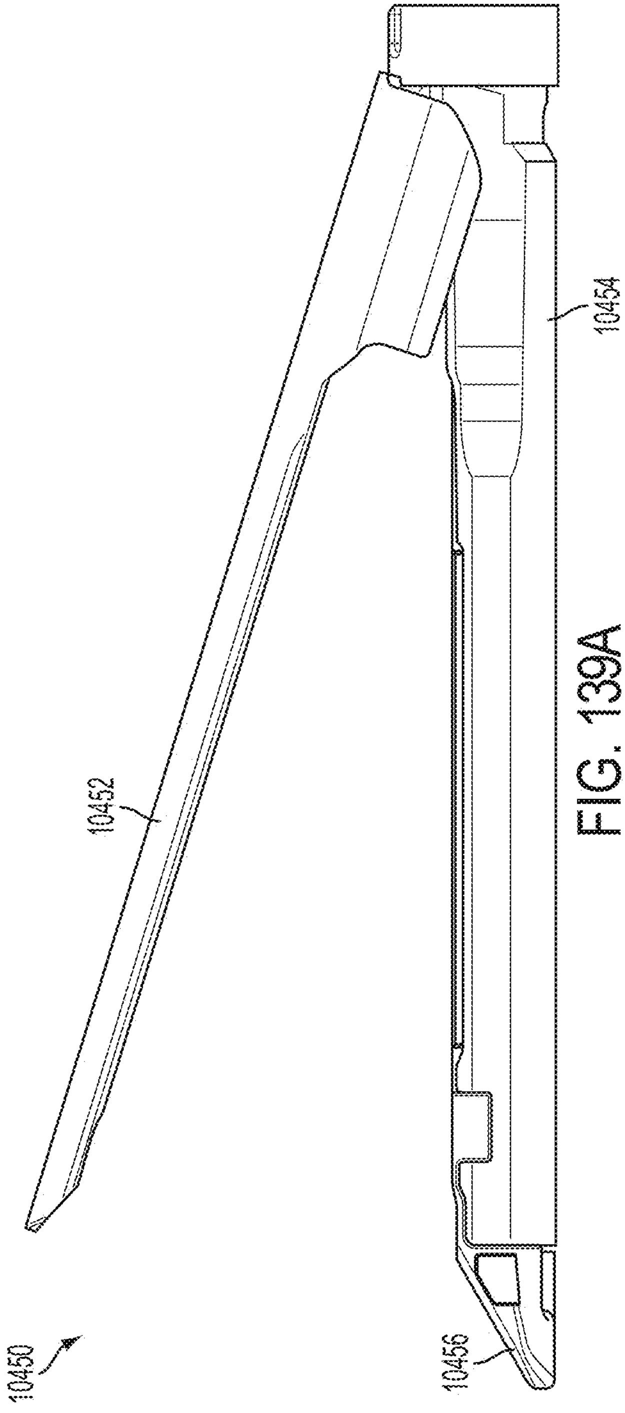
Figure 139B:
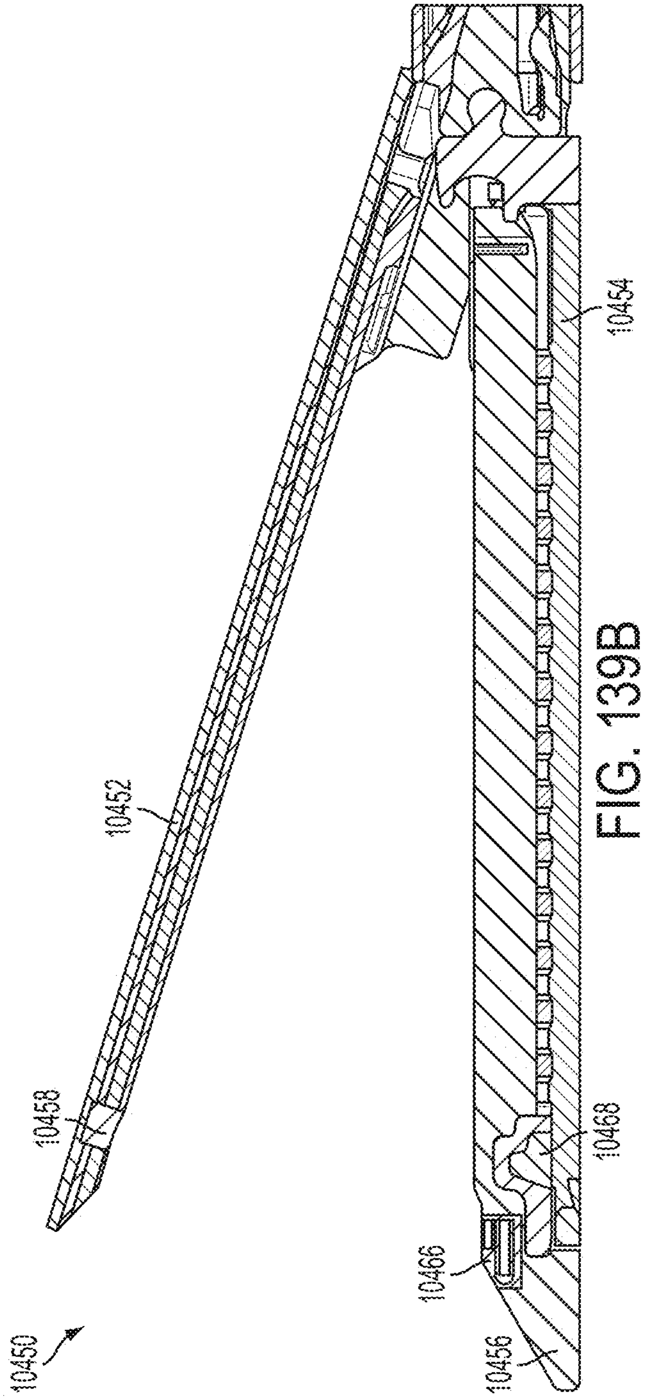
Figure 139C:
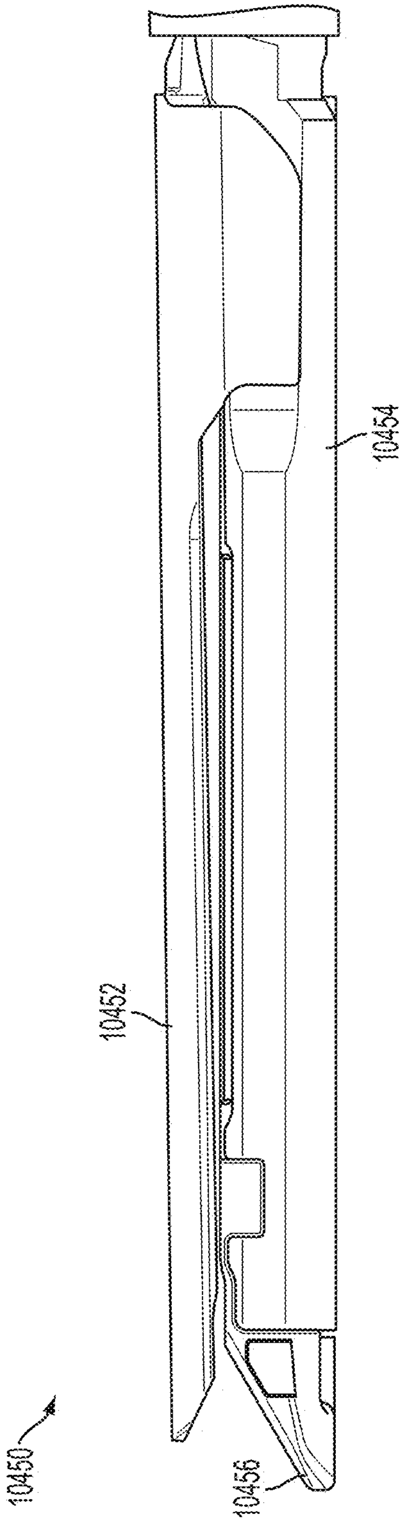
Figure 139D:
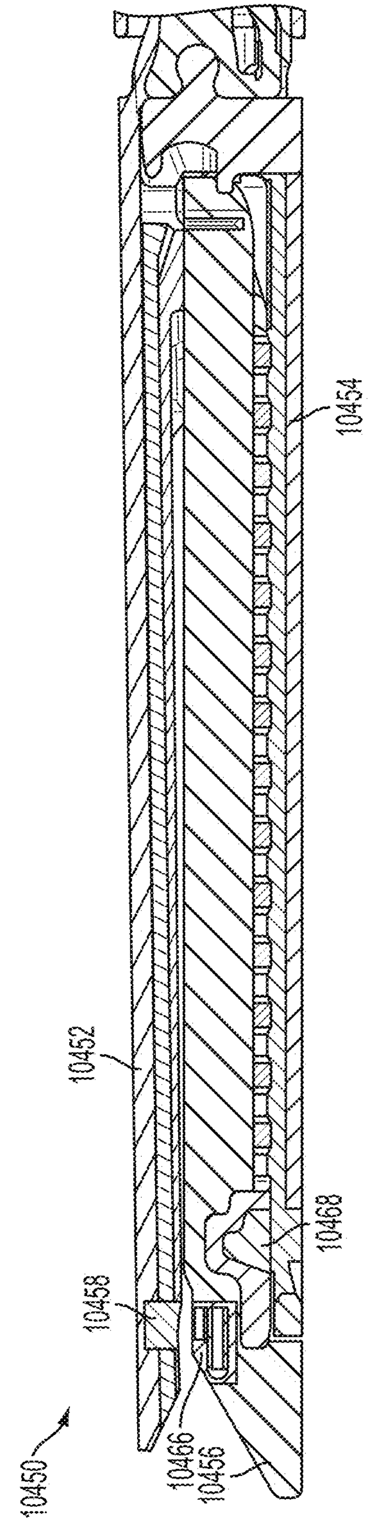
Figure 140:
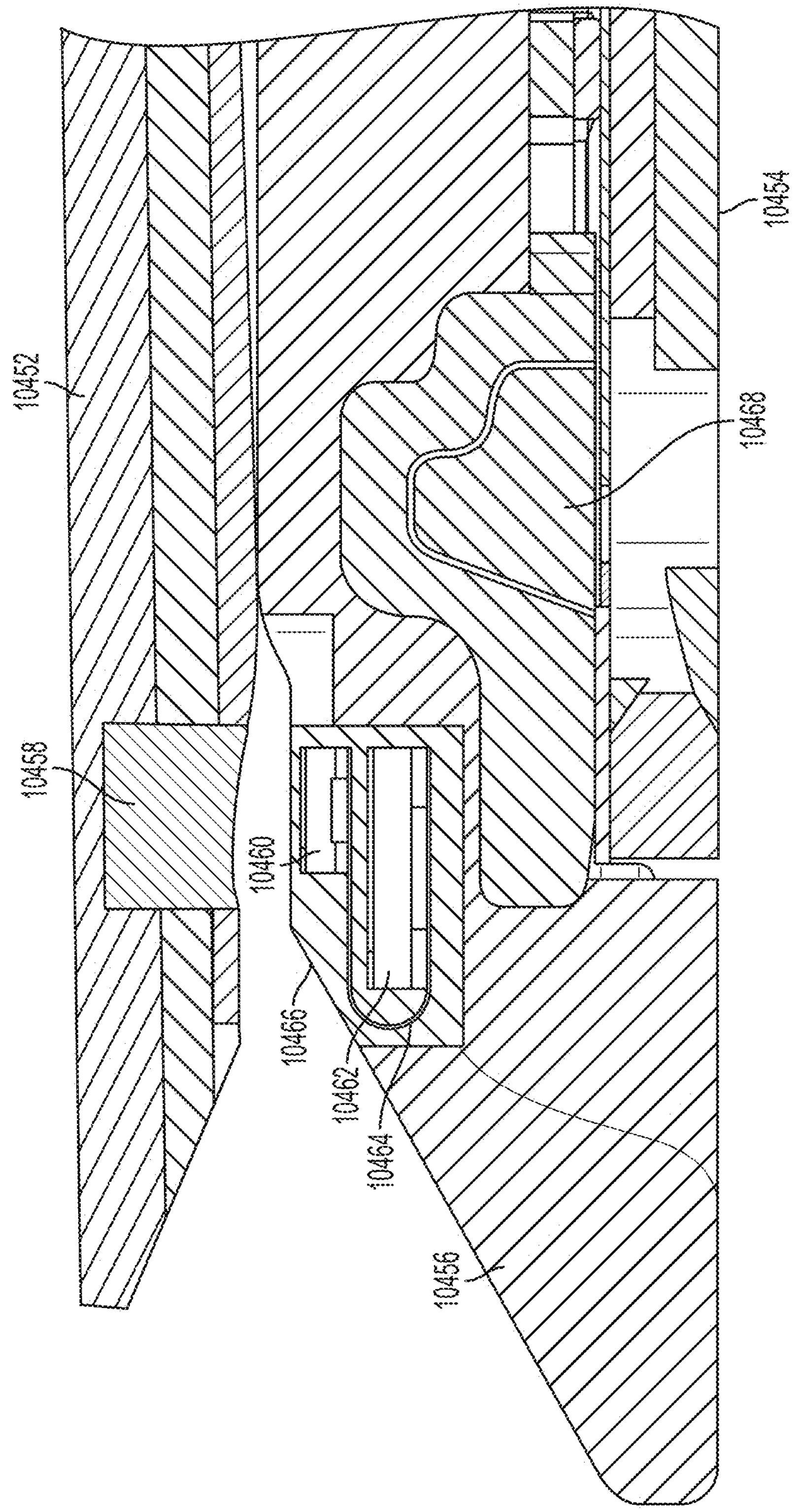
Figure 141:
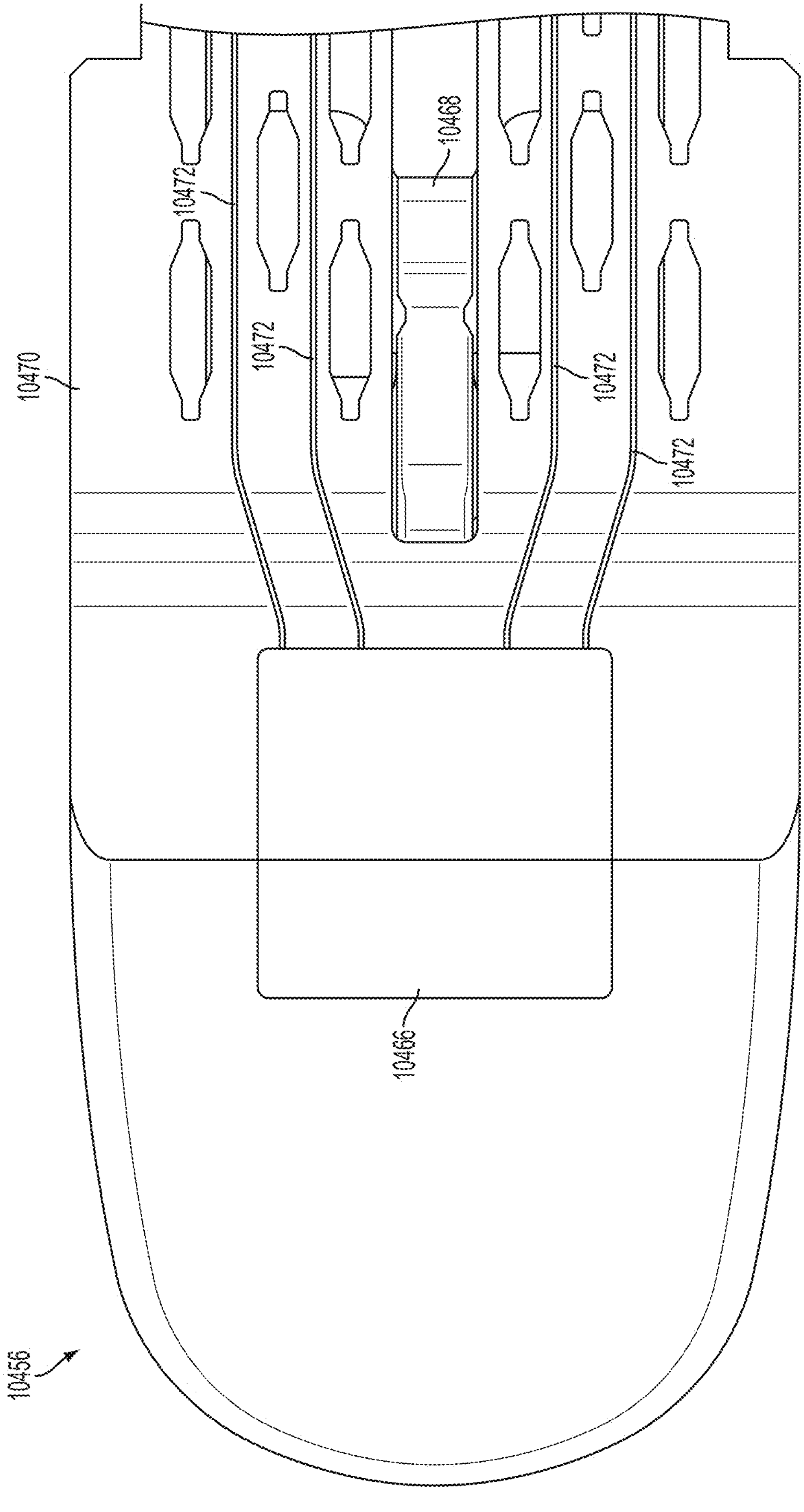
Figure 142A:
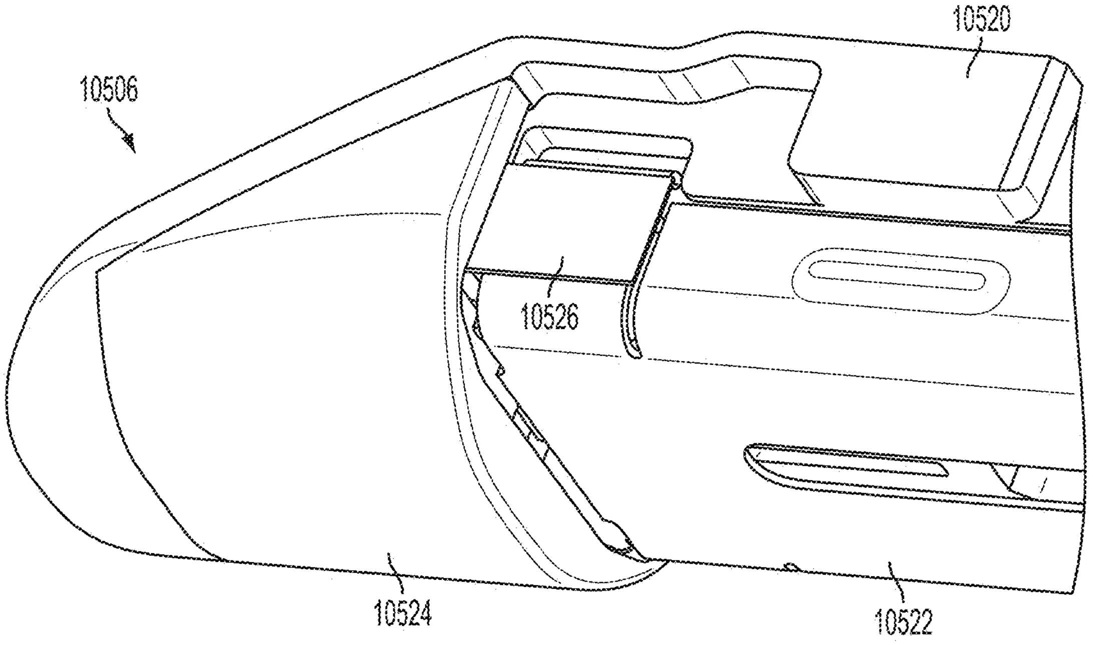
Figure 142B:
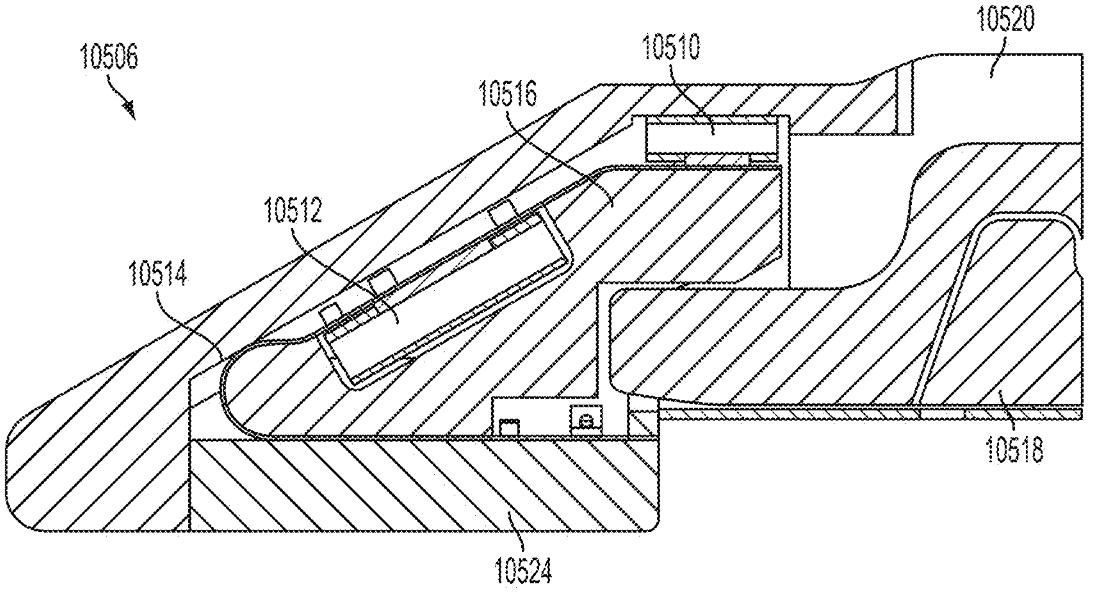
Figure 143A:
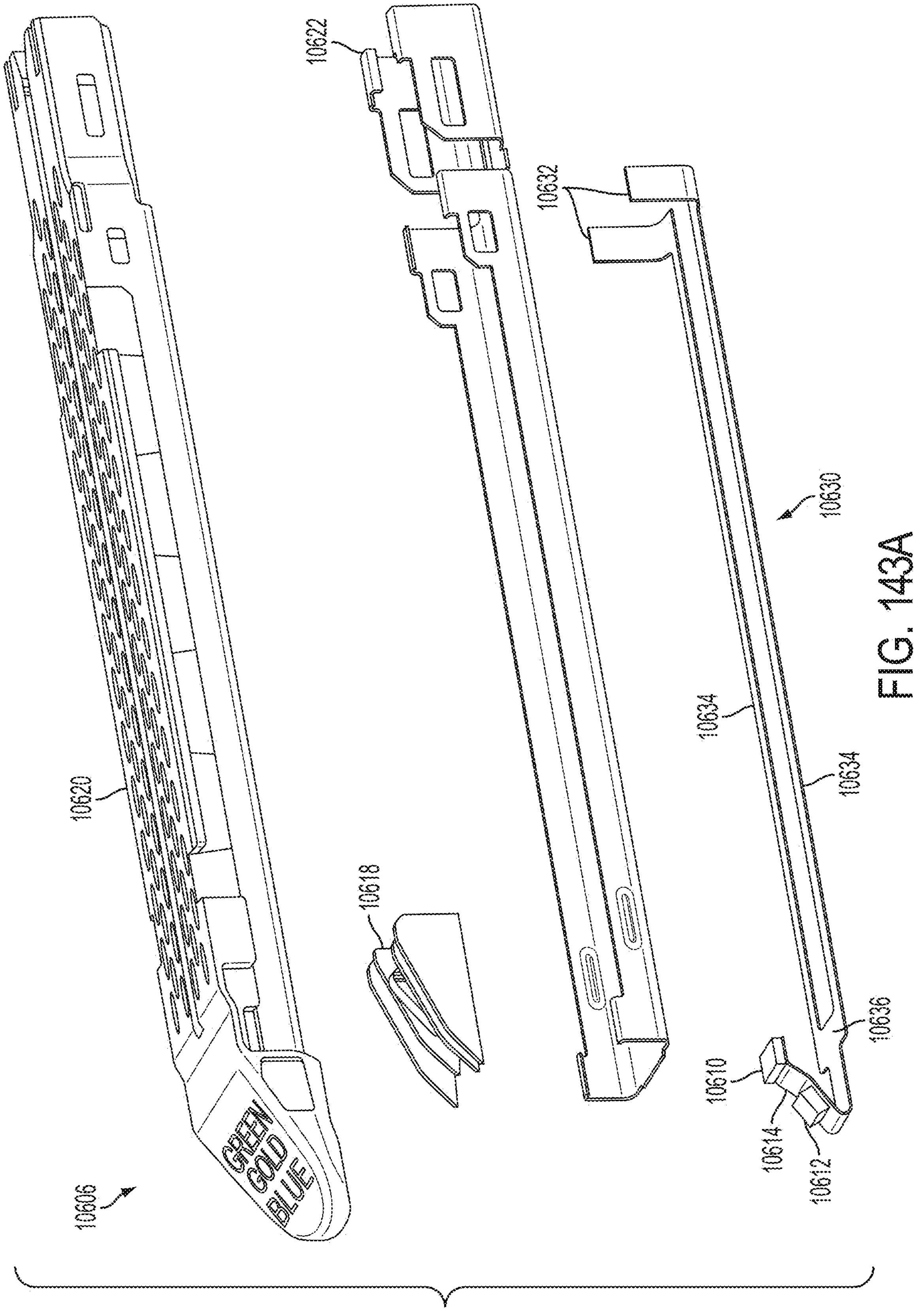
Figure 143B:
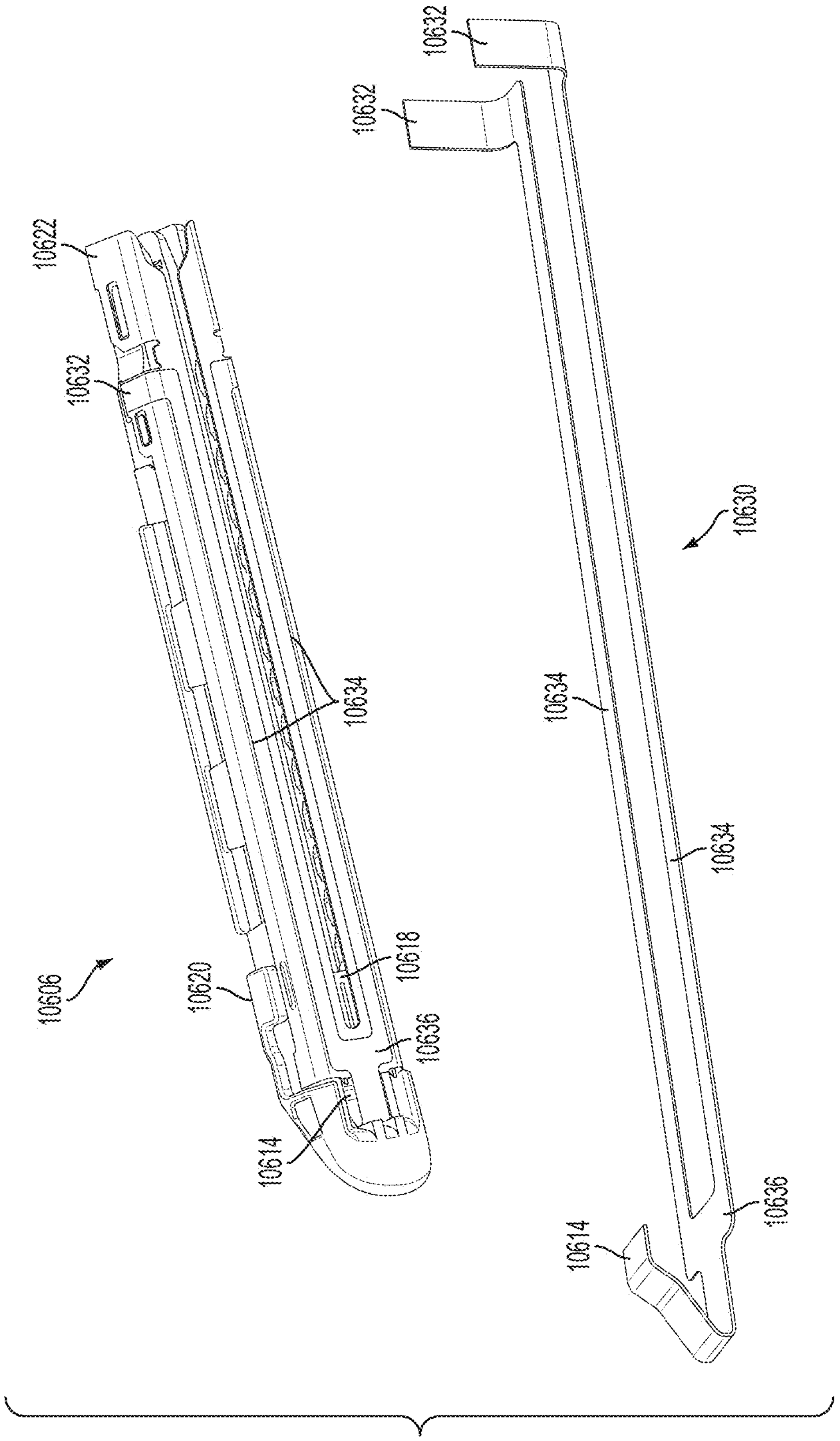
Figure 143C:
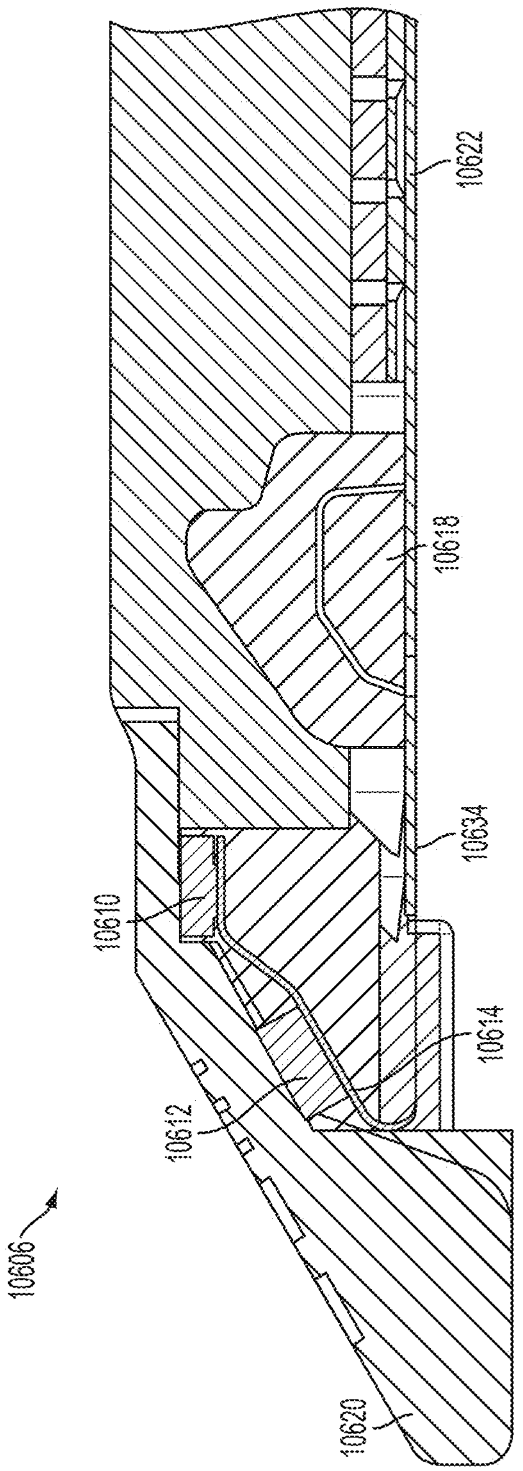
Figure 144A:
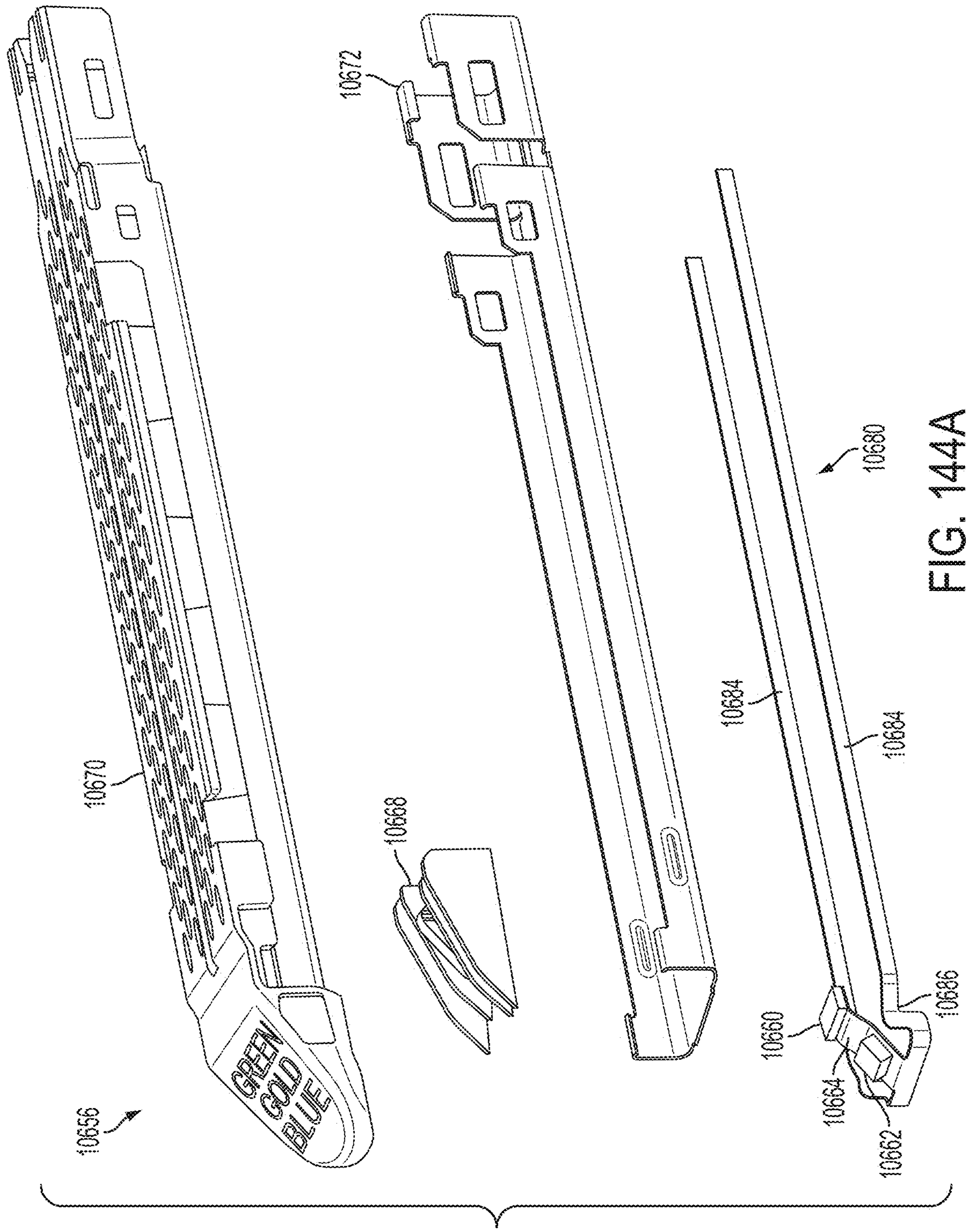
Figure 144B:
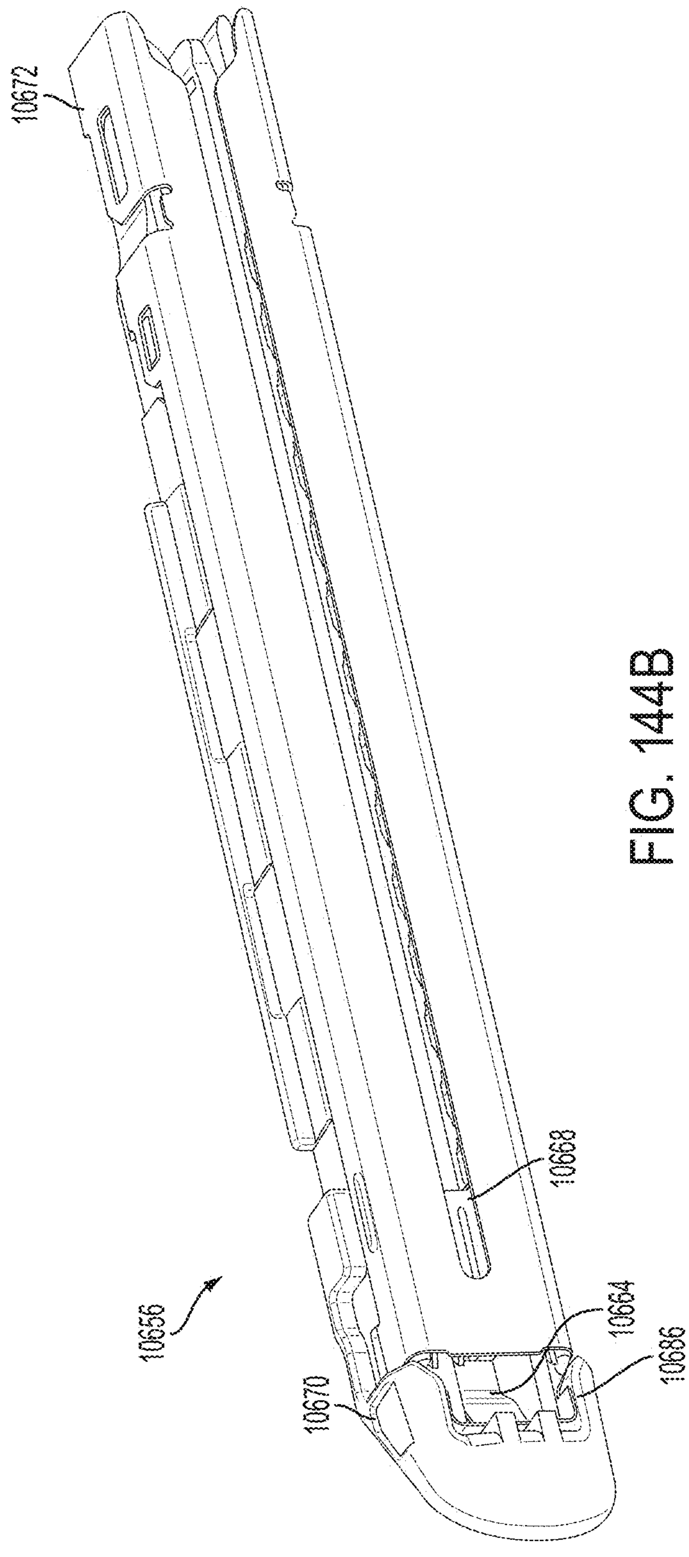
Figure 144C:
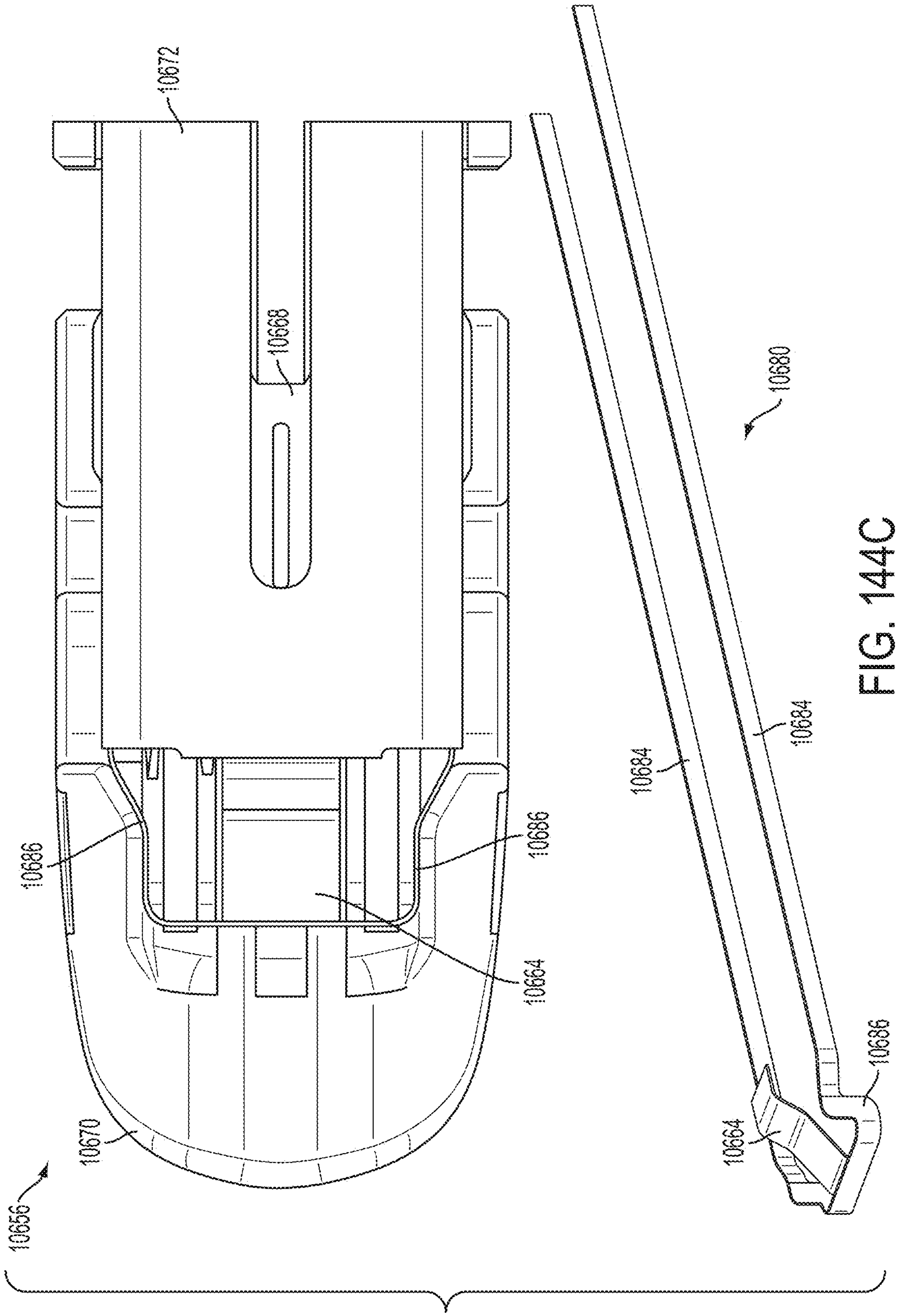
Figure 144D:
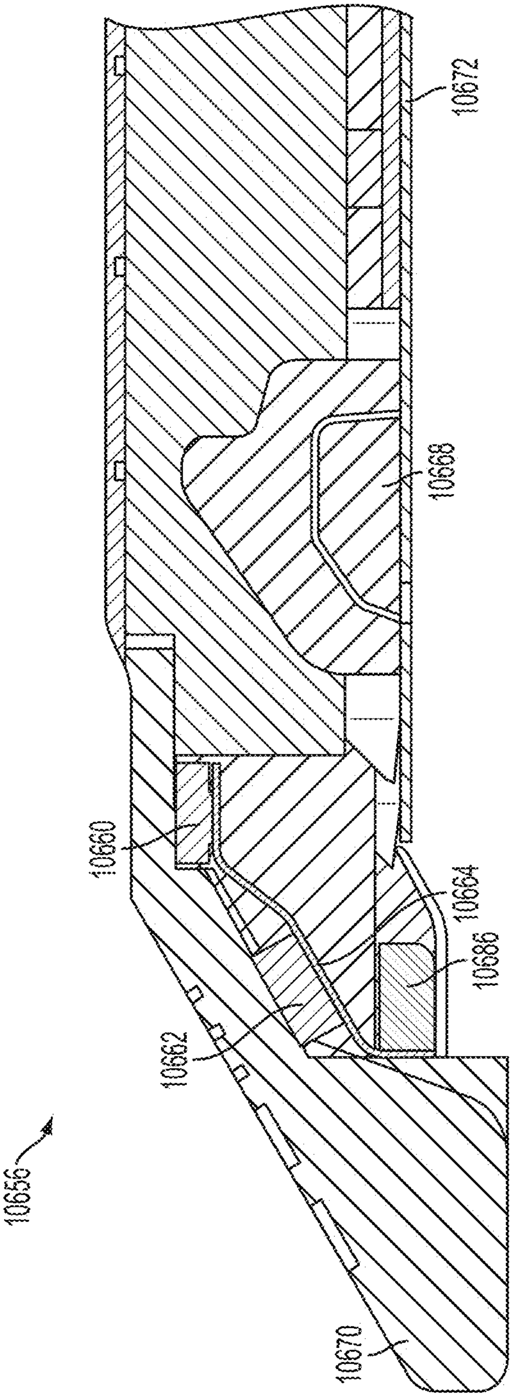
Figure 144E:
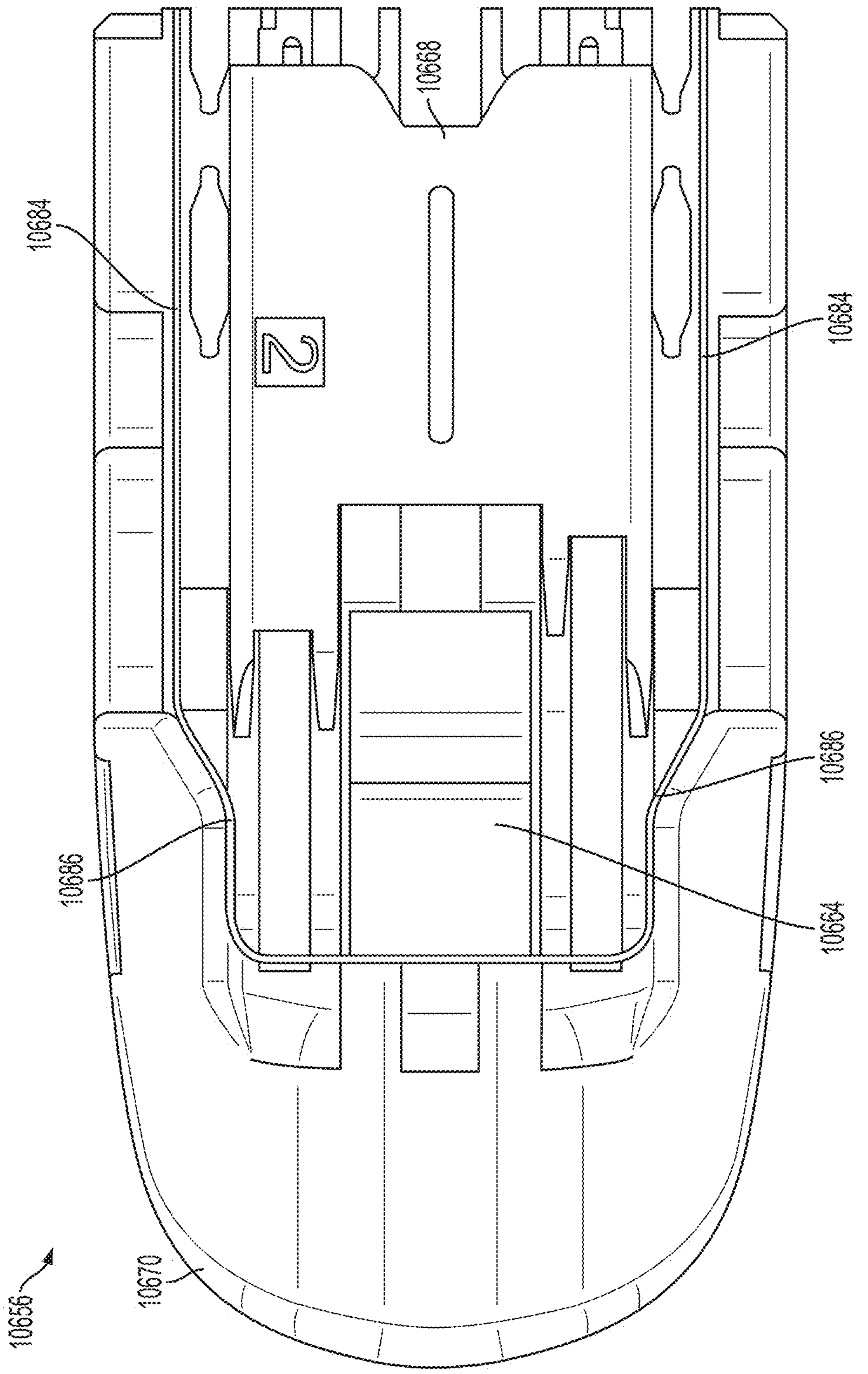
Figure 144F:
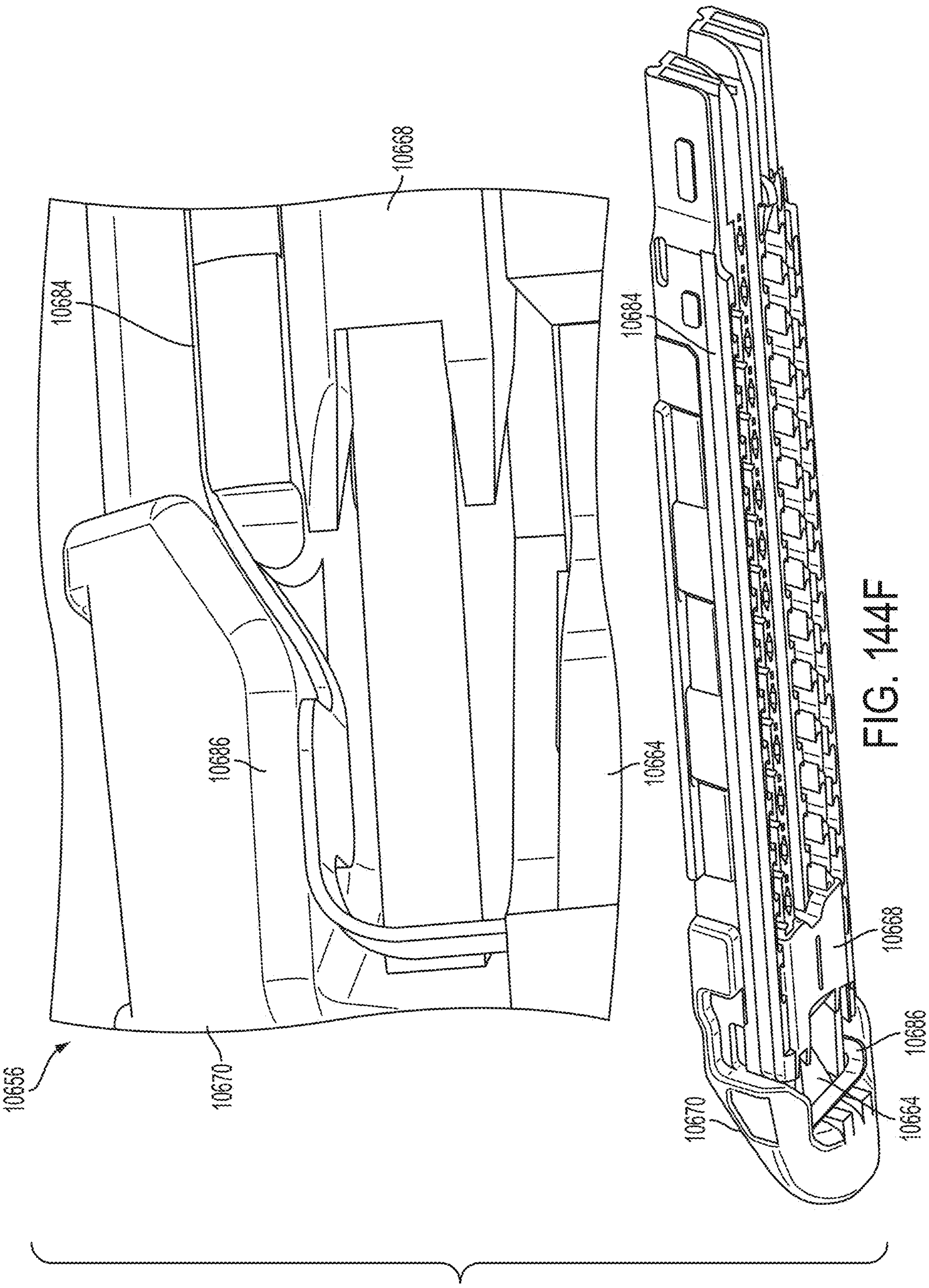
Figure 145A:
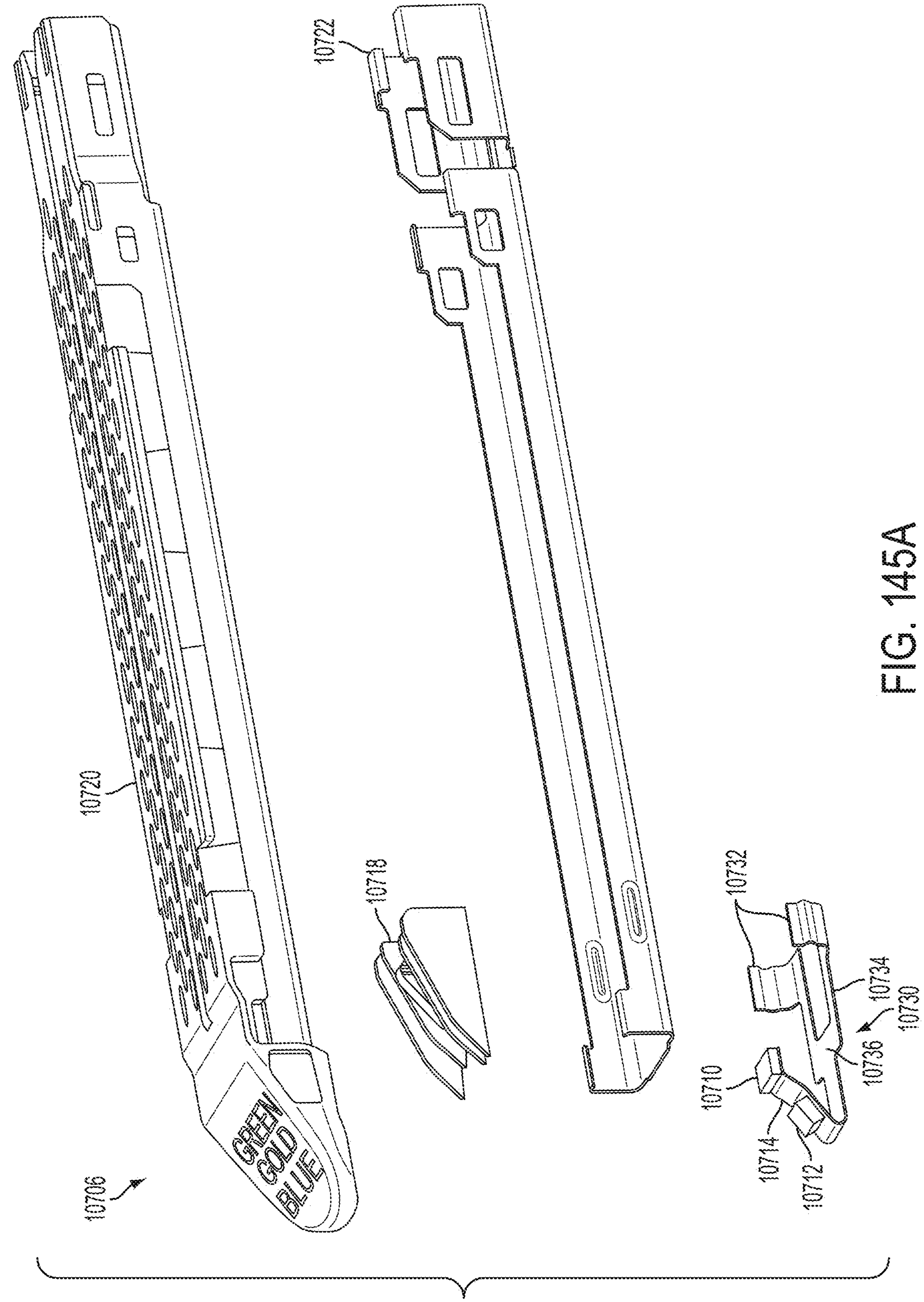
Figure 145B:
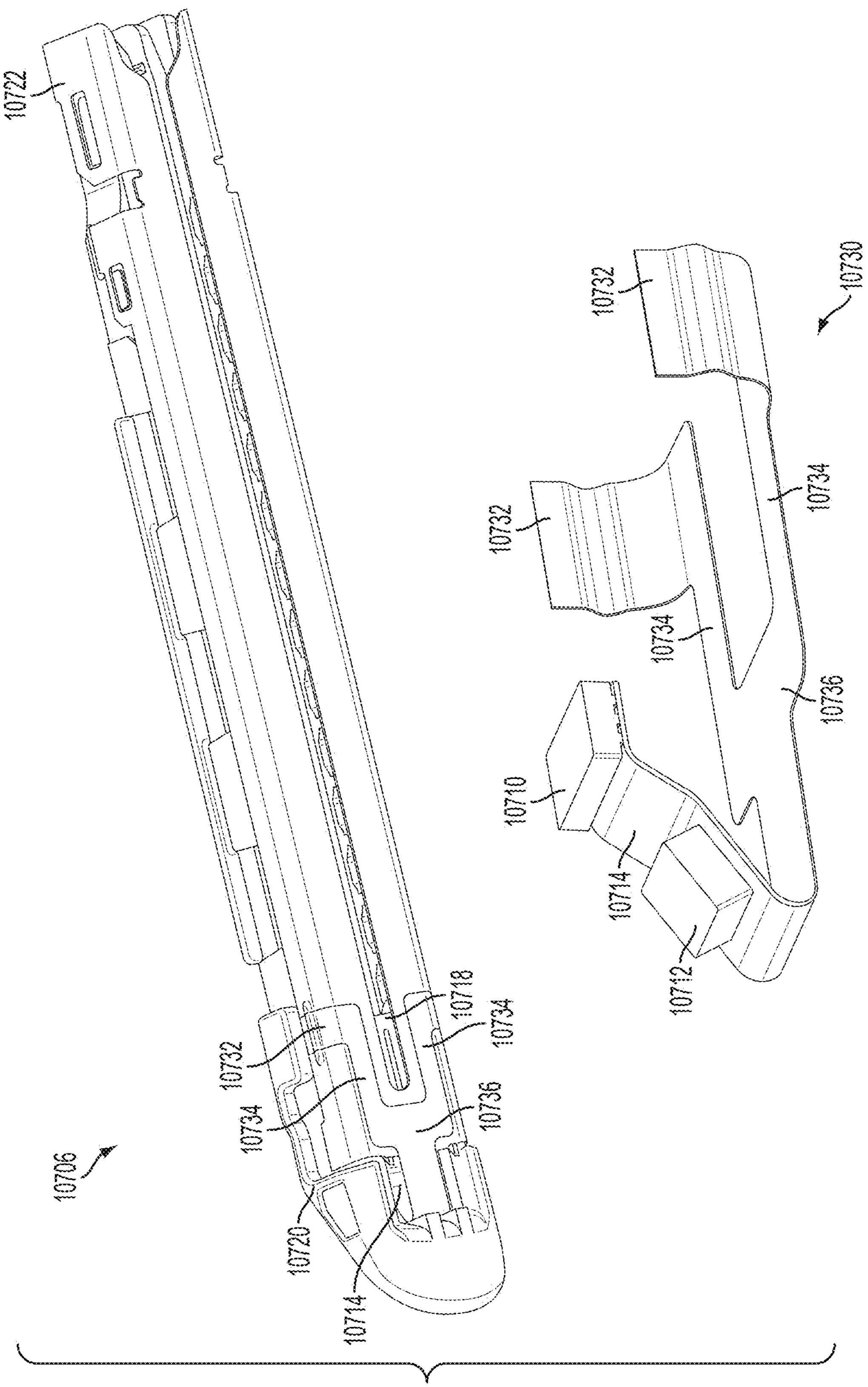
Figure 146A:
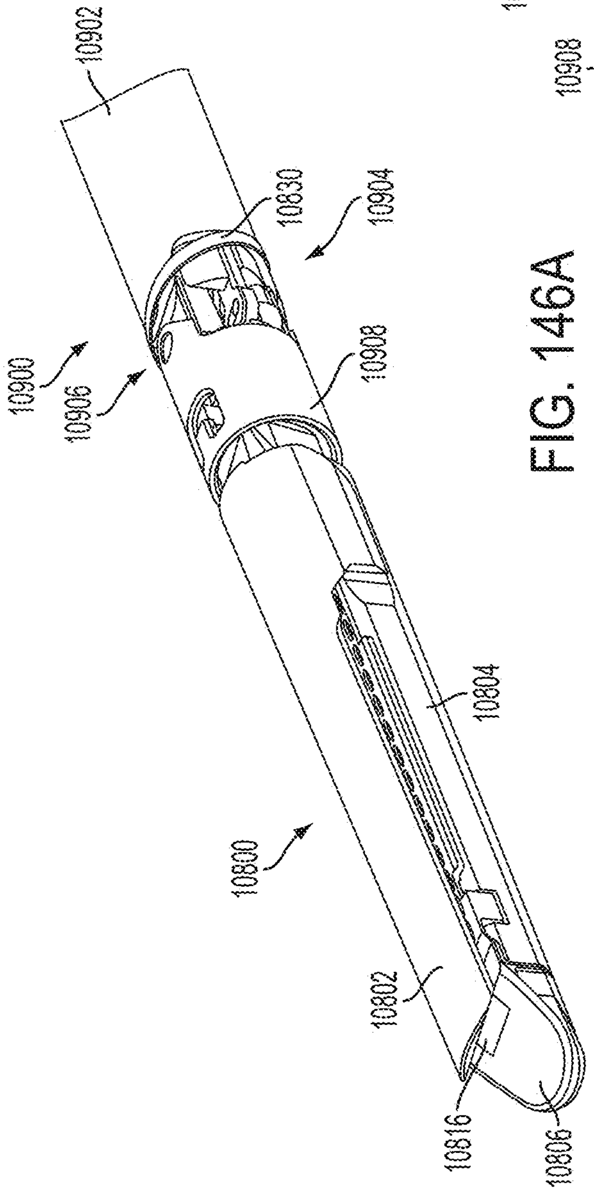
Figure 146B:
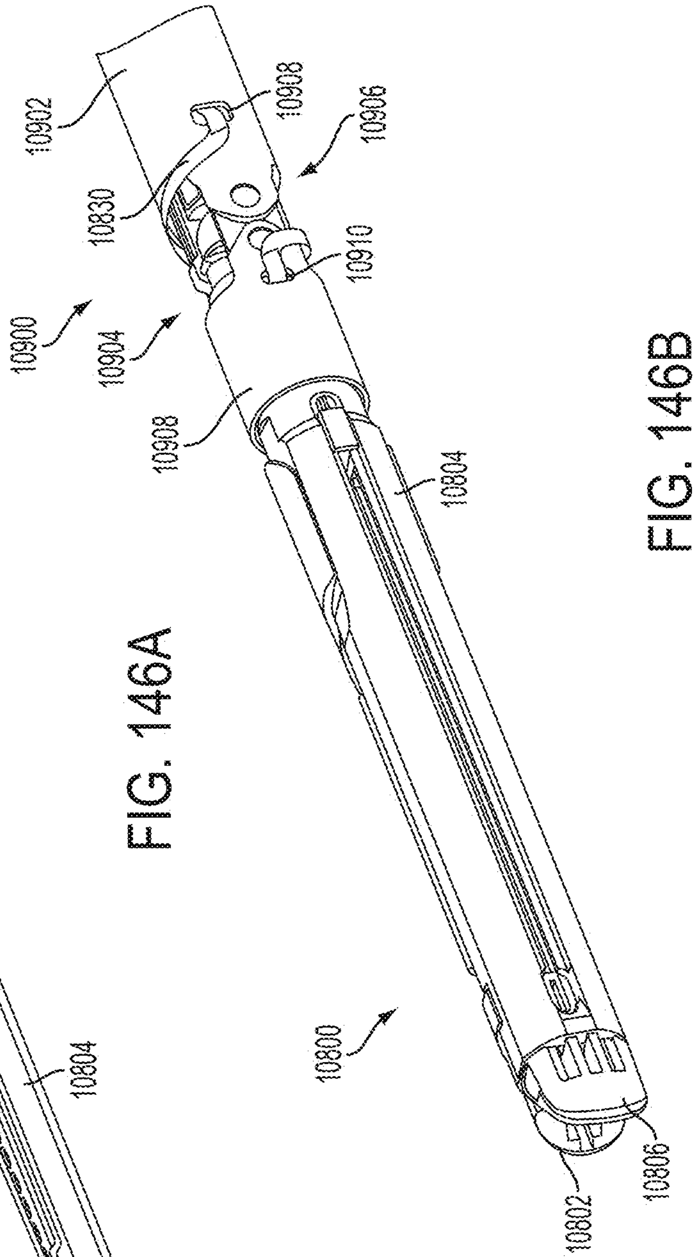
Figure 146D:
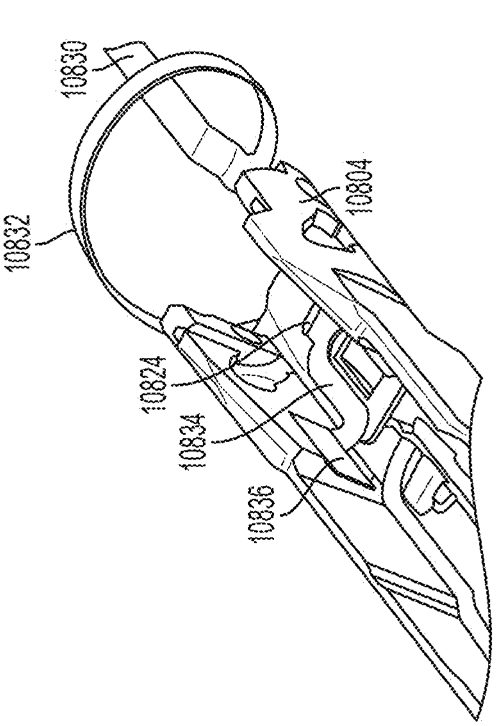
Figure 146F:
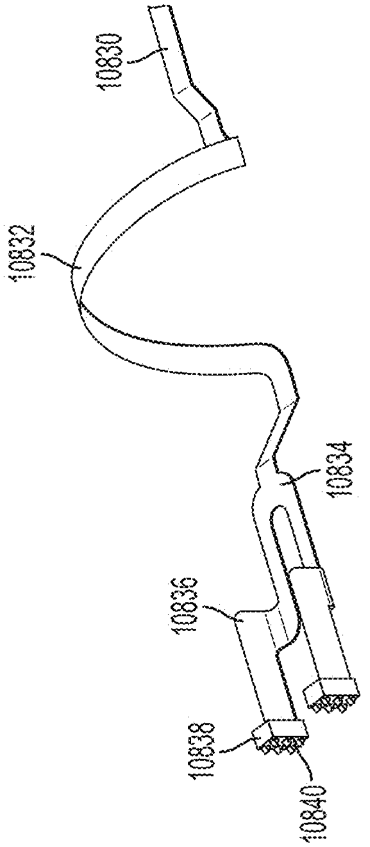
Figure 146C:
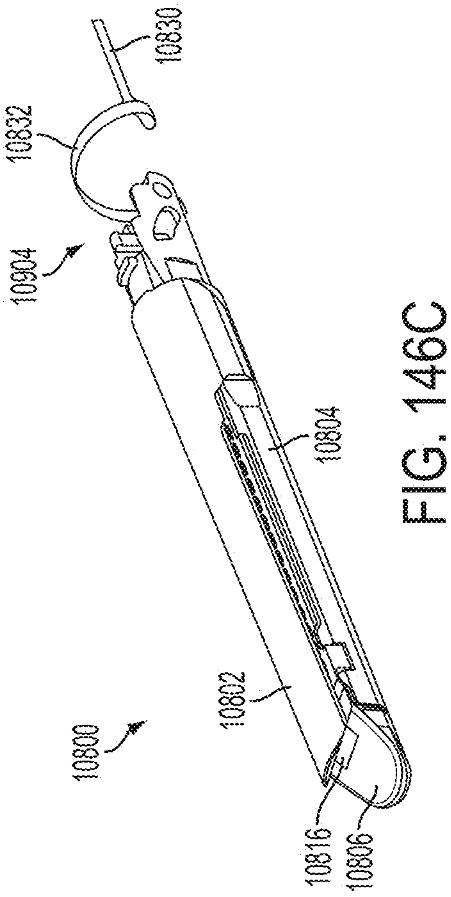
Figure 146E:
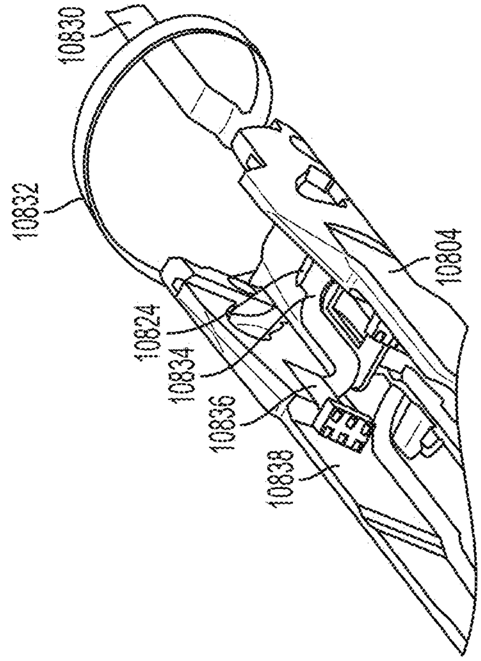
Figure 147:
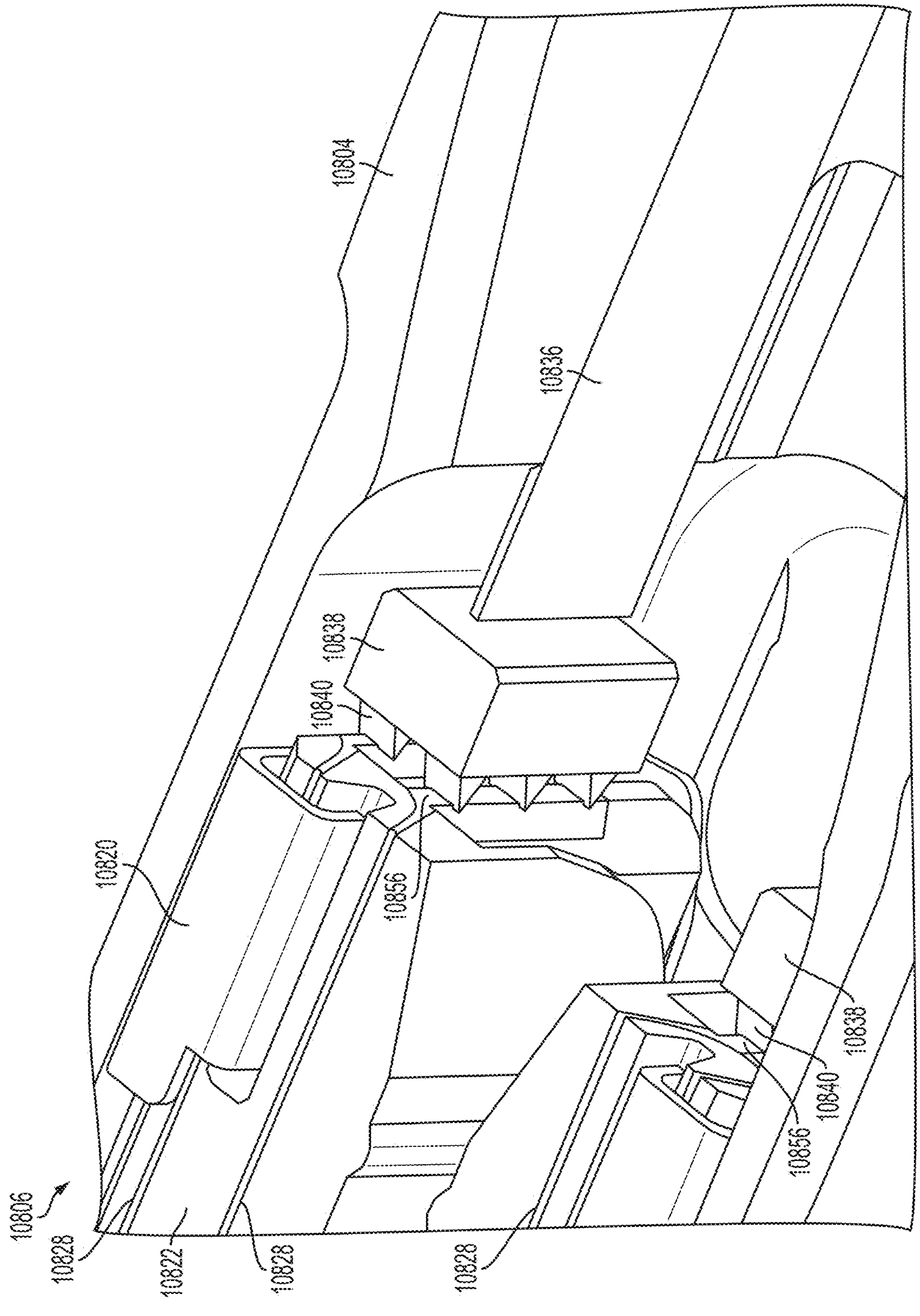
Figure 148A:
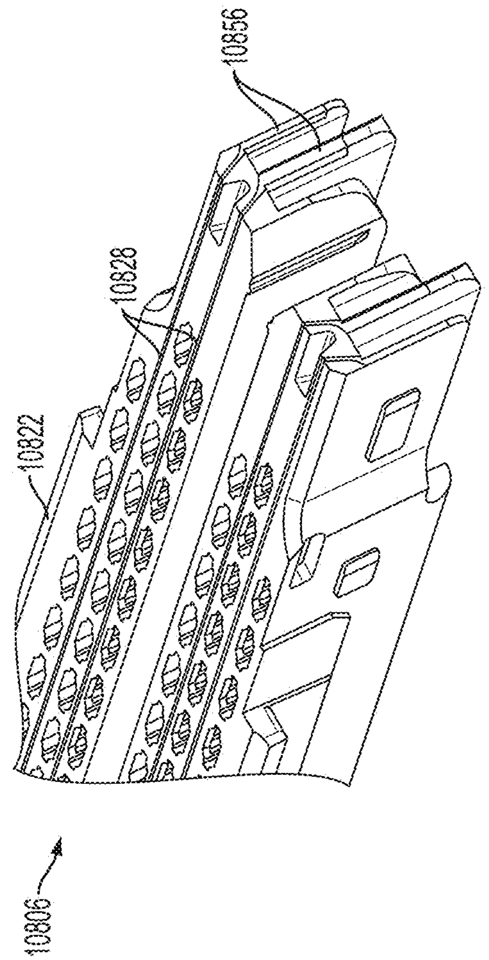
Figure 148B:
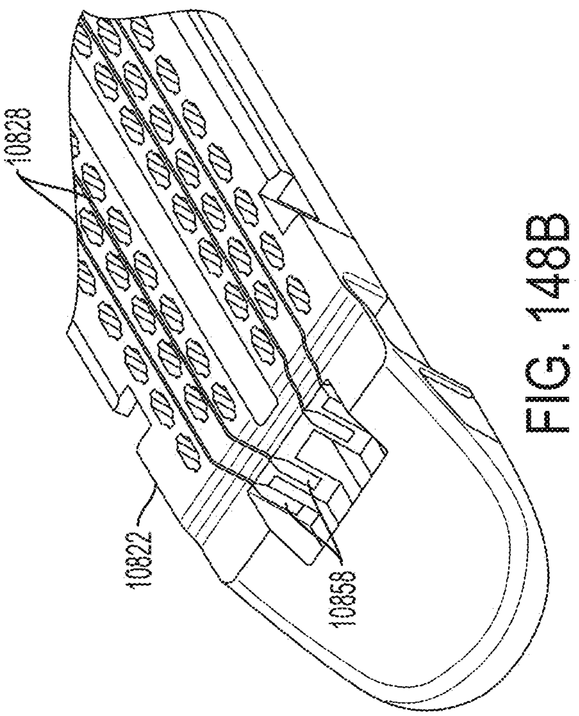
Figure 148C:
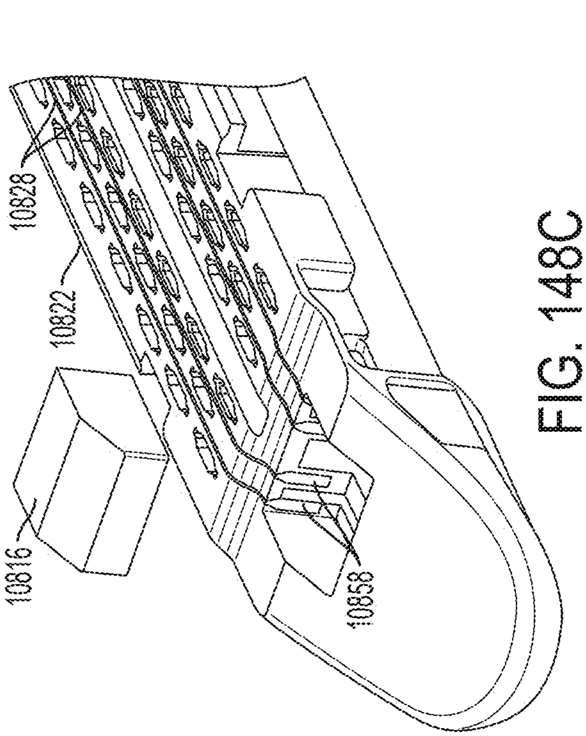
Figure 148D:
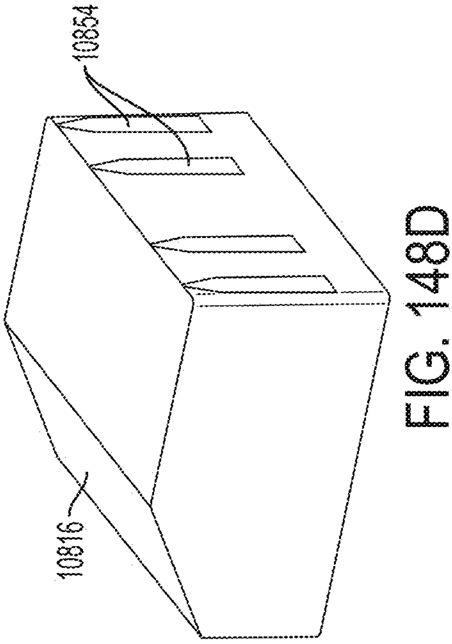
Figure 149A:
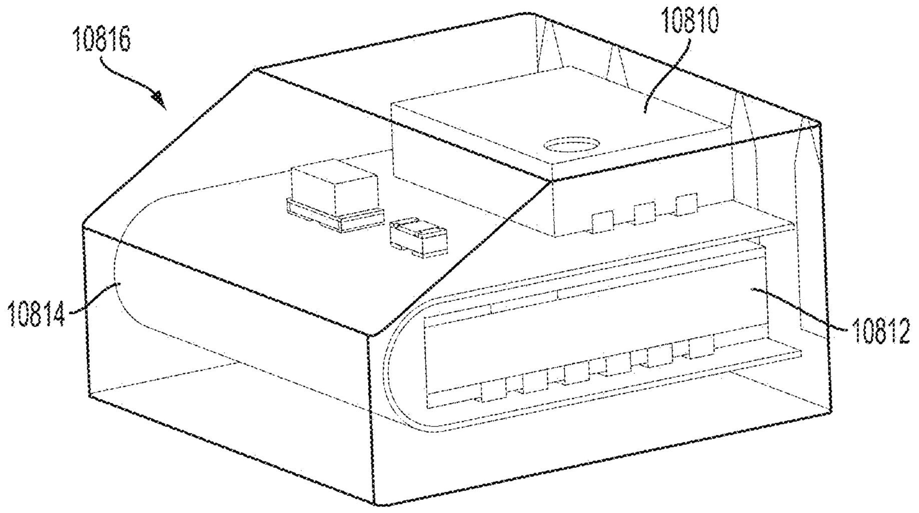
Figure 149B:
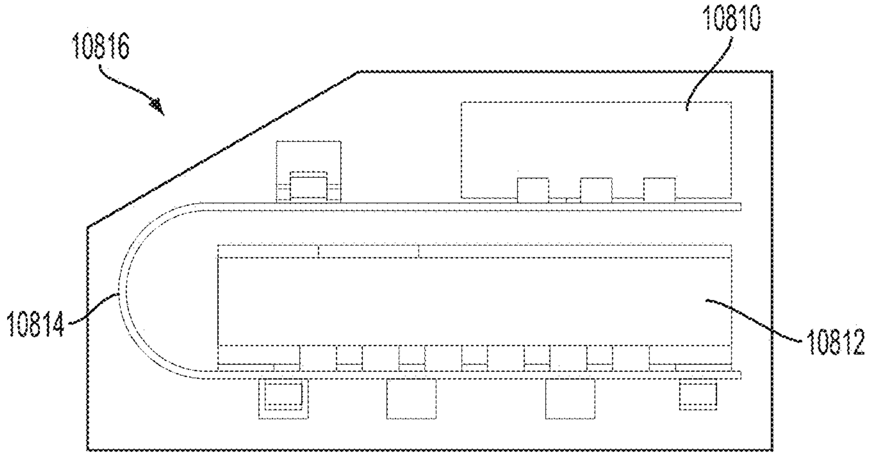
Figure 150:
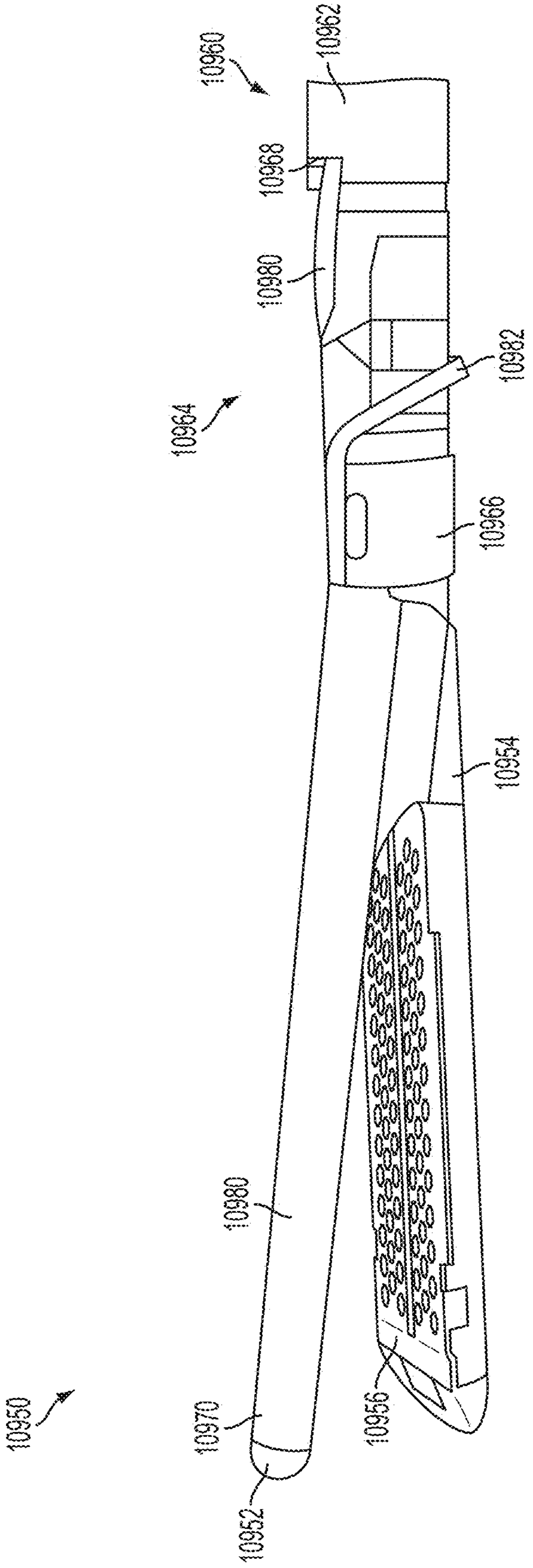
Figure 151C:
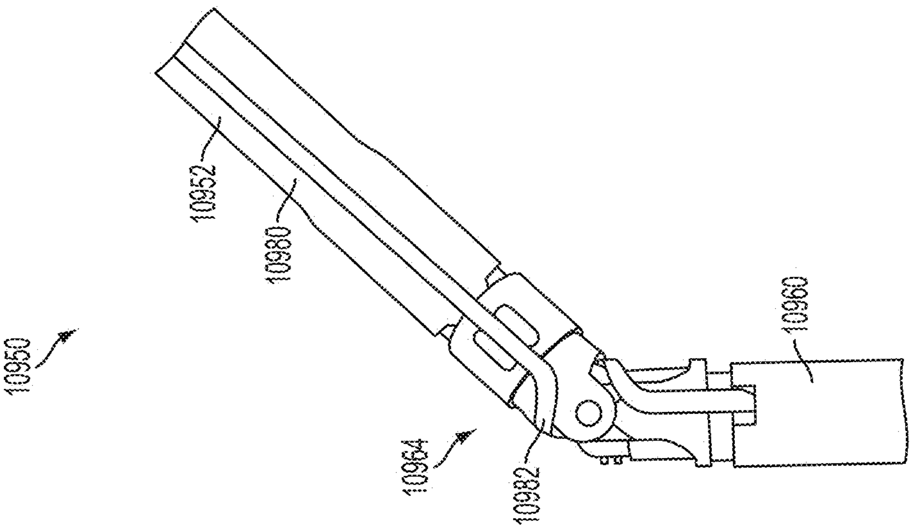
Figure 151B:
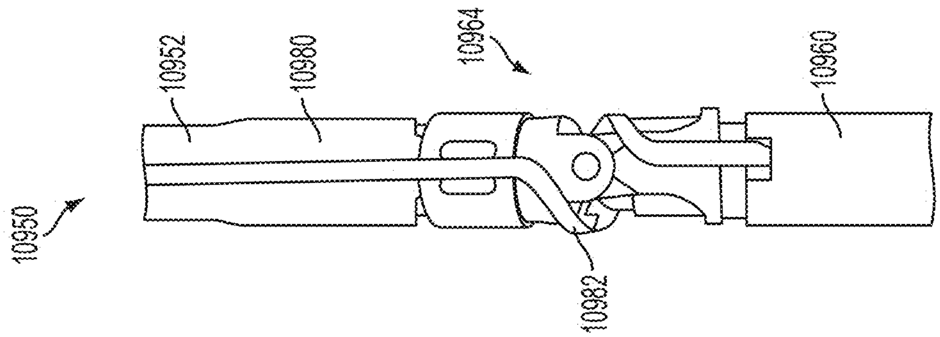
Figure 151A:
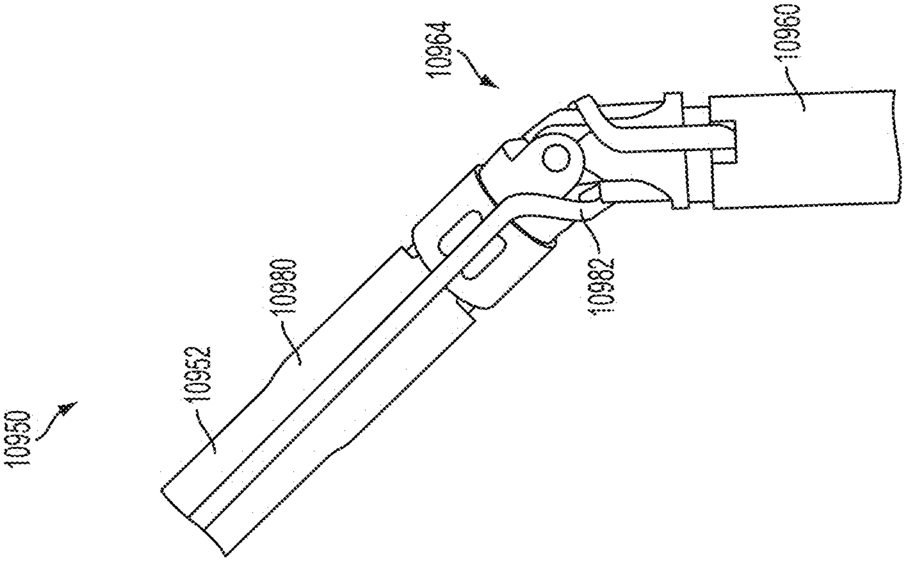
Figure 152:
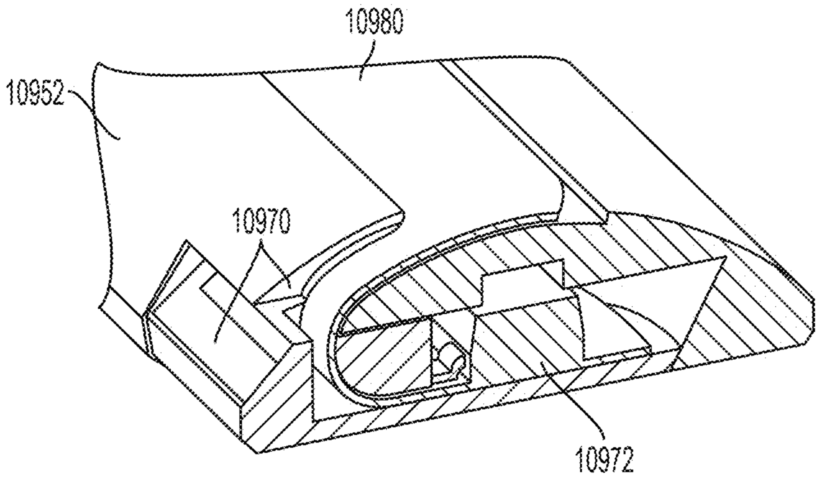
Figure 153:
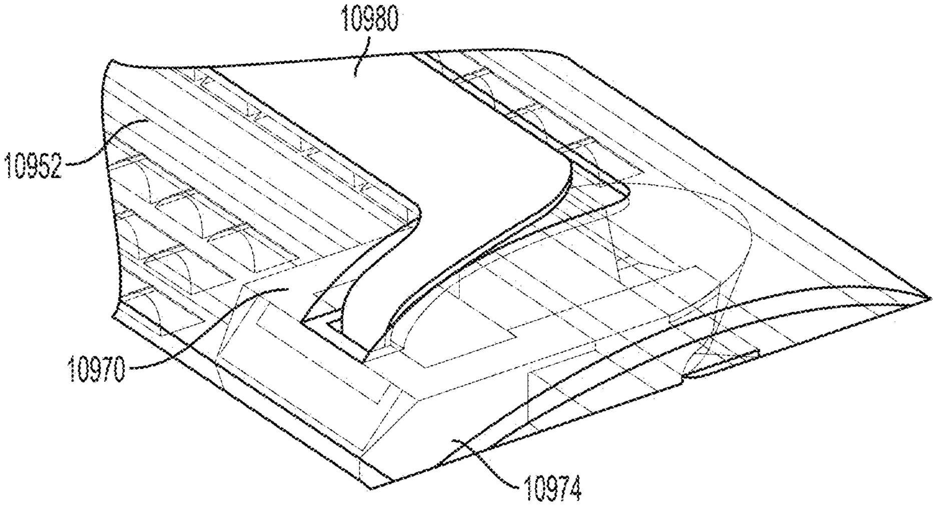

FIG. 126B illustrates a sideways cross-sectional view of one embodiment of an end effector comprising a magnet and a Hall effect sensor in communication with processor;

FIG. 127 illustrates one embodiment of the operable dimensions that relate to the operation of the Hall effect sensor;

FIG. 128A illustrates an external side view of an embodiment of a staple cartridge;

FIG. 128B illustrates various dimensions possible between the lower surface of the push-off lug and the top of the Hall effect sensor;

FIG. 128C illustrates an external side view of an embodiment of a staple cartridge;

FIG. 128D illustrates various dimensions possible between the lower surface of the push-off lug and the upper surface of the staple cartridge above the Hall effect sensor;

FIG. 129A further illustrates a front-end cross-sectional view 10054 of the anvil 10002 and the central axis point of the anvil;

FIG. 129B is a cross sectional view of a magnet shown in FIG. 129A;

FIGS. 130A-130E illustrate one embodiment of an end effector that comprises a magnet where FIG. 130A illustrates a front-end cross-sectional view of the end effector, FIG. 130B illustrates a front-end cutaway view of the anvil and the magnet in situ, FIG. 130C illustrates a perspective cutaway view of the anvil and the magnet, FIG. 130D illustrates a side cutaway view of the anvil and the magnet, and FIG. 130E illustrates a top cutaway view of the anvil and the magnet;

FIGS. 131A-131E illustrate another embodiment of an end effector that comprises a magnet where FIG. 131A illustrates a front-end cross-sectional view of the end effector, FIG. 131B illustrates a front-end cutaway view of the anvil and the magnet, in situ, FIG. 131C illustrates a perspective cutaway view of the anvil and the magnet, FIG. 131D illustrates a side cutaway view of the anvil and the magnet, and FIG. 131E illustrates a top cutaway view of the anvil and magnet;

FIG. 132 illustrates contact points between the anvil and either the staple cartridge and/or the elongated channel;

FIGS. 133A and 133B illustrate one embodiment of an end effector that is operable to use conductive surfaces at the distal contact point to create an electrical connection;

FIGS. 134A-134C illustrate one embodiment of an end effector that is operable to use conductive surfaces to form an electrical connection where FIG. 134A illustrates an end effector comprising an anvil, an elongated channel, and a staple cartridge, FIG. 134B illustrates the inside surface of the anvil further comprising first conductive surfaces located distally from the staple-forming indents, and FIG. 134C illustrates the staple cartridge comprising a cartridge body and first conductive surfaces located such that they can come into contact with a second conductive surface located on the staple cartridge;

FIGS. 135A and 135B illustrate one embodiment of an end effector that is operable to use conductive surfaces to form an electrical connection where FIG. 135A illustrates an end effector comprising an anvil, an elongated channel, and a staple cartridge and FIG. 109B 135B is a close-up view of the staple cartridge illustrating the first conductive surface located such that it can come into contact with second conductive surfaces;

FIGS. 136A and 136B illustrate one embodiment of an end effector that is operable to use conductive surfaces to form an electrical connection where FIG. 136A illustrates an end effector comprising an anvil, an elongated channel, and a staple cartridge and FIG. 136B is a close-up view of the staple cartridge illustrating the anvil further comprising a magnet and an inside surface, which further comprises a number of staple-forming indents;

FIGS. 137A-137C illustrate one embodiment of an end effector that is operable to use the proximal contact point to form an electrical connection where FIG. 137A illustrates the end effector, which comprises an anvil, an elongated channel, and a staple cartridge, FIG. 137B is a close-up view of a pin as it rests within an aperture defined in the elongated channel for that purpose, and FIG. 137C illustrates an alternate embodiment, with an alternate location for a second conductive surface on the surface of the aperture;

FIG. 138 illustrates one embodiment of an end effector with a distal sensor plug;

FIG. 139A illustrates the end effector shown in FIG. 138 with the anvil in an open position;

FIG. 139B illustrates a cross-sectional view of the end effector shown in FIG. 139A with the anvil in an open position;

FIG. 139C illustrates the end effector shown in FIG. 138 with the anvil in a closed position;

FIG. 139D illustrates a cross sectional view of the end effector shown in FIG. 139C with the anvil in a closed position;

FIG. 140 provides a close-up view of the cross section of the distal end of the end effector;

FIG. 141 illustrates a close-up top view of the staple cartridge that comprises a distal sensor plug;

FIG. 142A is a perspective view of the underside of a staple cartridge that comprises a distal sensor plug;

FIG. 142B illustrates a cross sectional view of the distal end of the staple cartridge;

FIGS. 143A-143C illustrate one embodiment of a staple cartridge that comprises a flex cable connected to a Hall effect sensor and processor where FIG. 143A is an exploded view of the staple cartridge, FIG. 143B illustrates the assembly of the staple cartridge and the flex cable in greater detail, and FIG. 143C illustrates a cross sectional view of the staple cartridge to illustrate the placement of the Hall effect sensor, processor, and conductive coupling within the distal end of the staple cartridge, in accordance with the present embodiment;

FIG. 144A-144F illustrate one embodiment of a staple cartridge that comprises a flex cable connected to a Hall effect sensor and a processor where FIG. 144A is an exploded view of the staple cartridge, FIG. 144B illustrates the assembly of the staple cartridge, FIG. 144C illustrates the underside of an assembled staple cartridge, and also illustrates the flex cable in greater detail, FIG. 144D illustrates a cross sectional view of the staple cartridge to illustrate the placement of the Hall effect sensor, processor, and conductive coupling, FIG. 144E illustrates the underside of the staple cartridge without the cartridge tray and including the wedge sled, in its most distal position, and FIG. 144F illustrates the staple cartridge without the cartridge tray in order to illustrate a possible placement for the cable traces;

FIGS. 145A and 145B illustrates one embodiment of a staple cartridge that comprises a flex cable, a Hall effect sensor, and a processor where FIG. 145A is an exploded view of the staple cartridge and FIG. 145B illustrates the assembly of the staple cartridge and the flex cable in greater detail;

FIG. 146A illustrates a perspective view of an end effector coupled to a shaft assembly;

FIG. 146B illustrates a perspective view of an underside of the end effector and shaft assembly shown in FIG. 146A;

FIG. 146C illustrates the end effector shown in FIGS. 146A and 146B with a flex cable and without the shaft assembly;

FIGS. 146D and 146E illustrate an elongated channel portion of the end effector shown in FIGS. 146A and 146B without the anvil or the staple cartridge, to illustrate how the flex cable shown in FIG. 146C can be seated within the elongated channel;

FIG. 146F illustrates the flex cable, shown in FIGS. 146C-120E 146C-146E, alone;

FIG. 147 illustrates a close up view of the elongated channel shown in FIGS. 146D and 146E with a staple cartridge coupled thereto;

FIGS. 148A-148D further illustrate one embodiment of a staple cartridge operative with the present embodiment of an end effector where FIG. 148A illustrates a close up view of the proximal end of the staple cartridge, FIG. 148B illustrates a close-up view of the distal end of the staple cartridge, with a space for a distal sensor plug, FIG. 148C further illustrates the distal sensor plug, and FIG. 148D illustrates the proximal-facing side of the distal sensor plug;

FIGS. 149A and 149B illustrate one embodiment of a distal sensor plug where FIG. 149A illustrates a cutaway view of the distal sensor plug and FIG. 149B further illustrates the Hall effect sensor and the processor operatively coupled to the flex board such that they are capable of communicating;

FIG. 150 illustrates an embodiment of an end effector with a flex cable operable to provide power to sensors and electronics in the distal tip of the anvil portion;

FIGS. 151A-151C illustrate the operation of the articulation joint and flex cable of the end effector where FIG. 151A illustrates a top view of the end effector with the end effector pivoted −45 degrees with respect to the shaft assembly, FIG. 151B illustrates a top view of the end effector, and FIG. 151C illustrates a top view of the end effector with the end effector pivoted +45 degrees with respect to the shaft assembly;

FIG. 152 illustrates cross-sectional view of the distal tip of an embodiment of an anvil with sensors and electronics; and FIG. 153 illustrates a cutaway view of the distal tip of the anvil.

DESCRIPTION

Certain example embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting example embodiments. The features illustrated or described in connection with one example embodiment may be combined with the features of other embodiments. Such modifications and variations are intended to be included within the scope of the present embodiment of the invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present embodiment of the invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute.

Various example devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

FIGS. 1-6 depict a motor-driven surgical cutting and fastening instrument 10 that may or may not be reused. In the illustrated embodiment, the instrument 10 includes a housing 12 that comprises a handle 14 that is configured to be grasped, manipulated and actuated by the clinician. The housing 12 is configured for operable attachment to an interchangeable shaft assembly 200 that has a surgical end effector 300 operably coupled thereto that is configured to perform one or more surgical tasks or procedures. As the present Detailed Description proceeds, it will be understood that the various unique and novel arrangements of the various forms of interchangeable shaft assemblies disclosed herein may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate the interchangeable shaft assemblies disclosed herein and their respective equivalents. The term "frame" may refer to a portion of a handheld surgical instrument. The term "frame" may also represent a portion of a robotically controlled surgical instrument and/or a portion of the robotic system that may be used to operably control a surgical instrument. For example, the interchangeable shaft assemblies disclosed herein may be employed with various robotic systems, instruments, components and methods disclosed in U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, is incorporated by reference herein in its entirety.

Figure 1:
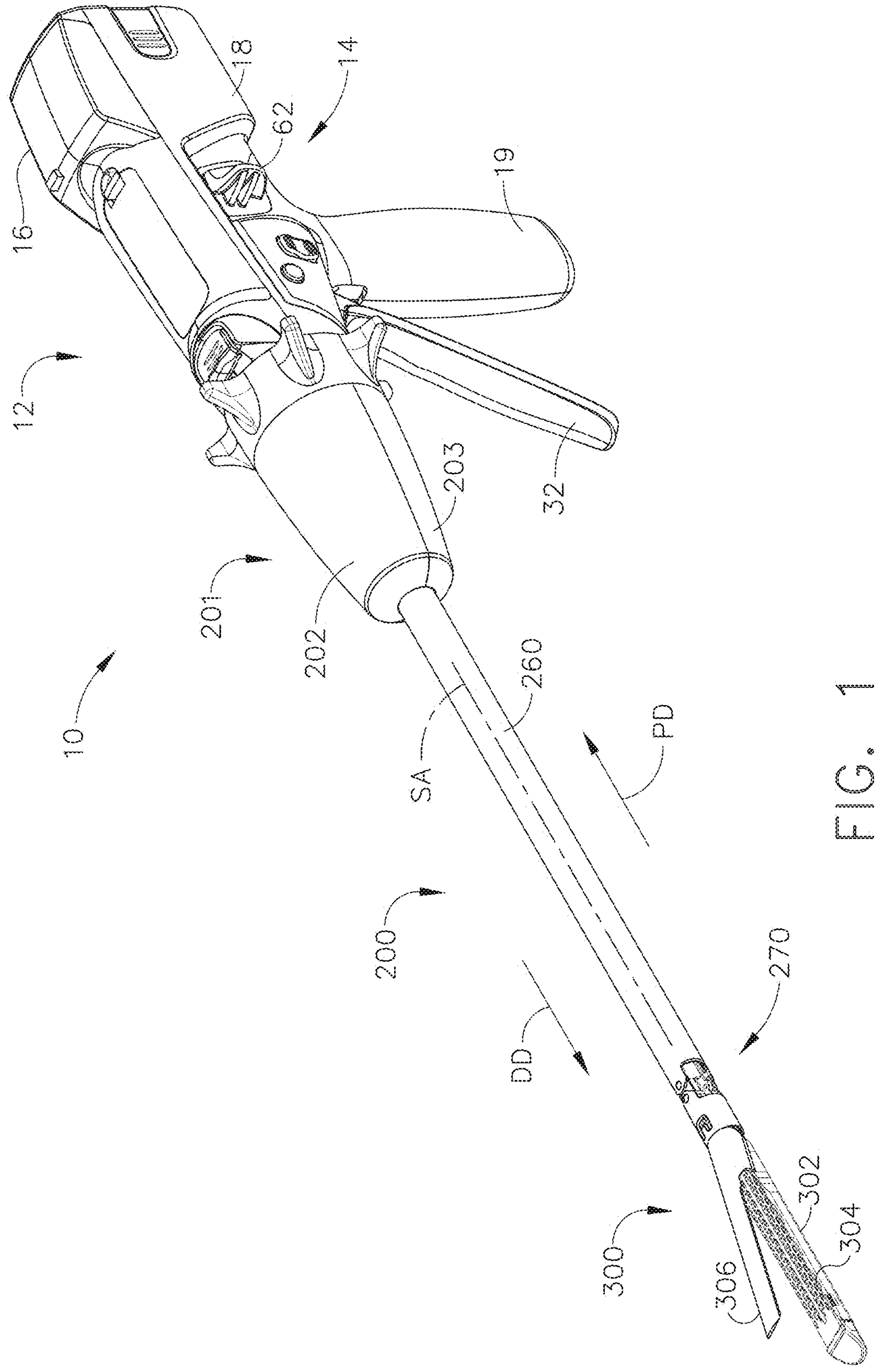
FIG. 1 is a perspective view of a surgical instrument that has an interchangeable shaft assembly operably coupled thereto.
Figure 2:
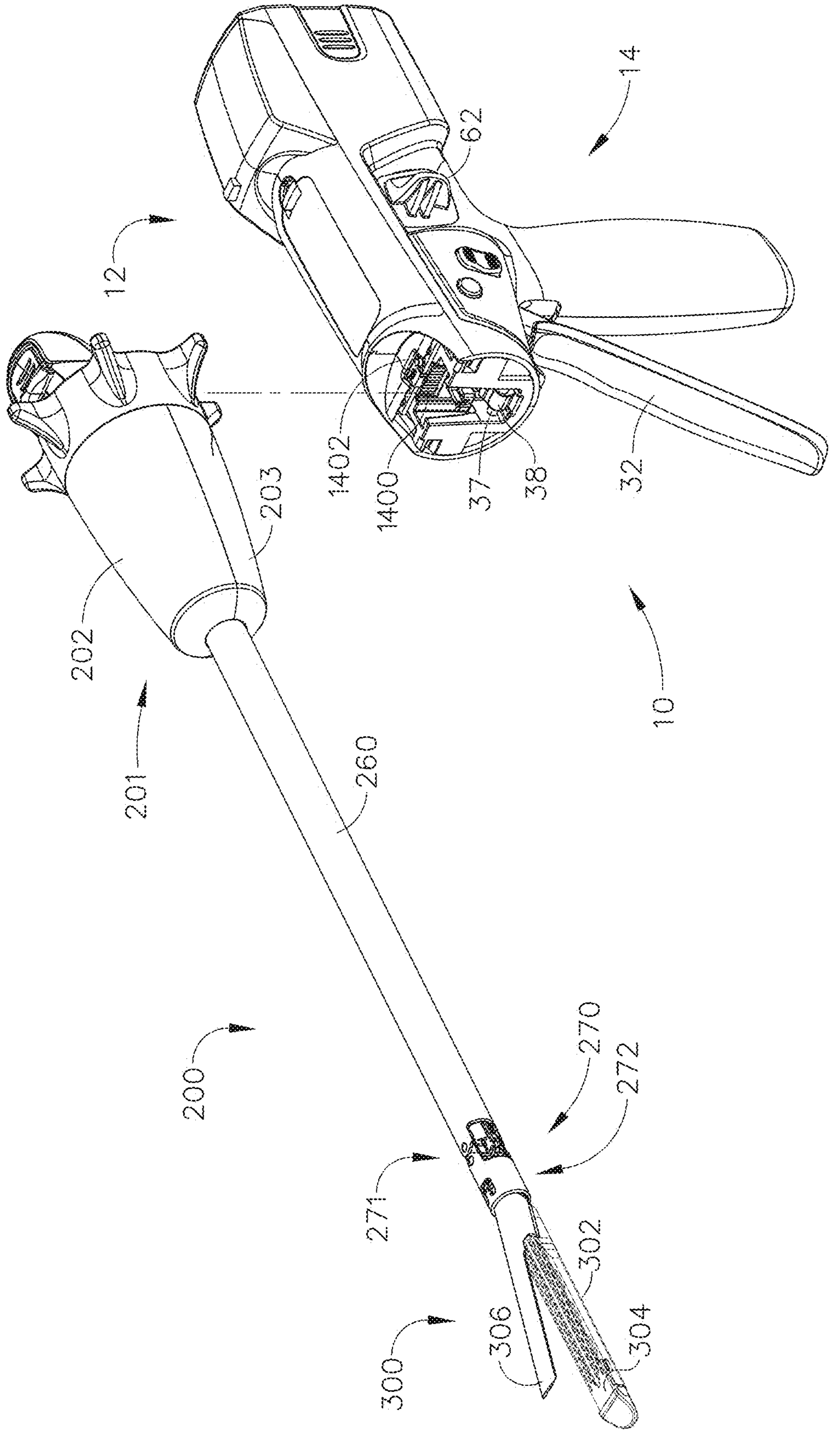
FIG. 2 is an exploded assembly view of the interchangeable shaft assembly and surgical instrument of FIG. 1.
Figure 3:
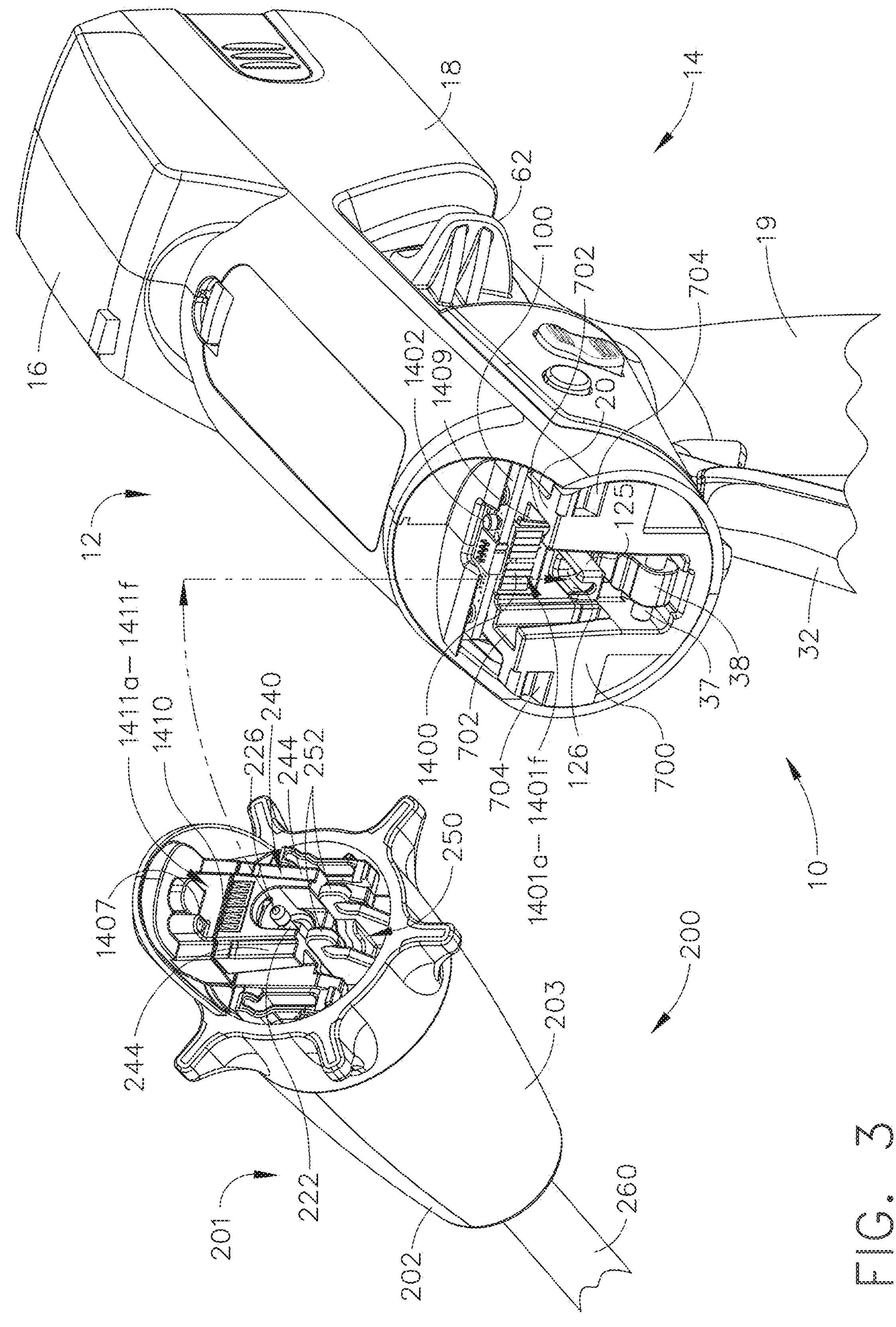
FIG. 3 is another exploded assembly view showing portions of the interchangeable shaft assembly and surgical instrument of FIGS. 1 and 2.

The housing 12 depicted in FIGS. 1-3 is shown in connection with an interchangeable shaft assembly 200 that includes an end effector 300 that comprises a surgical cutting and fastening device that is configured to operably support a surgical staple cartridge 304 therein. The housing 12 may be configured for use in connection with interchangeable shaft assemblies that include end effectors that are adapted to support different sizes and types of staple cartridges, have different shaft lengths, sizes, and types, etc. In addition, the housing 12 may also be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

Figure 4:
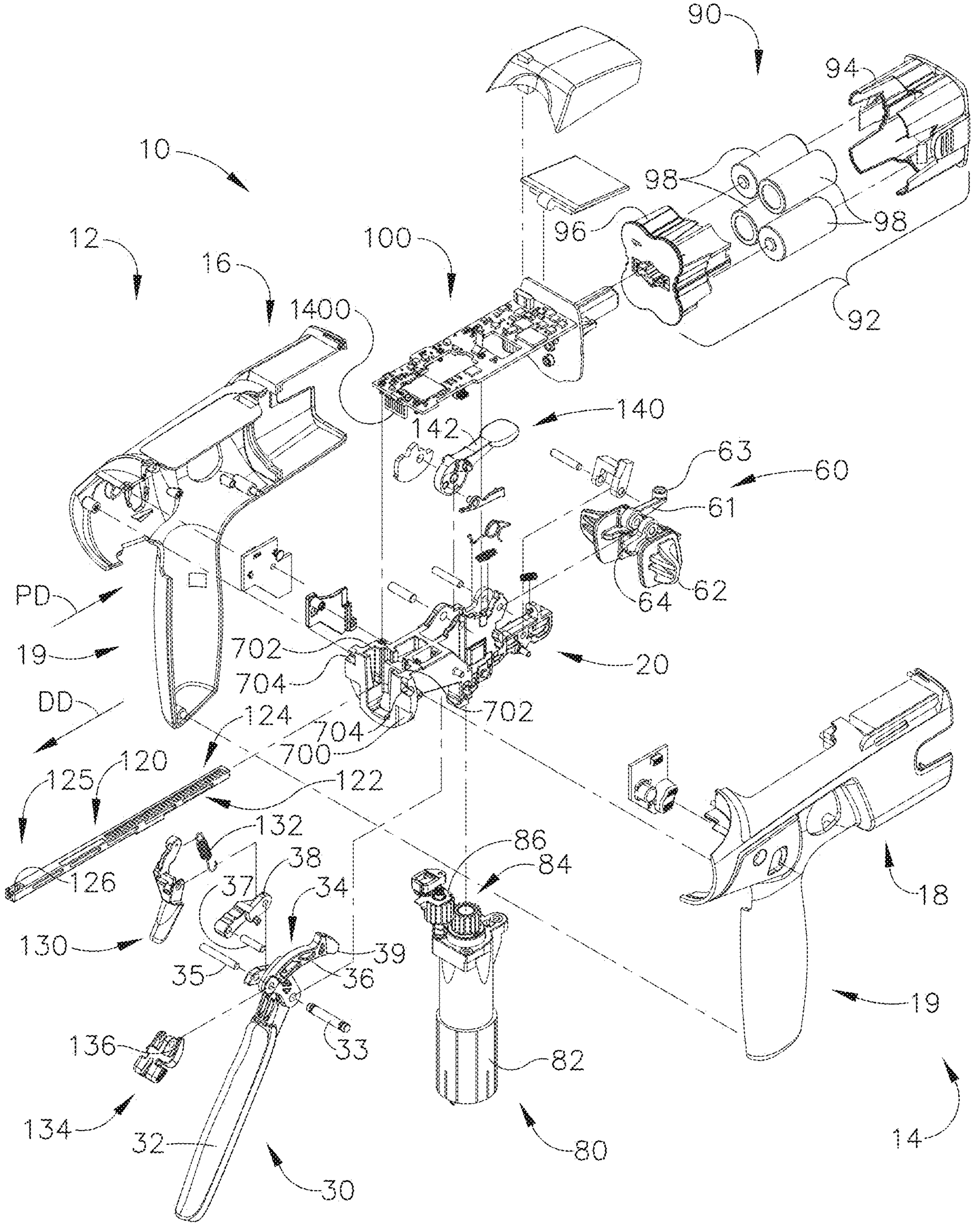
FIG. 4 is an exploded assembly view of a portion of the surgical instrument of FIGS. 1-3.
Figure 5:
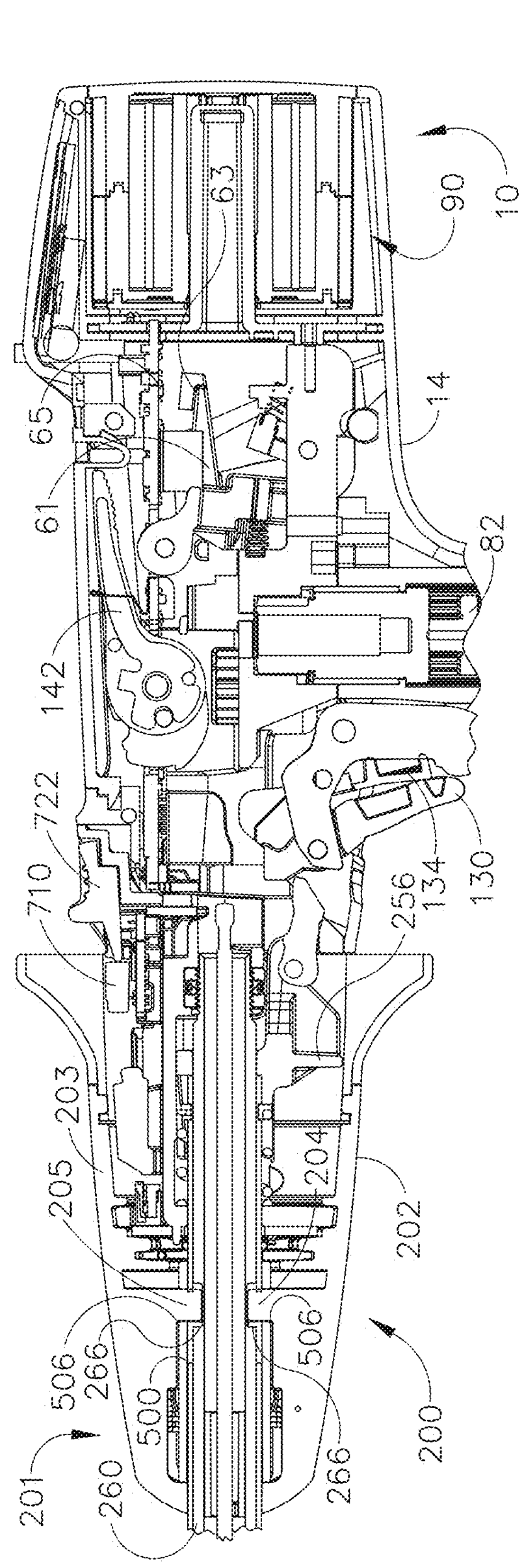
FIG. 5 is a cross-sectional side view of a portion of the surgical instrument of FIG. 4 with the firing trigger in a fully actuated position.
Figure 6:
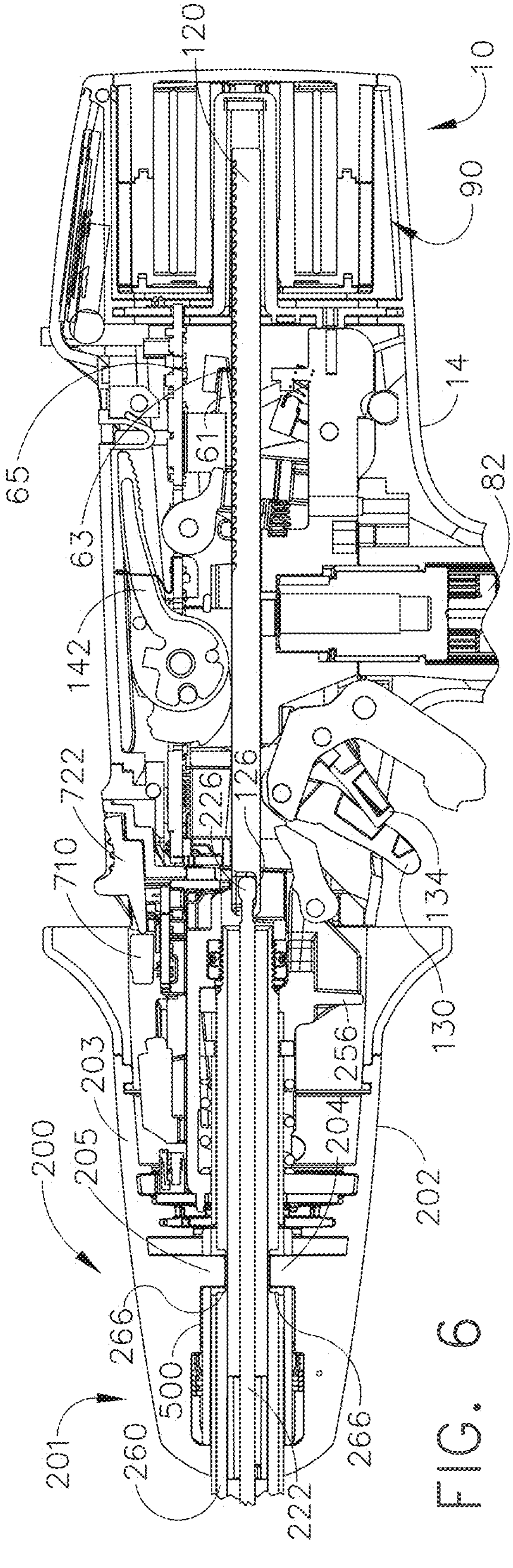
FIG. 6 is another cross-sectional view of a portion of the surgical instrument of FIG. 5 with the firing trigger in an unactuated position.

FIG. 1 illustrates the surgical instrument 10 with an interchangeable shaft assembly 200 operably coupled thereto. FIGS. 2 and 3 illustrate attachment of the interchangeable shaft assembly 200 to the housing 12 or handle 14. As shown in FIG. 4, the handle 14 may comprise a pair of interconnectable handle housing segments 16 and 18 that may be interconnected by screws, snap features, adhesive, etc. In the illustrated arrangement, the handle housing segments 16, 18 cooperate to form a pistol grip portion 19 that can be gripped and manipulated by the clinician. As will be discussed in further detail below, the handle 14 operably supports a plurality of drive systems therein that are configured to generate and apply various control motions to corresponding portions of the interchangeable shaft assembly that is operably attached thereto.

Referring now to FIG. 4, the handle 14 may further include a frame 20 that operably supports a plurality of drive systems. For example, the frame 20 can operably support a "first" or closure drive system, generally designated as 30, which may be employed to apply closing and opening motions to the interchangeable shaft assembly 200 that is operably attached or coupled thereto. In at least one form, the closure drive system 30 may include an actuator in the form of a closure trigger 32 that is pivotally supported by the frame 20. More specifically, as illustrated in FIG. 4, the closure trigger 32 is pivotally coupled to the housing 14 by a pin 33. Such arrangement enables the closure trigger 32 to be manipulated by a clinician such that when the clinician grips the pistol grip portion 19 of the handle 14, the closure trigger 32 may be easily pivoted from a starting or "unactuated" position to an "actuated" position and more particularly to a fully compressed or fully actuated position. The closure trigger 32 may be biased into the unactuated position by spring or other biasing arrangement (not shown). In various forms, the closure drive system 30 further includes a closure linkage assembly 34 that is pivotally coupled to the closure trigger 32. As shown in FIG. 4, the closure linkage assembly 34 may include a first closure link 36 and a second closure link 38 that are pivotally coupled to the closure trigger 32 by a pin 35. The second closure link 38 may also be referred to herein as an "attachment member" and include a transverse attachment pin 37.

Still referring to FIG. 4, it can be observed that the first closure link 36 may have a locking wall or end 39 thereon that is configured to cooperate with a closure release assembly 60 that is pivotally coupled to the frame 20. In at least one form, the closure release assembly 60 may comprise a release button assembly 62 that has a distally protruding locking pawl 64 formed thereon. The release button assembly 62 may be pivoted in a counterclockwise direction by a release spring (not shown). As the clinician depresses the closure trigger 32 from its unactuated position towards the pistol grip portion 19 of the handle 14, the first closure link 36 pivots upward to a point wherein the locking pawl 64 drops into retaining engagement with the locking wall 39 on the first closure link 36 thereby preventing the closure trigger 32 from returning to the unactuated position. See FIG. 18. Thus, the closure release assembly 60 serves to lock the closure trigger 32 in the fully actuated position. When the clinician desires to unlock the closure trigger 32 to permit it to be biased to the unactuated position, the clinician simply pivots the closure release button assembly 62 such that the locking pawl 64 is moved out of engagement with the locking wall 39 on the first closure link 36. When the locking pawl 64 has been moved out of engagement with the first closure link 36, the closure trigger 32 may pivot back to the unactuated position. Other closure trigger locking and release arrangements may also be employed.

Figure 13:
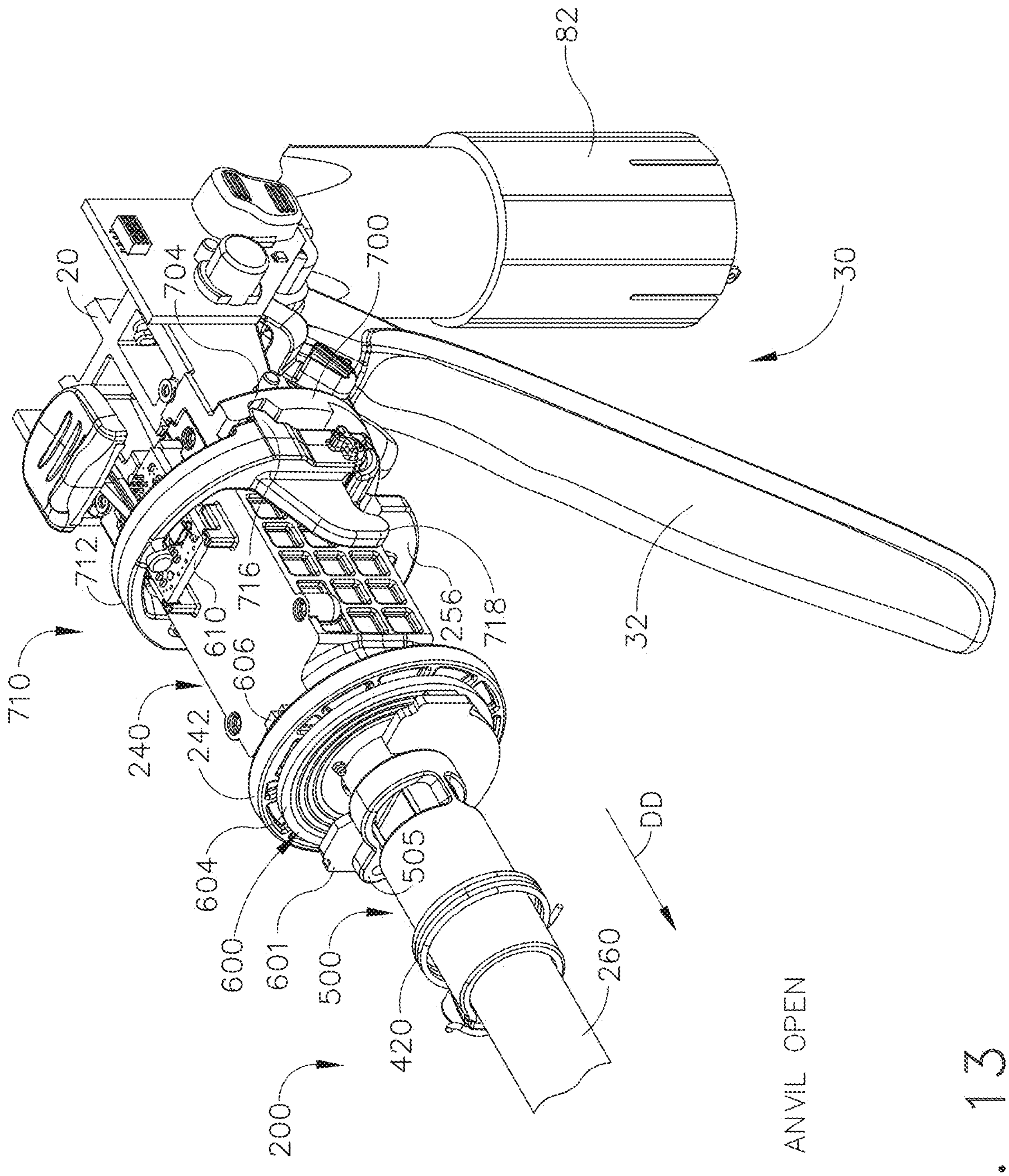
FIG. 13 is a perspective view of a portion of the interchangeable shaft assembly of FIG. 11 operably coupled to a portion of the surgical instrument of FIG. 1 illustrated with the closure trigger thereof in an unactuated position.
Figure 14:
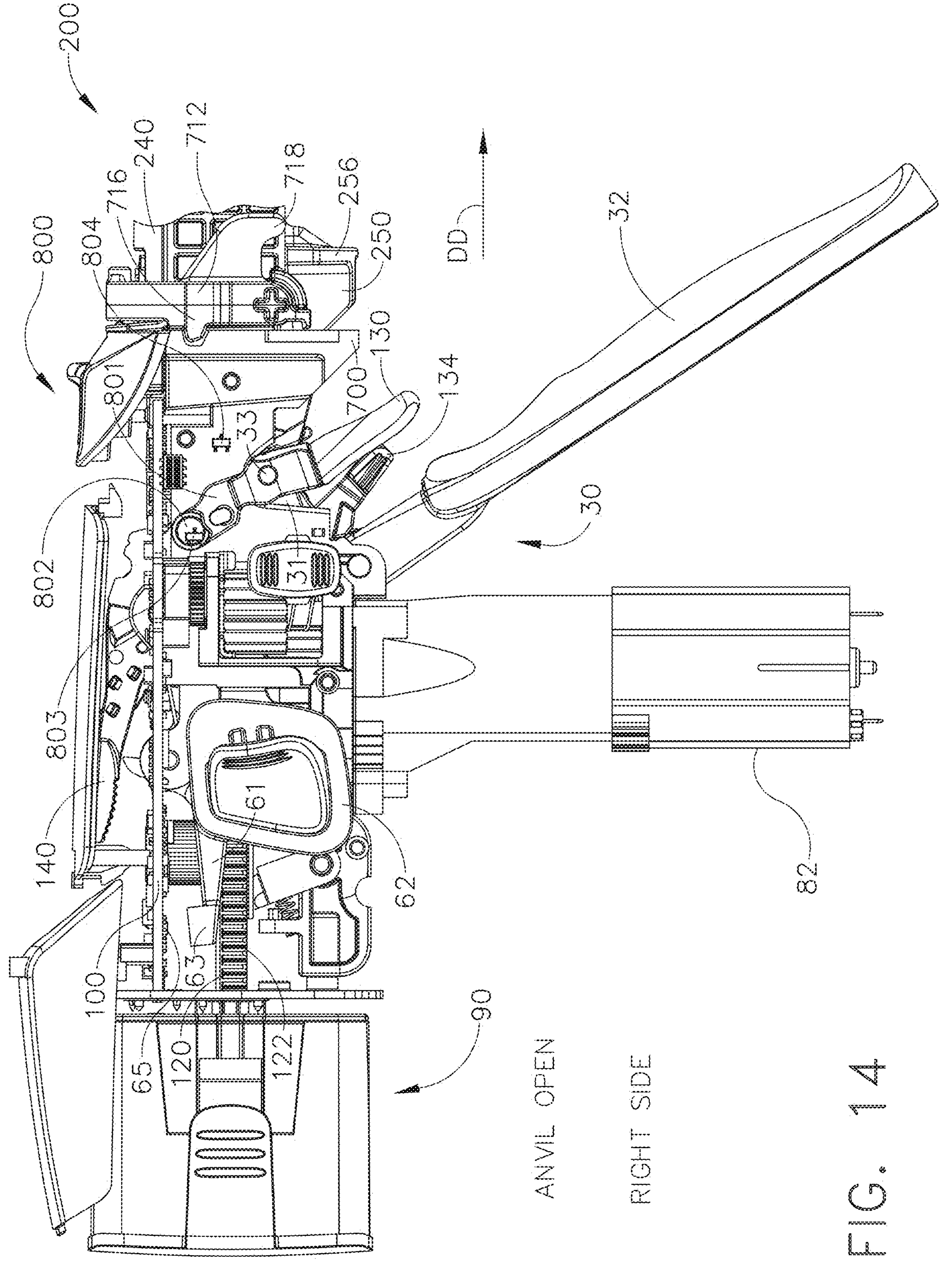
FIG. 14 is a right side elevational view of the interchangeable shaft assembly and surgical instrument of FIG. 13.
Figure 15:
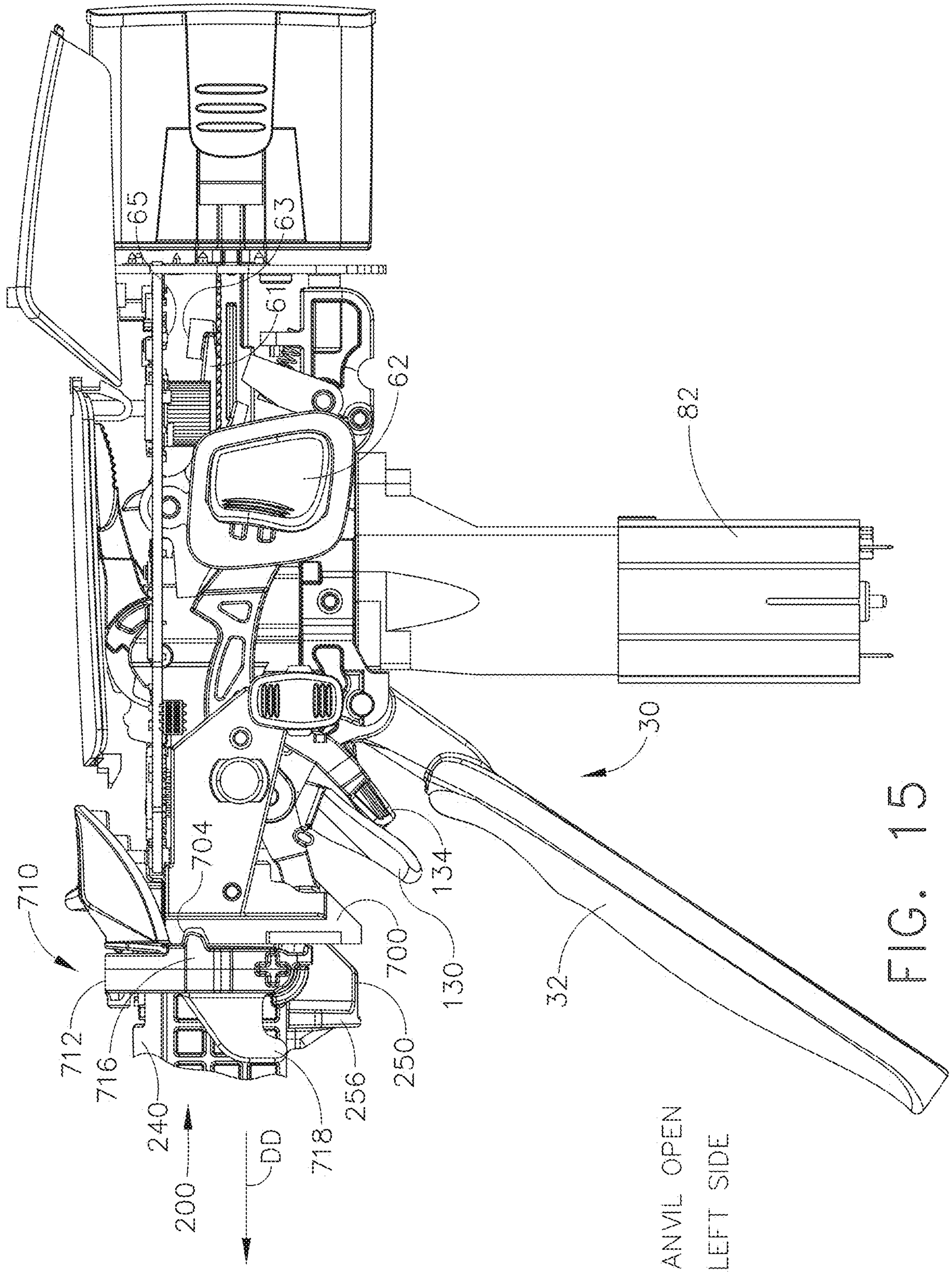
FIG. 15 is a left side elevational view of the interchangeable shaft assembly and surgical instrument of FIGS. 13 and 14.
Figure 16:
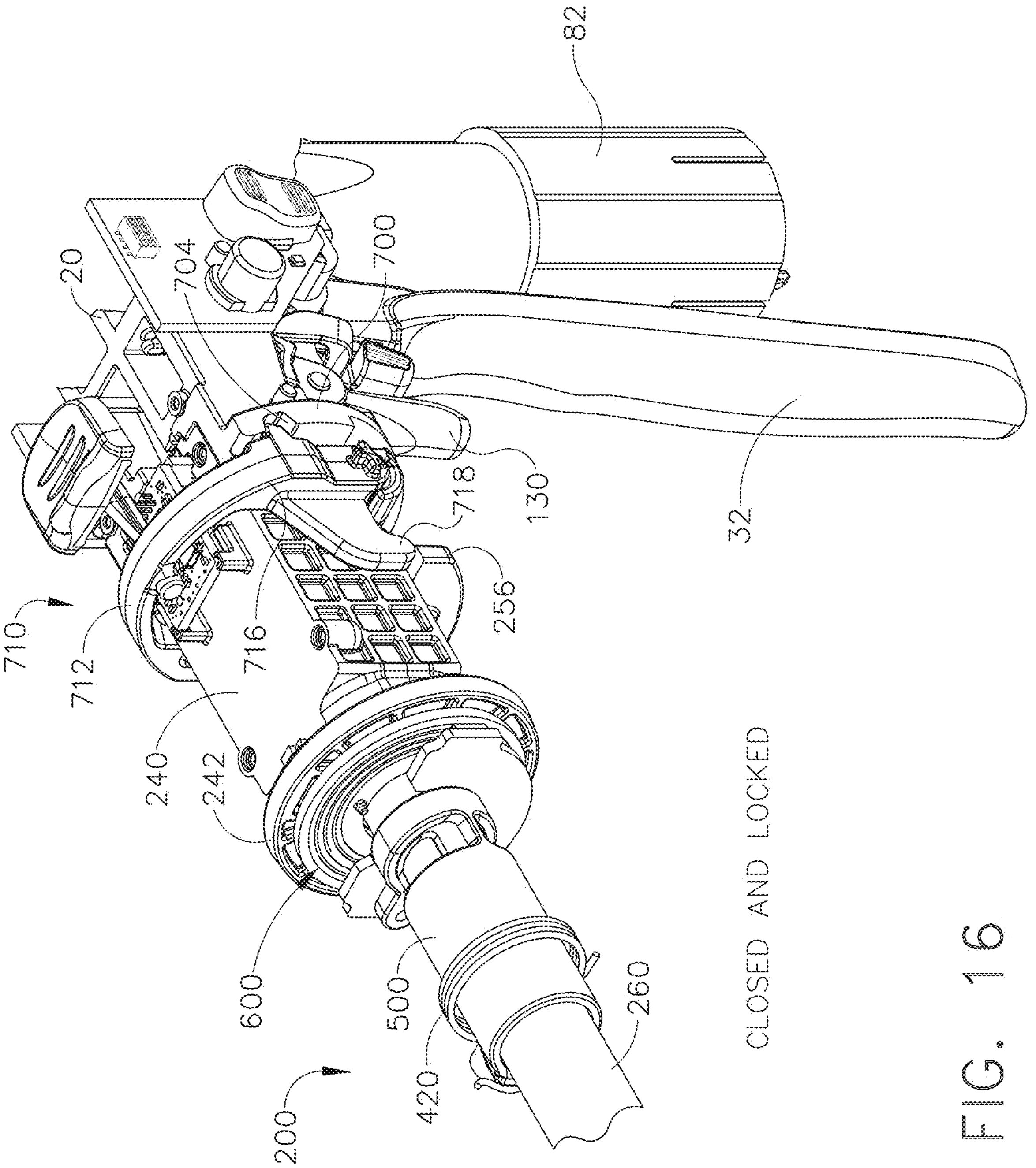
FIG. 16 is a perspective view of a portion of the interchangeable shaft assembly of FIG. 11 operably coupled to a portion of the surgical instrument of FIG. 1 illustrated with the closure trigger thereof in an actuated position and a firing trigger thereof in an unactuated position.
Figure 17:
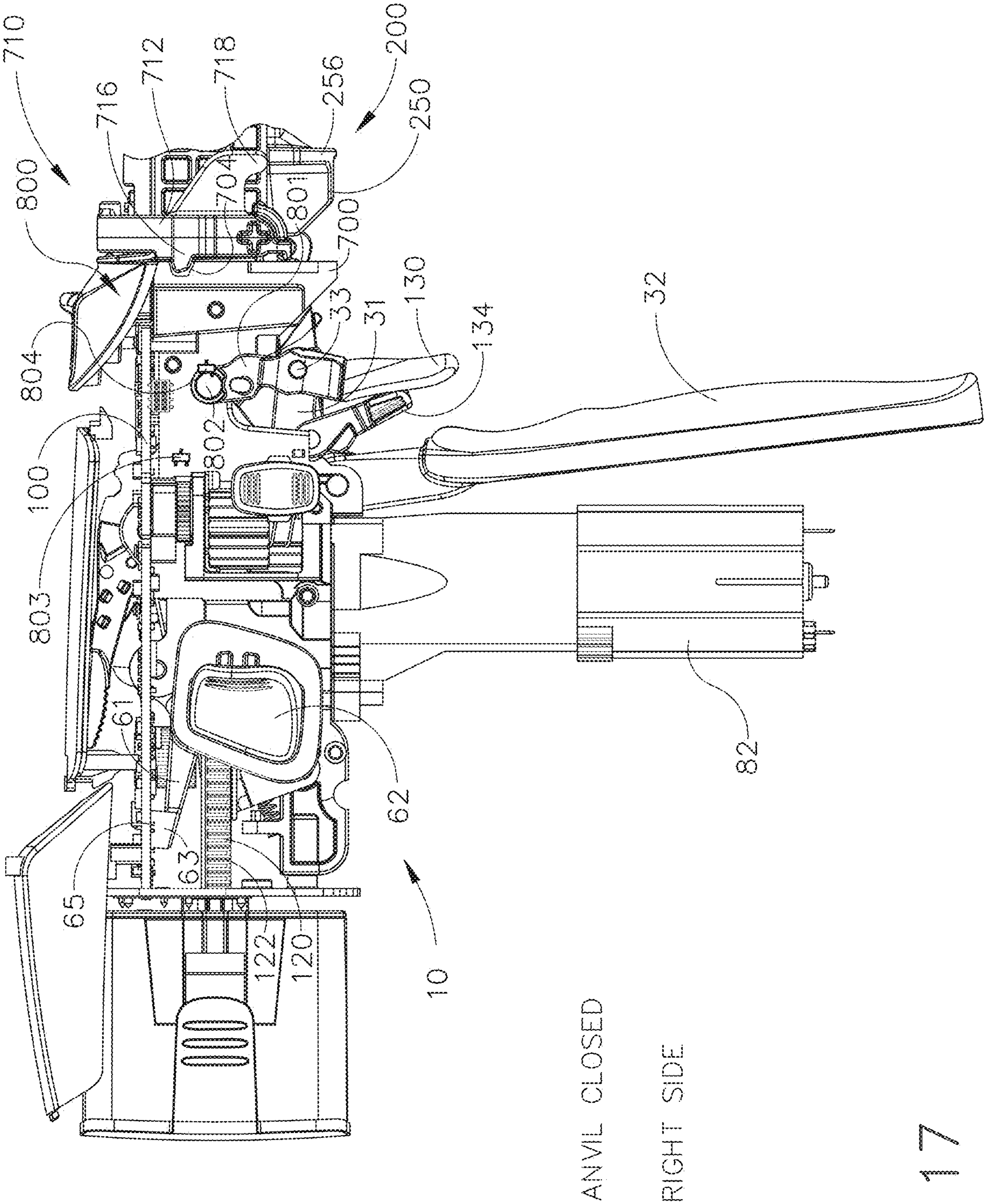
FIG. 17 is a right side elevational view of the interchangeable shaft assembly and surgical instrument of FIG. 16.
Figure 18:
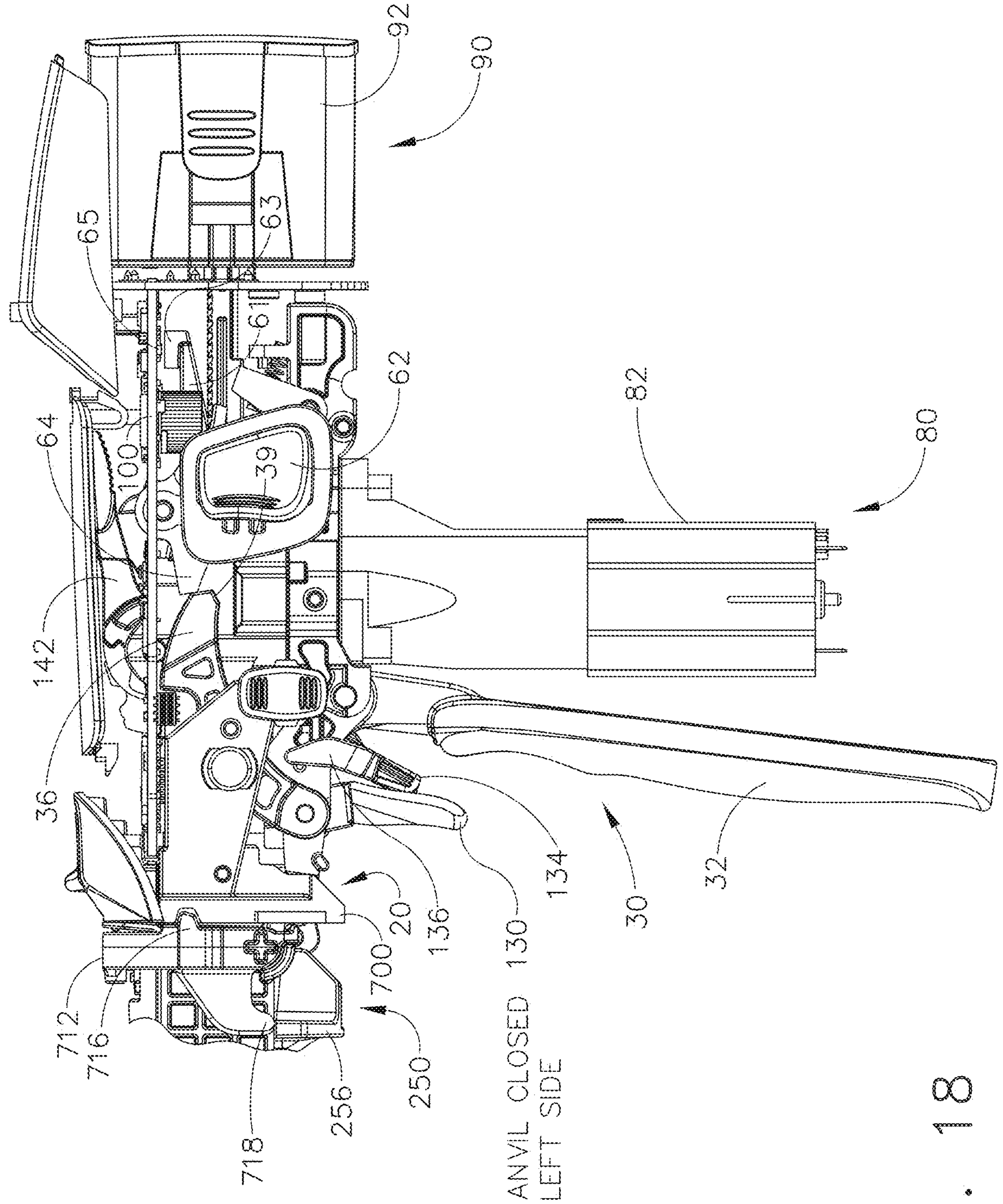
FIG. 18 is a left side elevational view of the interchangeable shaft assembly and surgical instrument of FIGS. 16 and 17.
Figure 18A:
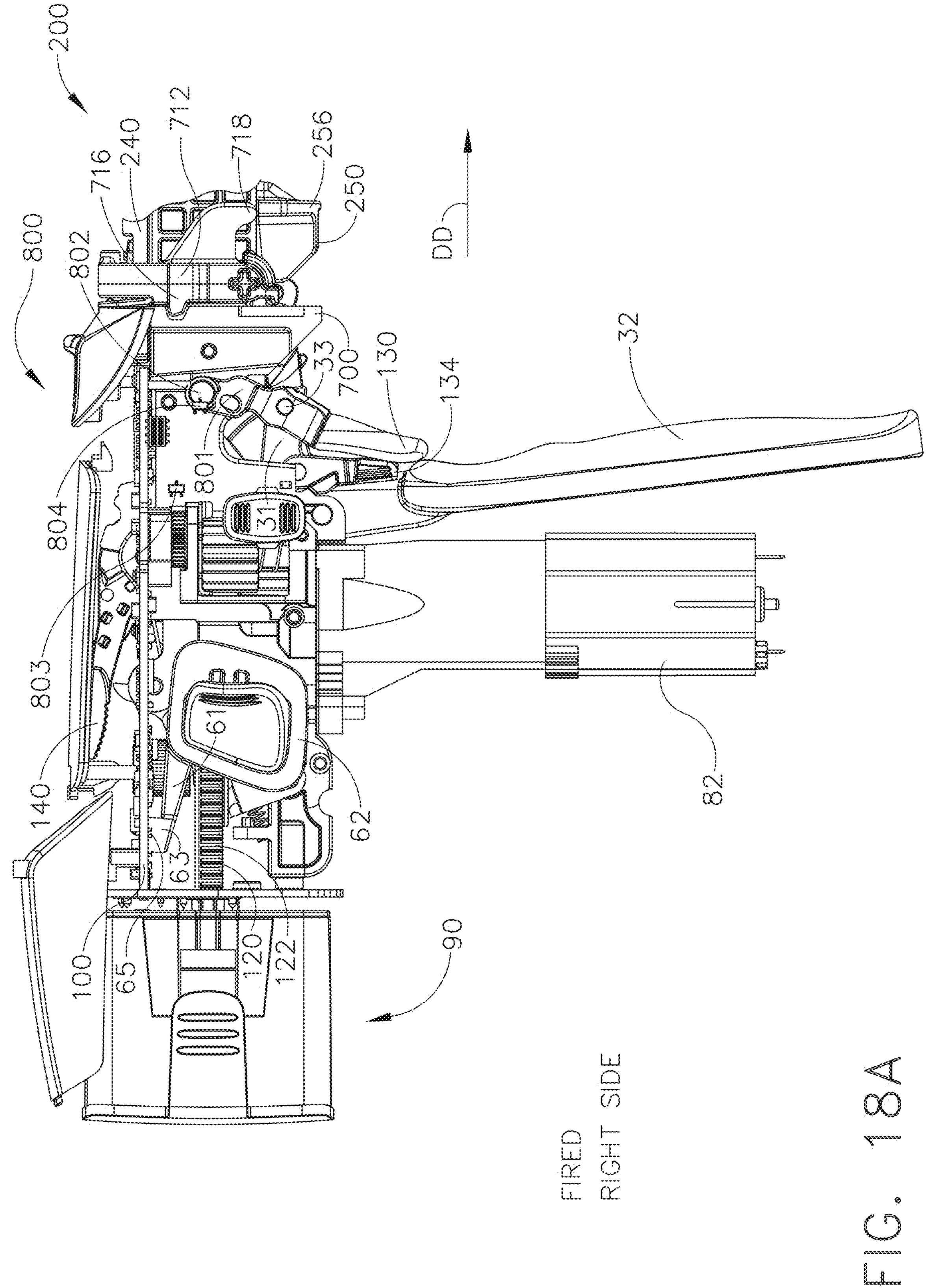
FIG. 18A is a right side elevational view of the interchangeable shaft assembly of FIG. 11 operably coupled to a portion of the surgical instrument of FIG. 1 illustrated with the closure trigger thereof in an actuated position and the firing trigger thereof in an actuated position.

Further to the above, FIGS. 13-15 illustrate the closure trigger 32 in its unactuated position which is associated with an open, or unclamped, configuration of the shaft assembly 200 in which tissue can be positioned between the jaws of the shaft assembly 200. FIGS. 16-18 illustrate the closure trigger 32 in its actuated position which is associated with a closed, or clamped, configuration of the shaft assembly 200 in which tissue is clamped between the jaws of the shaft assembly 200. Upon comparing FIGS. 14 and 17, the reader will appreciate that, when the closure trigger 32 is moved from its unactuated position (FIG. 14) to its actuated position (FIG. 17), the closure release button 62 is pivoted between a first position (FIG. 14) and a second position (FIG. 17). The rotation of the closure release button 62 can be referred to as being an upward rotation; however, at least a portion of the closure release button 62 is being rotated toward the circuit board 100. Referring to FIG. 4, the closure release button 62 can include an arm 61 extending therefrom and a magnetic element 63, such as a permanent magnet, for example, mounted to the arm 61. When the closure release button 62 is rotated from its first position to its second position, the magnetic element 63 can move toward the circuit board 100. The circuit board 100 can include at least one sensor configured to detect the movement of the magnetic element 63. In at least one embodiment, a Hall effect sensor 65, for example, can be mounted to the bottom surface of the circuit board 100. The Hall effect sensor 65 can be configured to detect changes in a magnetic field surrounding the Hall effect sensor 65 caused by the movement of the magnetic element 63. The Hall effect sensor 65 can be in signal communication with a microcontroller 1500 (FIG. 19), for example, which can determine whether the closure release button 62 is in its first position, which is associated with the unactuated position of the closure trigger 32 and the open configuration of the end effector, its second position, which is associated with the actuated position of the closure trigger 32 and the closed configuration of the end effector, and/or any position between the first position and the second position.

In at least one form, the handle 14 and the frame 20 may operably support another drive system referred to herein as a firing drive system 80 that is configured to apply firing motions to corresponding portions of the interchangeable shaft assembly attached thereto. The firing drive system may 80 also be referred to herein as a "second drive system". The firing drive system 80 may employ an electric motor 82, located in the pistol grip portion 19 of the handle 14. In various forms, the motor 82 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The motor 82 may be powered by a power source 90 that in one form may comprise a removable power pack 92. As shown in FIG. 4, for example, the power pack 92 may comprise a proximal housing portion 94 that is configured for attachment to a distal housing portion 96. The proximal housing portion 94 and the distal housing portion 96 are configured to operably support a plurality of batteries 98 therein. Batteries 98 may each comprise, for example, a Lithium Ion ("LI") or other suitable battery. The distal housing portion 96 is configured for removable operable attachment to a control circuit board assembly 100 which is also operably coupled to the motor 82. A number of batteries 98 may be connected in series may be used as the power source for the surgical instrument 10. In addition, the power source 90 may be replaceable and/or rechargeable.

As outlined above with respect to other various forms, the electric motor 82 can include a rotatable shaft (not shown) that operably interfaces with a gear reducer assembly 84 that is mounted in meshing engagement with a with a set, or rack, of drive teeth 122 on a longitudinally-movable drive member 120. In use, a voltage polarity provided by the power source 90 can operate the electric motor 82 in a clockwise direction wherein the voltage polarity applied to the electric motor by the battery can be reversed in order to operate the electric motor 82 in a counter-clockwise direction. When the electric motor 82 is rotated in one direction, the drive member 120 will be axially driven in the distal direction "DD". When the motor 82 is driven in the opposite rotary direction, the drive member 120 will be axially driven in a proximal direction "PD". The handle 14 can include a switch which can be configured to reverse the polarity applied to the electric motor 82 by the power source 90. As with the other forms described herein, the handle 14 can also include a sensor that is configured to detect the position of the drive member 120 and/or the direction in which the drive member 120 is being moved.

Actuation of the motor 82 can be controlled by a firing trigger 130 that is pivotally supported on the handle 14. The firing trigger 130 may be pivoted between an unactuated position and an actuated position. The firing trigger 130 may be biased into the unactuated position by a spring 132 or other biasing arrangement such that when the clinician releases the firing trigger 130, it may be pivoted or otherwise returned to the unactuated position by the spring 132 or biasing arrangement. In at least one form, the firing trigger 130 can be positioned "outboard" of the closure trigger 32 as was discussed above. In at least one form, a firing trigger safety button 134 may be pivotally mounted to the closure trigger 32 by pin 35. The safety button 134 may be positioned between the firing trigger 130 and the closure trigger 32 and have a pivot arm 136 protruding therefrom. See FIG. 4. When the closure trigger 32 is in the unactuated position, the safety button 134 is contained in the handle 14 where the clinician cannot readily access it and move it between a safety position preventing actuation of the firing trigger 130 and a firing position wherein the firing trigger 130 may be fired. As the clinician depresses the closure trigger 32, the safety button 134 and the firing trigger 130 pivot down wherein they can then be manipulated by the clinician.

As discussed above, the handle 14 can include a closure trigger 32 and a firing trigger 130. Referring to FIGS. 14-18A, the firing trigger 130 can be pivotably mounted to the closure trigger 32. The closure trigger 32 can include an arm 31 extending therefrom and the firing trigger 130 can be pivotably mounted to the arm 31 about a pivot pin 33. When the closure trigger 32 is moved from its unactuated position (FIG. 14) to its actuated position (FIG. 17), the firing trigger 130 can descend downwardly, as outlined above. After the safety button 134 has been moved to its firing position, referring primarily to FIG. 18A, the firing trigger 130 can be depressed to operate the motor of the surgical instrument firing system. In various instances, the handle 14 can include a tracking system, such as system 800, for example, configured to determine the position of the closure trigger 32 and/or the position of the firing trigger 130. With primary reference to FIGS. 14, 17, and 18A, the tracking system 800 can include a magnetic element, such as permanent magnet 802, for example, which is mounted to an arm 801 extending from the firing trigger 130. The tracking system 800 can comprise one or more sensors, such as a first Hall effect sensor 803 and a second Hall effect sensor 804, for example, which can be configured to track the position of the magnet 802. Upon comparing FIGS. 14 and 17, the reader will appreciate that, when the closure trigger 32 is moved from its unactuated position to its actuated position, the magnet 802 can move between a first position adjacent the first Hall effect sensor 803 and a second position adjacent the second Hall effect sensor 804. Upon comparing FIGS. 17 and 18A, the reader will further appreciate that, when the firing trigger 130 is moved from an unfired position (FIG. 17) to a fired position (FIG. 18A), the magnet 802 can move relative to the second Hall effect sensor 804. The sensors 803 and 804 can track the movement of the magnet 802 and can be in signal communication with a microcontroller on the circuit board 100. With data from the first sensor 803 and/or the second sensor 804, the microcontroller can determine the position of the magnet 802 along a predefined path and, based on that position, the microcontroller can determine whether the closure trigger 32 is in its unactuated position, its actuated position, or a position therebetween. Similarly, with data from the first sensor 803 and/or the second sensor 804, the microcontroller can determine the position of the magnet 802 along a predefined path and, based on that position, the microcontroller can determine whether the firing trigger 130 is in its unfired position, its fully fired position, or a position therebetween.

As indicated above, in at least one form, the longitudinally movable drive member 120 has a rack of teeth 122 formed thereon for meshing engagement with a corresponding drive gear 86 of the gear reducer assembly 84. At least one form also includes a manually-actuatable "bailout" assembly 140 that is configured to enable the clinician to manually retract the longitudinally movable drive member 120 should the motor 82 become disabled. The bailout assembly 140 may include a lever or bailout handle assembly 142 that is configured to be manually pivoted into ratcheting engagement with teeth 124 also provided in the drive member 120. Thus, the clinician can manually retract the drive member 120 by using the bailout handle assembly 142 to ratchet the drive member 120 in the proximal direction "PD". U.S. Pat. No. 8,608,045 discloses bailout arrangements and other components, arrangements and systems that may also be employed with the various instruments disclosed herein. U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045, is hereby incorporated by reference in its entirety.

Figure 7:
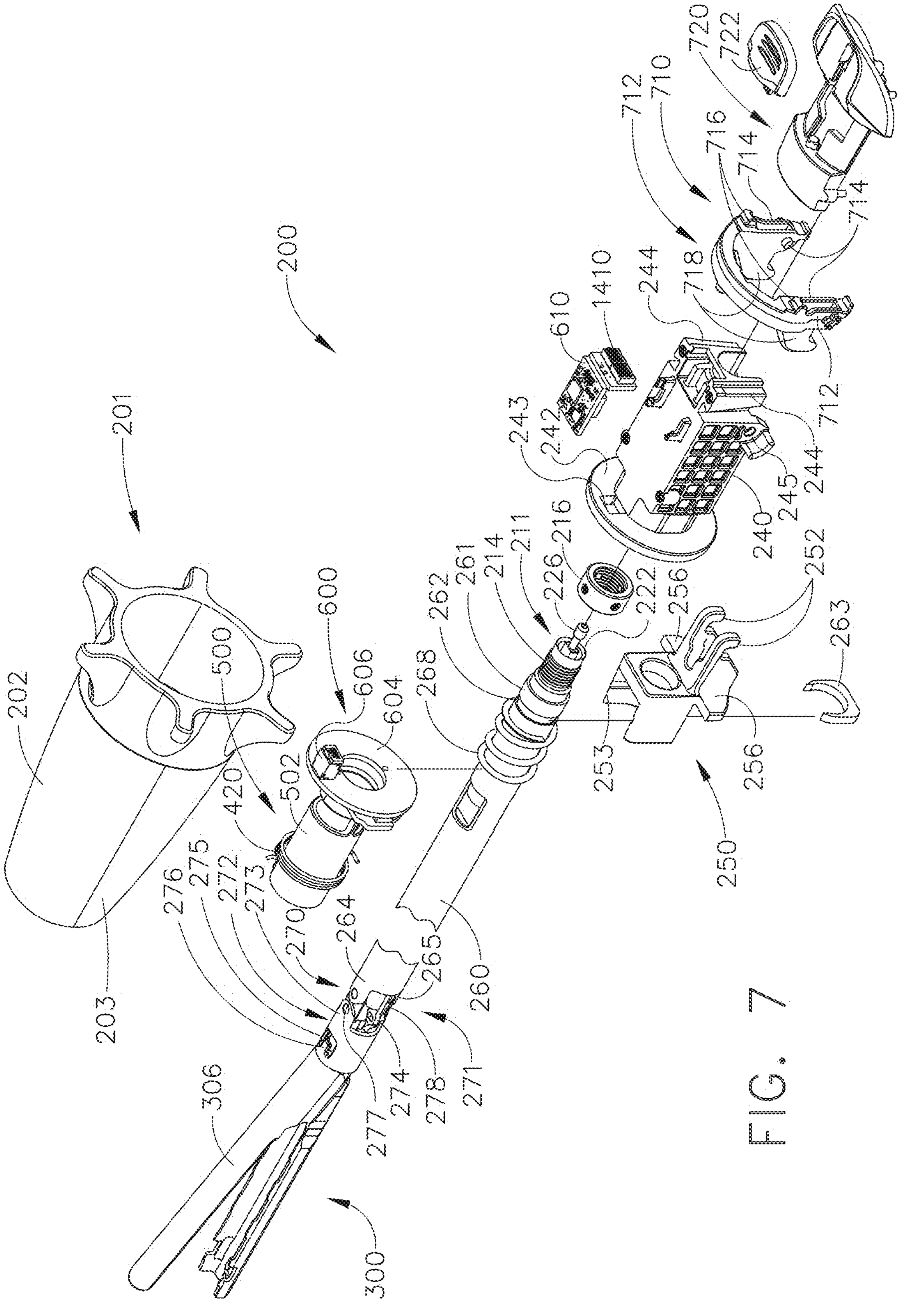
FIG. 7 is an exploded assembly view of one form of an interchangeable shaft assembly.
Figure 8:
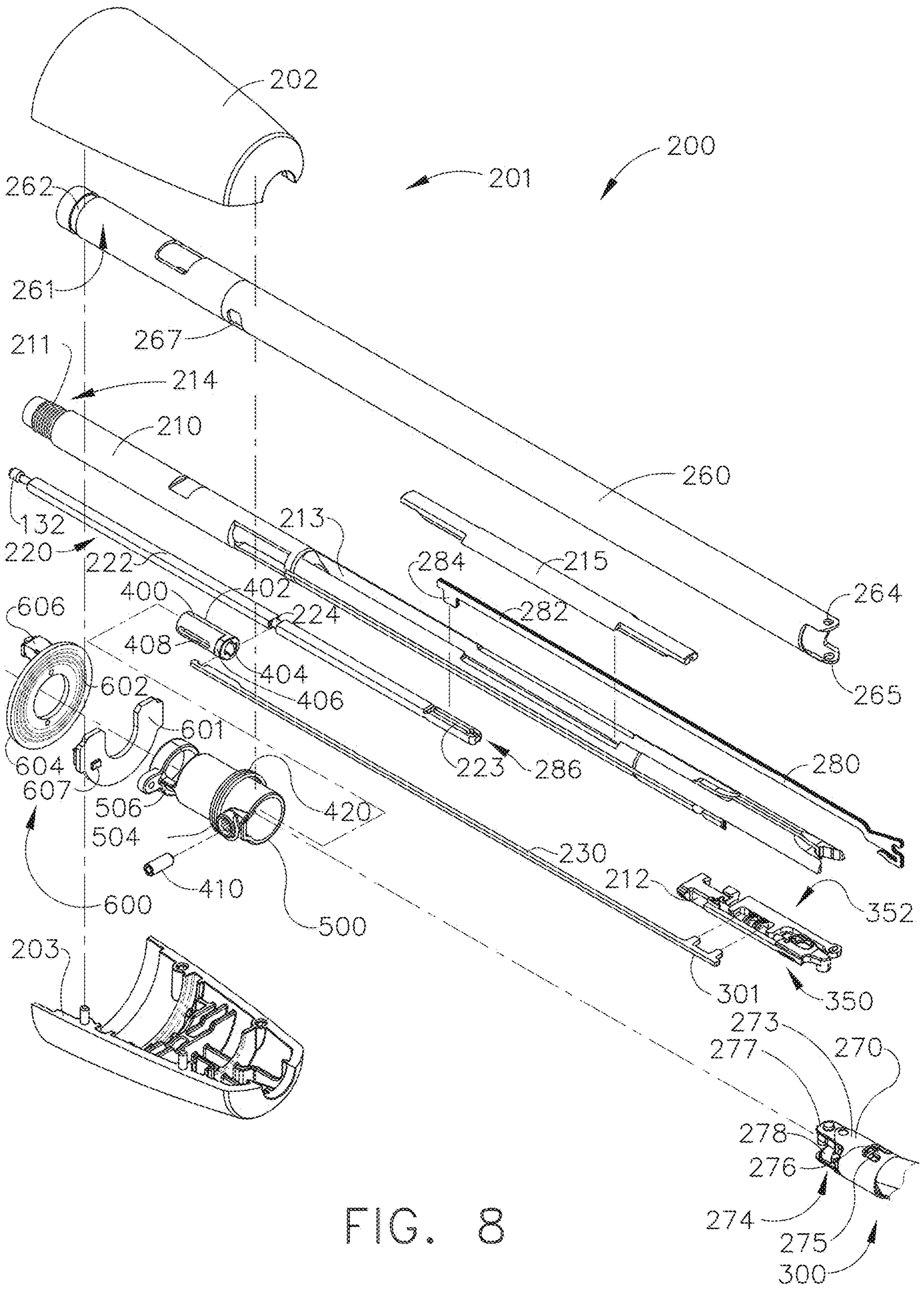
FIG. 8 is another exploded assembly view of portions of the interchangeable shaft assembly of FIG. 7.

Turning now to FIGS. 1 and 7, the interchangeable shaft assembly 200 includes a surgical end effector 300 that comprises an elongated channel 302 that is configured to operably support a staple cartridge 304 therein. The end effector 300 may further include an anvil 306 that is pivotally supported relative to the elongated channel 302. The interchangeable shaft assembly 200 may further include an articulation joint 270 and an articulation lock 350 (FIG. 8) which can be configured to releasably hold the end effector 300 in a desired position relative to a shaft axis SA-SA. Details regarding the construction and operation of the end effector 300, the articulation joint 270 and the articulation lock 350 are set forth in U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541. The entire disclosure of U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541 is hereby incorporated by reference herein. As shown in FIGS. 7 and 8, the interchangeable shaft assembly 200 can further include a proximal housing or nozzle 201 comprised of nozzle portions 202 and 203. The interchangeable shaft assembly 200 can further include a closure tube 260 which can be utilized to close and/or open the anvil 306 of the end effector 300. Primarily referring now to FIGS. 8 and 9, the shaft assembly 200 can include a spine 210 which can be configured to fixably support a shaft frame portion 212 of the articulation lock 350. See FIG. 8. The spine 210 can be configured to, one, slidably support a firing member 220 therein and, two, slidably support the closure tube 260 which extends around the spine 210. The spine 210 can also be configured to slidably support a proximal articulation driver 230. The articulation driver 230 has a distal end 231 that is configured to operably engage the articulation lock 350. The articulation lock 350 interfaces with an articulation frame 352 that is adapted to operably engage a drive pin (not shown) on the end effector frame (not shown). As indicated above, further details regarding the operation of the articulation lock 350 and the articulation frame may be found in U.S. patent application Ser. No. 13/803,086. In various circumstances, the spine 210 can comprise a proximal end 211 which is rotatably supported in a chassis 240. In one arrangement, for example, the proximal end 211 of the spine 210 has a thread 214 formed thereon for threaded attachment to a spine bearing 216 configured to be supported within the chassis 240. See FIG. 7. Such an arrangement facilitates rotatable attachment of the spine 210 to the chassis 240 such that the spine 210 may be selectively rotated about a shaft axis SA-SA relative to the chassis 240.

Referring primarily to FIG. 7, the interchangeable shaft assembly 200 includes a closure shuttle 250 that is slidably supported within the chassis 240 such that it may be axially moved relative thereto. As shown in FIGS. 3 and 7, the closure shuttle 250 includes a pair of proximally-protruding hooks 252 that are configured for attachment to the attachment pin 37 that is attached to the second closure link 38 as will be discussed in further detail below. A proximal end 261 of the closure tube 260 is coupled to the closure shuttle 250 for relative rotation thereto. For example, a U shaped connector 263 is inserted into an annular slot 262 in the proximal end 261 of the closure tube 260 and is retained within vertical slots 253 in the closure shuttle 250. See FIG. 7. Such an arrangement serves to attach the closure tube 260 to the closure shuttle 250 for axial travel therewith while enabling the closure tube 260 to rotate relative to the closure shuttle 250 about the shaft axis SA-SA. A closure spring 268 is journaled on the closure tube 260 and serves to bias the closure tube 260 in the proximal direction "PD" which can serve to pivot the closure trigger into the unactuated position when the shaft assembly is operably coupled to the handle 14.

In at least one form, the interchangeable shaft assembly 200 may further include an articulation joint 270. Other interchangeable shaft assemblies, however, may not be capable of articulation. As shown in FIG. 7, for example, the articulation joint 270 includes a double pivot closure sleeve assembly 271. According to various forms, the double pivot closure sleeve assembly 271 includes an end effector closure sleeve assembly 272 having upper and lower distally projecting tangs 273, 274. An end effector closure sleeve assembly 272 includes a horseshoe aperture 275 and a tab 276 for engaging an opening tab on the anvil 306 in the various manners described in U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541, which has been incorporated by reference herein. As described in further detail therein, the horseshoe aperture 275 and tab 276 engage a tab on the anvil when the anvil 306 is opened. An upper double pivot link 277 includes upwardly projecting distal and proximal pivot pins that engage respectively an upper distal pin hole in the upper proximally projecting tang 273 and an upper proximal pin hole in an upper distally projecting tang 264 on the closure tube 260. A lower double pivot link 278 includes upwardly projecting distal and proximal pivot pins that engage respectively a lower distal pin hole in the lower proximally projecting tang 274 and a lower proximal pin hole in the lower distally projecting tang 265. See also FIG. 8.

In use, the closure tube 260 is translated distally (direction "DD") to close the anvil 306, for example, in response to the actuation of the closure trigger 32. The anvil 306 is closed by distally translating the closure tube 260 and thus the shaft closure sleeve assembly 272, causing it to strike a proximal surface on the anvil 360 in the manner described in the aforementioned reference U.S. patent application Ser. No. 13/803,086. As was also described in detail in that reference, the anvil 306 is opened by proximally translating the closure tube 260 and the shaft closure sleeve assembly 272, causing tab 276 and the horseshoe aperture 275 to contact and push against the anvil tab to lift the anvil 306. In the anvil-open position, the shaft closure tube 260 is moved to its proximal position.

As indicated above, the surgical instrument 10 may further include an articulation lock 350 of the types and construction described in further detail in U.S. patent application Ser. No. 13/803,086 which can be configured and operated to selectively lock the end effector 300 in position. Such arrangement enables the end effector 300 to be rotated, or articulated, relative to the shaft closure tube 260 when the articulation lock 350 is in its unlocked state. In such an unlocked state, the end effector 300 can be positioned and pushed against soft tissue and/or bone, for example, surrounding the surgical site within the patient in order to cause the end effector 300 to articulate relative to the closure tube 260. The end effector 300 may also be articulated relative to the closure tube 260 by an articulation driver 230.

Figure 9:
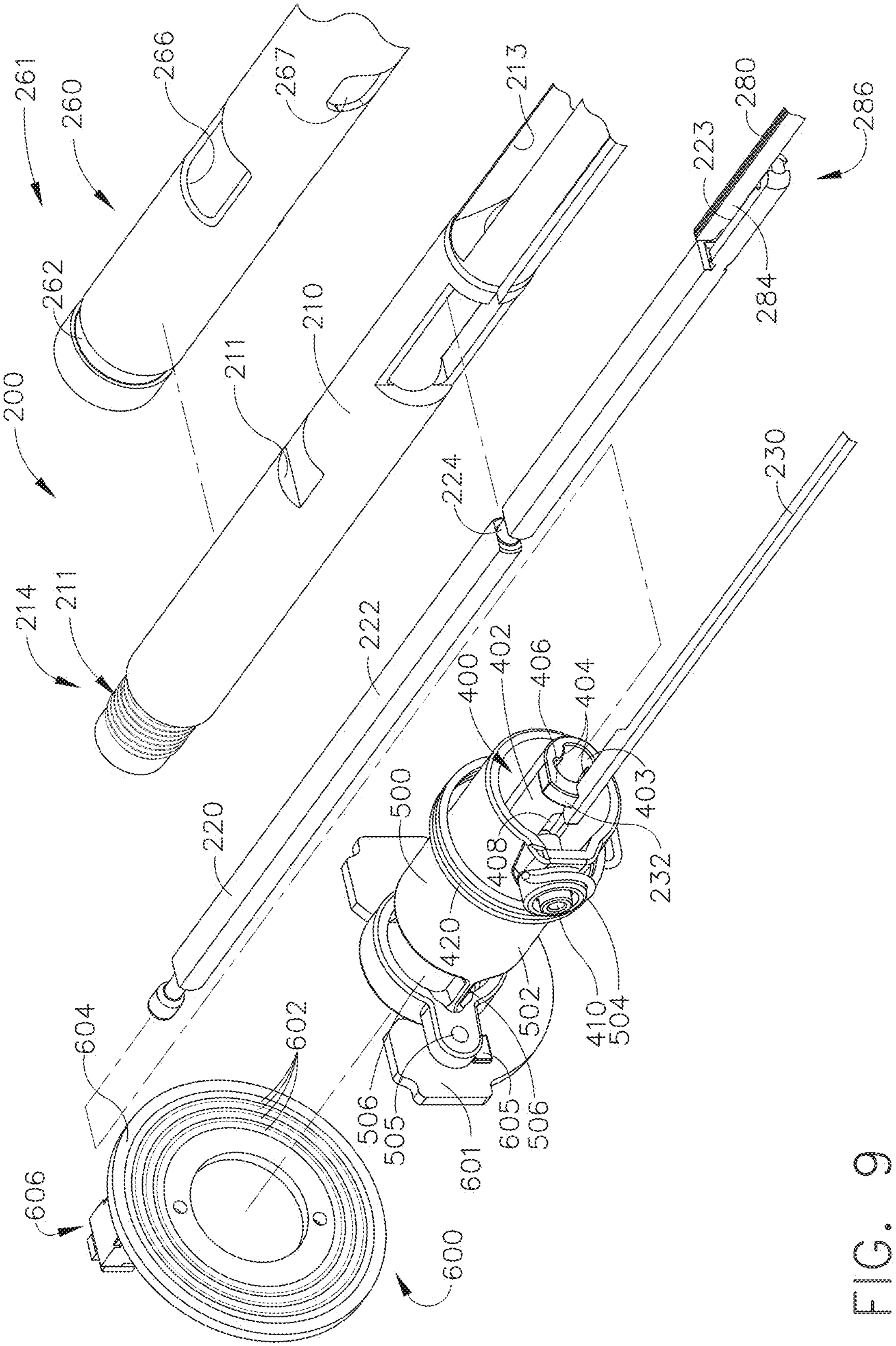
FIG. 9 is another exploded assembly view of portions of the interchangeable shaft assembly of FIGS. 7 and 8.

As was also indicated above, the interchangeable shaft assembly 200 further includes a firing member 220 that is supported for axial travel within the shaft spine 210. The firing member 220 includes an intermediate firing shaft portion 222 that is configured for attachment to a distal cutting portion or knife bar 280. The firing member 220 may also be referred to herein as a "second shaft" and/or a "second shaft assembly". As shown in FIGS. 8 and 9, the intermediate firing shaft portion 222 may include a longitudinal slot 223 in the distal end thereof which can be configured to receive a tab 284 on the proximal end 282 of the distal knife bar 280. The longitudinal slot 223 and the proximal end 282 can be sized and configured to permit relative movement therebetween and can comprise a slip joint 286. The slip joint 286 can permit the intermediate firing shaft portion 222 of the firing drive 220 to be moved to articulate the end effector 300 without moving, or at least substantially moving, the knife bar 280. Once the end effector 300 has been suitably oriented, the intermediate firing shaft portion 222 can be advanced distally until a proximal sidewall of the longitudinal slot 223 comes into contact with the tab 284 in order to advance the knife bar 280 and fire the staple cartridge positioned within the channel 302 As can be further seen in FIGS. 8 and 9, the shaft spine 210 has an elongate opening or window 213 therein to facilitate assembly and insertion of the intermediate firing shaft portion 222 into the shaft frame 210. Once the intermediate firing shaft portion 222 has been inserted therein, a top frame segment 215 may be engaged with the shaft frame 212 to enclose the intermediate firing shaft portion 222 and knife bar 280 therein. Further description of the operation of the firing member 220 may be found in U.S. patent application Ser. No. 13/803,086.

Further to the above, the shaft assembly 200 can include a clutch assembly 400 which can be configured to selectively and releasably couple the articulation driver 230 to the firing member 220. In one form, the clutch assembly 400 includes a lock collar, or sleeve 402, positioned around the firing member 220 wherein the lock sleeve 402 can be rotated between an engaged position in which the lock sleeve 402 couples the articulation driver 360 to the firing member 220 and a disengaged position in which the articulation driver 360 is not operably coupled to the firing member 200. When lock sleeve 402 is in its engaged position, distal movement of the firing member 220 can move the articulation driver 360 distally and, correspondingly, proximal movement of the firing member 220 can move the articulation driver 230 proximally. When lock sleeve 402 is in its disengaged position, movement of the firing member 220 is not transmitted to the articulation driver 230 and, as a result, the firing member 220 can move independently of the articulation driver 230. In various circumstances, the articulation driver 230 can be held in position by the articulation lock 350 when the articulation driver 230 is not being moved in the proximal or distal directions by the firing member 220.

Referring primarily to FIG. 9, the lock sleeve 402 can comprise a cylindrical, or an at least substantially cylindrical, body including a longitudinal aperture 403 defined therein configured to receive the firing member 220. The lock sleeve 402 can comprise diametrically-opposed, inwardly-facing lock protrusions 404 and an outwardly-facing lock member 406. The lock protrusions 404 can be configured to be selectively engaged with the firing member 220. More particularly, when the lock sleeve 402 is in its engaged position, the lock protrusions 404 are positioned within a drive notch 224 defined in the firing member 220 such that a distal pushing force and/or a proximal pulling force can be transmitted from the firing member 220 to the lock sleeve 402. When the lock sleeve 402 is in its engaged position, the second lock member 406 is received within a drive notch 232 defined in the articulation driver 230 such that the distal pushing force and/or the proximal pulling force applied to the lock sleeve 402 can be transmitted to the articulation driver 230. In effect, the firing member 220, the lock sleeve 402, and the articulation driver 230 will move together when the lock sleeve 402 is in its engaged position. On the other hand, when the lock sleeve 402 is in its disengaged position, the lock protrusions 404 may not be positioned within the drive notch 224 of the firing member 220 and, as a result, a distal pushing force and/or a proximal pulling force may not be transmitted from the firing member 220 to the lock sleeve 402. Correspondingly, the distal pushing force and/or the proximal pulling force may not be transmitted to the articulation driver 230. In such circumstances, the firing member 220 can be slid proximally and/or distally relative to the lock sleeve 402 and the proximal articulation driver 230.

Figure 10:
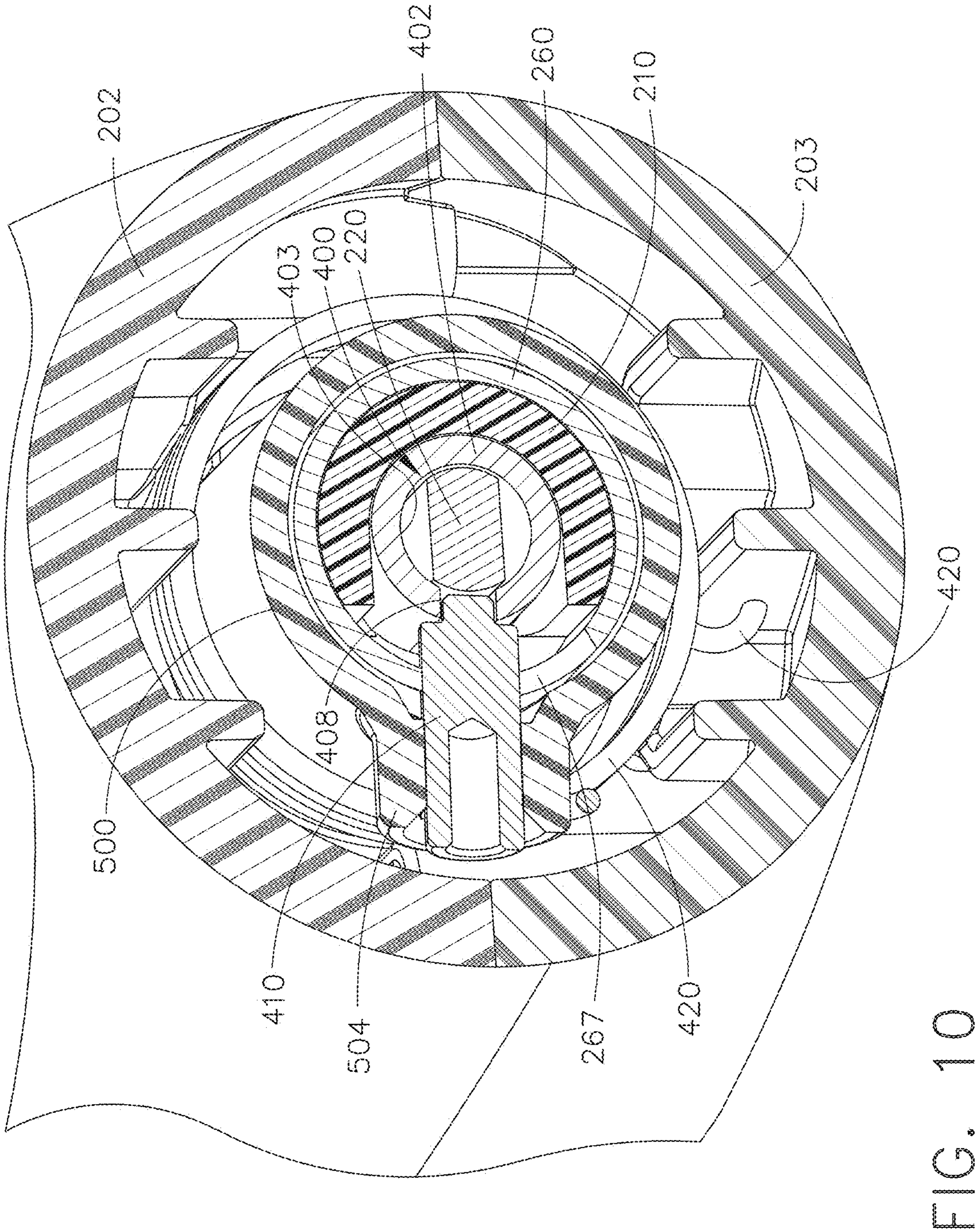
FIG. 10 is a cross-sectional view of a portion of the interchangeable shaft assembly of FIGS. 7-9.

As shown in FIGS. 8-12, the shaft assembly 200 further includes a switch drum 500 that is rotatably received on the closure tube 260. The switch drum 500 comprises a hollow shaft segment 502 that has a shaft boss 504 formed thereon for receive an outwardly protruding actuation pin 410 therein. In various circumstances, the actuation pin 410 extends through a slot 267 into a longitudinal slot 408 provided in the lock sleeve 402 to facilitate axial movement of the lock sleeve 402 when it is engaged with the articulation driver 230. A rotary torsion spring 420 is configured to engage the boss 504 on the switch drum 500 and a portion of the nozzle housing 203 as shown in FIG. 10 to apply a biasing force to the switch drum 500. The switch drum 500 can further comprise at least partially circumferential openings 506 defined therein which, referring to FIGS. 5 and 6, can be configured to receive circumferential mounts 204, 205 extending from the nozzle halves 202, 203 and permit relative rotation, but not translation, between the switch drum 500 and the proximal nozzle 201. As shown in those Figures, the mounts 204 and 205 also extend through openings 266 in the closure tube 260 to be seated in recesses 211 in the shaft spine 210. However, rotation of the nozzle 201 to a point where the mounts 204, 205 reach the end of their respective slots 506 in the switch drum 500 will result in rotation of the switch drum 500 about the shaft axis SA-SA. Rotation of the switch drum 500 will ultimately result in the rotation of eth actuation pin 410 and the lock sleeve 402 between its engaged and disengaged positions. Thus, in essence, the nozzle 201 may be employed to operably engage and disengage the articulation drive system with the firing drive system in the various manners described in further detail in U.S. patent application Ser. No. 13/803,086.

As also illustrated in FIGS. 8-12, the shaft assembly 200 can comprise a slip ring assembly 600 which can be configured to conduct electrical power to and/or from the end effector 300 and/or communicate signals to and/or from the end effector 300, for example. The slip ring assembly 600 can comprise a proximal connector flange 604 mounted to a chassis flange 242 extending from the chassis 240 and a distal connector flange 601 positioned within a slot defined in the shaft housings 202, 203. The proximal connector flange 604 can comprise a first face and the distal connector flange 601 can comprise a second face which is positioned adjacent to and movable relative to the first face. The distal connector flange 601 can rotate relative to the proximal connector flange 604 about the shaft axis SA-SA. The proximal connector flange 604 can comprise a plurality of concentric, or at least substantially concentric, conductors 602 defined in the first face thereof. A connector 607 can be mounted on the proximal side of the connector flange 601 and may have a plurality of contacts (not shown) wherein each contact corresponds to and is in electrical contact with one of the conductors 602. Such an arrangement permits relative rotation between the proximal connector flange 604 and the distal connector flange 601 while maintaining electrical contact therebetween. The proximal connector flange 604 can include an electrical connector 606 which can place the conductors 602 in signal communication with a shaft circuit board 610 mounted to the shaft chassis 240, for example. In at least one instance, a wiring harness comprising a plurality of conductors can extend between the electrical connector 606 and the shaft circuit board 610. The electrical connector 606 may extend proximally through a connector opening 243 defined in the chassis mounting flange 242. See FIG. 7. U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552, is incorporated by reference in its entirety. U.S. patent application Ser. No. 13/800,025, entitled STAPLE CARTRIDGE TISSUE THICKNESS SENSOR SYSTEM, filed on Mar. 13, 2013, now U.S. Patent Application Publication No. 2014/0263552, is incorporated by reference in its entirety. Further details regarding slip ring assembly 600 may be found in U.S. patent application Ser. No. 13/803,086.

Figure 11:
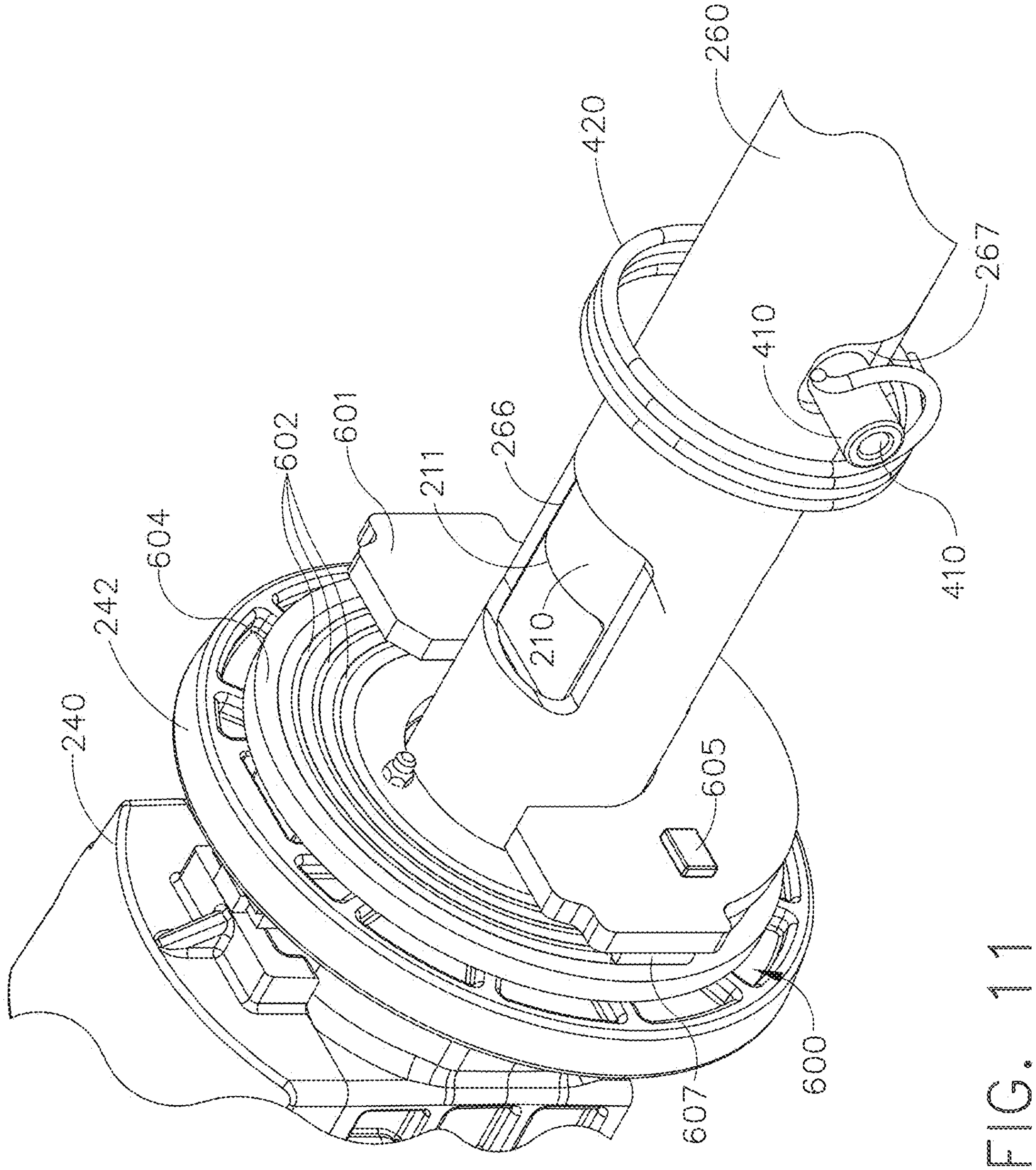
FIG. 11 is a perspective view of a portion of the shaft assembly of FIGS. 7-10 with the switch drum omitted for clarity.
Figure 12:
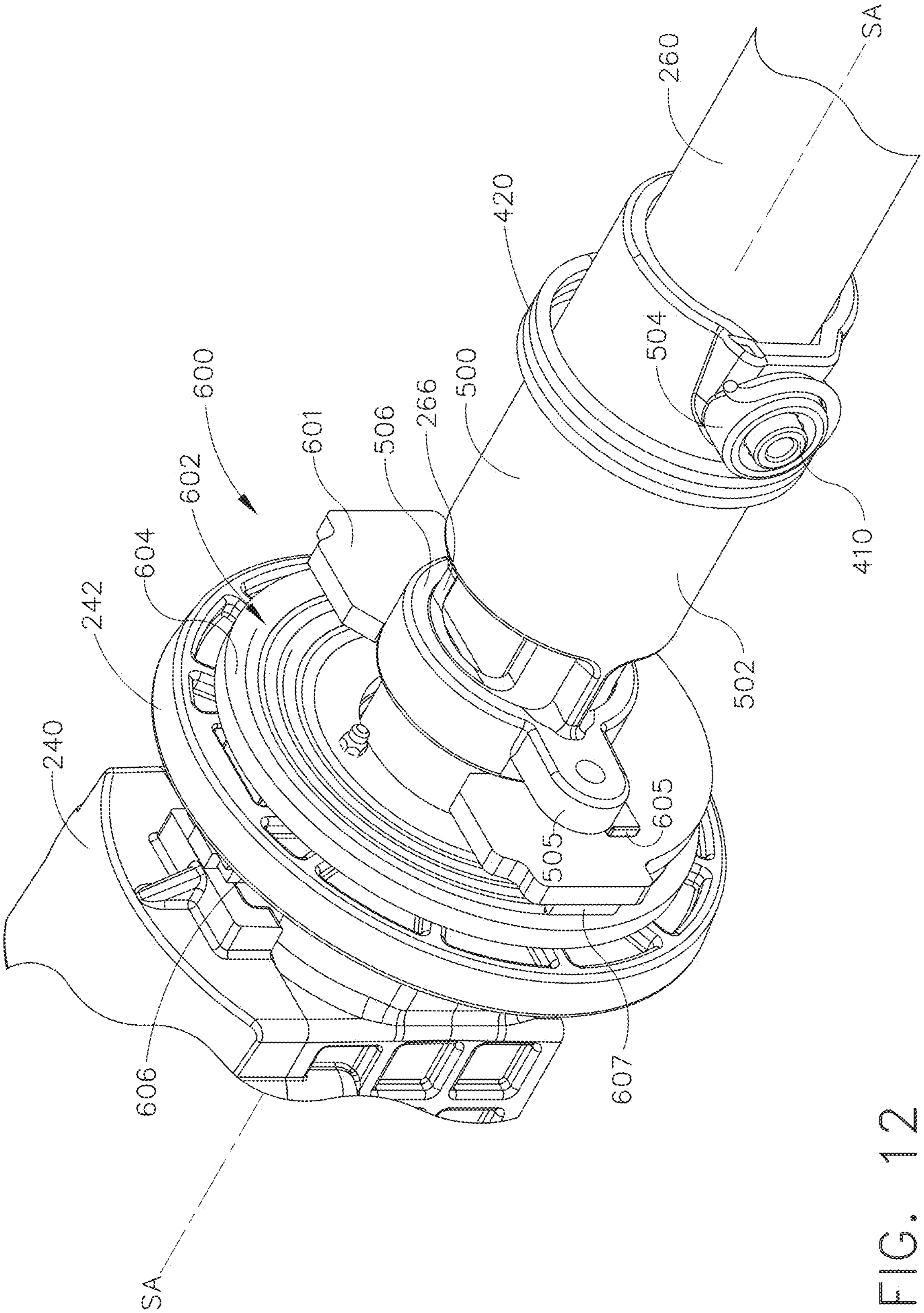
FIG. 12 is another perspective view of the portion of the interchangeable shaft assembly of FIG. 11 with the switch drum mounted thereon.

As discussed above, the shaft assembly 200 can include a proximal portion which is fixably mounted to the handle 14 and a distal portion which is rotatable about a longitudinal axis. The rotatable distal shaft portion can be rotated relative to the proximal portion about the slip ring assembly 600, as discussed above. The distal connector flange 601 of the slip ring assembly 600 can be positioned within the rotatable distal shaft portion. Moreover, further to the above, the switch drum 500 can also be positioned within the rotatable distal shaft portion. When the rotatable distal shaft portion is rotated, the distal connector flange 601 and the switch drum 500 can be rotated synchronously with one another. In addition, the switch drum 500 can be rotated between a first position and a second position relative to the distal connector flange 601. When the switch drum 500 is in its first position, the articulation drive system may be operably disengaged from the firing drive system and, thus, the operation of the firing drive system may not articulate the end effector 300 of the shaft assembly 200. When the switch drum 500 is in its second position, the articulation drive system may be operably engaged with the firing drive system and, thus, the operation of the firing drive system may articulate the end effector 300 of the shaft assembly 200. When the switch drum 500 is moved between its first position and its second position, the switch drum 500 is moved relative to distal connector flange 601. In various instances, the shaft assembly 200 can comprise at least one sensor configured to detect the position of the switch drum 500. Turning now to FIGS. 11 and 12, the distal connector flange 601 can comprise a Hall effect sensor 605, for example, and the switch drum 500 can comprise a magnetic element, such as permanent magnet 505, for example. The Hall effect sensor 605 can be configured to detect the position of the permanent magnet 505. When the switch drum 500 is rotated between its first position and its second position, the permanent magnet 505 can move relative to the Hall effect sensor 605. In various instances, Hall effect sensor 605 can detect changes in a magnetic field created when the permanent magnet 505 is moved. The Hall effect sensor 605 can be in signal communication with the shaft circuit board 610 and/or the handle circuit board 100, for example. Based on the signal from the Hall effect sensor 605, a microcontroller on the shaft circuit board 610 and/or the handle circuit board 100 can determine whether the articulation drive system is engaged with or disengaged from the firing drive system.

Referring again to FIGS. 3 and 7, the chassis 240 includes at least one, and preferably two, tapered attachment portions 244 formed thereon that are adapted to be received within corresponding dovetail slots 702 formed within a distal attachment flange portion 700 of the frame 20. Each dovetail slot 702 may be tapered or, stated another way, be somewhat V-shaped to seatingly receive the attachment portions 244 therein. As can be further seen in FIGS. 3 and 7, a shaft attachment lug 226 is formed on the proximal end of the intermediate firing shaft 222. As will be discussed in further detail below, when the interchangeable shaft assembly 200 is coupled to the handle 14, the shaft attachment lug 226 is received in a firing shaft attachment cradle 126 formed in the distal end 125 of the longitudinal drive member 120. See FIGS. 3 and 6.

Various shaft assembly embodiments employ a latch system 710 for removably coupling the shaft assembly 200 to the housing 12 and more specifically to the frame 20. As shown in FIG. 7, for example, in at least one form, the latch system 710 includes a lock member or lock yoke 712 that is movably coupled to the chassis 240. In the illustrated embodiment, for example, the lock yoke 712 has a U-shape with two spaced downwardly extending legs 714. The legs 714 each have a pivot lug 716 formed thereon that are adapted to be received in corresponding holes 245 formed in the chassis 240. Such arrangement facilitates pivotal attachment of the lock yoke 712 to the chassis 240. The lock yoke 712 may include two proximally protruding lock lugs 714 that are configured for releasable engagement with corresponding lock detents or grooves 704 in the distal attachment flange 700 of the frame 20. See FIG. 3. In various forms, the lock yoke 712 is biased in the proximal direction by spring or biasing member (not shown). Actuation of the lock yoke 712 may be accomplished by a latch button 722 that is slidably mounted on a latch actuator assembly 720 that is mounted to the chassis 240. The latch button 722 may be biased in a proximal direction relative to the lock yoke 712. As will be discussed in further detail below, the lock yoke 712 may be moved to an unlocked position by biasing the latch button the in distal direction which also causes the lock yoke 712 to pivot out of retaining engagement with the distal attachment flange 700 of the frame 20. When the lock yoke 712 is in "retaining engagement" with the distal attachment flange 700 of the frame 20, the lock lugs 716 are retainingly seated within the corresponding lock detents or grooves 704 in the distal attachment flange 700.

When employing an interchangeable shaft assembly that includes an end effector of the type described herein that is adapted to cut and fasten tissue, as well as other types of end effectors, it may be desirable to prevent inadvertent detachment of the interchangeable shaft assembly from the housing during actuation of the end effector. For example, in use the clinician may actuate the closure trigger 32 to grasp and manipulate the target tissue into a desired position. Once the target tissue is positioned within the end effector 300 in a desired orientation, the clinician may then fully actuate the closure trigger 32 to close the anvil 306 and clamp the target tissue in position for cutting and stapling. In that instance, the first drive system 30 has been fully actuated. After the target tissue has been clamped in the end effector 300, it may be desirable to prevent the inadvertent detachment of the shaft assembly 200 from the housing 12. One form of the latch system 710 is configured to prevent such inadvertent detachment.

As can be most particularly seen in FIG. 7, the lock yoke 712 includes at least one and preferably two lock hooks 718 that are adapted to contact corresponding lock lug portions 256 that are formed on the closure shuttle 250. Referring to FIGS. 13-15, when the closure shuttle 250 is in an unactuated position (i.e., the first drive system 30 is unactuated and the anvil 306 is open), the lock yoke 712 may be pivoted in a distal direction to unlock the interchangeable shaft assembly 200 from the housing 12. When in that position, the lock hooks 718 do not contact the lock lug portions 256 on the closure shuttle 250. However, when the closure shuttle 250 is moved to an actuated position (i.e., the first drive system 30 is actuated and the anvil 306 is in the closed position), the lock yoke 712 is prevented from being pivoted to an unlocked position. See FIGS. 16-18. Stated another way, if the clinician were to attempt to pivot the lock yoke 712 to an unlocked position or, for example, the lock yoke 712 was in advertently bumped or contacted in a manner that might otherwise cause it to pivot distally, the lock hooks 718 on the lock yoke 712 will contact the lock lugs 256 on the closure shuttle 250 and prevent movement of the lock yoke 712 to an unlocked position.

Attachment of the interchangeable shaft assembly 200 to the handle 14 will now be described with reference to FIG. 3. To commence the coupling process, the clinician may position the chassis 240 of the interchangeable shaft assembly 200 above or adjacent to the distal attachment flange 700 of the frame 20 such that the tapered attachment portions 244 formed on the chassis 240 are aligned with the dovetail slots 702 in the frame 20. The clinician may then move the shaft assembly 200 along an installation axis IA that is perpendicular to the shaft axis SA-SA to seat the attachment portions 244 in "operable engagement" with the corresponding dovetail receiving slots 702. In doing so, the shaft attachment lug 226 on the intermediate firing shaft 222 will also be seated in the cradle 126 in the longitudinally movable drive member 120 and the portions of pin 37 on the second closure link 38 will be seated in the corresponding hooks 252 in the closure yoke 250. As used herein, the term "operable engagement" in the context of two components means that the two components are sufficiently engaged with each other so that upon application of an actuation motion thereto, the components may carry out their intended action, function and/or procedure.

As discussed above, at least five systems of the interchangeable shaft assembly 200 can be operably coupled with at least five corresponding systems of the handle 14. A first system can comprise a frame system which couples and/or aligns the frame or spine of the shaft assembly 200 with the frame 20 of the handle 14. Another system can comprise a closure drive system 30 which can operably connect the closure trigger 32 of the handle 14 and the closure tube 260 and the anvil 306 of the shaft assembly 200. As outlined above, the closure tube attachment yoke 250 of the shaft assembly 200 can be engaged with the pin 37 on the second closure link 38. Another system can comprise the firing drive system 80 which can operably connect the firing trigger 130 of the handle 14 with the intermediate firing shaft 222 of the shaft assembly 200.

As outlined above, the shaft attachment lug 226 can be operably connected with the cradle 126 of the longitudinal drive member 120. Another system can comprise an electrical system which can signal to a controller in the handle 14, such as microcontroller, for example, that a shaft assembly, such as shaft assembly 200, for example, has been operably engaged with the handle 14 and/or, two, conduct power and/or communication signals between the shaft assembly 200 and the handle 14. For instance, the shaft assembly 200 can include an electrical connector 1410 that is operably mounted to the shaft circuit board 610. The electrical connector 1410 is configured for mating engagement with a corresponding electrical connector 1400 on the handle control board 100. Further details regaining the circuitry and control systems may be found in U.S. patent application Ser. No. 13/803,086, the entire disclosure of which was previously incorporated by reference herein. The fifth system may consist of the latching system for releasably locking the shaft assembly 200 to the handle 14.

Figure 19:
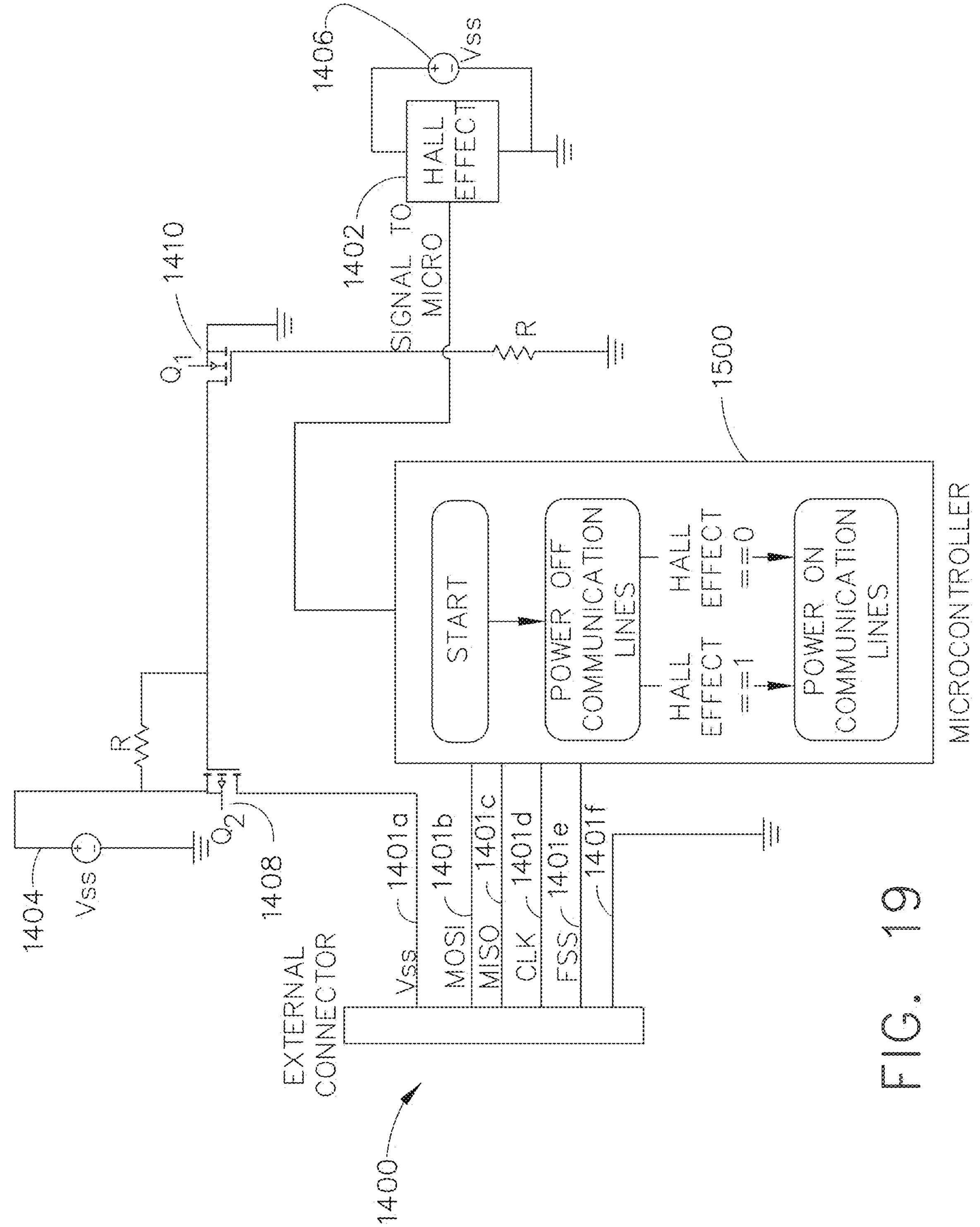
FIG. 19 is a schematic of a system for powering down an electrical connector of a surgical instrument handle when a shaft assembly is not coupled thereto.

Referring again to FIGS. 2 and 3, the handle 14 can include an electrical connector 1400 comprising a plurality of electrical contacts. Turning now to FIG. 19, the electrical connector 1400 can comprise a first contact 1401*a*, a second contact 1401*b*, a third contact 1401*c*, a fourth contact 1401*d*, a fifth contact 1401*e*, and a sixth contact 1401*f*, for example. While the illustrated embodiment utilizes six contacts, other embodiments are envisioned which may utilize more than six contacts or less than six contacts.

As illustrated in FIG. 19, the first contact 1401*a* can be in electrical communication with a transistor 1408, contacts 1401*b*-1401*e* can be in electrical communication with a microcontroller 1500, and the sixth contact 1401*f* can be in electrical communication with a ground. In certain circumstances, one or more of the electrical contacts 1401*b*-1401*e* may be in electrical communication with one or more output channels of the microcontroller 1500 and can be energized, or have a voltage potential applied thereto, when the handle 1042 is in a powered state. In some circumstances, one or more of the electrical contacts 1401*b*-1401*e* may be in electrical communication with one or more input channels of the microcontroller 1500 and, when the handle 14 is in a powered state, the microcontroller 1500 can be configured to detect when a voltage potential is applied to such electrical contacts. When a shaft assembly, such as shaft assembly 200, for example, is assembled to the handle 14, the electrical contacts 1401*a*-1401*f* may not communicate with each other. When a shaft assembly is not assembled to the handle 14, however, the electrical contacts 1401*a*-1401*f* of the electrical connector 1400 may be exposed and, in some circumstances, one or more of the contacts 1401*a*-1401*f* may be accidentally placed in electrical communication with each other. Such circumstances can arise when one or more of the contacts 1401*a*-1401*f* come into contact with an electrically conductive material, for example. When this occurs, the microcontroller 1500 can receive an erroneous input and/or the shaft assembly 200 can receive an erroneous output, for example. To address this issue, in various circumstances, the handle 14 may be unpowered when a shaft assembly, such as shaft assembly 200, for example, is not attached to the handle 14.

In other circumstances, the handle 1042 can be powered when a shaft assembly, such as shaft assembly 200, for example, is not attached thereto. In such circumstances, the microcontroller 1500 can be configured to ignore inputs, or voltage potentials, applied to the contacts in electrical communication with the microcontroller 1500, i.e., contacts 1401*b*-1401*e*, for example, until a shaft assembly is attached to the handle 14. Even though the microcontroller 1500 may be supplied with power to operate other functionalities of the handle 14 in such circumstances, the handle 14 may be in a powered-down state. In a way, the electrical connector 1400 may be in a powered-down state as voltage potentials applied to the electrical contacts 1401*b*-1401*e* may not affect the operation of the handle 14. The reader will appreciate that, even though contacts 1401*b*-1401*e* may be in a powered-down state, the electrical contacts 1401*a* and 1401*f*, which are not in electrical communication with the microcontroller 1500, may or may not be in a powered-down state. For instance, sixth contact 1401*f* may remain in electrical communication with a ground regardless of whether the handle 14 is in a powered-up or a powered-down state.

Furthermore, the transistor 1408, and/or any other suitable arrangement of transistors, such as transistor 1410, for example, and/or switches may be configured to control the supply of power from a power source 1404, such as a battery 90 within the handle 14, for example, to the first electrical contact 1401*a* regardless of whether the handle 14 is in a powered-up or a powered-down state. In various circumstances, the shaft assembly 200, for example, can be configured to change the state of the transistor 1408 when the shaft assembly 200 is engaged with the handle 14. In certain circumstances, further to the below, a Hall effect sensor 1402 can be configured to switch the state of transistor 1410 which, as a result, can switch the state of transistor 1408 and ultimately supply power from power source 1404 to first contact 1401*a*. In this way, both the power circuits and the signal circuits to the connector 1400 can be powered down when a shaft assembly is not installed to the handle 14 and powered up when a shaft assembly is installed to the handle 14.

In various circumstances, referring again to FIG. 19, the handle 14 can include the Hall effect sensor 1402, for example, which can be configured to detect a detectable element, such as a magnetic element 1407 (FIG. 3), for example, on a shaft assembly, such as shaft assembly 200, for example, when the shaft assembly is coupled to the handle 14. The Hall effect sensor 1402 can be powered by a power source 1406, such as a battery, for example, which can, in effect, amplify the detection signal of the Hall effect sensor 1402 and communicate with an input channel of the microcontroller 1500 via the circuit illustrated in FIG. 19. Once the microcontroller 1500 has a received an input indicating that a shaft assembly has been at least partially coupled to the handle 14, and that, as a result, the electrical contacts 1401*a*-1401*f* are no longer exposed, the microcontroller 1500 can enter into its normal, or powered-up, operating state. In such an operating state, the microcontroller 1500 will evaluate the signals transmitted to one or more of the contacts 1401*b*-1401*e* from the shaft assembly and/or transmit signals to the shaft assembly through one or more of the contacts 1401*b*-1401*e* in normal use thereof. In various circumstances, the shaft assembly 200 may have to be fully seated before the Hall effect sensor 1402 can detect the magnetic element 1407. While a Hall effect sensor 1402 can be utilized to detect the presence of the shaft assembly 200, any suitable system of sensors and/or switches can be utilized to detect whether a shaft assembly has been assembled to the handle 14, for example. In this way, further to the above, both the power circuits and the signal circuits to the connector 1400 can be powered down when a shaft assembly is not installed to the handle 14 and powered up when a shaft assembly is installed to the handle 14.

In various embodiments, any number of magnetic sensing elements may be employed to detect whether a shaft assembly has been assembled to the handle 14, for example. For example, the technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

Referring to FIG. 19, the microcontroller 1500 may generally comprise a microprocessor ("processor") and one or more memory units operationally coupled to the processor. By executing instruction code stored in the memory, the processor may control various components of the surgical instrument, such as the motor, various drive systems, and/or a user display, for example. The microcontroller 1500 may be implemented using integrated and/or discrete hardware elements, software elements, and/or a combination of both. Examples of integrated hardware elements may include processors, microprocessors, microcontrollers, integrated circuits, application specific integrated circuits (ASIC), programmable logic devices (PLD), digital signal processors (DSP), field programmable gate arrays (FPGA), logic gates, registers, semiconductor devices, chips, microchips, chip sets, microcontrollers, system-on-chip (SoC), and/or system-in-package (SIP). Examples of discrete hardware elements may include circuits and/or circuit elements such as logic gates, field effect transistors, bipolar transistors, resistors, capacitors, inductors, and/or relays. In certain instances, the microcontroller 1500 may include a hybrid circuit comprising discrete and integrated circuit elements or components on one or more substrates, for example.

Referring to FIG. 19, the microcontroller 1500 may be an LM 4F230H5QR, available from Texas Instruments, for example. In certain instances, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available. Other microcontrollers may be readily substituted for use with the present disclosure. Accordingly, the present disclosure should not be limited in this context.

As discussed above, the handle 14 and/or the shaft assembly 200 can include systems and configurations configured to prevent, or at least reduce the possibility of, the contacts of the handle electrical connector 1400 and/or the contacts of the shaft electrical connector 1410 from becoming shorted out when the shaft assembly 200 is not assembled, or completely assembled, to the handle 14. Referring to FIG. 3, the handle electrical connector 1400 can be at least partially recessed within a cavity 1409 defined in the handle frame 20. The six contacts 1401*a*-1401*f* of the electrical connector 1400 can be completely recessed within the cavity 1409. Such arrangements can reduce the possibility of an object accidentally contacting one or more of the contacts 1401*a*-1401*f*. Similarly, the shaft electrical connector 1410 can be positioned within a recess defined in the shaft chassis 240 which can reduce the possibility of an object accidentally contacting one or more of the contacts 1411*a*-1411*f* of the shaft electrical connector 1410. With regard to the particular embodiment depicted in FIG. 3, the shaft contacts 1411*a*-1411*f* can comprise male contacts. In at least one embodiment, each shaft contact 1411*a*-1411*f* can comprise a flexible projection extending therefrom which can be configured to engage a corresponding handle contact 1401*a*-1401*f*, for example. The handle contacts 1401*a*-1401*f* can comprise female contacts. In at least one embodiment, each handle contact 1401*a*-1401*f* can comprise a flat surface, for example, against which the male shaft contacts 1401*a*-1401*f* can wipe, or slide, against and maintain an electrically conductive interface therebetween. In various instances, the direction in which the shaft assembly 200 is assembled to the handle 14 can be parallel to, or at least substantially parallel to, the handle contacts 1401*a*-1401*f* such that the shaft contacts 1411*a*-1411*f* slide against the handle contacts 1401*a*-1401*f* when the shaft assembly 200 is assembled to the handle 14. In various alternative embodiments, the handle contacts 1401*a*-1401*f* can comprise male contacts and the shaft contacts 1411*a*-1411*f* can comprise female contacts. In certain alternative embodiments, the handle contacts 1401*a*-1401*f* and the shaft contacts 1411*a*-1411*f* can comprise any suitable arrangement of contacts.

In various instances, the handle 14 can comprise a connector guard configured to at least partially cover the handle electrical connector 1400 and/or a connector guard configured to at least partially cover the shaft electrical connector 1410. A connector guard can prevent, or at least reduce the possibility of, an object accidentally touching the contacts of an electrical connector when the shaft assembly is not assembled to, or only partially assembled to, the handle. A connector guard can be movable. For instance, the connector guard can be moved between a guarded position in which it at least partially guards a connector and an unguarded position in which it does not guard, or at least guards less of, the connector. In at least one embodiment, a connector guard can be displaced as the shaft assembly is being assembled to the handle. For instance, if the handle comprises a handle connector guard, the shaft assembly can contact and displace the handle connector guard as the shaft assembly is being assembled to the handle. Similarly, if the shaft assembly comprises a shaft connector guard, the handle can contact and displace the shaft connector guard as the shaft assembly is being assembled to the handle. In various instances, a connector guard can comprise a door, for example. In at least one instance, the door can comprise a beveled surface which, when contacted by the handle or shaft, can facilitate the displacement of the door in a certain direction. In various instances, the connector guard can be translated and/or rotated, for example. In certain instances, a connector guard can comprise at least one film which covers the contacts of an electrical connector. When the shaft assembly is assembled to the handle, the film can become ruptured. In at least one instance, the male contacts of a connector can penetrate the film before engaging the corresponding contacts positioned underneath the film.

As described above, the surgical instrument can include a system which can selectively power-up, or activate, the contacts of an electrical connector, such as the electrical connector 1400, for example. In various instances, the contacts can be transitioned between an unactivated condition and an activated condition. In certain instances, the contacts can be transitioned between a monitored condition, a deactivated condition, and an activated condition. For instance, the microcontroller 1500, for example, can monitor the contacts 1401*a*-1401*f* when a shaft assembly has not been assembled to the handle 14 to determine whether one or more of the contacts 1401*a*-1401*f* may have been shorted. The microcontroller 1500 can be configured to apply a low voltage potential to each of the contacts 1401*a*-1401*f* and assess whether only a minimal resistance is present at each of the contacts. Such an operating state can comprise the monitored condition. In the event that the resistance detected at a contact is high, or above a threshold resistance, the microcontroller 1500 can deactivate that contact, more than one contact, or, alternatively, all of the contacts. Such an operating state can comprise the deactivated condition. If a shaft assembly is assembled to the handle 14 and it is detected by the microcontroller 1500, as discussed above, the microcontroller 1500 can increase the voltage potential to the contacts 1401*a*-1401*f*. Such an operating state can comprise the activated condition.

The various shaft assemblies disclosed herein may employ sensors and various other components that require electrical communication with the controller in the housing. These shaft assemblies generally are configured to be able to rotate relative to the housing necessitating a connection that facilitates such electrical communication between two or more components that may rotate relative to each other. When employing end effectors of the types disclosed herein, the connector arrangements must be relatively robust in nature while also being somewhat compact to fit into the shaft assembly connector portion.

Figure 20:
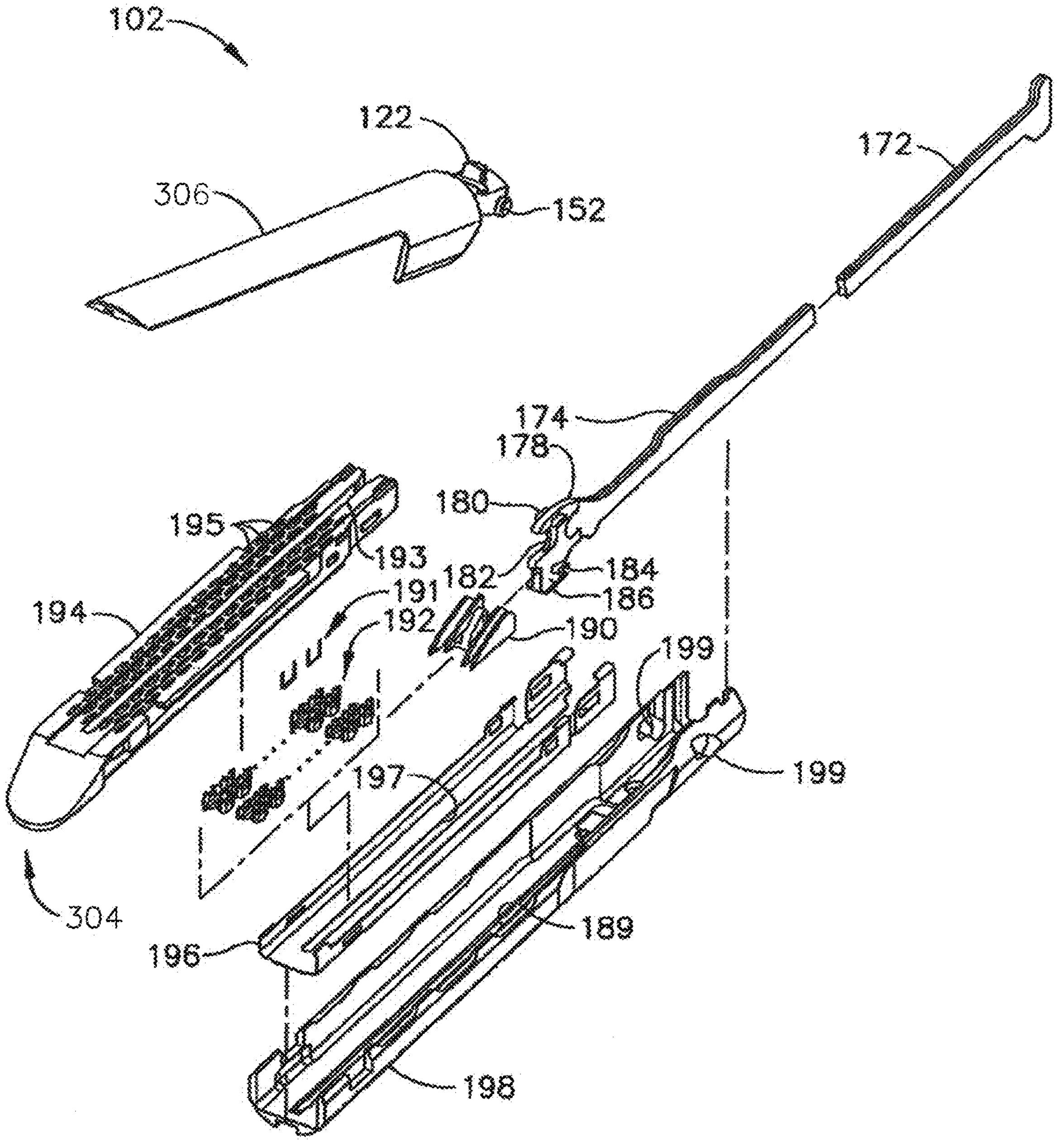
FIG. 20 is an exploded view of one embodiment of an end effector of the surgical instrument of FIG. 1.

Referring to FIG. 20, a non-limiting form of the end effector 300 is illustrated. As described above, the end effector 300 may include the anvil 306 and the staple cartridge 304. In this non-limiting embodiment, the anvil 306 is coupled to an elongate channel 198. For example, apertures 199 can be defined in the elongate channel 198 which can receive pins 152 extending from the anvil 306 and allow the anvil 306 to pivot from an open position to a closed position relative to the elongate channel 198 and staple cartridge 304. In addition, FIG. 20 shows a firing bar 172, configured to longitudinally translate into the end effector 300. The firing bar 172 may be constructed from one solid section, or in various embodiments, may include a laminate material comprising, for example, a stack of steel plates. A distally projecting end of the firing bar 172 can be attached to an E-beam 178 that can, among other things, assist in spacing the anvil 306 from a staple cartridge 304 positioned in the elongate channel 198 when the anvil 306 is in a closed position. The E-beam 178 can also include a sharpened cutting edge 182 which can be used to sever tissue as the E-beam 178 is advanced distally by the firing bar 172. In operation, the E-beam 178 can also actuate, or fire, the staple cartridge 304. The staple cartridge 304 can include a molded cartridge body 194 that holds a plurality of staples 191 resting upon staple drivers 192 within respective upwardly open staple cavities 195. A wedge sled 190 is driven distally by the E-beam 178, sliding upon a cartridge tray 196 that holds together the various components of the replaceable staple cartridge 304. The wedge sled 190 upwardly cams the staple drivers 192 to force out the staples 191 into deforming contact with the anvil 306 while a cutting surface 182 of the E-beam 178 severs clamped tissue.

Further to the above, the E-beam 178 can include upper pins 180 which engage the anvil 306 during firing. The E-beam 178 can further include middle pins 184 and a bottom foot 186 which can engage various portions of the cartridge body 194, cartridge tray 196 and elongate channel 198. When a staple cartridge 304 is positioned within the elongate channel 198, a slot 193 defined in the cartridge body 194 can be aligned with a slot 197 defined in the cartridge tray 196 and a slot 189 defined in the elongate channel 198. In use, the E-beam 178 can slide through the aligned slots 193, 197, and 189 wherein, as indicated in FIG. 20, the bottom foot 186 of the E-beam 178 can engage a groove running along the bottom surface of channel 198 along the length of slot 189, the middle pins 184 can engage the top surfaces of cartridge tray 196 along the length of longitudinal slot 197, and the upper pins 180 can engage the anvil 306. In such circumstances, the E-beam 178 can space, or limit the relative movement between, the anvil 306 and the staple cartridge 304 as the firing bar 172 is moved distally to fire the staples from the staple cartridge 304 and/or incise the tissue captured between the anvil 306 and the staple cartridge 304. Thereafter, the firing bar 172 and the E-beam 178 can be retracted proximally allowing the anvil 306 to be opened to release the two stapled and severed tissue portions (not shown).

Figure 21A:
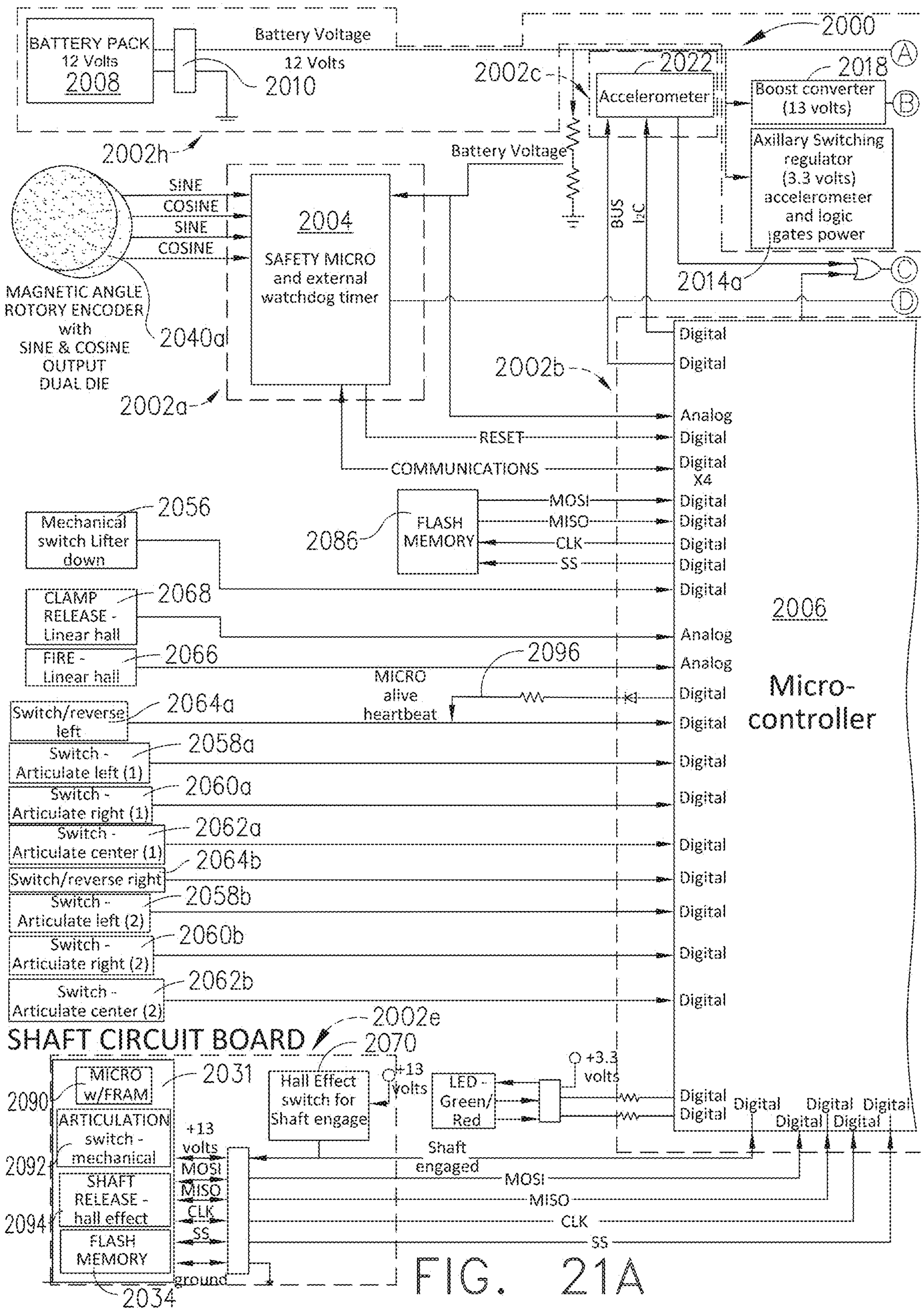
FIGS. 21A-21B is a circuit diagram of the surgical instrument of FIG. 1 spanning two drawings sheets.
Figure 21B:
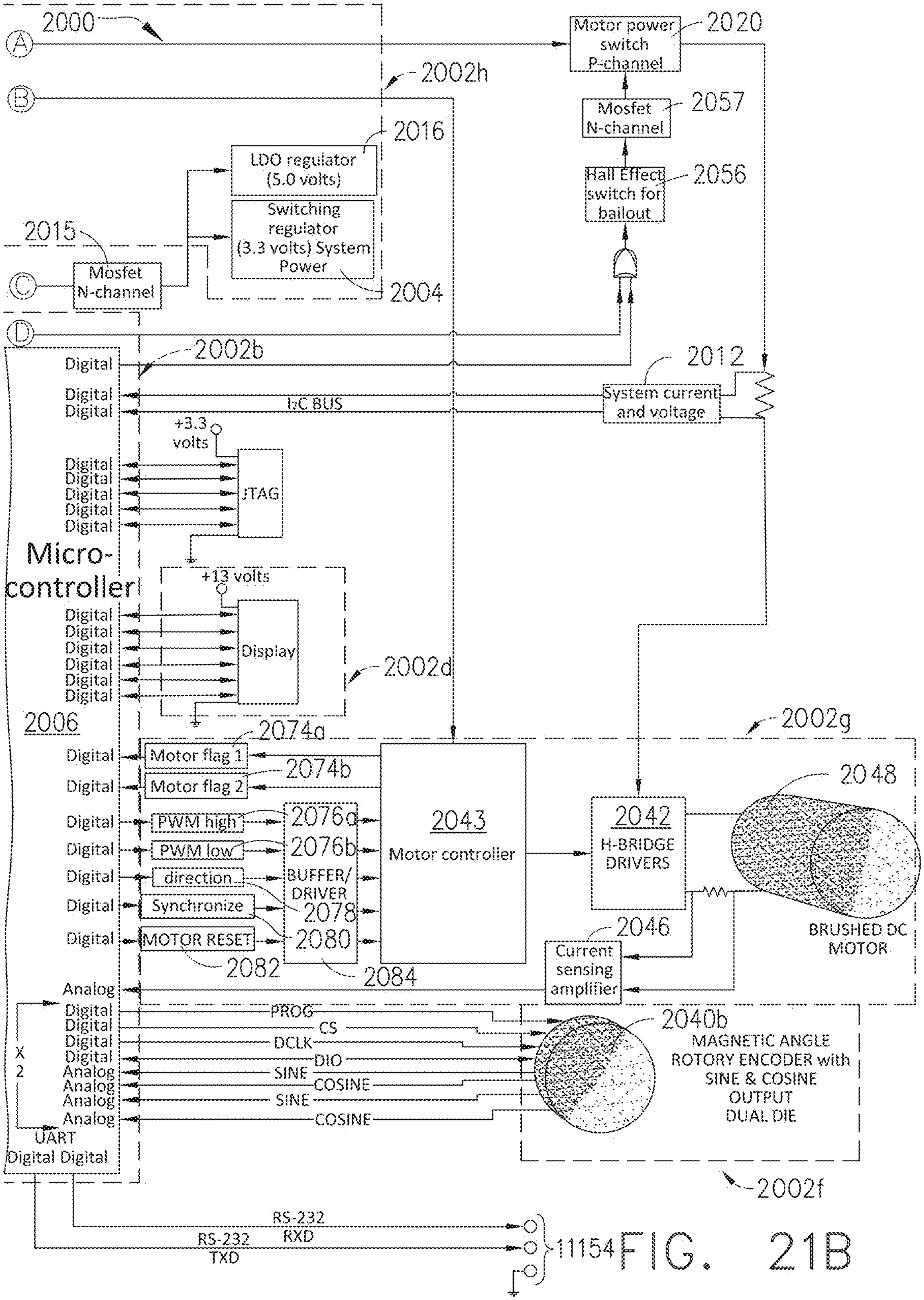

Having described a surgical instrument 10 in general terms, the description now turns to a detailed description of various electrical/electronic component of the surgical instrument 10. Turning now to FIGS. 21A-21B, where one embodiment of a segmented circuit 2000 comprising a plurality of circuit segments 2002*a*-2002*g* is illustrated. The segmented circuit 2000 comprising the plurality of circuit segments 2002*a*-2002*g* is configured to control a powered surgical instrument, such as, for example, the surgical instrument 10 illustrated in FIGS. 1-18A, without limitation. The plurality of circuit segments 2002*a*-2002*g* is configured to control one or more operations of the powered surgical instrument 10. A safety processor segment 2002*a* (Segment 1) comprises a safety processor 2004. A primary processor segment 2002*b* (Segment 2) comprises a primary processor 2006. The safety processor 2004 and/or the primary processor 2006 are configured to interact with one or more additional circuit segments 2002*c*-2002*g* to control operation of the powered surgical instrument 10. The primary processor 2006 comprises a plurality of inputs coupled to, for example, one or more circuit segments 2002*c*-2002*g*, a battery 2008, and/or a plurality of switches 2058*a*-2070. The segmented circuit 2000 may be implemented by any suitable circuit, such as, for example, a printed circuit board assembly (PCBA) within the powered surgical instrument 10. It should be understood that the term processor as used herein includes any microprocessor, microcontroller, or other basic computing device that incorporates the functions of a computer's central processing unit (CPU) on an integrated circuit or at most a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one embodiment, the main processor 2006 may be any single core or multicore processor such as those known under the trade name ARM Cortex by Texas Instruments. In one embodiment, the safety processor 2004 may be a safety microcontroller platform comprising two microcontroller-based families such as TMS570 and RM4x known under the trade name Hercules ARM Cortex R4, also by Texas Instruments. Nevertheless, other suitable substitutes for microcontrollers and safety processor may be employed, without limitation. In one embodiment, the safety processor 2004 may be configured specifically for IEC 61508 and ISO 26262 safety critical applications, among others, to provide advanced integrated safety features while delivering scalable performance, connectivity, and memory options.

In certain instances, the main processor 2006 may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle SRAM, internal ROM loaded with StellarisWare® software, 2 KB EEPROM, one or more PWM modules, one or more QEI analog, one or more 12-bit ADC with 12 analog input channels, among other features that are readily available for the product datasheet. Other processors may be readily substituted and, accordingly, the present disclosure should not be limited in this context.

In one embodiment, the segmented circuit 2000 comprises an acceleration segment 2002*c* (Segment 3). The acceleration segment 2002*c* comprises an acceleration sensor 2022. The acceleration sensor 2022 may comprise, for example, an accelerometer. The acceleration sensor 2022 is configured to detect movement or acceleration of the powered surgical instrument 10. In some embodiments, input from the acceleration sensor 2022 is used, for example, to transition to and from a sleep mode, identify an orientation of the powered surgical instrument, and/or identify when the surgical instrument has been dropped. In some embodiments, the acceleration segment 2002*c* is coupled to the safety processor 2004 and/or the primary processor 2006.

In one embodiment, the segmented circuit 2000 comprises a display segment 2002*d* (Segment 4). The display segment 2002*d* comprises a display connector 2024 coupled to the primary processor 2006. The display connector 2024 couples the primary processor 2006 to a display 2028 through one or more display driver integrated circuits 2026. The display driver integrated circuits 2026 may be integrated with the display 2028 and/or may be located separately from the display 2028. The display 2028 may comprise any suitable display, such as, for example, an organic light-emitting diode (OLED) display, a liquid-crystal display (LCD), and/or any other suitable display. In some embodiments, the display segment 2002*d* is coupled to the safety processor 2004.

In some embodiments, the segmented circuit 2000 comprises a shaft segment 2002*e* (Segment 5). The shaft segment 2002*e* comprises one or more controls for a shaft 2004 coupled to the surgical instrument 10 and/or one or more controls for an end effector 2006 coupled to the shaft 2004. The shaft segment 2002*e* comprises a shaft connector 2030 configured to couple the primary processor 2006 to a shaft PCBA 2031. The shaft PCBA 2031 comprises a first articulation switch 2036, a second articulation switch 2032, and a shaft PCBA EEPROM 2034. In some embodiments, the shaft PCBA EEPROM 2034 comprises one or more parameters, routines, and/or programs specific to the shaft 2004 and/or the shaft PCBA 2031. The shaft PCBA 2031 may be coupled to the shaft 2004 and/or integral with the surgical instrument 10. In some embodiments, the shaft segment 2002*e* comprises a second shaft EEPROM 2038. The second shaft EEPROM 2038 comprises a plurality of algorithms, routines, parameters, and/or other data corresponding to one or more shafts 2004 and/or end effectors 2006 which may be interfaced with the powered surgical instrument 10.

In some embodiments, the segmented circuit 2000 comprises a position encoder segment 2002*f* (Segment 6). The position encoder segment 2002*f* comprises one or more magnetic rotary position encoders 2040*a*-2040*b*. The one or more magnetic rotary position encoders 2040*a*-2040*b* are configured to identify the rotational position of a motor 2048, a shaft 2004, and/or an end effector 2006 of the surgical instrument 10. In some embodiments, the magnetic rotary position encoders 2040*a*-2040*b* may be coupled to the safety processor 2004 and/or the primary processor 2006.

In some embodiments, the segmented circuit 2000 comprises a motor segment 2002*g* (Segment 7). The motor segment 2002*g* comprises a motor 2048 configured to control one or more movements of the powered surgical instrument 10. The motor 2048 is coupled to the primary processor 2006 by an H-Bridge driver 2042 and one or more H-bridge field-effect transistors (FETs) 2044. The H-bridge FETs 2044 are coupled to the safety processor 2004. A motor current sensor 2046 is coupled in series with the motor 2048 to measure the current draw of the motor 2048. The motor current sensor 2046 is in signal communication with the primary processor 2006 and/or the safety processor 2004. In some embodiments, the motor 2048 is coupled to a motor electromagnetic interference (EMI) filter 2050.

The segmented circuit 2000 comprises a power segment 2002*h* (Segment 8). A battery 2008 is coupled to the safety processor 2004, the primary processor 2006, and one or more of the additional circuit segments 2002*c*-2002*g*. The battery 2008 is coupled to the segmented circuit 2000 by a battery connector 2010 and a current sensor 2012. The current sensor 2012 is configured to measure the total current draw of the segmented circuit 2000. In some embodiments, one or more voltage converters 2014*a*, 2014*b*, 2016 are configured to provide predetermined voltage values to one or more circuit segments 2002*a*-2002*g*. For example, in some embodiments, the segmented circuit 2000 may comprise 3.3V voltage converters 2014*a*-2014*b* and/or 5V voltage converters 2016. A boost converter 2018 is configured to provide a boost voltage up to a predetermined amount, such as, for example, up to 13V. The boost converter 2018 is configured to provide additional voltage and/or current during power intensive operations and prevent brownout or low-power conditions.

In some embodiments, the safety segment 2002*a* comprises a motor power interrupt 2020. The motor power interrupt 2020 is coupled between the power segment 2002*h* and the motor segment 2002*g*. The safety segment 2002*a* is configured to interrupt power to the motor segment 2002*g* when an error or fault condition is detected by the safety processor 2004 and/or the primary processor 2006 as discussed in more detail herein. Although the circuit segments 2002*a*-2002*g* are illustrated with all components of the circuit segments 2002*a*-2002*h* located in physical proximity, one skilled in the art will recognize that a circuit segment 2002*a*-2002*h* may comprise components physically and/or electrically separate from other components of the same circuit segment 2002*a*-2002*g*. In some embodiments, one or more components may be shared between two or more circuit segments 2002*a*-2002*g*.

In some embodiments, a plurality of switches 2056-2070 are coupled to the safety processor 2004 and/or the primary processor 2006. The plurality of switches 2056-2070 may be configured to control one or more operations of the surgical instrument 10, control one or more operations of the segmented circuit 2000, and/or indicate a status of the surgical instrument 10. For example, a bail-out door switch 2056 is configured to indicate the status of a bail-out door. A plurality of articulation switches, such as, for example, a left side articulation left switch 2058*a*, a left side articulation right switch 2060*a*, a left side articulation center switch 2062*a*, a right side articulation left switch 2058*b*, a right side articulation right switch 2060*b*, and a right side articulation center switch 2062*b* are configured to control articulation of a shaft 2004 and/or an end effector 2006. A left side reverse switch 2064*a* and a right side reverse switch 2064*b* are coupled to the primary processor 2006. In some embodiments, the left side switches comprising the left side articulation left switch 2058*a*, the left side articulation right switch 2060*a*, the left side articulation center switch 2062*a*, and the left side reverse switch 2064*a* are coupled to the primary processor 2006 by a left flex connector 2072*a*. The right side switches comprising the right side articulation left switch 2058*b*, the right side articulation right switch 2060*b*, the right side articulation center switch 2062*b*, and the right side reverse switch 2064*b* are coupled to the primary processor 2006 by a right flex connector 2072*b*. In some embodiments, a firing switch 2066, a clamp release switch 2068, and a shaft engaged switch 2070 are coupled to the primary processor 2006.

The plurality of switches 2056-2070 may comprise, for example, a plurality of handle controls mounted to a handle of the surgical instrument 10, a plurality of indicator switches, and/or any combination thereof. In various embodiments, the plurality of switches 2056-2070 allow a surgeon to manipulate the surgical instrument, provide feedback to the segmented circuit 2000 regarding the position and/or operation of the surgical instrument, and/or indicate unsafe operation of the surgical instrument 10. In some embodiments, additional or fewer switches may be coupled to the segmented circuit 2000, one or more of the switches 2056-2070 may be combined into a single switch, and/or expanded to multiple switches. For example, in one embodiment, one or more of the left side and/or right side articulation switches 2058*a*-2064*b* may be combined into a single multi-position switch.

In one embodiment, the safety processor 2004 is configured to implement a watchdog function, among other safety operations. The safety processor 2004 and the primary processor 2006 of the segmented circuit 2000 are in signal communication. A microprocessor alive heartbeat signal is provided at output 2096. The acceleration segment 2002*c* comprises an accelerometer 2022 configured to monitor movement of the surgical instrument 10. In various embodiments, the accelerometer 2022 may be a single, double, or triple axis accelerometer. The accelerometer 2022 may be employed to measures proper acceleration that is not necessarily the coordinate acceleration (rate of change of velocity). Instead, the accelerometer sees the acceleration associated with the phenomenon of weight experienced by a test mass at rest in the frame of reference of the accelerometer 2022. For example, the accelerometer 2022 at rest on the surface of the earth will measure an acceleration g=9.8 $m/s^2$ (gravity) straight upwards, due to its weight. Another type of acceleration that accelerometer 2022 can measure is g-force acceleration. In various other embodiments, the accelerometer 2022 may comprise a single, double, or triple axis accelerometer. Further, the acceleration segment 2002*c* may comprise one or more inertial sensors to detect and measure acceleration, tilt, shock, vibration, rotation, and multiple degrees-of-freedom (DoF). A suitable inertial sensor may comprise an accelerometer (single, double, or triple axis), a magnetometer to measure a magnetic field in space such as the earth's magnetic field, and/or a gyroscope to measure angular velocity.

In one embodiment, the safety processor 2004 is configured to implement a watchdog function with respect to one or more circuit segments 2002*c*-2002*h*, such as, for example, the motor segment 2002*g*. In this regards, the safety processor 2004 employs the watchdog function to detect and recover from malfunctions of the primary processor 2006. During normal operation, the safety processor 2004 monitors for hardware faults or program errors of the primary processor 2004 and to initiate corrective action or actions. The corrective actions may include placing the primary processor 2006 in a safe state and restoring normal system operation. In one embodiment, the safety processor 2004 is coupled to at least a first sensor. The first sensor measures a first property of the surgical instrument 10. In some embodiments, the safety processor 2004 is configured to compare the measured property of the surgical instrument 10 to a predetermined value. For example, in one embodiment, a motor sensor 2040*a* is coupled to the safety processor 2004. The motor sensor 2040*a* provides motor speed and position information to the safety processor 2004. The safety processor 2004 monitors the motor sensor 2040*a* and compares the value to a maximum speed and/or position value and prevents operation of the motor 2048 above the predetermined values. In some embodiments, the predetermined values are calculated based on real-time speed and/or position of the motor 2048, calculated from values supplied by a second motor sensor 2040*b* in communication with the primary processor 2006, and/or provided to the safety processor 2004 from, for example, a memory module coupled to the safety processor 2004.

In some embodiments, a second sensor is coupled to the primary processor 2006. The second sensor is configured to measure the first physical property. The safety processor 2004 and the primary processor 2006 are configured to provide a signal indicative of the value of the first sensor and the second sensor respectively. When either the safety processor 2004 or the primary processor 2006 indicates a value outside of an acceptable range, the segmented circuit 2000 prevents operation of at least one of the circuit segments 2002*c*-2002*h*, such as, for example, the motor segment 2002*g*. For example, in the embodiment illustrated in FIGS. 21A-21B, the safety processor 2004 is coupled to a first motor position sensor 2040*a* and the primary processor 2006 is coupled to a second motor position sensor 2040*b*. The motor position sensors 2040*a*, 2040*b* may comprise any suitable motor position sensor, such as, for example, a magnetic angle rotary input comprising a sine and cosine output. The motor position sensors 2040*a*, 2040*b* provide respective signals to the safety processor 2004 and the primary processor 2006 indicative of the position of the motor 2048.

The safety processor 2004 and the primary processor 2006 generate an activation signal when the values of the first motor sensor 2040*a* and the second motor sensor 2040*b* are within a predetermined range. When either the primary processor 2006 or the safety processor 2004 to detect a value outside of the predetermined range, the activation signal is terminated and operation of at least one circuit segment 2002*c*-2002*h*, such as, for example, the motor segment 2002*g*, is interrupted and/or prevented. For example, in some embodiments, the activation signal from the primary processor 2006 and the activation signal from the safety processor 2004 are coupled to an AND gate. The AND gate is coupled to a motor power switch 2020. The AND gate maintains the motor power switch 2020 in a closed, or on, position when the activation signal from both the safety processor 2004 and the primary processor 2006 are high, indicating a value of the motor sensors 2040*a*, 2040*b* within the predetermined range. When either of the motor sensors 2040*a*, 2040*b* detect a value outside of the predetermined range, the activation signal from that motor sensor 2040*a*, 2040*b* is set low, and the output of the AND gate is set low, opening the motor power switch 2020. In some embodiments, the value of the first sensor 2040*a* and the second sensor 2040*b* is compared, for example, by the safety processor 2004 and/or the primary processor 2006. When the values of the first sensor and the second sensor are different, the safety processor 2004 and/or the primary processor 2006 may prevent operation of the motor segment 2002*g*.

In some embodiments, the safety processor 2004 receives a signal indicative of the value of the second sensor 2040*b* and compares the second sensor value to the first sensor value. For example, in one embodiment, the safety processor 2004 is coupled directly to a first motor sensor 2040*a*. A second motor sensor 2040*b* is coupled to a primary processor 2006, which provides the second motor sensor 2040*b* value to the safety processor 2004, and/or coupled directly to the safety processor 2004. The safety processor 2004 compares the value of the first motor sensor 2040 to the value of the second motor sensor 2040*b*. When the safety processor 2004 detects a mismatch between the first motor sensor 2040*a* and the second motor sensor 2040*b*, the safety processor 2004 may interrupt operation of the motor segment 2002*g*, for example, by cutting power to the motor segment 2002*g*.

In some embodiments, the safety processor 2004 and/or the primary processor 2006 is coupled to a first sensor 2040*a* configured to measure a first property of a surgical instrument and a second sensor 2040*b* configured to measure a second property of the surgical instrument. The first property and the second property comprise a predetermined relationship when the surgical instrument is operating normally. The safety processor 2004 monitors the first property and the second property. When a value of the first property and/or the second property inconsistent with the predetermined relationship is detected, a fault occurs. When a fault occurs, the safety processor 2004 takes at least one action, such as, for example, preventing operation of at least one of the circuit segments, executing a predetermined operation, and/or resetting the primary processor 2006. For example, the safety processor 2004 may open the motor power switch 2020 to cut power to the motor circuit segment 2002*g* when a fault is detected.

In one embodiment, the safety processor 2004 is configured to execute an independent control algorithm. In operation, the safety processor 2004 monitors the segmented circuit 2000 and is configured to control and/or override signals from other circuit components, such as, for example, the primary processor 2006, independently. The safety processor 2004 may execute a preprogrammed algorithm and/or may be updated or programmed on the fly during operation based on one or more actions and/or positions of the surgical instrument 10. For example, in one embodiment, the safety processor 2004 is reprogrammed with new parameters and/or safety algorithms each time a new shaft and/or end effector is coupled to the surgical instrument 10. In some embodiments, one or more safety values stored by the safety processor 2004 are duplicated by the primary processor 2006. Two-way error detection is performed to ensure values and/or parameters stored by either of the processors 2004, 2006 are correct.

In some embodiments, the safety processor 2004 and the primary processor 2006 implement a redundant safety check. The safety processor 2004 and the primary processor 2006 provide periodic signals indicating normal operation. For example, during operation, the safety processor 2004 may indicate to the primary processor 2006 that the safety processor 2004 is executing code and operating normally. The primary processor 2006 may, likewise, indicate to the safety processor 2004 that the primary processor 2006 is executing code and operating normally. In some embodiments, communication between the safety processor 2004 and the primary processor 2006 occurs at a predetermined interval. The predetermined interval may be constant or may be variable based on the circuit state and/or operation of the surgical instrument 10.

Figure 22:
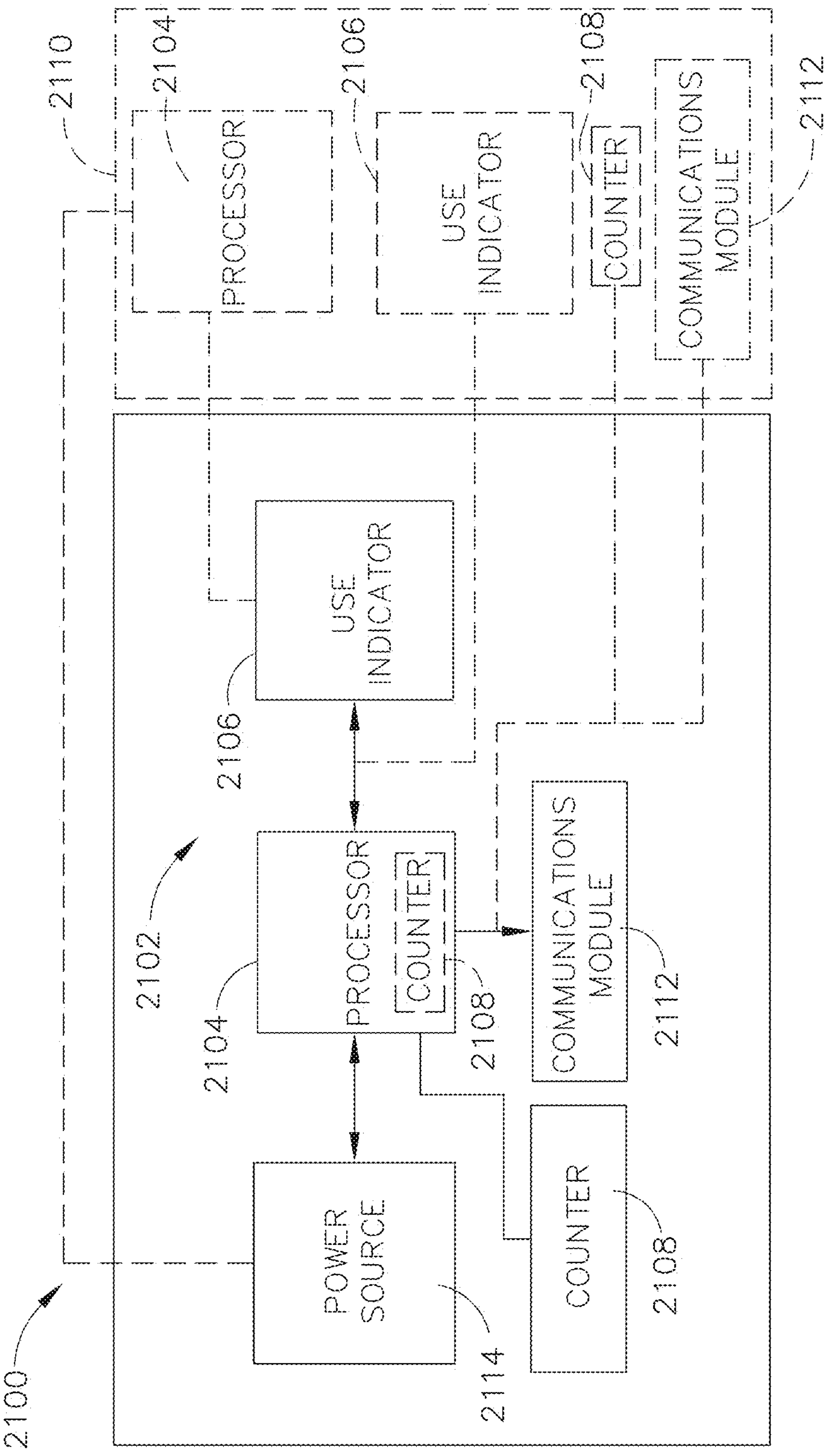
FIG. 22 illustrates one instance of a power assembly comprising a usage cycle circuit configured to generate a usage cycle count of the battery back.

FIG. 22 illustrates one example of a power assembly 2100 comprising a usage cycle circuit 2102 configured to monitor a usage cycle count of the power assembly 2100. The power assembly 2100 may be coupled to a surgical instrument 2110. The usage cycle circuit 2102 comprises a processor 2104 and a use indicator 2106. The use indicator 2106 is configured to provide a signal to the processor 2104 to indicate a use of the battery back 2100 and/or a surgical instrument 2110 coupled to the power assembly 2100. A "use" may comprise any suitable action, condition, and/or parameter such as, for example, changing a modular component of a surgical instrument 2110, deploying or firing a disposable component coupled to the surgical instrument 2110, delivering electrosurgical energy from the surgical instrument 2110, reconditioning the surgical instrument 2110 and/or the power assembly 2100, exchanging the power assembly 2100, recharging the power assembly 2100, and/or exceeding a safety limitation of the surgical instrument 2110 and/or the battery back 2100.

In some instances, a usage cycle, or use, is defined by one or more power assembly 2100 parameters. For example, in one instance, a usage cycle comprises using more than 5% of the total energy available from the power assembly 2100 when the power assembly 2100 is at a full charge level. In another instance, a usage cycle comprises a continuous energy drain from the power assembly 2100 exceeding a predetermined time limit. For example, a usage cycle may correspond to five minutes of continuous and/or total energy draw from the power assembly 2100. In some instances, the power assembly 2100 comprises a usage cycle circuit 2102 having a continuous power draw to maintain one or more components of the usage cycle circuit 2102, such as, for example, the use indicator 2106 and/or a counter 2108, in an active state.

The processor 2104 maintains a usage cycle count. The usage cycle count indicates the number of uses detected by the use indicator 2106 for the power assembly 2100 and/or the surgical instrument 2110. The processor 2104 may increment and/or decrement the usage cycle count based on input from the use indicator 2106. The usage cycle count is used to control one or more operations of the power assembly 2100 and/or the surgical instrument 2110. For example, in some instances, a power assembly 2100 is disabled when the usage cycle count exceeds a predetermined usage limit. Although the instances discussed herein are discussed with respect to incrementing the usage cycle count above a predetermined usage limit, those skilled in the art will recognize that the usage cycle count may start at a predetermined amount and may be decremented by the processor 2104. In this instance, the processor 2104 initiates and/or prevents one or more operations of the power assembly 2100 when the usage cycle count falls below a predetermined usage limit.

The usage cycle count is maintained by a counter 2108. The counter 2108 comprises any suitable circuit, such as, for example, a memory module, an analog counter, and/or any circuit configured to maintain a usage cycle count. In some instances, the counter 2108 is formed integrally with the processor 2104. In other instances, the counter 2108 comprises a separate component, such as, for example, a solid state memory module. In some instances, the usage cycle count is provided to a remote system, such as, for example, a central database. The usage cycle count is transmitted by a communications module 2112 to the remote system. The communications module 2112 is configured to use any suitable communications medium, such as, for example, wired and/or wireless communication. In some instances, the communications module 2112 is configured to receive one or more instructions from the remote system, such as, for example, a control signal when the usage cycle count exceeds the predetermined usage limit.

In some instances, the use indicator 2106 is configured to monitor the number of modular components used with a surgical instrument 2110 coupled to the power assembly 2100. A modular component may comprise, for example, a modular shaft, a modular end effector, and/or any other modular component. In some instances, the use indicator 2106 monitors the use of one or more disposable components, such as, for example, insertion and/or deployment of a staple cartridge within an end effector coupled to the surgical instrument 2110. The use indicator 2106 comprises one or more sensors for detecting the exchange of one or more modular and/or disposable components of the surgical instrument 2110.

In some instances, the use indicator 2106 is configured to monitor single patient surgical procedures performed while the power assembly 2100 is installed. For example, the use indicator 2106 may be configured to monitor firings of the surgical instrument 2110 while the power assembly 2100 is coupled to the surgical instrument 2110. A firing may correspond to deployment of a staple cartridge, application of electrosurgical energy, and/or any other suitable surgical event. The use indicator 2106 may comprise one or more circuits for measuring the number of firings while the power assembly 2100 is installed. The use indicator 2106 provides a signal to the processor 2104 when a single patient procedure is performed and the processor 2104 increments the usage cycle count.

In some instances, the use indicator 2106 comprises a circuit configured to monitor one or more parameters of the power source 2114, such as, for example, a current draw from the power source 2114. The one or more parameters of the power source 2114 correspond to one or more operations performable by the surgical instrument 2110, such as, for example, a cutting and sealing operation. The use indicator 2106 provides the one or more parameters to the processor 2104, which increments the usage cycle count when the one or more parameters indicate that a procedure has been performed.

In some instances, the use indicator 2106 comprises a timing circuit configured to increment a usage cycle count after a predetermined time period. The predetermined time period corresponds to a single patient procedure time, which is the time required for an operator to perform a procedure, such as, for example, a cutting and sealing procedure. When the power assembly 2100 is coupled to the surgical instrument 2110, the processor 2104 polls the use indicator 2106 to determine when the single patient procedure time has expired. When the predetermined time period has elapsed, the processor 2104 increments the usage cycle count. After incrementing the usage cycle count, the processor 2104 resets the timing circuit of the use indicator 2106.

In some instances, the use indicator 2106 comprises a time constant that approximates the single patient procedure time. In one embodiment, the usage cycle circuit 2102 comprises a resistor-capacitor (RC) timing circuit 2506. The RC timing circuit comprises a time constant defined by a resistor-capacitor pair. The time constant is defined by the values of the resistor and the capacitor. In one embodiment, the usage cycle circuit 2552 comprises a rechargeable battery and a clock. When the power assembly 2100 is installed in a surgical instrument, the rechargeable battery is charged by the power source. The rechargeable battery comprises enough power to run the clock for at least the single patient procedure time. The clock may comprise a real time clock, a processor configured to implement a time function, or any other suitable timing circuit.

Referring back to FIG. 2, in some instances, the use indicator 2106 comprises a sensor configured to monitor one or more environmental conditions experienced by the power assembly 2100. For example, the use indicator 2106 may comprise an accelerometer. The accelerometer is configured to monitor acceleration of the power assembly 2100. The power assembly 2100 comprises a maximum acceleration tolerance. Acceleration above a predetermined threshold indicates, for example, that the power assembly 2100 has been dropped. When the use indicator 2106 detects acceleration above the maximum acceleration tolerance, the processor 2104 increments a usage cycle count. In some instances, the use indicator 2106 comprises a moisture sensor. The moisture sensor is configured to indicate when the power assembly 2100 has been exposed to moisture. The moisture sensor may comprise, for example, an immersion sensor configured to indicate when the power assembly 2100 has been fully immersed in a cleaning fluid, a moisture sensor configured to indicate when moisture is in contact with the power assembly 2100 during use, and/or any other suitable moisture sensor.

In some instances, the use indicator 2106 comprises a chemical exposure sensor. The chemical exposure sensor is configured to indicate when the power assembly 2100 has come into contact with harmful and/or dangerous chemicals. For example, during a sterilization procedure, an inappropriate chemical may be used that leads to degradation of the power assembly 2100. The processor 2104 increments the usage cycle count when the use indicator 2106 detects an inappropriate chemical.

In some instances, the usage cycle circuit 2102 is configured to monitor the number of reconditioning cycles experienced by the power assembly 2100. A reconditioning cycle may comprise, for example, a cleaning cycle, a sterilization cycle, a charging cycle, routine and/or preventative maintenance, and/or any other suitable reconditioning cycle. The use indicator 2106 is configured to detect a reconditioning cycle. For example, the use indicator 2106 may comprise a moisture sensor to detect a cleaning and/or sterilization cycle. In some instances, the usage cycle circuit 2102 monitors the number of reconditioning cycles experienced by the power assembly 2100 and disables the power assembly 2100 after the number of reconditioning cycles exceeds a predetermined threshold.

The usage cycle circuit 2102 may be configured to monitor the number of power assembly 2100 exchanges. The usage cycle circuit 2102 increments the usage cycle count each time the power assembly 2100 is exchanged. When the maximum number of exchanges is exceeded the usage cycle circuit 2102 locks out the power assembly 2100 and/or the surgical instrument 2110. In some instances, when the power assembly 2100 is coupled the surgical instrument 2110, the usage cycle circuit 2102 identifies the serial number of the power assembly 2100 and locks the power assembly 2100 such that the power assembly 2100 is usable only with the surgical instrument 2110. In some instances, the usage cycle circuit 2102 increments the usage cycle each time the power assembly 2100 is removed from and/or coupled to the surgical instrument 2110.

In some instances, the usage cycle count corresponds to sterilization of the power assembly 2100. The use indicator 2106 comprises a sensor configured to detect one or more parameters of a sterilization cycle, such as, for example, a temperature parameter, a chemical parameter, a moisture parameter, and/or any other suitable parameter. The processor 2104 increments the usage cycle count when a sterilization parameter is detected. The usage cycle circuit 2102 disables the power assembly 2100 after a predetermined number of sterilizations. In some instances, the usage cycle circuit 2102 is reset during a sterilization cycle, a voltage sensor to detect a recharge cycle, and/or any suitable sensor. The processor 2104 increments the usage cycle count when a reconditioning cycle is detected. The usage cycle circuit 2102 is disabled when a sterilization cycle is detected. The usage cycle circuit 2102 is reactivated and/or reset when the power assembly 2100 is coupled to the surgical instrument 2110. In some instances, the use indicator comprises a zero power indicator. The zero power indicator changes state during a sterilization cycle and is checked by the processor 2104 when the power assembly 2100 is coupled to a surgical instrument 2110. When the zero power indicator indicates that a sterilization cycle has occurred, the processor 2104 increments the usage cycle count.

A counter 2108 maintains the usage cycle count. In some instances, the counter 2108 comprises a non-volatile memory module. The processor 2104 increments the usage cycle count stored in the non-volatile memory module each time a usage cycle is detected. The memory module may be accessed by the processor 2104 and/or a control circuit, such as, for example, the control circuit 200. When the usage cycle count exceeds a predetermined threshold, the processor 2104 disables the power assembly 2100. In some instances, the usage cycle count is maintained by a plurality of circuit components. For example, in one instance, the counter 2108 comprises a resistor (or fuse) pack. After each use of the power assembly 2100, a resistor (or fuse) is burned to an open position, changing the resistance of the resistor pack. The power assembly 2100 and/or the surgical instrument 2110 reads the remaining resistance. When the last resistor of the resistor pack is burned out, the resistor pack has a predetermined resistance, such as, for example, an infinite resistance corresponding to an open circuit, which indicates that the power assembly 2100 has reached its usage limit. In some instances, the resistance of the resistor pack is used to derive the number of uses remaining.

In some instances, the usage cycle circuit 2102 prevents further use of the power assembly 2100 and/or the surgical instrument 2110 when the usage cycle count exceeds a predetermined usage limit. In one instance, the usage cycle count associated with the power assembly 2100 is provided to an operator, for example, utilizing a screen formed integrally with the surgical instrument 2110. The surgical instrument 2110 provides an indication to the operator that the usage cycle count has exceeded a predetermined limit for the power assembly 2100, and prevents further operation of the surgical instrument 2110.

In some instances, the usage cycle circuit 2102 is configured to physically prevent operation when the predetermined usage limit is reached. For example, the power assembly 2100 may comprise a shield configured to deploy over contacts of the power assembly 2100 when the usage cycle count exceeds the predetermined usage limit. The shield prevents recharge and use of the power assembly 2100 by covering the electrical connections of the power assembly 2100.

In some instances, the usage cycle circuit 2102 is located at least partially within the surgical instrument 2110 and is configured to maintain a usage cycle count for the surgical instrument 2110. FIG. 22 illustrates one or more components of the usage cycle circuit 2102 within the surgical instrument 2110 in phantom, illustrating the alternative positioning of the usage cycle circuit 2102. When a predetermined usage limit of the surgical instrument 2110 is exceeded, the usage cycle circuit 2102 disables and/or prevents operation of the surgical instrument 2110. The usage cycle count is incremented by the usage cycle circuit 2102 when the use indicator 2106 detects a specific event and/or requirement, such as, for example, firing of the surgical instrument 2110, a predetermined time period corresponding to a single patient procedure time, based on one or more motor parameters of the surgical instrument 2110, in response to a system diagnostic indicating that one or more predetermined thresholds are met, and/or any other suitable requirement. As discussed above, in some instances, the use indicator 2106 comprises a timing circuit corresponding to a single patient procedure time. In other instances, the use indicator 2106 comprises one or more sensors configured to detect a specific event and/or condition of the surgical instrument 2110.

In some instances, the usage cycle circuit 2102 is configured to prevent operation of the surgical instrument 2110 after the predetermined usage limit is reached. In some instances, the surgical instrument 2110 comprises a visible indicator to indicate when the predetermined usage limit has been reached and/or exceeded. For example, a flag, such as a red flag, may pop-up from the surgical instrument 2110, such as from the handle, to provide a visual indication to the operator that the surgical instrument 2110 has exceeded the predetermined usage limit. As another example, the usage cycle circuit 2102 may be coupled to a display formed integrally with the surgical instrument 2110. The usage cycle circuit 2102 displays a message indicating that the predetermined usage limit has been exceeded. The surgical instrument 2110 may provide an audible indication to the operator that the predetermined usage limit has been exceeded. For example, in one instance, the surgical instrument 2110 emits an audible tone when the predetermined usage limit is exceeded and the power assembly 2100 is removed from the surgical instrument 2110. The audible tone indicates the last use of the surgical instrument 2110 and indicates that the surgical instrument 2110 should be disposed or reconditioned.

In some instances, the usage cycle circuit 2102 is configured to transmit the usage cycle count of the surgical instrument 2110 to a remote location, such as, for example, a central database. The usage cycle circuit 2102 comprises a communications module 2112 configured to transmit the usage cycle count to the remote location. The communications module 2112 may utilize any suitable communications system, such as, for example, wired or wireless communications system. The remote location may comprise a central database configured to maintain usage information. In some instances, when the power assembly 2100 is coupled to the surgical instrument 2110, the power assembly 2100 records a serial number of the surgical instrument 2110. The serial number is transmitted to the central database, for example, when the power assembly 2100 is coupled to a charger. In some instances, the central database maintains a count corresponding to each use of the surgical instrument 2110. For example, a bar code associated with the surgical instrument 2110 may be scanned each time the surgical instrument 2110 is used. When the use count exceeds a predetermined usage limit, the central database provides a signal to the surgical instrument 2110 indicating that the surgical instrument 2110 should be discarded.

The surgical instrument 2110 may be configured to lock and/or prevent operation of the surgical instrument 2110 when the usage cycle count exceeds a predetermined usage limit. In some instances, the surgical instrument 2110 comprises a disposable instrument and is discarded after the usage cycle count exceeds the predetermined usage limit. In other instances, the surgical instrument 2110 comprises a reusable surgical instrument which may be reconditioned after the usage cycle count exceeds the predetermined usage limit. The surgical instrument 2110 initiates a reversible lockout after the predetermined usage limit is met. A technician reconditions the surgical instrument 2110 and releases the lockout, for example, utilizing a specialized technician key configured to reset the usage cycle circuit 2102.

Figure 23:
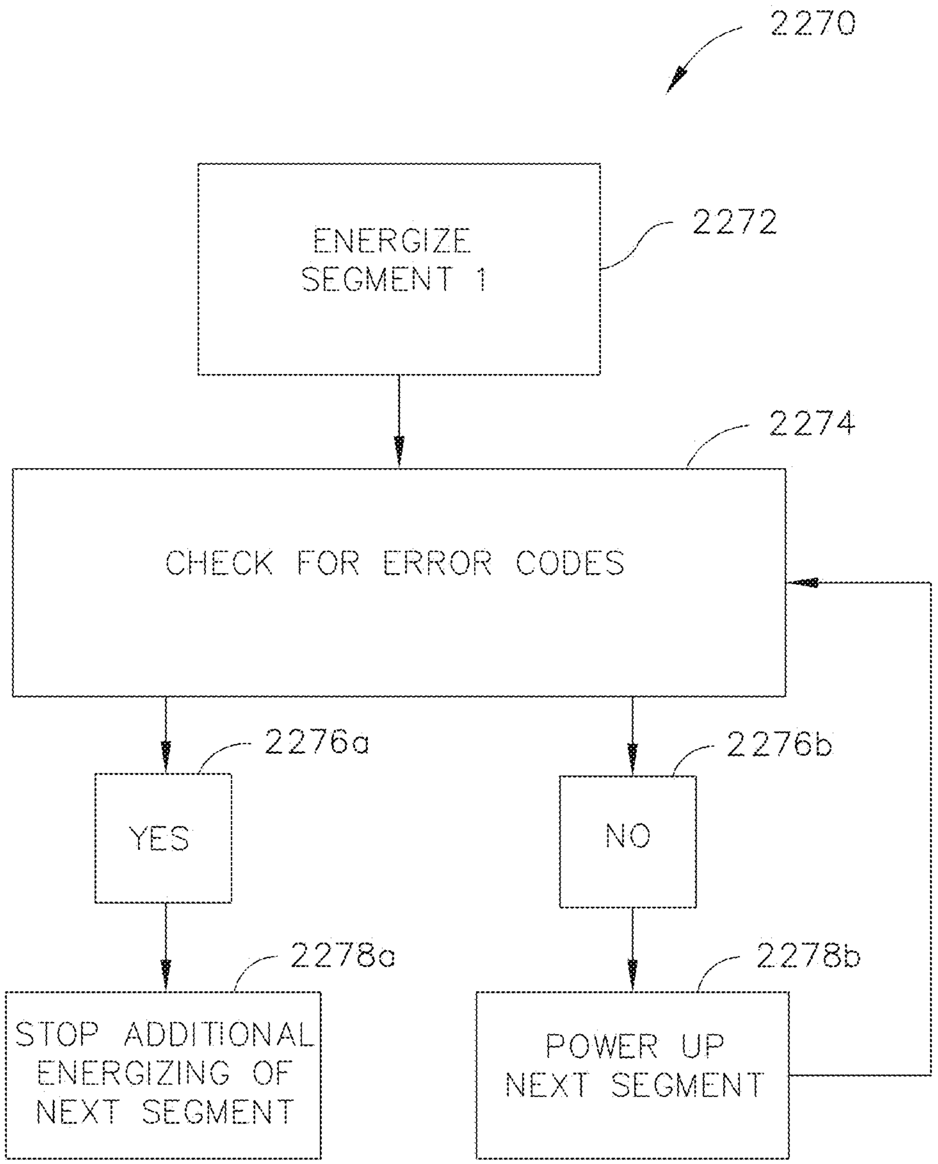
FIG. 23 illustrates one embodiment of a process for sequentially energizing a segmented circuit.

In some embodiments, the segmented circuit 2000 is configured for sequential start-up. An error check is performed by each circuit segment **2002*a*-2002*g* prior to energizing the next sequential circuit segment 2002*a*-2002*g*. FIG. 23 illustrates one embodiment of a process for sequentially energizing a segmented circuit 2270, such as, for example, the segmented circuit 2000. When a battery 2008 is coupled to the segmented circuit 2000, the safety processor 2004 is energized 2272. The safety processor 2004 performs a self-error check 2274. When an error is detected 2276*a*, the safety processor stops energizing the segmented circuit 2000 and generates an error code 2278*a*. When no errors are detected 2276*b*, the safety processor 2004 initiates 2278*b* power-up of the primary processor 2006. The primary processor 2006 performs a self-error check. When no errors are detected, the primary processor 2006 begins sequential power-up of each of the remaining circuit segments 2278*b*. Each circuit segment is energized and error checked by the primary processor 2006. When no errors are detected, the next circuit segment is energized 2278*b*. When an error is detected, the safety processor 2004 and/or the primary process stops energizing the current segment and generates an error 2278***a*. The sequential start-up continues until all of the circuit segments 2002*a*-2002*g* have been energized. In some embodiments, the segmented circuit 2000 transitions from sleep mode following a similar sequential power-up process 11250.

Figure 24:
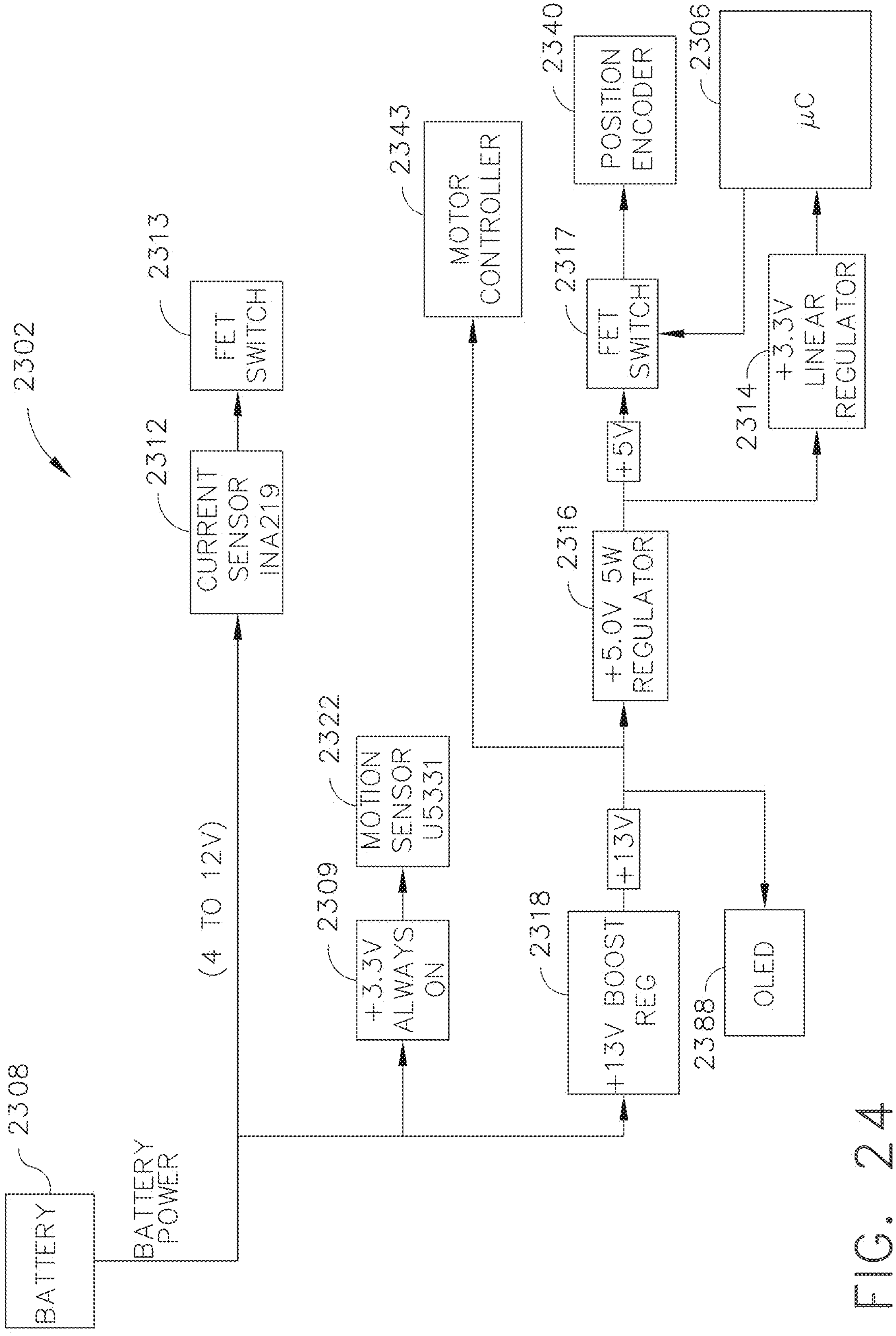
FIG. 24 illustrates one embodiment of a power segment comprising a plurality of daisy chained power converters.

FIG. 24 illustrates one embodiment of a power segment 2302 comprising a plurality of daisy chained power converters 2314, 2316, 2318. The power segment 2302 comprises a battery 2308. The battery 2308 is configured to provide a source voltage, such as, for example, 12V. A current sensor 2312 is coupled to the battery 2308 to monitor the current draw of a segmented circuit and/or one or more circuit segments. The current sensor 2312 is coupled to an FET switch 2313. The battery 2308 is coupled to one or more voltage converters 2309, 2314, 2316. An always on converter 2309 provides a constant voltage to one or more circuit components, such as, for example, a motion sensor 2322. The always on converter 2309 comprises, for example, a 3.3V converter. The always on converter 2309 may provide a constant voltage to additional circuit components, such as, for example, a safety processor (not shown). The battery 2308 is coupled to a boost converter 2318. The boost converter 2318 is configured to provide a boosted voltage above the voltage provided by the battery 2308. For example, in the illustrated embodiment, the battery 2308 provides a voltage of 12V. The boost converter 2318 is configured to boost the voltage to 13V. The boost converter 2318 is configured to maintain a minimum voltage during operation of a surgical instrument, for example, the surgical instrument 10 illustrated in FIGS. 69-71. Operation of a motor can result in the power provided to the primary processor 2306 dropping below a minimum threshold and creating a brownout or reset condition in the primary processor 2306. The boost converter 2318 ensures that sufficient power is available to the primary processor 2306 and/or other circuit components, such as the motor controller 2343, during operation of the surgical instrument 10. In some embodiments, the boost converter 2318 is coupled directly one or more circuit components, such as, for example, an OLED display 2388.

The boost converter 2318 is coupled to one or more step-down converters to provide voltages below the boosted voltage level. A first voltage converter 2316 is coupled to the boost converter 2318 and provides a first stepped-down voltage to one or more circuit components. In the illustrated embodiment, the first voltage converter 2316 provides a voltage of 5V. The first voltage converter 2316 is coupled to a rotary position encoder 2340. A FET switch 2317 is coupled between the first voltage converter 2316 and the rotary position encoder 2340. The FET switch 2317 is controlled by the processor 2306. The processor 2306 opens the FET switch 2317 to deactivate the position encoder 2340, for example, during power intensive operations. The first voltage converter 2316 is coupled to a second voltage converter 2314 configured to provide a second stepped-down voltage. The second stepped-down voltage comprises, for example, 3.3V. The second voltage converter 2314 is coupled to a processor 2306. In some embodiments, the boost converter 2318, the first voltage converter 2316, and the second voltage converter 2314 are coupled in a daisy chain configuration. The daisy chain configuration allows the use of smaller, more efficient converters for generating voltage levels below the boosted voltage level. The embodiments, however, are not limited to the particular voltage range(s) described in the context of this specification.

Figure 25:
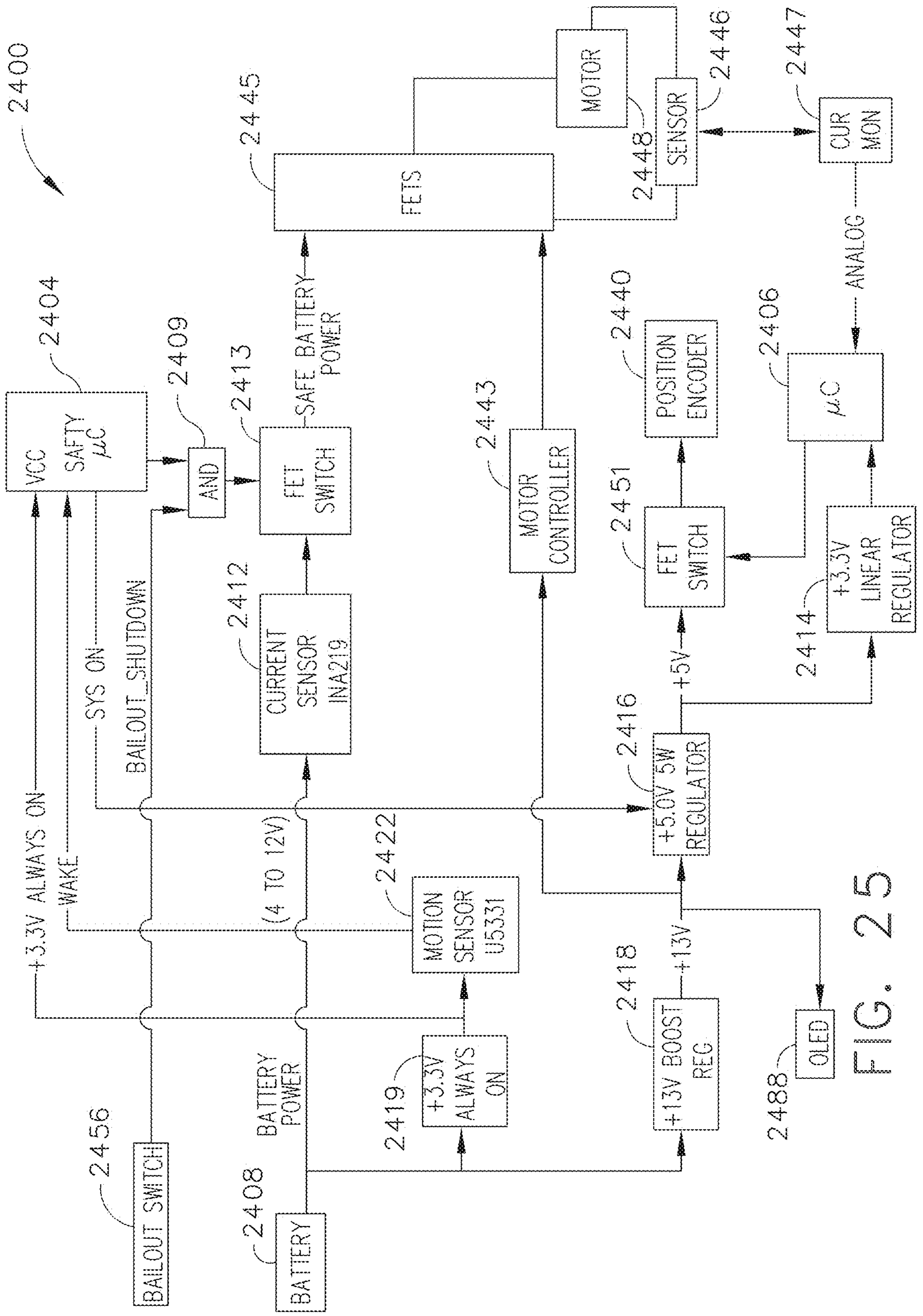
FIG. 25 illustrates one embodiment of a segmented circuit configured to maximize power available for critical and/or power intense functions.

FIG. 25 illustrates one embodiment of a segmented circuit 2400 configured to maximize power available for critical and/or power intense functions. The segmented circuit 2400 comprises a battery 2408. The battery 2408 is configured to provide a source voltage such as, for example, 12V. The source voltage is provided to a plurality of voltage converters 2409, 2418. An always-on voltage converter 2409 provides a constant voltage to one or more circuit components, for example, a motion sensor 2422 and a safety processor 2404. The always-on voltage converter 2409 is directly coupled to the battery 2408. The always-on converter 2409 provides a voltage of 3.3V, for example. The embodiments, however, are not limited to the particular voltage range(s) described in the context of this specification.

The segmented circuit 2400 comprises a boost converter 2418. The boost converter 2418 provides a boosted voltage above the source voltage provided by the battery 2408, such as, for example, 13V. The boost converter 2418 provides a boosted voltage directly to one or more circuit components, such as, for example, an OLED display 2488 and a motor controller 2443. By coupling the OLED display 2488 directly to the boost converter 2418, the segmented circuit 2400 eliminates the need for a power converter dedicated to the OLED display 2488. The boost converter 2418 provides a boosted voltage to the motor controller 2443 and the motor 2448 during one or more power intensive operations of the motor 2448, such as, for example, a cutting operation. The boost converter 2418 is coupled to a step-down converter 2416. The step-down converter 2416 is configured to provide a voltage below the boosted voltage to one or more circuit components, such as, for example, 5V. The step-down converter 2416 is coupled to, for example, a FET switch 2451 and a position encoder 2440. The FET switch 2451 is coupled to the primary processor 2406. The primary processor 2406 opens the FET switch 2451 when transitioning the segmented circuit 2400 to sleep mode and/or during power intensive functions requiring additional voltage delivered to the motor 2448. Opening the FET switch 2451 deactivates the position encoder 2440 and eliminates the power draw of the position encoder 2440. The embodiments, however, are not limited to the particular voltage range(s) described in the context of this specification.

The step-down converter 2416 is coupled to a linear converter 2414. The linear converter 2414 is configured to provide a voltage of, for example, 3.3V. The linear converter 2414 is coupled to the primary processor 2406. The linear converter 2414 provides an operating voltage to the primary processor 2406. The linear converter 2414 may be coupled to one or more additional circuit components. The embodiments, however, are not limited to the particular voltage range(s) described in the context of this specification.

The segmented circuit 2400 comprises a bailout switch 2456. The bailout switch 2456 is coupled to a bailout door on the surgical instrument 10. The bailout switch 2456 and the safety processor 2404 are coupled to an AND gate 2419. The AND gate 2419 provides an input to a FET switch 2413. When the bailout switch 2456 detects a bailout condition, the bailout switch 2456 provides a bailout shutdown signal to the AND gate 2419. When the safety processor 2404 detects an unsafe condition, such as, for example, due to a sensor mismatch, the safety processor 2404 provides a shutdown signal to the AND gate 2419. In some embodiments, both the bailout shutdown signal and the shutdown signal are high during normal operation and are low when a bailout condition or an unsafe condition is detected. When the output of the AND gate 2419 is low, the FET switch 2413 is opened and operation of the motor 2448 is prevented. In some embodiments, the safety processor 2404 utilizes the shutdown signal to transition the motor 2448 to an off state in sleep mode. A third input to the FET switch 2413 is provided by a current sensor 2412 coupled to the battery 2408. The current sensor 2412 monitors the current drawn by the circuit 2400 and opens the FET switch 2413 to shut-off power to the motor 2448 when an electrical current above a predetermined threshold is detected. The FET switch 2413 and the motor controller 2443 are coupled to a bank of FET switches 2445 configured to control operation of the motor 2448.

A motor current sensor 2446 is coupled in series with the motor 2448 to provide a motor current sensor reading to a current monitor 2447. The current monitor 2447 is coupled to the primary processor 2406. The current monitor 2447 provides a signal indicative of the current draw of the motor 2448. The primary processor 2406 may utilize the signal from the motor current 2447 to control operation of the motor, for example, to ensure the current draw of the motor 2448 is within an acceptable range, to compare the current draw of the motor 2448 to one or more other parameters of the circuit 2400 such as, for example, the position encoder 2440, and/or to determine one or more parameters of a treatment site. In some embodiments, the current monitor 2447 may be coupled to the safety processor 2404.

In some embodiments, actuation of one or more handle controls, such as, for example, a firing trigger, causes the primary processor 2406 to decrease power to one or more components while the handle control is actuated. For example, in one embodiment, a firing trigger controls a firing stroke of a cutting member. The cutting member is driven by the motor 2448. Actuation of the firing trigger results in forward operation of the motor 2448 and advancement of the cutting member. During firing, the primary processor 2406 closes the FET switch 2451 to remove power from the position encoder 2440. The deactivation of one or more circuit components allows higher power to be delivered to the motor 2448. When the firing trigger is released, full power is restored to the deactivated components, for example, by closing the FET switch 2451 and reactivating the position encoder 2440.

In some embodiments, the safety processor 2404 controls operation of the segmented circuit 2400. For example, the safety processor 2404 may initiate a sequential power-up of the segmented circuit 2400, transition of the segmented circuit 2400 to and from sleep mode, and/or may override one or more control signals from the primary processor 2406. For example, in the illustrated embodiment, the safety processor 2404 is coupled to the step-down converter 2416. The safety processor 2404 controls operation of the segmented circuit 2400 by activating or deactivating the step-down converter 2416 to provide power to the remainder of the segmented circuit 2400.

Figure 26:
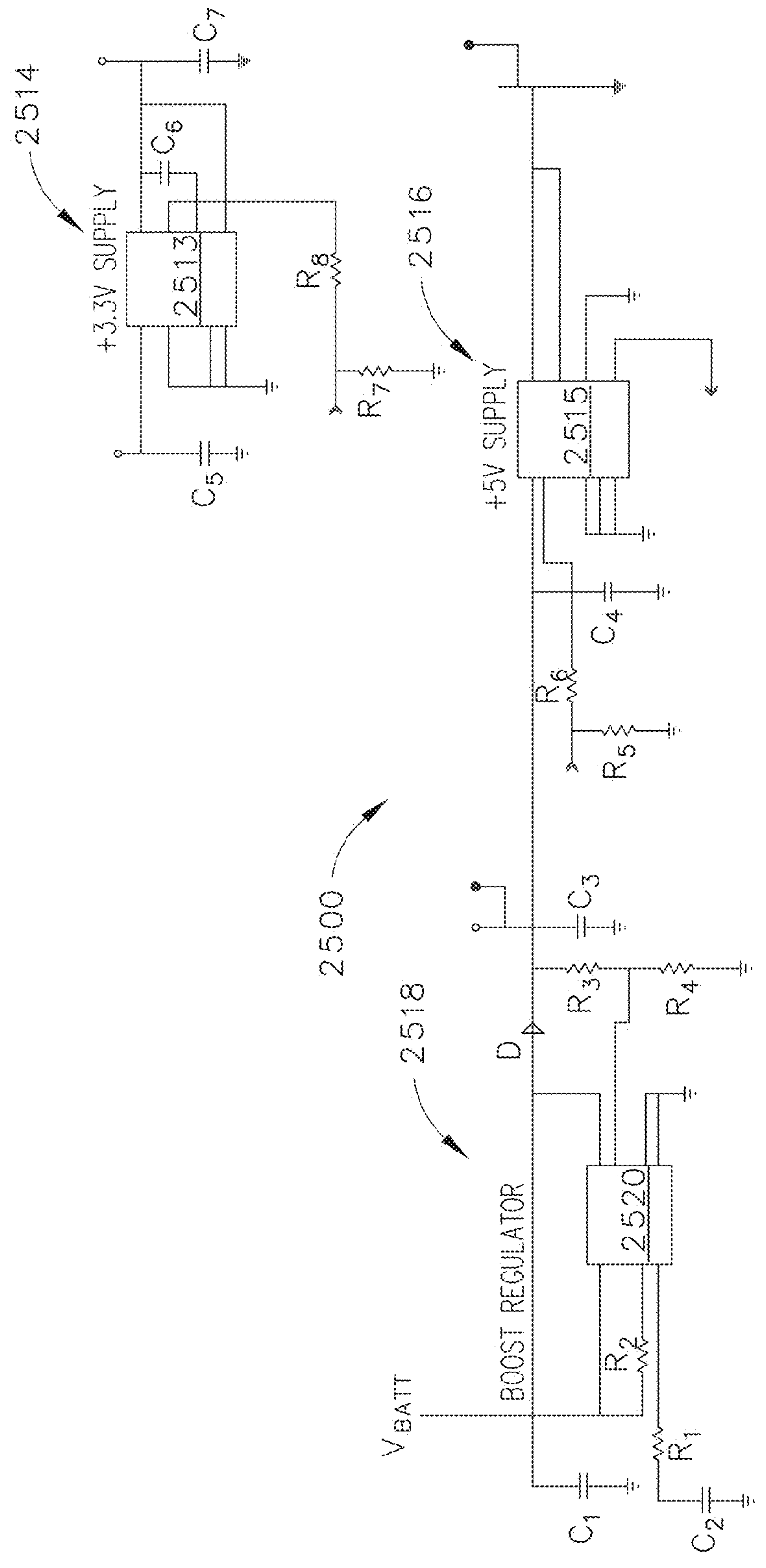
FIG. 26 illustrates one embodiment of a power system comprising a plurality of daisy chained power converters configured to be sequentially energized.

FIG. 26 illustrates one embodiment of a power system 2500 comprising a plurality of daisy chained power converters 2514, 2516, 2518 configured to be sequentially energized. The plurality of daisy chained power converters 2514, 2516, 2518 may be sequentially activated by, for example, a safety processor during initial power-up and/or transition from sleep mode. The safety processor may be powered by an independent power converter (not shown). For example, in one embodiment, when a battery voltage $V_{BATT}$ is coupled to the power system 2500 and/or an accelerometer detects movement in sleep mode, the safety processor initiates a sequential start-up of the daisy chained power converters 2514, 2516, 2518. The safety processor activates the 13V boost section 2518. The boost section 2518 is energized and performs a self-check. In some embodiments, the boost section 2518 comprises an integrated circuit 2520 configured to boost the source voltage and to perform a self check. A diode D prevents power-up of a 5V supply section 2516 until the boost section 2518 has completed a self-check and provided a signal to the diode D indicating that the boost section 2518 did not identify any errors. In some embodiments, this signal is provided by the safety processor. The embodiments, however, are not limited to the particular voltage range(s) described in the context of this specification.

The 5V supply section 2516 is sequentially powered-up after the boost section 2518. The 5V supply section 2516 performs a self-check during power-up to identify any errors in the 5V supply section 2516. The 5V supply section 2516 comprises an integrated circuit 2515 configured to provide a step-down voltage from the boost voltage and to perform an error check. When no errors are detected, the 5V supply section 2516 completes sequential power-up and provides an activation signal to the 3.3V supply section 2514. In some embodiments, the safety processor provides an activation signal to the 3.3V supply section 2514. The 3.3V supply section comprises an integrated circuit 2513 configured to provide a step-down voltage from the 5V supply section 2516 and perform a self-error check during power-up. When no errors are detected during the self-check, the 3.3V supply section 2514 provides power to the primary processor. The primary processor is configured to sequentially energize each of the remaining circuit segments. By sequentially energizing the power system 2500 and/or the remainder of a segmented circuit, the power system 2500 reduces error risks, allows for stabilization of voltage levels before loads are applied, and prevents large current draws from all hardware being turned on simultaneously in an uncontrolled manner. The embodiments, however, are not limited to the particular voltage range(s) described in the context of this specification.

In one embodiment, the power system 2500 comprises an over voltage identification and mitigation circuit. The over voltage identification and mitigation circuit is configured to detect a monopolar return current in the surgical instrument and interrupt power from the power segment when the monopolar return current is detected. The over voltage identification and mitigation circuit is configured to identify ground floatation of the power system. The over voltage identification and mitigation circuit comprises a metal oxide varistor. The over voltage identification and mitigation circuit comprises at least one transient voltage suppression diode.

Figure 27:
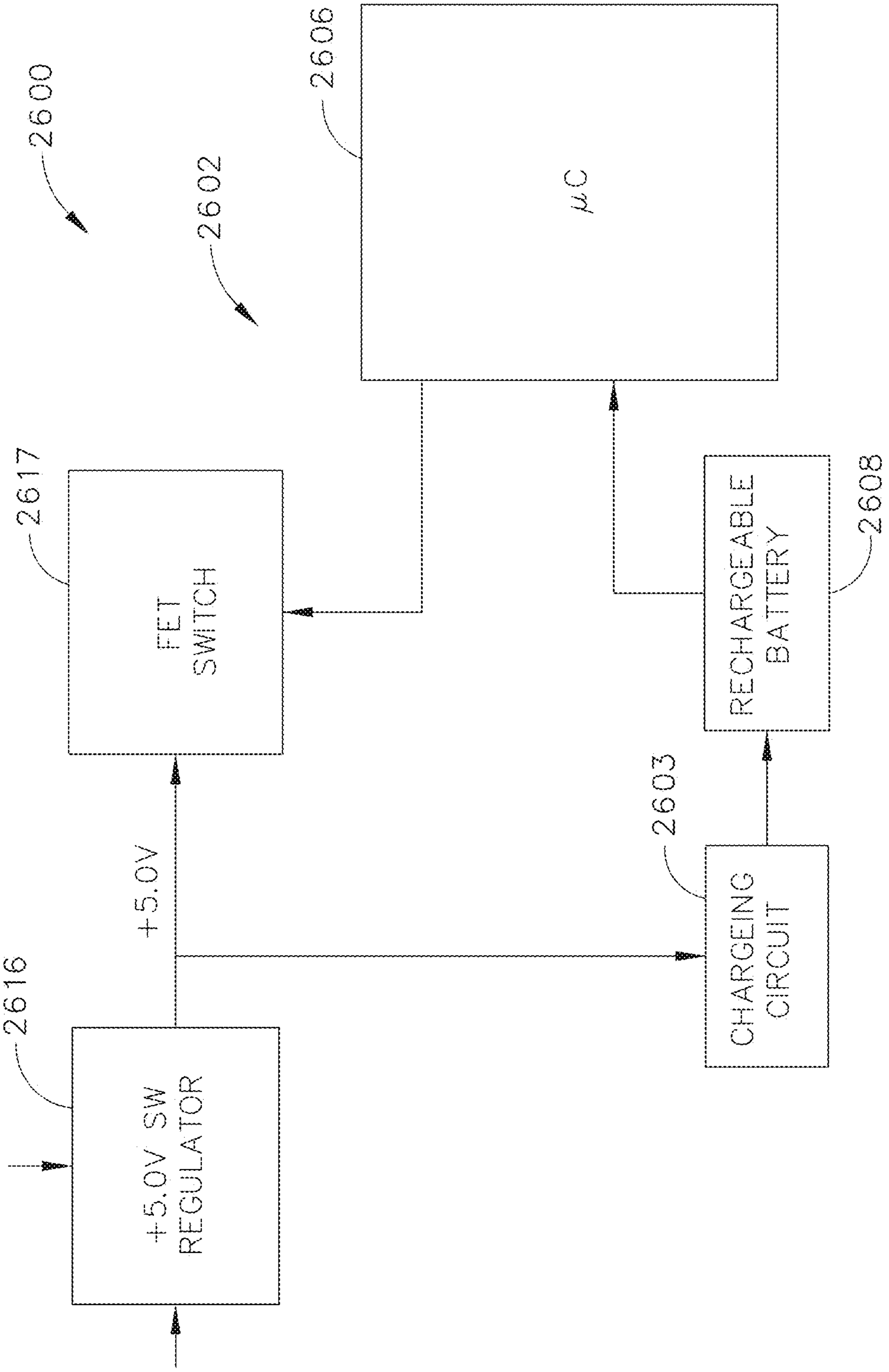
FIG. 27 illustrates one embodiment of a segmented circuit comprising an isolated control section.

FIG. 27 illustrates one embodiment of a segmented circuit 2600 comprising an isolated control section 2602. The isolated control section 2602 isolates control hardware of the segmented circuit 2600 from a power section (not shown) of the segmented circuit 2600. The control section 2602 comprises, for example, a primary processor 2606, a safety processor (not shown), and/or additional control hardware, for example, a FET Switch 2617. The power section comprises, for example, a motor, a motor driver, and/or a plurality of motor MOSFETS. The isolated control section 2602 comprises a charging circuit 2603 and a rechargeable battery 2608 coupled to a 5V power converter 2616. The charging circuit 2603 and the rechargeable battery 2608 isolate the primary processor 2606 from the power section. In some embodiments, the rechargeable battery 2608 is coupled to a safety processor and any additional support hardware. Isolating the control section 2602 from the power section allows the control section 2602, for example, the primary processor 2606, to remain active even when main power is removed, provides a filter, through the rechargeable battery 2608, to keep noise out of the control section 2602, isolates the control section 2602 from heavy swings in the battery voltage to ensure proper operation even during heavy motor loads, and/or allows for real-time operating system (RTOS) to be used by the segmented circuit 2600. In some embodiments, the rechargeable battery 2608 provides a stepped-down voltage to the primary processor, such as, for example, 3.3V. The embodiments, however, are not limited to the particular voltage range(s) described in the context of this specification.

Figure 28:
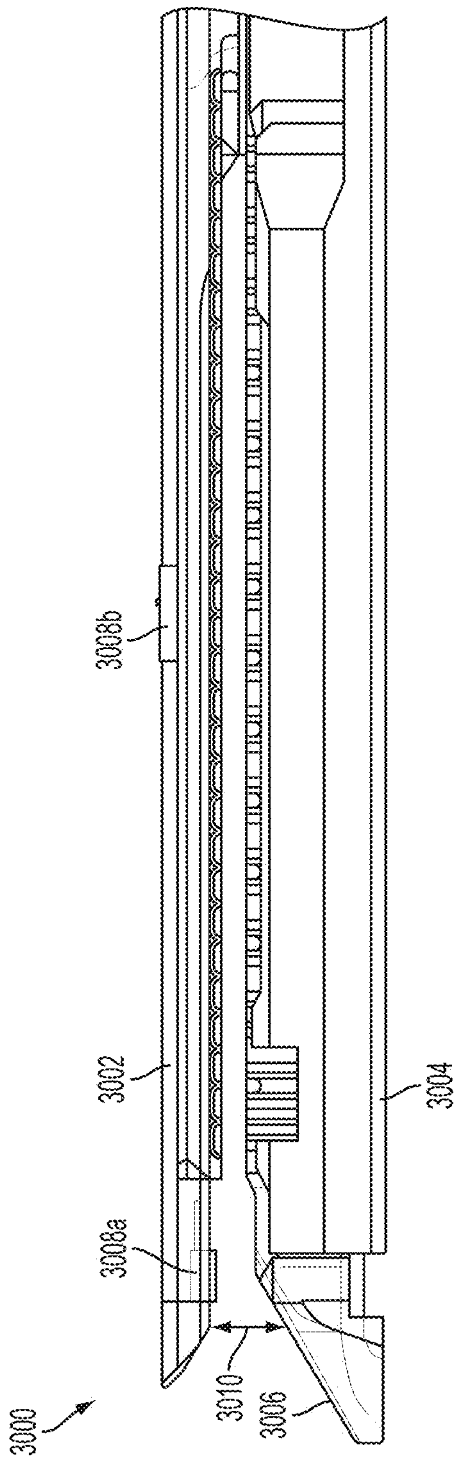
FIG. 28 illustrates one embodiment of an end effector comprising a first sensor and a second sensor.

Use of Multiple Sensors with One Sensor Affecting a Second Sensor's Output or Interpretation FIG. 28 illustrates one embodiment of an end effector 3000 comprising a first sensor 3008*a* and a second sensor 3008*b*. The end effector 3000 is similar to the end effector 300 described above. The end effector 3000 comprises a first jaw member, or anvil, 3002 pivotally coupled to a second jaw member 3004. The second jaw member 3004 is configured to receive a staple cartridge 3006 therein. The staple cartridge 3006 comprises a plurality of staples (not shown). The plurality of staples is deployable from the staple cartridge 3006 during a surgical operation. The end effector 3000 comprises a first sensor 3008*a*. The first sensor 3008*a* is configured to measure one or more parameters of the end effector 3000. For example, in one embodiment, the first sensor 3008*a* is configured to measure the gap 3010 between the anvil 3002 and the second jaw member 3004. The first sensor 3008*a* may comprise, for example, a Hall effect sensor configured to detect a magnetic field generated by a magnet 3012 embedded in the second jaw member 3004 and/or the staple cartridge 3006. As another example, in one embodiment, the first sensor 3008*a* is configured to measure one or more forces exerted on the anvil 3002 by the second jaw member 3004 and/or tissue clamped between the anvil 3002 and the second jaw member 3004.

The end effector 3000 comprises a second sensor 3008*b*. The second sensor 3008*b* is configured to measure one or more parameters of the end effector 3000. For example, in various embodiments, the second sensor 3008*b* may comprise a strain gauge configured to measure the magnitude of the strain in the anvil 3002 during a clamped condition. The strain gauge provides an electrical signal whose amplitude varies with the magnitude of the strain. In various embodiments, the first sensor 3008*a* and/or the second sensor 3008*b* may comprise, for example, a magnetic sensor such as, for example, a Hall effect sensor, a strain gauge, a pressure sensor, a force sensor, an inductive sensor such as, for example, an eddy current sensor, a resistive sensor, a capacitive sensor, an optical sensor, and/or any other suitable sensor for measuring one or more parameters of the end effector 3000. The first sensor 3008*a* and the second sensor 3008*b* may be arranged in a series configuration and/or a parallel configuration. In a series configuration, the second sensor 3008*b* may be configured to directly affect the output of the first sensor 3008*a*. In a parallel configuration, the second sensor 3008*b* may be configured to indirectly affect the output of the first sensor 3008*a*.

In one embodiment, the one or more parameters measured by the first sensor 3008*a* are related to the one or more parameters measured by the second sensor 3008*b*. For example, in one embodiment, the first sensor 3008*a* is configured to measure the gap 3010 between the anvil 3002 and the second jaw member 3004. The gap 3010 is representative of the thickness and/or compressibility of a tissue section clamped between the anvil 3002 and the staple cartridge 3006. The first sensor 3008*a* may comprise, for example, a Hall effect sensor configured to detect a magnetic field generated by a magnet 3012 coupled to the second jaw member 3004 and/or the staple cartridge 3006. Measuring at a single location accurately describes the compressed tissue thickness for a calibrated full bit of tissue, but may provide inaccurate results when a partial bite of tissue is placed between the anvil 3002 and the second jaw member 3004. A partial bite of tissue, either a proximal partial bite or a distal partial bite, changes the clamping geometry of the anvil 3002.

In some embodiments, the second sensor 3008*b* is configured to detect one or more parameters indicative of a type of tissue bite, for example, a full bite, a partial proximal bite, and/or a partial distal bite. The measurement of the second sensor 3008*b* may be used to adjust the measurement of the first sensor 3008*a* to accurately represent a proximal or distal positioned partial bite's true compressed tissue thickness. For example, in one embodiment, the second sensor 3008*b* comprises a strain gauge, such as, for example, a micro-strain gauge, configured to monitor the amplitude of the strain in the anvil during a clamped condition. The amplitude of the strain of the anvil 3002 is used to modify the output of the first sensor 3008*a*, for example, a Hall effect sensor, to accurately represent a proximal or distal positioned partial bite's true compressed tissue thickness. The first sensor 3008*a* and the second sensor 3008*b* may be measured in real-time during a clamping operation. Real-time measurement allows time based information to be analyzed, for example, by the primary processor 2006, and used to select one or more algorithms and/or look-up tables to recognize tissue characteristics and clamping positioning to dynamically adjust tissue thickness measurements.

In some embodiments, the thickness measurement of the first sensor 3008*a* may be provided to an output device of a surgical instrument 10 coupled to the end effector 3000. For example, in one embodiment, the end effector 3000 is coupled to the surgical instrument 10 comprising a display 2028. The measurement of the first sensor 3008*a* is provided to a processor, for example, the primary processor 2006. The primary processor 2006 adjusts the measurement of the first sensor 3008*a* based on the measurement of the second sensor 3008*b* to reflect the true tissue thickness of a tissue section clamped between the anvil 3002 and the staple cartridge 3006. The primary processor 2006 outputs the adjusted tissue thickness measurement and an indication of full or partial bite to the display 2028. An operator may determine whether or not to deploy the staples in the staple cartridge 3006 based on the displayed values.

In some embodiments, the first sensor 3008*a* and the second sensor 3008*b* may be located in different environments, such as, for example, the first sensor 3008*a* being located within a patient at a treatment site and the second sensor 3008*b* being located externally to the patient. The second sensor 3008*b* may be configured to calibrate and/or modify the output of the first sensor 3008*a*. The first sensor 3008*a* and/or the second sensor 3008*b* may comprise, for example, an environmental sensor. Environmental sensors may comprise, for example, temperature sensors, humidity sensors, pressure sensors, and/or any other suitable environmental sensor.

Figure 29:
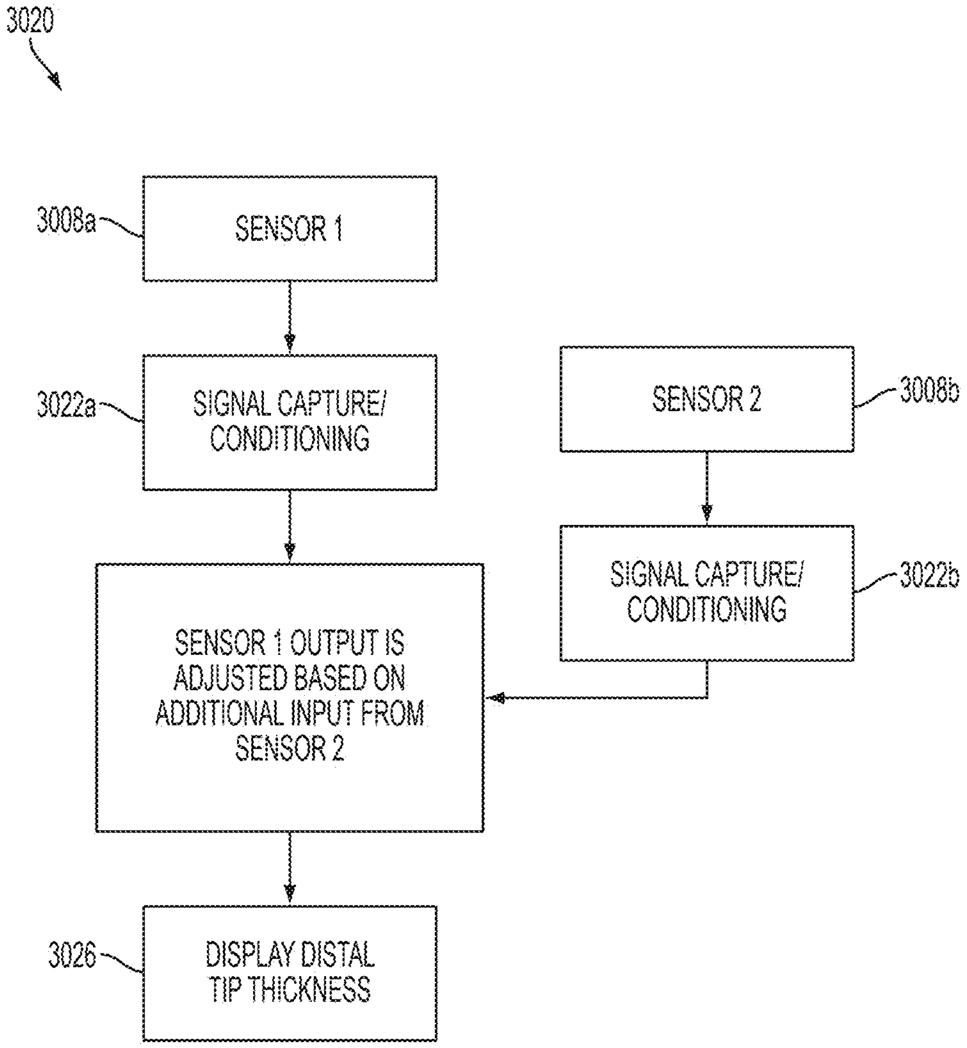
FIG. 29 is a logic diagram illustrating one embodiment of a process for adjusting the measurement of the first sensor based on input from the second sensor of the end effector illustrated in FIG. 28.

FIG. 29 is a logic diagram illustrating one embodiment of a process 3020 for adjusting the measurement of a first sensor 3008*a* based on input from a second sensor 3008*b*. A first signal is captured 3022*a* by the first sensor 3008*a*. The first signal 3022*a* may be conditioned based on one or more predetermined parameters, such as, for example, a smoothing function, a look-up table, and/or any other suitable conditioning parameters. A second signal is captured 3022*b* by the second sensor 3008*b*. The second signal 3022*b* may be conditioned based on one or more predetermined conditioning parameters. The first signal 3022*a* and the second signal 3022*b* are provided to a processor, such as, for example, the primary processor 2006. The processor 2006 adjusts the measurement of the first sensor 3022*a*, as represented by the first signal 3022*a*, based on the second signal 3022*b* from the second sensor. For example, in one embodiment, the first sensor 3022*a* comprises a Hall effect sensor and the second sensor 3022*b* comprises a strain gauge. The distance measurement of the first sensor 3022*a* is adjusted by the amplitude of the strain measured by the second sensor 3022*b* to determine the fullness of the bite of tissue in the end effector 3000. The adjusted measurement is displayed 3026 to an operator by, for example, a display 2026 embedded in the surgical instrument 10.

Figure 30:
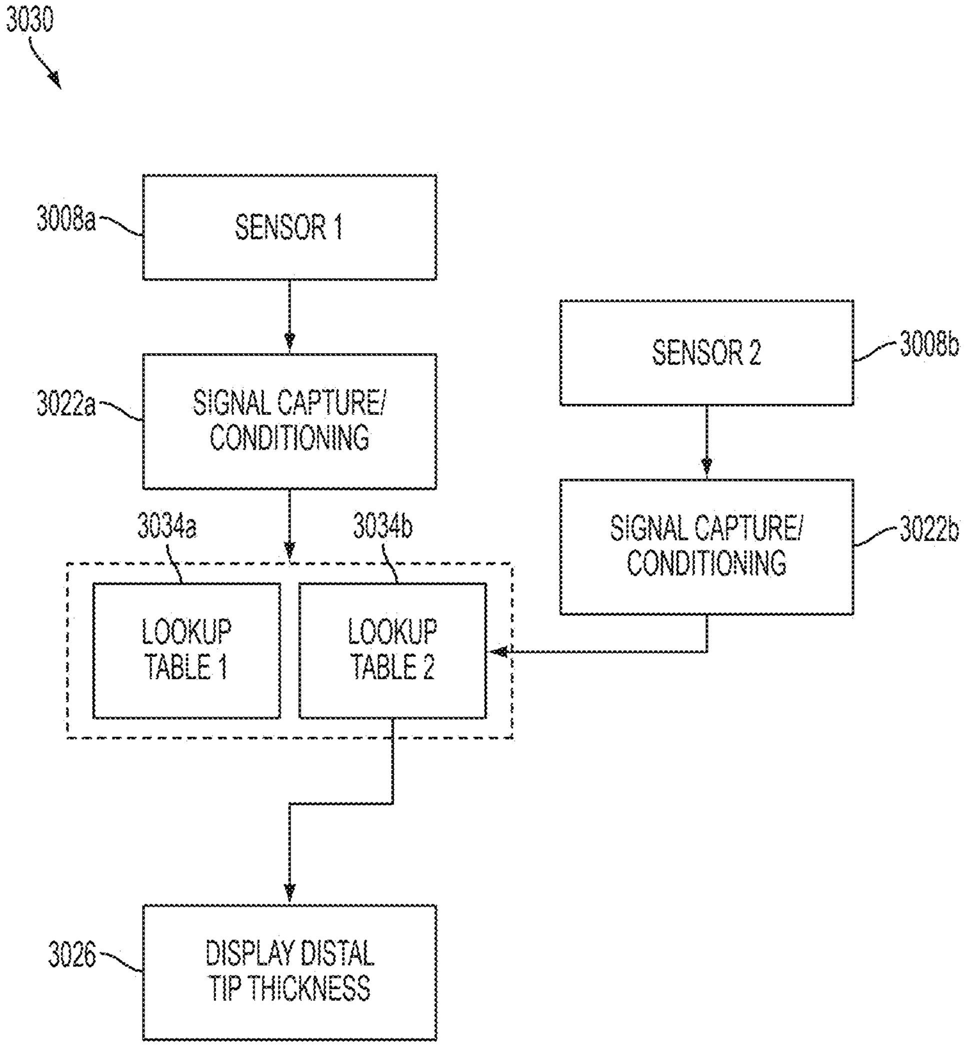
FIG. 30 is a logic diagram illustrating one embodiment of a process for determining a look-up table for a first sensor based on the input from a second sensor.

FIG. 30 is a logic diagram illustrating one embodiment of a process 3030 for determining a look-up table for a first sensor 3008*a* based on the input from a second sensor 3008*b*. The first sensor 3008*a* captures 3022*a* a signal indicative of one or more parameters of the end effector 3000. The first signal 3022*a* may be conditioned based on one or more predetermined parameters, such as, for example, a smoothing function, a look-up table, and/or any other suitable conditioning parameters. A second signal is captured 3022*b* by the second sensor 3008*b*. The second signal 3022*b* may be conditioned based on one or more predetermined conditioning parameters. The first signal 3022*a* and the second signal 3022*b* are provided to a processor, such as, for example, the primary processor 2006. The processor 2006 selects a look-up table from one or more available look-up tables 3034*a*, 3034*b* based on the value of the second signal. The selected look-up table is used to convert the first signal into a thickness measurement of the tissue located between the anvil 3002 and the staple cartridge 3006. The adjusted measurement is displayed 3026 to an operator by, for example, a display 2026 embedded in the surgical instrument 10.

Figure 31:
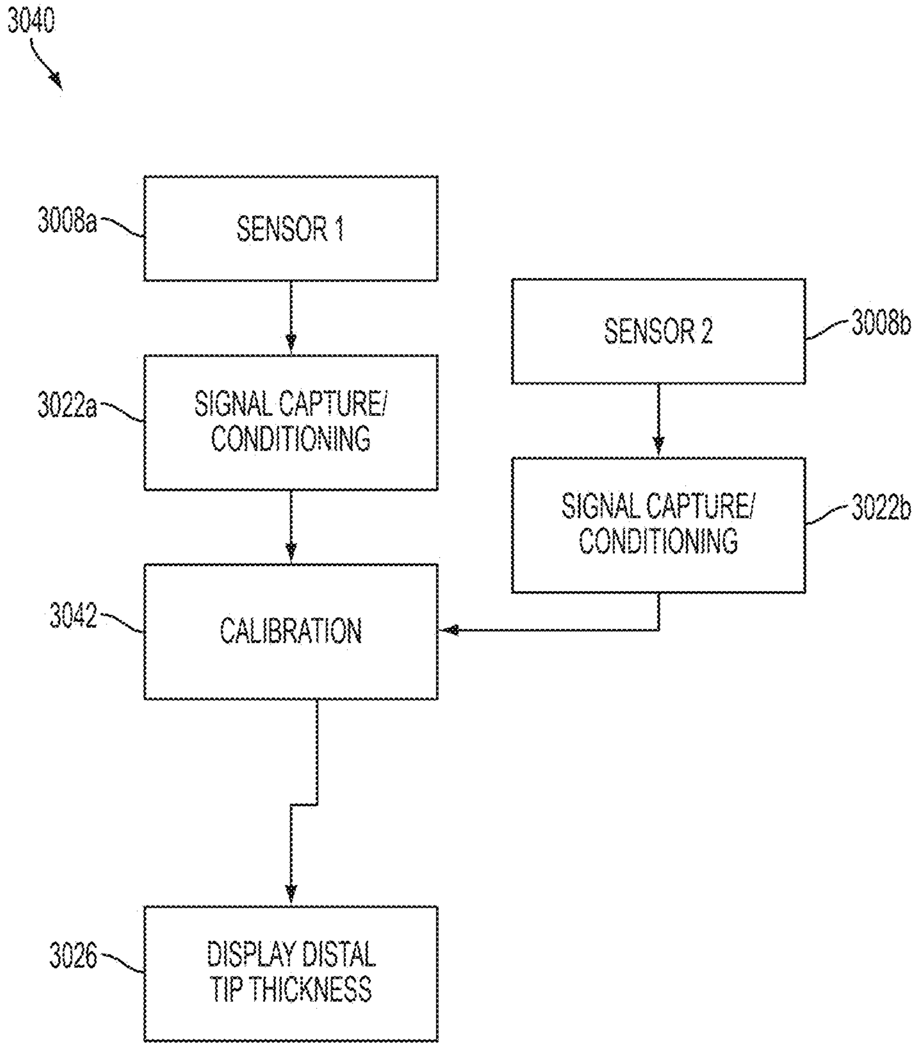
FIG. 31 is a logic diagram illustrating one embodiment of a process for calibrating a first sensor in response to an input from a second sensor.

FIG. 31 is a logic diagram illustrating one embodiment of a process 3040 for calibrating a first sensor 3008*a* in response to an input from a second sensor 3008*b*. The first sensor 3008*a* is configured to capture 3022*a* a signal indicative of one or more parameters of the end effector 3000. The first signal 3022*a* may be conditioned based on one or more predetermined parameters, such as, for example, a smoothing function, a look-up table, and/or any other suitable conditioning parameters. A second signal is captured 3022*b* by the second sensor 3008*b*. The second signal 3022*b* may be conditioned based on one or more predetermined conditioning parameters. The first signal 3022*a* and the second signal 3022*b* are provided to a processor, such as, for example, the primary processor 2006. The primary processor 2006 calibrates 3042 the first signal 3022*a* in response to the second signal 3022*b*. The first signal 3022*a* is calibrated 3042 to reflect the fullness of the bite of tissue in the end effector 3000. The calibrated signal is displayed 3026 to an operator by, for example, a display 2026 embedded in the surgical instrument 10.

Figure 32A:
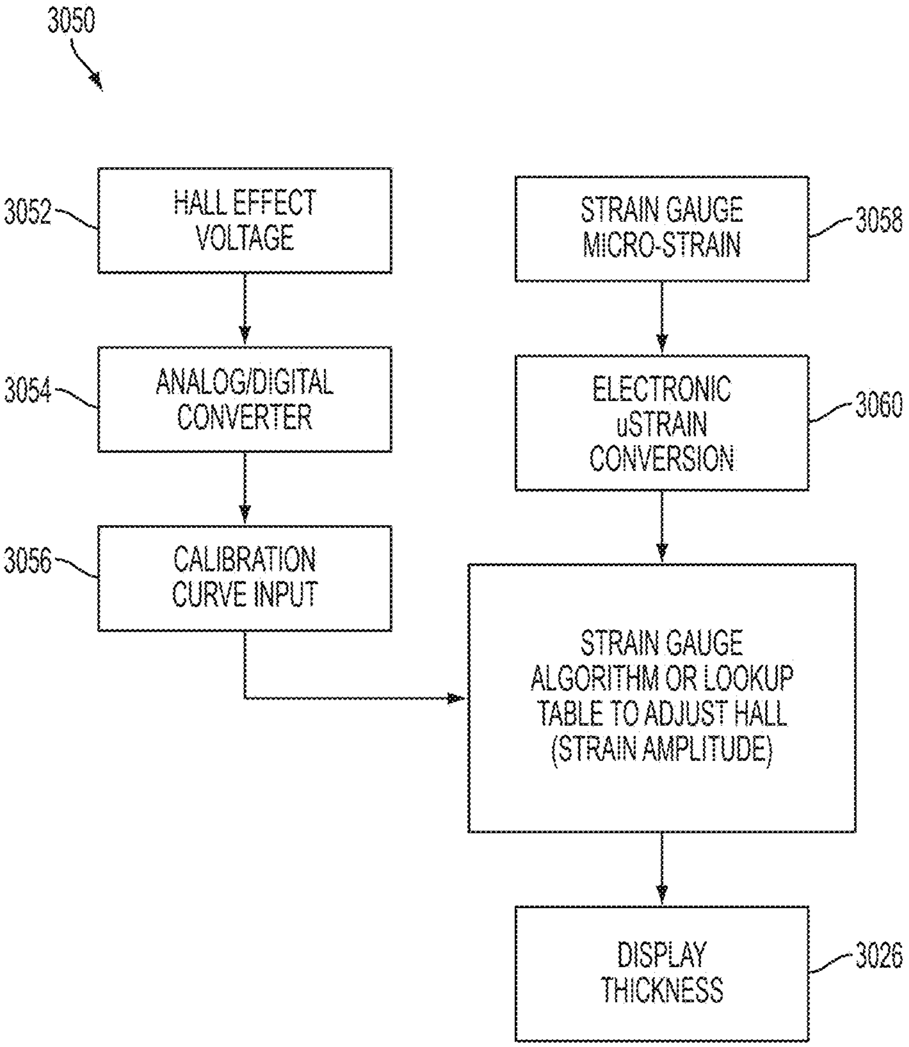
FIG. 32A is a logic diagram illustrating one embodiment of a process for determining and displaying the thickness of a tissue section clamped between an anvil and a staple cartridge of an end effector.

FIG. 32A is a logic diagram illustrating one embodiment of a process 3050 for determining and displaying the thickness of a tissue section clamped between the anvil 3002 and the staple cartridge 3006 of the end effector 3000. The process 3050 comprises obtaining a Hall effect voltage 3052, for example, through a Hall effect sensor located at the distal tip of the anvil 3002. The Hall effect voltage 3052 is provided to an analog to digital convertor 3054 and converted into a digital signal. The digital signal is provided to a processor, such as, for example, the primary processor 2006. The primary processor 2006 calibrates 3056 the curve input of the Hall effect voltage 3052 signal. A strain gauge 3058, such as, for example, a micro-strain gauge, is configured to measure one or more parameters of the end effector 3000, such as, for example, the amplitude of the strain exerted on the anvil 3002 during a clamping operation. The measured strain is converted 3060 to a digital signal and provided to the processor, such as, for example, the primary processor 2006. The primary processor 2006 uses one or more algorithms and/or lookup tables to adjust the Hall effect voltage 3052 in response to the strain measured by the strain gauge 3058 to reflect the true thickness and fullness of the bite of tissue clamped by the anvil 3002 and the staple cartridge 3006. The adjusted thickness is displayed 3026 to an operator by, for example, a display 2026 embedded in the surgical instrument 10.

Figure 32B:
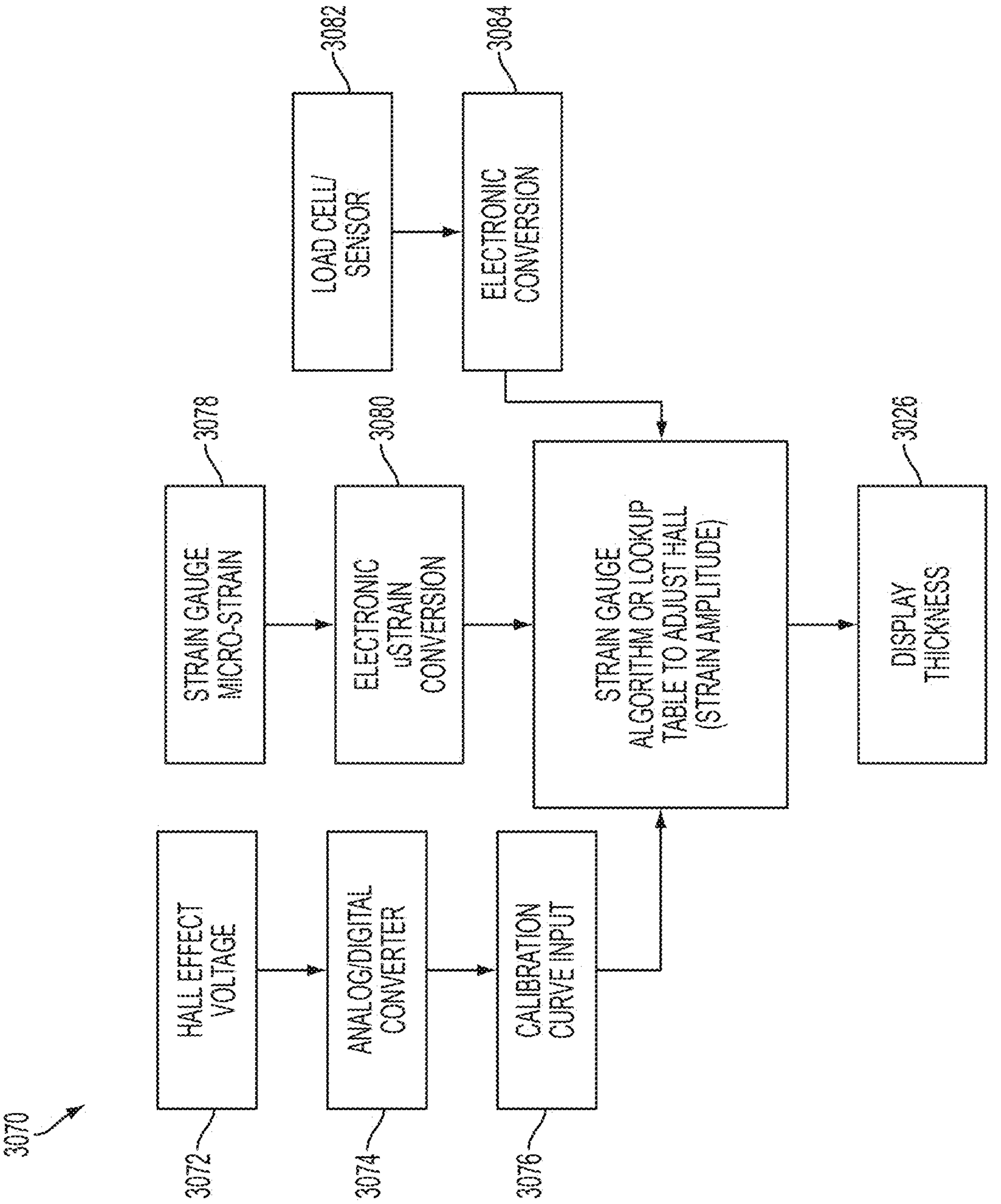
FIG. 32B is a logic diagram illustrating one embodiment of a process for determining and displaying the thickness of a tissue section clamped between the anvil and the staple cartridge of the end effector.

In some embodiments, the surgical instrument can further comprise a load cell or sensor 3082. The load sensor 3082 can be located, for instance, in the shaft assembly 200, described above, or in the housing 12, also described above. FIG. 32B is a logic diagram illustrating one embodiment of a process 3070 for determining and displaying the thickness of a tissue section clamped between the anvil 3002 and the staple cartridge 3006 of the end effector 3000. The process comprises obtaining a Hall effect voltage 3072, for example, through a Hall effect sensor located at the distal tip of the anvil 3002. The Hall effect voltage 3072 is provided to an analog to digital convertor 3074 and converted into a digital signal. The digital signal is provided to a processor, such as, for example, the primary processor 2006. The primary processor 2006 applies calibrates 3076 the curve input of the Hall effect voltage 3072 signal. A strain gauge 3078, such as, for example, a micro-strain gauge, is configured to measure one or more parameters of the end effector 3000, such as, for example, the amplitude of the strain exerted on the anvil 3002 during a clamping operation. The measured strain is converted 3080 to a digital signal and provided to the processor, such as, for example, the primary processor 2006. The load sensor 3082 measures the clamping force of the anvil 3002 against the staple cartridge 3006. The measured clamping force is converted 3084 to a digital signal and provided to the processor, such as for example, the primary processor 2006. The primary processor 2006 uses one or more algorithms and/or lookup tables to adjust the Hall effect voltage 3072 in response to the strain measured by the strain gauge 3078 and the clamping force measured by the load sensor 3082 to reflect the true thickness and fullness of the bite of tissue clamped by the anvil 3002 and the staple cartridge 3006. The adjusted thickness is displayed 3026 to an operator by, for example, a display 2026 embedded in the surgical instrument 10.

Figure 33:
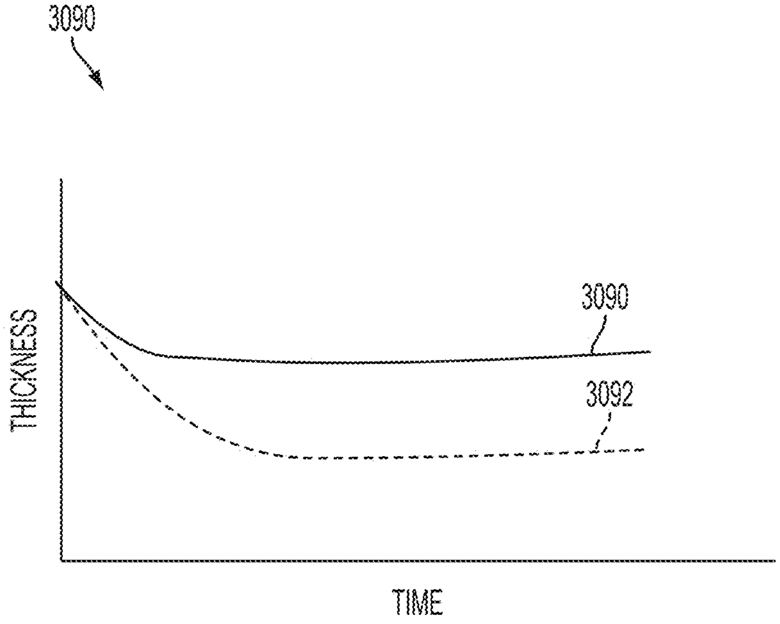
FIG. 33 is a graph illustrating an adjusted Hall effect thickness measurement compared to an unmodified Hall effect thickness measurement.

FIG. 33 is a graph 3090 illustrating an adjusted Hall effect thickness measurement 3094 compared to an unmodified Hall effect thickness measurement 3092. As shown in FIG. 33, the unmodified Hall effect thickness measurement 3092 indicates a thicker tissue measurement, as the single sensor is unable to compensate for partial distal/proximal bites that result in incorrect thickness measurements. The adjusted thickness measurement 3094 is generated by, for example, the process 3050 illustrated in FIG. 32A. The Hall effect thickness measurement 3092 is calibrated based on input from one or more additional sensors, such as, for example, a strain gauge. The adjusted Hall effect thickness 3094 reflects the true thickness of the tissue located between an anvil 3002 and a staple cartridge 3006.

Figure 34:
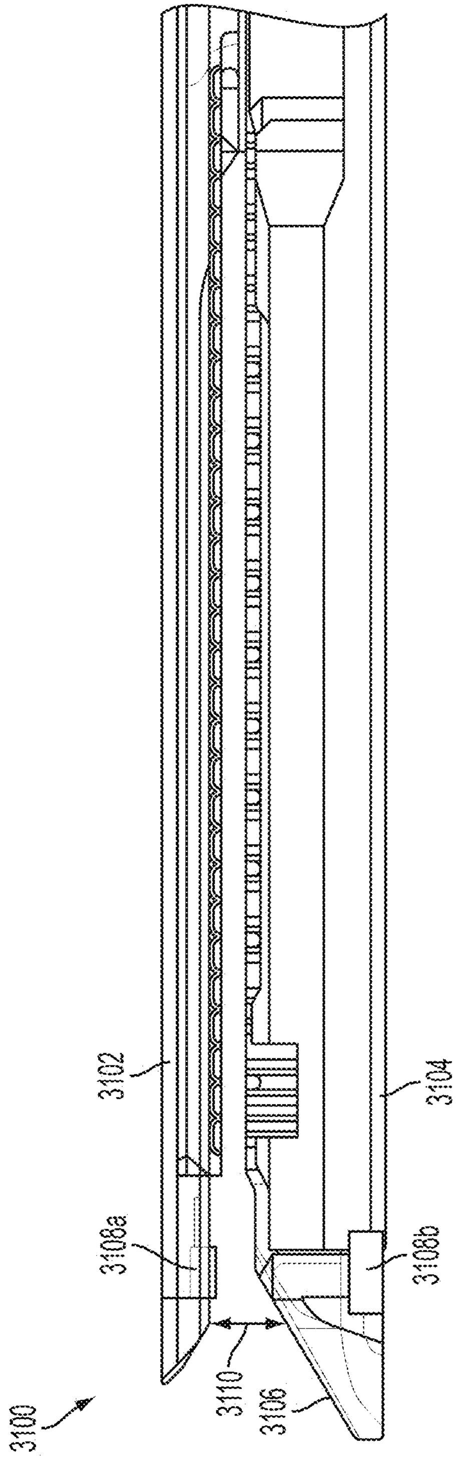
FIG. 34 illustrates one embodiment of an end effector comprising a first sensor and a second sensor.

FIG. 34 illustrates one embodiment of an end effector 3100 comprising a first sensor 3108*a* and a second sensor 3108*b*. The end effector 3100 is similar to the end effector 3000 illustrated in FIG. 28. The end effector 3100 comprises a first jaw member, or anvil, 3102 pivotally coupled to a second jaw member 3104. The second jaw member 3104 is configured to receive a staple cartridge 3106 therein. The end effector 3100 comprises a first sensor 3108*a* coupled to the anvil 3102. The first sensor 3108*a* is configured to measure one or more parameters of the end effector 3100, such as, for example, the gap 3110 between the anvil 3102 and the staple cartridge 3106. The gap 3110 may correspond to, for example, a thickness of tissue clamped between the anvil 3102 and the staple cartridge 3106. The first sensor 3108*a* may comprise any suitable sensor for measuring one or more parameters of the end effector. For example, in various embodiments, the first sensor 3108*a* may comprise a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor.

In some embodiments, the end effector 3100 comprises a second sensor 3108*b*. The second sensor 3108*b* is coupled to second jaw member 3104 and/or the staple cartridge 3106. The second sensor 3108*b* is configured to detect one or more parameters of the end effector 3100. For example, in some embodiments, the second sensor 3108*b* is configured to detect one or more instrument conditions such as, for example, a color of the staple cartridge 3106 coupled to the second jaw member 3104, a length of the staple cartridge 3106, a clamping condition of the end effector 3100, the number of uses/number of remaining uses of the end effector 3100 and/or the staple cartridge 3106, and/or any other suitable instrument condition. The second sensor 3108*b* may comprise any suitable sensor for detecting one or more instrument conditions, such as, for example, a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor.

The end effector 3100 may be used in conjunction with any of the processes shown in FIGS. 29-33. For example, in one embodiment, input from the second sensor 3108*b* may be used to calibrate the input of the first sensor 3108*a*. The second sensor 3108*b* may be configured to detect one or more parameters of the staple cartridge 3106, such as, for example, the color and/or length of the staple cartridge 3106. The detected parameters, such as the color and/or the length of the staple cartridge 3106, may correspond to one or more properties of the cartridge, such as, for example, the height of the cartridge deck, the thickness of tissue useable/optimal for the staple cartridge, and/or the pattern of the staples in the staple cartridge 3106. The known parameters of the staple cartridge 3106 may be used to adjust the thickness measurement provided by the first sensor 3108*a*. For example, if the staple cartridge 3106 has a higher deck height, the thickness measurement provided by the first sensor 3108*a* may be reduced to compensate for the added deck height. The adjusted thickness may be displayed to an operator, for example, through a display 2026 coupled to the surgical instrument 10.

Figure 35:
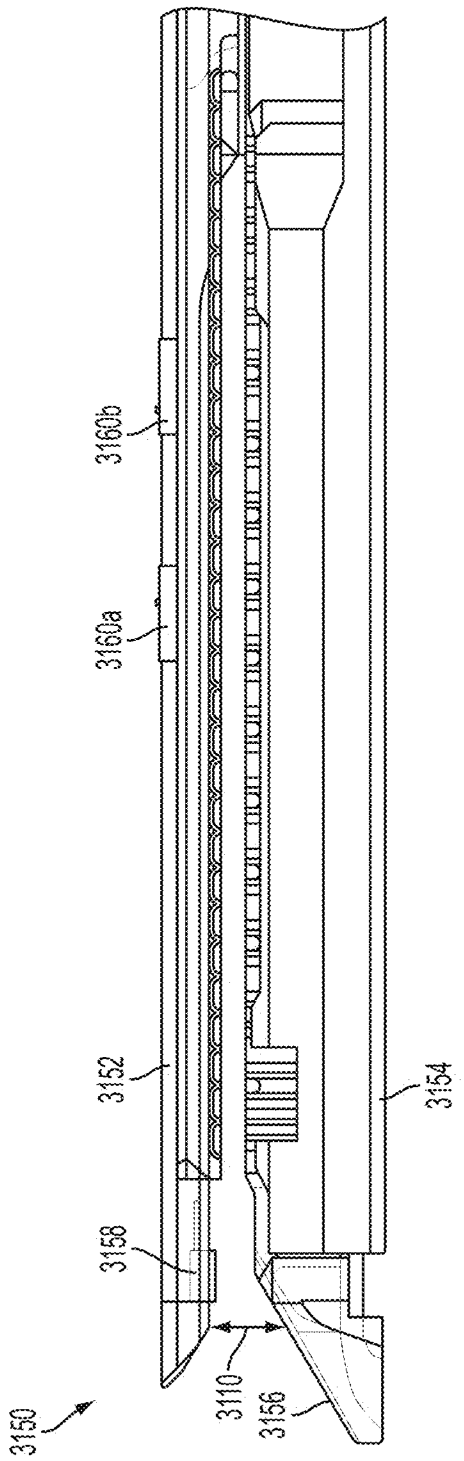
FIG. 35 illustrates one embodiment of an end effector comprising a first sensor and a plurality of second sensors.

FIG. 35 illustrates one embodiment of an end effector 3150 comprising a first sensor 3158 and a plurality of second sensors 3160*a*, 3160*b*. The end effector 3150 comprises a first jaw member, or anvil, 3152 and a second jaw member 3154. The second jaw member 3154 is configured to receive a staple cartridge 3156. The anvil 3152 is pivotally moveable with respect to the second jaw member 3154 to clamp tissue between the anvil 3152 and the staple cartridge 3156. The anvil comprises a first sensor 3158. The first sensor 3158 is configured to detect one or more parameters of the end effector 3150, such as, for example, the gap 3110 between the anvil 3152 and the staple cartridge 3156. The gap 3110 may correspond to, for example, a thickness of tissue clamped between the anvil 3152 and the staple cartridge 3156. The first sensor 3158 may comprise any suitable sensor for measuring one or more parameters of the end effector. For example, in various embodiments, the first sensor 3158 may comprise a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor.

In some embodiments, the end effector 3150 comprises a plurality of secondary sensors 3160*a*, 3160*b*. The secondary sensors 3160*a*, 3160*b* are configured to detect one or more parameters of the end effector 3150. For example, in some embodiments, the secondary sensors 3160*a*, 3160*b* are configured to measure an amplitude of strain exerted on the anvil 3152 during a clamping procedure. In various embodiments, the secondary sensors 3160*a*, 3160*b* may comprise a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor. The secondary sensors 3160*a*, 3160*b* may be configured to measure one or more identical parameters at different locations of the anvil 3152, different parameters at identical locations on the anvil 3152, and/or different parameters at different locations on the anvil 3152.

Figure 36:
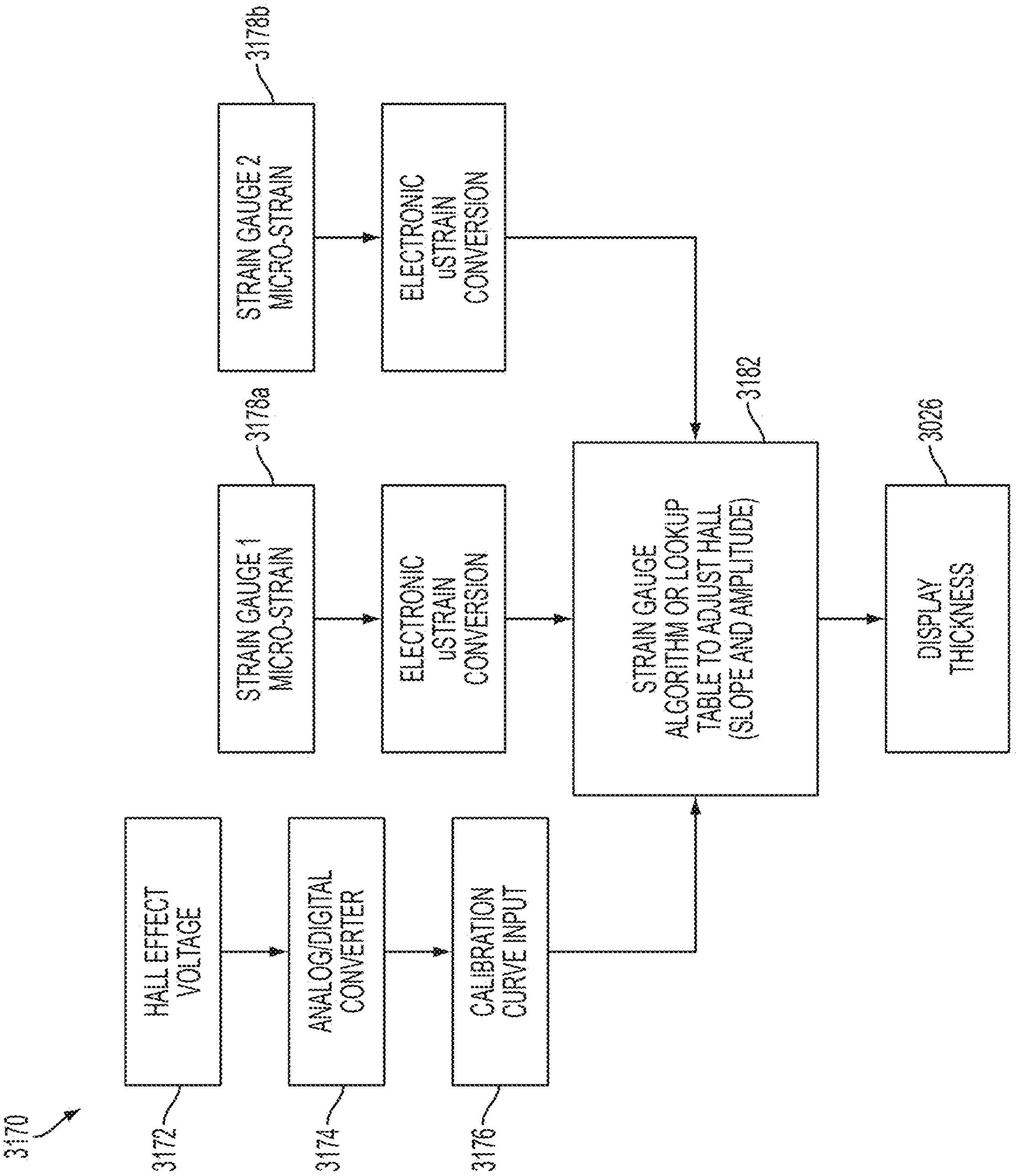
FIG. 36 is a logic diagram illustrating one embodiment of a process for adjusting a measurement of a first sensor in response to a plurality of secondary sensors.

FIG. 36 is a logic diagram illustrating one embodiment of a process 3170 for adjusting a measurement of a first sensor 3158 in response to a plurality of secondary sensors 3160*a*, 3160. In one embodiment, a Hall effect voltage is obtained 3172, for example, by a Hall effect sensor. The Hall effect voltage is converted 3174 by an analog to digital convertor. The converted Hall effect voltage signal is calibrated 3176. The calibrated curve represents the thickness of a tissue section located between the anvil 3152 and the staple cartridge 3156. A plurality of secondary measurements are obtained 3178*a*, 3178*b* by a plurality of secondary sensors, such as, for example, a plurality of strain gauges. The input of the strain gauges is converted 3180*a*, 3180*b* into one or more digital signals, for example, by a plurality of electronic μStrain conversion circuits. The calibrated Hall effect voltage and the plurality of secondary measurements are provided to a processor, such as, for example, the primary processor 2006. The primary processor utilizes the secondary measurements to adjust 3182 the Hall effect voltage, for example, by applying an algorithm and/or utilizing one or more look-up tables. The adjusted Hall effect voltage represents the true thickness and fullness of the bite of tissue clamped by the anvil 3152 and the staple cartridge 3156. The adjusted thickness is displayed 3026 to an operator by, for example, a display 2026 embedded in the surgical instrument 10.

Figure 37:
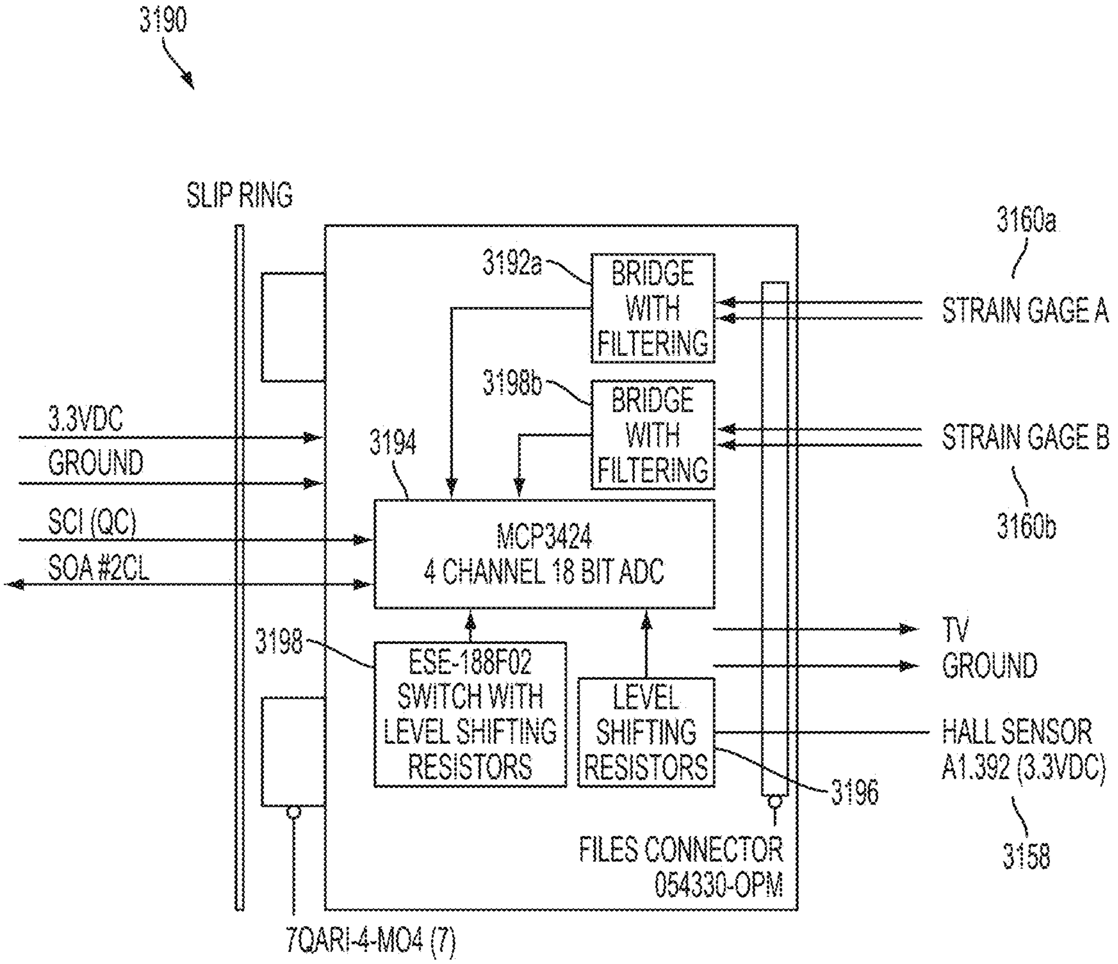
FIG. 37 illustrates one embodiment of a circuit configured to convert signals from a first sensor and a plurality of secondary sensors into digital signals receivable by a processor.

FIG. 37 illustrates one embodiment of a circuit 3190 configured to convert signals from the first sensor 3158 and the plurality of secondary sensors 3160*a*, 3160*b* into digital signals receivable by a processor, such as, for example, the primary processor 2006. The circuit 3190 comprises an analog-to-digital convertor 3194. In some embodiments, the analog-to-digital convertor 3194 comprises a 4-channel, 18-bit analog to digital convertor. Those skilled in the art will recognize that the analog-to-digital convertor 3194 may comprise any suitable number of channels and/or bits to convert one or more inputs from analog to digital signals. The circuit 3190 comprises one or more level shifting resistors 3196 configured to receive an input from the first sensor 3158, such as, for example, a Hall effect sensor. The level shifting resistors 3196 adjust the input from the first sensor, shifting the value to a higher or lower voltage depending on the input. The level shifting resistors 3196 provide the level-shifted input from the first sensor 3158 to the analog-to-digital convertor.

In some embodiments, a plurality of secondary sensors 3160*a*, 3160*b* are coupled to a plurality of bridges 3192*a*, 3192*b* within the circuit 3190. The plurality of bridges 3192*a*, 3192*b* may provide filtering of the input from the plurality of secondary sensors 3160*a*, 3160*b*. After filtering the input signals, the plurality of bridges 3192*a*, 3192*b* provide the inputs from the plurality of secondary sensors 3160*a*, 3160*b* to the analog-to-digital convertor 3194. In some embodiments, a switch 3198 coupled to one or more level shifting resistors may be coupled to the analog-to-digital convertor 3194. The switch 3198 is configured to calibrate one or more of the input signals, such as, for example, an input from a Hall effect sensor. The switch 3198 may be engaged to provide one or more level shifting signals to adjust the input of one or more of the sensors, such as, for example, to calibrate the input of a Hall effect sensor. In some embodiments, the adjustment is not necessary, and the switch 3198 is left in the open position to decouple the level shifting resistors. The switch 3198 is coupled to the analog-to-digital convertor 3194. The analog-to-digital convertor 3194 provides an output to one or more processors, such as, for example, the primary processor 2006. The primary processor 2006 calculates one or more parameters of the end effector 3150 based on the input from the analog-to-digital convertor 3194. For example, in one embodiment, the primary processor 2006 calculates a thickness of tissue located between the anvil 3152 and the staple cartridge 3156 based on input from one or more sensors 3158, 3160*a*, 3160*b*.

Figure 38:
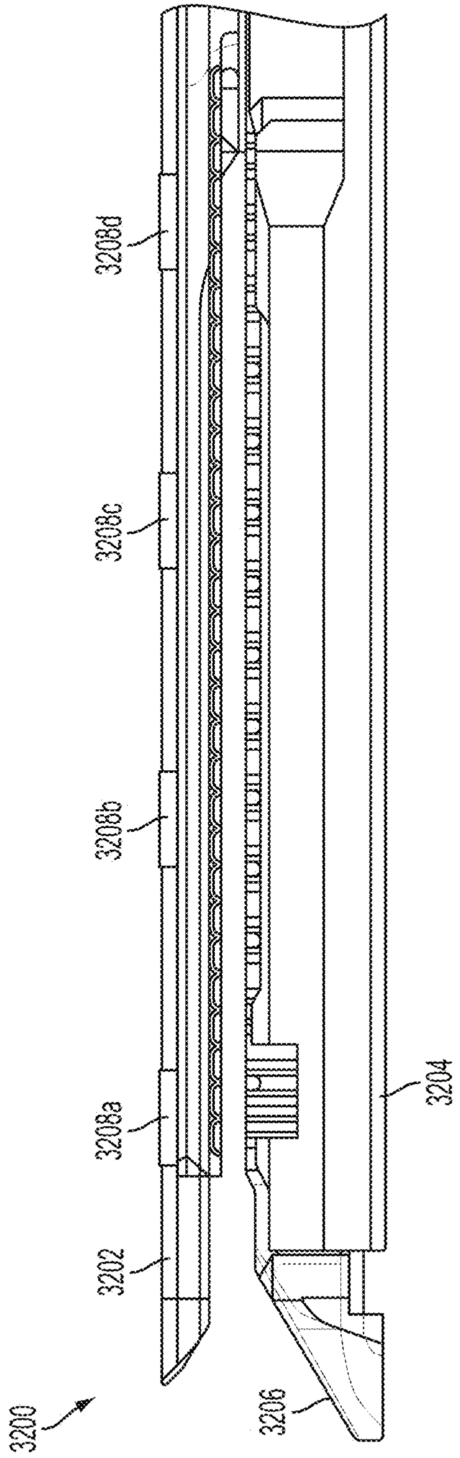
FIG. 38 illustrates one embodiment of an end effector comprising a plurality of sensors.

FIG. 38 illustrates one embodiment of an end effector 3200 comprising a plurality of sensors 3208*a*-3208*d*. The end effector 3200 comprises an anvil 3202 pivotally coupled to a second jaw member 3204. The second jaw member 3204 is configured to receive a staple cartridge 3206 therein. The anvil 3202 comprises a plurality of sensors 3208*a*-3208*d* thereon. The plurality of sensors 3208*a*-3208*d* is configured to detect one or more parameters of the end effector 3200, such as, for example, the anvil 3202. The plurality of sensors 3208*a*-3208*d* may comprise one or more identical sensors and/or different sensors. The plurality of sensors 3208*a*-3208*d* may comprise, for example, magnetic sensors, such as a Hall effect sensor, strain gauges, pressure sensors, inductive sensors, such as an eddy current sensor, resistive sensors, capacitive sensors, optical sensors, and/or any other suitable sensors or combination thereof. For example, in one embodiment, the plurality of sensors 3208*a*-3208*d* may comprise a plurality of strain gauges.

In one embodiment, the plurality of sensors 3208*a*-3208*d* allows a robust tissue thickness sensing process to be implemented. By detecting various parameters along the length of the anvil 3202, the plurality of sensors 3208*a*-3208*d* allow a surgical instrument, such as, for example, the surgical instrument 10, to calculate the tissue thickness in the jaws regardless of the bite, for example, a partial or full bite. In some embodiments, the plurality of sensors 3208*a*-3208*d* comprises a plurality of strain gauges. The plurality of strain gauges is configured to measure the strain at various points on the anvil 3202. The amplitude and/or the slope of the strain at each of the various points on the anvil 3202 can be used to determine the thickness of tissue in between the anvil 3202 and the staple cartridge 3206. The plurality of strain gauges may be configured to optimize maximum amplitude and/or slope differences based on clamping dynamics to determine thickness, tissue placement, and/or material properties of the tissue. Time based monitoring of the plurality of sensors 3208*a*-3208*d* during clamping allows a processor, such as, for example, the primary processor 2006, to utilize algorithms and look-up tables to recognize tissue characteristics and clamping positions and dynamically adjust the end effector 3200 and/or tissue clamped between the anvil 3202 and the staple cartridge 3206.

Figure 39:
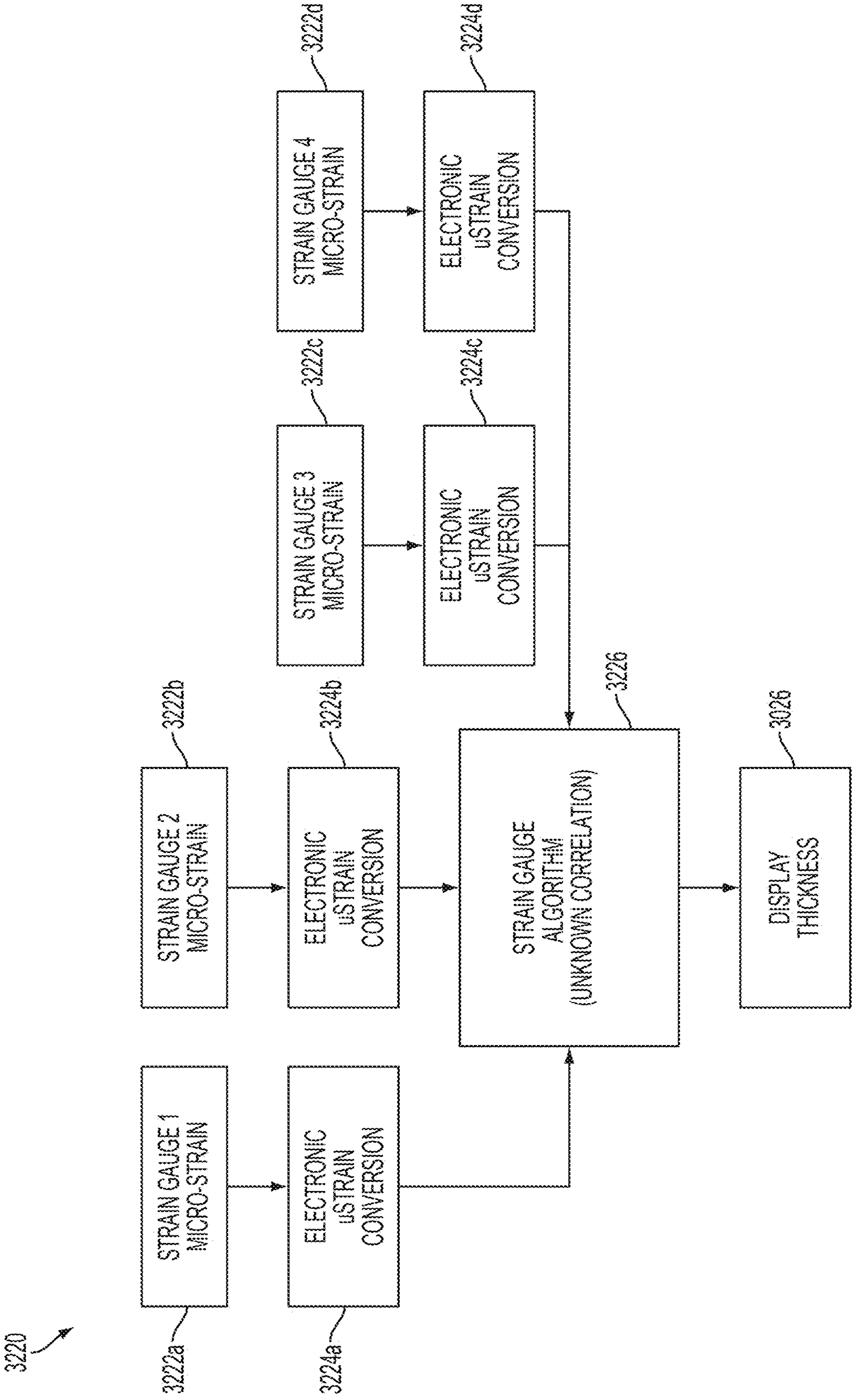
FIG. 39 is a logic diagram illustrating one embodiment of a process for determining one or more tissue properties based on a plurality of sensors.

FIG. 39 is a logic diagram illustrating one embodiment of a process 3220 for determining one or more tissue properties based on a plurality of sensors 3208*a*-3208*d*. In one embodiment, a plurality of sensors 3208*a*-3208*d* generate 3222*a*-3222*d* a plurality of signals indicative of one or more parameters of the end effector 3200. The plurality of generated signals is converted 3224*a*-3224*d* to digital signals and provided to a processor. For example, in one embodiment comprising a plurality of strain gauges, a plurality of electronic μStrain (micro-strain) conversion circuits convert 3224*a*-3224*d* the strain gauge signals to digital signals. The digital signals are provided to a processor, such as, for example, the primary processor 2006. The primary processor 2006 determines 3226 one or more tissue characteristics based on the plurality of signals. The processor 2006 may determine the one or more tissue characteristics by applying an algorithm and/or a look-up table. The one or more tissue characteristics are displayed 3026 to an operator, for example, by a display 2026 embedded in the surgical instrument 10.

Figure 40:
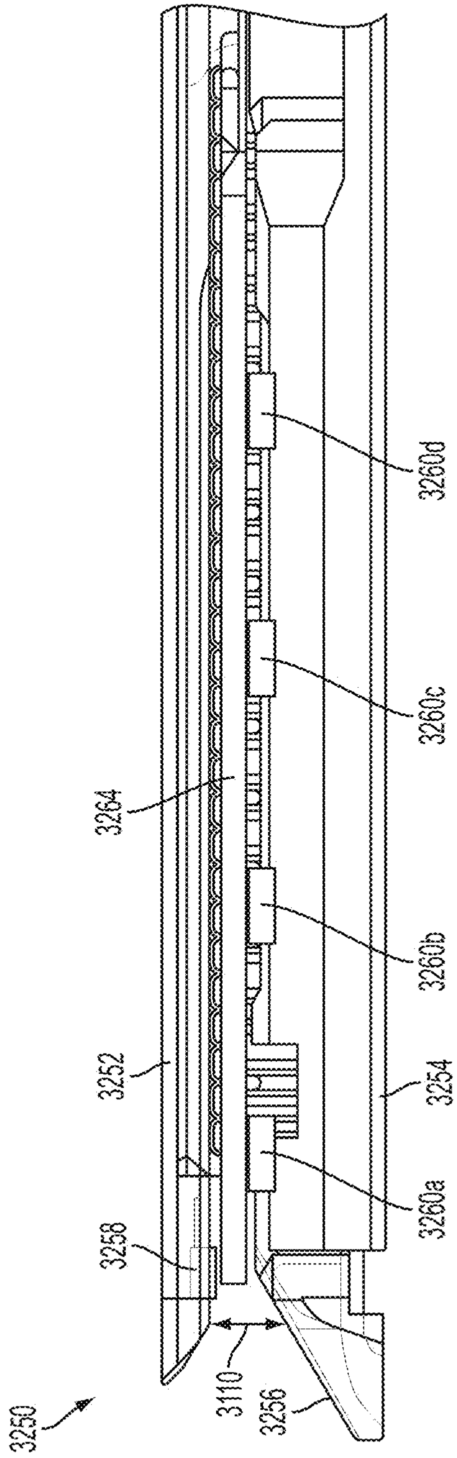
FIG. 40 illustrates one embodiment of an end effector comprising a plurality of sensors coupled to a second jaw member.

FIG. 40 illustrates one embodiment of an end effector 3250 comprising a plurality of sensors 3260*a*-3260*d* coupled to a second jaw member 3254. The end effector 3250 comprises an anvil 3252 pivotally coupled to a second jaw member 3254. The anvil 3252 is moveable relative to the second jaw member 3254 to clamp one or more materials, such as, for example, a tissue section 3264, therebetween. The second jaw member 3254 is configured to receive a staple cartridge 3256. A first sensor 3258 is coupled to the anvil 3252. The first sensor is configured to detect one or more parameters of the end effector 3150, such as, for example, the gap 3110 between the anvil 3252 and the staple cartridge 3256. The gap 3110 may correspond to, for example, a thickness of tissue clamped between the anvil 3252 and the staple cartridge 3256. The first sensor 3258 may comprise any suitable sensor for measuring one or more parameters of the end effector. For example, in various embodiments, the first sensor 3258 may comprise a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor.

A plurality of secondary sensors 3260*a*-3260*d* is coupled to the second jaw member 3254. The plurality of secondary sensors 3260*a*-3260*d* may be formed integrally with the second jaw member 3254 and/or the staple cartridge 3256. For example, in one embodiment, the plurality of secondary sensors 3260*a*-3260*d* is disposed on an outer row of the staple cartridge 3256 (see FIG. 41). The plurality of secondary sensors 3260*a*-3260*d* are configured to detect one or more parameters of the end effector 3250 and/or a tissue section 3264 clamped between the anvil 3252 and the staple cartridge 3256. The plurality of secondary sensors 3260*a*-3260*d* may comprise any suitable sensors for detecting one or more parameters of the end effector 3250 and/or the tissue section 3264, such as, for example, magnetic sensors, such as a Hall effect sensor, strain gauges, pressure sensors, inductive sensors, such as an eddy current sensor, resistive sensors, capacitive sensors, optical sensors, and/or any other suitable sensors or combination thereof. The plurality of secondary sensors 3260*a*-3260*d* may comprise identical sensors and/or different sensors.

In some embodiments, the plurality of secondary sensors 3260*a*-3260*d* comprises dual purpose sensors and tissue stabilizing elements. The plurality of secondary sensors 3260*a*-3260*d* comprise electrodes and/or sensing geometries configured to create a stabilized tissue condition when the plurality of secondary sensors 3260*a*-3260*d* are engaged with a tissue section 3264, such as, for example, during a clamping operation. In some embodiments, one or more of the plurality of secondary sensors 3260*a*-3260*d* may be replaced with non-sensing tissue stabilizing elements. The secondary sensors 3260*a*-3260*d* create a stabilized tissue condition by controlling tissue flow, staple formation, and/or other tissue conditions during a clamping, stapling, and/or other treatment process.

Figure 41:
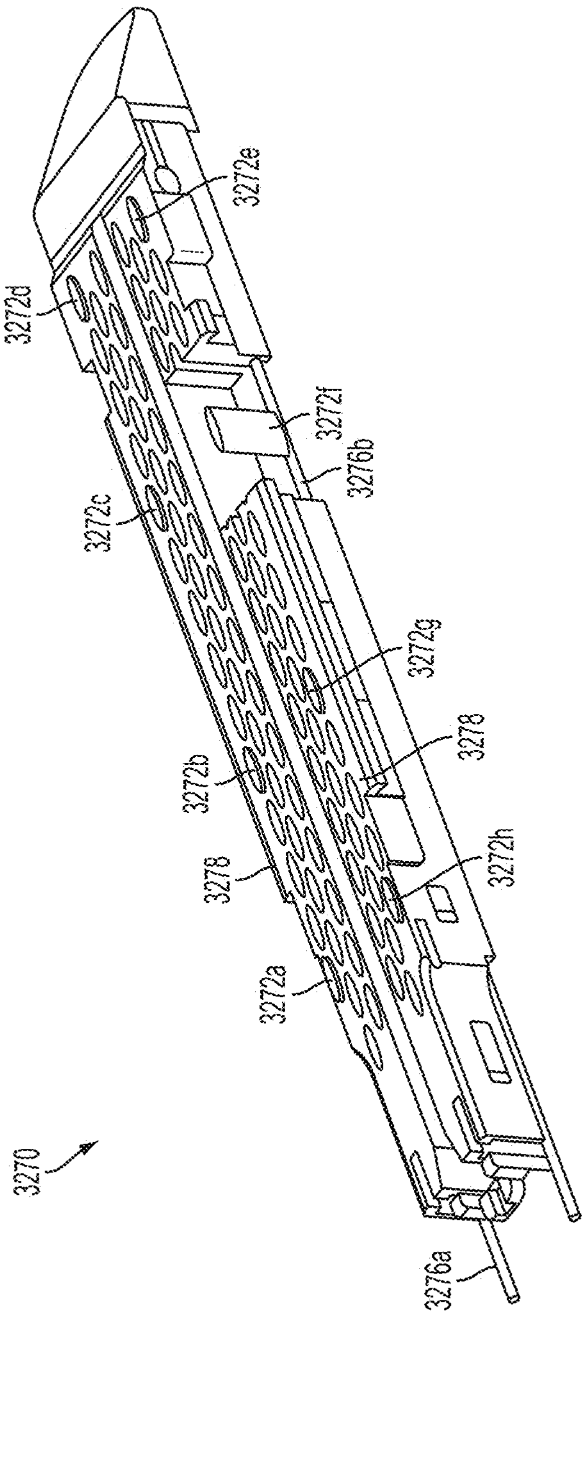
FIG. 41 illustrates one embodiment of a staple cartridge comprising a plurality of sensors formed integrally therein.

FIG. 41 illustrates one embodiment of a staple cartridge 3270 comprising a plurality of sensors 3272*a*-3272*h* formed integrally therein. The staple cartridge 3270 comprises a plurality of rows containing a plurality of holes for storing staples therein. One or more of the holes in the outer row 3278 are replaced with one of the plurality of sensors 3272*a*-3272*h*. A cut-away section 3274 is shown to illustrate a sensor 3272*f* coupled to a sensor wire 3276*b*. The sensor wires 3276*a*, 3276*b* may comprise a plurality of wires for coupling the plurality of sensors 3272*a*-3272*h* to one or more circuits of a surgical instrument, such as, for example, the surgical instrument 10. In some embodiments, one or more of the plurality of sensors 3272*a*-3272*h* comprise dual purpose sensor and tissue stabilizing elements having electrodes and/or sensing geometries configured to provide tissue stabilization. In some embodiments, the plurality of sensors 3272*a*-3272*h* may be replaced with and/or co-populated with a plurality of tissue stabilizing elements. Tissue stabilization may be provided by, for example, controlling tissue flow and/or staple formation during a clamping and/or stapling process. The plurality of sensors 3272*a*-3272*h* provide signals to one or more circuits of the surgical instrument 10 to enhance feedback of stapling performance and/or tissue thickness sensing.

Figure 42:
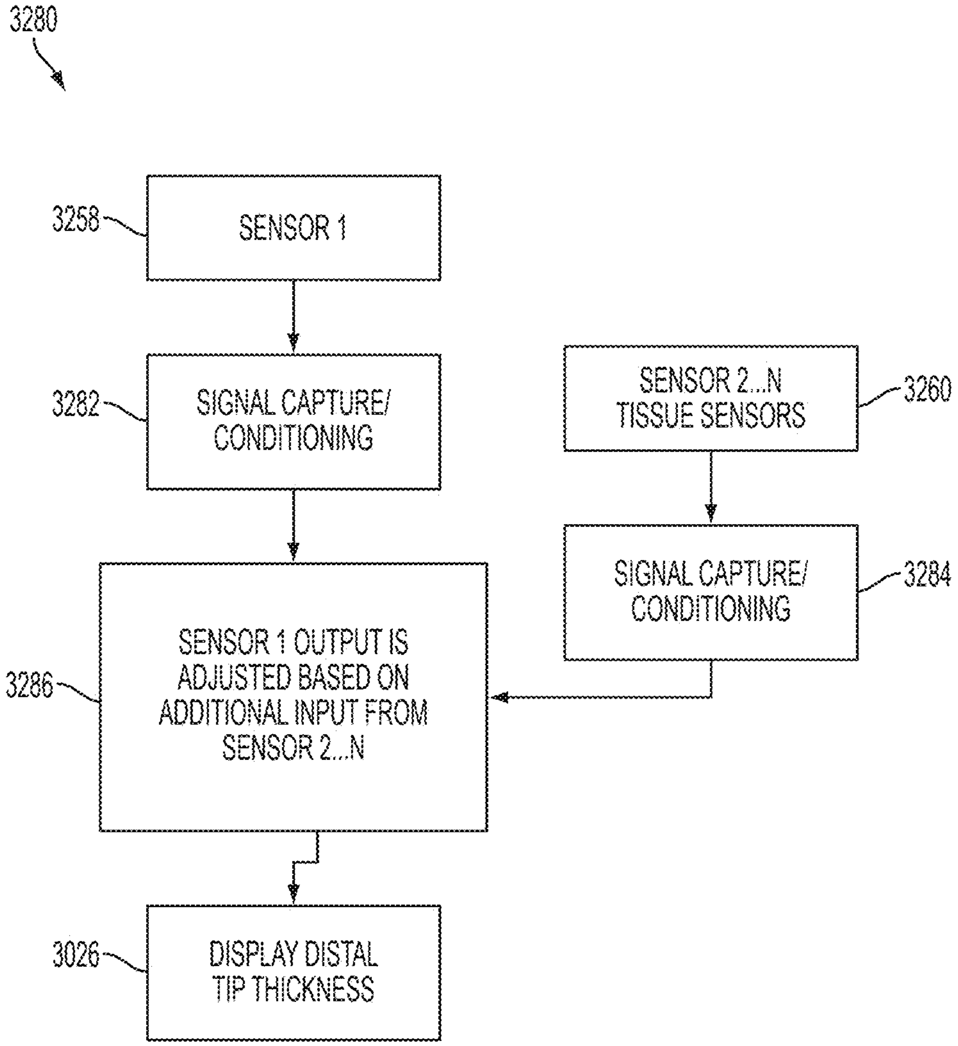
FIG. 42 is a logic diagram illustrating one embodiment of a process for determining one or more parameters of a tissue section clamped within an end effector.

FIG. 42 is a logic diagram illustrating one embodiment of a process 3280 for determining one or more parameters of a tissue section 3264 clamped within an end effector, such as, for example, the end effector 3250 illustrated in FIG. 40. In one embodiment, a first sensor 3258 is configured to detect one or more parameters of the end effector 3250 and/or a tissue section 3264 located between the anvil 3252 and the staple cartridge 3256. A first signal is generated 3282 by the first sensors 3258. The first signal is indicative of the one or more parameters detected by the first sensor 3258. One or more secondary sensors 3260 are configured to detect one or more parameters of the end effector 3250 and/or the tissue section 3264. The secondary sensors 3260 may be configured to detect the same parameters, additional parameters, or different parameters as the first sensor 3258. Secondary signals 3284 are generated by the secondary sensors 3260. The secondary signals 3284 are indicative of the one or more parameters detected by the secondary sensors 3260. The first signal and the secondary signals are provided to a processor, such as, for example, a primary processor 2006. The processor 2006 adjusts 3286 the first signal generated by the first sensor 3258 based on input generated by the secondary sensors 3260. The adjusted signal may be indicative of, for example, the true thickness of a tissue section 3264 and the fullness of the bite. The adjusted signal is displayed 3026 to an operator by, for example, a display 2026 embedded in the surgical instrument 10.

Figure 43:
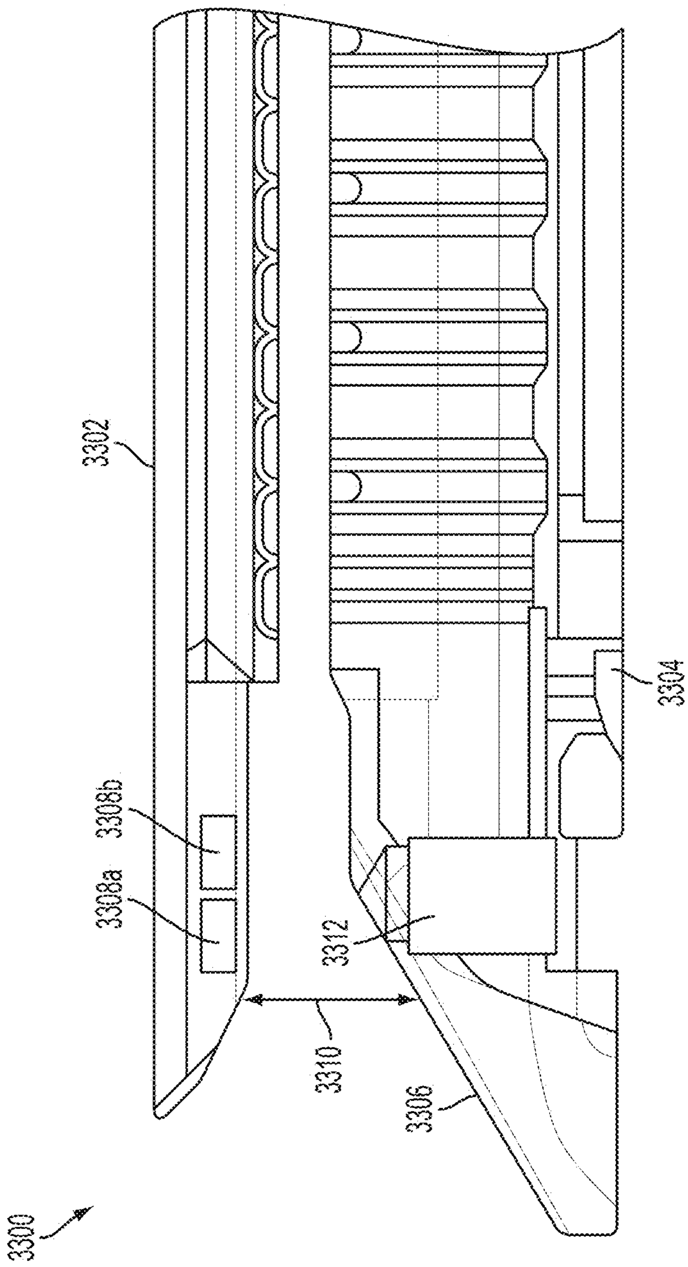
FIG. 43 illustrates one embodiment of an end effector comprising a plurality of redundant sensors.

FIG. 43 illustrates one embodiment of an end effector 3300 comprising a plurality of redundant sensors 3308*a*, 3308*b*. The end effector 3300 comprises a first jaw member, or anvil, 3302 pivotally coupled to a second jaw member 3304. the second jaw member 3304 is configured to receive a staple cartridge 3306 therein. The anvil 3302 is moveable with respect to the staple cartridge 3306 to grasp a material, such as, for example, a tissue section, between the anvil 3302 and the staple cartridge 3306. A plurality of sensors 3308*a*, 3308*b* is coupled to the anvil. The plurality of sensors 3308*a*, 3308*b* are configured to detect one or more parameters of the end effector 3300 and/or a tissue section located between the anvil 3302 and the staple cartridge 3306. In some embodiments, the plurality of sensors 3308*a*, 3308*b* are configured to detect a gap 3310 between the anvil 3302 and the staple cartridge 3306. The gap 3310 may correspond to, for example, the thickness of tissue located between the anvil 3302 and the staple cartridge 3306. The plurality of sensors 3308*a*, 3308*b* may detect the gap 3310 by, for example, detecting a magnetic field generated by a magnet 3312 coupled to the second jaw member 3304.

In some embodiments, the plurality of sensors 3308*a*, 3308*b* comprise redundant sensors. The redundant sensors are configured to detect the same properties of the end effector 3300 and/or a tissue section located between the anvil 3302 and the staple cartridge 3306. The redundant sensors may comprise, for example, Hall effect sensors configured to detect the gap 3310 between the anvil 3302 and the staple cartridge 3306. The redundant sensors provide signals representative of one or more parameters allowing a processor, such as, for example, the primary processor 2006, to evaluate the multiple inputs and determine the most reliable input. In some embodiments, the redundant sensors are used to reduce noise, false signals, and/or drift. Each of the redundant sensors may be measured in real-time during clamping, allowing time-based information to be analyzed and algorithms and/or look-up tables to recognize tissue characteristics and clamping positioning dynamically. The input of one or more of the redundant sensors may be adjusted and/or selected to identify the true tissue thickness and bite of a tissue section located between the anvil 3302 and the staple cartridge 3306.

Figure 44:
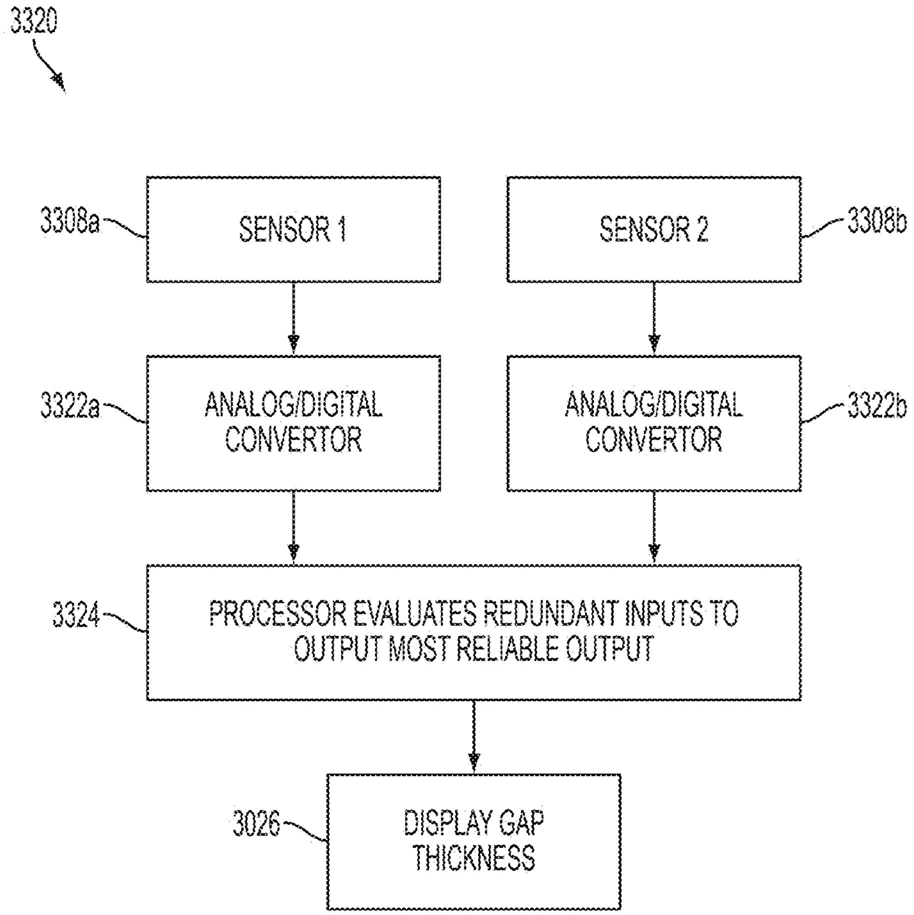
FIG. 44 is a logic diagram illustrating one embodiment of a process for selecting the most reliable output from a plurality of redundant sensors.

FIG. 44 is a logic diagram illustrating one embodiment of a process 3320 for selecting the most reliable output from a plurality of redundant sensors, such as, for example, the plurality of sensors 3308*a*, 3308*b* illustrated in FIG. 43. In one embodiment, a first signal is generated by a first sensor 3308*a*. The first signal is converted 3322*a* by an analog-to-digital convertor. One or more additional signals are generated by one or more redundant sensors 3308*b*. The one or more additional signals are converted 3322*b* by an analog-to-digital convertor. The converted signals are provided to a processor, such as, for example, the primary processor 2006. The primary processor evaluates 3324 the redundant inputs to determine the most reliable output. The most reliable output may be selected based on one or more parameters, such as, for example, algorithms, look-up tables, input from additional sensors, and/or instrument conditions. After selecting the most reliable output, the processor may adjust the output based on one or more additional sensors to reflect, for example, the true thickness and bite of a tissue section located between the anvil 3302 and the staple cartridge 3306. The adjusted most reliable output is displayed 3026 to an operator by, for example, a display 2026 embedded in the surgical instrument 10.

Figure 45:
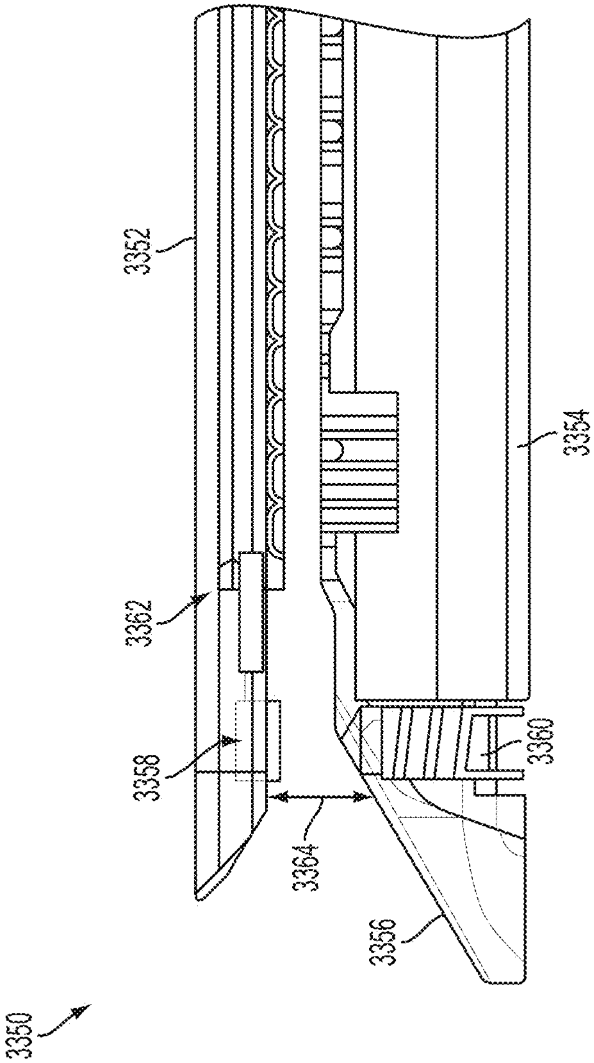
FIG. 45 illustrates one embodiment of an end effector comprising a sensor comprising a specific sampling rate to limit or eliminate false signals.

FIG. 45 illustrates one embodiment of an end effector 3350 comprising a sensor 3358 comprising a specific sampling rate to limit or eliminate false signals. The end effector 3350 comprises a first jaw member, or anvil, 3352 pivotably coupled to a second jaw member 3354. The second jaw member 3354 is configured to receive a staple cartridge 3356 therein. The staple cartridge 3356 contains a plurality of staples that may be delivered to a tissue section located between the anvil 3352 and the staple cartridge 3356. A sensor 3358 is coupled to the anvil 3352. The sensor 3358 is configured to detect one or more parameters of the end effector 3350, such as, for example, the gap 3364 between the anvil 3352 and the staple cartridge 3356. The gap 3364 may correspond to the thickness of a material, such as, for example, a tissue section, and/or the fullness of a bite of material located between the anvil 3352 and the staple cartridge 3356. The sensor 3358 may comprise any suitable sensor for detecting one or more parameters of the end effector 3350, such as, for example, a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor.

In one embodiment, the sensor 3358 comprises a magnetic sensor configured to detect a magnetic field generated by an electromagnetic source 3360 coupled to the second jaw member 3354 and/or the staple cartridge 3356. The electromagnetic source 3360 generates a magnetic field detected by the sensor 3358. The strength of the detected magnetic field may correspond to, for example, the thickness and/or fullness of a bite of tissue located between the anvil 3352 and the staple cartridge 3356. In some embodiments, the electromagnetic source 3360 generates a signal at a known frequency, such as, for example, 1 MHz. In other embodiments, the signal generated by the electromagnetic source 3360 may be adjustable based on, for example, the type of staple cartridge 3356 installed in the second jaw member 3354, one or more additional sensor, an algorithm, and/or one or more parameters.

In one embodiment, a signal processor 3362 is coupled to the end effector 3350, such as, for example, the anvil 3352. The signal processor 3362 is configured to process the signal generated by the sensor 3358 to eliminate false signals and to boost the input from the sensor 3358. In some embodiments, the signal processor 3362 may be located separately from the end effector 3350, such as, for example, in the handle 14 of a surgical instrument 10. In some embodiments, the signal processor 3362 is formed integrally with and/or comprises an algorithm executed by a general processor, such as, for example, the primary processor 2006. The signal processor 3362 is configured to process the signal from the sensor 3358 at a frequency substantially equal to the frequency of the signal generated by the electromagnetic source 3360. For example, in one embodiment, the electromagnetic source 3360 generates a signal at a frequency of 1 MHz. The signal is detected by the sensor 3358. The sensor 3358 generates a signal indicative of the detected magnetic field which is provided to the signal processor 3362. The signal is processed by the signal processor 3362 at a frequency of 1 MHz to eliminate false signals. The processed signal is provided to a processor, such as, for example, the primary processor 2006. The primary processor 2006 correlates the received signal to one or more parameters of the end effector 3350, such as, for example, the gap 3364 between the anvil 3352 and the staple cartridge 3356.

Figure 46:
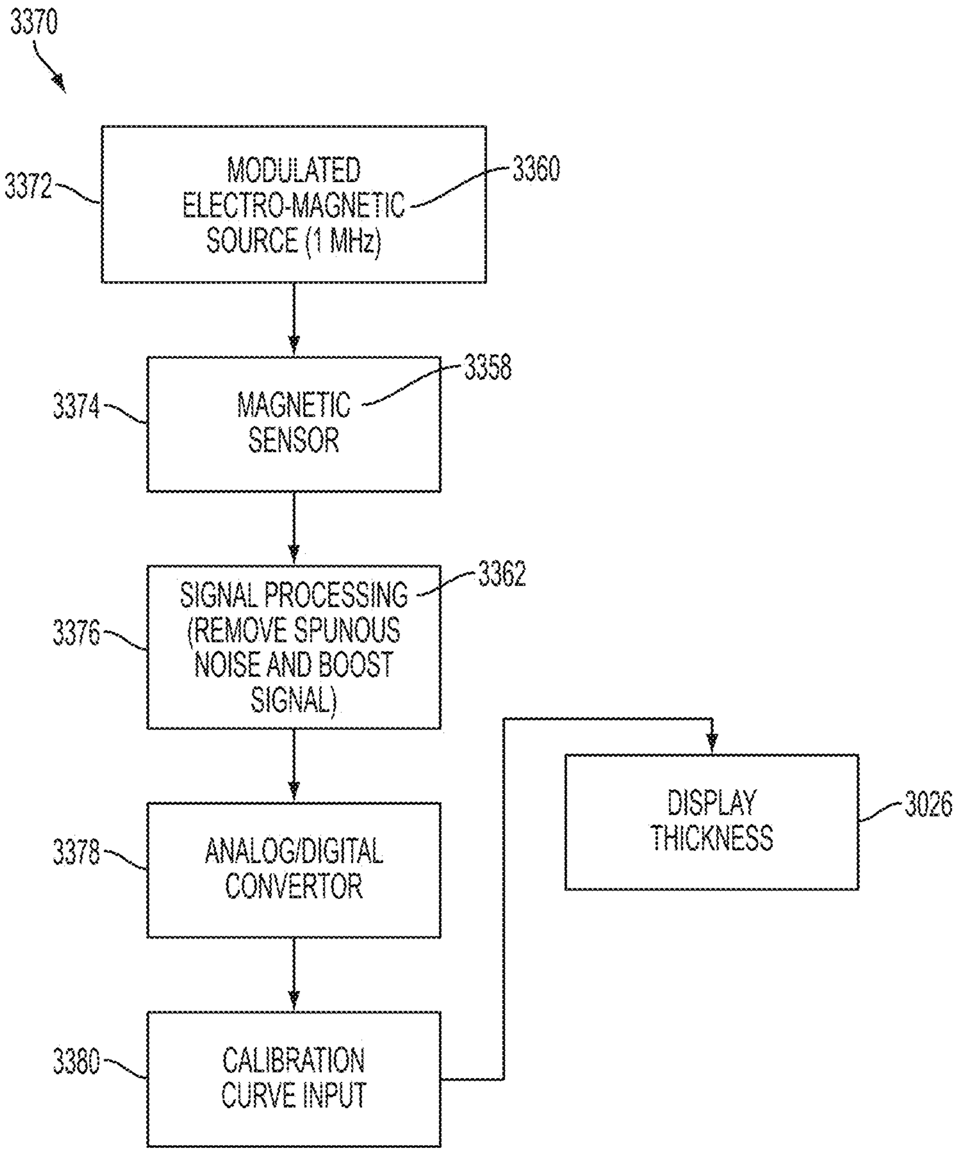
FIG. 46 is a logic diagram illustrating one embodiment of a process for generating a thickness measurement for a tissue section located between an anvil and a staple cartridge of an end effector.

FIG. 46 is a logic diagram illustrating one embodiment of a process 3370 for generating a thickness measurement for a tissue section located between an anvil and a staple cartridge of an end effector, such as, for example, the end effector 3350 illustrated in FIG. 45. In one embodiment of the process 3370, a signal is generated 3372 by a modulated electromagnetic source 3360. The generated signal may comprise, for example, a 1 MHz signal. A magnetic sensor 3358 is configured to detect 3374 the signal generated by the electromagnetic source 3360. The magnetic sensor 3358 generates a signal indicative of the detected magnetic field and provides the signal to a signal processor 3362. The signal processor 3362 processes 3376 the signal to remove noise, false signals, and/or to boost the signal. The processed signal is provided to an analog-to-digital convertor for conversion 3378 to a digital signal. The digital signal may be calibrated 3380, for example, by application of a calibration curve input algorithm and/or look-up table. The signal processing 3376, conversion 3378, and calibration 3380 may be performed by one or more circuits. The calibrated signal is displayed 3026 to a user by, for example, a display 2026 formed integrally with a surgical instrument 10.

Figure 47:
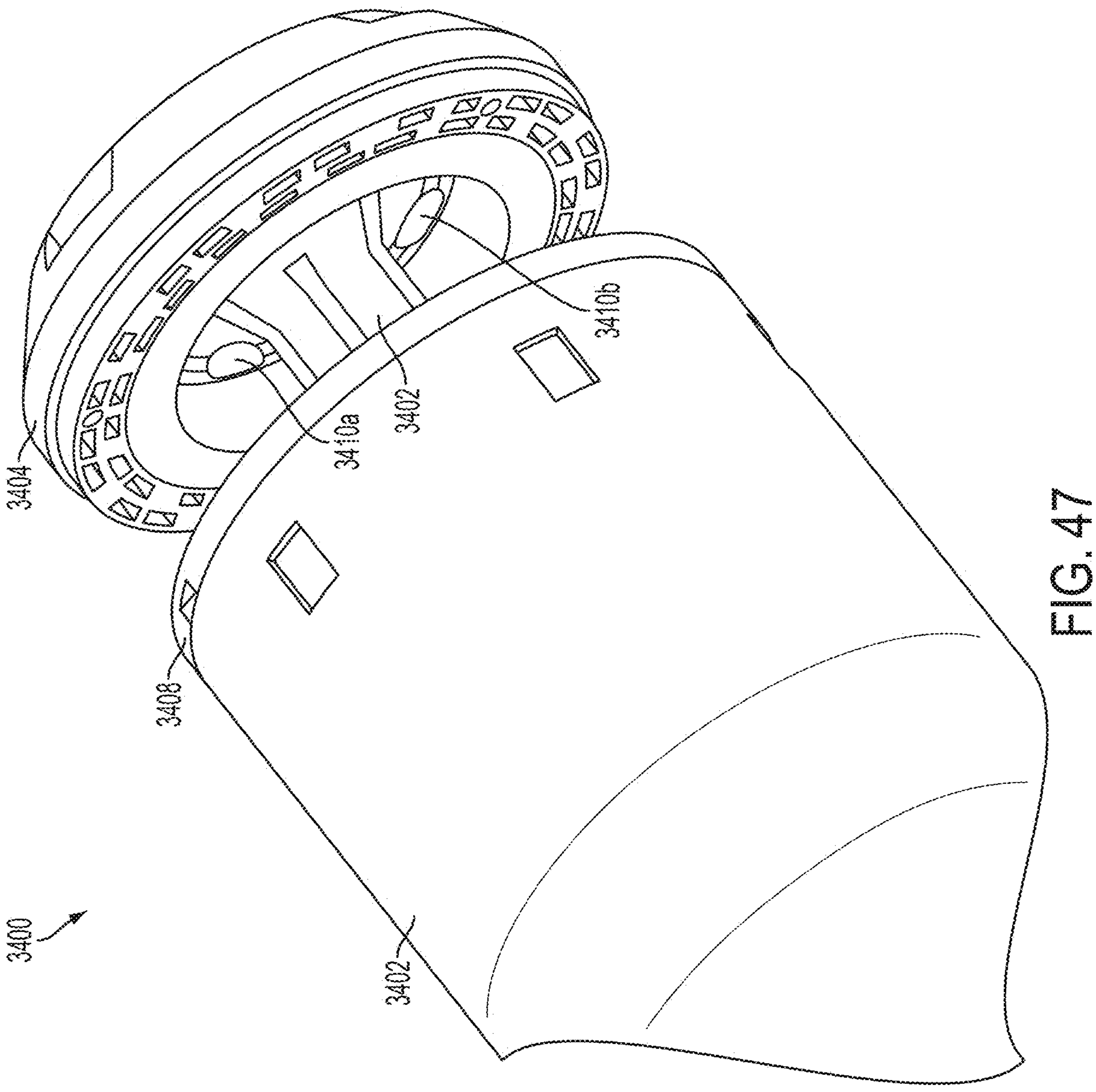
FIG. 47 illustrates one embodiment of a circular stapler.

Although the various embodiments so far described comprise an end effector having first and second jaw members pivotally coupled, the described embodiments are not so limited. For example, in one embodiment, the end effector may comprise a circular stapler end effector. FIG. 47 illustrates one embodiment of a circular stapler 3400 configured to implement one or more of the processes described in FIGS. 28-46. The circular stapler 3400 comprises a body 3402. The body 3402 may be coupled to a shaft, such as, for example, the shaft assembly 200 of the surgical instrument 10. The body 3402 is configured to receive a staple cartridge and/or one or more staples therein (not shown). An anvil 3404 is moveably coupled to the body 3402. The anvil 3404 may be coupled to the body 3402 by, for example, a shaft 3406. The shaft 3406 is receivable within a cavity within the body (not shown). In some embodiments, a breakaway washer 3408 is coupled to the anvil 3404. The breakaway washer 3408 may comprise a buttress or reinforcing material during stapling.

In some embodiments, the circular stapler 3400 comprises a plurality of sensors 3410*a*, 3410*b*. The plurality of sensor 3410*a*, 3410*b* is configured to detect one or more parameters of the circular stapler 3400 and/or a tissue section located between the body 3402 and the anvil 3404. The plurality of sensors 3410*a*, 3410*b* may be coupled to any suitable portion of the anvil 3404, such as, for example, being positioned under the breakaway washer 3408. The plurality of sensors 3410*a*, 3410*b* may be arranged in any suitable arrangement, such as, for example, being equally spaced about the perimeter of the anvil 3404. The plurality of sensors 3410*a*, 3410*b* may comprise any suitable sensors for detecting one or more parameters of the end effector 3400 and/or a tissue section located between the body 3402 and the anvil 3404. For example, the plurality of sensors 3410*a*, 3410*b* may comprise magnetic sensors, such as a Hall effect sensor, strain gauges, pressure sensors, inductive sensors, such as an eddy current sensor, resistive sensors, capacitive sensors, optical sensors, any combination thereof, and/or any other suitable sensor.

In one embodiment, the plurality of sensors 3410*a*, 3410*b* comprise a plurality of pressure sensors positioned under the breakaway washer 3408. Each of the sensors 3410*a*, 3410*b* is configured to detect a pressure generated by the presence of compressed tissue between the body 3402 and the anvil 3404. In some embodiments the plurality of sensors 3410*a*, 3410*b* are configured to detect the impedance of a tissue section located between the anvil 3404 and the body 3402. The detected impedance may be indicative of the thickness and/or fullness of tissue located between the anvil 3404 and the body 3402. The plurality of sensors 3410*a*, 3410*b* generate a plurality of signals indicative of the detected pressure. The plurality of generated signals is provided to a processor, such as, for example, the primary processor 2006. The primary processor 2006 applies one or more algorithms and/or look-up tables based on the input from the plurality of sensors 3410*a*, 3410*b* to determine one or more parameters of the end effector 3400 and/or a tissue section located between the body 3402 and the anvil 3404. For example, in one embodiment comprising a plurality of pressure sensors, the processor 2006 is configured to apply an algorithm to quantitatively compare the output of the plurality of sensors 3410*a*, 3410*b* with respect to each other and with respect to a predetermined threshold. In one embodiment, if the delta, or difference, between the outputs of the plurality of sensors 3410*a*, 3410*b* is greater than a predetermined threshold, feedback is provided to the operator indicating a potential uneven loading condition. In some embodiments, the end effector 3400 may be coupled to a shaft comprising one or more additional sensors, such as, for example, the drive shaft 3504 described in connection to FIG. 50 below.

Figure 48A:
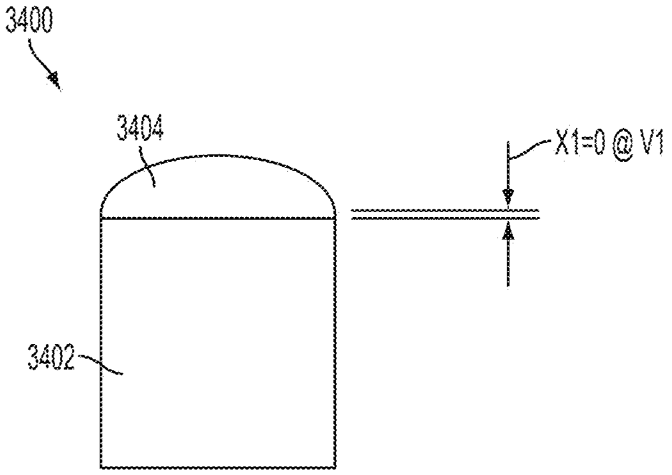
FIGS. 48A-48D illustrate a clamping process of the circular stapler illustrated in FIG. 47, where
Figure 48B:
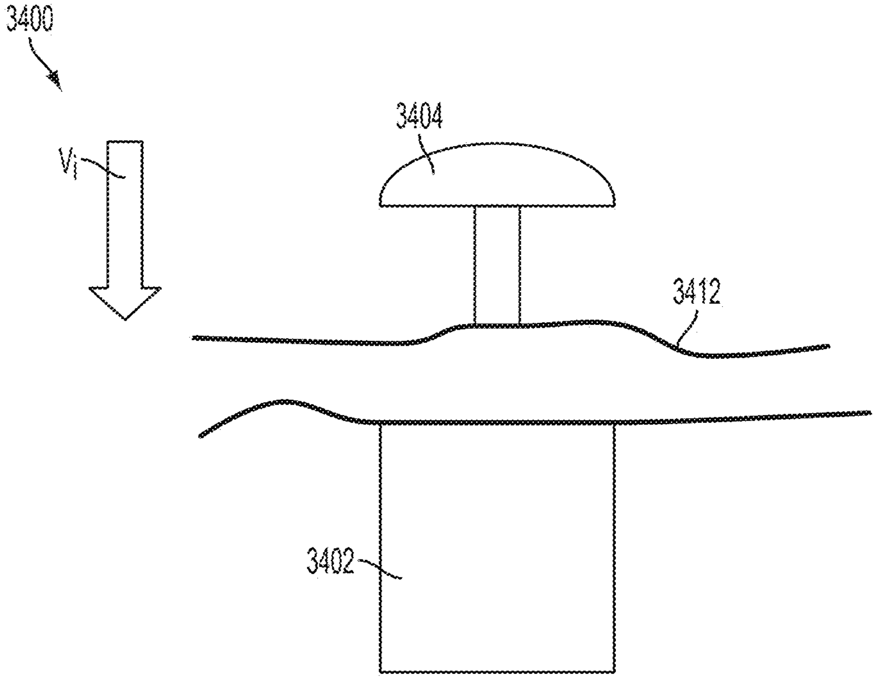
Figure 48C:
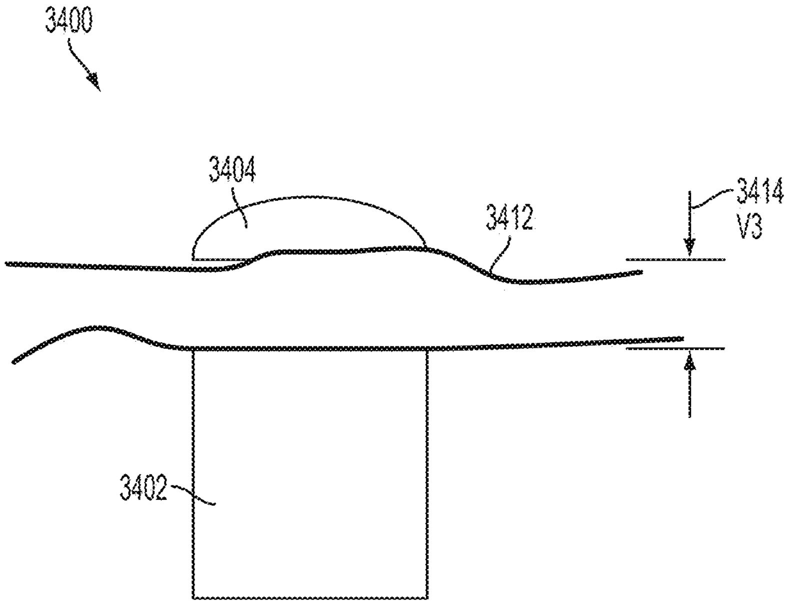
Figure 48D:
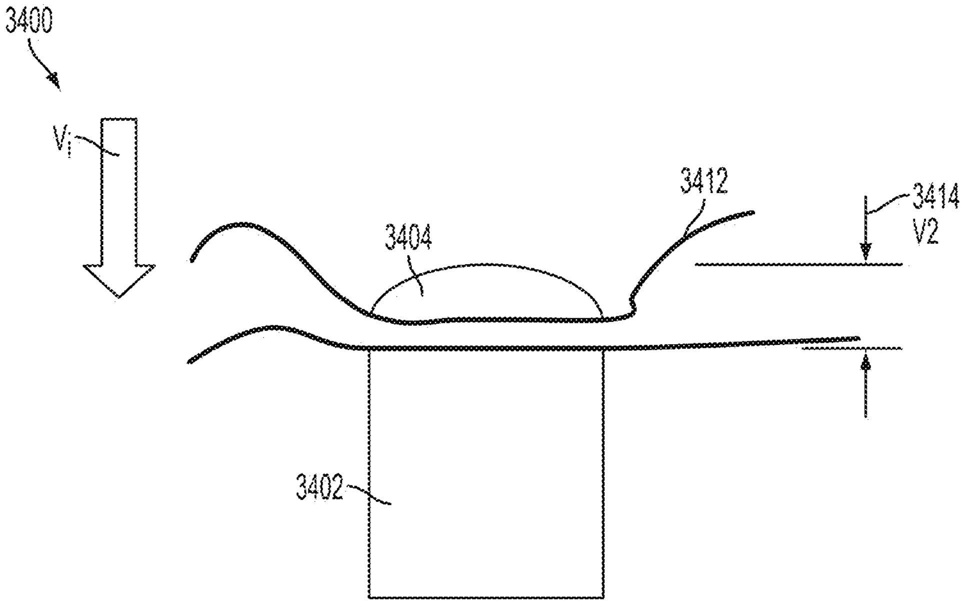

FIGS. 48A-48D illustrate a clamping process of the circular stapler 3400 illustrated in FIG. 47. FIG. 48A illustrates the circular stapler 3400 in an initial position with the anvil 3404 and the body 3402 in a closed configuration. The circular stapler 3400 is positioned at a treatment site in the closed configuration. Once the circular stapler 3400 is positioned, the anvil 3404 is moved distally to disengage with the body 3402 and create a gap configured to receive a tissue section 3412 therein, as illustrated in FIG. 48B. The tissue section 3412 is compressed to a predetermined compression 3414 between the anvil 3404 and the body 3402, as shown in FIG. 48C. The tissue section 3412 is further compressed between the anvil 3404 and the body 3402. The additional compression deploys one or more staples from the body 3402 into the tissue section 3412. The staples are shaped by the anvil 3404. FIG. 48D illustrates the circular stapler 3400 in position corresponding to staple deployment. Proper staple deployment is dependent on obtaining a proper bite of tissue between the body 3402 and the anvil 3404. The plurality of sensors 3410*a*, 3410*b* disposed on the anvil 3404 allow a processor to determine that a proper bite of tissue is located between the anvil 3404 and the body 3402 prior to deployment of the staples.

Figure 49:
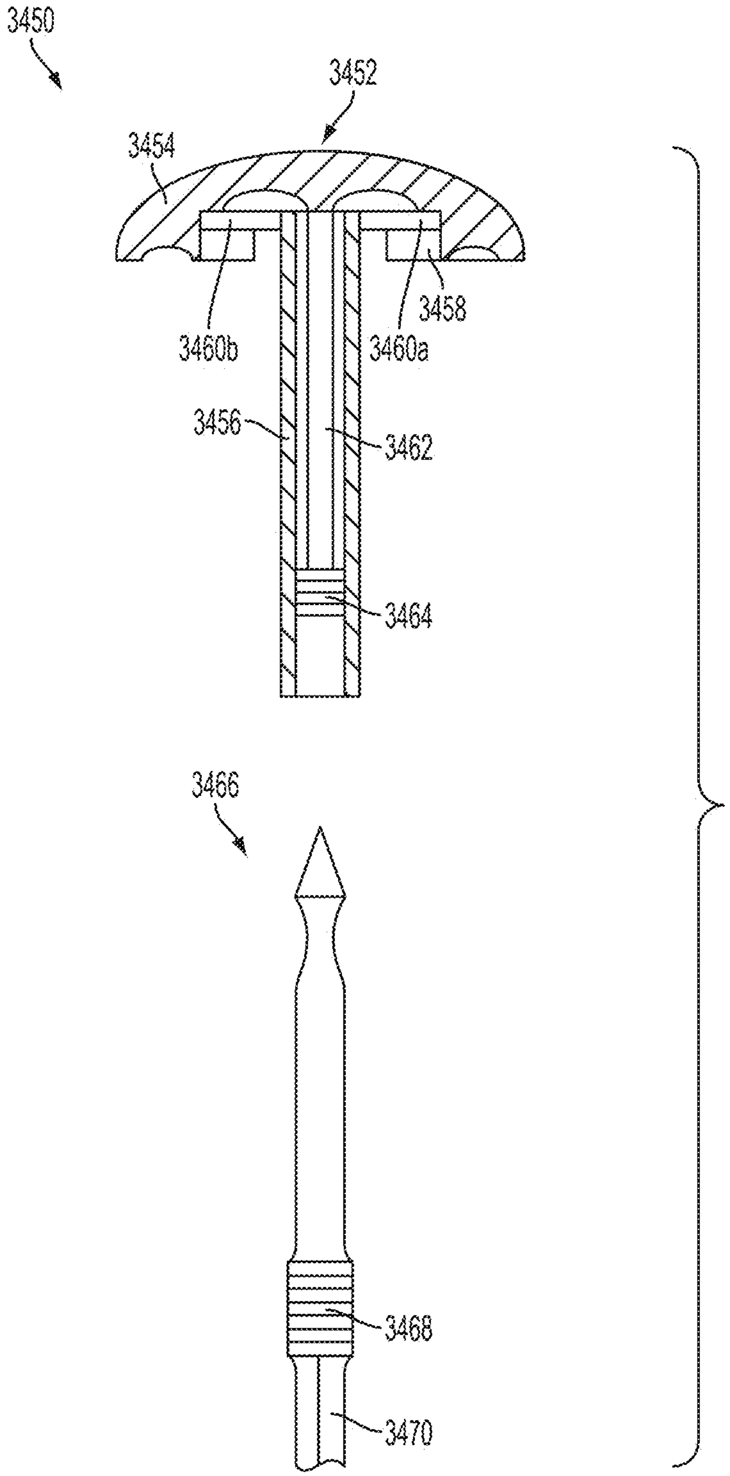
FIG. 49 illustrates one embodiment of a circular staple anvil and an electrical connector configured to interface therewith.

FIG. 49 illustrates one embodiment of a circular staple anvil 3452 and an electrical connector 3466 configured to interface therewith. The anvil 3452 comprises an anvil head 3454 coupled to an anvil shaft 3456. A breakaway washer 3458 is coupled to the anvil head 3452. A plurality of pressure sensors 3460*a*, 3460*b* are coupled to the anvil head 3452 between the anvil head 3452 and the breakaway washer 3458. A flex circuit 3462 is formed on the shaft 3456. The flex circuit 3462 is coupled to the plurality of pressure sensors 3460*a*, 3460*b*. One or more contacts 3464 are formed on the shaft 3456 to couple the flex circuit 3462 to one or more circuits, such as, for example, the control circuit 2000 of the surgical instrument 10. The flex circuit 3462 may be coupled to the one or more circuits by an electrical connector 3466. The electrical connector 3466 is coupled to the anvil 3454. For example, in one embodiment, the shaft 3456 is hollow and configured to receive the electrical connector 3466 therein. The electrical connector 3466 comprises a plurality of contacts 3468 configured to interface with the contacts 3464 formed on the anvil shaft 3456. The plurality of contacts 3468 on the electrical connector 3466 are coupled to a flex circuit 3470 which is coupled the one or more circuits, such as, for example, a control circuit 2000.

Figure 50:
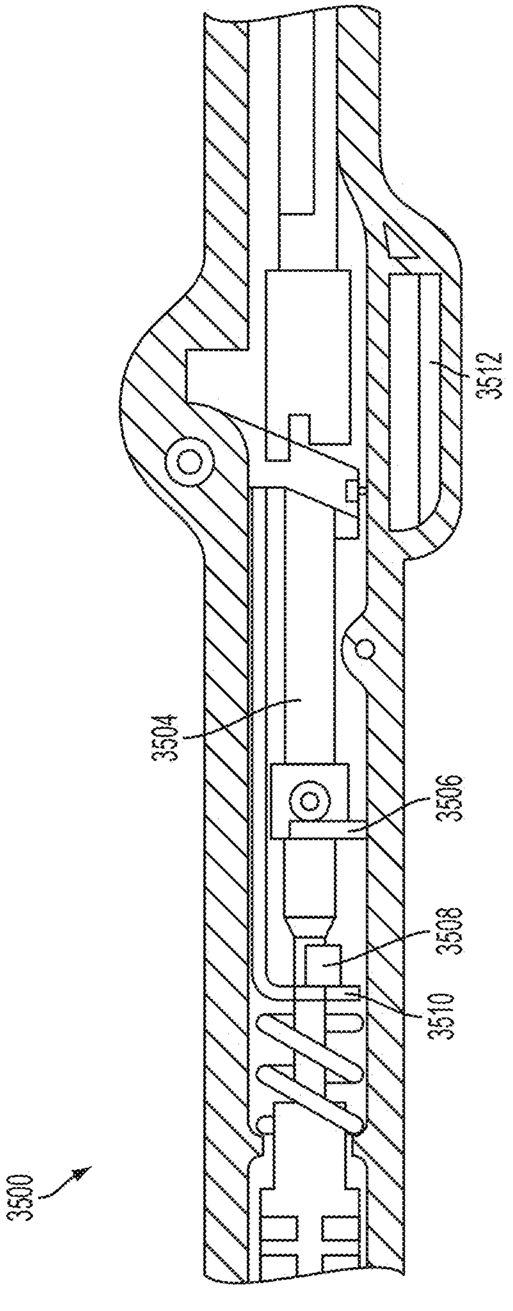
FIG. 50 illustrates one embodiment of a surgical instrument comprising a sensor coupled to a drive shaft of the surgical instrument.

FIG. 50 illustrates one embodiment of a surgical instrument 3500 comprising a sensor 3506 coupled to a drive shaft 3504 of the surgical instrument 3500. The surgical instrument 3500 may be similar to the surgical instrument 10 described above. The surgical instrument 3500 comprises a handle 3502 and a drive shaft 3504 coupled to a distal end of the handle. The drive shaft 3504 is configured to receive an end effector (not shown) at the distal end. A sensor 3506 is fixedly mounted in the drive shaft 3504. The sensor 3506 is configured to detect one or more parameters of the drive shaft 3504. The sensor 3506 may comprise any suitable sensor, such as, for example, a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor.

In some embodiments, the sensor 3506 comprises a magnetic Hall effect sensor. A magnet 3508 is located within the drive shaft 3504. The sensor 3506 is configured to detect a magnetic field generated by the magnet 3508. The magnet 3508 is coupled to a spring-backed bracket 3510. The spring-backed bracket 3510 is coupled to the end effector. The spring-backed bracket 3510 is moveable in response to an action of the end effector, for example, compression of an anvil towards a body and/or second jaw member. The spring-backed bracket 3510 moves the magnet 3508 in response to the movement of the end effector. The sensor 3506 detects the change in the magnetic field generated by the magnet 3508 and generates a signal indicative of the movement of the magnet 3508. The movement of the magnet 3508 may correspond to, for example, the thickness of tissue clamped by the end effector. The thickness of the tissue may be displayed to an operator by, for example, a display 3512 embedded in the handle 3502 of the surgical instrument 3500. In some embodiments, the Hall effect sensor 3508 may be combined with one or more additional sensors, such as, for example, the pressure sensors illustrated in FIG. 47.

Figure 51:
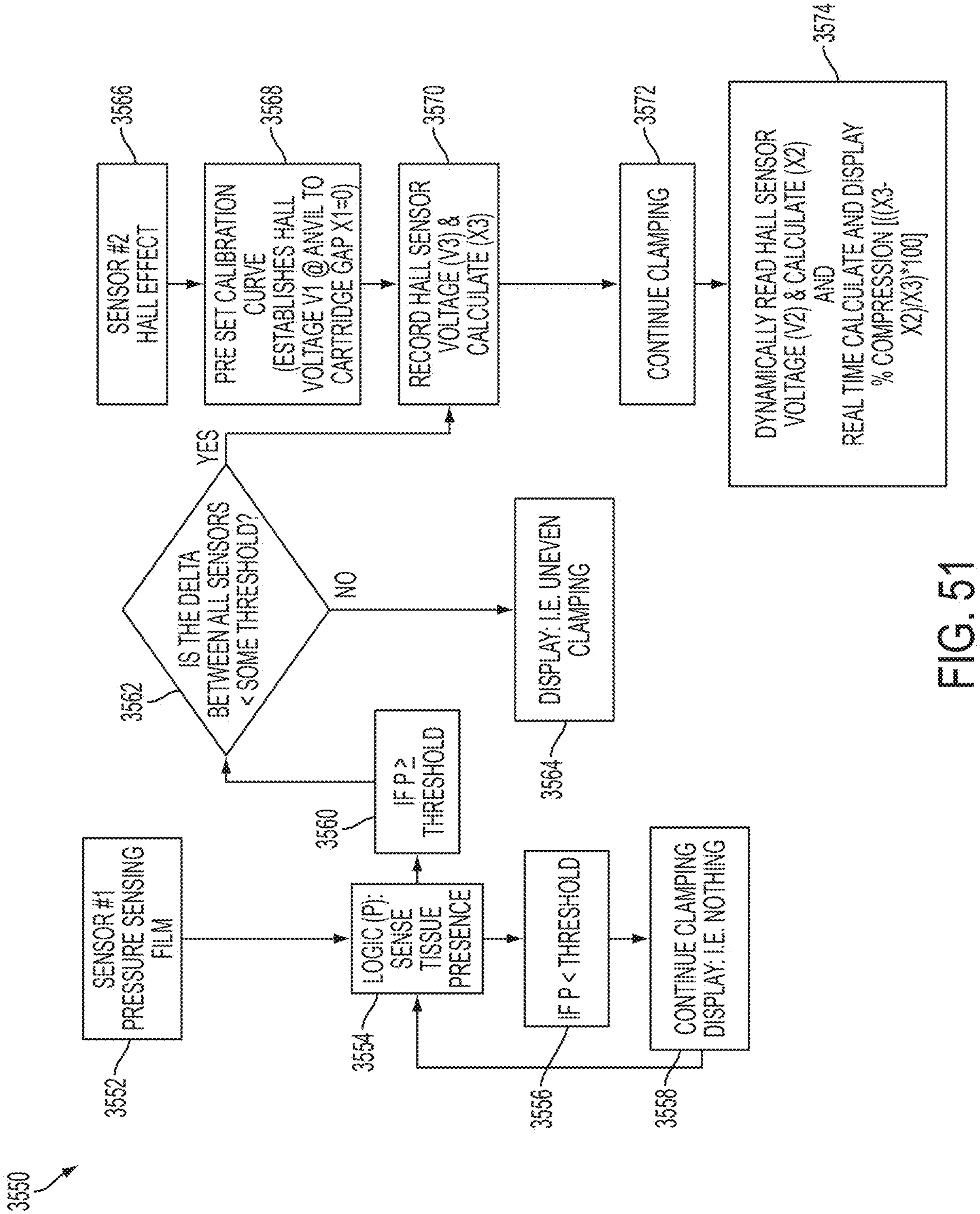
FIG. 51 is a flow chart illustrating one embodiment of a process for determining uneven tissue loading in an end effector.

FIG. 51 is a flow chart illustrating one embodiment of a process 3550 for determining uneven tissue loading in an end effector, for example, the end effector 3400 illustrated in FIG. 47 coupled to the surgical instrument 3500 illustrated in FIG. 50. In one embodiment, the process 3550 comprises utilizing one or more first sensors 3552, such as, for example, a plurality of pressure sensors, to detect 3554 the presence of tissue within an end effector. During a clamping operation of the end effector 3400, the input from the pressure sensors, P, is analyzed to determine the value of P. If P is less 3556 than a predetermined threshold, the end effector 3400 continues 3558 the clamping operation. If P is greater than or equal to 3560 the predetermined threshold, clamping is stopped. The delta (difference) between the plurality of sensors 3552 is compared 3562. If the delta is greater than a predetermined delta, the surgical instrument 3500 displays 3564 a warning to the user. The warning may comprise, for example, a message indicating that there is uneven clamping in the end effector. If the delta is less than or equal to the predetermined delta, the input of the one or more sensors 3552 is compared to an input from an additional sensor 3566.

In some embodiments, a second sensor 3566 is configured to detect one or more parameters of the surgical instrument 3500. For example, in one some embodiments, a magnetic sensor, such as, for example, a Hall effect sensor, is located in a shaft 3504 of the surgical instrument 3500. The second sensor 3566 generates a signal indicative of the one or more parameters of the surgical instrument 3500. A preset calibration curve is applied 3568 to the input from the second sensor 3566. The preset calibration curve may adjust 3568 a signal generated by the second sensor 3566, such as, for example, a Hall voltage generated by a Hall effect sensor. For example, in one embodiment, the Hall effect voltage is adjusted such that the generated Hall effect voltage is set at a predetermined value when the gap between the anvil 3404 and the body 3402, X1, is equal to zero. The adjusted sensor 3566 input is used to calculate 3570 a distance, X3, between the anvil 3404 and the body 3402 when the pressure threshold P is met. The clamping process is continued 3572 to deploy a plurality of staples into the tissue section clamped in the end effector 3400. The input from the second sensor 3566 changes dynamically during the clamping procedure and is used to calculate the distance, X2, between the anvil 3404 and the body 3402 in real-time. A real-time percent compression is calculated 3574 and displayed to an operator. In one embodiment, the percent compression is calculated as: [((X3−X2)/X3)*100].

In some embodiments, one or more of the sensors illustrated in FIGS. 28-50 are used to indicate: whether the anvil is attached to the body of the surgical device; the compressed tissue gap; and/or whether the anvil is in a proper position for removing the device, or any combination of these indicators.

In some embodiments, one or more of the sensors illustrated in FIGS. 28-50 are used to affect device performance. One or more control parameters of a surgical device 10 may be adjusted by at least one sensor output. For example, in some embodiments, the speed control of a firing operation may be adjusted by the output of one or more sensors, such as, for example, a Hall effect sensor. In some embodiments, one or more the sensors may adjust a closure and/or clamping operation based on load and/or tissue type. In some embodiments, multiple stage compression sensors allow the surgical instrument 10 to stop closure at a predetermined load and/or a predetermined displacement. The control circuit 2000 may apply one or more predetermined algorithms to apply varying compression to a tissue section to determine a tissue type, for example, based on a tissue response. The algorithms may be varied based on closure rate and/or predetermined tissue parameters. In some embodiments, one or more sensors are configured to detect a tissue property and one or more sensors are configured to detect a device property and/or configuration parameter. For example, in one embodiment, capacitive blocks may be formed integrally with a staple cartridge to measure skew.

Circuitry and Sensors for Powered Medical Device

Figure 52:
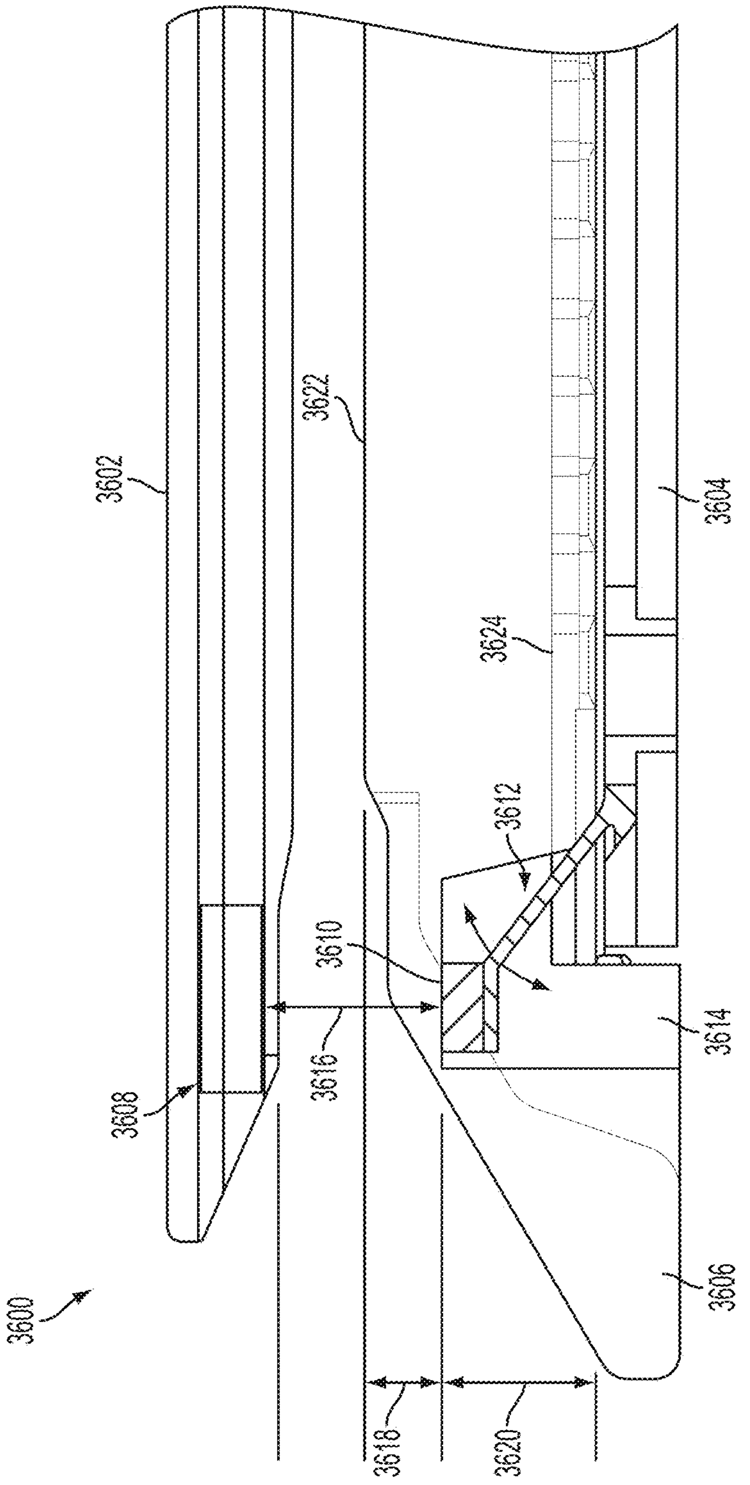
FIG. 52 illustrates one embodiment of an end effector configured to determine one or more parameters of a tissue section during a clamping operation.

FIG. 52 illustrates one embodiment of an end effector 3600 configured to determine one or more parameters of a tissue section during a clamping operation. The end effector 3600 comprises a first jaw member, or anvil, 3602 pivotally coupled to a second jaw member 3604. The second jaw member 3604 is configured to receive a staple cartridge 3606 therein. The staple cartridge 3606 contains a plurality of staples (not shown) configured to be deployed into a tissue section during a clamping and stapling operation. The staple cartridge 3606 comprises a staple cartridge deck 3622 having a predetermined height. The staple cartridge 3606 further comprises a slot 3624 defined within the body of the staple cartridge, similar to slot 193 described above. A Hall effect sensor 3608 is configured to detect the distance 3616 between the Hall effect sensor 3608 and a magnet 3610 coupled to the second jaw member 3604. The distance 3616 between the Hall effect sensor 3608 and the magnet 3610 is indicative of a thickness of tissue located between the anvil 3602 and the staple cartridge deck 3622.

The second jaw member 3604 is configured to receive a plurality of staple cartridge 3606 types. The types of staple cartridge 3606 may vary by, for example, containing different length staples, comprising a buttress material, and/or containing different types of staples. In some embodiments, the height 3618 of the staple cartridge deck 3622 may vary based on the type of staple cartridge 3606 coupled to the second jaw member 3604. The varying cartridge height 3618 may result in an inaccurate thickness measurement by the Hall effect sensor 3608. For example, in one embodiment, a first cartridge comprises a first cartridge deck height X and a second cartridge comprises a second cartridge deck height Y, where Y>X. A fixed Hall effect sensor 3608 and fixed magnet will produce an accurate thickness measurement only for one of the two cartridge deck heights. In some embodiments, an adjustable magnet is used to compensate for various deck heights.

In some embodiments, the second jaw member 3604 and the staple cartridge 3606 comprise a magnet cavity 3614. The magnet cavity 3614 is configured to receive the magnet 3610 therein. The magnet is coupled to a spring-arm 3612. The spring-arm 3612 is configured to bias the magnet towards the upper surface of the magnet cavity 3614. A depth 3620 of the magnet cavity 3614 varies depending on the deck height 3618 of the staple cartridge 3606. For example, each staple cartridge 3606 may define a cavity depth 3620 such that the upper surface of the cavity 3614 is a set distance from the plane of the deck 3622. The magnet 3610 is biased against the upper surface of the cavity 3614. The magnetic reference of the magnet 3610, as viewed by the Hall effect sensor 3608, is consistent relative to all cartridge decks but variable relative to the slot 3624. For example, in some embodiments, the upper-biased magnet 3610 and the cavity 3614 provide a set distance 3616 from the Hall effect sensor 3608 to the magnet 3610, regardless of the staple cartridge 3606 inserted into the second jaw member 3604. The set distance 3616 allows the Hall effect sensor 3608 to generate an accurate thickness measurement irrespective of the staple cartridge 3606 type. In some embodiments, the depth 3620 of the cavity 3614 may be adjusted to calibrate the Hall effect sensor 3608 for one or more surgical procedures.

Figure 53A:
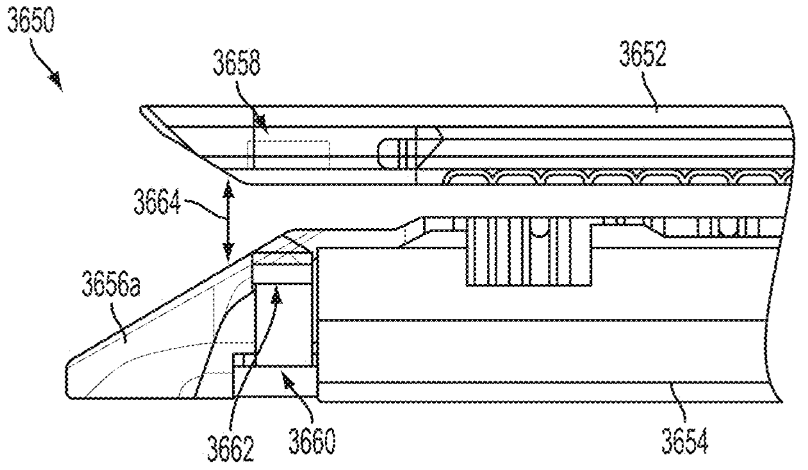
FIGS. 53A and 53B illustrate an embodiment of an end effector configured to normalize a Hall effect voltage irrespective of a deck height of a staple cartridge.
Figure 53B:
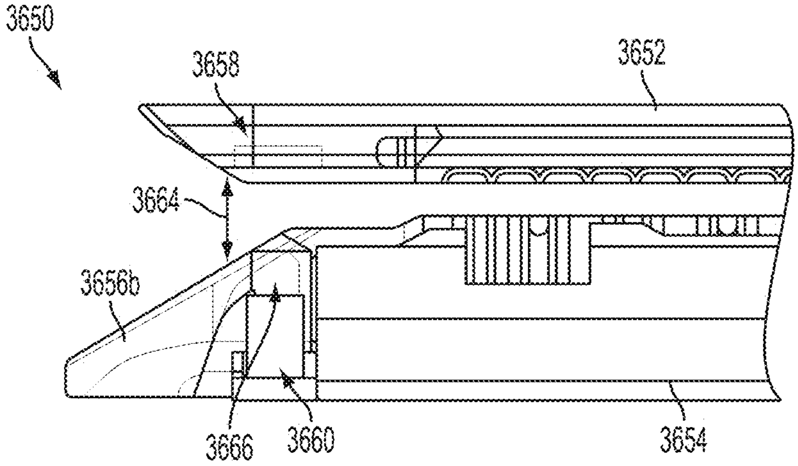

FIGS. 53A and 53B illustrate an embodiment of an end effector 3650 configured to normalize a Hall effect voltage irrespective of a deck height of a staple cartridge 3656. FIG. 53A illustrates one embodiment of the end effector 3650 comprising a first cartridge **3656*a* inserted therein. The end effector 3650 comprises a first jaw member, or anvil, 3652 pivotally coupled to a second jaw member 3654 to grasp tissue therebetween. The second jaw member 3654 is configured to receive a staple cartridge 3656*a*. The staple cartridge 3656*a* may comprise a variety of staple lengths, buttress materials, and/or deck heights. A magnetic sensor 3658, such as, for example, a Hall effect sensor, is coupled to the anvil 3652. The magnetic sensor 3658 is configured to detect a magnetic field generated by a magnet 3660**. The detected magnetic field strength is indicative of the distance

3664 between the magnetic sensor 3658 and the magnet 3660, which may be indicative of, for example, a thickness of a tissue section grasped between the anvil 3652 and the staple cartridge 3656. As noted above, various staple cartridges 3656*a* may comprise varying deck heights which create differences in the calibrated compression gap 3664.

In some embodiments, a magnetic attenuator 3662 is coupled to the staple cartridge 3656*a*. The magnetic attenuator 3662 is configured to attenuate the magnetic flux generated to by the magnet 3660. The magnetic attenuator 3662 is calibrated to produce a magnetic flux based on the height of the staple cartridge 3656*a*. By attenuating the magnet 3660 based on the staple cartridge 3656 type, the magnetic attenuator 3662 normalizes the magnetic sensor 3658 signal to the same calibration level for various deck heights. The magnetic attenuator 3662 may comprise any suitable magnet attenuator, such as, for example, a ferrous metallic cap. The magnetic attenuator 3662 is molded into the staple cartridge 3656*a* such that the magnetic attenuator 3662 is positioned above the magnet 3660 when the staple cartridge 3656 is inserted into the second jaw member 3654.

In some embodiments, attenuation of the magnet 3660 is not required for the deck height of the staple cartridge. FIG. 53B illustrates one embodiment of the end effector 3650 comprising a second staple cartridge 3656*b* coupled to the second jaw member 3654. The second staple cartridge 3656*b* comprises a deck height matching the calibration of the magnet 3660 and the Hall effect sensor 3658, and therefore does not require attenuation. As shown in FIG. 53B, the second staple cartridge 3656*b* comprises a cavity 3666 in place of the magnetic attenuator 3662 of the first staple cartridge 3656*a*. In some embodiments, larger and/or smaller attenuation members are provided depending on the height of the cartridge deck. The design of the attenuation member 3662 shape may be optimized to create features in the response signal generated by the Hall effect sensor 3658 that allow for the distinction of one or more additional cartridge attributes.

Figure 54:
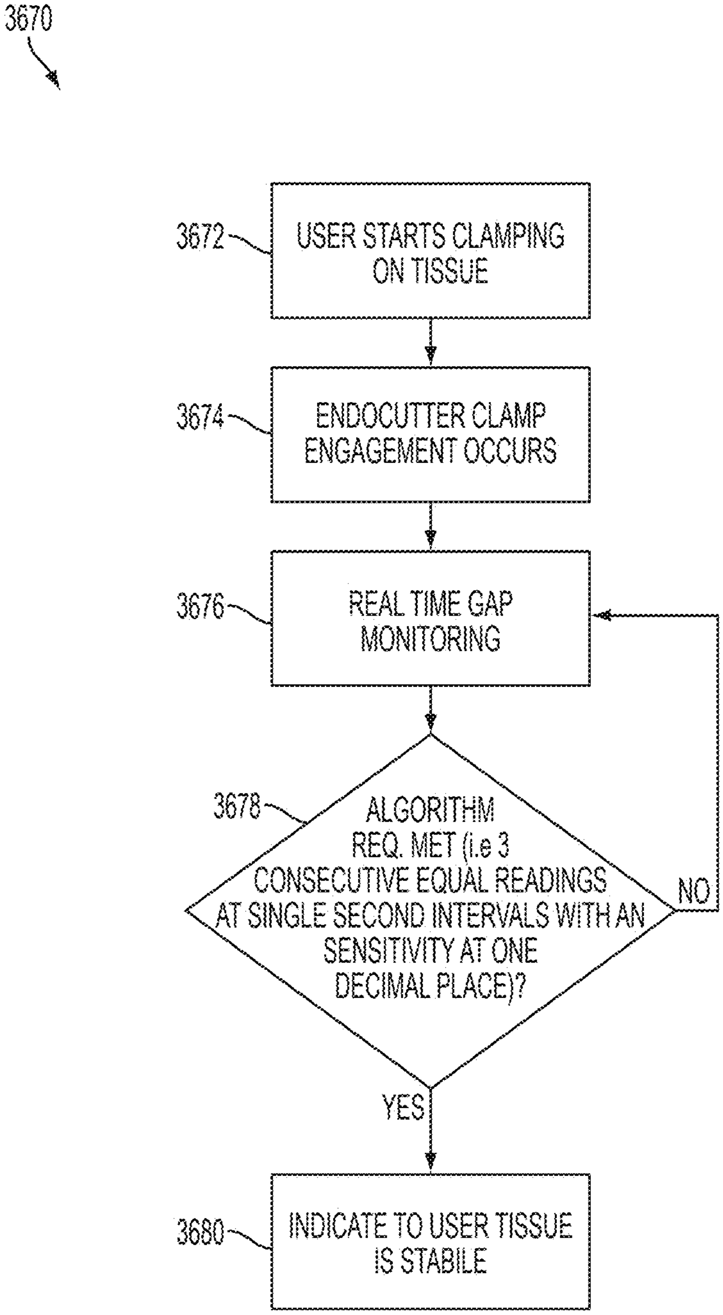
FIG. 54 is a logic diagram illustrating one embodiment of a process for determining when the compression of tissue within an end effector, such as, for example, the end effector illustrated in FIGS. 53A-53B, has reached a steady state.

FIG. 54 is a logic diagram illustrating one embodiment of a process 3670 for determining when the compression of tissue within an end effector, such as, for example, the end effector 3650 illustrated in FIGS. 53A-53B, has reached a steady state. In some embodiments, a clinician initiates 3672 a clamping procedure to clamp tissue within the end effector, for example, between an anvil 3652 and staple cartridge 3656. The end effector engages 3674 with tissue during the clamping procedure. Once the tissue has been engaged 3674, the end effector begins 3676 real time gap monitoring. The real time gap monitoring monitors the gap between, for example, the anvil 3652 and the staple cartridge 3656 of the end effector 3650. The gap may be monitored by, for example, a sensor 3658, such as a Hall effect sensor, coupled to the end effector 3650. The sensor 3658 may be coupled to a processor, such as, for example, the primary processor 2006. The processor determines 3678 when tissue clamping requirements of the end effector 3650 and/or the staple cartridge 3656 have been met. Once the processor determines that the tissue has stabilized, the process indicates 3680 to the user that the tissue has stabilized. The indication may be provided by, for example, a display embedded within a surgical instrument 10.

In some embodiments, the gap measurement is provided by a Hall effect sensor. The Hall effect sensor may be located, for example, at the distal tip of an anvil 3652. The Hall effect sensor is configured to measure the gap between the anvil 3652 and a staple cartridge 3656 deck at the distal tip. The measured gap may be used to calculate a jaw closure gap and/or to monitor a change in tissue compression of a tissue section clamped in the end effector 3650. In one embodiment, the Hall effect sensor is coupled to a processor, such as, for example, the primary processor 2006. The processor is configured to receive real time measurements from the Hall effect sensor and compare the received signal to a predetermined set of criteria. For example, in one embodiment, a logic equation at equally spaced intervals, such as one second, is used to indicate stabilization of a tissue section to the user when a gap reading remains unchanged for a predetermined interval, such as, for example, 3.0 seconds. Tissue stabilization may also be indicated after a predetermined time period, such as, for example, 15.0 seconds. As another example, tissue stabilization may be indicated when yn=yn+1=yn+2, where y equals a gap measurement of the Hall effect sensor and n is a predetermined measurement interval. A surgical instrument 10 may display an indication to a user, such as, for example, a graphical and/or numerical representation, when stabilization has occurred.

Figure 55:
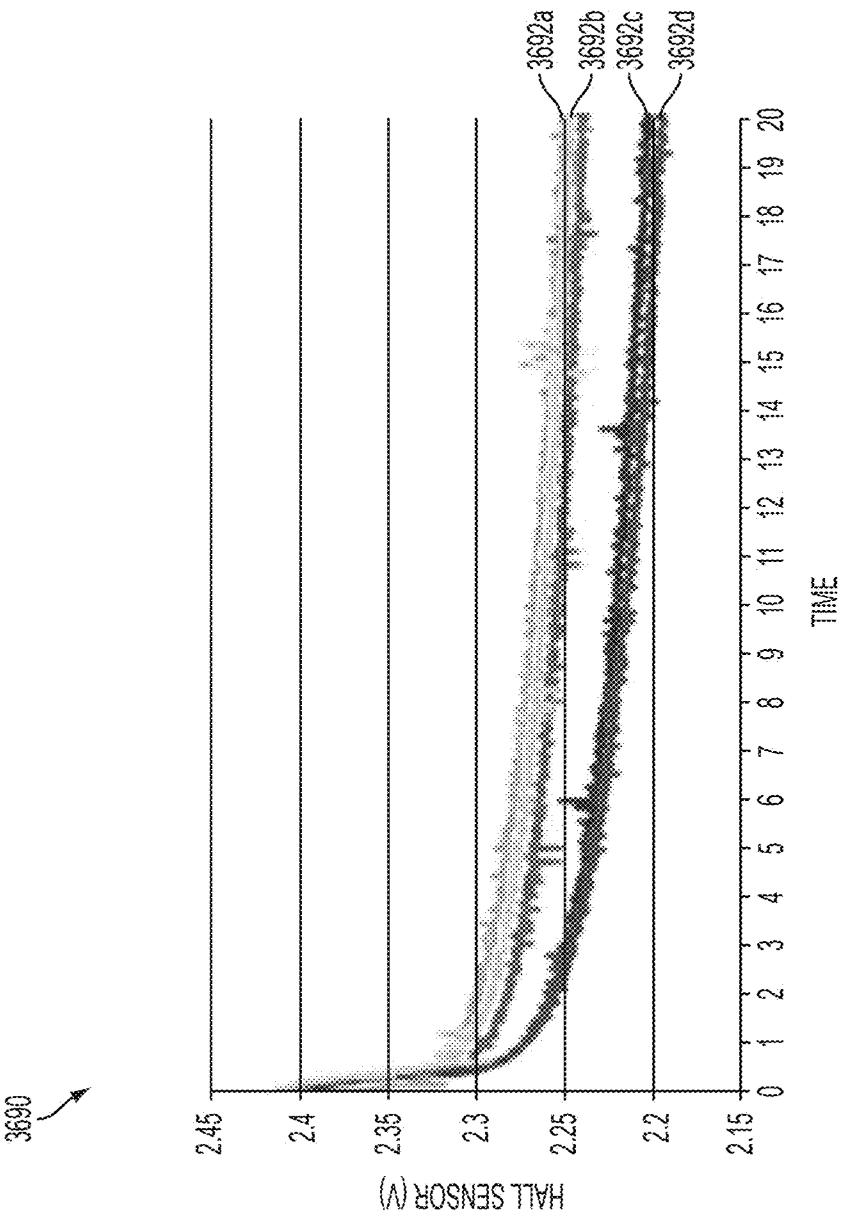
FIG. 55 is a graph illustrating various Hall effect sensor readings.

FIG. 55 is a graph 3690 illustrating various Hall effect sensor readings 3692*a*-3692*d*. As shown in graph 3690, a thickness, or compression, of a tissue section stabilizes after a predetermined time period. A processor, such as, for example, the primary processor 2006, may be configured to indicate when the calculated thickness from a sensor, such as a Hall effect sensor, is relatively consistent or constant over a predetermined time period. The processor 2006 may indicate to a user, for example, through a number display, that the tissue has stabilized.

Figure 56:
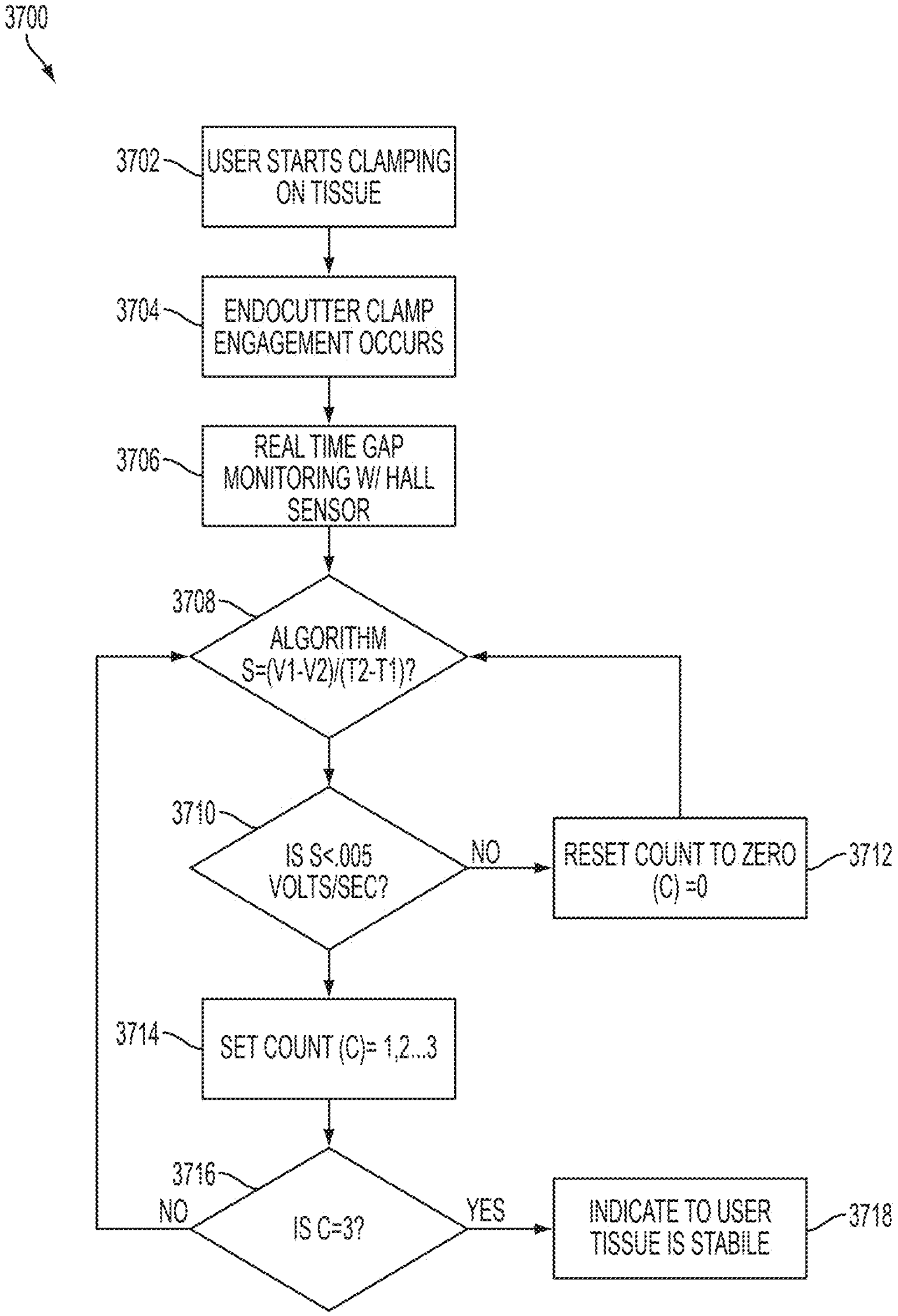
FIG. 56 is a logic diagram illustrating one embodiment of a process for determining when the compression of tissue within an end effector, such as, for example, the end effector illustrated in FIGS. 53A-53B, has reached a steady state.

FIG. 56 is a logic diagram illustrating one embodiment of a process 3700 for determining when the compression of tissue within an end effector, such as, for example, the end effector 3650 illustrated in FIGS. 53A-53B, has reached a steady state. In some embodiments, a clinician initiates 3702 a clamping procedure to clamp tissue within the end effector, for example, between an anvil 3652 and staple cartridge 3656. The end effector engages 3704 with tissue during the clamping procedure. Once the tissue has been engaged 3704, the end effector begins 3706 real time gap monitoring. The real time gap monitoring technique monitors 3706 the gap between, for example, the anvil 3652 and the staple cartridge 3656 of the end effector 3650. The gap may be monitored 3706 by, for example, a sensor 3658, such as a Hall effect sensor, coupled to the end effector 3650. The sensor 3658 may be coupled to a processor, such as, for example, the primary processor 2006. The processor is configured to execute one or more algorithms determine when tissue section compressed by the end effector 3650 has stabilized.

For example, in the embodiment illustrated in FIG. 56, the process 3700 is configured to utilize a slop calculation to determine stabilization of tissue. The processor calculates 3708 the slope, S, of an input from a sensor, such as a Hall effect sensor. The slope may be calculated 3708 by, for example, the equation S=((V_1−V_2))/((T_1−T_2)). The processor compares 3710 the calculated slope to a predetermined value, such as, for example, 0.005 volts/sec. If the value of the calculated slope is greater than the predetermined value, the processor resets 3712 a count, C, to zero. If the calculated slope is less than or equal to the predetermined value, the processor increments 3714 the value of the count C. The count, C, is compared 3716 to a predetermined threshold value, such as, for example, 3. If the value of the count C is greater than or equal to the predetermined threshold value, the processor indicates 3718 to the user that the tissue section has stabilized. If the value of the count C is less than the predetermined threshold value, the processor continues monitoring the sensor 3658. In various embodiments, the slope of the sensor input, the change in the slope, and/or any other suitable change in the input signal may be monitored.

In some embodiments, an end effector, such as for example, the end effectors 3600, 3650 illustrated in FIGS. 52, 53A, and 53B may comprise a cutting member deployable therein. The cutting member may comprise, for example, an I-Beam configured to simultaneously cut a tissue section located between an anvil 3602 and a staple cartridge 3608 and to deploy staples from the staple cartridge 3608. In some embodiments, the I-Beam may comprise only a cutting member and/or may only deploy one or more staples. Tissue flow during firing may affect the proper formation of staples. For example, during I-Beam deployment, fluid in the tissue may cause the thickness of tissue to temporarily increase, causing improper deployment of staples.

Figure 57:
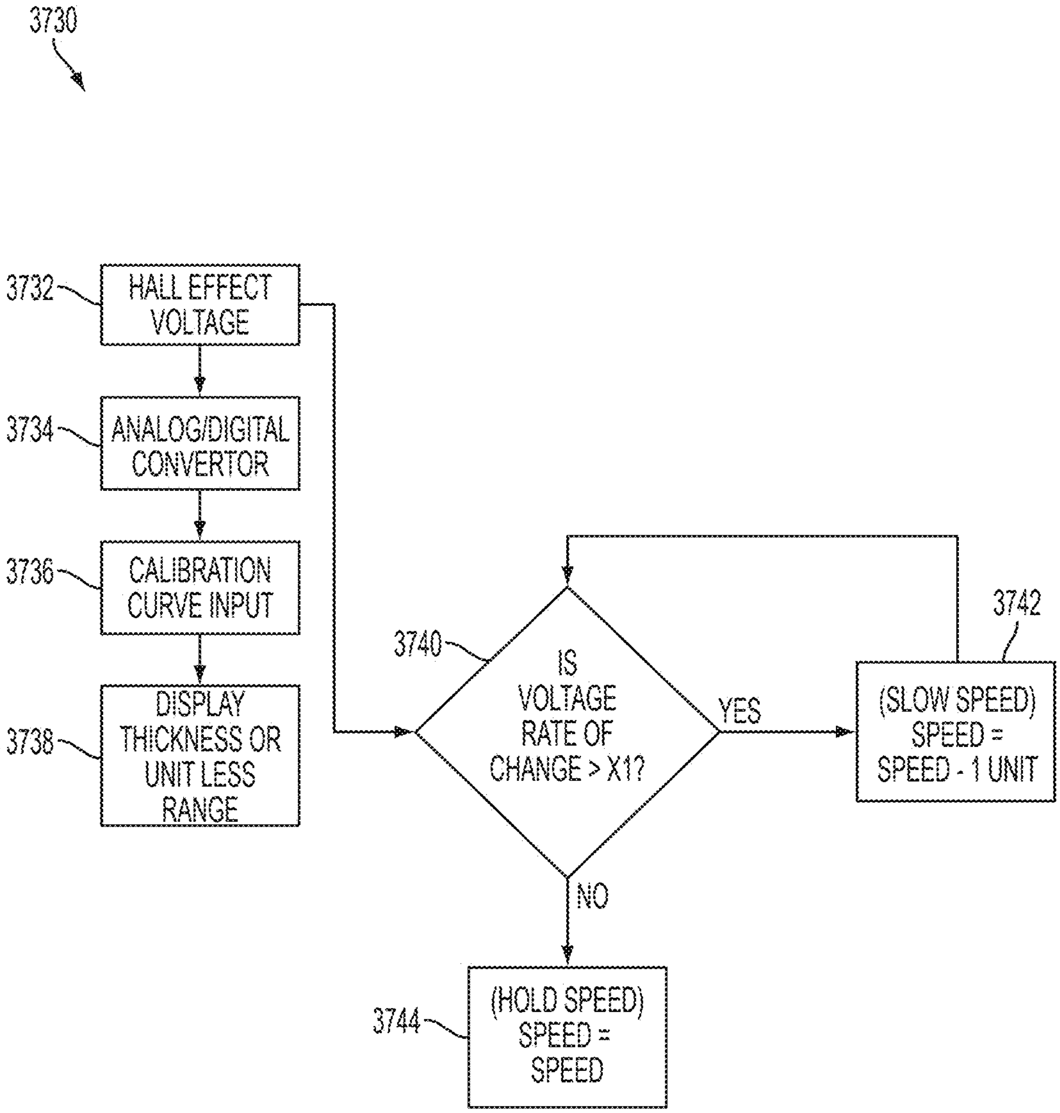
FIG. 57 is a logic diagram illustrating one embodiment of a process for controlling an end effector to improve proper staple formation during deployment.

FIG. 57 is a logic diagram illustrating one embodiment of a process 3730 for controlling an end effector to improve proper staple formation during deployment. The control process 3730 comprises generating 3732 a sensor measurement indicative of the thickness of a tissue section within the end effector 3650, such as for example, a Hall effect voltage generated by a Hall effect sensor. The sensor measurement is converted 3734 to a digital signal by an analog-to-digital convertor. The digital signal is calibrated 3736. The calibration 3736 may be performed by, for example, a processor and/or a dedicated calibration circuit. The digital signal is calibrated 3736 based on one or more calibration curve inputs. The calibrated digital signal is displayed 3738 to an operator by, for example, a display 2026 embedded in a surgical instrument 10. The calibrated signal may be displayed 3738 as a thickness measurement of a tissue section grasped between the anvil 3652 and the staple cartridge 3656 and/or as a unit-less range.

In some embodiments, the generated 3732 Hall effect voltage is used to control an I-beam. For example, in the illustrated embodiment, the Hall effect voltage is provided to a processor configured to control deployment of an I-Beam within an end effector, such as, for example, the primary processor 2006. The processor receives the Hall effect voltage and calculates the voltage rate of change over a predetermined time period. The processor compares 3740 the calculated rate of change to a predetermined value, x1. If the calculated rate of change is greater than the predetermined value, x1, the processor slows 3742 the speed of the I-Beam. The speed may be reduced by, for example, decrementing a speed variable by a predetermined unit. If the calculated voltage rate of change is less than or equal to the predetermine value, x1, the processor maintains 3744 the current speed of the I-Beam.

In some embodiments, the processor may temporarily reduce the speed of the I-Beam to compensate, for example, for thicker tissue, uneven loading, and/or any other tissue characteristic. For example, in one embodiment, the processor is configured to monitor 3740 the rate of voltage change of a Hall effect sensor. If the rate of change monitored 3740 by the processor exceeds a first predetermine value, x1, the processor slows down or stops deployment of the I-Beam until the rate of change is less than a second predetermined value, x2. When the rate of change is less than the second predetermined value, x2, the processor may return the I-beam to normal speed. In some embodiments, the sensor input may be generated by for example, a pressure sensor, a strain gauge, a Hall effect sensor, and/or any other suitable sensor. In some embodiments, the processor may implement one or more pause points during deployment of an I-Beam. For example, in some embodiments, the processor may implement three predetermined pause points, at which the processor pauses deployment of the I-Beam for a predetermined time period. The pause points are configured to provide optimized tissue flow control.

Figure 58:
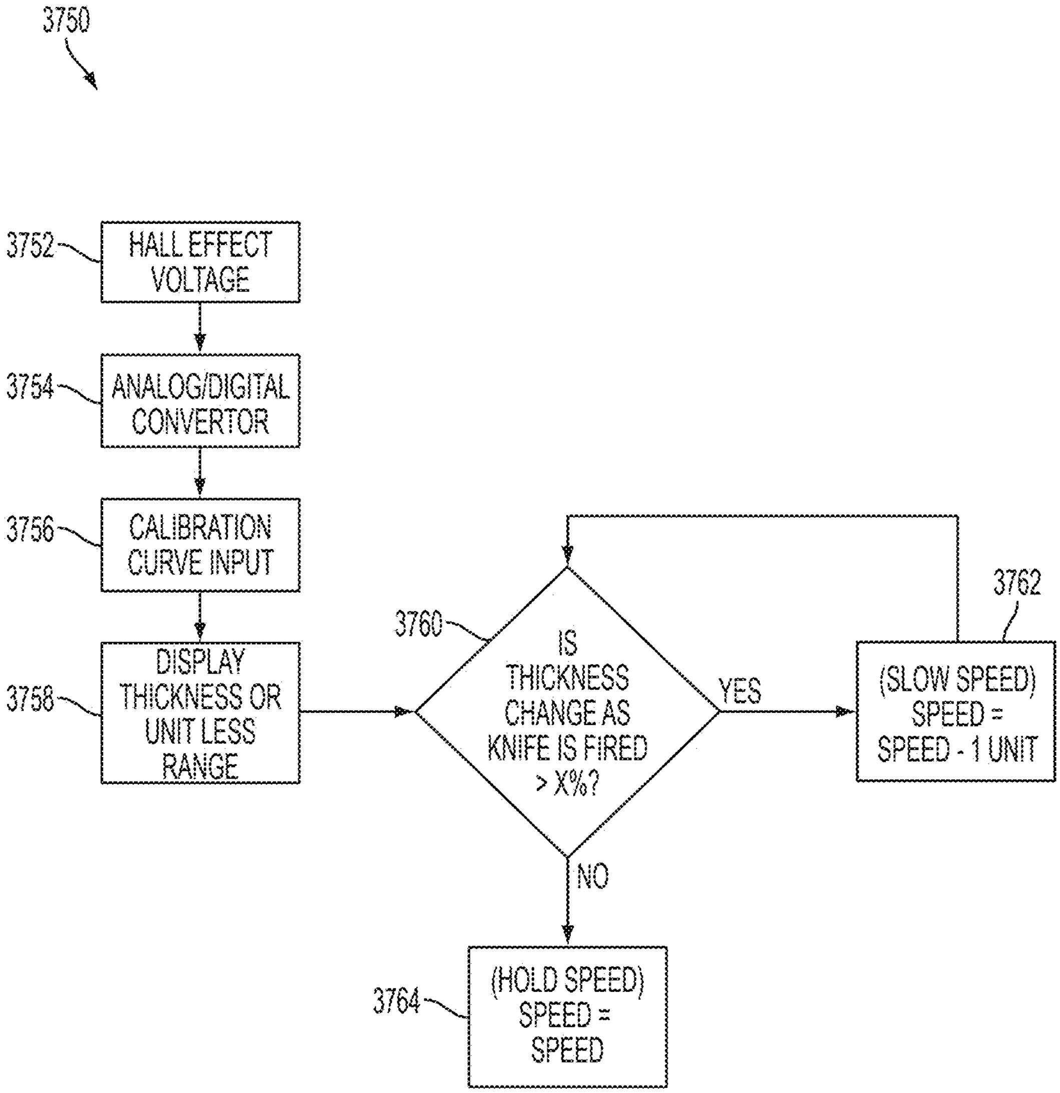
FIG. 58 is a logic diagram illustrating one embodiment of a process for controlling an end effector to allow for fluid evacuation and provide improved staple formation.

FIG. 58 is a logic diagram illustrating one embodiment of a process 3750 for controlling an end effector to allow for fluid evacuation and provide improved staple formation. The process 3750 comprises generating 3752 a sensor measurement, such as, for example, a Hall effect voltage. The sensor measurement may be indicative of, for example, the thickness of a tissue section grasped between an anvil 3652 and a staple cartridge 3656 of an end effector 3650. The generated signal is provided to an analog-to-digital convertor for conversion 3754 to a digital signal. The converted signal is calibrated 3756 based on one or more inputs, such as, for example, a second sensor input and/or a predetermined calibration curve. The calibrated signal is representative of one or more parameters of the end effector 3650, such as, for example, the thickness of a tissue section grasped therein. The calibrated thickness measurement may be displayed to a user as a thickness and/or as a unit-less range. The calibrated thickness may be displayed by, for example, a display 2026 embedded in a surgical instrument 10 coupled to the end effector 3650.

In some embodiments, the calibrated thickness measurement is used to control deployment of an I-Beam and/or other firing member within the end effector 3650. The calibrated thickness measurement is provided to a processor. The processor compares 3760 the change in the calibrated thickness measurement to a predetermined threshold percentage, x. If the rate of change of the thickness measurement is greater than x, the processor slows 3762 the speed, or rate of deployment, of the I-Beam within the end effector. The processor may slow 3762 the speed of the I-Beam by, for example, decrementing a speed variable by a predetermined unit. If the rate of change of the thickness measurement is less than or equal to x, the processor maintains 3764 the speed of the I-Beam within the end effector 3650. The real time feedback of tissue thickness and/or compression allows the surgical instrument 10 to affect the firing speed to allow for fluid evacuation and/or provide improved staple form.

In some embodiments, the sensor reading generated 3752 by the sensor, for example, a Hall effect voltage, may be adjusted by one or more additional sensor inputs. For example, in one embodiment, a generated 3752 Hall effect voltage may be adjusted by an input from a micro-strain gauge sensor on the anvil 3652. The micro-strain gauge may be configured to monitor the strain amplitude of the anvil 3652. The generated 3752 Hall effect voltage may be adjusted by the monitored strain amplitude to indicate, for example, partial proximal or distal tissue bites. Time based monitoring of the micro-strain and Hall effect sensor output during clamping allows one or more algorithms and/or look-up tables to recognize tissue characteristics and clamping positioning and dynamically adjust tissue thickness measurements to control firing speed of, for example, an I-Beam. In some embodiments, the processor may implement one or more pause points during deployment of an I-Beam. For example, in some embodiments, the processor may implement three predetermined pause points, at which the processor pauses deployment of the I-Beam for a predetermined time period. The pause points are configured to provide optimized tissue flow control.

Figure 59A:
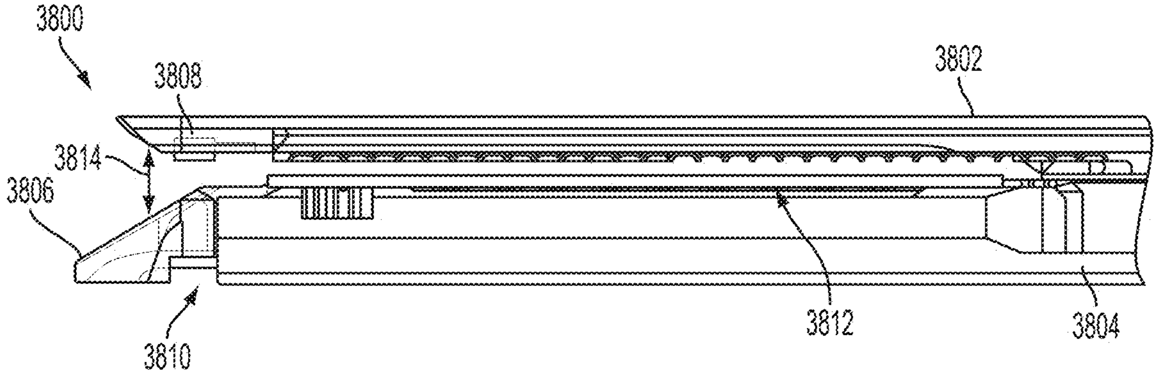
FIGS. 59A-59B illustrate one embodiment of an end effector comprising a pressure sensor.
Figure 59B:
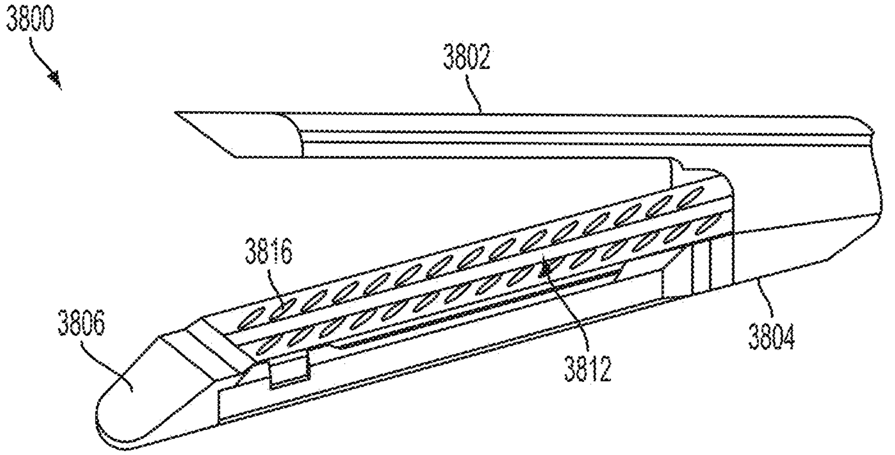

FIGS. 59A-59B illustrate one embodiment of an end effector 3800 comprising a pressure sensor. The end effector 3800 comprises a first jaw member, or anvil, 3802 pivotally coupled to a second jaw member 3804. The second jaw member 3804 is configured to receive a staple cartridge 3806 therein. The staple cartridge 3806 comprises a plurality of staples. A first sensor 3808 is coupled to the anvil 3802 at a distal tip. The first sensor 3808 is configured to detect one or more parameters of the end effector, such as, for example, the distance, or gap 3814, between the anvil 3802 and the staple cartridge 3806. The first sensor 3808 may comprise any suitable sensor, such as, for example, a magnetic sensor. A magnet 3810 may be coupled to the second jaw member 3804 and/or the staple cartridge 3806 to provide a magnetic signal to the magnetic sensor.

In some embodiments, the end effector 3800 comprises a second sensor 3812. The second sensor 3812 is configured to detect one or more parameters of the end effector 3800 and/or a tissue section located therebetween. The second sensor 3812 may comprise any suitable sensor, such as, for example, one or more pressure sensors. The second sensor 3812 may be coupled to the anvil 3802, the second jaw member 3804, and/or the staple cartridge 3806. A signal from the second sensor 3812 may be used to adjust the measurement of the first sensor 3808 to adjust the reading of the first sensor to accurately represent proximal and/or distal positioned partial bites true compressed tissue thickness. In some embodiments, the second sensor 3812 may be surrogate with respect to the first sensor 3808.

In some embodiments, the second sensor 3812 may comprise, for example, a single continuous pressure sensing film and/or an array of pressure sensing films. The second sensor 3812 is coupled to the deck of the staple cartridge 3806 along the central axis covering, for example, a slot 3816 configured to receive a cutting and/or staple deployment member. The second sensor 3812 provides signals indicate of the amplitude of pressure applied by the tissue during a clamping procedure. During firing of the cutting and/or deployment member, the signal from the second sensor 3812 may be severed, for example, by cutting electrical connections between the second sensor 3812 and one or more circuits. In some embodiments, a severed circuit of the second sensor 3812 may be indicative of a spent staple cartridge 3806. In other embodiments, the second sensor 3812 may be positioned such that deployment of a cutting and/or deployment member does not sever the connection to the second sensor 3812.

Figure 60:
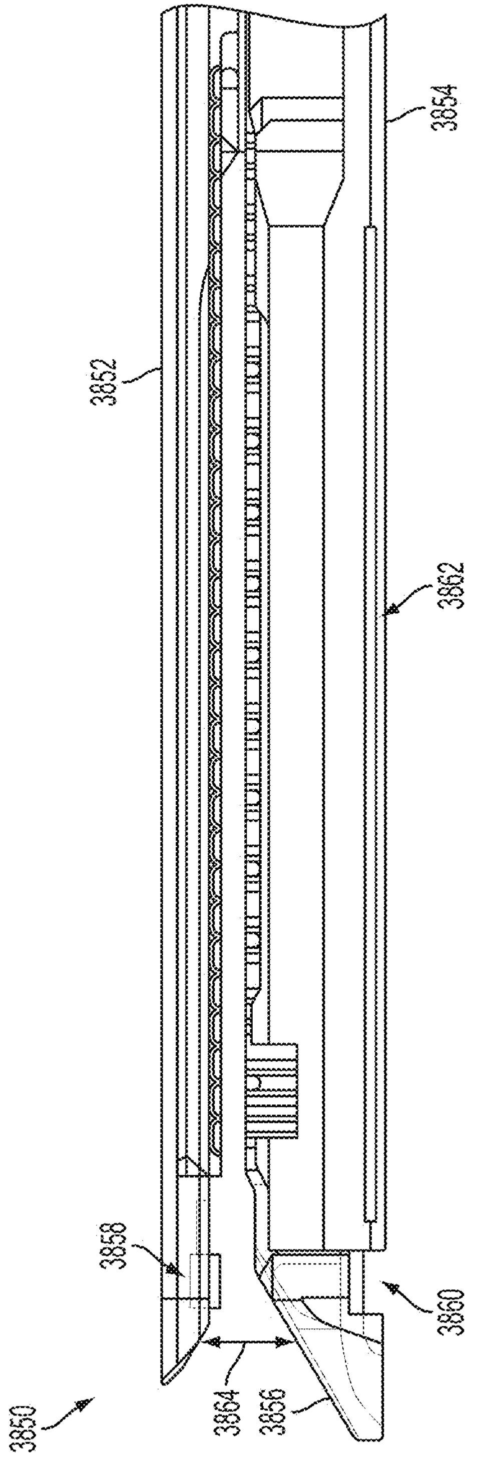
FIG. 60 illustrates one embodiment of an end effector comprising a second sensor located between a staple cartridge and a second jaw member.

FIG. 60 illustrates one embodiment of an end effector 3850 comprising a second sensor 3862 located between a staple cartridge 3806 and a second jaw member 3804. The end effector 3850 comprises a first jaw member, or anvil, 3852 pivotally coupled to a second jaw member 3854. The second jaw member 3854 is configured to receive a staple cartridge 3856 therein. A first sensor 3858 is coupled to the anvil 3852 at a distal tip. The first sensor 3858 is configured to detect one or more parameters of the end effector 3850, such as, for example, the distance, or gap 3864, between the anvil 3852 and the staple cartridge 3856. The first sensor 3858 may comprise any suitable sensor, such as, for example, a magnetic sensor. A magnet 3860 may be coupled to the second jaw member 3854 and/or the staple cartridge 3856 to provide a magnetic signal to the magnetic sensor. In some embodiments, the end effector 3850 comprises a second sensor 3862 similar in all respect to the second sensor 3812 of FIGS. 59A-59B, except that it is located between the staple cartridge 3856 and the second jaw member 3864.

Figure 61:
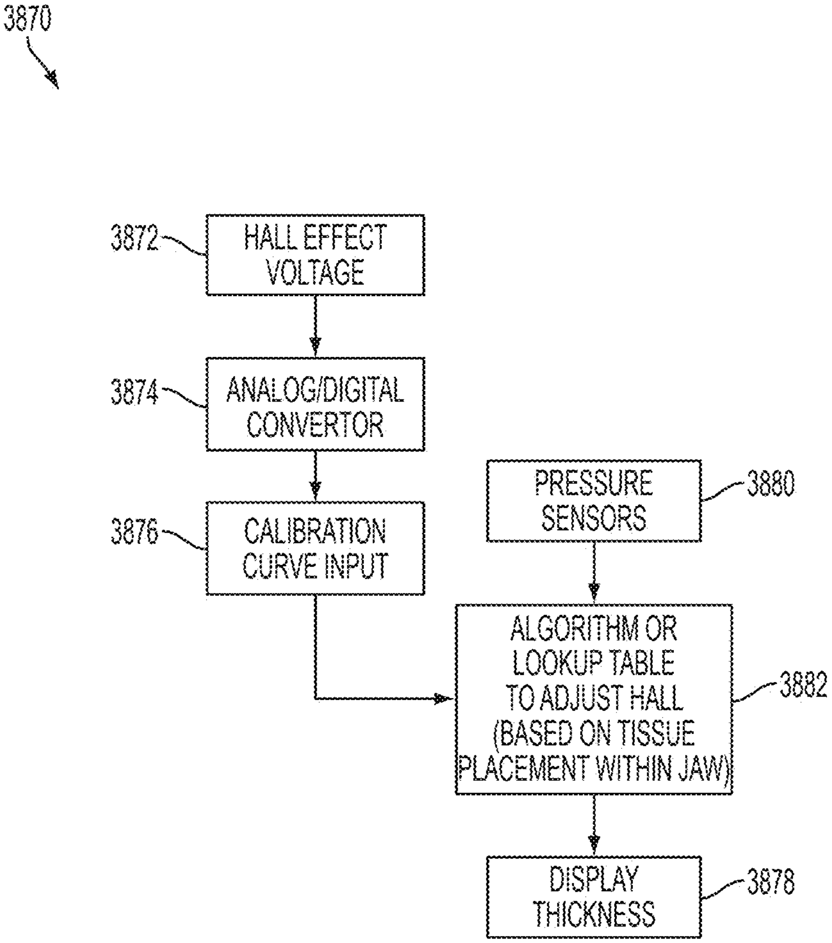
FIG. 61 is a logic diagram illustrating one embodiment of a process for determining and displaying the thickness of a tissue section clamped in an end effector, according to FIGS. 59A-59B or FIG. 60.

FIG. 61 is a logic diagram illustrating one embodiment of a process 3870 for determining and displaying the thickness of a tissue section clamped in an end effector 3800 or 3850, according to FIGS. 59A-59B or FIG. 60. The process comprises obtaining a Hall effect voltage 3872, for example, through a Hall effect sensor located at the distal tip of the anvil 3802. The Hall effect voltage 3872 is proved to an analog to digital converter 3874 and converted into a digital signal. The digital signal is provided to a process, such as for example the primary processor 2006. The primary processor 2006 calibrates 3874 the curve input of the Hall effect voltage 3872 signal. Pressure sensors, such as for example second sensor 3812, is configured to measure 3880 one or more parameters of, for example, the end effector 3800, such as for example the amount of pressure being exerted by the anvil 3802 on the tissue clamped in the end effector 3800. In some embodiments the pressure sensors may comprise a single continuous pressure sensing film and/or array of pressure sensing films. The pressure sensors may thus be operable determine variations in the measure pressure at different locations between the proximal and distal ends of the end effector 3800. The measured pressure is provided to the processor, such as for example the primary processor 2006. The primary processor 2006 uses one or more algorithms and/or lookup tables to adjust 3882 the Hall effect voltage 3872 in response to the pressure measured by the pressure sensors 3880 to more accurately reflect the thickness of the tissue clamped between, for example, the anvil 3802 and the staple cartridge 3806. The adjusted thickness is displayed 3878 to an operator by, for example, a display 2026 embedded in the surgical instrument 10.

Figure 62:
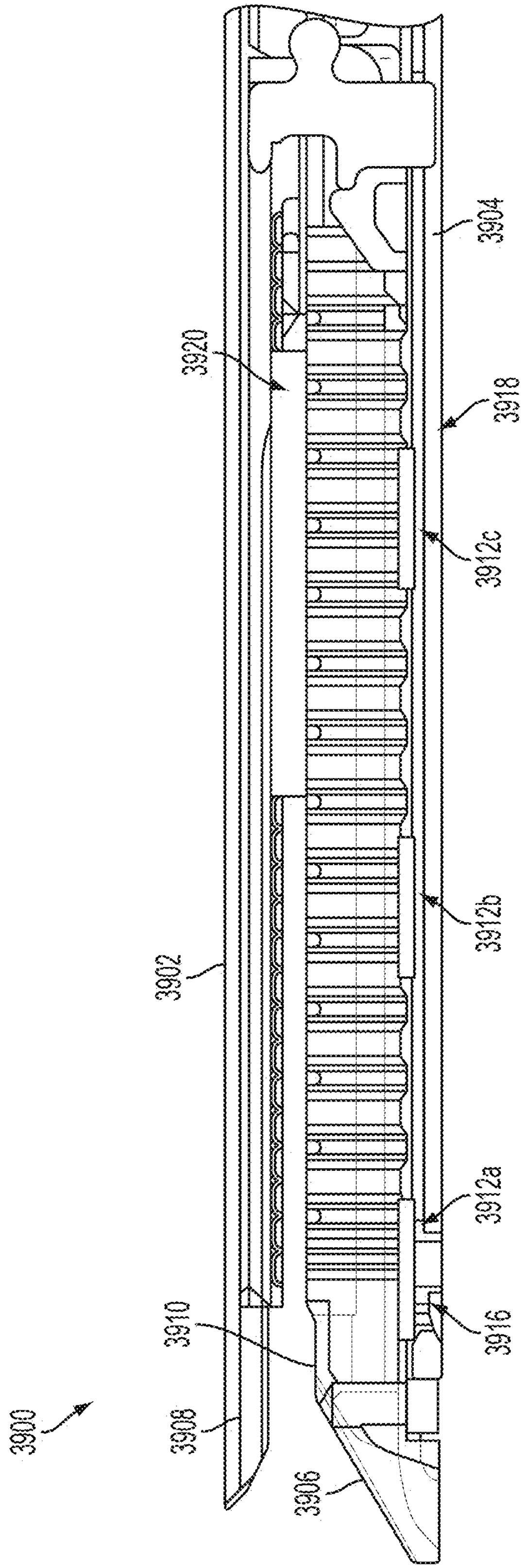
FIG. 62 illustrates one embodiment of an end effector comprising a plurality of second sensors located between a staple cartridge and an elongated channel.

FIG. 62 illustrates one embodiment of an end effector 3900 comprising a plurality of second sensors 3192$a$-3192$b$ located between a staple cartridge 3906 and an elongated channel 3916. The end effector 3900 comprises a first jaw member or anvil 3902 pivotally coupled to a second jaw member or elongated channel 3904. The elongated channel 3904 is configured to receive a staple cartridge 3906 therein. The anvil 3902 further comprises a first sensor 3908 located in the distal tip. The first sensor 3908 is configured to detect one or more parameters of the end effector 3900, such as, for example, the distance, or gap, between the anvil 3902 and the staple cartridge 3906. The first sensor 3908 may comprise any suitable sensor, such as, for example, a magnetic sensor. A magnet 3910 may be coupled to the elongated channel 3904 and/or the staple cartridge 3906 to provide a magnetic signal to the first sensor 3908. In some embodiments, the end effector 3900 comprises a plurality of second sensors 3912$a$-3912$c$ located between the staple cartridge 3906 and the elongated channel 3904. The second sensors 3912$a$-3912$c$ may comprise any suitable sensors, such as for instance piezo-resistive pressure film strips. In some embodiments, the second sensors 3912$a$-3912$c$ may be uniformly distributed between the distal and proximal ends of the end effector 3900.

In some embodiments, signals from the second sensors 3912$a$-3912$c$ may be used to adjust the measurement of the first sensor 3908. For instance, the signals from the second sensors 3912$a$-3912$c$ may be used to adjust the reading of the first sensor 3908 to accurately represent the gap between the anvil 3908 and the staple cartridge 3906, which may vary between the distal and proximal ends of the end effector 3900, depending on the location and/or density of tissue 3920 between the anvil 3902 and the staple cartridge 3906. FIG. 11 illustrates an example of a partial bite of tissue 3920. As illustrated for purposes of this example, the tissue is located only in the proximal area of the end effector 3900, creating a high pressure 3918 area near the proximal area of the end effector 3900 and a corresponding low pressure 3916 area near the distal end of the end effector.

Figure 63A:
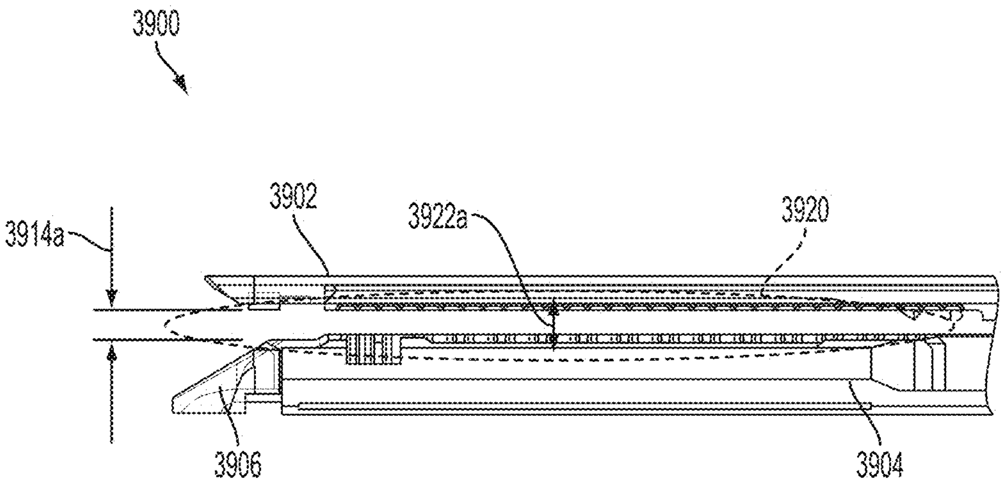
FIGS. 63A and 63B further illustrate the effect of a full versus partial bite of tissue.
Figure 63B:
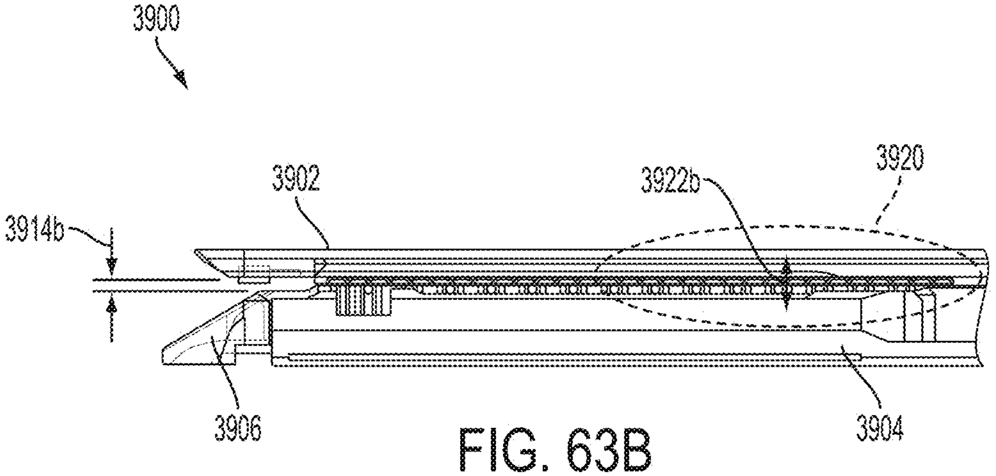

FIGS. 63A and 63B further illustrate the effect of a full versus partial bite of tissue 3920. FIG. 63A illustrates the end effector 3900 with a full bite of tissue 3920, where the tissue 3920 is of uniform density. With a full bite of tissue 3920 of uniform density, the measured first gap 3914*a* at the distal tip of the end effector 3900 may be approximately the same as the measured second gap 3922*a* in the middle or proximal end of the end effector 3900. For example, the first gap 3914*a* may measure 2.4 mm, and the second gap may measure 2.3 mm. FIG. 63B illustrates an end effector 3900 with a partial bite of tissue 3920, or alternatively a full bit of tissue 3920 of non-uniform density. In this case, the first gap 3914*b* will measure less than the second gap 3922*b* measured at the thickest or densest portion of the tissue 3920. For example, the first gap may measure 1.0 mm, while the second gap may measure 1.9 mm. In the conditions illustrated in FIGS. 63A and 63B, signals from the second sensors 3912*a*-3912*c*, such as for instance measured pressure at different points along the length of the end effector 3900, may be employed by the instrument to determine tissue 3920 placement and/or material properties of the tissue 3920. The instrument may further be operable to use measured pressure over time to recognize tissue characteristics and tissue position, and dynamically adjust tissue thickness measurements.

Figure 64:
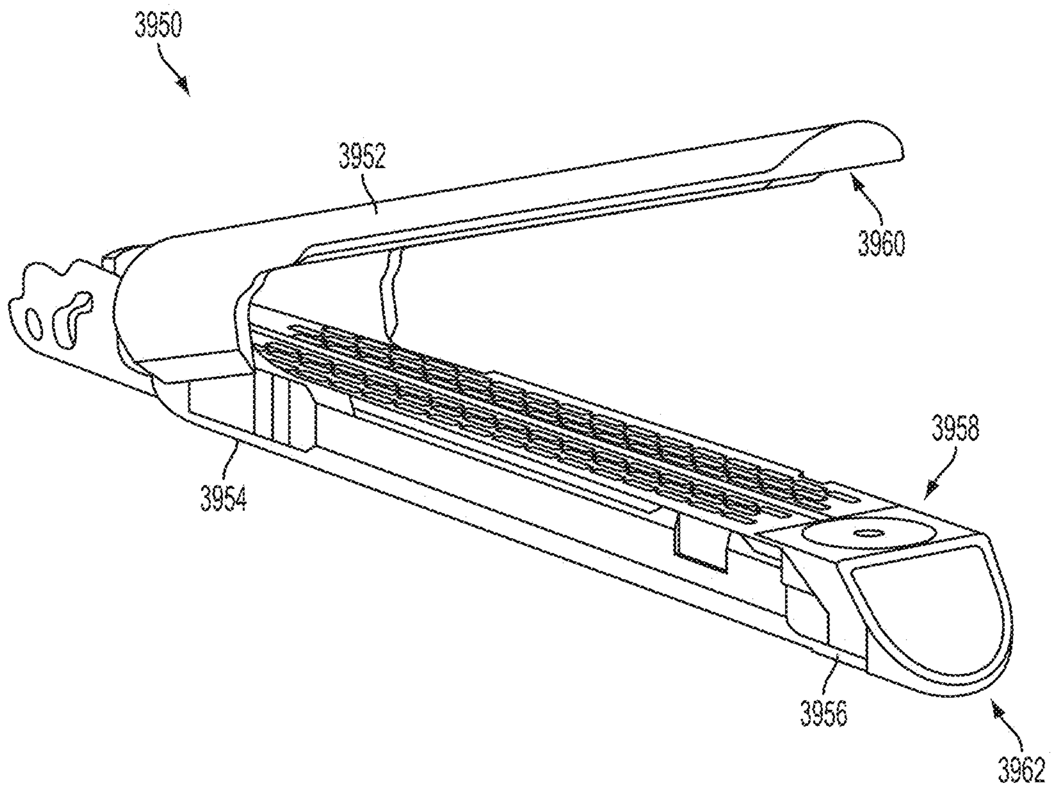
FIG. 64 illustrates one embodiment of an end effector comprising a coil and oscillator circuit for measuring the gap between the anvil and the staple cartridge.

FIG. 64 illustrates one embodiment of an end effector 3950 comprising a coil 3958 and oscillator circuit 3962 for measuring the gap between the anvil and the staple cartridge 3956. The end effector 3950 comprises a first jaw member or anvil 3952 pivotally coupled to a second jaw member or elongated channel 3954. The elongated channel 3954 is configured to receive a staple cartridge 3956 therein. In some embodiments the staple cartridge 3954 further comprises a coil 3958 and an oscillator circuit 3962 located at the distal end. The coil 3958 and oscillator circuit 3962 are operable as eddy current sensors and/or inductive sensors. The coil 3958 and oscillator circuit 3962 can detect eddy currents and/or induction as a target 3960, such as for instance the distal tip of the anvil 3952, approaches the coil 3958. The eddy current and/or induction detected by the coil 3958 and oscillator circuit 3962 can be used to detect the distance or gap between the anvil 3952 and staple cartridge 3956.

Figure 65:
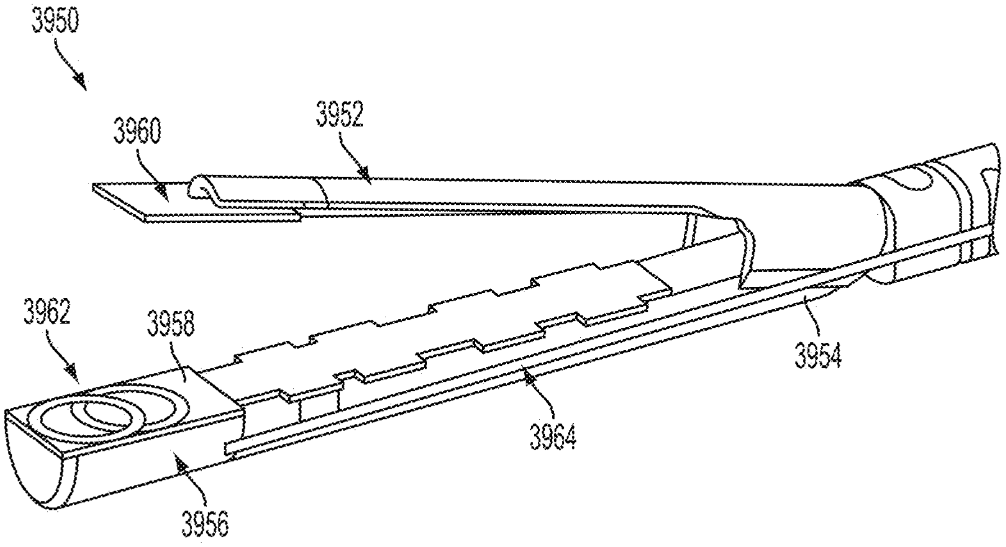
FIG. 65 illustrates and alternate view of the end effector. As illustrated, in some embodiments external wiring may supply power to the oscillator circuit.

FIG. 65 illustrates and alternate view of the end effector 3950. As illustrated, in some embodiments external wiring 3964 may supply power to the oscillator circuit 3962. The external wiring 3964 may be placed along the outside of the elongated channel 3954.

Figure 66:
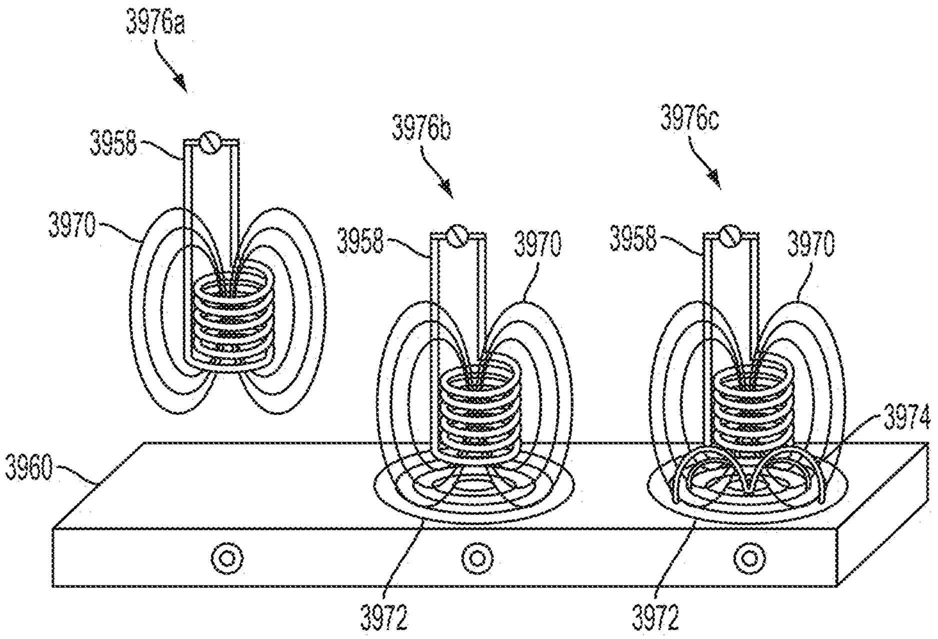
FIG. 66 illustrates examples of the operation of a coil to detect eddy currents in a target.

FIG. 66 illustrates examples of the operation of a coil 3958 to detect eddy currents 3972 in a target 3960. Alternating current flowing through the coil 3958 at a chose frequency generates a magnetic field 3970 around the coil 3958. When the coil 3958 is at is position 3976*a* a certain distance away from the target 3960, the coil 3958 will not induce an eddy current 3972. When the coil 3958 is at a position 3976*b* close to an electrically conductive target 3960 and eddy current 3972 is produced in the target 3960. When the coil 3958 is at a position 3976*c* near a flaw in the target 3960, the flaw may disrupt the eddy current circulation; in this case, the magnetic coupling with the coil 3958 is changed and a defect signal 3974 can be read by measuring the coil impedance variation.

Figure 67:
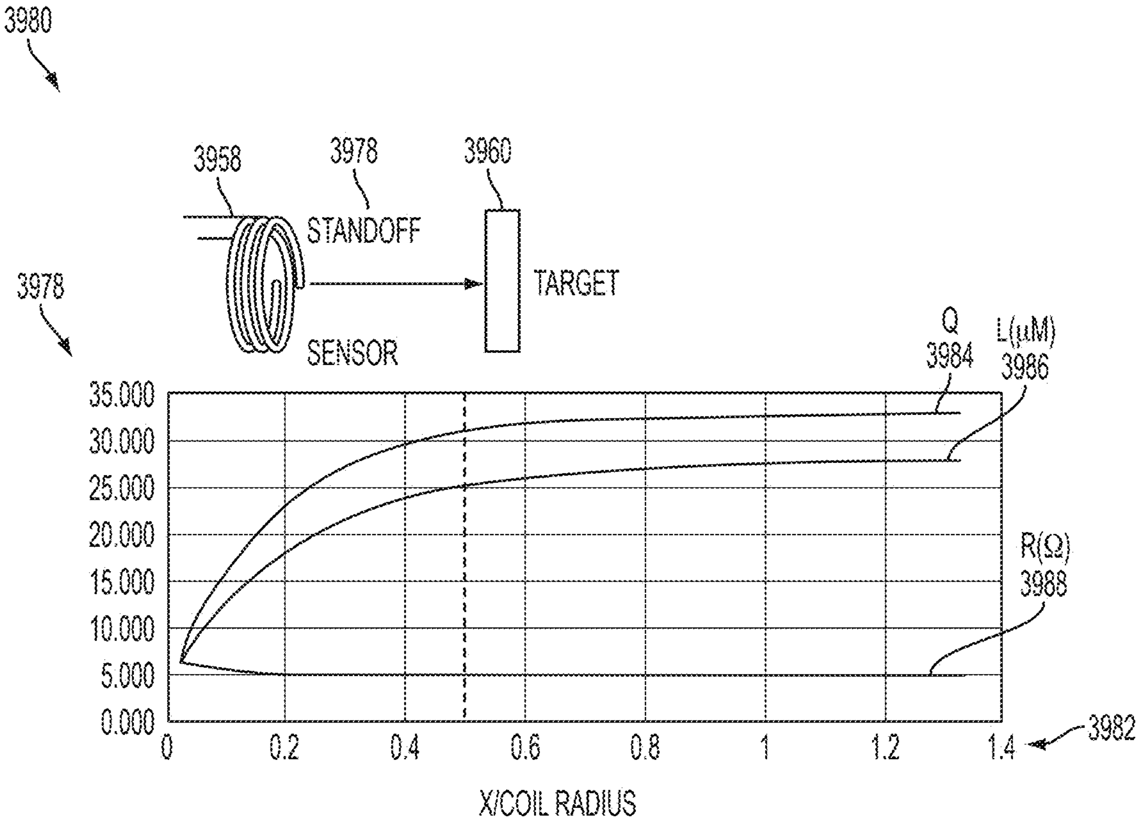
FIG. 67 illustrates a graph of a measured quality factor, the measured inductance, and measure resistance of the radius of a coil as a function of the coil's standoff to a target.

FIG. 67 illustrates a graph 3980 of a measured quality factor 3984, the measured inductance 3986, and measure resistance 3988 of the radius of a coil 3958 as a function of the coil's 3958 standoff 3978 to a target 3960. The quality factor 3984 depends on the standoff 3978, while both the inductance 3986 and resistance 3988 are functions of displacement. A higher quality factor 3984 results in a more purely reactive sensor. The specific value of the inductance 3986 is constrained only by the need for a manufacturable coil 3958 and a practical circuit design that burns a reasonable amount of energy at a reasonable frequency. Resistance 3988 is a parasitic effect.

The graph 3980 illustrates how inductance 3986, resistance 3988, and the quality factor 3984 depend on the target standoff 3978. As the standoff 3978 increases, the inductance 3986 increases by a factor of four, the resistance 3988 decreases slightly and as a consequence the quality factor 3984 increases. The change in all three parameters is highly nonlinear and each curve tends to decay roughly exponentially as standoff 3978 increases. The rapid loss of sensitivity with distance strictly limits the range of an eddy current sensor to approximately ½ the coil diameter.

Figure 68:
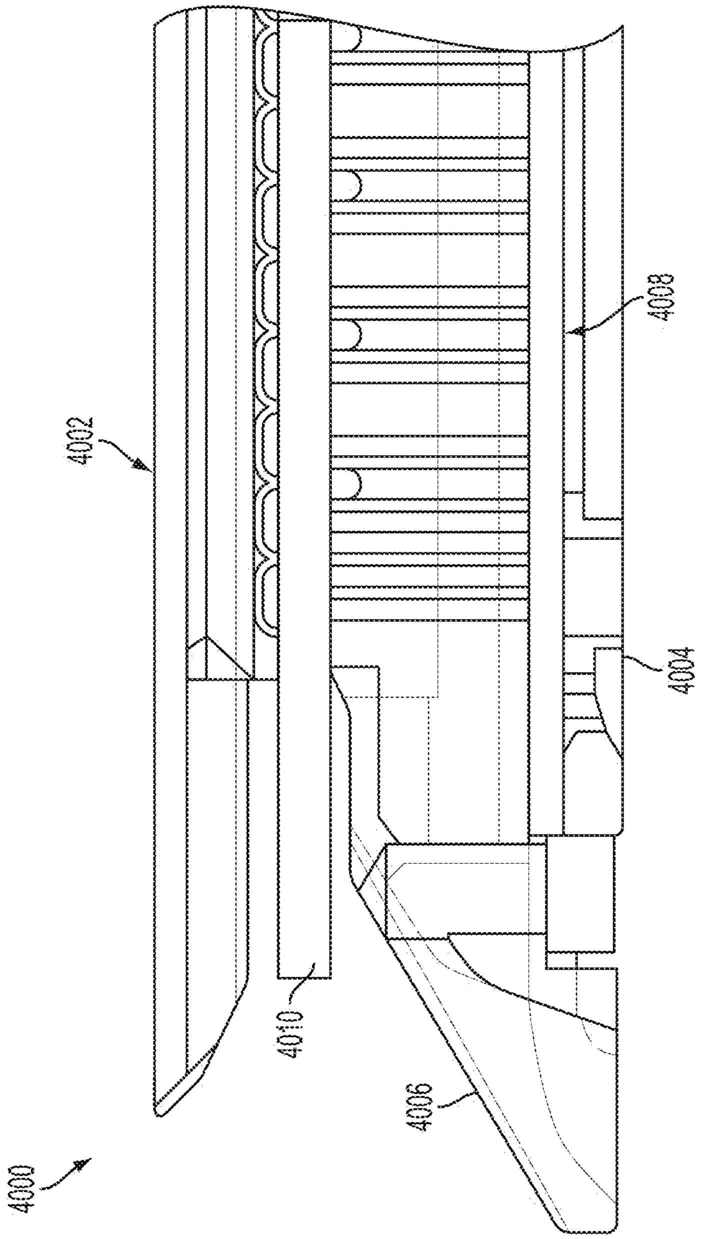
FIG. 68 illustrates one embodiment of an end effector comprising an emitter and sensor placed between the staple cartridge and the elongated channel.

FIG. 68 illustrates one embodiment of an end effector 4000 comprising an emitter and sensor 4008 placed between the staple cartridge 4006 and the elongated channel 4004. The end effector 4000 comprises a first jaw member or anvil 4002 pivotally coupled to a second jaw member or elongated channel 4004. The elongated channel 3904 is configured to receive a staple cartridge 4006 therein. In some embodiments, the end effector 4000 further comprises an emitter and sensor 4008 located between the staple cartridge 4006 and the elongated channel 4004. The emitter and sensor 4008 can be any suitable device, such as for instance a MEMS ultrasonic transducer. In some embodiments, the emitter and sensor may be placed along the length of the end effector 4000.

Figure 69:
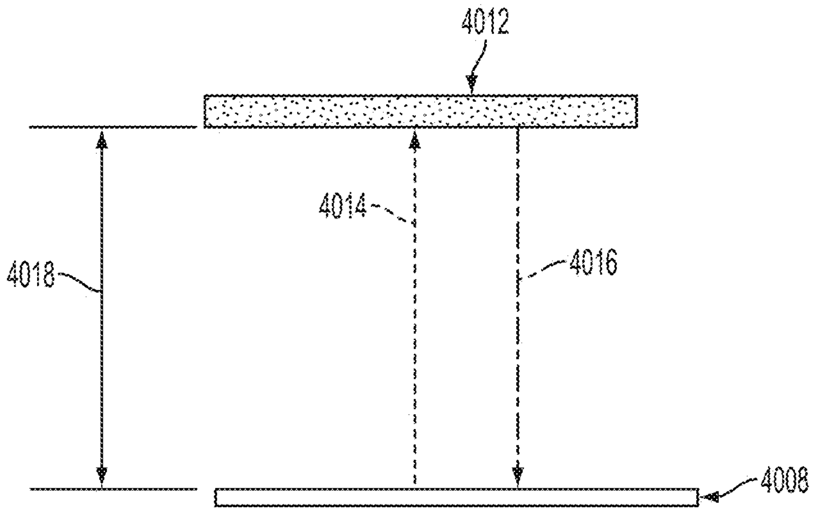
FIG. 69 illustrates an embodiment of an emitter and sensor in operation.

FIG. 69 illustrates an embodiment of an emitter and sensor 4008 in operation. The emitter and sensor 4008 may be operable to emit a pulse 4014 and sense the reflected signal 4016 of the pulse 4014. The emitter and sensor 4008 may further be operable to measure the time of flight 4018 between the issuance of the pulse 4014 and the reception of the reflected signal 4016. The measured time of flight 4018 can be used to determine the thickness of tissue compressed in the end effector 4000 along the entire length of the end effector 4000. In some embodiments, the emitter and sensor 4008 may be coupled to a processor, such as for instance the primary processor 2006. The processor 2006 may be operable to use the time of flight 4018 to determine additional information about the tissue, such as for instance whether the tissue was diseased, bunched, or damaged. The surgical instrument can further be operable to convey this information to the operator of the instrument.

Figure 70:
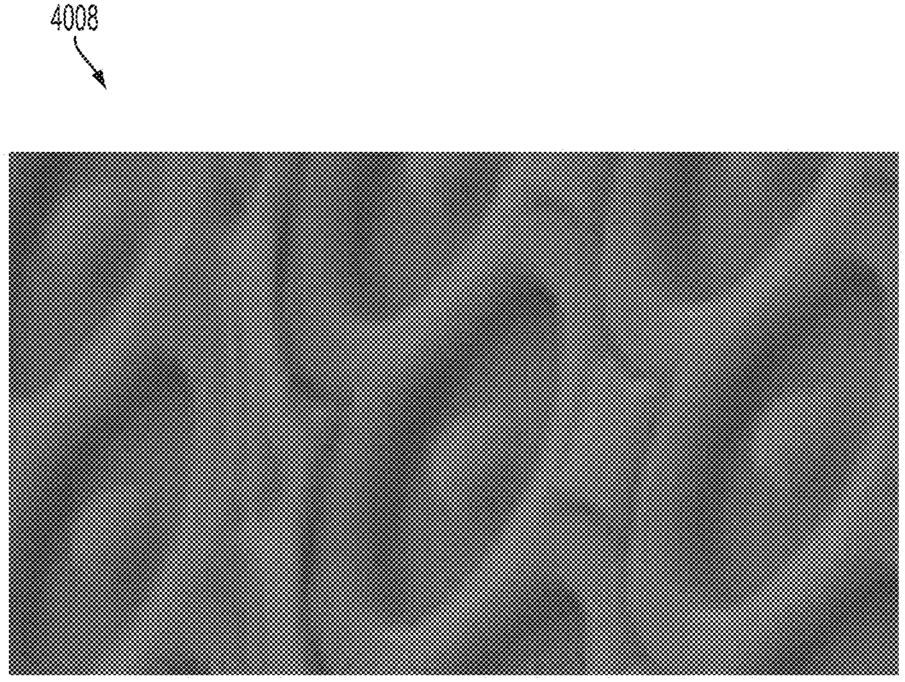
FIG. 70 illustrates the surface of an embodiment of an emitter and sensor comprising a MEMS transducer.

FIG. 70 illustrates the surface of an embodiment of an emitter and sensor 4008 comprising a MEMS transducer.

Figure 71:
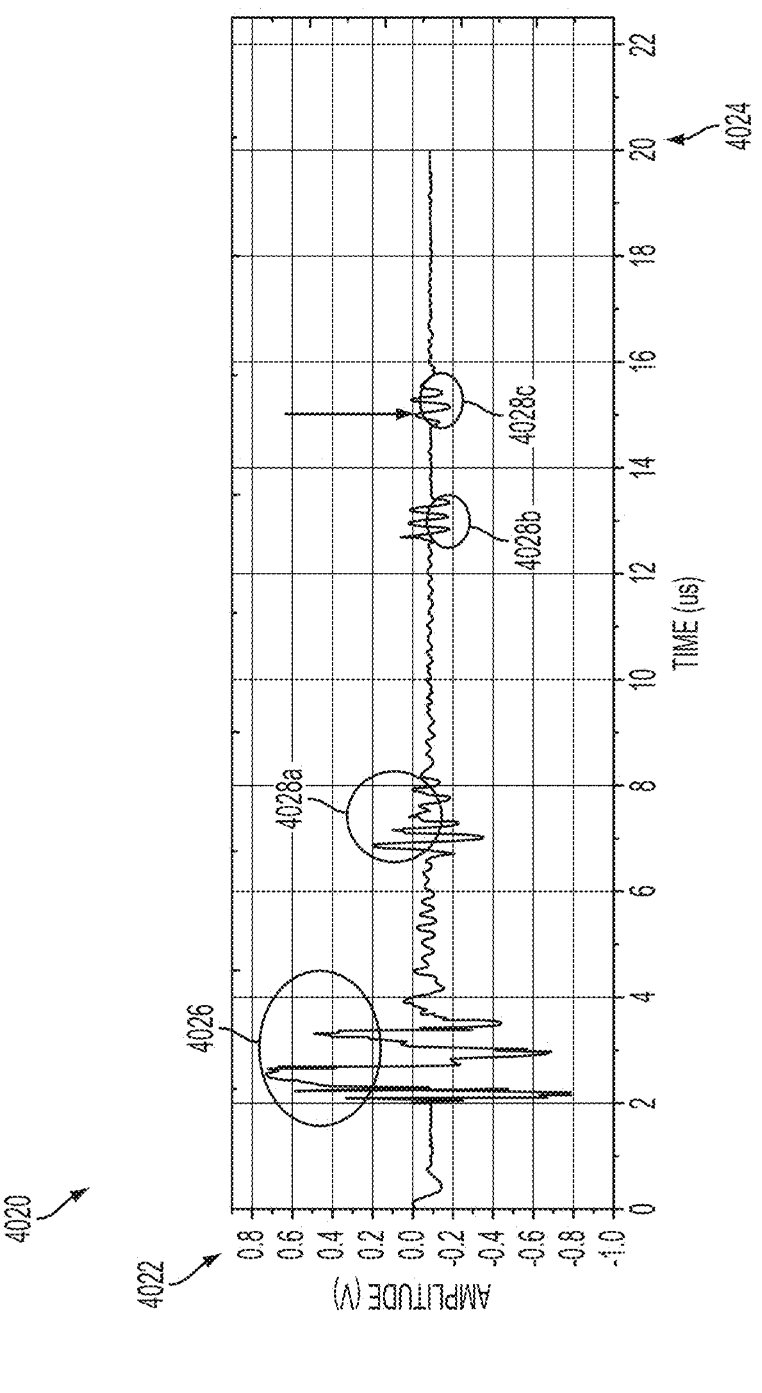
FIG. 71 illustrates a graph of an example of the reflected signal that may be measured by the emitter and sensor of FIG. 69.

FIG. 71 illustrates a graph 4020 of an example of the reflected signal 4016 that may be measured by the emitter and sensor 4008 of FIG. 69. FIG. 71 illustrates the amplitude 4022 of the reflected signal 4016 as a function of time 4024. As illustrated, the amplitude of the transmitted pulse 4026 is greater than the amplitude of the reflected pulses 4028*a*-4028*c*. The amplitude of the transmitted pulse 4026 may be of a known or expected value. The first reflected pulse 4028*a* may be, for example, from the tissue enclosed by the end effector 4000. The second reflected pulse 4028*b* may be, for example, from the lower surface of the anvil 4002. The third reflected pulse 4028*c* may be, for example, from the upper surface of the anvil 4002.

Figure 72:
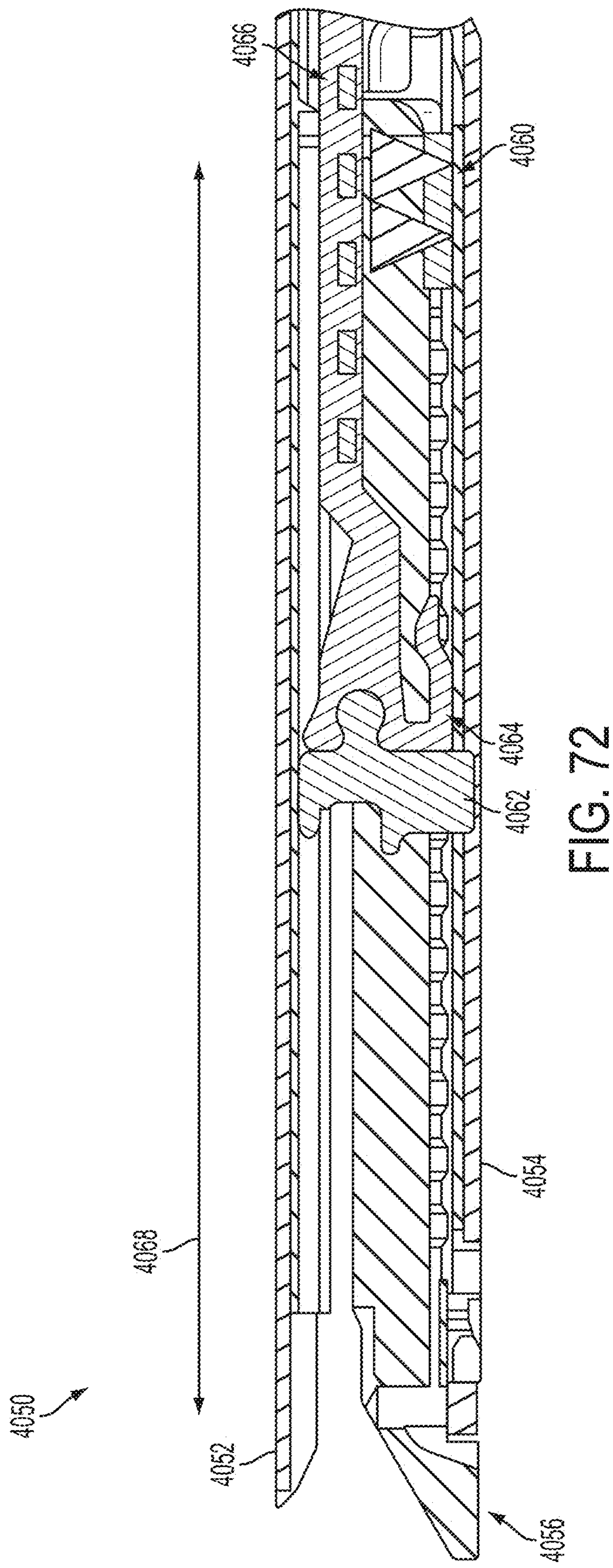
FIG. 72 illustrates an embodiment of an end effector that is configured to determine the location of a cutting member or knife.

FIG. 72 illustrates an embodiment of an end effector 4050 that is configured to determine the location of a cutting member or knife 4058. The end effector 4050 comprises a first jaw member or anvil 4052 pivotally coupled to a second jaw member or elongated channel 4054. The elongated channel 4054 is configured to receive a staple cartridge 4056 therein. The staple cartridge 4056 further comprises a slot 4058 (not shown) and a cutting member or knife 4062 located therein. The knife 4062 is operably coupled to a knife bar 4064. The knife bar 4064 is operable to move the knife 4062 from the proximal end of the slot 4058 to the distal end. The end effector 4050 may further comprise an optical sensor 4060 located near the proximal end of the slot 4058. The optical sensor may be coupled to a processor, such as for instance the primary processor 2006. The optical sensor 4060 may be operable to emit an optical signal towards the knife bar 4064. The knife bar 4064 may further comprise a code strip 4066 along its length. The code strip 4066 may comprise cut-outs, notches, reflective pieces, or any other configuration that is optically readable. The code strip 4066 is placed such that the optical signal from the optical sensor 4060 will reflect off or through the code strip 4066. As the knife 4062 and knife bar 4064 move 4068 along the slot 4058, the optical sensor 4060 will detect the reflection of the emitted optical signal coupled to the code strip 4066. The optical sensor 4060 may be operable to communicate the detected signal to the processor 2006. The processor 2006 may be configured to use the detected signal to determine the position of the knife 4062. The position of the knife 4062 may be sensed more precisely by designing the code strip 4066 such that the detected optical signal has a gradual rise and fall.

Figure 73:
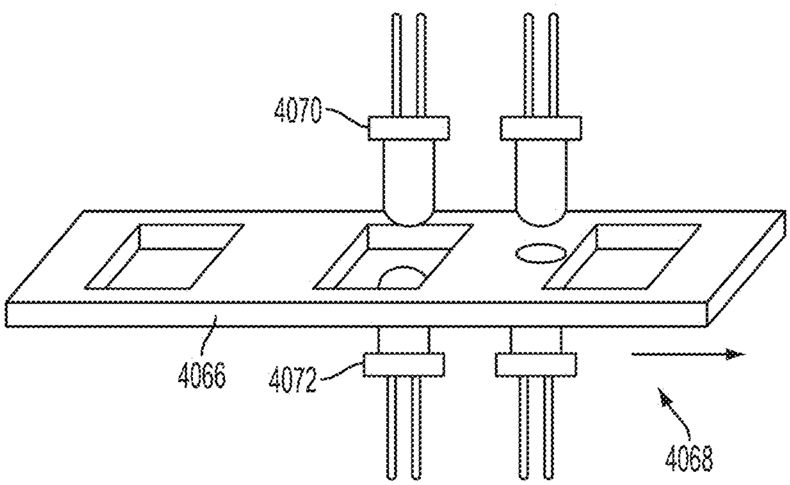
FIG. 73 illustrates an example of the code strip in operation with red LEDs and an infrared LEDs.

FIG. 73 illustrates an example of the code strip 4066 in operation with red LEDs 4070 and infrared LEDs 4072. For purposes of this example only, the code strip 4066 comprises cut-outs. As the code strip 4066 moves 4068, the light emitted by the red LEDs 4070 will be interrupted as the cut-outs passed before it. The infrared LEDs 4072 will therefore detect the motion 4068 of the code strip 4066, and therefore, by extension, the motion of the knife 4062.

Monitoring Device Degradation Based on Component Evaluation

Figure 74:
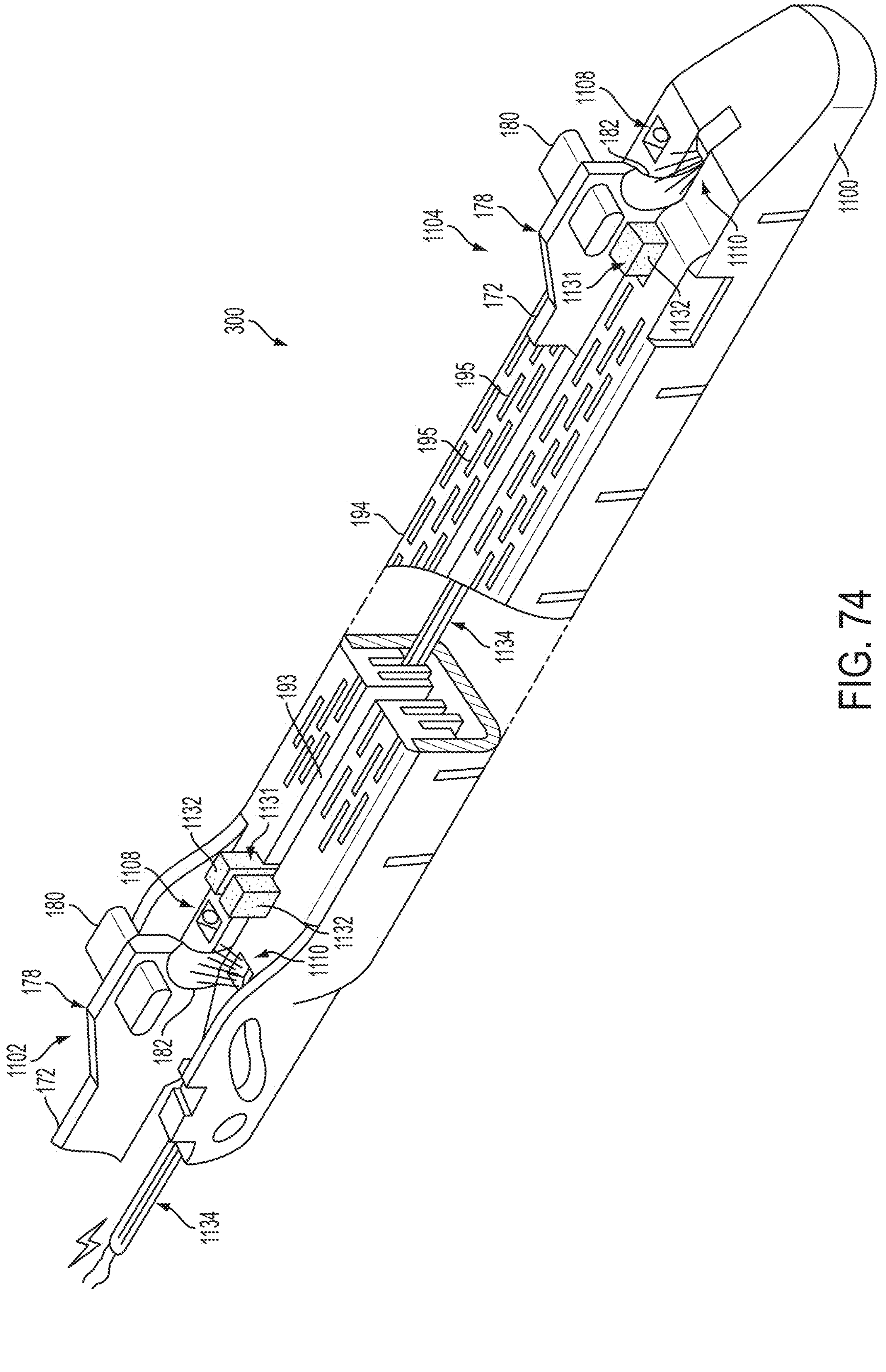
FIG. 74 illustrates a partial perspective view of an end effector of a surgical instrument comprising a staple cartridge according to various embodiments described herein.

FIG. 74 depicts a partial view of the end effector 300 of the surgical instrument 10. In the example form depicted in FIG. 74, the end effector 300 comprises a staple cartridge 1100 which is similar in many respects to the staple cartridge 304 (FIG. 20). Several parts of the end effector 300 are omitted to enable a clearer understanding of the present disclosure. In certain instances, the end effector 300 may include a first jaw such as, for example, the anvil 306 (FIG. 20) and a second jaw such as, for example, the channel 198 (FIG. 20). In certain instances, as described above, the channel 198 may accommodate a staple cartridge such as, for example, the staple cartridge 304 or the staple cartridge 1100, for example. At least one of the channel 198 and the anvil 306 may be movable relative to the other one of the channel 198 and the anvil 306 to capture tissue between the staple cartridge 1100 and the anvil 306. Various actuation assemblies are described herein to facilitation motion of the channel 198 and/or the anvil 306 between an open configuration (FIG. 1) and a closed configuration (FIG. 75), for example In certain instances, as described above, the E-beam 178 can be advanced distally to deploy the staples 191 into the captured tissue and/or advance the cutting edge 182 between a plurality of positions to engage and cut the captured tissue. As illustrated in FIG. 74, the cutting edge 182 can be advanced distally along a path defined by the slot 193, for example. In certain instances, the cutting edge 182 can be advanced from a proximal portion 1102 of the staple cartridge 1100 to a distal portion 1104 of the staple cartridge 1100 to cut the captured tissue, as illustrated in FIG. 74. In certain instances, the cutting edge 182 can be retracted proximally from the distal portion 1104 to the proximal portion 1102 by retraction of the E-beam 178 proximally, for example.

Figure 75:
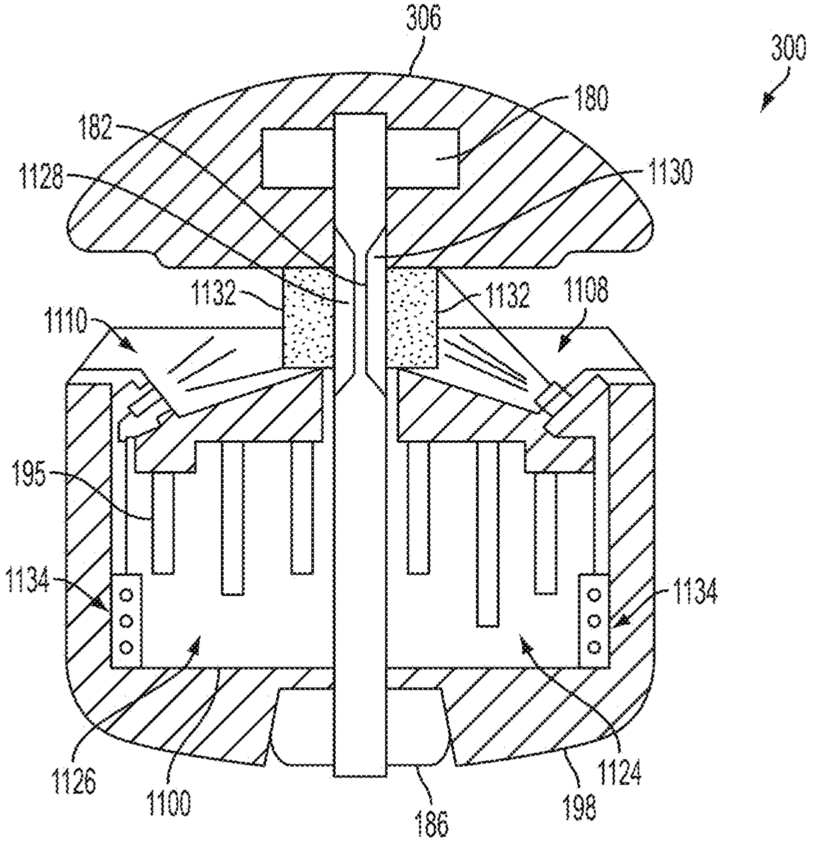
FIG. 75 illustrates a elevational view of a portion of the end effector of FIG. 74 according to various embodiments described herein.
Figure 76:
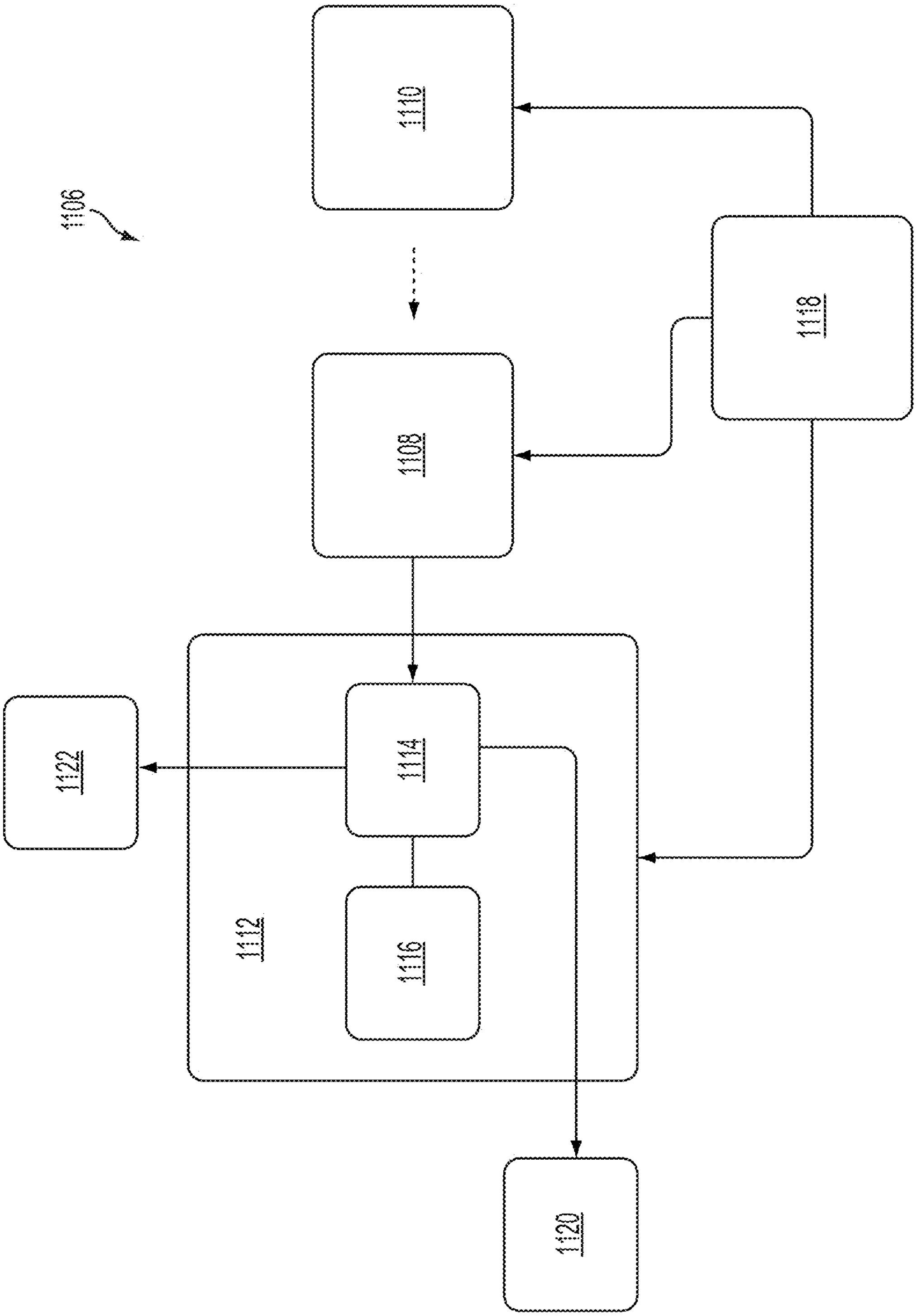
FIG. 76 illustrates a logic diagram of a module of the surgical instrument of FIG. 74 according to various embodiments described herein.

In certain instances, the cutting edge 182 can be employed to cut tissue captured by the end effector 300 in multiple procedures. The reader will appreciate that repetitive use of the cutting edge 182 may affect the sharpness of the cutting edge 182. The reader will also appreciate that as the sharpness of the cutting edge 182 decreases, the force required to cut the captured tissue with the cutting edge 182 may increase. Referring to FIGS. 74-76, in certain instances, the surgical instrument 10 may comprise a module 1106 (FIG. 76) for monitoring the sharpness of the cutting edge 182 during, before, and/or after operation of the surgical instrument 10 in a surgical procedure, for example. In certain instances, the module 1106 can be employed to test the sharpness of the cutting edge 182 prior to utilizing the cutting edge 182 to cut the captured tissue. In certain instances, the module 1106 can be employed to test the sharpness of the cutting edge 182 after the cutting edge 182 has been used to cut the captured tissue. In certain instances, the module 1106 can be employed to test the sharpness of the cutting edge 182 prior to and after the cutting edge 182 is used to cut the captured tissue. In certain instances, the module 1106 can be employed to test the sharpness of the cutting edge 1106 at the proximal portion 1102 and/or at the distal portion 1104.

Referring to FIGS. 74-76, the module 1106 may include one or more sensors such as, for example, an optical sensor 1108; the optical sensor 1108 of the module 1106 can be employed to test the reflective ability of the cutting edge 182, for example. In certain instances, the ability of the cutting edge 182 to reflect light may correlate with the sharpness of the cutting edge 182. In other words, a decrease in the sharpness of the cutting edge 182 may result in a decrease in the ability of the cutting edge 182 to reflect the light. Accordingly, in certain instances, the dullness of the cutting edge 182 can be evaluated by monitoring the intensity of the light reflected from the cutting edge 182, for example. In certain instances, the optical sensor 1108 may define a light sensing region. The optical sensor 1108 can be oriented such that the optical sensing region is disposed in the path of the cutting edge 182, for example. The optical sensor 1108 may be employed to sense the light reflected from the cutting edge 182 while the cutting edge 182 is in the optical sensing region, for example. A decrease in intensity of the reflected light beyond a threshold can indicate that the sharpness of the cutting edge 182 has decreased beyond an acceptable level.

Referring again to FIGS. 74-76, the module 1106 may include one or more lights sources such as, for example, a light source 1110. In certain instances, the module 1106 may include a microcontroller 1112 ("controller") which may be operably coupled to the optical sensor 1108, as illustrated in FIG. 76. In certain instances, the controller 1112 may include a microprocessor 1114 ("processor") and one or more computer readable mediums or memory units 1116 ("memory"). In certain instances, the memory 1116 may store various program instructions, which when executed may cause the processor 1114 to perform a plurality of functions and/or calculations described herein. In certain instances, the memory 1116 may be coupled to the processor 1114, for example. A power source 1118 can be configured to supply power to the controller 1112, the optical sensors 1108, and/or the light sources 1110, for example. In certain instances, the power source 1118 may comprise a battery (or "battery pack" or "power pack"), such as a Li ion battery, for example. In certain instances, the battery pack may be configured to be releasably mounted to the handle 14 for supplying power to the surgical instrument 10. A number of battery cells connected in series may be used as the power source 4428. In certain instances, the power source 1118 may be replaceable and/or rechargeable, for example.

The controller 1112 and/or other controllers of the present disclosure may be implemented using integrated and/or discrete hardware elements, software elements, and/or a combination of both. Examples of integrated hardware elements may include processors, microprocessors, microcontrollers, integrated circuits, ASICs, PLDs, DSPs, FPGAs, logic gates, registers, semiconductor devices, chips, microchips, chip sets, microcontrollers, SoC, and/or SIP. Examples of discrete hardware elements may include circuits and/or circuit elements such as logic gates, field effect transistors, bipolar transistors, resistors, capacitors, inductors, and/or relays. In certain instances, the controller 1112 may include a hybrid circuit comprising discrete and integrated circuit elements or components on one or more substrates, for example.

In certain instances, the controller 1112 and/or other controllers of the present disclosure may be an LM 4F230H5QR, available from Texas Instruments, for example. In certain instances, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle SRAM, internal ROM loaded with StellarisWare® software, 2 KB EEPROM, one or more PWM modules, one or more QEI analog, one or more 12-bit ADC with 12 analog input channels, among other features that are readily available. Other microcontrollers may be readily substituted for use with the present disclosure. Accordingly, the present disclosure should not be limited in this context.

In certain instances, the light source 1110 can be employed to emit light which can be directed at the cutting edge 182 in the optical sensing region, for example. The optical sensor 1108 may be employed to measure the intensity of the light reflected from the cutting edge 182 while in the optical sensing region in response to exposure to the light emitted by the light source 1110. In certain instances, the processor 1114 may receive one or more values of the measured intensity of the reflected light and may store the one or more values of the measured intensity of the reflected light on the memory 1116, for example. The stored values can be detected and/or recorded before, after, and/or during a plurality of surgical procedures performed by the surgical instrument 10, for example.

In certain instances, the processor 1114 may compare the measured intensity of the reflected light to a predefined threshold values that may be stored on the memory 1116, for example. In certain instances, the controller 1112 may conclude that the sharpness of the cutting edge 182 has dropped below an acceptable level if the measured light intensity exceeds the predefined threshold value by 1%, 5%, 10%, 25%, 50%, 100% and/or more than 100%, for example. In certain instances, the processor 1114 can be employed to detect a decreasing trend in the stored values of the measured intensity of the light reflected from the cutting edge 182 while in the optical sensing region.

In certain instances, the surgical instrument 10 may include one or more feedback systems such as, for example, the feedback system 1120. In certain instances, the processor 1114 can employ the feedback system 1120 to alert a user if the measured light intensity of the light reflected from cutting edge 182 while in the optical sensing region is beyond the stored threshold value, for example. In certain instances, the feedback system 1120 may comprise one or more visual feedback systems such as display screens, backlights, and/or LEDs, for example. In certain instances, the feedback system 1120 may comprise one or more audio feedback systems such as speakers and/or buzzers, for example. In certain instances, the feedback system 1120 may comprise one or more haptic feedback systems, for example. In certain instances, the feedback system 1120 may comprise combinations of visual, audio, and/or tactile feedback systems, for example.

In certain instances, the surgical instrument 10 may comprise a firing lockout mechanism 1122 which can be employed to prevent advancement of the cutting edge 182. Various suitable firing lockout mechanisms are described in greater detail in U.S. Patent Publication No. 2014/0001231, entitled FIRING SYSTEM LOCKOUT ARRANGEMENTS FOR SURGICAL INSTRUMENTS, and filed Jun. 28, 2012, which is hereby incorporated by reference herein in its entirety. In certain instances, as illustrated in FIG. 76, the processor 1114 can be operably coupled to the lockout mechanism 1122; the processor 1114 may employ the lockout mechanism 1122 to prevent advancement of the cutting edge 182 in the event it is determined that the measured intensity of the light reflected from the cutting edge 182 is beyond the stored threshold, for example. In other words, the processor 1114 may activate the lockout mechanism 1122 if the cutting edge is not sufficiently sharp to cut the tissue captured by the end effector 300.

In certain instances, the optical sensor 1108 and the light source 1110 can be housed at a distal portion of the shaft assembly 200. In certain instances, the sharpness of cutting edge 182 can be evaluated by the optical sensor 1108, as described above, prior to transitioning the cutting edge 182 into the end effector 300. The firing bar 172 (FIG. 20) may advance the cutting edge 182 through the optical sensing region defined by the optical sensor 1108 while the cutting edge 182 is in the shaft assembly 182 and prior to entering the end effector 300, for example. In certain instances, the sharpness of cutting edge 182 can be evaluated by the optical sensor 1108 after retracting the cutting edge 182 proximally from the end effector 300. The firing bar 172 (FIG. 20) may retract the cutting edge 182 through the optical sensing region defined by the optical sensor 1108 after retracting the cutting edge 182 from the end effector 300 into the shaft assembly 200, for example.

In certain instances, the optical sensor 1108 and the light source 1110 can be housed at a proximal portion of the end effector 300 which can be proximal to the staple cartridge 1100, for example. The sharpness of cutting edge 182 can be evaluated by the optical sensor 1108 after transitioning the cutting edge 182 into the end effector 300 but prior to engaging the staple cartridge 1100, for example. In certain instances, the firing bar 172 (FIG. 20) may advance the cutting edge 182 through the optical sensing region defined by the optical sensor 1108 while the cutting edge 182 is in the end effector 300 but prior to engaging the staple cartridge 1100, for example.

In various instances, the sharpness of cutting edge 182 can be evaluated by the optical sensor 1108 as the cutting edge 182 is advanced by the firing bar 172 through the slot 193. As illustrated in FIG. 74, the optical sensor 1108 and the light source 1110 can be housed at the proximal portion 1102 of the staple cartridge 1100, for example; and the sharpness of cutting edge 182 can be evaluated by the optical sensor 1108 at the proximal portion 1102, for example. The firing bar 172 (FIG. 20) may advance the cutting edge 182 through the optical sensing region defined by the optical sensor 1108 at the proximal portion 1102 before the cutting edge 182 engages tissue captured between the staple cartridge 1100 and the anvil 306, for example. In certain instances, as illustrated in FIG. 74, the optical sensor 1108 and the light source 1110 can be housed at the distal portion 1104 of the staple cartridge 1100, for example. The sharpness of cutting edge 182 can be evaluated by the optical sensor 1108 at the distal portion 1104. In certain instances, the firing bar 172 (FIG. 20) may advance the cutting edge 182 through the optical sensing region defined by the optical sensor 1108 at the distal portion 1104 after the cutting edge 182 has passed through the tissue captured between the staple cartridge 1100 and the anvil 306, for example.

Referring again to FIG. 74, the staple cartridge 1100 may comprise a plurality of optical sensors 1108 and a plurality of corresponding light sources 1110, for example. In certain instances, a pair of the optical sensor 1108 and the light source 1110 can be housed at the proximal portion 1102 of the staple cartridge 1100, for example; and a pair of the optical sensor 1108 and the light source 1110 can be housed at the distal portion 1104 of the staple cartridge 1100, for example. In such instances, the sharpness of the cutting edge 182 can be evaluated a first time at the proximal portion 1102 prior to engaging the tissue, for example, and a second time at the distal portion 1104 after passing through the captured tissue, for example.

The reader will appreciate that an optical sensor 1108 may evaluate the sharpness of the cutting edge 182 a plurality of times during a surgical procedure. For example, the sharpness of the cutting edge can be evaluated a first time during advancement of the cutting edge 182 through the slot 193 in a firing stroke, and a second time during retraction of the cutting edge 182 through the slot 193 in a return stroke, for example. In other words, the light reflected from the cutting edge 182 can be measured by the same optical sensor 1108 once as the cutting edge is advanced through the optical sensing region, and once as the cutting edge 182 is retracted through the optical sensing region, for example.

The reader will appreciate that the processor 1114 may receive a plurality of readings of the intensity of the light reflected from the cutting edge 182 from one or more of the optical sensors 1108. In certain instances, the processor 1114 may be configured to discard outliers and calculate an average reading from the plurality of readings, for example. In certain instances, the average reading can be compared to a threshold stored in the memory 1116, for example. In certain instances, the processor 1114 may be configured to alert a user through the feedback system 1120 and/or activate the lockout mechanism 1122 if it is determined that the calculated average reading is beyond the threshold stored in the memory 1116, for example.

Figure 77:
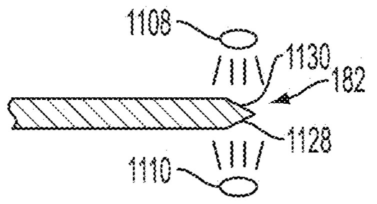
FIG. 77 illustrates a partial view of a cutting edge, an optical sensor, and a light source of the surgical instrument of FIG. 74 according to various embodiments described herein.
Figure 78:
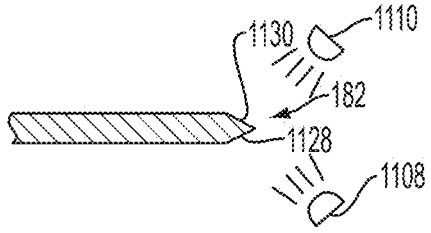
FIG. 78 illustrates a partial view of a cutting edge, an optical sensor, and a light source of the surgical instrument of FIG. 74 according to various embodiments described herein.

In certain instances, as illustrated in FIGS. 75, 77, and 78, a pair of the optical sensor 1108 and the light source 1110 can be positioned on opposite sides of the staple cartridge 1100. In other words, the optical sensor 1108 can be positioned on a first side 1124 of the slot 193, for example, and the light source 1110 can be positioned on a second side 1126, opposite the first side 1124, of the slot 193, for example. In certain instances, the pair of the optical sensor 1108 and the light source 1110 can be substantially disposed in a plane transecting the staple cartridge 1100, as illustrated in FIG. 75. The pair of the optical sensor 1108 and the light source 1110 can be oriented to define an optical sensing region that is positioned, or at least substantially positioned, on the plane transecting the staple cartridge 1100, for example. Alternatively, the pair of the optical sensor 1108 and the light source 1110 can be oriented to define an optical sensing region that is positioned proximal to the plane transecting the staple cartridge 1100, for example, as illustrated in FIG. 78.

Figure 79:
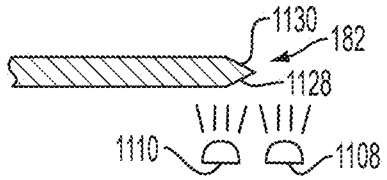
FIG. 79 illustrates a partial view of a cutting edge, an optical sensor, and a light source of the surgical instrument of FIG. 74 according to various embodiments described herein.

In certain instances, a pair of the optical sensor 1108 and the light source 1110 can be positioned on a same side of the staple cartridge 1100. In other words, as illustrated in FIG. 79, the pair of the optical sensor 1108 and the light source 1110 can be positioned on a first side of the cutting edge 182, e.g. the side 1128, as the cutting edge 182 is advanced through the slot 193. In such instances, the light source 1110 can be oriented to direct light at the side 1128 of the cutting edge 182; and the intensity of the light reflected from the side 1128, as measured by the optical sensor 1108, may represent the sharpness of the side 1128.

Figure 80:
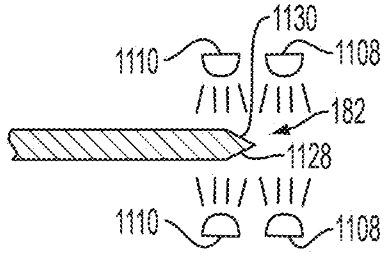
FIG. 80 illustrates a partial view of a cutting edge, optical sensors, and light sources of the surgical instrument of FIG. 74 according to various embodiments described herein.

In certain instances, as illustrated in FIG. 80, a second pair of the optical sensor 1108 and the light source 1110 can be positioned on a second side of the cutting edge 182, e.g. the side 1130, for example. The second pair can be employed to evaluate the sharpness of the side 1130. For example, the light source 1110 of the second pair can be oriented to direct light at the side 1130 of the cutting edge 182; and the intensity of the light reflected from the side 1130, as measured by the optical sensor 1108 of the second pair, may represent the sharpness of the side 1130. In certain instances, the processor can be configured to assess the sharpness of the cutting edge 182 based upon the measured intensities of the light reflected from the sides 1128 and 1130 of the cutting edge 182, for example.

Figure 81:
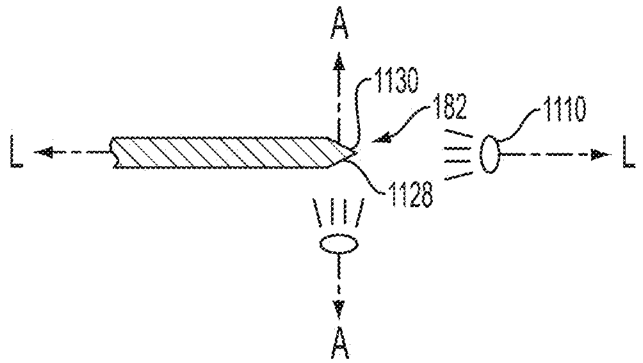
FIG. 81 illustrates a partial view of a cutting edge, an optical sensor, and a light source of the surgical instrument of FIG. 74 according to various embodiments described herein.

In certain instances, as illustrated in FIG. 75, a pair of the optical sensor 1108 and the light source 1110 can be housed at the distal portion 1104 of the staple cartridge 1100. As illustrated in FIG. 81, the light source 1108 can be positioned, or at least substantially positioned, on an axis LL which extends longitudinally along the path of the cutting edge 182 through the slot 193, for example. In addition, the light source 1110 can be positioned distal to the cutting edge 182 and oriented to direct light at the cutting edge 182 as the cutting edge is advanced toward the light source 1110, for example. Furthermore, the optical sensor 1108 can be positioned, or at least substantially positioned, along an axis AA that intersects the axis LL, as illustrated in FIG. 81. In certain instances, the axis AA may be perpendicular to the axis LL, for example. In any event, the optical sensor 1108 can be oriented to define an optical sensing region at the intersection of the axis LL and the axis AA, for example.

The reader will appreciate that the position, orientation and/or number of optical sensors and corresponding light sources described herein in connection with the surgical instrument 10 are example embodiments intended for illustration purposes. Various other arrangements of optical sensors and light sources can be employed by the present disclosure to evaluate the sharpness of the cutting edge 182.

The reader will appreciate that advancement of the cutting edge 182 through the tissue captured by the end effector 300 may cause the cutting edge to collect tissue debris and/or bodily fluids during each firing of the surgical instrument 10. Such debris may interfere with the ability of the module

Figure 82:
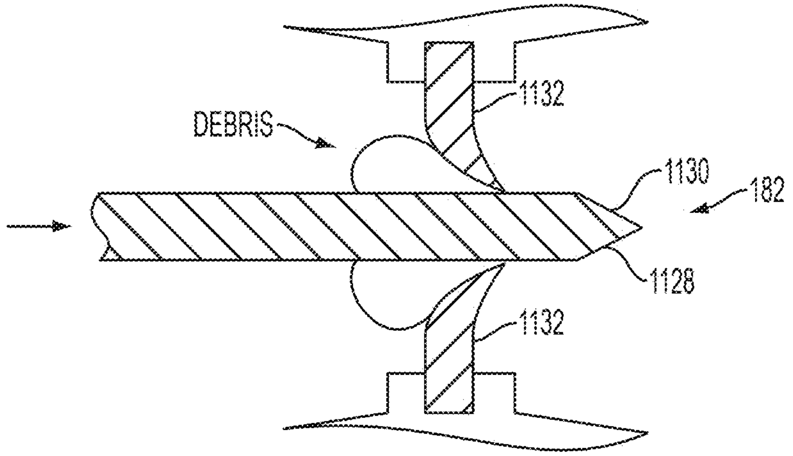
FIG. 82 illustrates a partial view of a cutting edge between cleaning blades of the surgical instrument of FIG. 74 according to various embodiments described herein.
Figure 83:
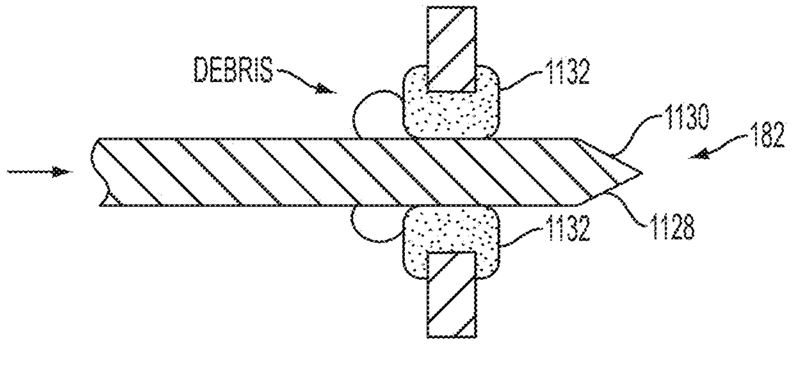
FIG. 83 illustrates a partial view of a cutting edge between cleaning sponges of the surgical instrument of FIG. 74 according to various embodiments described herein.

1106 to accurately evaluate the sharpness of the cutting edge 182. In certain instances, the surgical instrument 10 can be equipped with one or more cleaning mechanisms which can be employed to clean the cutting edge 182 prior to evaluating the sharpness of the cutting edge 182, for example. In certain instances, as illustrated in FIG. 82, a cleaning mechanism 1131 may comprise one or more cleaning members 1132, for example. In certain instances, the cleaning members 1132 can be disposed on opposite sides of the slot 193 to receive the cutting edge 182 therebetween (See FIG. 82) as the cutting edge 182 is advanced through the slot 193, for example. In certain instances, as illustrated in FIG. 82, the cleaning members 1132 may comprise wiper blades, for example. In certain instances, as illustrated in FIG. 830, the cleaning members 1132 may comprise sponges, for example. The reader will appreciate that various other cleaning members can be employed to clean the cutting edge 182, for example.

Referring to FIG. 74, in certain instances, the staple cartridge 1100 may include a first pair of the optical sensor 1108 and the light source 1110, which can be housed in the proximal portion 1102 of the staple cartridge 1100, for example. Furthermore, as illustrated in FIG. 74, the staple cartridge 1100 may include a first pair of the cleaning members 1132, which can be housed in the proximal portion 1102 on opposite sides of the slot 193. The first pair of the cleaning members 1132 can be positioned distal to the first pair of the optical sensor 1108 and the light source 1110, for example. As illustrated in FIG. 74, the staple cartridge 1100 may include a second pair of the optical sensor 1108 and the light source 1110, which can be housed in the distal portion 1104 of the staple cartridge 1100, for example. As illustrated in FIG. 74, the staple cartridge 1100 may include a second pair of the cleaning members 1132, which can be housed in the distal portion 1104 on opposite sides of the slot 193. The second pair of the cleaning members 1132 can be positioned proximal to the second pair of the optical sensor 1108 and the light source 1110.

Further to the above, as illustrated in FIG. 74, the cutting edge 182 may be advanced distally in a firing stroke to cut tissue captured by the end effector 300. As the cutting edge is advanced, a first evaluation of the sharpness of the cutting edge 182 can be performed by the first pair of the optical sensor 1108 and the light source 1110 prior to tissue engagement by the cutting edge 182, for example. A second evaluation of the sharpness of the cutting edge 182 can be performed by the second pair of the optical sensor 1108 and the light source 1110 after the cutting edge 182 has transected the captured tissue, for example. The cutting edge 182 may be advanced through the second pair of the cleaning members 1132 prior to the second evaluation of the sharpness of the cutting edge 182 to remove any debris collected by the cutting edge 182 during the transection of the captured tissue.

Further to the above, as illustrated in FIG. 74, the cutting edge 182 may be retracted proximally in a return stroke. As the cutting edge is retracted, a third evaluation of the sharpness of the cutting edge 182 can be performed by the first pair of the optical sensor 1108 and the light source 1110 during the return stroke. The cutting edge 182 may be retracted through the first pair of the cleaning members 1132 prior to the third evaluation of the sharpness of the cutting edge 182 to remove any debris collected by the cutting edge 182 during the transection of the captured tissue, for example.

In certain instances, one or more of the lights sources 1110 may comprise one or more optical fiber cables. In certain instances, one or more flex circuits 1134 can be employed to transmit energy from the power source 1118 to the optical sensors 1108 and/or the light sources 1110. In certain instances, the flex circuits 1134 may be configured to transmit one or more of the readings of the optical sensors 1108 to the controller 1112, for example.

Figure 84:
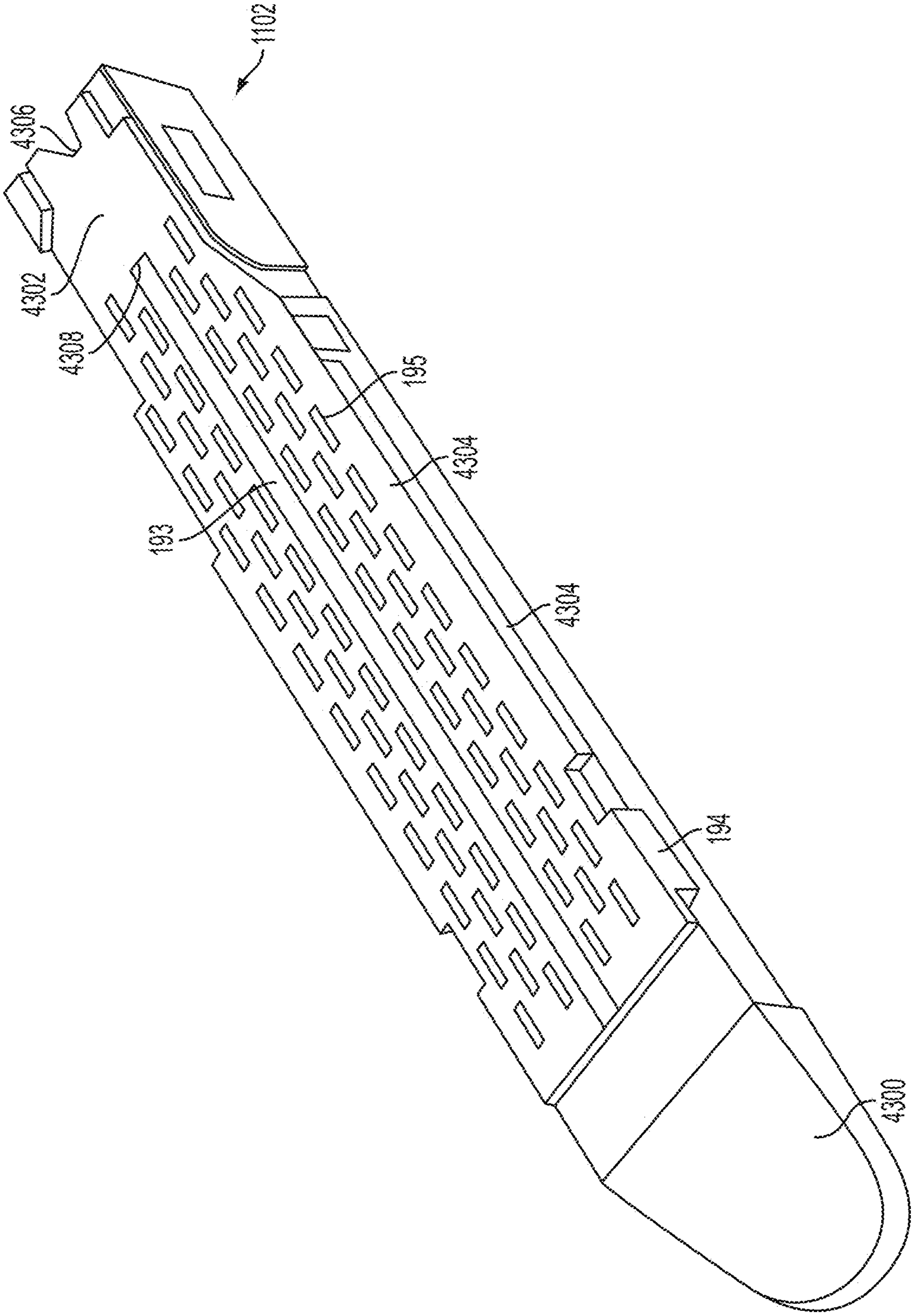
FIG. 84 illustrates a perspective view of a staple cartridge including a sharpness testing member according to various embodiments described herein.

Referring now to FIG. 84, a staple cartridge 4300 is depicted; the staple cartridge 4300 is similar in many respects to the staple cartridge 304 (FIG. 20). For example, the staple cartridge 4300 can be employed with the end effector 300. In certain instances, as illustrated in FIG. 84, the staple cartridge 4300 may comprise a sharpness testing member 4302 which can be employed to test the sharpness of the cutting edge 182. In certain instances, the sharpness testing member 4302 can be attached to and/or integrated with the cartridge body 194 of the staple cartridge 4300, for example. In certain instances, the sharpness testing member 4302 can be disposed in the proximal portion 1102 of the staple cartridge 4300, for example. In certain instances, as illustrated in FIG. 84, the sharpness testing member 4302 can be disposed onto a cartridge deck 4304 of the staple cartridge 4300, for example.

In certain instances, as illustrated in FIG. 84, the sharpness testing member 4302 can extend across the slot 193 of the staple cartridge 4300 to bridge, or at least partially bridge, the gap defined by the slot 193, for example. In certain instances, the sharpness testing member 4302 may interrupt, or at least partially interrupt, the path of the cutting edge 182. The cutting edge 182 may engage, cut, and/or pass through the sharpness testing member 4302 as the cutting edge 182 is advanced during a firing stroke, for example. In certain instances, the cutting edge 182 may be configured to engage, cut, and/or pass through the sharpness testing member 4302 prior to engaging tissue captured by the end effector 300 in a firing stroke, for example. In certain instances, the cutting edge 182 may be configured to engage the sharpness testing member 4302 at a proximal end 4306 of the sharpness testing member 4302, and exit and/or disengage the sharpness testing member 4302 at a distal end 4308 of the sharpness testing member 4302, for example. In certain instances, the cutting edge 182 can travel and/or cut through the sharpness testing member 4302 a distance (D) between the proximal end 4306 and the distal end 4308, for example, as the cutting edge 182 is advanced during a firing stroke.

Figure 85:
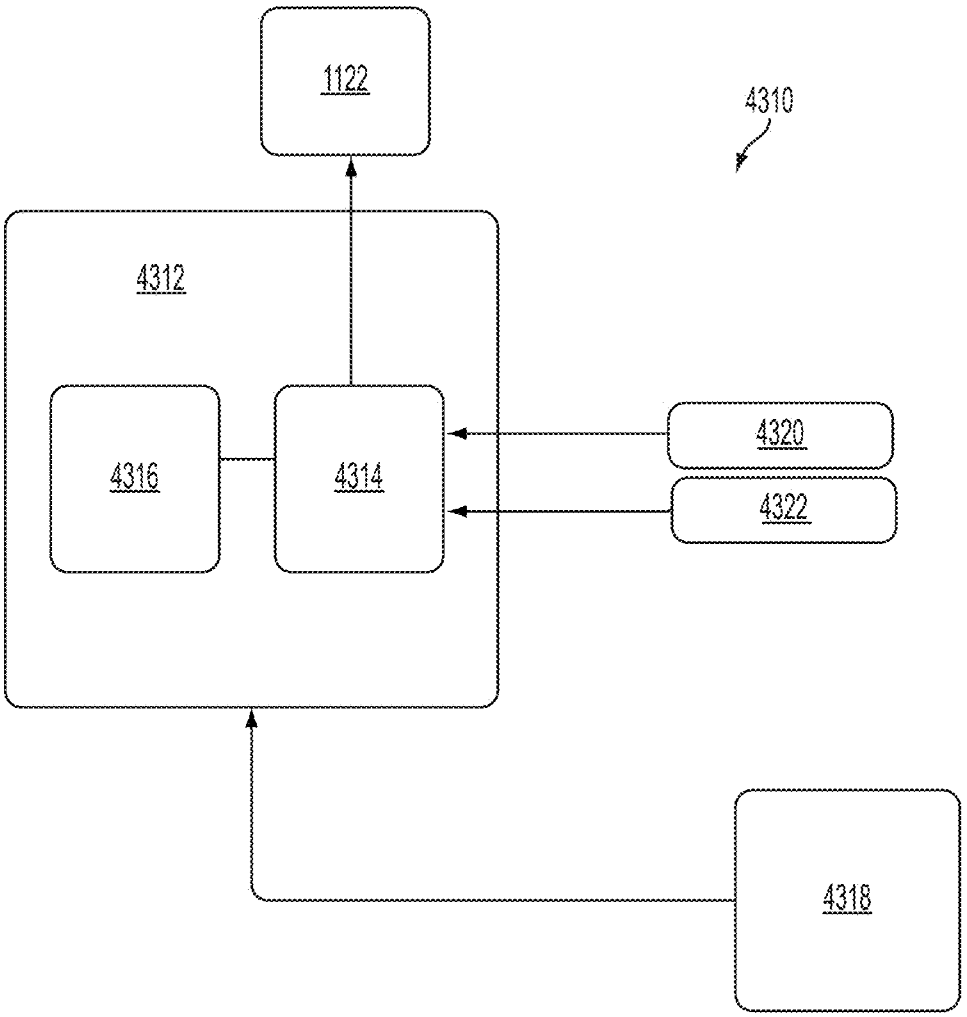
FIG. 85 illustrates a logic diagram of a module of a surgical instrument according to various embodiments described herein.

Referring primarily to FIGS. 84 and 85, the surgical instrument 10 may comprise a sharpness testing module 4310 for testing the sharpness of the cutting edge 182, for example. In certain instances, the module 4310 can evaluate the sharpness of the cutting edge 182 by testing the ability of the cutting edge 182 to be advanced through the sharpness testing member 4302. For example, the module 4310 can be configured to observe the time period the cutting edge 182 takes to fully transect and/or completely pass through at least a predetermined portion of the sharpness testing member 4302. If the observed time period exceeds a predetermined threshold, the module 4310 may conclude that the sharpness of the cutting edge 182 has dropped below an acceptable level, for example.

In certain instances, the module 4310 may include a microcontroller 4312 ("controller") which may include a microprocessor 4314 ("processor") and one or more computer readable mediums or memory units 4316 ("memory"). In certain instances, the memory 4316 may store various program instructions, which when executed may cause the processor 4314 to perform a plurality of functions and/or calculations described herein. In certain instances, the memory 4316 may be coupled to the processor 4314, for example. A power source 4318 can be configured to supply power to the controller 4312, for example. In certain instances, the power source 4138 may comprise a battery (or "battery pack" or "power pack"), such as a Li ion battery, for example. In certain instances, the battery pack may be configured to be releasably mounted to the handle 14. A number of battery cells connected in series may be used as the power source 4318. In certain instances, the power source 4318 may be replaceable and/or rechargeable, for example.

In certain instances, the processor 4313 can be operably coupled to the feedback system 1120 and/or the lockout mechanism 1122, for example.

Referring to FIGS. 84 and 85, the module 4310 may comprise one or more position sensors. Example position sensors and positioning systems suitable for use with the present disclosure are described in U.S. patent application Ser. No. 13/803,210, entitled SENSOR ARRANGEMENTS FOR ABSOLUTE POSITIONING SYSTEM FOR SURGICAL INSTRUMENTS, and filed Mar. 14, 2013, now U.S. Pat. No. 9,808,244, the disclosure of which is hereby incorporated by reference herein in its entirety. In certain instances, the module 4310 may include a first position sensor 4320 and a second position sensor 4322. In certain instances, the first position sensor 4320 can be employed to detect a first position of the cutting edge 182 at the proximal end 4306 of the sharpness testing member 4302, for example; and the second position sensor 4322 can be employed to detect a second position of the cutting edge 182 at the distal end 4308 of the sharpness cutting member 4302, for example.

In certain instances, the position sensors 4320 and 4322 can be employed to provide first and second position signals, respectively, to the microcontroller 4312. It will be appreciated that the position signals may be analog signals or digital values based on the interface between the microcontroller 4312 and the position sensors 4320 and 4322. In one embodiment, the interface between the microcontroller 4312 and the position sensors 4320 and 4322 can be a standard serial peripheral interface (SPI), and the position signals can be digital values representing the first and second positions of the cutting edge 182, as described above.

Further to the above, the processor 4314 may determine the time period between receiving the first position signal and receiving the second position signal. The determined time period may correspond to the time it takes the cutting edge 182 to advance through the sharpness testing member 4302 from the first position at the proximal end 4306 of the sharpness testing member 4302, for example, to the second position at the distal end 4308 of the sharpness testing member 4302, for example. In at least one example, the controller 4312 may include a time element which can be activated by the processor 4314 upon receipt of the first position signal, and deactivated upon receipt of the second position signal. The time period between the activation and deactivation of the time element may correspond to the time it takes the cutting edge 182 to advance from the first position to the second position, for example. The time element may comprise a real time clock, a processor configured to implement a time function, or any other suitable timing circuit.

In various instances, the controller 4312 can compare the time period it takes the cutting edge 182 to advance from the first position to the second position to a predefined threshold value to assess whether the sharpness of the cutting edge 182 has dropped below an acceptable level, for example. In certain instances, the controller 4312 may conclude that the sharpness of the cutting edge 182 has dropped below an acceptable level if the measured time period exceeds the predefined threshold value by 1%, 5%, 10%, 25%, 50%, 100% and/or more than 100%, for example.

Figure 86:
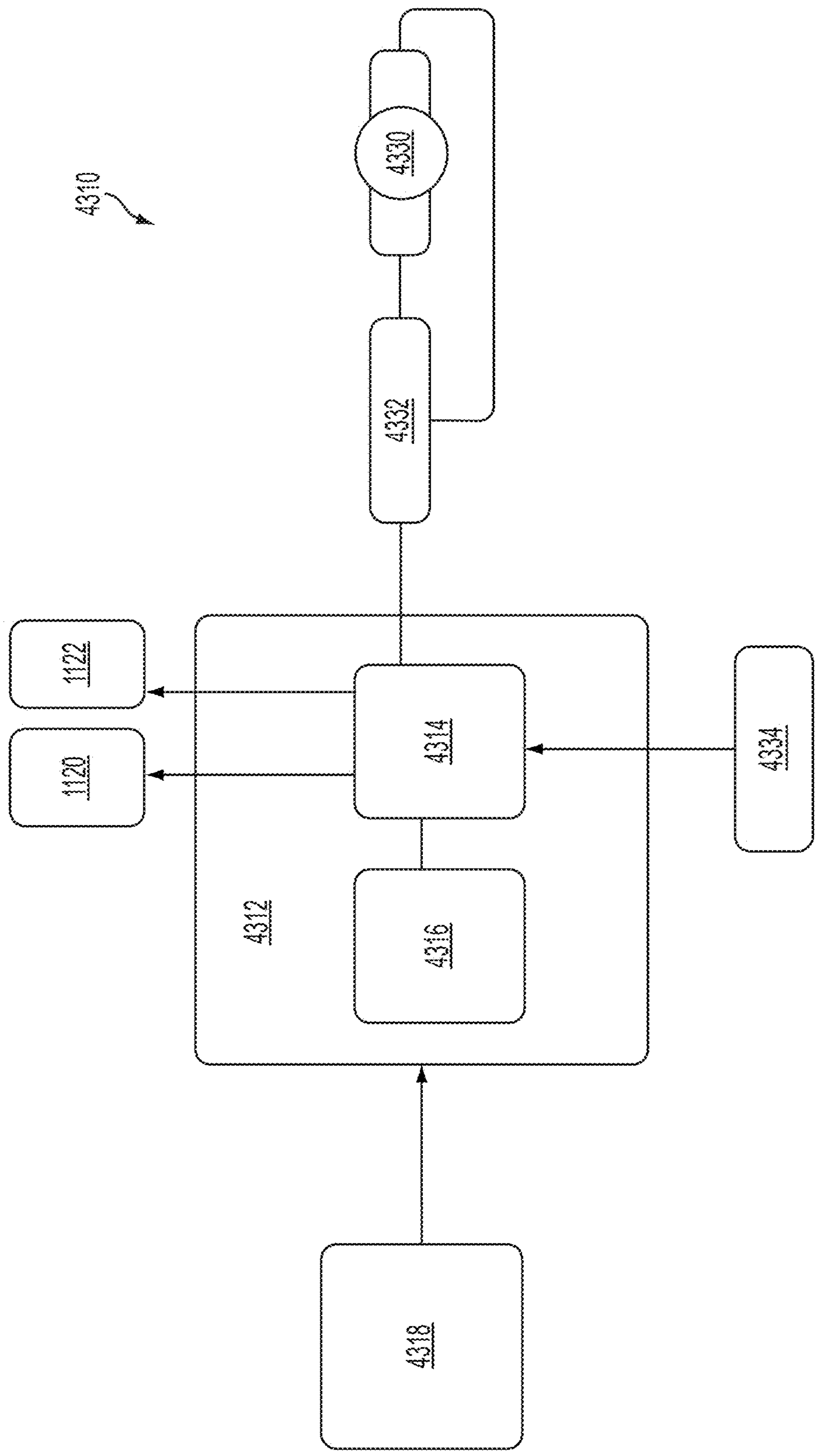
FIG. 86 illustrates a logic diagram of a module of a surgical instrument according to various embodiments described herein.

Referring to FIG. 86, in various instances, an electric motor 4330 can drive the firing bar 172 (FIG. 20) to advance the cutting edge 182 during a firing stroke and/or to retract the cutting edge 182 during a return stroke, for example. A motor driver 4332 can control the electric motor 4330; and a microcontroller such as, for example, the microcontroller 4312 can be in signal communication with the motor driver 4332. As the electric motor 4330 advances the cutting edge 182, the microcontroller 4312 can determine the current drawn by the electric motor 4330, for example. In such instances, the force required to advance the cutting edge 182 can correspond to the current drawn by the electric motor 4330, for example. Referring still to FIG. 86, the microcontroller 4312 of the surgical instrument 10 can determine if the current drawn by the electric motor 4330 increases during advancement of the cutting edge 182 and, if so, can calculate the percentage increase of the current.

In certain instances, the current drawn by the electric motor 4330 may increase significantly while the cutting edge 182 is in contact with the sharpness testing member 4302 due to the resistance of the sharpness testing member 4302 to the cutting edge 182. For example, the current drawn by the electric motor 4330 may increase significantly as the cutting edge 182 engages, passes and/or cuts through the sharpness testing member 4302. The reader will appreciate that the resistance of the sharpness testing member 4302 to the cutting edge 182 depends, in part, on the sharpness of the cutting edge 182; and as the sharpness of the cutting edge 182 decreases from repetitive use, the resistance of the sharpness testing member 4302 to the cutting edge 182 will increase. Accordingly, the value of the percentage increase of the current drawn by the motor 4330 while the cutting edge is in contact with the sharpness testing member 4302 can increase as the sharpness of the cutting edge 182 decreases from repetitive use, for example.

In certain instances, the determined value of the percentage increase of the current drawn by the motor 4330 can be the maximum detected percentage increase of the current drawn by the motor 4330. In various instances, the microcontroller 4312 can compare the determined value of the percentage increase of the current drawn by the motor 4330 to a predefined threshold value of the percentage increase of the current drawn by the motor 4330. If the determined value exceeds the predefined threshold value, the microcontroller 4312 may conclude that the sharpness of the cutting edge 182 has dropped below an acceptable level, for example.

In certain instances, as illustrated in FIG. 86, the processor 4314 can be in communication with the feedback system 1120 and/or the lockout mechanism 1122, for example. In certain instances, the processor 4314 can employ the feedback system 1120 to alert a user if the determined value of the percentage increase of the current drawn by the motor 4330 exceeds the predefined threshold value, for example. In certain instances, the processor 4314 may employ the lockout mechanism 1122 to prevent advancement of the cutting edge 182 if the determined value of the percentage increase of the current drawn by the motor 4330 exceeds the predefined threshold value, for example.

In various instances, the microcontroller 43312 can utilize an algorithm to determine the change in current drawn by the electric motor 4330. For example, a current sensor can detect the current drawn by the electric motor 4330 during the firing stroke. The current sensor can continually detect the current drawn by the electric motor and/or can intermittently detect the current draw by the electric motor. In various instances, the algorithm can compare the most recent current reading to the immediately proceeding current reading, for example. Additionally or alternatively, the algorithm can compare a sample reading within a time period X to a previous current reading. For example, the algorithm can compare the sample reading to a previous sample reading within a previous time period X, such as the immediately proceeding time period X, for example. In other instances, the algorithm can calculate the trending average of current drawn by the motor. The algorithm can calculate the average current draw during a time period X that includes the most recent current reading, for example, and can compare that average current draw to the average current draw during an immediately proceeding time period time X, for example.

Figure 87:
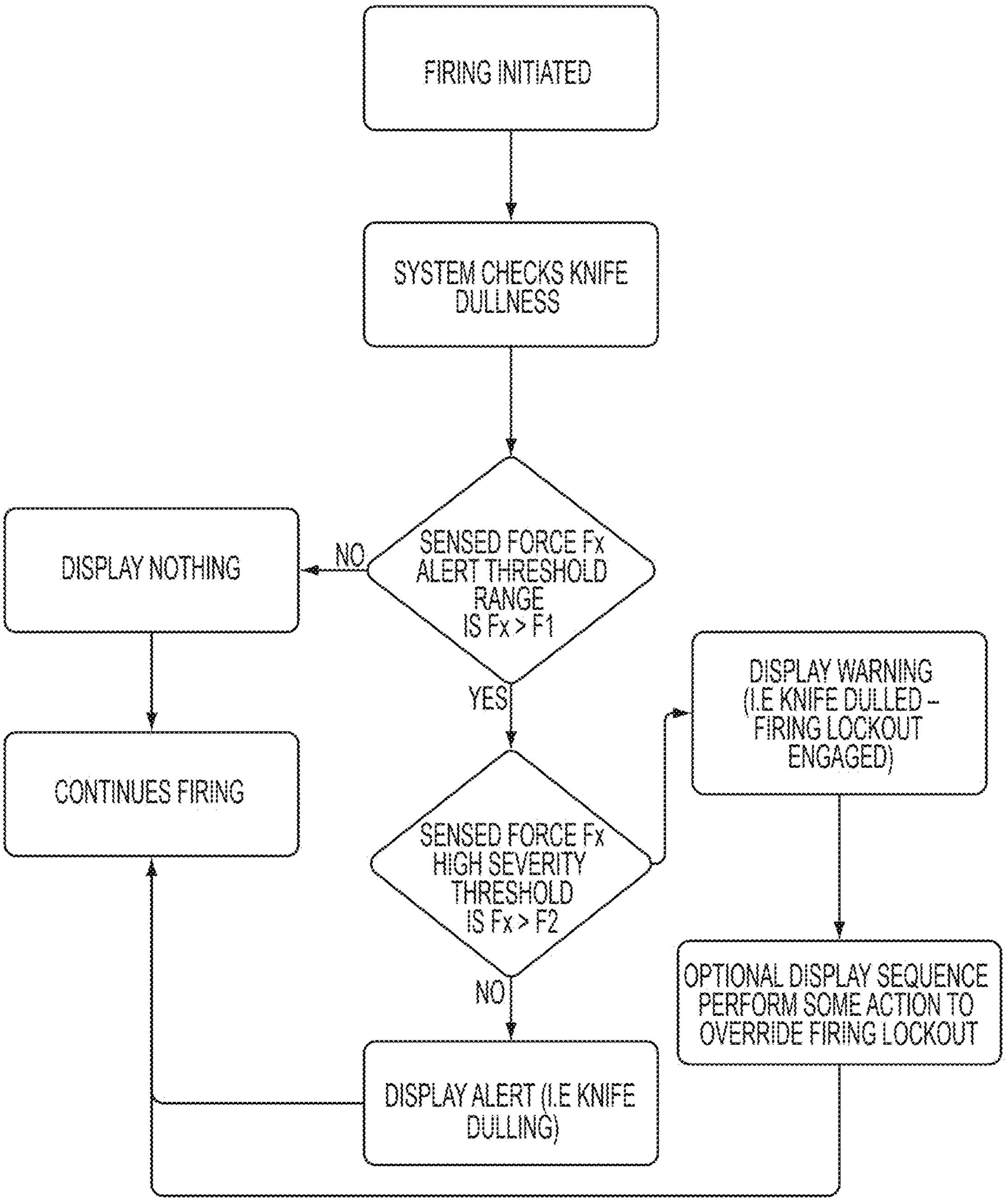
FIG. 87 illustrates a logic diagram outlining a method for evaluating sharpness of a cutting edge of a surgical instrument according to various embodiments described herein.

Referring to FIG. 87, a method is depicted for evaluating the sharpness of the cutting edge 182 of the surgical instrument 10; and various responses are outlined in the event the sharpness of the cutting edge 182 drops to and/or below an alert threshold and/or a high severity threshold, for example. In various instances, a microcontroller such as, for example, the microcontroller 4312 can be configured to implement the method depicted in FIG. 87. In certain instances, the surgical instrument 10 may include a load cell 4334 (FIG. 86); as illustrated in FIG. 86, the microcontroller 4312 may be in communication with the load cell 4334. In certain instances, the load cell 4334 may include a force sensor such as, for example, a strain gauge, which can be operably coupled to the firing bar 172, for example. In certain instances, the microcontroller 4312 may employ the load cell 4334 to monitor the force (Fx) applied to the cutting edge 182 as the cutting edge 182 is advanced during a firing stroke.

Figure 88:
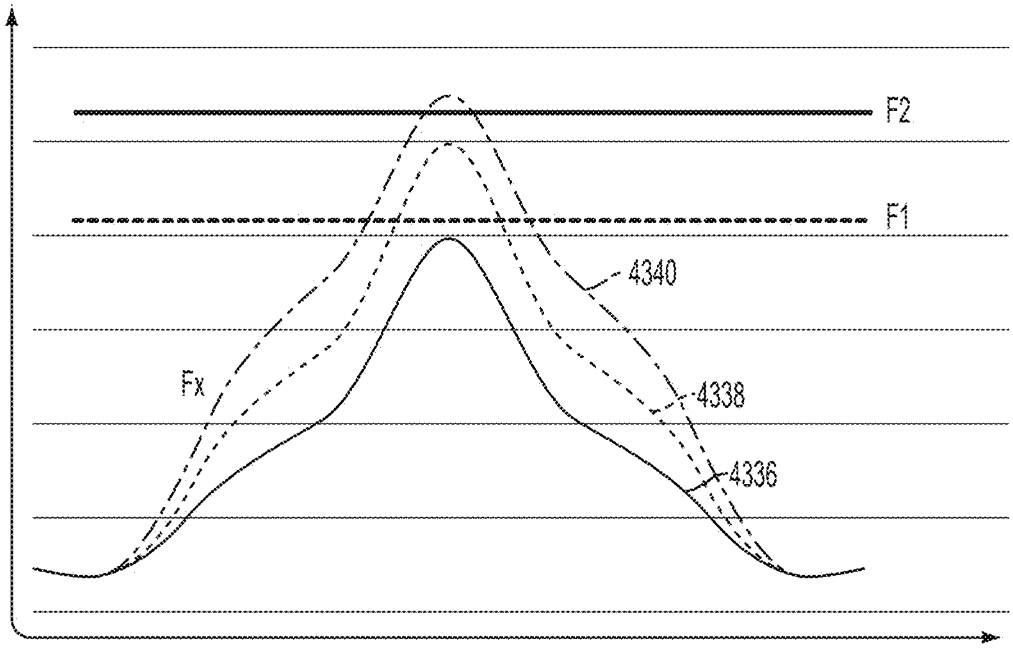
FIG. 88 illustrates a chart of the forces applied against a cutting edge of a surgical instrument by the sharpness testing member of FIG. 84 at various sharpness levels according to various embodiments described herein.

In certain instances, as illustrated in FIG. 88, the load cell 4334 can be configured to monitor the force (Fx) applied to the cutting edge 182 while the cutting edge 182 is engaged and/or in contact with the sharpness testing member 4302, for example. The reader will appreciate that the force (Fx) applied by the sharpness testing member 4302 to the cutting edge 182 while the cutting edge 182 is engaged and/or in contact with the sharpness testing member 4302 may depend, at least in part, on the sharpness of the cutting edge 182. In certain instances, a decrease in the sharpness of the cutting edge 182 can result in an increase in the force (FX) required for the cutting edge 182 to cut or pass through the sharpness testing member 4302. For example, as illustrated in FIG. 88, graphs 4336, 4338, and 4340 represent the force (Fx) applied to the cutting edge 182 while the cutting edge 182 travels a predefined distance (D) through three identical, or at least substantially identical, sharpness testing members 4302. The graph 4336 corresponds to a first sharpness of the cutting edge 182; the graph 4338 corresponds to a second sharpness of the cutting edge 182; and the graph 4340 corresponds to a third sharpness of the cutting edge 182. The first sharpness is greater than the second sharpness, and the second sharpness is greater than the third sharpness.

In certain instances, the microcontroller 4312 may compare a maximum value of the monitored force (Fx) applied to the cutting edge 182 to one or more predefined threshold values. In certain instances, as illustrated in FIG. 88, the predefined threshold values may include an alert threshold (F1) and/or a high severity threshold (F2). In certain instances, as illustrated in the graph 4336 of FIG. 88, the monitored force (Fx) can be less than the alert threshold (F1), for example. In such instances, as illustrated in FIG. 87, the sharpness of the cutting edge 182 is at a good level and the microcontroller 4312 may take no action to alert a user as to the status of the cutting edge 182 or may inform the user that the sharpness of the cutting edge 182 is within an acceptable range.

In certain instances, as illustrated in the graph 4338 of FIG. 88, the monitored force (Fx) can be more than the alert threshold (F1) but less than the high severity threshold (F2), for example. In such instances, as illustrated in FIG. 87, the sharpness of the cutting edge 182 can be dulling but still within an acceptable level. The microcontroller 4312 may take no action to alert a user as to the status of the cutting edge 182. Alternatively, the microcontroller 4312 may inform the user that the sharpness of the cutting edge 182 is within an acceptable range. Alternatively or additionally, the microcontroller 4312 may determine or estimate the number of cutting cycles remaining in the lifecycle of the cutting edge 182 and may alert the user accordingly.

In certain instances, the memory 4316 may include a database or a table that correlates the number of cutting cycles remaining in the lifecycle of the cutting edge 182 to predetermined values of the monitored force (Fx). The processor 4314 may access the memory 4316 to determine the number of cutting cycles remaining in the lifecycle of the cutting edge 182 which correspond to a particular measured value of the monitored force (Fx) and may alert the user to the number of cutting cycles remaining in the lifecycle of the cutting edge 182, for example.

In certain instances, as illustrated in the graph 4340 of FIG. 88, the monitored force (Fx) can be more than the high severity threshold (F2), for example. In such instances, as illustrated in FIG. 87, the sharpness of the cutting edge 182 can be below an acceptable level In response, the microcontroller 4312 may employ the feedback system 1120 to warn the user that the cutting edge 182 is too dull for safe use, for example. In certain instances, the microcontroller 4312 may employ the lockout mechanism 1122 to prevent advancement of the cutting edge 182 upon detection that the monitored force (Fx) exceeds the high severity threshold (F2), for example. In certain instances, the microcontroller 4312 may employ the feedback system 1122 to provide instructions to the user for overriding the lockout mechanism 1122, for example.

Figure 89:
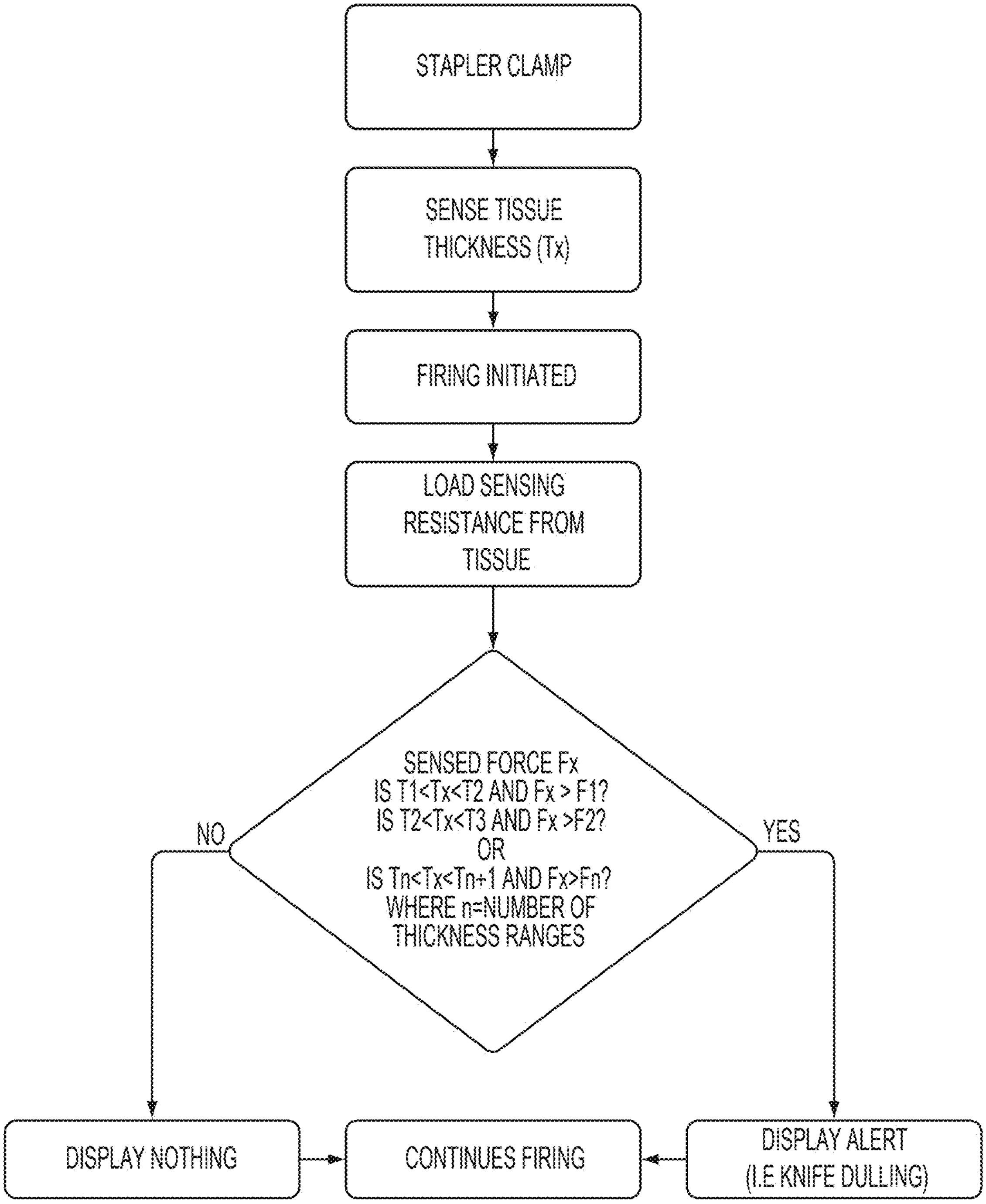
FIG. 89 illustrates a flow chart outlining a method for determining whether a cutting edge of a surgical instrument is sufficiently sharp to transect tissue captured by the surgical instrument according to various embodiments described herein.

Referring to FIG. 89, a method is depicted for determining whether a cutting edge such as, for example, the cutting edge 182 is sufficiently sharp to be employed in transecting a tissue of a particular tissue thickness that is captured by the end effector 300, for example. In certain instances, the microcontroller 4312 can be implemented to perform the method depicted in FIG. 16, for example. As described above, repetitive use of the cutting edge 182 may dull or reduce the sharpness of the cutting edge 182 which may increase the force required for the cutting edge 182 to transect the captured tissue. In other words, the sharpness level of the cutting edge 182 can be defined by the force required for the cutting edge 182 to transect the captured tissue, for example. The reader will appreciate that the force required for the cutting edge 182 to transect a captured tissue may also depend on the thickness of the captured tissue. In certain instances, the greater the thickness of the captured tissue, the greater the force required for the cutting edge 182 to transect the captured tissue at the same sharpness level, for example.

In certain instances, the cutting edge 182 may be sufficiently sharp for transecting a captured tissue comprising a first thickness but may not be sufficiently sharp for transecting a captured tissue comprising a second thickness greater than the first thickness, for example. In certain instances, a sharpness level of the cutting edge 182, as defined by the force required for the cutting edge 182 to transect a captured tissue, may be adequate for transecting the captured tissue if the captured tissue comprises a tissue thickness that is in a particular range of tissue thicknesses, for example. In certain instances, as illustrated in FIG. 90, the memory 4316 can store one or more predefined ranges of tissue thicknesses of tissue captured by the end effector 300; and predefined threshold forces associated with the predefined ranges of tissue thicknesses. In certain instances, each predefined threshold force may represent a minimum sharpness level of the cutting edge 182 that is suitable for transecting a captured tissue comprising a tissue thickness (Tx) encompassed by the range of tissue thicknesses that is associated with the predefined threshold force. In certain instances, if the force (Fx) required for the cutting edge 182 to transect the captured tissue, comprising the tissue thickness (Tx), exceeds the predefined threshold force associated with the predefined range of tissue thicknesses that encompasses the tissue thickness (Tx), the cutting edge 182 may not be sufficiently sharp to transect the captured tissue, for example.

In certain instances, the predefined threshold forces and their corresponding predefined ranges of tissue thicknesses can be stored in a database and/or a table on the memory 4316 such as, for example, a table 4342, as illustrated in FIG. 90. In certain instances, the processor 4314 can be configured to receive a measured value of the force (Fx) required for the cutting edge 182 to transect a captured tissue and a measured value of the tissue thickness (Tx) of the captured tissue. The processor 4314 may access the table 4342 to determine the predefined range of tissue thicknesses that encompasses the measured tissue thickness (Tx). In addition, the processor 4314 may compare the measured force (Fx) to the predefined threshold force associated with the predefined range of tissue thicknesses that encompasses the tissue thickness (Tx). In certain instances, if the measured force (Fx) exceeds the predefined threshold force, the processor 4314 may conclude that the cutting edge 182 may not be sufficiently sharp to transect the captured tissue, for example.

Further to the above, the processor 4314 may employ one or more tissue thickness sensing modules such as, for example, a tissue thickness sensing module 4336 to determine the thickness of the captured tissue. Various suitable tissue thickness sensing modules are described in the present disclosure. In addition, various tissue thickness sensing devices and methods, which are suitable for use with the present disclosure, are disclosed in U.S. Publication No. US 2011/0155781, entitled SURGICAL CUTTING INSTRUMENT THAT ANALYZES TISSUE THICKNESS, and filed Dec. 24, 2009, now U.S. Pat. No. 8,851,354, the entire disclosure of which is hereby incorporated by reference herein.

In certain instances, the processor 4314 may employ the load cell 4334 to measure the force (Fx) required for the cutting edge 182 to transect a captured tissue comprising a tissue thickness (Tx). The reader will appreciate that that the force applied to the cutting edge 182 by the captured tissue, while the cutting edge 182 is engaged and/or in contact with the captured tissue, may increase as the cutting edge 182 is advanced against the captured tissue up to the force (Fx) at which the cutting edge 182 may transect the captured tissue. In certain instances, the processor 4314 may employ the load cell 4334 to continually monitor the force applied by the captured tissue against the cutting edge 182 as the cutting edge 182 is advanced against the captured tissue. The processor 4314 may continually compare the monitored force to the predefined threshold force associated with the predefined tissue thickness range encompassing the tissue thickness (Tx) of the captured tissue. In certain instances, if the monitored force exceeds the predefined threshold force, the processor 4314 may conclude that the cutting edge is not sufficiently sharp to safely transect the captured tissue, for example.

The method described in FIG. 89 outline various example actions that can be taken by the processor 4313 in the event it is determined that the cutting edge 182 is not be sufficiently sharp to safely transect the captured tissue, for example. In certain instances, the microcontroller 4312 may warn the user that the cutting edge 182 is too dull for safe use, for example, through the feedback system 1120, for example. In certain instances, the microcontroller 4312 may employ the lockout mechanism 1122 to prevent advancement of the cutting edge 182 upon concluding that the cutting edge 182 is not sufficiently sharp to safely transect the captured tissue, for example. In certain instances, the microcontroller 4312 may employ the feedback system 1122 to provide instructions to the user for overriding the lockout mechanism 1122, for example.

Multiple Motor Control for Powered Medical Device

Figure 91:
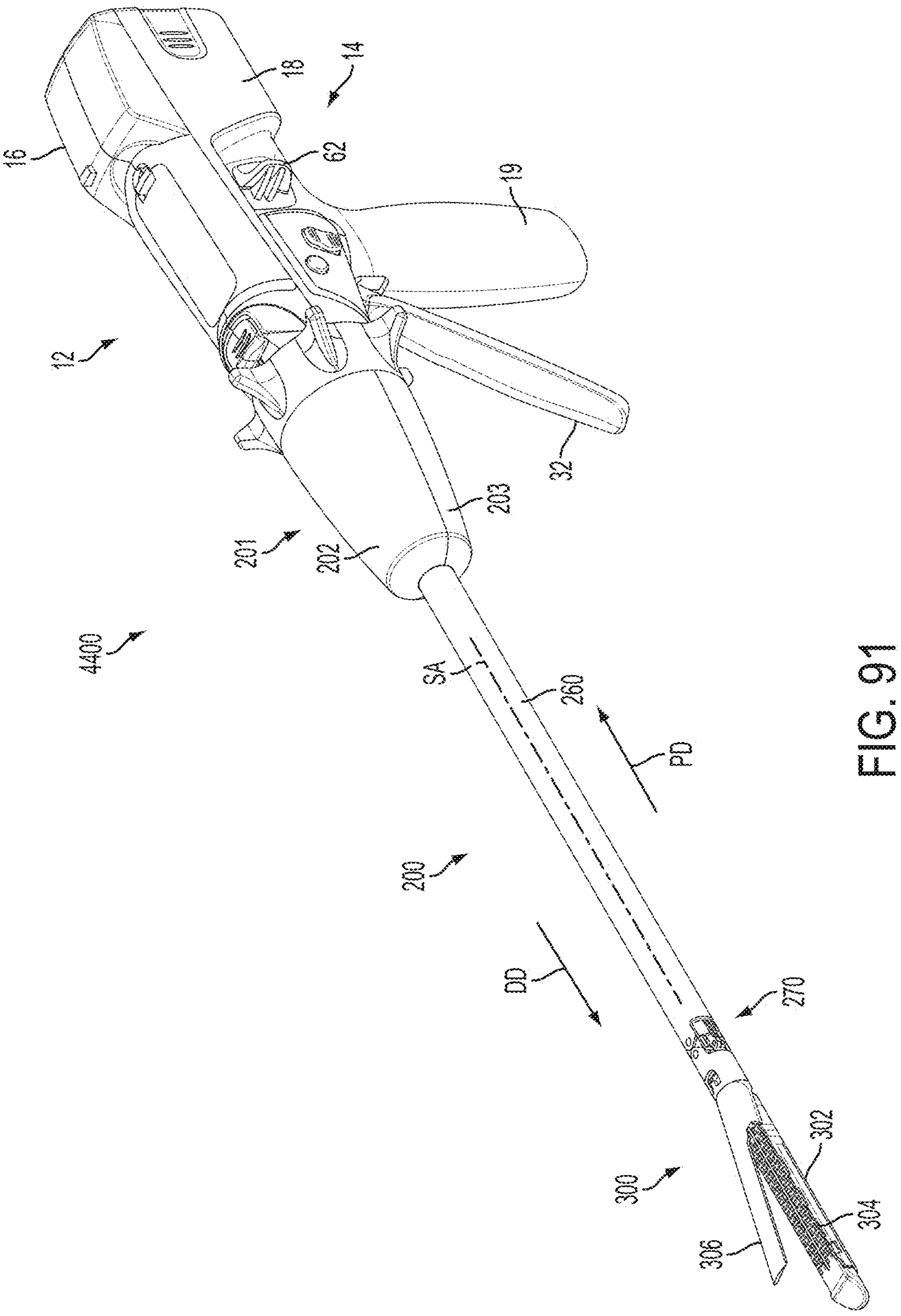
FIG. 91 illustrates a perspective view of a surgical instrument including a handle, a shaft assembly, and an end effector.
Figure 92:
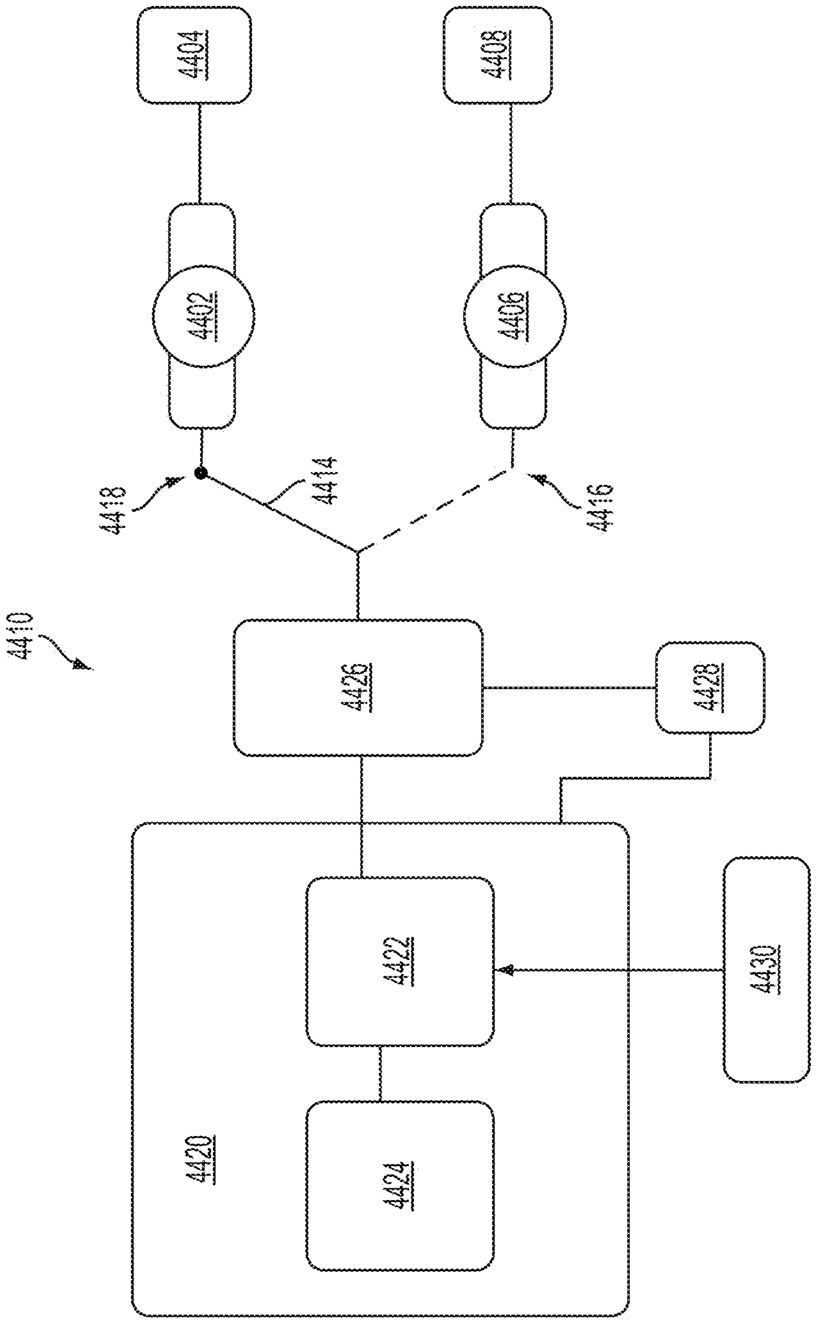
FIG. 92 illustrates a logic diagram of a common control module for use with a plurality of motors of the surgical instrument of FIG. 91.
Figure 93:
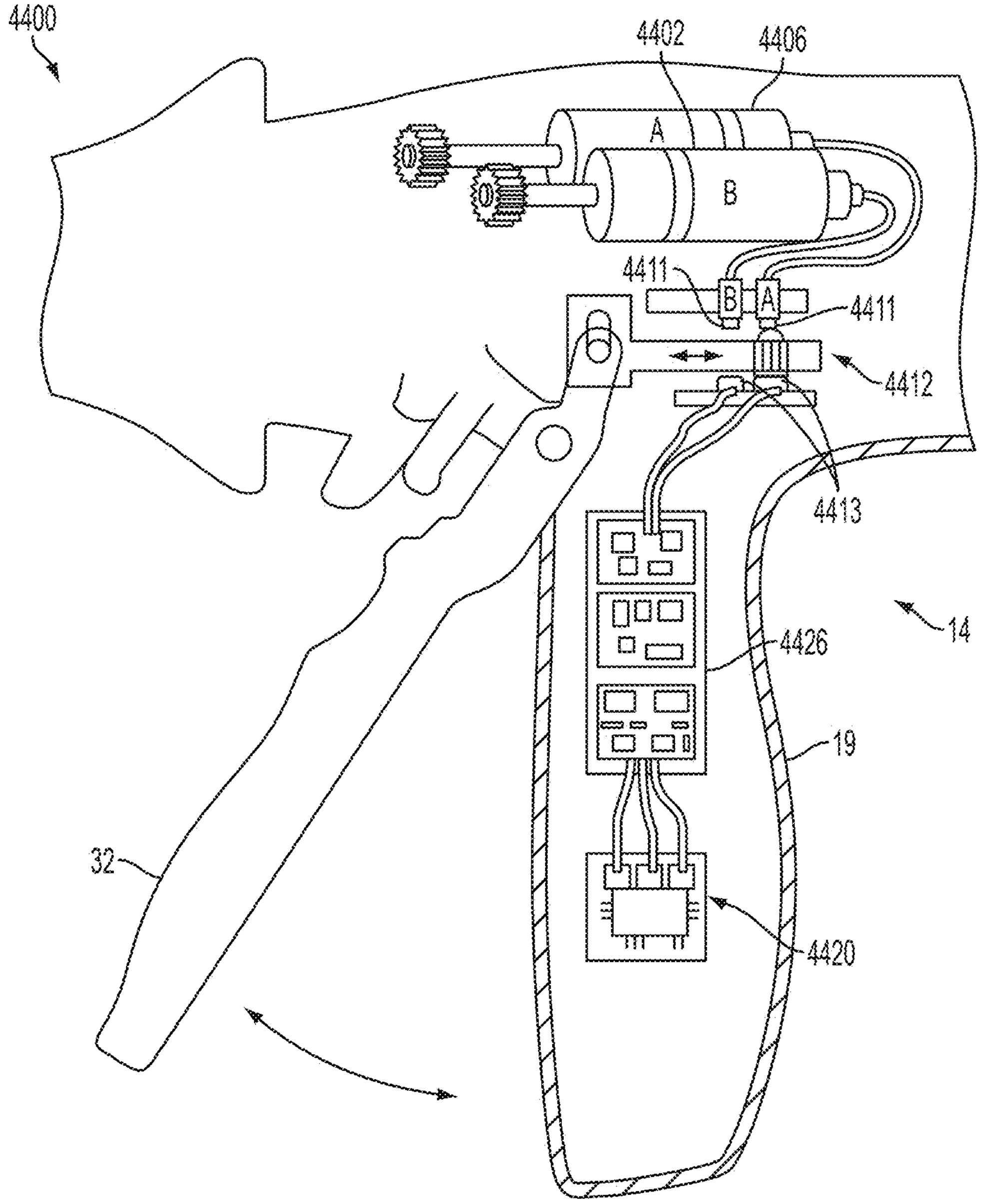
FIG. 93 illustrates a partial elevational view of the handle of the surgical instrument of FIG. 91 with a removed outer casing.

FIGS. 91-93 illustrate various embodiments of an apparatus, system, and method for employing a common control module with a plurality of motors in connection with a surgical instrument such as, for example, a surgical instrument 4400. The surgical instrument 4400 is similar in many respects to other surgical instruments described by the present disclosure such as, for example, the surgical instrument 10 of FIG. 1 which is described in greater detail above. For example, as illustrated in FIG. 91, the surgical instrument 4400 includes the housing 12, the handle 14, the closure trigger 32, the shaft assembly 200, and the surgical end effector 300. Accordingly, for conciseness and clarity of disclosure, a detailed description of certain features of the surgical instrument 4400, which are common with the surgical instrument 10, will not be repeated here.

Referring primarily to FIG. 92, the surgical instrument 4400 may include a plurality of motors which can be activated to perform various functions in connection with the operation of the surgical instrument 4400. In certain instances, a first motor can be activated to perform a first function; a second motor can be activated to perform a second function; and a third motor can be activated to perform a third function. In certain instances, the plurality of motors of the surgical instrument 4400 can be individually activated to cause articulation, closure, and/or firing motions in the end effector 300. The articulation, closure, and/or firing motions can be transmitted to the end effector 300 through the shaft assembly 200, for example.

In certain instances, as illustrated in FIG. 92, the surgical instrument 4400 may include a firing motor 4402. The firing motor 4402 may be operably coupled to a firing drive assembly 4404 which can be configured to transmit firing motions generated by the motor 4402 to the end effector 300. In certain instances, the firing motions generated by the motor 4402 may cause the staples 191 to be deployed from the staple cartridge 304 into tissue captured by the end effector 300 and/or the cutting edge 182 to be advanced to cut the captured tissue, for example.

In certain instances, as illustrated in FIG. 92, the surgical instrument 4400 may include an articulation motor 4406, for example. The motor 4406 may be operably coupled to an articulation drive assembly 4408 which can be configured to transmit articulation motions generated by the motor 4406 to the end effector 300. In certain instances, the articulation motions may cause the end effector 300 to articulate relative to the shaft assembly 200, for example. In certain instances, the surgical instrument 4400 may include a closure motor, for example. The closure motor may be operably coupled to a closure drive assembly which can be configured to transmit closure motions to the end effector 300. In certain instances, the closure motions may cause the end effector 300 to transition from an open configuration to an approximated configuration to capture tissue, for example. The reader will appreciate that the motors described herein and their corresponding drive assemblies are intended as examples of the types of motors and/or driving assemblies that can be employed in connection with the present disclosure. The surgical instrument 4400 may include various other motors which can be utilized to perform various other functions in connection with the operation of the surgical instrument 4400.

As described above, the surgical instrument 4400 may include a plurality of motors which may be configured to perform various independent functions. In certain instances, the plurality of motors of the surgical instrument 4400 can be individually or separately activated to perform one or more functions while the other motors remain inactive. For example, the articulation motor 4406 can be activated to cause the end effector 300 to be articulated while the firing motor 4402 remains inactive. Alternatively, the firing motor 4402 can be activated to fire the plurality of staples 191 and/or advance the cutting edge 182 while the articulation motor 4406 remains inactive.

In certain instances, the surgical instrument 4400 may include a common control module 4410 which can be employed with a plurality of motors of the surgical instrument 4400. In certain instances, the common control module 4410 may accommodate one of the plurality of motors at a time. For example, the common control module 4410 can be separably couplable to the plurality of motors of the surgical instrument 4400 individually. In certain instances, a plurality of the motors of the surgical instrument 4400 may share one or more common control modules such as the module 4410. In certain instances, a plurality of motors of the surgical instrument 4400 can be individually and selectively engaged the common control module 4410. In certain instances, the module 4410 can be selectively switched from interfacing with one of a plurality of motors of the surgical instrument 4400 to interfacing with another one of the plurality of motors of the surgical instrument 4400.

In at least one example, the module 4410 can be selectively switched between operable engagement with the articulation motor 4406 and operable engagement with the firing motor 4402. In at least one example, as illustrated in FIG. 92, a switch 4414 can be moved or transitioned between a plurality of positions and/or states such as a first position 4416 and a second position 4418, for example. In the first position 4416, the switch 4414 may electrically couple the module 4410 to the articulation motor 4406; and in the second position 4418, the switch 4414 may electrically couple the module 4410 to the firing motor 4402, for example. In certain instances, the module 4410 can be electrically coupled to the articulation motor 4406, while the switch 4414 is in the first position 4416, to control the operation of the motor 4406 to articulate the end effector 300 to a desired position. In certain instances, the module 4410 can be electrically coupled to the firing motor 4402, while the switch 4414 is in the second position 4418, to control the operation of the motor 4402 to fire the plurality of staples 191 and/or advance the cutting edge 182, for example. In certain instances, the switch 4414 may be a mechanical switch, an electromechanical switch, a solid state switch, or any suitable switching mechanism.

Referring now to FIG. 93, an outer casing of the handle 14 of the surgical instrument 4400 is removed and several features and elements of the surgical instrument 4400 are also removed for clarity of disclosure. In certain instances, as illustrated in FIG. 93, the surgical instrument 4400 may include an interface 4412 which can be selectively transitioned between a plurality of positions and/or states. In a first position and/or state, the interface 4412 may couple the module 4410 to a first motor such as, for example, the articulation motor 4406; and in a second position and/or state, the interface 4412 may couple the module 4410 to a second motor such as, for example, the firing motor 4402. Additional positions and/or states of the interface 4412 are contemplated by the present disclosure.

In certain instances, the interface 4412 is movable between a first position and a second position, wherein the module 4410 is coupled to a first motor in the first position and a second motor in the second position. In certain instances, the module 4410 is decoupled from first motor as the interface 4412 is moved from the first position; and the module 4410 is decoupled from second motor as the interface 4412 is moved from the second position. In certain instances, a switch or a trigger can be configured to transition the interface 4412 between the plurality of positions and/or states. In certain instances, a trigger can be movable to simultaneously effectuate the end effector and transition the control module 4410 from operable engagement with one of the motors of the surgical instrument 4400 to operable engagement with another one of the motors of the surgical instrument 4400.

In at least one example, as illustrated in FIG. 93, the closure trigger 32 can be operably coupled to the interface 4412 and can be configured to transition the interface 4412 between a plurality of positions and/or states. As illustrated in FIG. 93, the closure trigger 32 can be movable, for example during a closure stroke, to transition the interface 4412 from a first position and/or state to a second position and/or state while transitioning the end effector 300 to an approximated configuration to capture tissue by the end effector, for example.

In certain instances, in the first position and/or state, the module 4410 can be electrically coupled to a first motor such as, for example, the articulation motor 4406, and in the second position and/or state, the module 4410 can be electrically coupled to a second motor such as, for example, the firing motor 4402. In the first position and/or state, the module 4410 may be engaged with the articulation motor 4406 to allow the user to articulate the end effector 300 to a desired position; and the module 4410 may remain engaged with the articulation motor 4406 until the trigger 32 is actuated. As the user actuates the closure trigger 32 to capture tissue by the end effector 300 at the desired position, the interface 4412 can be transitioned or shifted to transition the module 4410 from operable engagement with the articulation motor 4406, for example, to operable engagement with the firing motor 4402, for example. Once operable engagement with the firing motor 4402 is established, the module 4410 may take control of the firing motor 4402; and the module 4410 may activate the motor 4402, in response to user input, to fire the plurality of staples 191 and/or advance the cutting edge 182, for example.

In certain instances, as illustrated in FIG. 93, the module 4410 may include a plurality of electrical and/or mechanical contacts 4411 adapted for coupling engagement with the interface 4412. The plurality of motors of the surgical instrument 4400, which share the module 4410, may each comprise one or more corresponding electrical and/or mechanical contacts 4413 adapted for coupling engagement with the interface 4412, for example.

In various instances, the motors of the surgical instrument 4400 can be electrical motors. In certain instances, one or more of the motors of the surgical instrument 4400 can be a DC brushed driving motor having a maximum rotation of, approximately, 25,000 RPM, for example. In other arrangements, the motors of the surgical instrument 4400 may include one or more motors selected from a group of motors comprising a brushless motor, a cordless motor, a synchronous motor, a stepper motor, or any other suitable electric motor.

In various instances, as illustrated in FIG. 92, the common control module 4410 may comprise a motor driver 4426 which may comprise one or more H-Bridge field-effect transistors (FETs). The motor driver 4426 may modulate the power transmitted from a power source 4428 to a motor coupled to the module 4410 based on input from a microcontroller 4420 ("controller"), for example. In certain instances, the controller 4420 can be employed to determine the current drawn by the motor, for example, while the motor is coupled to the module 4410, as described above.

In certain instances, the controller 4420 may include a microprocessor 4422 ("processor") and one or more computer readable mediums or memory units 4424 ("memory"). In certain instances, the memory 4424 may store various program instructions, which when executed may cause the processor 4422 to perform a plurality of functions and/or calculations described herein. In certain instances, one or more of the memory units 4424 may be coupled to the processor 4422, for example.

In certain instances, the power source 4428 can be employed to supply power to the controller 4420, for example. In certain instances, the power source 4428 may comprise a battery (or "battery pack" or "power pack"), such as a Li ion battery, for example. In certain instances, the battery pack may be configured to be releasably mounted to the handle 14 for supplying power to the surgical instrument 4400. A number of battery cells connected in series may be used as the power source 4428. In certain instances, the power source 4428 may be replaceable and/or rechargeable, for example.

In various instances, the processor 4422 may control the motor driver 4426 to control the position, direction of rotation, and/or velocity of a motor that is coupled to the module 4410. In certain instances, the processor 4422 can signal the motor driver 4426 to stop and/or disable a motor that is coupled to the module 4410. It should be understood that the term processor as used herein includes any suitable microprocessor, microcontroller, or other basic computing device that incorporates the functions of a computer's central processing unit (CPU) on an integrated circuit or at most a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 4422 may be any single core or multicore processor such as those known under the trade name ARM Cortex by Texas Instruments. In certain instances, the microcontroller 4420 may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle SRAM, internal ROM loaded with StellarisWare® software, 2 KB EEPROM, one or more PWM modules, one or more QEI analog, one or more 12-bit ADC with 12 analog input channels, among other features that are readily available for the product datasheet. Other microcontrollers may be readily substituted for use with the module 4410. Accordingly, the present disclosure should not be limited in this context.

In certain instances, the memory 4424 may include program instructions for controlling each of the motors of the surgical instrument 4400 that are couplable to the module 4410. For example, the memory 4424 may include program instructions for controlling the articulation motor 4406. Such program instructions may cause the processor 4422 to control the articulation motor 4406 to articulate the end effector 300 in accordance with user input while the articulation motor 4406 is coupled to the module 4410. In another example, the memory 4424 may include program instructions for controlling the firing motor 4402. Such program instructions may cause the processor 4422 to control the firing motor 4402 to fire the plurality of staples 191 and/or advance the cutting edge 182 in accordance with user input while the firing motor 4402 is coupled to the module 4410.

In certain instances, one or more mechanisms and/or sensors such as, for example, sensors 4430 can be employed to alert the processor 4422 to the program instructions that should be used in a particular setting. For example, the sensors 4430 may alert the processor 4422 to use the program instructions associated with articulation of the end effector 300 while the module 4410 is coupled to the articulation motor 4406; and the sensors 4430 may alert the processor 4422 to use the program instructions associated with firing the surgical instrument 4400 while the module 4410 is coupled to the firing motor 4402. In certain instances, the sensors 4430 may comprise position sensors which can be employed to sense the position of the switch 4414, for example. Accordingly, the processor 4422 may use the program instructions associated with articulation of the end effector 300 upon detecting, through the sensors 4430 for example, that the switch 4414 is in the first position 4416; and the processor 4422 may use the program instructions associated with firing the surgical instrument 4400 upon detecting, through the sensors 4430 for example, that the switch 4414 is in the second position 4418.

Figure 94:
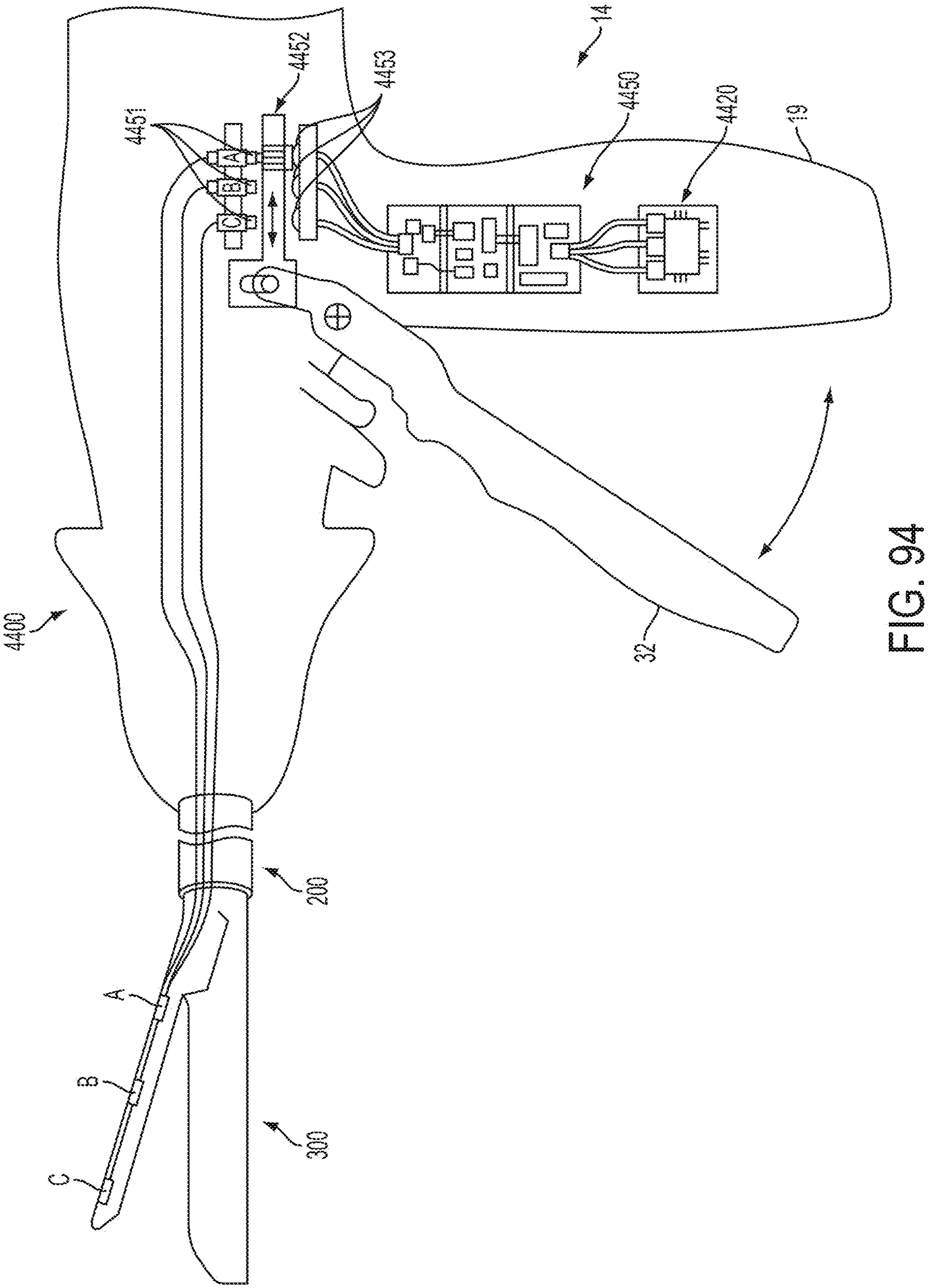
FIG. 94 illustrates a partial elevational view of the surgical instrument of FIG. 91 with a removed outer casing.

Referring now to FIG. 94, an outer casing of the surgical instrument 4400 is removed and several features and elements of the surgical instrument 4400 are also removed for clarity of disclosure. As illustrated in FIG. 94, the surgical instrument 4400 may include a plurality of sensors which can be employed to perform various functions in connection with the operation of the surgical instrument 4400. For example, as illustrated in FIG. 94, the surgical instrument 4400 may include sensors A, B, and/or C. In certain instances, the sensor A can be employed to perform a first function, for example; the sensor B can be employed to perform a second function, for example; and the sensor C can be employed to perform a third function, for example. In certain instances, the sensor A can be employed to sense a thickness of the tissue captured by the end effector 300 during a first segment of a closure stroke; the sensor B can be employed to sense the tissue thickness during a second segment of the closure stroke following the first segment; and the sensor C can be employed to sense the tissue thickness during a third segment of the closure stroke following the second segment, for example. In certain instances, the sensors A, B, and C can be disposed along the end effector 300, for example.

In certain instances, the sensors A, B, and C can be arranged, as illustrated in FIG. 94, such that the sensor A is disposed proximal to the sensor B, and the sensor C is disposed proximal to the sensor B, for example. In certain instances, as illustrated in FIG. 94, the sensor A can sense the tissue thickness of the tissue captured by the end effector 300 at a first position; the sensor B can sense the tissue thickness of the tissue captured by the end effector 300 at a second position distal to the first position; and the sensor C can sense the tissue thickness of the tissue captured by the end effector 300 at a third position distal to the second position, for example. The reader will appreciate that the sensors described herein are intended as examples of the types of sensors which can be employed in connection with the present disclosure. Other suitable sensors and sensing arrangements can be employed by the present disclosure.

In certain instances, the surgical instrument 4400 may include a common control module 4450 which can be similar in many respects to the module 4410. For example, the module 4450, like the module 4410, may comprise the controller 4420, the processor 4422, and/or the memory 4424. In certain instances, the power source 4428 can supply power to the module 4450, for example. In certain instances, the surgical instrument 4400 may include a plurality of sensors such as the sensors A, B, and C, for example, which can activated to perform various functions in connection with the operation of the surgical instrument 4400. In certain instances, one of the sensors A, B, and C, for example, can be individually or separately activated to perform one or more functions while the other sensors remain inactive. In certain instances, a plurality of sensors of the surgical instrument 4400 such as, for example, the sensors A, B, and C may share the module 4450. In certain instances, only one of the sensors A, B, and C can be coupled to the module 4450 at a time. In certain instances, the plurality of sensors of the surgical instrument 4400 can be individually and separately couplable to the module 4450, for example. In at least one example, the module 4450 can be selectively switched between operable engagement with sensor A, Sensor B, and/or Sensor C.

In certain instances, as illustrated in FIG. 94, the module 4450 can be disposed in the handle 14, for example, and the sensors that share the module 4450 can be disposed in the end effector 300, for example. The reader will appreciate that the module 4450 and/or the sensors that share the module 4450 are not limited to the above identified positions. In certain instances, the module 4450 and the sensors that share the module 4450 can be disposed in the end effector 300, for example. Other arrangements for the positions of the module 4450 and/or the sensors that share the module 4450 are contemplated by the present disclosure.

In certain instances, as illustrated in FIG. 94, an interface 4452 can be employed to manage the coupling and/or decoupling of the sensors of the surgical instrument 4400 to the module 4450. In certain instances, the interface 4452 can be selectively transitioned between a plurality of positions and/or states. In a first position and/or state, the interface 4452 may couple the module 4450 to the sensor A, for example; in a second position and/or state, the interface 4452 may couple the module 4450 to the sensor B, for example; and in a third position and/or state, the interface 4452 may couple the module 4450 to the sensor C, for example. Additional positions and/or states of the interface 4452 are contemplated by the present disclosure.

In certain instances, the interface 4452 is movable between a first position, a second position, and/or a third position, for example, wherein the module 4450 is coupled to a first sensor in the first position, a second sensor in the second position, and a third sensor in the third position. In certain instances, the module 4450 is decoupled from first sensor as the interface 4452 is moved from the first position; the module 4450 is decoupled from second sensor as the interface 4452 is moved from the second position; and the module 4450 is decoupled from third sensor as the interface 4452 is moved from the third position. In certain instances, a switch or a trigger can be configured to transition the interface 4452 between the plurality of positions and/or states. In certain instances, a trigger can be movable to simultaneously effectuate the end effector and transition the control module 4450 from operable engagement with one of the sensors that share the module 4450 to operable engagement with another one of the sensors that share the module 4450, for example.

In at least one example, as illustrated in FIG. 94, the closure trigger 32 can be operably coupled to the interface 4450 and can be configured to transition the interface 4450 between a plurality of positions and/or states. As illustrated in FIG. 94, the closure trigger 32 can be moveable between a plurality of positions, for example during a closure stroke, to transition the interface 4450 between a first position and/or state wherein the module 4450 is electrically coupled to the sensor A, for example, a second position and/or state wherein the module 4450 is electrically coupled to the sensor B, for example, and/or a third position and/or state wherein the module 4450 is electrically coupled to the sensor C, for example.

In certain instances, a user may actuate the closure trigger 32 to capture tissue by the end effector 300. Actuation of the closure trigger may cause the interface 4452 to be transitioned or shifted to transition the module 4450 from operable engagement with the sensor A, for example, to operable engagement with the sensor B, for example, and/or from operable engagement with sensor B, for example, to operable engagement with sensor C, for example.

In certain instances, the module 4450 may be coupled to the sensor A while the trigger 32 is in a first actuated position. As the trigger 32 is actuated past the first actuated position and toward a second actuated position, the module 4450 may be decoupled from the sensor A. Alternatively, the module 4450 may be coupled to the sensor A while the trigger 32 is in an unactuated position. As the trigger 32 is actuated past the unactuated position and toward a second actuated position, the module 4450 may be decoupled from the sensor A. In certain instances, the module 4450 may be coupled to the sensor B while the trigger 32 is in the second actuated position. As the trigger 32 is actuated past the second actuated position and toward a third actuated position, the module 4450 may be decoupled from the sensor B. In certain instances, the module 4450 may be coupled to the sensor C while the trigger 32 is in the third actuated position.

In certain instances, as illustrated in FIG. 94, the module 4450 may include a plurality of electrical and/or mechanical contacts 4451 adapted for coupling engagement with the interface 4452. The plurality of sensors of the surgical instrument 4400, which share the module 4450, may each comprise one or more corresponding electrical and/or mechanical contacts 4453 adapted for coupling engagement with the interface 4452, for example.

In certain instances, the processor 4422 may receive input from the plurality of sensors that share the module 4450 while the sensors are coupled to the module 4452. For example, the processor 4422 may receive input from the sensor A while the sensor A is coupled to the module 4450; the processor 4422 may receive input from the sensor B while the sensor B is coupled to the module 4450; and the processor 4422 may receive input from the sensor C while the sensor C is coupled to the module 4450. In certain instances, the input can be a measurement value such as, for example, a measurement value of a tissue thickness of tissue captured by the end effector 300. In certain instances, the processor 4422 may store the input from one or more of the sensors A, B, and C on the memory 4426. In certain instances, the processor 4422 may perform various calculations based on the input provided by the sensors A, B, and C, for example.

Local Display of Tissue Parameter Stabilization

Figure 95A:
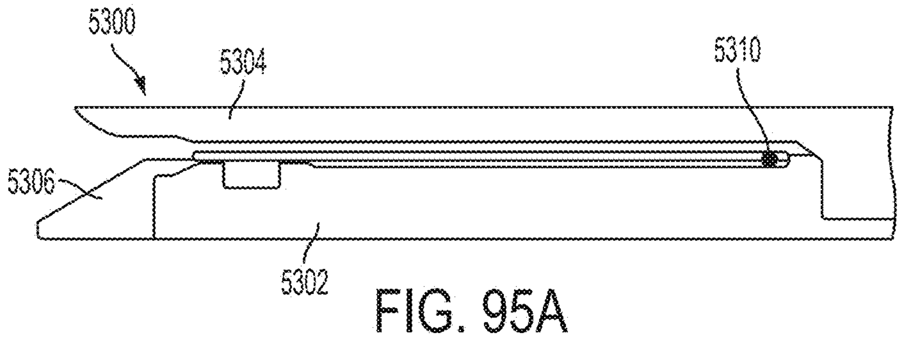
FIG. 95A illustrates a side angle view of an end effector with the anvil in a closed position, illustrating one located on either side of the cartridge deck.

FIGS. 95A and 1B illustrate one embodiment of an end effector 5300 comprising a staple cartridge 5306 that further comprises two light-emitting diodes (LEDs) 5310. The end effector 5300 is similar to the end effector 300 described above. The end effector comprises a first jaw member or anvil 5302, pivotally coupled to a second jaw member or elongated channel 5304. The elongated channel 5304 is configured to receive the staple cartridge 5306 therein. The staple cartridge 5306 comprises a plurality of staples (not shown). The plurality of staples are deployable from the staple cartridge 5306 during a surgical operation. The staple cartridge 5306 further comprises two LEDs 5310 mounted on the upper surface, or cartridge deck 5308 of the staple cartridge 5306. The LEDs 5310 are mounted such that they will be visible when the anvil 5304 is in a closed position. Furthermore, the LEDs 5310 can be sufficiently bright to be visible through any tissue that may be obscuring a direct view of the LEDs 5310. Additionally, one LED 5310 can be mounted on either side of the staple cartridge 5306 such that at least one LED 5310 is visible from either side of the end effector 5300. The LED 5310 can be mounted near the proximal end of the staple cartridge 530, as illustrated, or may be mounted at the distal end of the staple cartridge 5306.

The LEDs 5310 may be in communication with a processor or microcontroller, such as for instance microcontroller 1500 of FIG. 19. The microcontroller 1500 can be configured to detect a property of tissue compressed by the anvil 5304 against the cartridge deck 5308. Tissue that is enclosed by the end effector 5300 may change height as fluid within the tissue is exuded from the tissue's layers. Stapling the tissue before it has sufficiently stabilized may affect the effectiveness of the staples. Tissue stabilization is typically communicates as a rate of change, where the rate of change indicates how rapidly the tissue enclosed by the end effector is changing height.

The LEDs 5310 mounted to the staple cartridge 5306, in the view of the operator of the instrument, can be used to indicate rate at which the enclosed tissue is stabilizing and/or whether the tissue has reached a stable state. The LEDs 5310 can, for example, be configured to flash at a rate that directly correlates to the rate of stabilization of the tissue, that is, can flash quickly initially, flash slower as the tissue stabilizes, and remain steady when the tissue is stable. Alternatively, the LEDs 5310 can flash slowly initially, flash more quickly as the tissue stabilizes, and turn off when the tissue is stable.

The LEDs 5310 mounted on the staple cartridge 5306 can be used additionally or optionally to indicate other information. Examples of other information include, but are not limited to: whether the end effector 5300 is enclosing a sufficient amount of tissue, whether the staple cartridge 5306 is appropriate for the enclosed tissue, whether there is more tissue enclosed than is appropriate for the staple cartridge 5306, whether the staple cartridge 5306 is not compatible with the surgical instrument, or any other indicator that would be useful to the operator of the instrument. The LEDs 5310 can indicate information by either flashing at a particular rate, turning on or off at a particular instance, lighting in different colors for different information. The LEDs 5310 can alternatively or additionally be used to illuminate the area of operation. In some embodiments the LEDs 5310 can be selected to emit ultraviolet or infrared light to illuminate information not visible under normal light, where that information is printed on the staple cartridge 5300 or on a tissue compensator (not illustrated). Alternatively or additionally, the staples can be coated with a fluorescing dye and the wavelength of the LEDs 5310 chosen so that the LEDs 5310 cause the fluorescing dye to glow. By illuminating the staples with the LEDs 5310 allows the operator of the instrument to see the staples after they have been driven.

Figure 95B:
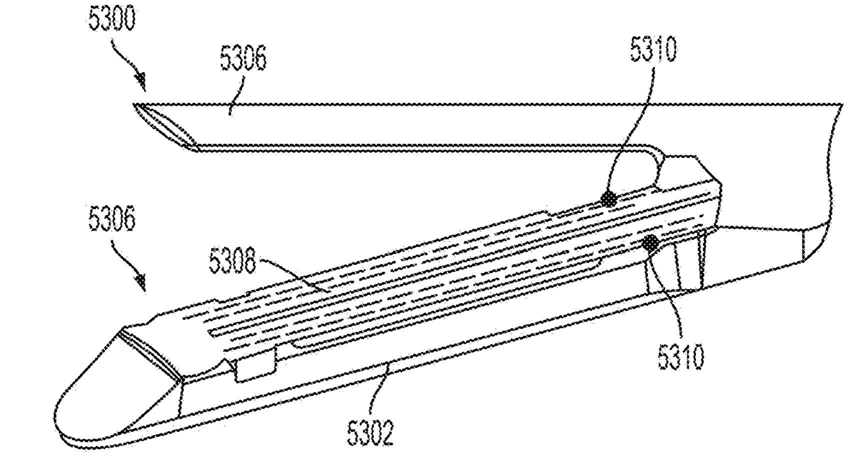
FIG. 95B illustrates a three-quarter angle view of the end effector with the anvil in an open position, and one LED located on either side of the cartridge deck.

Returning to FIGS. 95A and 95B, FIG. 95A illustrates a side angle view of the end effector 5300 with the anvil 5304 in a closed position. The illustrated embodiment comprises, by way of example, one LED 5310 located on either side of the cartridge deck 5308. FIG. 95B illustrates a three-quarter angle view of the end effector 5300 with the anvil 5304 in an open position, and one LED 5310 located on either side of the cartridge deck 5308.

Figure 96A:
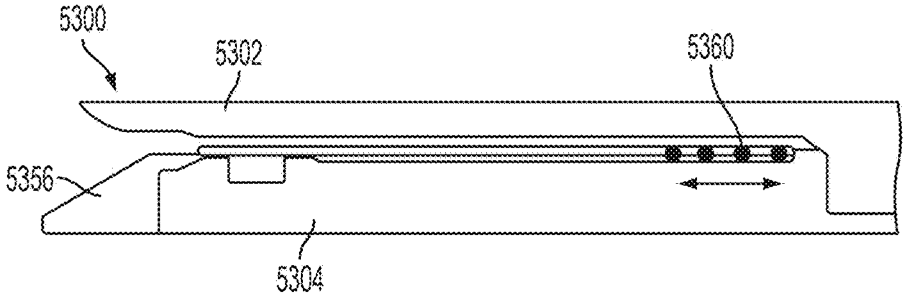
FIG. 96A illustrates a side angle view of an end effector with the anvil in a closed position and a plurality of LEDs located on either side of the cartridge deck.
Figure 96B:
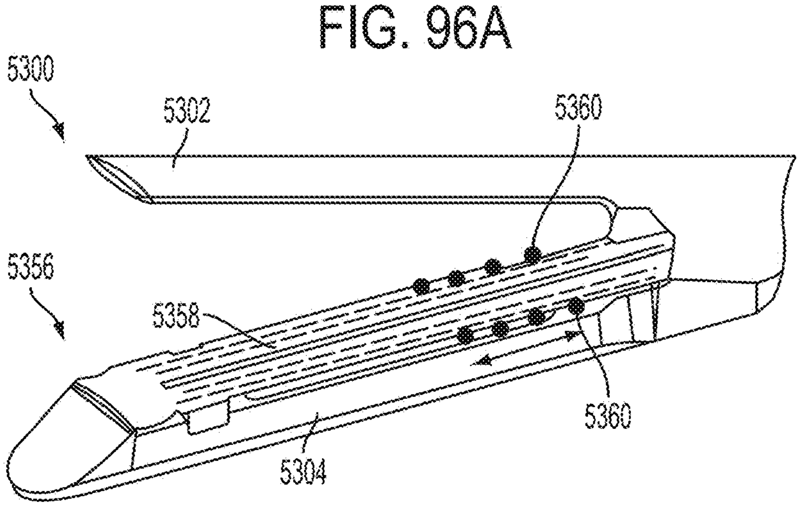
FIG. 96B illustrates a three-quarter angle view of the end effector with the anvil in an open position, and a plurality of LEDs located on either side of the cartridge deck.

FIGS. 96A and 96B illustrate one embodiment of the end effector 5300 comprising a staple cartridge 5356 that further comprises a plurality of LEDs 5360. The staple cartridge 5356 comprises a plurality of LEDs 5360 mounted on the cartridge deck 5358 of the staple cartridge 5356. The LEDs 5360 are mounted such that they will be visible when the anvil 5304 is in a closed position. Furthermore, the LEDs 5360 can be sufficiently bright to be visible through any tissue that may be obscuring a direct view of the LEDs 5360. Additionally, the same number of LEDs 5360 can be mounted on either side of the staple cartridge 5356 such that the same number of LEDs 5360 is visible from either side of the end effector 5300. The LEDs 5360 can be mounted near the proximal end of the staple cartridge 5356, as illustrated, or may be mounted at the distal end of the staple cartridge 5356.

The LEDs 5360 may be in communication with a processor or microcontroller, such as for instance microcontroller 1500 of FIG. 15. The microcontroller 1500 can be configured to detect a property of tissue compressed by the anvil 5304 against the cartridge deck 5358, such as the rate of stabilization of the tissue, as described above. The LEDs 5360 can be used to indicate the rate at which the enclose tissue is stabilizing and/or whether the tissue has reached a stable state. The LEDs 5360 can be configured, for instance, to light in sequence starting at the proximal end of the staple cartridge 5356 with each subsequent LED 5360 lighting at the rate at which the enclosed tissue is stabilizing; when the tissue is stable, all the LEDs 5360 can be lit. Alternatively, the LEDs 5360 can light in sequence beginning at the distal end of the staple cartridge 5356. Yet another alternative is for the LEDs 5360 to light in a sequential, repeating sequence, with the sequence starting at either the proximal or distal end of the LEDs 5360. The rate at which the LEDs 5360 light and/or the speed of the repeat can indicate the rate at which the enclosed tissue is stabilizing. It is understood that these are only examples of how the LEDs 5360 can indicate information about the tissue, and that other combinations of the sequence in which the LEDs 5360 light, the rate at which they light, and or their on or off state are possible. It is also understood that the LEDs 5360 can be used to communicate some other information to the operator of the surgical instrument, or to light the work area, as described above.

Returning to FIGS. 96A and 96B, FIG. 96A illustrates a side angle view of the end effector 5300 with the anvil 5304 in a closed position. The illustrated embodiment comprises, by way of example, a plurality of LEDs 5360 located on either side of the cartridge deck 5358. FIG. 96B illustrates a three-quarter angle view of the end effector 5300 with the anvil 5304 in an open position, illustrating a plurality of LEDs 5360 located on either side of the cartridge deck 5358.

Figure 97A:
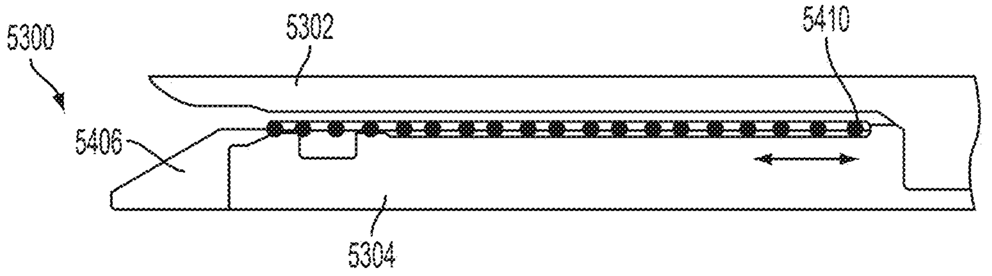
FIG. 97A illustrates a side angle view of an end effector with the anvil in a closed position, and a plurality of LEDs from the proximal to the distal end of the staple cartridge, on either side of the cartridge deck.
Figure 97B:
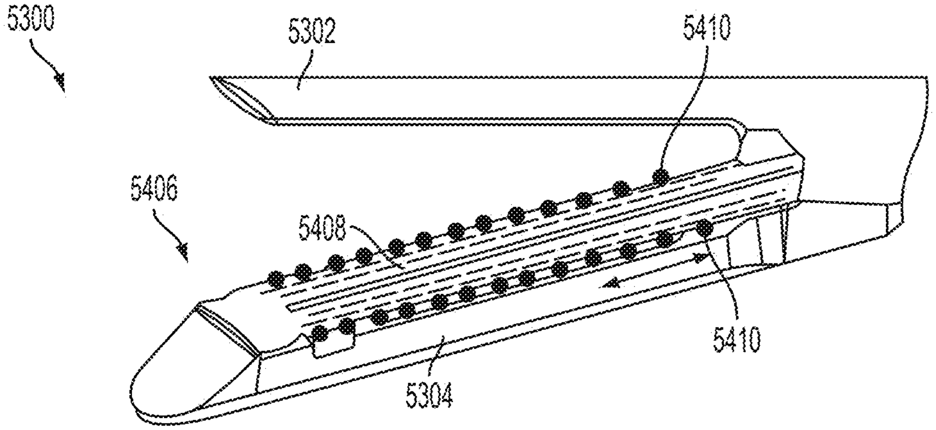
FIG. 97B illustrates a three-quarter angle view of the end effector with the anvil in an open position, illustrating a plurality of LEDs from the proximal to the distal end of the staple cartridge, and on either side of the cartridge deck.

FIGS. 97A and 97B illustrate one embodiment of the end effector 5300 comprising a staple cartridge 5406 that further comprises a plurality of LEDs 5410. The staple cartridge 5406 comprises a plurality of LEDs 5410 mounted on the cartridge deck 5408 of the staple cartridge 5406, with the LEDs 5410 placed continuously from the proximal to the distal end of the staple cartridge 5406. The LEDs 5410 are mounted such that they will be visible when the anvil 5302 is in a closed position. The same number of LEDs 5410 can be mounted on either side of the staple cartridge 5406 such that the same number of LEDs 5410 is visible from either side of the end effector 5300.

The LEDs 5410 can be in communication with a processor or microcontroller, such as for instance microcontroller 1500 of FIG. 15. The microcontroller 1500 can be configured to detect a property of tissue compressed by the anvil 5304 against the cartridge deck 5408, such as the rate of stabilization of the tissue, as described above. The LEDs 5410 can be configured to be turned on or off in sequences or groups as desired to indicate the rate of stabilization of the tissue and/or that the tissue is stable. The LEDs 5410 can further be configured communicate some other information to the operator of the surgical instrument, or to light the work area, as described above. Additionally or alternatively, the LEDs 5410 can be configured to indicate which areas of the end effector 5300 contain stable tissue, and or what areas of the end effector 5300 are enclosing tissue, and/or if those areas are enclosing sufficient tissue. The LEDs 5410 can further be configured to indicate if any portion of the enclosed tissue is unsuitable for the staple cartridge 5406.

Returning to FIGS. 97A and 97B, FIG. 97A illustrates a side angle view of the end effector 5300 with the anvil 5304 in a closed position. The illustrated embodiment comprises, by way of example, a plurality of LEDs 5410 from the proximal to the distal end of the staple cartridge 5406, on either side of the cartridge deck 5408. FIG. 97B illustrates a three-quarter angle view of the end effector 5300 with the anvil 5304 in an open position, illustrating a plurality of LEDs 5410 from the proximal to the distal end of the staple cartridge 5406, and on either side of the cartridge deck 5408.

Adjunct with Integrated Sensors to Quantify Tissue Compression

Figure 98A:
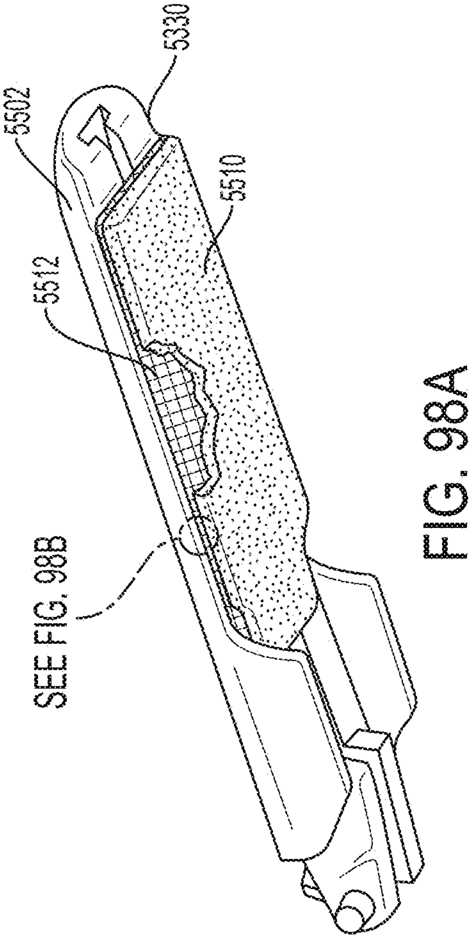
FIG. 98A illustrates an embodiment wherein the tissue compensator is removably attached to the anvil portion of the end effector.
Figure 98B:
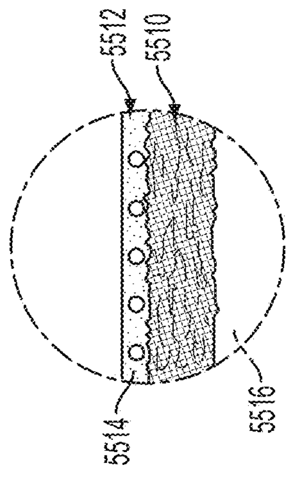
FIG. 98B illustrates a detail view of a portion of the tissue compensator shown in FIG. 98A.

FIG. 98A illustrates an embodiment of an end effector 5500 comprising a tissue compensator 5510 that further comprises a layer of conductive elements 5512. The end effector 5500 is similar to the end effector 300 described above. The end effector 5500 comprises a first jaw member, or anvil, 5502 pivotally coupled to a second jaw member 5504 (not shown). The second jaw member 5504 is configured to receive a staple cartridge 5506 therein (not shown). The staple cartridge 5506 comprises a plurality of staples (not shown). The plurality of staples 191 is deployable from the staple cartridge 3006 during a surgical operation. In some embodiments, the end effector 5500 further comprises a tissue compensator 5510 removably positioned on the anvil 5502 or on the staple cartridge 5506. FIG. 98B illustrates a detail view of a portion of the tissue compensator 5510 shown in FIG. 98A.

As described above, the plurality of staples 191 can be deployed between an unfired position and a fired position, such that staple legs 5530 move through and penetrate tissue 5518 compressed between the anvil 5502 and the staple cartridge 5506, and contact the anvil's 5502 staple-forming surface. In embodiments that include a tissue compensator 5510, the staple legs 5530 also penetrate and puncture the tissue compensator 5510. As the staple legs 5530 are deformed against the anvil's staple-forming surface, each staple 191 can capture a portion of the tissue 5518 and the tissue compensator 5510 and apply a compressive force to the tissue 5518. The tissue compensator 5510 thus remains in place with the staples 191 after the surgical instrument 10 is withdrawn from the patient's body. Because they are to be retained by the patient's body, the tissue compensators 5510 are composed of biodurable and/or biodegradable materials. The tissue compensators 5510 are described in further detail in U.S. Pat. No. 8,657,176, entitled TISSUE THICKNESS COMPENSATOR FOR SURGICAL STAPLER, which is incorporated herein by reference in its entirety.

Returning to FIG. 98A, in some embodiments, the tissue compensator 5510 comprises a layer of conductive elements 5512. The conductive elements 5512 can comprise any combination of conductive materials in any number of configurations, such as for instance coils of wire, a mesh or grid of wires, conductive strips, conductive plates, electrical circuits, microprocessors, or any combination thereof. The layer containing conductive elements 5512 can be located on the anvil-facing surface 5514 of the tissue compensator 5510. Alternatively or additionally, the layer of conductive elements 5512 can be located on the staple cartridge-facing surface 5516 of the tissue compensator 5510. Alternatively or additionally, the layer of conductive elements 5512 can be embedded within the tissue compensator 5510. Alternatively, the layer of conductive elements 5512 can comprise all of the tissue compensator 5510, such as when a conductive material is uniformly or non-uniformly distributed in the material comprising the tissue compensator 5510.

Figure 99:
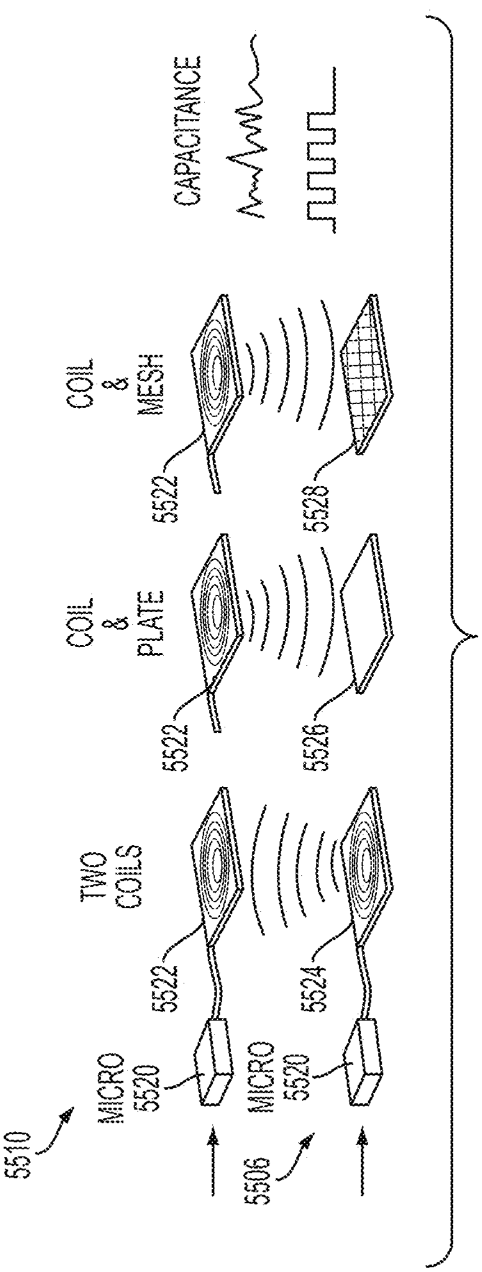
FIG. 99 illustrates various example embodiments that use the layer of conductive elements and conductive elements in the staple cartridge to detect the distance between the anvil and the upper surface of the staple cartridge.

FIG. 98A illustrates an embodiment wherein the tissue compensator 5510 is removably attached to the anvil 5502 portion of the end effector 5500. The tissue compensator 5510 would be so attached before the end effector 5500 would be inserted into a patient's body. Additionally or alternatively, a tissue compensator 5610 can be attached to a staple cartridge 5506 (not illustrated) after or before the staple cartridge 5506 is applied to the end effector 6600 and before the device is inserted into a patient's body FIG. 99 illustrates various example embodiments that use the layer of conductive elements 5512 and conductive elements 5524, 5526, and 5528 in the staple cartridge 5506 to detect the distance between the anvil 5502 and the upper surface of the staple cartridge 5506. The distance between the anvil 5502 and the staple cartridge 5506 indicates the amount and/or density of tissue 5518 compressed therebetween. This distance can additionally or alternatively indicate which areas of the end effector 5500 contain tissue. The tissue 5518 thickness, density, and/or location can be communicated to the operator of the surgical instrument 10.

In the illustrated example embodiments, the layer of conductive elements 5512 is located on the anvil-facing surface 5514 of the tissue compensator 5510, and comprises one or more coils of wire 5522 in communication with a microprocessor 5520. The microprocessor 5500 can be located in the end effector 5500 or any component thereof, or can be located in the housing 12 of the instrument, or can comprise any microprocessor or microcontroller previously described. In the illustrated example embodiments, the staple cartridge 5506 also includes conductive elements, which can be any one of: one or more coils of wire 5524, one or more conductive plates 5526, a mesh of wires 5528, or any other convenient configuration, or any combination thereof. The staple cartridge's 5506 conductive elements can be in communication with the same microprocessor 5520 or some other microprocessor in the instrument.

When the anvil 5502 is in a closed position and thus is compressing tissue 5518 against staple cartridge 5506, the layer of conductive elements 5512 of the tissue compensator 5510 can capacitively couple with the conductors in staple cartridge 5506. The strength of the capacitive field between the layer of conductive elements 5512 and the conductive elements of the staple cartridge 5506 can be used to determine the amount of tissue 5518 being compressed. Alternatively, the staple cartridge 5506 can comprise eddy current sensors in communication with a microprocessor 5520, wherein the eddy current sensors are operable to sense the distance between the anvil 5502 and the upper surface of the staple cartridge 5506 using eddy currents.

It is understood that other configurations of conductive elements are possible, and that the embodiments of FIG. 99 are by way of example only, and not limitation. For example, in some embodiments the layer of conductive elements 5512 can be located on the staple cartridge-facing surface 5516 of the tissue compensator 5510. Also, in some embodiments the conductive elements 5524, 5526, and/or 5528 can be located on or within the anvil 5502. Thus in some embodiments, the layer of conductive elements 5512 can capacitively couple with conductive elements in the anvil 5502 and thereby sense properties of tissue 5518 enclosed within the end effector.

It can also be recognized that tissue compensator 5512 can comprise a layer of conductive elements 5512 on both the anvil-facing surface 5514 and the cartridge-facing surface 5516. A system to detect the amount, density, and/or location of tissue 5518 compressed by the anvil 5502 against the staple cartridge 5506 can comprise conductors or sensors either in the anvil 5502, the staple cartridge 5506, or both. Embodiments that include conductors or sensors in both the anvil 5502 and the staple cartridge 5506 can optionally achieve enhanced results by allowing differential analysis of the signals that can be achieved by this configuration.

Figure 100B:
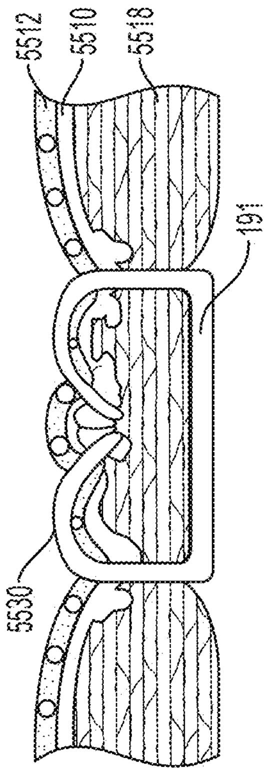
FIGS. 100A and 100B illustrate an embodiment of the tissue compensator comprising a layer of conductive elements in operation.
Figure 100A:
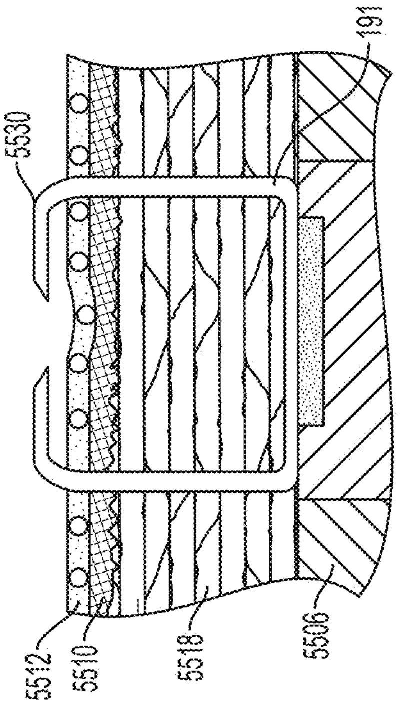

FIGS. 100A and 100B illustrate an embodiment of the tissue compensator 5510 comprising a layer of conductive elements 5512 in operation. FIG. 100A illustrates one of the plurality of staples 191 after it has been deployed. As illustrated, the staple 191 has penetrated both the tissue 5518 and the tissue compensator 5510. The layer of conductive elements 5512 may comprise, for example, mesh wires. Upon penetrating the layer of conductive elements 5512, the staple legs 5530 may puncture the mesh of wires, thus altering the conductivity of the layer of conductive elements 5512. This change in the conductivity can be used to indicate the locations of each of the plurality of staples 191. The location of the staples 191 can compared against the expected location of the staples, and this comparison can be used to determine if any staples did not fire or if any staples are not where they are expected to be.

FIG. 100A also illustrates staple legs 5530 that failed to completely deform. FIG. 100B illustrates staple legs 5530 that have properly and completely deformed. As illustrated in FIG. 100B, the layer of conductive elements 5512 can be punctured by the staple legs 5530 a second time, such as when the staple legs 5530 deform against the staple-forming surface of the anvil 5502 and turn back towards the tissue 5518. The secondary breaks in the layer of conductive elements 5512 can be used to indicate complete staple 191 formation, as illustrated in FIG. 100B, or incomplete staple 191 formation, as in FIG. 100A.

Figure 101A:
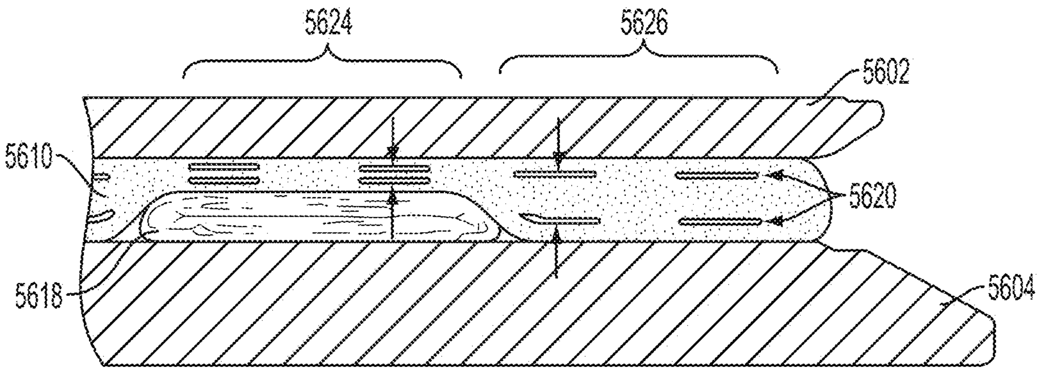
FIGS. 101A and 101B illustrate an embodiment of an end effector comprising a tissue compensator further comprising conductors embedded within.
Figure 101B:
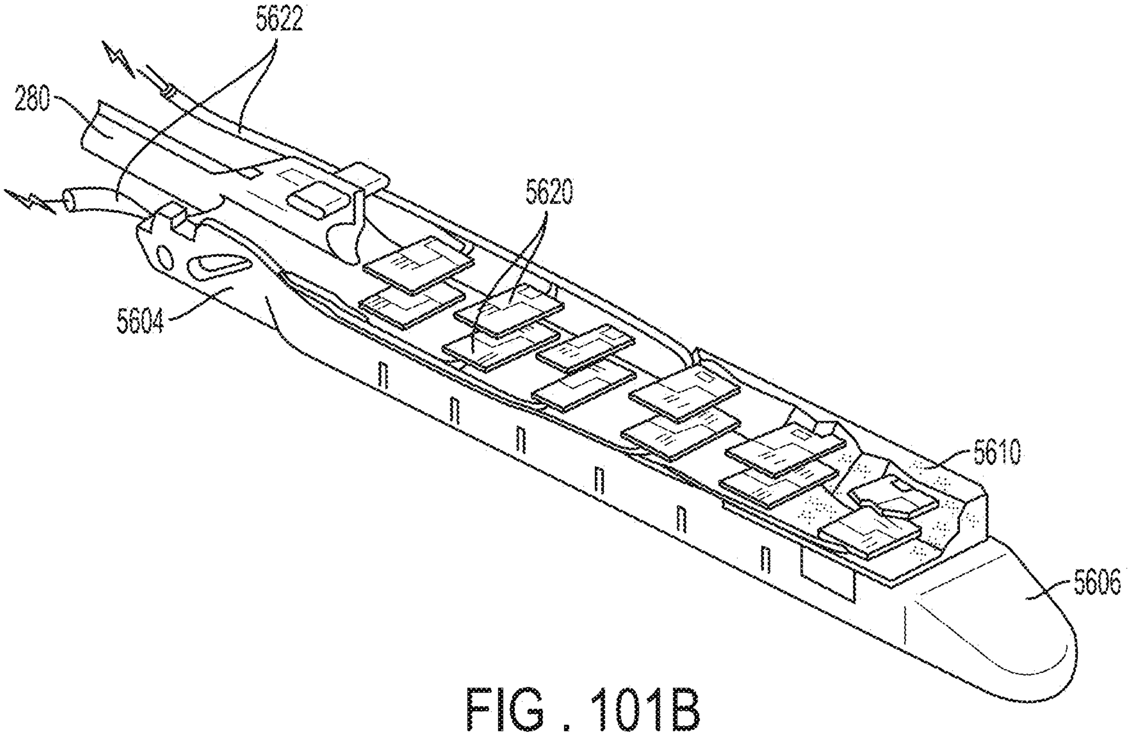

FIGS. 101A and 101B illustrate an embodiment of an end effector 5600 comprising a tissue compensator 5610 further comprising conductors 5620 embedded within. The end effector 5600 comprises a first jaw member, or anvil, 5602 pivotally coupled to a second jaw member 5604. The second jaw member 5604 is configured to receive a staple cartridge 5606 therein. In some embodiments, the end effector 5600 further comprises a tissue compensator 5610 removably positioned on the anvil 5602 or the staple cartridge 5606.

Turning first to FIG. 4B, FIG. 4B illustrates a cutaway view of the tissue compensator 5610 removably positioned on the staple cartridge 5606. The cutaway view illustrates an array of conductors 5620 embedded within the material that comprises the tissue compensator 5610. The array of conductors 5620 can be arranged in an opposing configuration, and the opposing elements can be separated by insulating material. The array of conductors 5620 are each coupled to one or more conductive wires 5622. The conductive wires 5622 allow the array of conductors 5620 to communicate with a microprocessor, such as for instance microprocessor 1500. The array of conductors 5620 may span the width of the tissue compensator 5610 such that they will be in the path of a cutting member or knife bar 280. As the knife bar 280 advances, it will sever, destroy, or otherwise disable the conductors 5620, and thereby indicate its position within the end effector 5600. The array of conductors 5610 can comprise conductive elements, electric circuits, microprocessors, or any combination thereof.

Turning now to FIG. 101A, FIG. 101A illustrates a close-up cutaway view of the end effector 5600 with the anvil 5602 in a closed position. In a closed position, the anvil 5602 can compress tissue 5618 and the tissue compensator 5610 against the staple cartridge 5606. In some cases, only a part of the end effector 5600 may be enclosing the tissue 5618. In areas of the end effector 5600 that are enclosing tissue 5618, the tissue compensator 5610 may be compressed 5624 a greater amount than areas that do not enclose tissue 5618, where the tissue compensator 5618 may remain uncompressed 5626 or be less compressed. In areas of greater compression 5624, the array of conductors 5620 will also be compressed, while in uncompressed 5626 areas, the array of conductors 5620 will be further apart. Hence, the conductivity, resistance, capacitance, and/or some other electrical property between the array of conductors 5620 can indicate which areas of the end effector 5600 contain tissue.

Figure 102A:
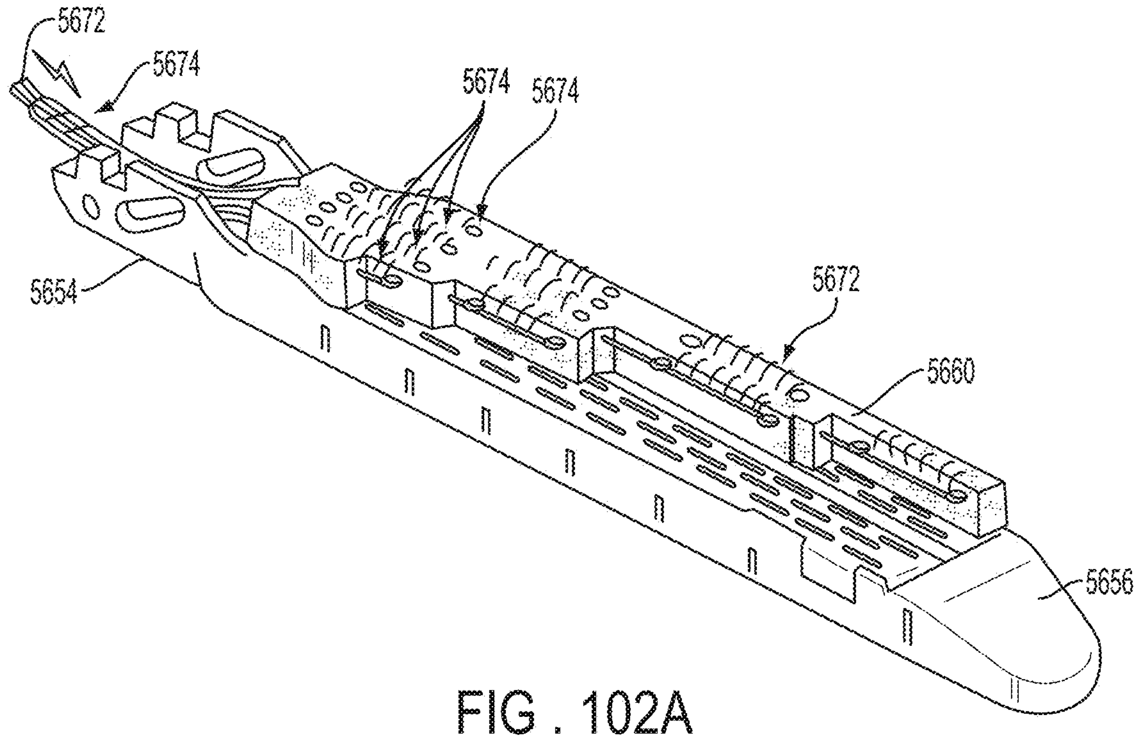
FIGS. 102A and 102B illustrate an embodiment of an end effector comprising a tissue compensator further comprising conductors embedded therein.
Figure 102B:
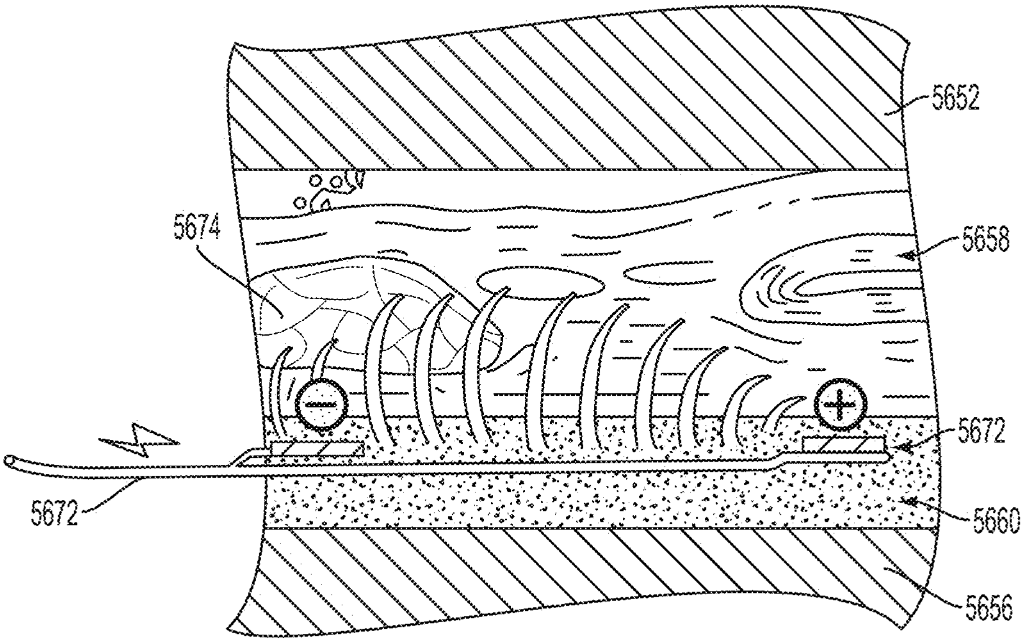

FIGS. 102A and 102B illustrate an embodiment of an end effector 5650 comprising a tissue compensator 5660 further comprising conductors 5662 embedded therein. The end effector 5650 comprises a first jaw member, or anvil, 5652 pivotally coupled to a second jaw member 5654. The second jaw member 5654 is configured to receive a staple cartridge 5656 therein. In some embodiments, the end effector 5650 further comprises a tissue compensator 5660 removably positioned on the anvil 5652 or the staple cartridge 5656.

FIG. 102A illustrates a cutaway view of the tissue compensator 5660 removably positioned on the staple cartridge 5656. The cutaway view illustrates conductors 5670 embedded within the material that comprises the tissue compensator 5660. Each of the conductors 5672 is coupled to a conductive wire 5672. The conductive wires 5672 allow the array of conductors 5672 to communicate with a microprocessor, such as for instance microprocessor 1500. The conductors 5672 may comprise conductive elements, electric circuits, microprocessors, or any combination thereof.

FIG. 102A illustrates a close-up side view of the end effector 5650 with the anvil 5652 in a closed position. In a closed position, the anvil 5652 can compress tissue 5658 and the tissue compensator 5660 against the staple cartridge 5656. The conductors 5672 embedded within the tissue compensator 5660 can be operable to apply pulses of electrical current 5674, at predetermined frequencies, to the tissue 5658. The same or additional conductors 5672 can detect the response of the tissue 5658 and transmit this response to a microprocessor or microcontroller located in the instrument. The response of the tissue 5658 to the electrical pulses 5674 can be used to determine a property of the tissue 5658. For example, the galvanic response of the tissue 5658 indicates the tissue's 5658 moisture content. As another example, measurement of the electrical impedance through the tissue 5658 could be used to determine the conductivity of the tissue 5648, which is an indicator of the tissue type. Other properties that can be determined include by way of example and not limitation: oxygen content, salinity, density, and/or the presence of certain chemicals. By combining data from several sensors, other properties could be determined, such as blood flow, blood type, the presence of antibodies, etc.

Figure 103:
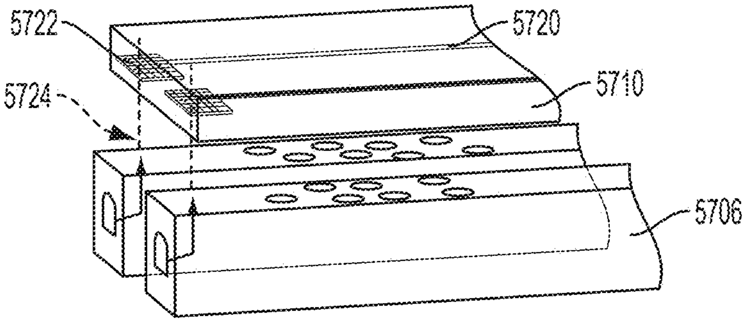
FIG. 103 illustrates an embodiment of a staple cartridge and a tissue compensator wherein the staple cartridge provides power to the conductive elements that comprise the tissue compensator.

FIG. 103 illustrates an embodiment of a staple cartridge 5706 and a tissue compensator 5710 wherein the staple cartridge 5706 provides power to the conductive elements 5720 that comprise the tissue compensator 5710. As illustrated, the staple cartridge 5706 comprises electrical contacts 5724 in the form of patches, spokes, bumps, or some other raised configuration. The tissue compensator 5710 comprises mesh or solid contact points 5722 that can electrically couple to the contacts 5724 on the staple cartridge 5706.

Figure 104A:
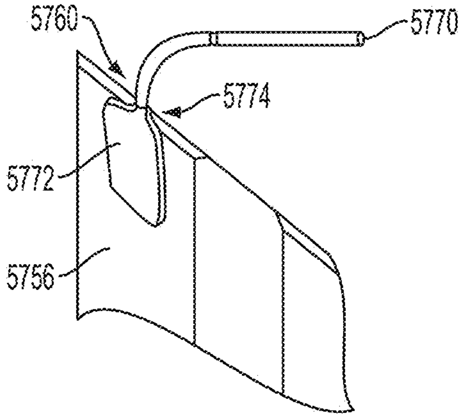
FIGS. 104A and 104B illustrate an embodiment of a staple cartridge and a tissue compensator wherein the staple cartridge provides power to the conductive elements that comprise the tissue compensator.
Figure 104B:
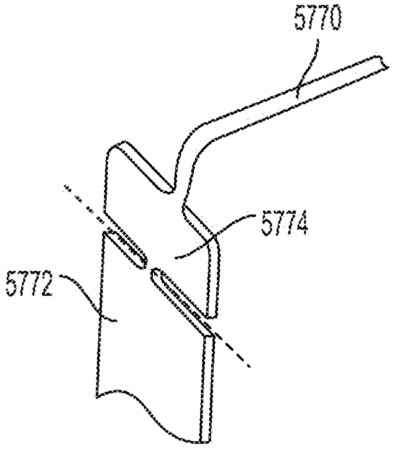

FIGS. 104A and 104B illustrate an embodiment of a staple cartridge 5756 and a tissue compensator 5760 wherein the staple cartridge provides power to the conductive elements 5770 that comprise the tissue compensator 5710. As illustrated in FIG. 104A, the tissue compensator 5760 comprises an extension or tab 5772 configured to come into contact with the staple cartridge 5756. The tab 5772 may contact and adhere to an electrical contact (not shown) on the staple cartridge 5756. The tab 5772 further comprises a break point 5774 located in a wire comprising the conductive elements 5770 of the tissue compensator 5760. When the tissue compensator 5760 is compressed, such as when an anvil is in a closed position towards the staple cartridge 5756, the break point 5774 will break, thus allowing the tissue compensator 5756 to become free from the staple cartridge 5756. FIG. 104B illustrates another embodiment employing a break point 5774 positioned in the tab 5772.

Figure 105A:
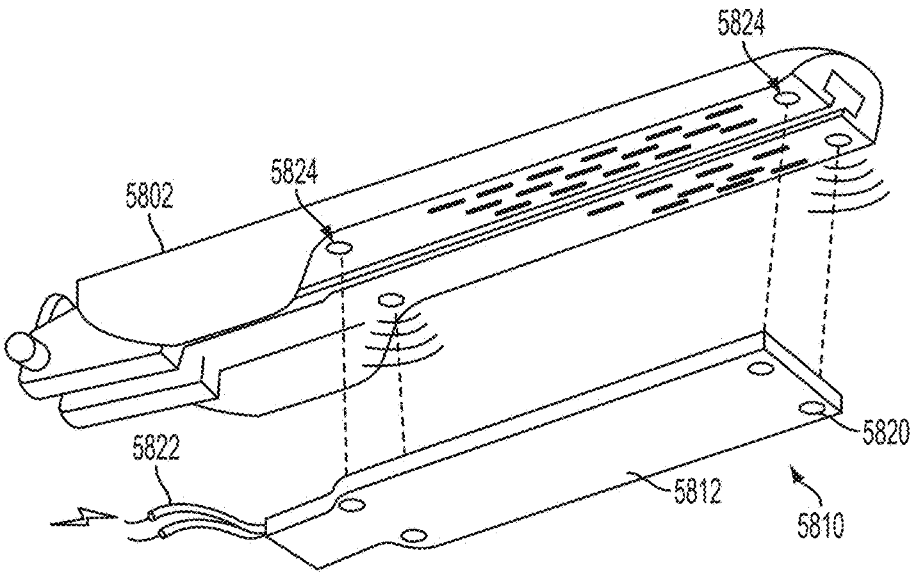
FIGS. 105A and 105B illustrate an embodiment of an end effector comprising position sensing elements and a tissue compensator.

FIGS. 105A and F8B illustrate an embodiment of an end effector 5800 comprising position sensing elements 5824 and a tissue compensator 5810. The end effector 5800 comprises a first jaw member, or anvil, 5802 pivotally coupled to a second jaw member 5804 (not shown). The second jaw member 5804 is configured to receive a staple cartridge 5806 (not shown) therein. In some embodiments, the end effector 5800 further comprises a tissue compensator 5810 removably positioned on the anvil 5802 or the staple cartridge 5806.

FIG. 105A illustrates the anvil 5804 portion of the end effector 5800. In some embodiments the anvil 5804 comprises position sensing elements 5824. The position sensing elements 5824 can comprise, for example, electrical contacts, magnets, RF sensors, etc. The position sensing elements 5824 can be located in key locations, such as for instance the corner points where the tissue compensator 5810 will be attached, or along the exterior edges of the anvil's 5802 tissue-facing surface. In some embodiments, the tissue compensator 5810 can comprise position indicating elements 5820. The position indicating elements 5820 can be located in corresponding locations to the position sensing elements 5824 on the anvil 5802, or in proximal locations, or in overlapping locations. The tissue compensator 5810 optionally further comprises a layer of conductive elements 5812. The layer of conductive elements 5812 and/or the position indicating elements 5820 can be electrically coupled to conductive wires 5822. The conductive wires 5822 can provide communication with a microprocessor, such as for instance microprocessor 1500.

FIG. F8B illustrates an embodiment the position sensing elements 5824 and position indicating elements 5820 in operation. When the tissue compensator 5810 is positioned, the anvil 5802 can sense 5826 that the tissue compensator 5810 is properly position. When the tissue compensator 5810 is misaligned or missing entirely, the anvil 5802 (or some other component) can sense 5826 that the tissue compensator 5810 is misaligned. If the misalignment is above a threshold magnitude, a warning can be signaled to the operator of the instrument, and/or a function of the instrument can be disabled to prevent the staples from being fired.

Figure 105B:
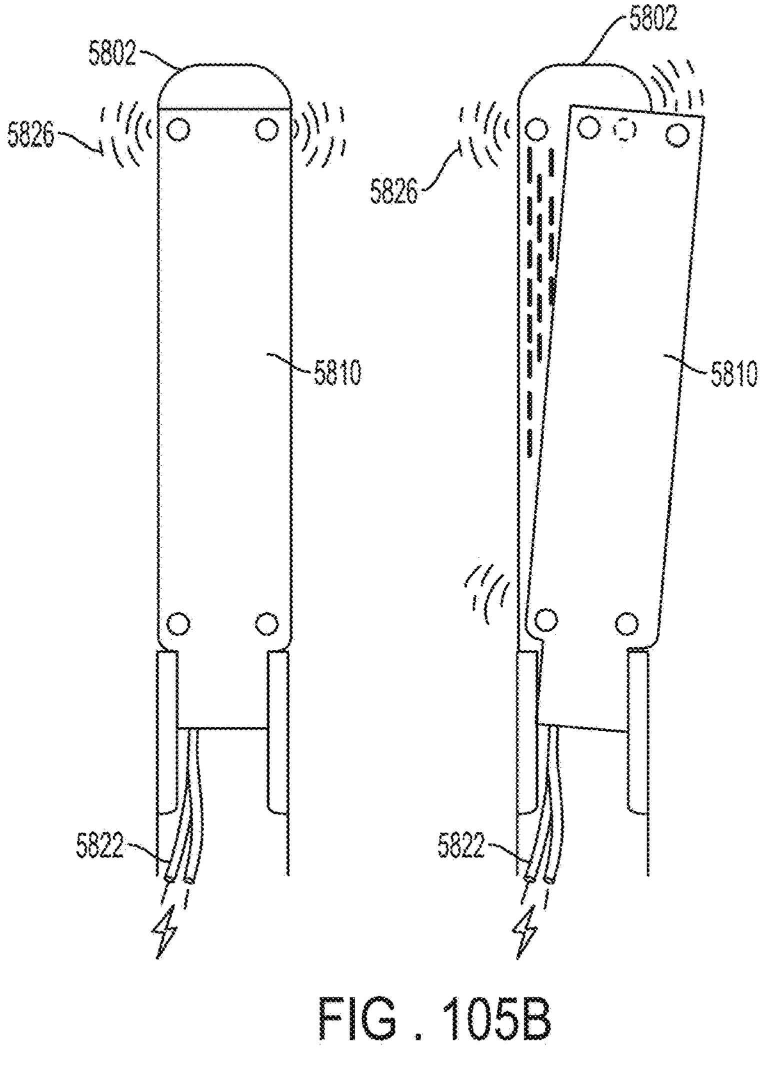

In FIGS. 105A and 105B the position sensing elements 5824 are illustrated as a part of the anvil 5804 by way of example only. It is understood that the position sensing elements 5824 can be located instead or additionally on the staple cartridge 5806. It is also understood that the location of the position sensing elements 5824 and the position indicating elements 5820 can be reversed, such that the tissue compensator 5810 is operable to indicate whether it is properly aligned.

Figure 106A:
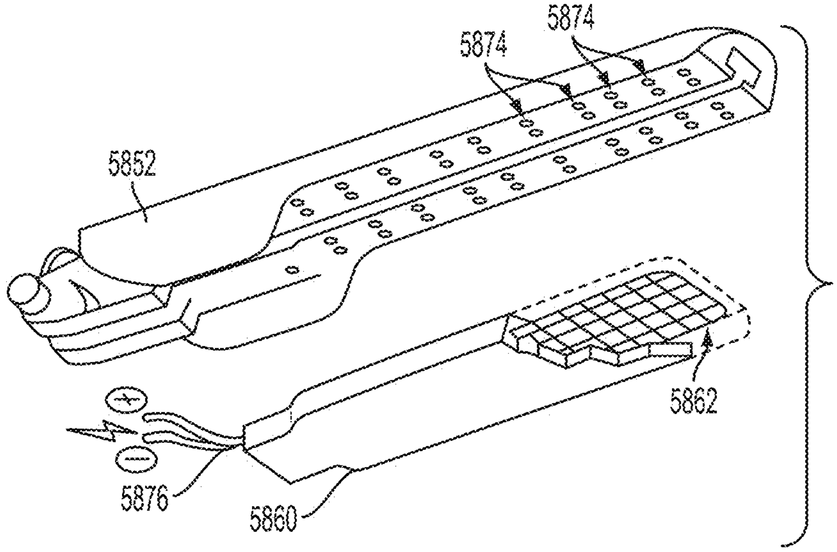
FIGS. 106A and 106B illustrate an embodiment of an end effector comprising position sensing elements and a tissue compensator.
Figure 106B:
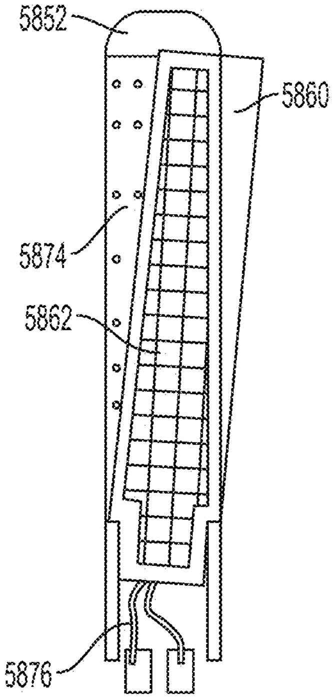

FIGS. 106A and F9B illustrate an embodiment of an end effector 5850 comprising position sensing elements 5874 and a tissue compensator 5860. The end effector 5850 comprises a first jaw member, or anvil, 5852 pivotally coupled to a second jaw member 5854 (not shown). The second jaw member 5854 is configured to receive a staple cartridge 5856 (not show) therein. In some embodiments, the end effector 5850 further comprises a tissue compensator 5860 removably positioned on the anvil 5852 or the staple cartridge 5856.

FIG. 106A illustrates the anvil 5852 portion of the end effector 5850. In some embodiments, the anvil 5854 comprises an array of conductive elements 5474. The array of conductive elements 5474 can comprise, for example, electrical contacts, magnets, RF sensors, etc. The array of conductive elements 5474 are arrayed along the length of the tissue-facing surface of the anvil 5852. In some embodiments, the tissue compensator 5860 can comprise a layer of conductive elements 5862, wherein the conductive elements comprise a grid or mesh of wires. The layer of conductive elements 5862 may be coupled to conductive wires 5876. The conductive wires 5862 can provide communication with a microprocessor, such as for instance microprocessor 1500.

FIG. 106A illustrates an embodiment wherein of the conductive elements 5474 of the anvil 5852 and the layer of conductive elements 5862 are operable to indicate whether the tissue compensator 5860 is misaligned or missing. As illustrated, the array of conductive elements 5874 is operable to electrically couple with the layer of conductive elements 5862. When the tissue compensator 5860 is misaligned or missing, the electrical coupling will be incomplete. If the misalignment is above a threshold magnitude, a warning can be signaled to the operator of the instrument, and/or a function of the instrument can be disabled to prevent the staples from being fired.

It is understood that the array of conductive elements 5874 may additionally or alternatively be located on the staple cartridge 5856. It is also understood that the any of the anvil 5852, staple cartridge 5856, and/or tissue compensator 5860 may be operable to indicate misalignment of the tissue compensator 5860.

Figure 107A:
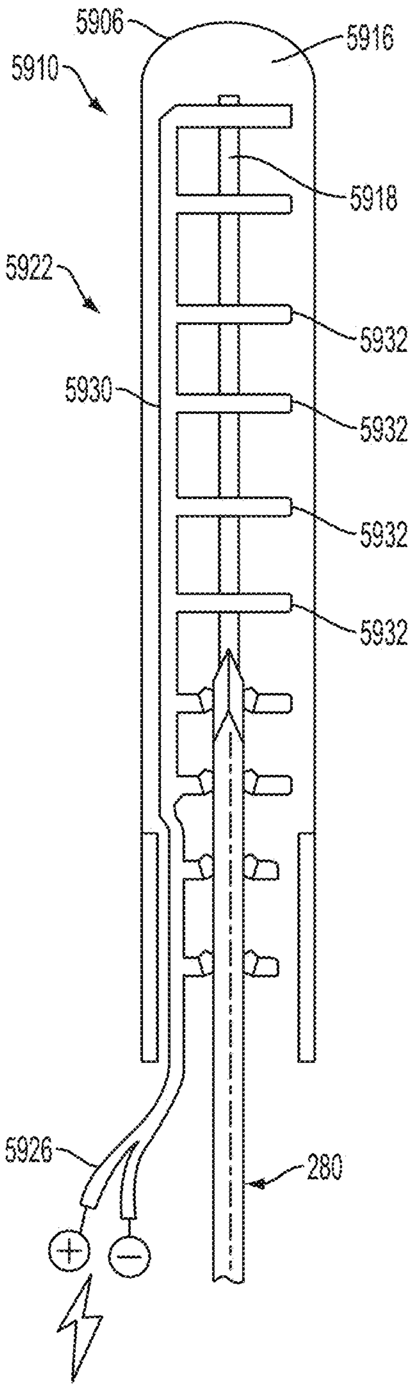
FIGS. 107A and 107B illustrate an embodiment of a staple cartridge and a tissue compensator that is operable to indicate the position of a cutting member or knife bar.
Figure 107B:
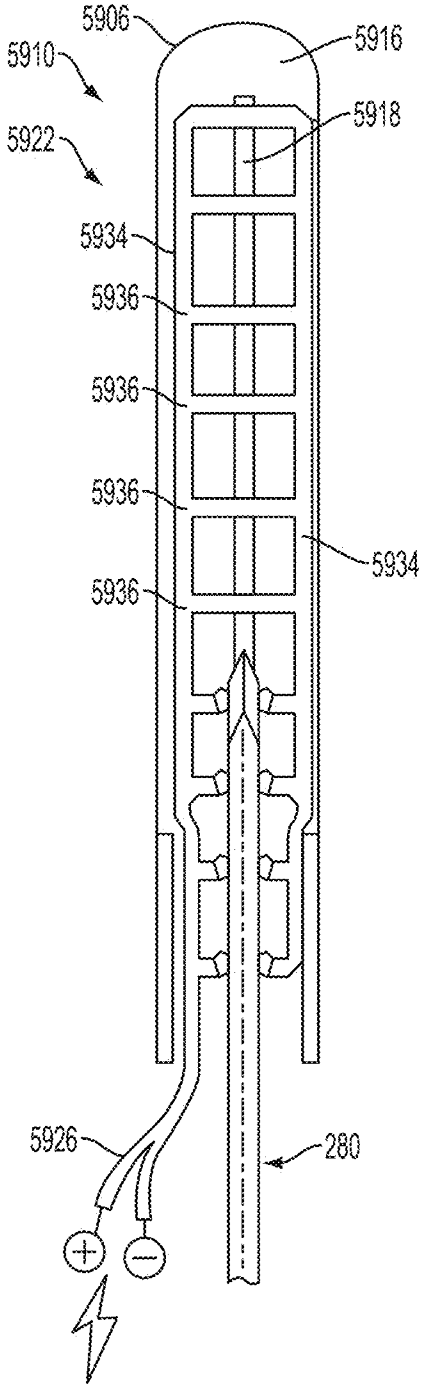

FIGS. 107A and 107B illustrate an embodiment of a staple cartridge 5906 and a tissue compensator 5910 that is operable to indicate the position of a cutting member or knife bar 280. FIG. 107A is a top-down view of the staple cartridge 5906 that has a tissue compensator 5920 placed on its upper surface 5916. The staple cartridge 5906 further comprises a cartridge channel 5918 operable to accept a cutting member or knife bar 280. FIG. 107A illustrates only the layer of conductive elements 5922 of the tissue compensator 5910, for clarity. As illustrated, the layer of conductive elements 5922 comprises a lengthwise segment 5930 that is located off-center. The lengthwise segment 5930 is coupled to conductive wires 5926. The conductive wires 5926 allow the layer of conductive elements 5922 to communicate with a microprocessor, such as for instance microprocessor 1500. The layer of conductive elements 5922 further comprises horizontal elements 5932 coupled to the lengthwise segment 5930 and spanning the width of the tissue compensator 5910, and thus crossing the path of the knife bar 280. As the knife bar 280 advances, it will sever the horizontal elements 5932 and thereby alter an electrical property of the layer of conductive elements 5922. For example, the advancing of the knife bar 280 may alter the resistance, capacitance, conductivity, or some other electrical property of the layer of conductive elements 5922. As each horizontal element 5932 is severed by the knife bar 280, the change in the electrical properties of the layer of conductive elements 5922 will indicate the position of the knife bar 280.

FIG. 107B illustrates an alternate configuration for the layer of conductive elements 5922. As illustrated, the layer of conductive elements 5922 comprises a lengthwise segment 5934 on either side of the cartridge channel 5918. The layer of conductive elements 5922 further comprises horizontal elements 5936 coupled to both of the lengthwise segments 5934, thus spanning the path of the knife bar 280. As the knife bar 280, the resistance, for example between the knife bar and the horizontal elements 5396 can be measured and used to determine the location of the knife bar 280. Other configurations of the layer of conductive elements 5922 can be used to accomplish the same result, such as for instance any of the arrangements illustrated in FIGS. 98A through 102B. For example, the layer of conductive elements 5922 can comprise a wire mesh or grid, such that as the knife bar 280 advances it can sever the wire mesh and thereby change the conductivity in the wire mesh. This change in conductivity can be used to indicate the position of the knife bar 280.

Other uses for the layer of conductive elements 5922 can be imagined. For example, a specific resistance can be created in the layer of conductive elements 592, or a binary ladder of resistors or conductors can be implemented, such that simple data can be stored in the tissue compensator 5910. This data can be extracted from the tissue compensator 5910 by conductive elements in the anvil and/or staple cartridge when either electrically couple with the layer of conductive elements 5922. The data can represent, for example, a serial number, a "use by" date, etc.

Polarity of Hall Magnet to Detect Misloaded Cartridge

Figure 108:
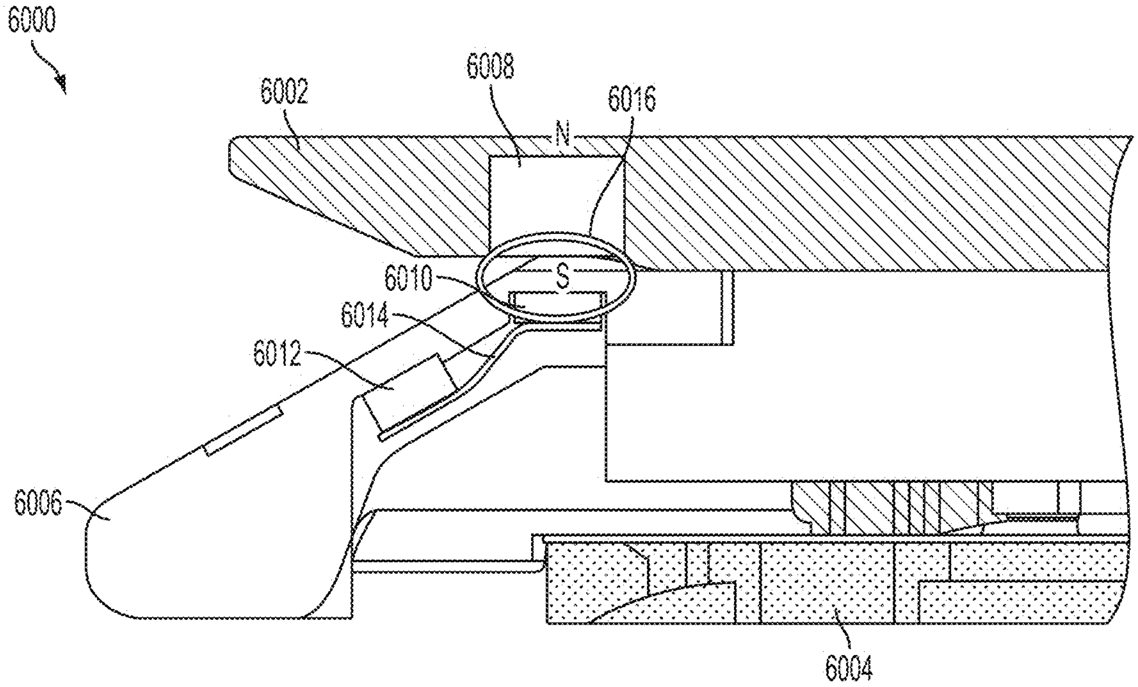
FIG. 108 illustrates one embodiment of an end effector comprising a magnet and a Hall effect sensor wherein the detected magnetic field can be used to identify a staple cartridge.

FIG. 108 illustrates one embodiment of an end effector 6000 comprising a magnet 6008 and a Hall effect sensor 6010 wherein the detected magnetic field 6016 can be used to identify a staple cartridge 6006. The end effector 6000 is similar to the end effector 300 described above. The end effector 6000 comprises a first jaw member or anvil 6002, pivotally coupled to a second jaw member or elongated channel 6004. The elongated channel 6004 is configured to operably support a staple cartridge 6006 therein. The staple cartridge 6006 is similar to the staple cartridge 304 described above. The anvil 6002 further comprises a magnet 6008. The staple cartridge 6006 further comprises a Hall effect sensor 6010 and a processor 6012. The Hall effect sensor 6010 is operable to communicate with the processor 6012 through a conductive coupling 6014. The Hall effect sensor 6010 is positioned within the staple cartridge 6006 to operatively couple with the magnet 6008 when the anvil 6002 is in a closed position. The Hall effect sensor 6010 can be operable to detect the magnetic field 6016 produced by the magnet 6008. The polarity of the magnetic field 6016 can be one of north or south depending on the orientation of the magnet 6008 within the anvil 6002. In the illustrated embodiment of FIG. 108, the magnet 6008 is oriented such that its south pole is directed towards the staple cartridge 6006. The Hall effect sensor 6010 can be operable to detect the magnetic field 6016 produced by a south pole. If the Hall effect sensor 6010 detects a magnetic south pole, then the staple cartridge 6006 can be identified as of a first type.

Figure 109:
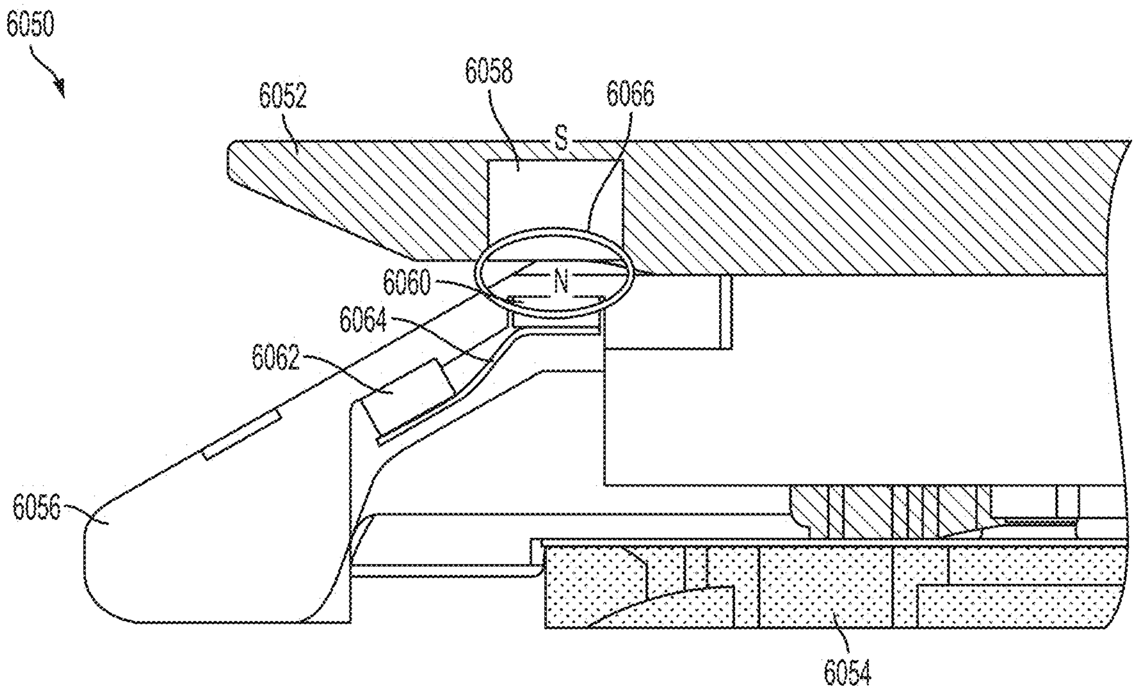
FIG. 109 illustrates on embodiment of an end effector comprising a magnet and a Hall effect sensor wherein the detected magnetic field can be used to identify a staple cartridge.

FIG. 109 illustrates on embodiment of an end effector 6050 comprising a magnet 6058 and a Hall effect sensor 6060 wherein the detected magnetic field 6066 can be used to identify a staple cartridge 6056. The end effector 6050 comprises a first jaw member or anvil 6052, pivotally coupled to a second jaw member or elongated channel 6054. The elongated channel 6054 is configured to operably support a staple cartridge 6056 therein. The anvil 6052 further comprises a magnet 6058. The staple cartridge 6056 further comprises a Hall effect sensor 6060 in communication with a processor 6062 over a conductive coupling 6064. The Hall effect sensor 6060 is positioned such that it will operatively couple with the magnet 6058 when the anvil 6052 is in a closed position. The Hall effect sensor 6060 can be operable to detect the magnetic field 6066 produced by the magnet 6058. In the illustrated embodiment, the magnet 6058 is oriented such that its north magnetic pole is directed towards the staple cartridge 6056. The Hall effect sensor 6060 can be operable to detect the magnetic field 6066 produced by a north pole. If the Hall effect sensor 6060 detects a north magnetic pole, then the staple cartridge 6056 an be identified as a second type.

It can be recognized that the second type staple cartridge 6056 of FIG. 109 can be substituted for the first type staple cartridge 6006 of FIG. 108, and vice versa. In FIG. 108, the second type staple cartridge 6056 would be operable to detect a magnetic north pole, but will detect a magnetic south pole instead. In this case, end effector 6000 will identify the staple cartridge 6056 as being of the second type. If the end effector 6000 did not expect a staple cartridge 6056 of the second type, the operator of the instrument can be alerted, and/or a function of the instrument can be disabled. The type of the staple cartridge 6056 can additionally or alternatively be used to identify some parameter of the staple cartridge 6056, such as for instance the length of the cartridge and/or the height and length of the staples.

Similarly, as shown in FIG. 109, the first type staple cartridge 6006 can be substituted for the second staple cartridge 6056. The first type staple cartridge 6006 would be operable to detect a south magnetic pole, but will instead detect a north magnetic pole. In this case, the end effector 6050 will identify the staple cartridge 6006 as being of the first type.

Figure 110:
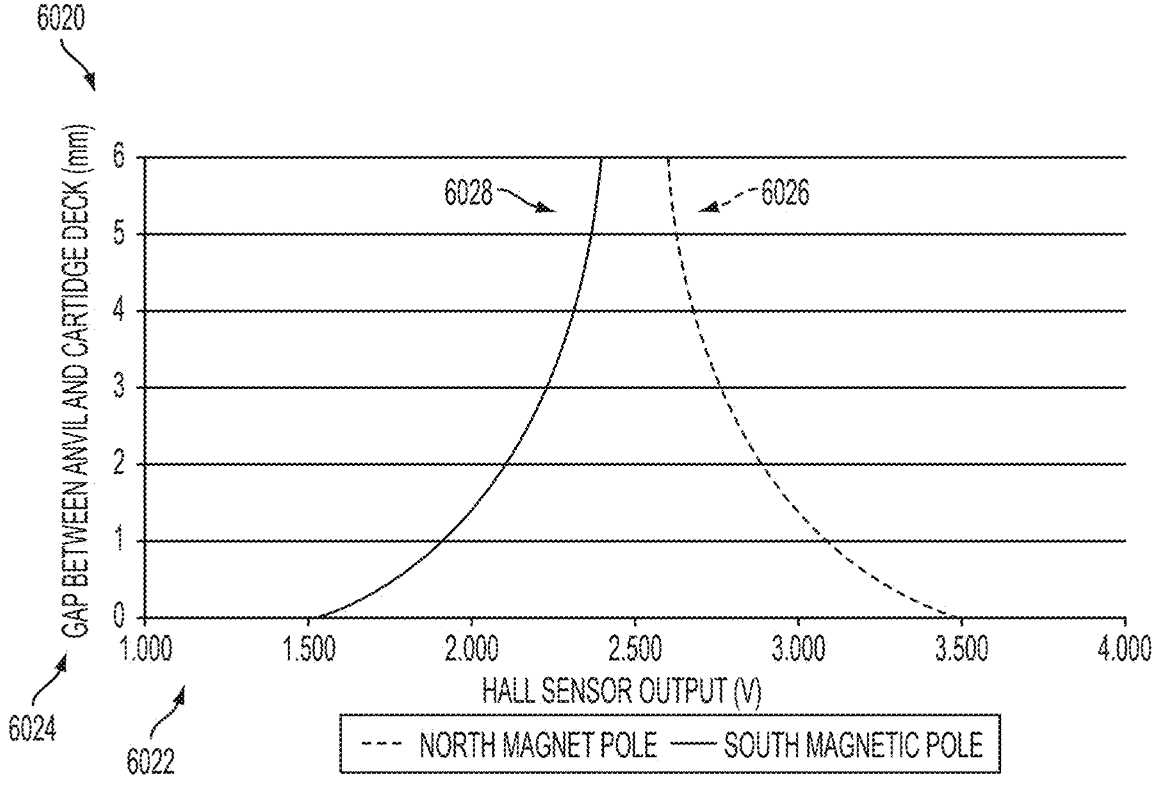
FIG. 110 illustrates a graph of the voltage detected by a Hall effect sensor located in the distal tip of a staple cartridge, such as is illustrated in FIGS. 108 and 109, in response to the distance or gap between a magnet located in the anvil and the Hall effect sensor in the staple cartridge, such as illustrated in FIGS. 108 and 109.

FIG. 110 illustrates a graph 6020 of the voltage 6022 detected by a Hall effect sensor located in the distal tip of a staple cartridge, such as is illustrated in FIGS. 108 and 109, in response to the distance or gap 6024 between a magnet located in the anvil and the Hall effect sensor in the staple cartridge, such as illustrated in FIGS. 108 and 109. As illustrated FIG. 110, when the magnet in the anvil is oriented such that its north pole is towards the staple cartridge, the voltage will tend towards a first value as the magnet comes in proximity to the Hall effect sensor; when the magnet is oriented with its south pole towards the staple cartridge, the voltage will tend towards a second, different value. The measured voltage can be used by the instrument to identify the staple cartridge.

Figure 111:
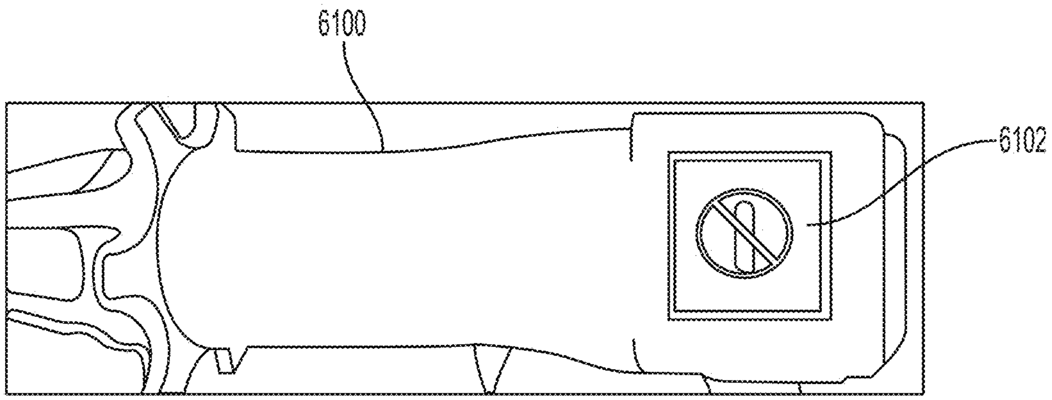
FIG. 111 illustrates one embodiment of the housing of the surgical instrument, comprising a display.

FIG. 111 illustrates one embodiment of the housing 6100 of the surgical instrument, comprising a display 6102. The housing 6100 is similar to the housing 12 described above. The display 6102 can be operable to convey information to the operator of the instrument, such as for instance, that the staple cartridge coupled to the end effector is inappropriate for the present application. Additionally or alternatively, the display 6102 can display the parameters of the staple cartridge, such as the length of the cartridge and/or the height and length of the staples.

Figure 112:
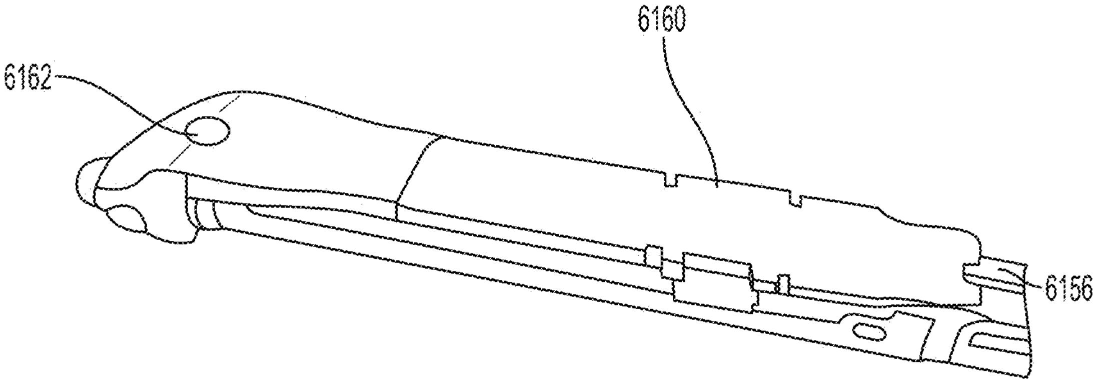
FIG. 112 illustrates one embodiment of a staple retainer comprising a magnet.

FIG. 112 illustrates one embodiment of a staple retainer 6160 comprising a magnet 6162. The staple retainer 6160 can be operably coupled to a staple cartridge 6156 and functions to prevent staples from exiting of the staple cartridge 6156. The staple retainer 6160 can be left in place when the staple cartridge 6156 is applied to an end effector. In some embodiments, the staple retainer 6160 comprises a magnet 6162 located in the distal area of the staple retainer 6160. The anvil of the end effector can comprise a Hall effect sensor operable to couple with the magnet 6162 in the staple retainer 6160. The Hall effect sensor can be operable to detect the properties of the magnet 6162, such as for instance the magnetic field strength and magnetic polarity. The magnetic field strength can be varied by, for example, placing the magnet 6162 in different locations and/or depths on or in the staple retainer 6160, or by selecting magnets 6162 of different compositions. The different properties of the magnet 6162 can be used to identify staple cartridges of different types.

Figure 113A:
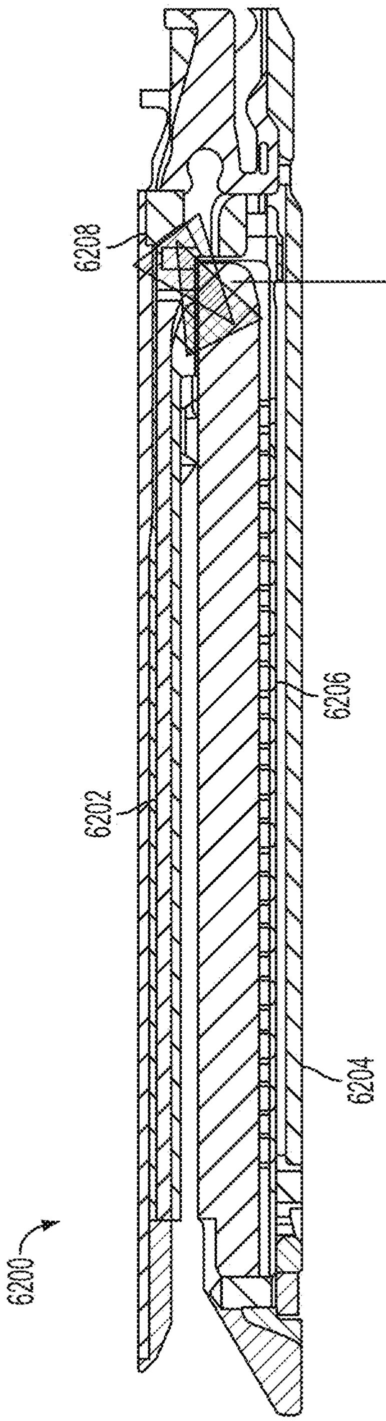
FIGS. 113A and 113B illustrate one embodiment of an end effector comprising a sensor for identifying staple cartridges of different types.
Figure 113B:
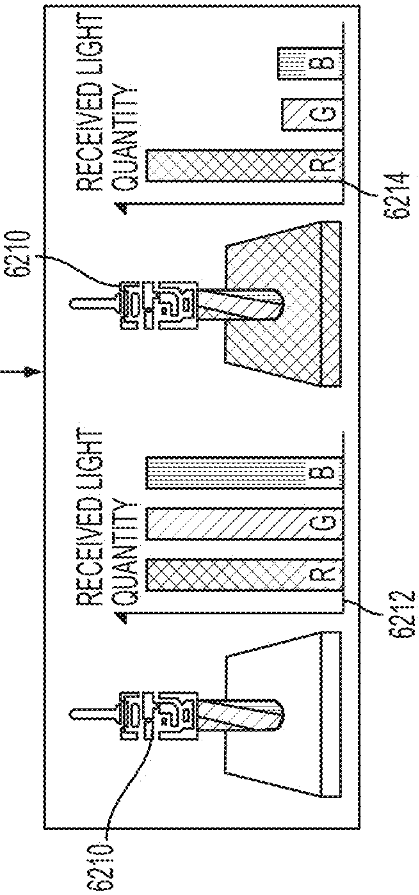

FIGS. 113A and 113B illustrate one embodiment of an end effector 6200 comprising a sensor 6208 for identifying staple cartridges 6206 of different types. The end effector 6200 comprises a first jaw member or anvil 6202, pivotally coupled to a second jaw member or elongated channel 6204. The elongated channel 6204 is configured to operably support a staple cartridge 6206 therein. The end effector 6200 further comprises a sensor 6208 located in the proximal area. The sensor 6208 can be any of an optical sensor, a magnetic sensor, an electrical sensor, or any other suitable sensor.

The sensor 6208 can be operable to detect a property of the staple cartridge 6206 and thereby identify the staple cartridge 6206 type. FIG. 113B illustrates an example where the sensor 6208 is an optical emitter and detector 6210. The body of the staple cartridge 6206 can be different colors, such that the color identifies the staple cartridge 6206 type. An optical emitter and detector 6210 can be operable to interrogate the color of the staple cartridge 6206 body. In the illustrated example, the optical emitter and detector 6210 can detect white 6212 by receiving reflected light in the red, green, and blue spectrums in equal intensity. The optical emitter and detector 6210 can detect red 6214 by receiving very little reflected light in the green and blue spectrums while receiving light in the red spectrum in greater intensity.

Alternately or additionally, the optical emitter and detector 6210, or another suitable sensor 6208, can interrogate and identify some other symbol or marking on the staple cartridge 6206. The symbol or marking can be any one of a barcode, a shape or character, a color-coded emblem, or any other suitable marking. The information read by the sensor 6208 can be communicated to a microcontroller in the surgical device 10, such as for instance microcontroller 1500. The microcontroller 1500 can be configured to communicate information about the staple cartridge 6206 to the operator of the instrument. For instance, the identified staple cartridge 6206 may not be appropriate for a given application; in such case, the operator of the instrument can be informed, and/or a function of the instrument s inappropriate. In such instance, microcontroller 1500 can optionally be configured to disable a function of surgical instrument can be disabled. Alternatively or additionally, microcontroller 1500 can be configured to inform the operator of the surgical instrument 10 of the parameters of the identified staple cartridge 6206 type, such as for instance the length of the staple cartridge 6206, or information about the staples, such as the height and length.

Smart Cartridge Wake Up Operation and Data Retention

In one embodiment the surgical instrument described herein comprises short circuit protection techniques for sensors and/or electronic components. To enable such sensors and other electronic technology both power and data signals are transferred between modular components of the surgical instrument. During assembly of modular sensor components electrical conductors that when connected are used to transfer power and data signals between the connected components are typically exposed.

Figure 114:
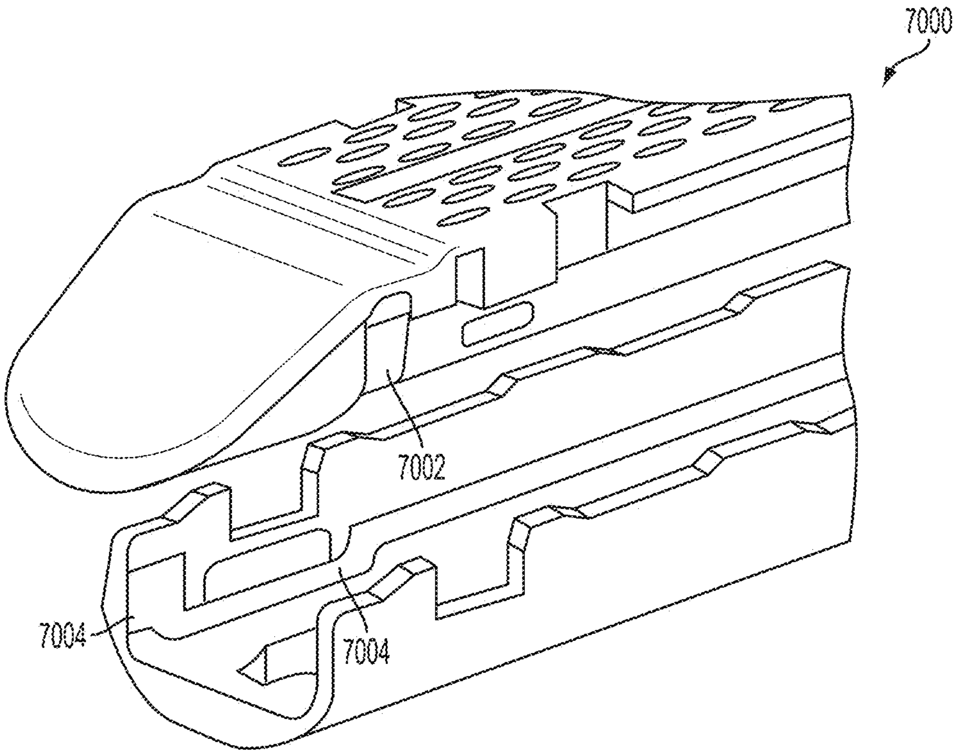
FIG. 114 is a partial view of an end effector with sensor power conductors for transferring power and data signals between the connected components of the surgical instrument according to one embodiment.
Figure 115:
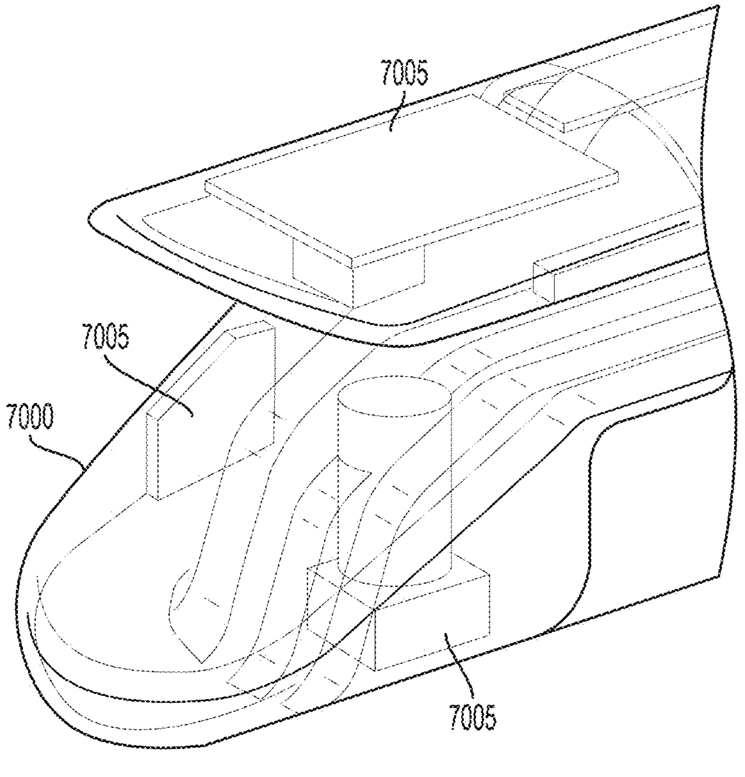

FIG. 114 is a partial view of an end effector 7000 with electrical conductors 7002, 7004 for transferring power and data signals between the connected components of the surgical instrument according to one embodiment. There is potential for these electrical conductors 7002, 7004 to become shorted and thus damage critical system electronic components. FIG. 115 is a partial view of the end effector 7000 shown in FIG. 114 showing sensors and/or electronic components 7005 located in the end effector. With reference now to both FIGS. 114 and 115, in various embodiments the surgical instruments disclosed throughout the present disclosure provide real time feedback about the compressibility and thickness of tissue using electronic sensors. Modular architectures will enable the configuration of custom modular shafts to employ job specific technologies. To enable sensors and other electronic circuit components in surgical instruments it is necessary to transfer both power and data signals between a secondary circuit comprising the modular sensor and/or electronic circuit components 7005. During the assembly of the modular sensors and/or electronic components 7005 the electrical conductors 7002, 7004 are exposed such that when connected, they are used to transfer power and data signals between the connected sensors and/or electronic components 7005. Because there is a potential for these electrical conductors 7002, 7004 to become short circuited during the assembly process and thus damage other system electronic circuits, various embodiments of the surgical instruments described herein comprise short circuit protection techniques for the sensors and/or electronic components 7005

Figure 116:
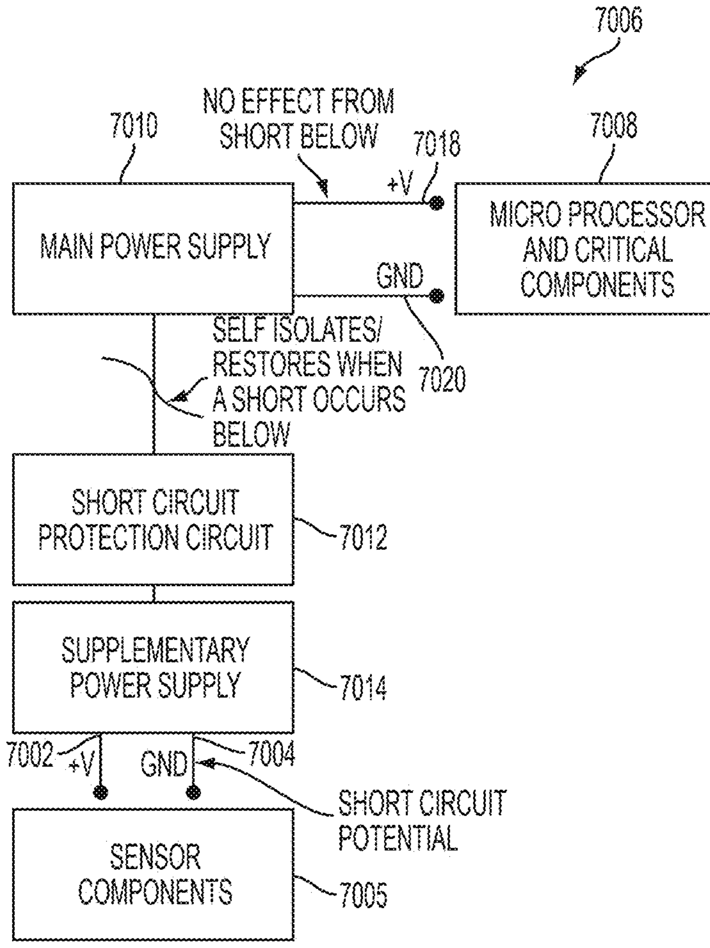

In one embodiment, the present disclosure provides a short circuit protection circuit 7012 for the sensors and/or electronic components 7005 of the secondary circuits of the surgical instrument. FIG. 116 is a block diagram of a surgical instrument electronic subsystem 7006 comprising a short circuit protection circuit 7012 for the sensors and/or electronic components 7005 according to one embodiment. A main power supply circuit 7010 is connected to a primary circuit comprising a microprocessor and other electronic components 7008 (processor 7008 hereinafter) through main power supply terminals 7018, 7020. The main power supply circuit 7010 also is connected to a short circuit protection circuit 7012. The short circuit protection circuit 7012 is coupled to a supplementary power supply circuit 7014, which supplies power to the sensors and/or electronic components 7005 via the electrical conductors 7002, 7004.

To reduce damage to the processor 7008 connected to the main power supply terminals 7018, 7020, during a short circuit between the electrical conductors 7002, 7004 of the power supply terminals feeding the sensors and/or electronic components 7005, a self isolating/restoring short circuit protection circuit 7012 is provided. In one embodiment, the short circuit protection circuit 7012 may be implemented by coupling a supplementary power supply circuit 7014 to the main power supply circuit 7010. In circumstances when the supplementary power supply circuit 7014 power conductors 7002, 7004 are shorted, the supplementary power supply circuit 7014 isolates itself from the main power supply circuit 7010 to prevent damage to the processor 7008 of the surgical instrument. Thus, there is virtually no effect to the processor 7008 and other electronic circuit components coupled to the main power supply terminals 7018, 7020 when a short circuit occurs in the electrical conductors 7002, 7004 of the supplementary power supply circuit 7014. Accordingly, in the event that a short circuit occurs between the electrical conductors 7002, 7004 of the supplementary power supply circuit 7014, the main power supply circuit 7010 is unaffected and remains active to supply power to the protected processor 7008 such that the processor 7008 can monitor the short circuit condition. When the short circuit between the electrical conductors 7002, 7004 of the supplementary power supply circuit 7014 is remedied, the supplementary power supply circuit 7014 rejoins the main power supply circuit 7010 and is available once again to supply power to the sensor components 7005. The short circuit protection circuit 7012 also may be monitored to indicate one or more short circuit conditions to the end user of the surgical instrument. The short circuit protection circuit 7012 also may be monitored to lockout the firing of the surgical instrument when a short circuit event is indicated. Many supplementary protection circuits may be networked together to isolate, detect, or protect other circuit functions.

Accordingly, in one aspect, the present disclosure provides a short circuit protection circuit 7012 for electrical conductors 7002, 7004 in the end effector 7000 (FIGS. 114 and 115) or other elements of the surgical instrument. In one embodiment, the short circuit protection circuit 7012 employs a supplementary self-isolating/restoring power supply circuit 7014 coupled to the main power supply circuit 7010. The short circuit protection circuit 7012 may be monitored to indicate one or more short circuit conditions to the end user of the surgical instrument. In the event of a short circuit, the short circuit protection circuit 7012 may be employed to lock-out the surgical instrument from being fired or other device operations. Many other supplementary protection circuits may be networked together to isolate, detect, or protect other circuit functions.

Figure 117:
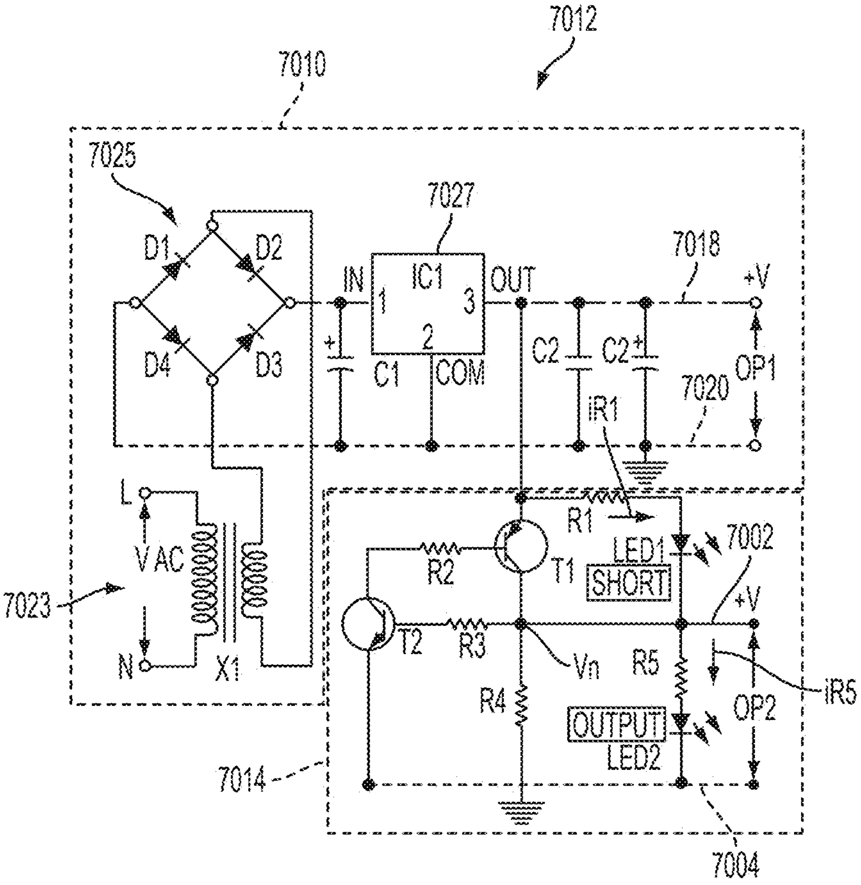

FIG. 117 is a short circuit protection circuit 7012 comprising a supplementary power supply circuit 7014 coupled to a main power supply circuit 7010, according to one embodiment. The main power supply circuit 7010 comprises a transformer 7023 (X1) coupled to a full wave rectifier 7025 implemented with diodes 91-94. The full wave rectifier 7025 is coupled to the voltage regulator 7027. The output (OUT) of the voltage regulator 7027 is coupled to both the output terminals 7018, 7020 of the main power supply circuit 7010 (OP1) and the supplementary power supply circuit 7014. An input capacitor C1 filters the input voltage in the voltage regulator 7027 and one or more capacitors C2 filter the output the of the voltage regulator 7027.

In the embodiment illustrated in FIG. 117, the supplementary power supply circuit 7014 comprises a pair of transistors T1, T2 configured to control the power supply output OP2 between the electrical conductors 7002, 7004. During normal operation when the electrical conductors 7002, 7004 are not shorted, the output OP2 supplies power to the sensor components 7005. Once the transistors T1 and T2 are turned ON (activated) and begin conducting current, the current from the output of the voltage regulator 7027 is shunted by the first transistor T1 such that no current flows through R1 and $i_{R1}$=0. The output voltage of the regulator +V is applied at the node such the $V_n$~+V, which is then the output voltage OP2 of the supplementary power supply circuit 7014 and the first transistor T1 drives the current to the sensor components 7005 through the output terminal 7002, where output terminal 7004 is the current return path. A portion of the output current $i_{R5}$ is diverted through R5 to drive the output indicator LED2. The current though the LED2 is $i_{R5}$. As long as the node voltage $V_n$ is above the threshold necessary to turn ON (activate) the second transistor T2, the supplementary power supply circuit 7014 operates as a power supply circuit to feed the sensors and/or electronic components 7005.

When the electrical conductors 7002, 7004 of the secondary circuit are shorted, the node voltage $V_n$ drops to ground or zero and the second transistor T2 turns OFF and stops conducting, which turns OFF the first transistor T1. When the first transistor T1 is cut-OFF, the output voltage +V of the voltage regulator 7027 causes current $i_{R1}$ to flow through the short circuit indicator LED1 and through to ground via the short circuit between the electrical conductors 7002, 7004. Thus, no current flows through R5 and $i_{R5}$=0A and $+V_{OP2}$=0V. The supplementary power supply circuit 7014 isolates itself from the main power supply circuit 7010 until the short circuit is removed. During the short circuit only the short circuit indicator LED1 is energized while the output indicator LED2 is not. When the short circuit between the electrical conductors 7002, 7004 is removed, the node voltage $V_n$ rises until T2 turns ON and subsequently turning T1 ON. When T1 and T2 are turned ON (are biased in a conducting state such as saturation), until the node voltage $V_n$ reaches $+V_{OP2}$ and the supplementary power supply circuit 7014 resumes its power supply function for the sensor components 7005. Once the supplementary power supply circuit 7014 restores its power supply function, the short circuit indicator LED1 turns OFF and the output indicator LED2 turns ON. The cycle is repeated in the event of another short circuit between the supplementary power supply circuit 7014 electrical conductors 7002, 7004.

Figure 118:
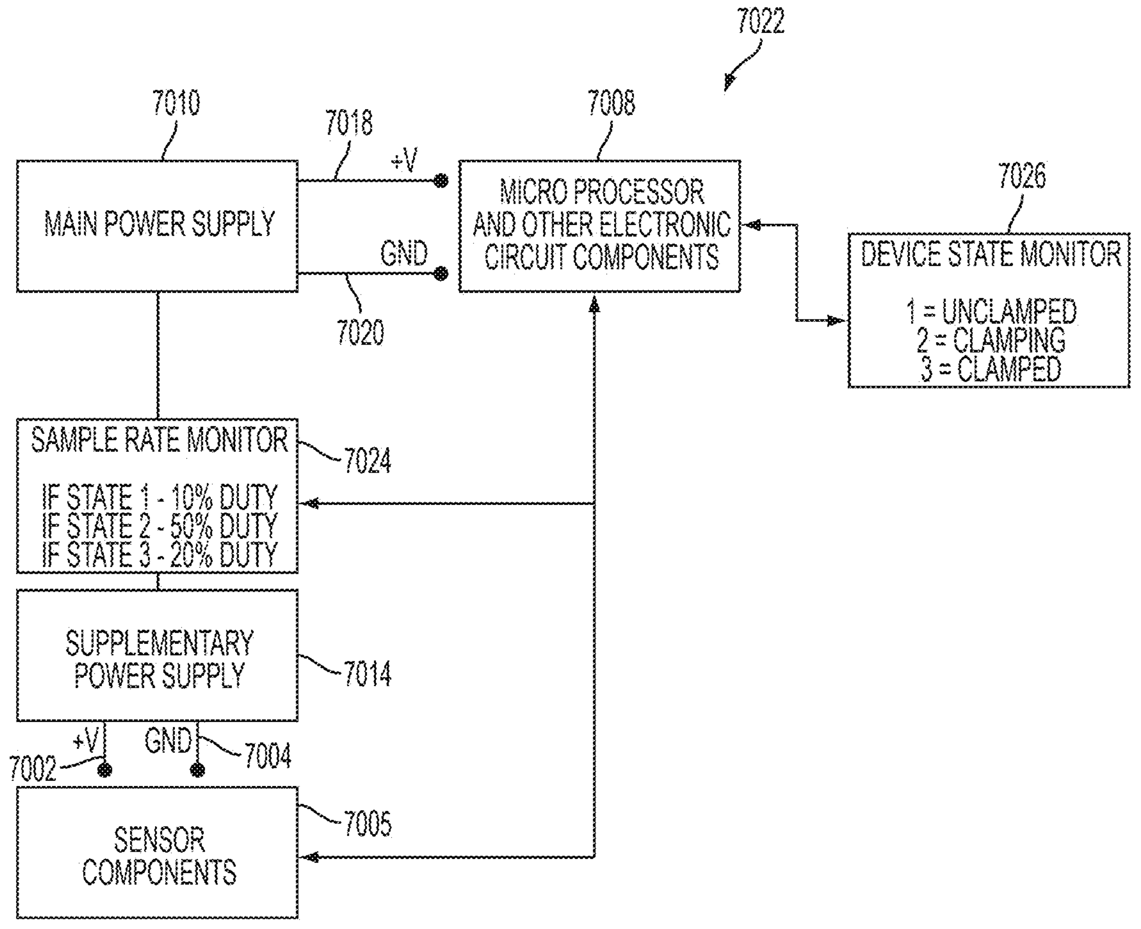

In one embodiment, a sample rate monitor is provided to enable power reduction by limiting sample rates and/or duty cycle of the sensor components when the surgical instrument is in a non-sensing state. FIG. 118 is a block diagram of a surgical instrument electronic subsystem 7022 comprising a sample rate monitor 7024 to provide power reduction by limiting sample rates and/or duty cycle of the sensors and/or electronic components 7005 of the secondary circuit when the surgical instrument is in a non-sensing state, according to one embodiment. As shown in FIG. 118, the surgical instrument electronic subsystem 7022 comprises a processor 7008 coupled to a main power supply circuit 7010. The main power supply circuit 7010 is coupled to a sample rate monitor circuit 7024. A supplementary power supply circuit 7014 is coupled to the sample rate 7024 as powers the sensors and/or electronic components 7005 via the electrical conductors 7002, 7004. The primary circuit comprising the processor 7008 is coupled to a device state monitor 7026. In various embodiments, the surgical instrument electronic subsystem 7022 provides real time feedback about the compressibility and thickness of tissue using the sensors and/or electronic components 7005 as previously described herein. The modular architecture of the surgical instrument enables the configuration of custom modular shafts to employ function job specific technologies. To enable such additional functionality, electronic connection points and components are employed to transfer both power and signal between modular components of the surgical instrument. An increase in the number of sensors and/or electronic components 7005 increases the power consumption of the surgical instrument system 7022 and creates the need for various techniques for reducing power consumption of the surgical instrument system 7022.

In one embodiment, to reduce power consumption, a surgical instrument configured with sensors and/or electronic components 7005 (secondary circuit) comprises a sample rate monitor 7024, which can be implemented as a hardware circuit or software technique to reduce the sample rate and/or duty cycle for the sensors and/or electronic components 7005. The sample rate monitor 7024 operates in conjunction with the device state monitor 7026. The device state monitor 7026 senses the state of various electrical/mechanical subsystems of the surgical instrument. In the embodiment illustrated in FIG. 118, the device state monitor 7026 whether the state of the end effector is in an unclamped (State 1), a clamping (State 2), or a clamped (State 3) state of operation.

The sample rate monitor 7024 sets the sample rate and/or duty cycle for the sensor components 7005 based on the state of the end effector determined by the device state monitor 7026. In one aspect, the sample rate monitor 7024 may set the duty cycle to about 10% when the end effector is in State 1, to about 50% when the end effector is in State 2, or about 20% when the end effector is in State 3. In various other embodiments, the duty cycle and/or sample rate set by the sample rate monitor 7024 may take on ranges of values. For example, in another aspect, the sample rate monitor 7024 may set the duty cycle to a value between about 5% to about 15% when the end effector is in State 1, to a value of about 45% to about 55% when the end effector is in State 2, or to a value of about 15% to about 25% when the end effector is in State 3. In various other embodiments, the duty cycle and/or sample rate set by the sample rate monitor 7024 may take on additional ranges of values. For example, in another aspect, the sample rate monitor 7024 may set the duty cycle to a value between about 1% to about 20% when the end effector is in State 1, to a value of about 20% to about 80% when the end effector is in State 2, or to a value of about 1% to about 50% when the end effector is in State 3. In various other embodiments, the duty cycle and/or sample rate set by the sample rate monitor 7024 may take on additional ranges of values.

In one aspect, the sample rate monitor 7024 may be implemented by creating a supplementary circuit/software coupled to a main circuit/software. When the supplementary circuit/software determines that the surgical instrument system 7022 is in a non-sensing condition, the sample rate monitor 7024 enters the sensors and/or electronic components 7005 into a reduced sampling or duty cycle mode reducing the power load on the main circuit. The main power supply circuit 7010 will still be active to supply power, so that the protected processor 7008 of the primary circuit can monitor the condition. When the surgical instrument system 7022 enters a condition requiring more rigorous sensing activity the sample rate monitor 7024 increases the supplementary circuit sample rate or duty cycle. The circuit could utilize a mixture of integrated circuits, solid state components, microprocessors, and firmware. The reduced sample rate or duty cycle mode circuit also may be monitored to indicate the condition to the end user of the surgical instrument system 7022. The circuit/software might also be monitored to lockout the firing or function of the device in the event the device is in the power saving mode.

In one embodiment, the sample rate monitor 7024 hardware circuit or software technique reduce the sample rate and/or duty cycle for the sensors and/or electronic components 7005 to reduce power consumption of the surgical instrument. The reduced sample rate and/or duty cycle may be monitored to indicate one or more conditions to the end user of the surgical instrument. In the event of a reduced sample rate and/or duty cycle condition in the surgical instrument the protection circuit/software may be configured to lock-out the surgical instrument from being fired or otherwise operated.

Figure 119:
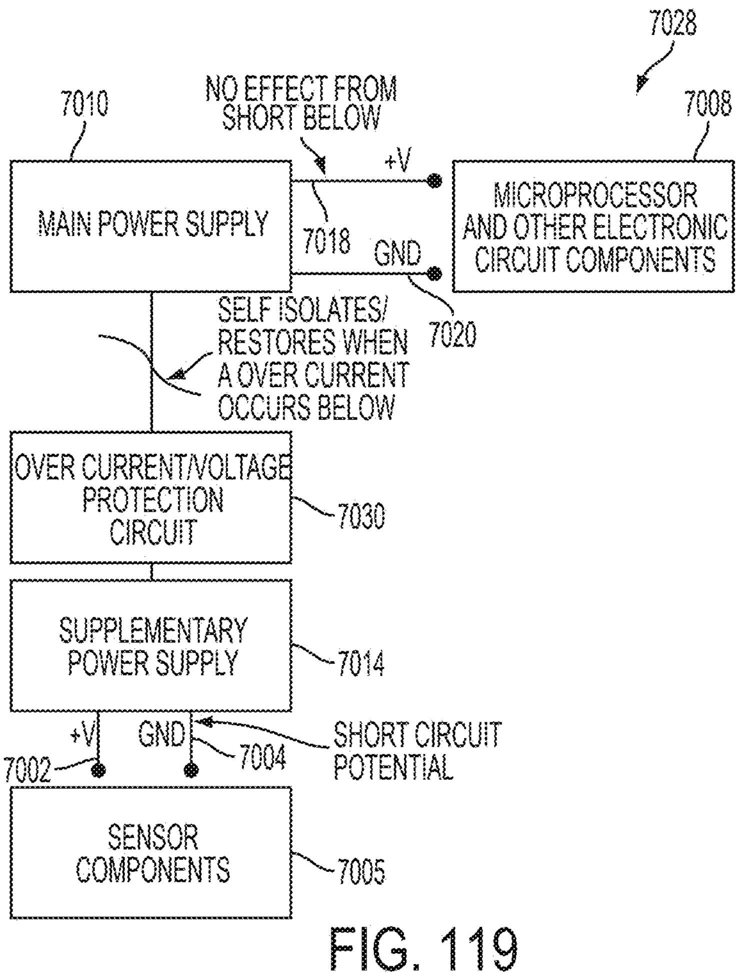

In one embodiment, the present disclosure provides an over current and/or a voltage protection circuit for sensors and/or electronic components of a surgical instrument. FIG. 119 is a block diagram of a surgical instrument electronic subsystem 7028 comprising an over current and/or over voltage protection circuit 7030 for sensors and/or electronic components 7005 of the secondary circuit of a surgical instrument, according to one embodiment. In various embodiments, the surgical instrument electronic subsystem 7028 provides real time feedback about the compressibility and thickness of tissue using the sensors and/or electronic components 7005 of the secondary circuit as previously described herein. The modular architecture of the surgical instrument enables the configuration of custom modular shafts to employ function job specific technologies. To enable the sensors and/or electronic components 7005, additional electronic connection points and components to transfer both power and signal between modular components are added. There is potential for these additional conductors for the sensors and/or electronic components 7005 from the modular pieces to be shorted and or damaged causing large draws of current that could damage fragile processor 7008 circuits or and other electronic components of the primary circuit. In one embodiment, the over current/voltage protection circuit 7030 protects the conductors for the sensors and/or electronic components 7005 on a surgical instrument using a supplementary self-isolating/restoring circuit 7014 coupled to the main power supply circuit 7010. The operation of one embodiment of the supplementary self-isolating/ restoring circuit 7014 is described in connection with FIG. 117 and will not be repeated here for conciseness and clarity of disclosure.

In one embodiment, to reduce electronic damage during large current draws in a sensing surgical instrument, the electronic subsystem 7028 of the surgical instrument comprises an over current/voltage protection circuit 7030 for the conductors for the sensors and/or electronic components 7005. The over current/voltage protection circuit 7030 may be implemented by creating a supplementary circuit coupled to a main power supply circuit 7010 circuit. In the case that the supplementary circuit electrical conductors 7002, 7004 experience higher levels of current than expected, the over current/voltage protection circuit 7030 isolates the current from the main power supply circuit 7010 circuit to prevent damage. The main power supply circuit 7010 circuit will still be active to supply power, so that the protected main processor 7008 can monitor the condition. When a large current draw in the supplementary power supply circuit 7014 is remedied, the supplementary power supply circuit 7014 rejoins the main power supply circuit 7010 and is available to supply power to the sensors and/or electronic components 7005 (e.g., the secondary circuit). The over current/voltage protection circuit 7030 may utilize a mixture of integrated circuits, solid state components, micro-processors, firmware, circuit breaker, fuses, or PTC (positive temperature coefficient) type technologies.

In various embodiments, the over current/voltage protection circuit 7030 also may be monitored to indicate the over current/voltage condition to the end user of the device. The over current/voltage protection circuit 7030 also may be monitored to lockout the firing of the surgical instrument when the over current/voltage condition event is indicated. The over current/voltage protection circuit 7030 also may be monitored to indicate one or more over current/voltage conditions to the end user of the device. In the event of over current/voltage condition in the device the over current/voltage protection circuit 7030 may lock-out the surgical instrument from being fired or lock-out other operations of the surgical instrument.

Figure 120:
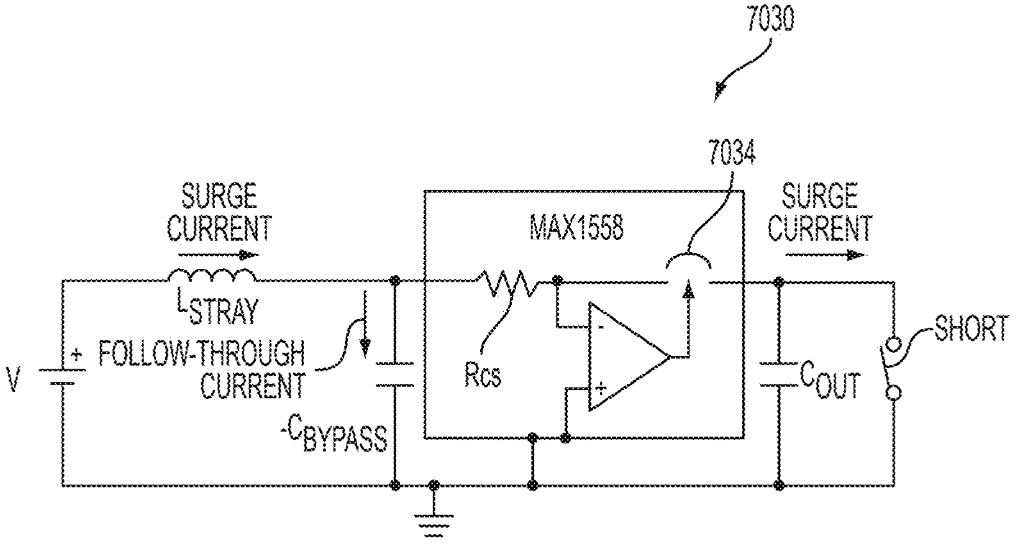

FIG. 120 is an over current/voltage protection circuit 7030 for sensors and electronic components 7005 (FIG. 119) of the secondary circuit of a surgical instrument, according to one embodiment. The over current/voltage protection circuit 7030 provides a current path during a hard short circuit (SHORT) at the output of the over current/voltage protection circuit 7030, and also provides a path for follow-through current through a bypass capacitor $C_{BYPASS}$ driven by stray inductance $L_{STRAY}$.

In one embodiment, the over current/voltage protection circuit 7030 comprises a current limited switch 7032 with autoreset. The current limited switch 7032 comprises a current sense resistor $R_{CS}$ coupled to an amplifier A. When the amplifier A senses a surge current above a predetermined threshold, the amplifier activates a circuit breaker CB to open the current path to interrupt the surge current. In one embodiment, the current limited switch 7032 with autoreset may be implemented with a MAX1558 integrated circuit by Maxim. The current limited switch 7032 with autoreset. Autoreset latches the switch 7032 off if it is shorted for more than 20 ms, saving system power. The shorted output (SHORT) is then tested to determine when the short is removed to automatically restart the channel. Low quiescent supply current (45 μA) and standby current (3 μA) conserve battery power in the surgical instrument. The current limited switch 7032 with autoreset safety features ensure that the surgical instrument is protected. Built-in thermal-overload protection limits power dissipation and junction temperature. Accurate, programmable current-limiting circuits, protects the input supply against both overload and short-circuit conditions. Fault blanking of 20 ms duration enables the circuit to ignore transient faults, such as those caused when hot swapping a capacitive load, preventing false alarms to the host system. In one embodiment, the current limited switch 7032 with autoreset also features a reverse-current protection circuitry to block current flow from the output to the input when the switch 7032 is off.

Figure 121:
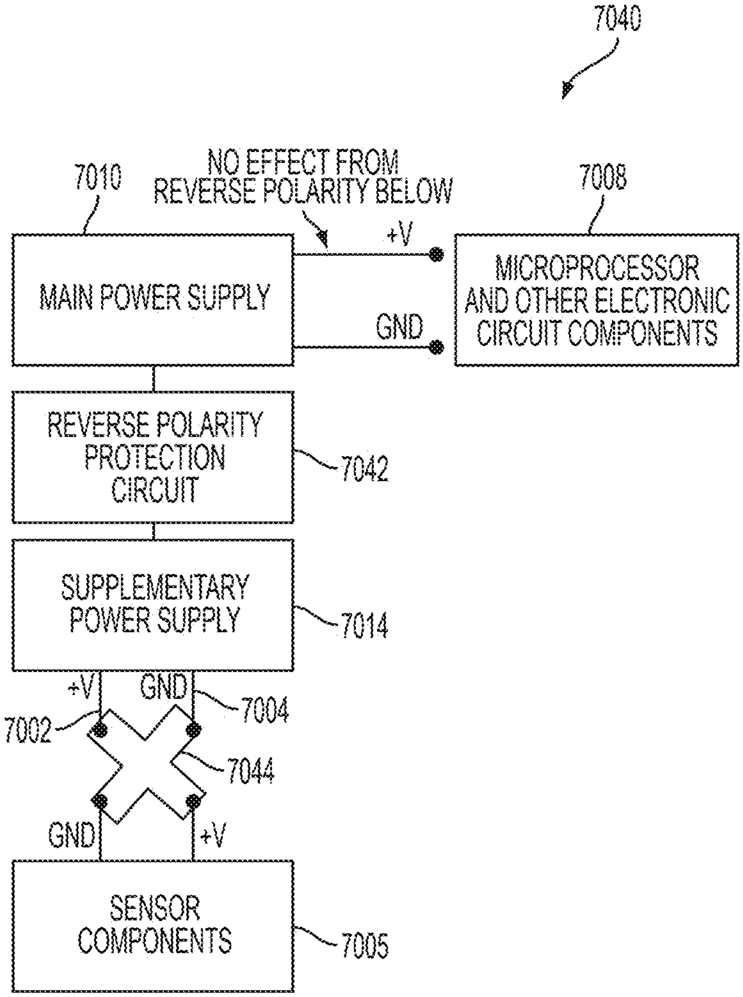

In one embodiment, the present disclosure provides a reverse polarity protection for sensors and/or electronic components in a surgical instrument. FIG. 121 is a block diagram of a surgical instrument electronic subsystem 7040 with a reverse polarity protection circuit 7042 for sensors and/or electronic components 7005 of the secondary circuit according to one embodiment. Reverse polarity protection is provided for exposed leads (electrical conductors 7002, 7004) of a surgical instrument using a supplementary self-isolating/restoring circuit referred to herein as a supplementary power supply circuit 7014 coupled to the main power supply circuit 7010. The reverse polarity protection circuit 7042 may be monitored to indicate one or more reverse polarity conditions to the end user of the device. In the event of reverse polarity applied to the device the protection circuit 7042 might lock-out the device from being fired or other device critical operations.

In various embodiments, the surgical instruments described herein provide real time feedback about the compressibility and thickness of tissue using sensors and/or electronic components 7005. The modular architecture of the surgical instrument enables the configuration of custom modular shafts to employ job specific technologies. To enable sensors and/or electronic components 7005, both power and data signals are transferred between the modular components. During the assembly of modular components there are typically exposed electrical conductors that when connected are used to transfer power and data signals between the connected components. There is potential for these conductors to become powered with reverse polarity.

Accordingly, in one embodiment, the surgical instrument electronic subsystem 7040 is configured to reduce electronic damage during the application of a reverse polarity connection 7044 in a sensing surgical instrument. The surgical instrument electronic subsystem 7040 employs a polarity protection circuit 7042 inline with the exposed electrical conductors 7002, 7004. In one embodiment, the polarity protection circuit 7042 may be implemented by creating a supplementary power supply circuit 7014 coupled to a main power supply circuit 7010. In the case that the supplementary power supply circuit 7014 electrical conductors 7002, 7004 become powered with reverse polarity it isolates the power from the main power supply circuit 7010 to prevent damage. The main power supply circuit 7010 will still be active to supply power, so that the protected processor 7008 of the main circuit can monitor the condition. When the reverse polarity in the supplementary power supply circuit 7014 is remedied, the supplementary power supply circuit 7014 rejoins the main power supply circuit 7010 and is available to supply power to the secondary circuit. The reverse polarity protection circuit 7042 also may be monitored to indicate that the reverse polarity condition to the end user of the device. The reverse polarity protection circuit 7042 also may be monitored to lockout the firing of the device if a reverse polarity event is indicated.

Figure 122:
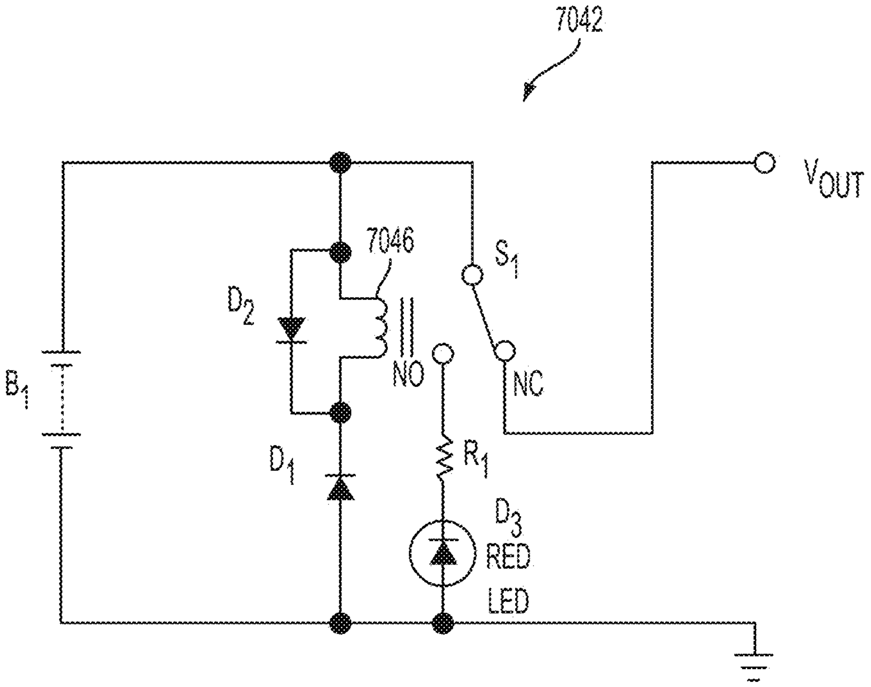

FIG. 122 is a reverse polarity protection circuit 7042 for sensors and/or electronic components 7005 of the secondary circuit of a surgical instrument according to one embodiment. During normal operation, the relay switch S1 comprises output contacts in the normally closed (NC) position and the battery voltage $B_1$ of the main power supply circuit 7010 (FIG. 121) is applied to $V_{OUT}$ coupled to the secondary circuit. The diode $D_1$ blocks current from flowing through the coil 7046 (inductor) of the relay switch $S_1$. When the polarity of the battery $B_1$ is reversed, diode $D_1$ conducts and current flows through the coil 7046 of the relay switch $S_1$ energizing the relay switch S1 to place the output contacts in the normally open (NO) position and thus disconnecting the reverse voltage from $V_{OUT}$ coupled to the secondary circuit. Once the switch $S_1$ is in the NO position, current from the positive terminal of the battery $B_1$ flows through LED $D_3$ and resistor $R_1$ to prevent the battery $B_1$ from shorting out. Diode $D_2$ is a clamping diode to protect from spikes generated by the coil 7046 during switching.

Figure 123:
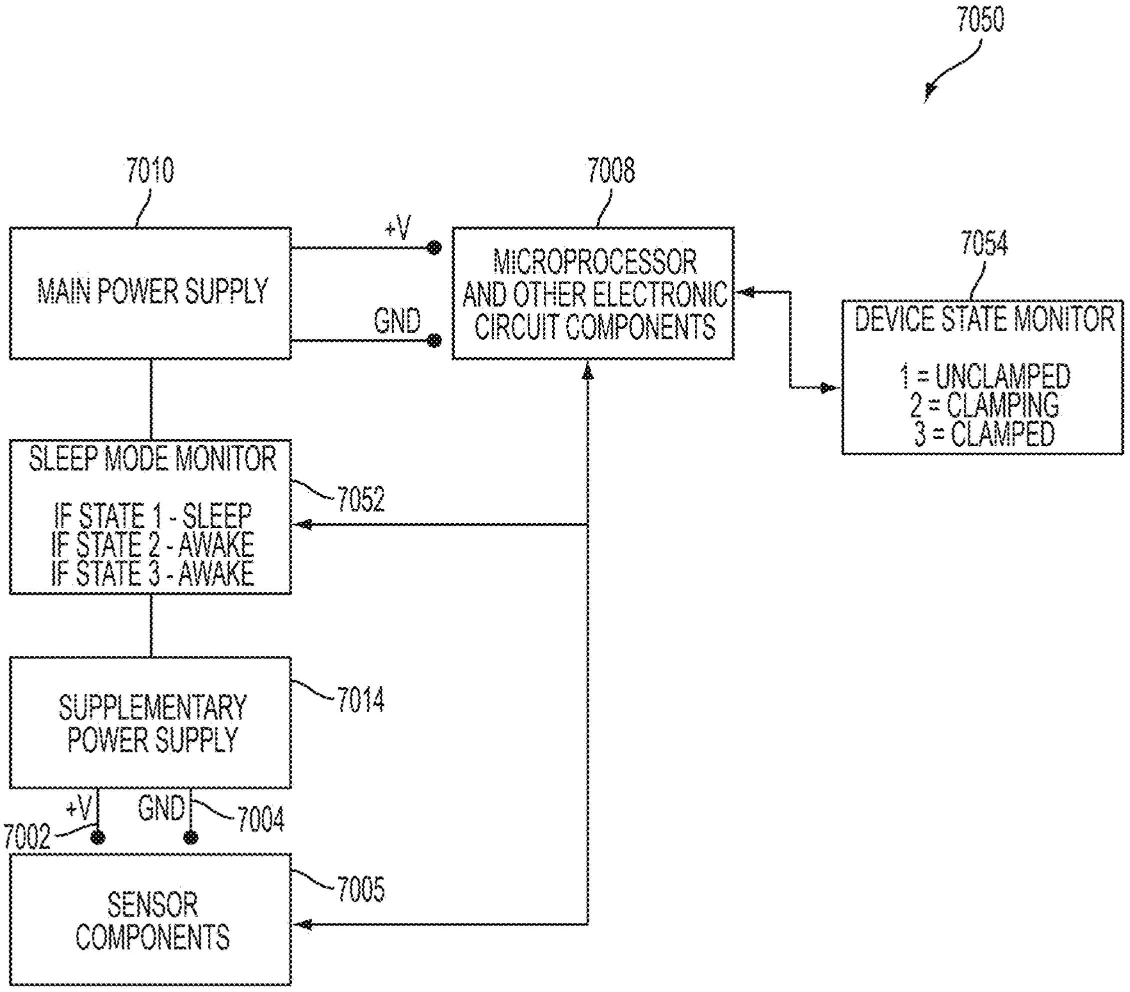

In one embodiment, the surgical instruments described herein provide a power reduction technique utilizing a sleep mode for sensors on a modular device. FIG. 123 is a block diagram of a surgical instrument electronic subsystem 7050 with power reduction utilizing a sleep mode monitor 7052 for sensors and/or electronic components 7005 according to one embodiment. In one embodiment, the sleep mode monitor 7052 for the sensors and/or electronic components 7005 of the secondary circuit may be implemented as a circuit and/or as a software routine to reduce the power consumption of a surgical instrument. The sleep mode monitor 7052 protection circuit may be monitored to indicate one or more sleep mode conditions to the end user of the device. In the event of a sleep mode condition in the device, the sleep mode monitor 7052 protection circuit/software may be configured to lock-out the device from being fired or operated by the user.

In various embodiments, the surgical instruments described herein provide real time feedback about the compressibility and thickness of tissue using electronic sensors 7005. The modular architecture enables the surgical instrument to be configured with custom modular shafts to employ job specific technologies. To enable sensors and/or electronic components 7005, additional electronic connection points and components may be employed to transfer both power and data signal between the modular components. As the number of sensors and/or electronic components 7005 increases, the power consumption of the surgical instrument increases, thus creating a need for techniques to reduce the power consumption of the surgical instrument.

In one embodiment, the electronic subsystem 7050 comprises a sleep mode monitor 7052 circuit and/or software for the sensors 7005 to reduce power consumption of the sensing surgical instrument. The sleep mode monitor 7052 may be implemented by creating a supplementary power supply circuit 7014 coupled to a main power supply circuit 7010. A device state monitor 7054 monitors whether the surgical instrument is in a 1=Unclamped State, 2=Clamping State, or a 3=Clamped State. When the sleep mode monitor 7052 software determines that the surgical instrument is in a non-sensing (1=Unclamped State) condition the sleep mode monitor 7052 enters the sensors and/or electronic components 7005 of the secondary circuit into a sleep mode to reduce the power load on the main power supply circuit 7010. The main power supply circuit 7010 will still be active to supply power, so that the protected processor 7008 of the primary circuit can monitor the condition. When the surgical instrument enters a condition requiring sensor activity the supplementary power supply circuit 7014 is awakened and rejoins the main power supply circuit 7010. The sleep mode monitor 7051 circuit can utilize a mixture of integrated circuits, solid state components, micro-processors, and/or firmware. The sleep mode monitor 7051 circuit also may be monitored to indicate the condition to the end user of the device. The sleep mode monitor 7051 circuit may also be monitored to lockout the firing or function of the device in the event the device is in a sleep mode.

Figure 124:
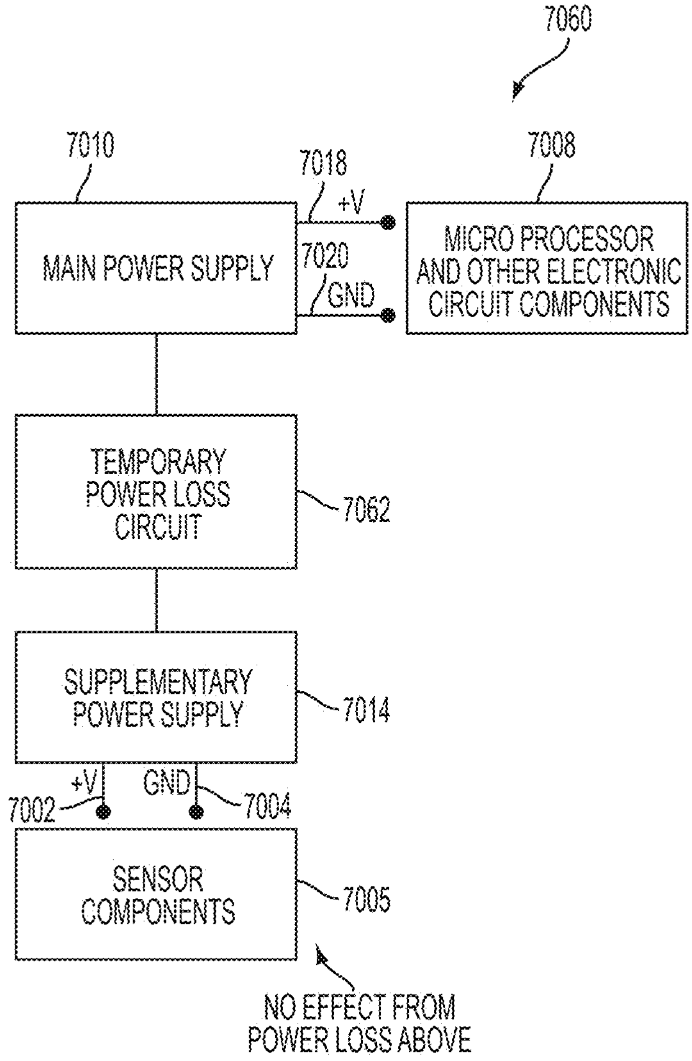

In one embodiment the present disclosure provides protection against intermittent power loss for sensors and/or electronic components in modular surgical instruments. FIG. 124 is a block diagram of a surgical instrument electronic subsystem 7060 comprising a temporary power loss circuit 7062 to provide protection against intermittent power loss for sensors and/or electronic components 7005 of the secondary circuit in modular surgical instruments.

In various embodiments, the surgical instruments described herein provide real time feedback about the compressibility and thickness of tissue using sensors and/or electronic components 7005. The modular architecture enables the surgical instrument to be configured with custom modular shafts to employ job specific technologies. To enable sensors and/or electronic components 7005 additional electronic connection points and components may be employed to transfer both power and signal between the modular components. As the number of electrical connection points increase, the potential for sensors and/or electronic components 7005 to experience short term intermittent power loss increases.

In accordance with one embodiment, the temporary power loss circuit 7062 is configured to reduce device operation error from short term intermittent power loss in a sensing surgical instrument. The temporary power loss circuit 7062 has the capacity to deliver continuous power for short periods of time in the event the power from the main power supply circuit 7010 is interrupted. The temporary power loss circuit 7062 may comprises capacitive elements, batteries, and/or other electronic elements capable of leveling, detecting, or storing power.

As shown in FIG. 124, the temporary power loss circuit 7062 may be implemented by creating a supplementary circuit/software coupled to a main circuit/software. In the case that the supplementary circuit/software experiences a sudden power loss from the main power source, the sensors and/or electronic components 7005 powered by the supplementary power supply circuit 7014 would be unaffected for short period times. During the power loss the supplementary power supply circuit 7014 may be powered by capacitive elements, batteries, and/or other electronic elements that are capable of leveling or storing power. The temporary power loss circuit 7062 implemented either in hardware or software also may be monitored to lockout the firing or function of the surgical instrument in the event the device is in the power saving mode. In the event of an intermittent power loss condition in the surgical instrument the temporary power loss circuit 7062 implemented either in hardware or software may lock-out the surgical instrument from being fired or operated.

Figure 125:
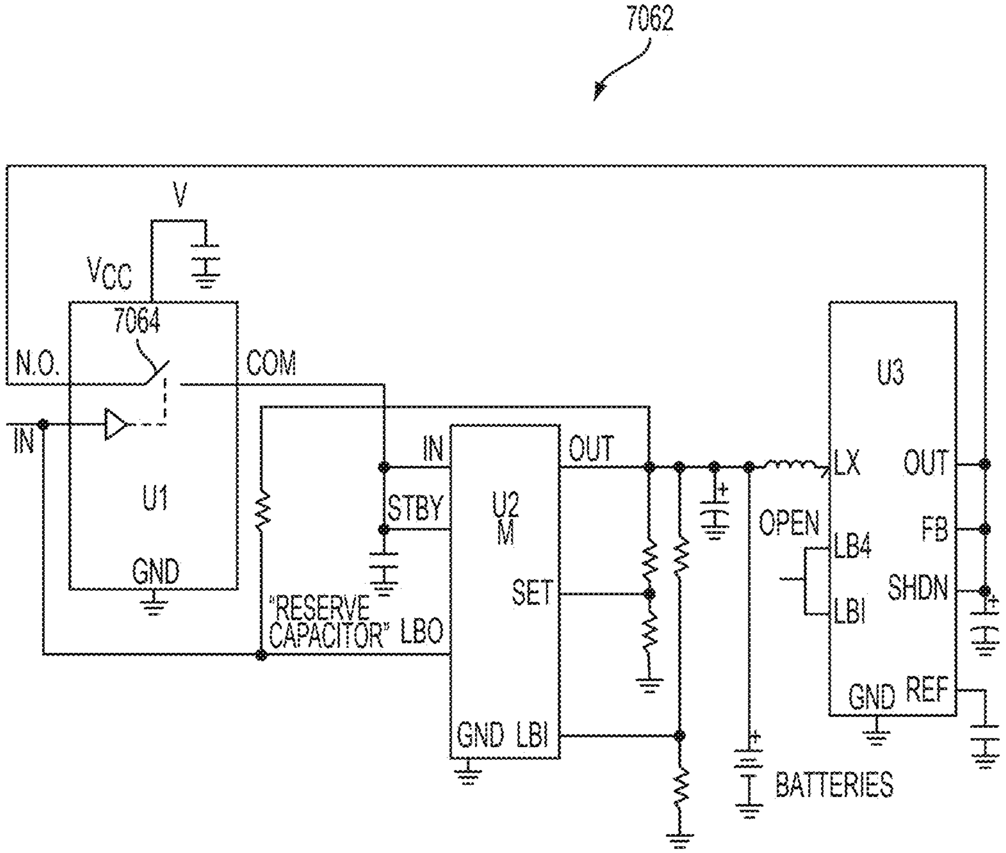

FIG. 125 illustrates one embodiment of a temporary power loss circuit 7062 implemented as a hardware circuit. The temporary power loss circuit 7062 hardware circuit is configured to reduce surgical instrument operation error from short term intermittent power loss. The temporary power loss circuit 7062 has the capacity to deliver continuous power for short periods of time in the event the power from the main power supply circuit 7010 (FIG. 124) is interrupted. The temporary power loss circuit 7062 employs capacitive elements, batteries, and/or other electronic elements that are capable of leveling, detecting, or storing power. The temporary power loss circuit 7062 may be monitored to indicate one or more conditions to the end user of the surgical instrument. In the event of an intermittent power loss condition in the surgical instrument, the temporary power loss circuit 7062 protection circuit/software might lock-out the device from being fired or operated.

In the illustrated embodiment, the temporary power loss circuit 7062 comprises an analog switch integrated circuit U1. In one embodiment, the analog switch integrated circuit U1 is a single-pole/single-throw (SPST), low-voltage, single-supply, CMOS analog switch such as the MAX4501 provided by Maxim. In one embodiment, the analog switch integrated circuit U1 is normally open (NO). In other embodiments, the analog switch integrated circuit U1 may be normally closed (NC). The input IN activates the NO analog switch 7064 to connect the output of a step-up DC-DC converter U3 to the input of a linear regulator U2 via a standby "RESERVE CAPACITOR." The output of the linear regulator U2 is coupled to the input of the DC-DC converter U3. The linear regulator U2 maximizes battery life by combining ultra-low supply currents and low dropout voltages. In one embodiment, the linear regulator U2 is a MAX882 integrated circuit provided by Maxim.

The batteries are also coupled to the input of the step-up DC-DC converter U3. The step-up DC-DC converter U3 may be a compact, high-efficiency, step-up DC-DC converter with a built-in synchronous rectifier to improve efficiency and reduce size and cost by eliminating the need for an external Schottky diode. In one embodiment, the step-up DC-DC converter U3 is a MAX1674 integrated circuit by Maxim.

Smart Cartridge Technology

FIGS. 126A and 126B illustrate one embodiment of an end effector 10000 comprising a magnet 10008 and a Hall effect sensor 10010 in communication with a processor 10012. The end effector 10000 is similar to the end effector 300 described above. The end effector comprises a first jaw member, or anvil 10002, pivotally coupled to a second jaw member, or elongated channel 10004. The elongated channel 10004 is configured to operably support a staple cartridge 10006 therein. The staple cartridge 10006 is similar to the staple cartridge 304 described above. The anvil 10008 comprises a magnet 10008. The staple cartridge comprises a Hall effect sensor 10010 and a processor 10012. The Hall effect sensor 10010 is operable to communicate with the processor 10012 through a conductive coupling 10014. The Hall effect sensor 10010 is positioned within the staple cartridge 10006 to operatively couple with the magnet 10008 when the anvil 10002 is in a closed position. The Hall effect sensor 10010 can be configured to detect changes in the magnetic field surrounding the Hall effect sensor 10010 caused by the movement of or location of magnet 10008.

FIG. 127 illustrates one embodiment of the operable dimensions that relate to the operation of the Hall effect sensor 10010. A first dimension 10020 is between the bottom of the center of the magnet 10008 and the top of the staple cartridge 10006. The first dimension 10020 can vary with the size and shape of the staple cartridge 10006, such as for instance between 0.0466 inches, 0.0325 inches, 0.0154 inches, or 0.0154 inches, or any reasonable value. A second dimension 10022 is between the bottom of the center of the magnet 10008 and the top of the Hall effect sensor 10010. The second dimension can also vary with the size and shape of the staple cartridge 10006, such as for instance 0.0666 inches, 0.0525 inches, 0.0354 inches, 0.0347 inches, or any reasonable value. A third dimension 10024 is between the top of the processor 10012 and the lead-in surface 10028 of the staple cartridge 10006. The third dimension can also vary with the size and the shape of the staple cartridge, such as for instance 0.0444 inches, 0.0440 inches, 0.0398 inches, 0.0356 inches, or any reasonable value. An angle 10026 is the angle between the anvil 10002 and the top of the staple cartridge 10006. The angle 10026 also can vary with the size and shape of the staple cartridge 10006, such as for instance 0.91 degrees, 0.68 degrees, 0.62 degrees, 0.15 degrees, or any reasonable value.

FIGS. 128A through 128D further illustrate dimensions that can vary with the size and shape of a staple cartridge 10006 and effect the operation of the Hall effect sensor 10010. FIG. 128A illustrates an external side view of an embodiment of a staple cartridge 10006. The staple cartridge 10006 comprises a push-off lug 10036. When the staple cartridge 10006 is operatively coupled with the end effector 10000 as illustrated in FIG. 126A, the push-off lug 10036 rests on the side of the elongated channel 10004.

FIG. 128B illustrates various dimensions possible between the lower surface 10038 of the push-off lug 10036 and the top of the Hall effect sensor 10010 (not pictured). A first dimension 10030*a* is possible with black, blue, green or gold staple cartridges 10006, where the color of the body of the staple cartridge 10006 may be used to identify various aspects of the staple cartridge 10006. The first dimension 10030*a* can be, for instance, 0.005 inches below the lower surface 10038 of the push-off lug 10036. A second dimension 10030*b* is possible with gray staple cartridges 10006, and can be 0.060 inches above the lower surface 10038 of the push-off lug 10036. A third dimension 10030*c* is possible with white staple cartridges 10006, and can be 0.030 inches above the lower-surface 10038 of the push-off lug 10036.

FIG. 128C illustrates an external side view of an embodiment of a staple cartridge 10006. The staple cartridge 10006 comprises a push-off lug 10036 with a lower surface 10038. The staple cartridge 10006 further comprises an upper surface 10046 immediately above the Hall effect sensor 10010 (not pictured). FIG. 128D illustrates various dimensions possible between the lower surface 10038 of the push-off lug 10038 and the upper surface 10046 of the staple cartridge 10006 above the Hall effect sensor 10010. A first dimension 10040 is possible for black, blue, green or gold staple cartridges 10006, and can be, for instance, 0.015 inches above the lower surface 10038 of the push-off lug 10036. A second dimension 10042 is possible for gray staple cartridges 10006, and can be, for instance, 0.080 inches. A third dimension 10044 is possible for white staple cartridges 10006, and can be, for instance, 0.050.

It is understood that the references to the color of the body of a staple cartridge 10006 is for convenience and by way of example only. It is understood that other staple cartridge 10006 body colors are possible. It is also understood that the dimensions given for FIGS. 128A through 128D are also example and non-limiting.

FIG. 129A illustrates various embodiments of magnets 10058*a*-10058*d* of various sizes, according to how each magnet 10058*a*-10058*d* may fit in the distal end of an anvil, such as anvil 10002 illustrated in FIGS. 126A-126B. A magnet 10058*a*-10058*d* can be positioned in the distal tip of the anvil 10002 at a given distance 10050 from the anvil's pin or pivot point 10052. It is understood that this distance 10050 may vary with the construction of the end effector and staple cartridge and/or the desired position of the magnet. FIG. 129B further illustrates a front-end cross-sectional view 10054 of the anvil 10002 and the central axis point of the anvil 10002. FIG. 129A also illustrates an example

10056 of how various embodiments of magnets 10058*a*-10058*d* may fit within the same anvil 10002.

FIGS. 130A-130E illustrate one embodiment of an end effector 10100 that comprises, by way of example, a magnet 10058*a* as illustrated in FIGS. 129A-129B. FIG. 130A illustrates a front-end cross-sectional view of the end effector 10100. The end effector 10100 is similar to the end effector 300 described above. The end effector 10100 comprises a first jaw member or anvil 10102, a second jaw member or elongated channel 10104, and a staple cartridge 10106 operatively coupled to the elongated channel 10104. The anvil 10102 further comprises the magnet 10058*a*. The staple cartridge 10106 further comprises a Hall effect sensor 10110. The anvil 10102 is here illustrated in a closed position. FIG. 130B illustrates a front-end cutaway view of the anvil 10102 and the magnet 10058*a*, in situ. FIG. 130C illustrates a perspective cutaway view of the anvil 10102 and the magnet 10058*a*, in an optional location. FIG. 130D illustrates a side cutaway view of the anvil 10102 and the magnet 10058*a*, in an optional location. FIG. 130E illustrates a top cutaway view of the anvil 10102 and the magnet 10058*a*, in an optional location.

FIGS. 131A-131E illustrate one embodiment of an end effector 10150 that comprises, by way of example, a magnet 10058*d* as illustrated in FIGS. 129A-129B. FIG. 131A illustrates a front-end cross-sectional view of the end effector 10150. The end effector 10150 comprises an anvil 10152, an elongated channel 10154, and a staple cartridge 10156. The anvil 10152 further comprises magnet 10058*d*. The staple cartridge 10156 further comprises a Hall effect sensor 10160. FIG. 131B illustrates a front-end cutaway view of the anvil 10150 and the magnet 10058*d*, in situ. FIG. 131C illustrates a perspective cutaway view of the anvil 10152 and the magnet 10058*d* in an optional location. FIG. 131D illustrates a side cutaway view of the anvil 10152 and the magnet 10058*d* in an optional location. FIG. 131E illustrates a top cutaway view of the anvil 10152 and magnet 10058*d* in an optional location.

FIG. 132 illustrates an end effector 300 as described above, and illustrates contact points between the anvil 306 and either the staple cartridge 304 and/or the elongated channel 302. Contact points between the anvil 306 and the staple cartridge 304 and/or the elongated channel 302 can be used to determine the position of the anvil 306 and/or provide a point for an electrical contact between the anvil 306 and the staple cartridge 304, and/or the anvil 306 and the elongated channel 302. Distal contact point 10170 can provide a contact point between the anvil 306 and the staple cartridge 304. Proximal contact point 10172 can provide a contact point between the anvil 306 and the elongated channel 302.

FIGS. 133A and 133B illustrate one embodiment of an end effector 10200 that is operable to use conductive surfaces at the distal contact point to create an electrical connection. The end effector 10200 is similar to the end effector 300 described above. The end effector comprises an anvil 10202, an elongated channel 10204, and a staple cartridge 10206. The anvil 10202 further comprises a magnet 10208 and an inside surface 10210, which further comprises a number of staple-forming indents 10212. In some embodiments, the inside surface 10210 of the anvil 10202 further comprises a first conductive surface 10214 surrounding the staple-forming indents 10212. The first conductive surface 10214 can come into contact with second conductive surfaces 10222 on the staple cartridge 10206, as illustrated in FIG. 107B. FIG. 107B illustrates a close-up view of the cartridge body 10216 of the staple cartridge 10206. The cartridge body 10216 comprises a number of staple cavities 10218 designed to hold staples (not pictured). In some embodiments the staple cavities 10218 further comprise staple cavity extensions 10220 that protrude above the surface of the cartridge body 10216. The staple cavity extensions 10220 can be coated with the second conductive surfaces 10222. Because the staple cavity extensions 10222 protrude above the surface of the cartridge body 10216, the second conductive surfaces 10222 will come into contact with the first conductive surfaces 10214 when the anvil 10202 is in a closed position. In this manner the anvil 10202 can form an electrical contact with the staple cartridge 10206.

FIGS. 134A-134C illustrate one embodiment of an end effector 10250 that is operable to use conductive surfaces to form an electrical connection. FIG. 134A illustrates the end effector 10250 comprises an anvil 10252, an elongated channel 10254, and a staple cartridge 10256. The anvil further comprises a magnet 10258 and an inside surface 10260, which further comprises staple-forming indents 10262. In some embodiments the inside surface 10260 of the anvil 10250 can further comprise first conductive surfaces 10264, located, by way of example, distally from the staple-forming indents 10262, as illustrated in FIG. 134B. The first conductive surfaces 10264 are located such that they can come into contact with a second conductive surface 10272 located on the staple cartridge 10256, as illustrated in FIG. 134C. FIG. 134C illustrates the staple cartridge 10256, which comprises a cartridge body 10266. The cartridge body 10266 further comprises an upper surface 10270, which in some embodiments can be coated with the second conductive surface 10272. The first conductive surfaces 10264 are located on the inside surface 10260 of the anvil 10252 such that they come into contact with the second conductive surface 10272 when the anvil 10252 is in a closed position. In this manner the anvil 10250 can form an electrical contact with the staple cartridge 10256.

FIGS. 135A and 135B illustrate one embodiment of an end effector 10300 that is operable to use conductive surfaces to form an electrical connection. The end effector 10300 comprises an anvil 10302, an elongated channel 10304, and a staple cartridge 10306. The anvil 10302 further comprises a magnet 10308 and an inside surface 10310, which further comprises a number of staple-forming indents 10312. In some embodiments the inside surface 10310 further comprises a first conductive surface 10314 surrounding some of the staple-forming indents 10312. The first conductive surface is located such that it can come into contact with second conductive surfaces 10322 as illustrated in FIG. 109B. FIG. 109B illustrates a close-up view of the staple cartridge 10306. The staple cartridge 10306 comprises a cartridge body 10316 which further comprises an upper surface 10320. In some embodiments, the leading edge of the upper surface 10320 can be coated with second conductive surfaces 10322. The first conductive surface 10312 is positioned such that it will come into contact with the second conductive surfaces 10322 when the anvil 10302 is in a closed position. In this manner the anvil 10302 can form an electrical connection with the staple cartridge 10306.

FIGS. 136A and 136B illustrate one embodiment of an end effector 10350 that is operable to use conductive surfaces to form an electrical connection. FIG. 136A illustrates an end effector 10350 comprising an anvil 10352, an elongated channel 10354, and a staple cartridge 10356. The anvil 10352 further comprises a magnet 10358 and an inside surface 10360, which further comprises a number of staple-forming indents 10362. In some embodiments the inside surface 10360 further comprises a first conductive surface 10364 surrounding some of the staple-forming indents 10362. The first conductive surface is located such that it can come into contact with second conductive surfaces 10372 as illustrated in FIG. 136B. FIG. 136B illustrates a close-up view of the staple cartridge 10356. The staple cartridge 10356 comprises a cartridge body 10366 which further comprises an upper surface 10370. In some embodiments, the leading edge of the upper surface 10327 can be coated with second conductive surfaces 10372. The first conductive surface 10362 is positioned such that it will come into contact with the second conductive surfaces 10372 when the anvil 10352 is in a closed position. In this manner the anvil 10352 can form an electrical connection with the staple cartridge 10356.

FIGS. 137A-137C illustrate one embodiment of an end effector 10400 that is operable to use the proximal contact point 10408 to form an electrical connection. FIG. 137A illustrate the end effector 10400, which comprises an anvil 10402, an elongated channel 10404, and a staple cartridge 10406. The anvil 10402 further comprises pins 10410 that extend from the anvil 10402 and allow the anvil to pivot between an open and a closed position relative to the elongated channel 10404 and the staple cartridge 10406. FIG. 137B is a close-up view of a pin 10410 as it rests within an aperture 10418 defined in the elongated channel 10404 for that purpose. In some embodiments, pin 10410 further comprises a first conductive surface 10412 located on the exterior of the pin 10410. In some embodiments the aperture 10418 further comprises a second conductive surface 10141 on its outside surface. As the anvil 10402 moves between a closed and an open position, the first conductive surface 10412 on the pin 10410 rotates and comes into contact with the second conductive surface 10414 on the surface of the aperture 10418, thus forming an electrical contact. FIG. 137C illustrates an alternate embodiment, with an alternate location for a second conductive surface 10416 on the surface of the aperture 10418.

FIG. 138 illustrates one embodiment of an end effector 10450 with a distal sensor plug 10466. End effector 10450 comprises a first jaw member or anvil 10452, a second jaw member or elongated channel 10454, and a staple cartridge 10466. The staple cartridge 10466 further comprises the distal sensor plug 10466, located at the distal end of the staple cartridge 10466.

FIG. 139A illustrates the end effector 10450 with the anvil 10452 in an open position. FIG. 139B illustrates a cross-sectional view of the end effector 10450 with the anvil 10452 in an open position. As illustrated, the anvil 10452 may further comprise a magnet 10458, and the staple cartridge 10456 may further comprise the distal sensor plug 10466 and a wedge sled, 10468, which is similar to the wedge sled 190 described above. FIG. 139C illustrates the end effector 10450 with the anvil 10452 in a closed position. FIG. 139D illustrates a cross sectional view of the end effector 10450 with the anvil 10452 in a closed position. As illustrated, the anvil 10452 may further comprise a magnet 10458, and the staple cartridge 10456 may further comprise the distal sensor plug 10466 and a wedge sled 10468. As illustrated, when the anvil 10452 is in a closed position relative to the staple cartridge 10456, the magnet 10458 is in proximity to the distal sensor plug 10466.

FIG. 140 provides a close-up view of the cross section of the distal end of the end effector 10450. As illustrated, the distal sensor plug 10466 may further comprise a Hall effect sensor 10460 in communication with a processor 10462. The Hall effect sensor 10460 can be operatively connected to a flex board 10464. The processor 10462 can also be operatively connect to the flex board 10464, such that the flex board 10464 provides a communication path between the Hall effect sensor 10460 and the processor 10462. The anvil 10452 is illustrated in a closed position, and as illustrated, when the anvil 10452 is in a closed position the magnet 10458 is in proximity to the Hall effect sensor 10460.

FIG. 141 illustrates a close-up top view of the staple cartridge 10456 that comprises a distal sensor plug 10466. Staple cartridge 10456 further comprises a cartridge body 10470. The cartridge body 10470 further comprises electrical traces 10472. Electrical traces 10472 provide power to the distal sensor plug 10466, and are connected to a power source at the proximal end of the staple cartridge 10456 as described in further detail below. Electrical traces 10472 can be placed in the cartridge body 10470 by various methods, such as for instance laser etching.

FIGS. 142A and 142B illustrate one embodiment of a staple cartridge 10506 with a distal sensor plug 10516. FIG. 142A is a perspective view of the underside of the staple cartridge 10506. The staple cartridge 10506 comprises a cartridge body 10520 and a cartridge tray 10522. The staple cartridge 10506 further comprises a distal sensor cover 10524 that encloses the lower area of the distal end of the staple cartridge 10506. The cartridge tray 10522 further comprises an electrical contact 10526. FIG. 142B illustrates a cross sectional view of the distal end of the staple cartridge 10506. As illustrated, the staple cartridge 10506 can further comprise a distal sensor plug 10516 located within the cartridge body 10520. The distal sensor plug 10516 further comprises a Hall effect sensor 10510 and a processor 10512, both operatively connected to a flex board 10514. The distal sensor plug 10516 can be connected to the electrical contact 10526, and can thus use conductivity in the cartridge tray 10522 as a source of power. FIG. 142B further illustrates the distal sensor cover 10524, which encloses the distal sensor plug 10516 within the cartridge body 10520.

FIGS. 143A-143C illustrate one embodiment of a staple cartridge 10606 that comprises a flex cable 10630 connected to a Hall effect sensor 10610 and processor 10612. The staple cartridge 10606 is similar to the staple cartridge 10606 is similar to the staple cartridge 306 described above. FIG. 143A is an exploded view of the staple cartridge 10606. The staple cartridge comprises 10606 a cartridge body 10620, a wedge sled 10618, a cartridge tray 10622, and a flex cable 10630. The flex cable 10630 further comprises electrical contacts 10632 at the proximal end of the staple cartridge 10606, placed to make an electrical connection when the staple cartridge 10606 is operatively coupled with an end effector, such as end effector 10800 described below. The electrical contacts 10632 are integrated with cable traces 10634, which extend along some of the length of the staple cartridge 10606. The cable traces 10634 connect 10636 near the distal end of the staple cartridge 10606 and this connection 10636 joins with a conductive coupling 10614. A Hall effect sensor 10610 and a processor 10612 are operatively coupled to the conductive coupling 10614 such that the Hall effect sensor 10610 and the processor 10612 are able to communicate.

FIG. 143B illustrates the assembly of the staple cartridge 10606 and the flex cable 10630 in greater detail. As illustrated, the cartridge tray 10622 encloses the underside of the cartridge body 10620, thereby enclosing the wedge sledge 10618. The flex cable 10630 can be located on the exterior of the cartridge tray 10622, with the conductive coupling 10614 positioned within the distal end of the cartridge body 10620 and the electrical contacts 10632 located on the outside near the proximal end. The flex cable 10630 can be placed on the exterior of the cartridge tray 10622 by any appropriate means, such as for instance bonding or laser etching.

FIG. 143C illustrates a cross sectional view of the staple cartridge 10606 to illustrate the placement of the Hall effect sensor 10610, processor 10612, and conductive coupling 10614 within the distal end of the staple cartridge, in accordance with the present embodiment.

FIG. 144A-144F illustrate one embodiment of a staple cartridge 10656 that comprises a flex cable 10680 connected to a Hall effect sensor 10660 and a processor 10662. FIG. 144A is an exploded view of the staple cartridge 10656. The staple cartridge comprises a cartridge body 10670, a wedge sled 10668, a cartridge tray 10672, and a flex cable 10680. The flex cable 10680 further comprises cable traces 10684 that extend along some of the length of the staple cartridge 10656. Each of the cable traces 10684 have an angle 10686 near their distal end, and connect therefrom to a conductive coupling 10664. A Hall effect sensor 10660 and a processor 10662 are operatively coupled to the conductive coupling 10664 such that the Hall effect sensor 10660 and the processor 10662 are able to communicate.

FIG. 144B illustrates the assembly of the staple cartridge 10656. The cartridge tray 10672 encloses the underside of the cartridge body 10670, thereby enclosing the wedge sled 10668. The flex cable 10680 is located between the cartridge body 10670 and the cartridge tray 10672. As such, in the illustration only the angle 10686 and the conductive coupling 10664 are visible.

FIG. 144C illustrates the underside of an assembled staple cartridge 10656, and also illustrates the flex cable 10680 in greater detail. In an assembled staple cartridge 10656, the conductive coupling 10664 is located in the distal end of the staple cartridge 10656. Because the flex cable 10680 can be located between the cartridge body 10670 and the cartridge tray 10672, only the angle 10686 ends of the cable traces 10684 would be visible from the underside of the staple cartridge 10656, as well as the conductive coupling 10664.

FIG. 144D illustrates a cross sectional view of the staple cartridge 10656 to illustrate the placement of the Hall effect sensor 10660, processor 10662, and conductive coupling 10664. Also illustrated is an angle 10686 of a cable trace 10684, to illustrate where the angle 10686 could be placed. The cable traces 10684 are not pictured.

FIG. 144E illustrates the underside of the staple cartridge 10656 without the cartridge tray 10672 and including the wedge sled 10668, in its most distal position. The staple cartridge 10656 is illustrated without the cartridge tray 10672 in order to illustrate a possible placement for the cable traces 10684, which are otherwise obscured by the cartridge tray 10672. As illustrated, the cable traces 10684 can be placed inside the cartridge body 10670. The angle 10686 optionally allows the cable traces 10684 to occupy a narrower space in the distal end of the cartridge body 10670.

FIG. 144F also illustrates the staple cartridge 10656 without the cartridge tray 10672 in order to illustrate a possible placement for the cable traces 10684. As illustrated the cable traces 10684 can be placed along the length of the exterior of cartridge body 10670. Furthermore, the cable traces 10684 can form an angle 10686 to enter the interior of the distal end of the cartridge body 10670.

FIGS. 145A and 145B illustrates one embodiment of a staple cartridge 10706 that comprises a flex cable 10730, a Hall effect sensor 10710, and a processor 10712. FIG. 145A is an exploded view of the staple cartridge 10706. The staple cartridge 10706 comprises a cartridge body 10720, a wedge sled 10718, a cartridge tray 10722, and a flex cable 10730. The flex cable 10730 further comprises electrical contacts 10732 placed to make an electrical connection when the staple cartridge 10706 is operatively coupled with an end effector. The electrical contacts 10732 are integrated with cable traces 10734. The cable traces connect 10736 near the distal end of the staple cartridge 10706, and this connection 10736 joins with a conductive coupling 10714. A Hall effect sensor 10710 and a processor 10712 are operatively connected to the conductive coupling 10714 such that the are able to communicate.

FIG. 145B illustrates the assembly of the staple cartridge 10706 and the flex cable 10730 in greater detail. As illustrated, the cartridge tray 10722 encloses the underside of the cartridge body 10720, thereby enclosing the wedge sled 10718. The flex cable 10730 can be located on the exterior of the cartridge tray 10722 with the conductive coupling 10714 positioned within the distal end of the cartridge body 10720. The flex cable 10730 can be placed on the exterior of the cartridge tray 10722 by any appropriate means, such as for instance bonding or laser etching.

FIGS. 146A-146F illustrate one embodiment of an end effector 10800 with a flex cable 10840 operable to provide power to a staple cartridge 10806 that comprises a distal sensor plug 10816. The end effector 10800 is similar to the end effector 300 described above. The end effector 10800 comprises a first jaw member or anvil 10802, a second jaw member or elongated channel 10804, and a staple cartridge 10806 operatively coupled to the elongated channel 10804. The end effector 10800 is operatively coupled to a shaft assembly 10900. The shaft assembly 10900 is similar to shaft assembly 200 described above. The shaft assembly 10900 further comprises a closure tube 10902 that encloses the exterior of the shaft assembly 10900. In some embodiments the shaft assembly 10900 further comprises an articulation joint 10904, which includes a double pivot closure sleeve assembly 10906. The double pivot closure sleeve assembly 10906 includes an end effector closure sleeve assembly 10908 that is operable to couple with the end effector 10800.

FIG. 146A illustrates a perspective view of the end effector 10800 coupled to the shaft assembly 10900. In various embodiments, the shaft assembly 10900 further comprises a flex cable 10830 that is configured to not interfere with the function of the articulation joint 10904, as described in further detail below. FIG. 146B illustrates a perspective view of the underside of the end effector 10800 and shaft assembly 10900. In some embodiments, the closure tube 10902 of the shaft assembly 10900 further comprises a first aperture 10908, through which the flex cable 10908 can extend. The close sleeve assembly 10908 further comprises a second aperture 10910, through which the flex cable 10908 can also pass.

FIG. 146C illustrates the end effector 10800 with the flex cable 10830 and without the shaft assembly 10900. As illustrated, in some embodiments the flex cable 10830 can include a single coil 10832 operable to wrap around the articulation joint 10904, and thereby be operable to flex with the motion of the articulation joint 10904.

FIGS. 146D and 146E illustrate the elongated channel 10804 portion of the end effector 10800 without the anvil 10802 or the staple cartridge 10806, to illustrate how the flex cable 10830 can be seated within the elongated channel 10804. In some embodiments, the elongated channel 10804 further comprises a third aperture 10824 for receiving the flex cable 10830. Within the body of the elongated channel 10804 the flex cable splits 10834 to form extensions 10836 on either side of the elongated channel 10804. FIG. 146E further illustrates that connectors 10838 can be operatively coupled to the flex cable extensions 10836.

FIG. 146F illustrates the flex cable 10830 alone. As illustrated, the flex cable 10830 comprises a single coil 10832 operative to wrap around the articulation joint 10904, and a split 10834 that attaches to extensions 10836. The extensions can be coupled to connectors 10838 that have on their distal facing surfaces prongs 10840 for coupling to the staple cartridge 10806, as described below.

FIG. 147 illustrates a close up view of the elongated channel 10804 with a staple cartridge 10806 coupled thereto. The staple cartridge 10804 comprises a cartridge body 10822 and a cartridge tray 10820. In some embodiments the staple cartridge 10806 further comprises electrical traces 10828 that are coupled to proximal contacts 10856 at the proximal end of the staple cartridge 10806. The proximal contacts 10856 can be positioned to form a conductive connection with the prongs 10840 of the connectors 10838 that are coupled to the flex cable extensions 10836. Thus, when the staple cartridge 10806 is operatively coupled with the elongated channel 10804, the flex cable 10830, through the connectors 10838 and the connector prongs 10840, can provide power to the staple cartridge 10806.

FIGS. 148A-148D further illustrate one embodiment of a staple cartridge 10806 operative with the present embodiment of an end effector 10800. FIG. 148A illustrates a close up view of the proximal end of the staple cartridge 10806. As discussed above, the staple cartridge 10806 comprises electrical traces 10828 that, at the proximal end of the staple cartridge 10806, form proximal contacts 10856 that are operable to couple with the flex cable 10830 as described above. FIG. 148B illustrates a close-up view of the distal end of the staple cartridge 10806, with a space for a distal sensor plug 10816, described below. As illustrated, the electrical traces 10828 can extend along the length of the staple cartridge body 10822 and, at the distal end, form distal contacts 10856. FIG. 148C further illustrates the distal sensor plug 10816, which in some embodiments is shaped to be received by the space formed for it in the distal end of the staple cartridge 10806. FIG. 148D illustrates the proximal-facing side of the distal sensor plug 10816. As illustrated, the distal sensor plug 10816 has sensor plug contacts 10854, positioned to couple with the distal contacts 10858 of the staple cartridge 10806. Thus, in some embodiments the electrical traces 10828 can be operative to provide power to the distal sensor plug 10816.

FIGS. 149A and 149B illustrate one embodiment of a distal sensor plug 10816. FIG. 149A illustrates a cutaway view of the distal sensor plug 10816. As illustrated, the distal sensor plug 10816 comprises a Hall effect sensor 10810 and a processor 10812. The distal sensor plug 10816 further comprises a flex board 10814. As further illustrated in FIG. 149B, the Hall effect sensor 10810 and the processor 10812 are operatively coupled to the flex board 10814 such that they are capable of communicating.

FIG. 150 illustrates an embodiment of an end effector 10960 with a flex cable 10980 operable to provide power to sensors and electronics 10972 in the distal tip of the anvil 19052 portion. The end effector 10950 comprises a first jaw member or anvil 10962, a second jaw member or elongated channel 10964, and a staple cartridge 10956 operatively coupled to the elongated channel 10952. The end effector 10960 is operatively coupled to a shaft assembly 10960. The shaft assembly 10960 further comprises a closure tube 10962 that encloses the shaft assembly 10960. In some embodiments the shaft assembly 10960 further comprises an articulation joint 10964, which includes a double pivot closure sleeve assembly 10966.

In various embodiments, the end effector 10950 further comprises a flex cable 19080 that is configured to not interfere with the function of the articulation joint 10964. In some embodiments, the closure tube 10962 comprises a first aperture 10968 through which the flex cable 10980 can extend. In some embodiments, flex cable 10980 further comprises a loop or coil 10982 that wraps around the articulation joint 10964 such that the flex cable 10980 does not interfere with the operation of the articulation joint 10964, as further described below. In some embodiments, the flex cable 10980 extends along the length of the anvil 10951 to a second aperture 10970 in the distal tip of the anvil 10951.

FIGS. 151A-151C illustrate the operation of the articulation joint 10964 and flex cable 19080 of the end effector 10950. FIG. 151A illustrates a top view of the end effector 10952 with the end effector 109650 pivoted −45 degrees with respect to the shaft assembly 10960. As illustrated, the coil 10982 of the flex cable 10980 flexes with the articulation joint 10964 such that the flex cable 10980 does not interfere with the operation of the articulation joint. 10964. FIG. 151B illustrates a top view of the end effector 10950. As illustrated, the coil 10982 wraps around the articulation joint 10964 once. FIG. 151C illustrates a top view of the end effector 10950 with the end effector 10950 pivoted +45 degrees with respect to the shaft assembly 10960. As illustrated, the coil 10982 of the flex cable 10980 flexes with the articulation joint 10964 such that the flex cable 10980 does not interfere with the operation of the articulation joint 10964.

FIG. 152 illustrates cross-sectional view of the distal tip of an embodiment of an anvil 10952 with sensors and electronics 10972. The anvil 10952 comprises a flex cable 10980, as described with respect to FIGS. 150 and 151A-151C. As illustrated in FIG. 152, the anvil 10952 further comprises a second aperture 10970 through which the flex cable 10980 can pass such that the flex cable 10980 can enter a housing 10974 in the within the anvil 10952. Within the housing 10974 the flex cable 10980 can operably couple to sensors and electronics 10972 located within the housing 10974 and thereby provide power to the sensors and electronics 10972.

FIG. 153 illustrates a cutaway view of the distal tip of the anvil 10952. FIG. 153 illustrates an embodiment of the housing 10974 that can contain sensors and electronics 10972 as illustrated by FIG. 152.

In accordance with various embodiments, the surgical instruments described herein may comprise one or more processors (e.g., microprocessor, microcontroller) coupled to various sensors. In addition, to the processor(s), a storage (having operating logic) and communication interface, are coupled to each other.

As described earlier, the sensors may be configured to detect and collect data associated with the surgical device. The processor processes the sensor data received from the sensor(s).

The processor may be configured to execute the operating logic. The processor may be any one of a number of single or multi-core processors known in the art. The storage may comprise volatile and non-volatile storage media configured to store persistent and temporal (working) copy of the operating logic.

In various embodiments, the operating logic may be configured to perform the initial processing, and transmit the data to the computer hosting the application to determine and generate instructions. For these embodiments, the operating logic may be further configured to receive information from and provide feedback to a hosting computer. In alternate embodiments, the operating logic may be configured to assume a larger role in receiving information and determining the feedback. In either case, whether determined on its own or responsive to instructions from a hosting computer, the operating logic may be further configured to control and provide feedback to the user.

In various embodiments, the operating logic may be implemented in instructions supported by the instruction set architecture (ISA) of the processor, or in higher level languages and compiled into the supported ISA. The operating logic may comprise one or more logic units or modules. The operating logic may be implemented in an object oriented manner. The operating logic may be configured to be executed in a multi-tasking and/or multi-thread manner. In other embodiments, the operating logic may be implemented in hardware such as a gate array.

In various embodiments, the communication interface may be configured to facilitate communication between a peripheral device and the computing system. The communication may include transmission of the collected biometric data associated with position, posture, and/or movement data of the user's body part(s) to a hosting computer, and transmission of data associated with the tactile feedback from the host computer to the peripheral device. In various embodiments, the communication interface may be a wired or a wireless communication interface. An example of a wired communication interface may include, but is not limited to, a Universal Serial Bus (USB) interface. An example of a wireless communication interface may include, but is not limited to, a Bluetooth interface.

For various embodiments, the processor may be packaged together with the operating logic. In various embodiments, the processor may be packaged together with the operating logic to form a SiP. In various embodiments, the processor may be integrated on the same die with the operating logic. In various embodiments, the processor may be packaged together with the operating logic to form a System on Chip (SoC).

Various embodiments may be described herein in the general context of computer executable instructions, such as software, program modules, and/or engines being executed by a processor. Generally, software, program modules, and/or engines include any software element arranged to perform particular operations or implement particular abstract data types. Software, program modules, and/or engines can include routines, programs, objects, components, data structures and the like that perform particular tasks or implement particular abstract data types. An implementation of the software, program modules, and/or engines components and techniques may be stored on and/or transmitted across some form of computer-readable media. In this regard, computer-readable media can be any available medium or media useable to store information and accessible by a computing device. Some embodiments also may be practiced in distributed computing environments where operations are performed by one or more remote processing devices that are linked through a communications network. In a distributed computing environment, software, program modules, and/or engines may be located in both local and remote computer storage media including memory storage devices. A memory such as a random access memory (RAM) or other dynamic storage device may be employed for storing information and instructions to be executed by the processor. The memory also may be used for storing temporary variables or other intermediate information during execution of instructions to be executed by the processor.

Although some embodiments may be illustrated and described as comprising functional components, software, engines, and/or modules performing various operations, it can be appreciated that such components or modules may be implemented by one or more hardware components, software components, and/or combination thereof. The functional components, software, engines, and/or modules may be implemented, for example, by logic (e.g., instructions, data, and/or code) to be executed by a logic device (e.g., processor). Such logic may be stored internally or externally to a logic device on one or more types of computer-readable storage media. In other embodiments, the functional components such as software, engines, and/or modules may be implemented by hardware elements that may include processors, microprocessors, circuits, circuit elements (e.g., transistors, resistors, capacitors, inductors, and so forth), integrated circuits, ASICs, PLDs, DSPs, FPGAs, logic gates, registers, semiconductor device, chips, microchips, chip sets, and so forth.

Examples of software, engines, and/or modules may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more of the modules described herein may comprise one or more embedded applications implemented as firmware, software, hardware, or any combination thereof. One or more of the modules described herein may comprise various executable modules such as software, programs, data, drivers, application APIs, and so forth. The firmware may be stored in a memory of the controller and/or the controller which may comprise a nonvolatile memory (NVM), such as in bit-masked ROM or flash memory. In various implementations, storing the firmware in ROM may preserve flash memory. The NVM may comprise other types of memory including, for example, programmable ROM (PROM), erasable programmable ROM (EPROM), EEPROM, or battery backed RAM such as dynamic RAM (DRAM), Double-Data-Rate DRAM (DDRAM), and/or synchronous DRAM (SDRAM).

In some cases, various embodiments may be implemented as an article of manufacture. The article of manufacture may include a computer readable storage medium arranged to store logic, instructions and/or data for performing various operations of one or more embodiments. In various embodiments, for example, the article of manufacture may comprise a magnetic disk, optical disk, flash memory or firmware containing computer program instructions suitable for execution by a general purpose processor or application specific processor. The embodiments, however, are not limited in this context.

The functions of the various functional elements, logical blocks, modules, and circuits elements described in connection with the embodiments disclosed herein may be implemented in the general context of computer executable instructions, such as software, control modules, logic, and/or logic modules executed by the processing unit. Generally, software, control modules, logic, and/or logic modules comprise any software element arranged to perform particular operations. Software, control modules, logic, and/or logic modules can comprise routines, programs, objects, components, data structures and the like that perform particular tasks or implement particular abstract data types. An implementation of the software, control modules, logic, and/or logic modules and techniques may be stored on and/or transmitted across some form of computer-readable media. In this regard, computer-readable media can be any available medium or media useable to store information and accessible by a computing device. Some embodiments also may be practiced in distributed computing environments where operations are performed by one or more remote processing devices that are linked through a communications network. In a distributed computing environment, software, control modules, logic, and/or logic modules may be located in both local and remote computer storage media including memory storage devices.

Additionally, it is to be appreciated that the embodiments described herein illustrate example implementations, and that the functional elements, logical blocks, modules, and circuits elements may be implemented in various other ways which are consistent with the described embodiments. Furthermore, the operations performed by such functional elements, logical blocks, modules, and circuits elements may be combined and/or separated for a given implementation and may be performed by a greater number or fewer number of components or modules. As will be apparent to those of skill in the art upon reading the present disclosure, each of the individual embodiments described and illustrated herein has discrete components and features which may be readily separated from or combined with the features of any of the other several aspects without departing from the scope of the present disclosure. Any recited method can be carried out in the order of events recited or in any other order which is logically possible.

It is worthy to note that any reference to "one embodiment" or "an embodiment" means that a particular feature, structure, or characteristic described in connection with the embodiment is comprised in at least one embodiment. The appearances of the phrase "in one embodiment" or "in one aspect" in the specification are not necessarily all referring to the same embodiment.

Unless specifically stated otherwise, it may be appreciated that terms such as "processing," "computing," "calculating," "determining," or the like, refer to the action and/or processes of a computer or computing system, or similar electronic computing device, such as a general purpose processor, a DSP, ASIC, FPGA or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers or other such information storage, transmission or display devices.

It is worthy to note that some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, also may mean that two or more elements are not in direct contact with each other, but yet still co-operate or interact with each other. With respect to software elements, for example, the term "coupled" may refer to interfaces, message interfaces, API, exchanging messages, and so forth.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The disclosed embodiments have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and when necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely examples and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that when a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even when a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical application to thereby enable one of ordinary skill in the art to utilize the various embodiments and with various modifications as are suited to the particular use contemplated. It is intended that the claims submitted herewith define the overall scope.

What is claimed is:

1. A surgical staple cartridge, comprising:

a cartridge body defining a plurality of holes;

a plurality of staples stored in at least some of the holes;

a plurality of sensors positioned in at least some of the holes, each configured to generate a sensor output receivable by a control circuit of a surgical stapling instrument, wherein the plurality of sensors comprises:

a first sensor at a first longitudinal position along the cartridge body; and a second sensor at a second longitudinal position along the cartridge body, wherein the second longitudinal position is different from the first longitudinal position.

2. The surgical staple cartridge of claim 1, wherein the plurality of sensors comprises a series of longitudinally spaced sensors.

3. The surgical staple cartridge of claim 2, wherein the plurality of sensors are configured to:

serially sense a parameter; and generate the sensor outputs based on the serially sensed parameter.

4. The surgical staple cartridge of claim 1, wherein each of the sensors is configured to generate the sensor output corresponding to a sensed tissue parameter associated with tissue clamped between the surgical staple cartridge and an anvil of the surgical stapling instrument.

5. The surgical staple cartridge of claim 4, wherein the sensed tissue parameter comprises a tissue thickness.

6. The surgical staple cartridge of claim 4, wherein the plurality of sensors comprises a plurality of strain gauges.

7. The surgical staple cartridge of claim 4, wherein each of the sensors comprises an electrode, and wherein the electrodes are configured to sense tissue and stabilize tissue.

8. The surgical staple cartridge of claim 1, wherein the cartridge comprises a deck surface, wherein the plurality of holes is defined in the deck surface, and wherein the sensors are positioned in the holes to protrude from the deck surface.

9. The surgical staple cartridge of claim 1, wherein the holes are arranged in a plurality of longitudinal rows, and wherein the first sensor and the second sensors are positioned in the same longitudinal row.

10. The surgical staple cartridge of claim 9, wherein the plurality of longitudinal cavity rows comprises an outermost row, and wherein the first sensor and the second sensor are positioned in the outermost row.

11. The surgical staple cartridge of claim 10, further comprising a wire extending longitudinally within the cartridge body for communicably coupling the first sensor and the second sensor to the control circuit.

12. The surgical staple cartridge of claim 10, wherein the outermost row is positioned on a first side of the cartridge body, wherein the plurality of longitudinal rows further comprises a second outermost row on a second side of the cartridge body, wherein the plurality of sensors further comprises a third senor and a fourth sensor positioned in the second outermost row.

13. The surgical staple cartridge of claim 1, wherein the first sensor is positioned in a distal most hole of the outermost row.

14. The surgical staple cartridge of claim 1, configured to be inserted into a surgical stapling instrument which comprises an anvil comprising a plurality of anvil sensors configured to sense a tissue parameter, and wherein the sensors of the surgical staple cartridge are configured to sense the same tissue parameter as the plurality of anvil sensors.

15. A surgical staple cartridge, comprising:

a cartridge body defining a plurality of holes;

a plurality of staples stored in at least some of the holes; and a series of longitudinally spaced sensors positioned in at least some of the holes, wherein each of the sensors is configured to generate a sensor output receivable by a control circuit of a surgical stapling instrument.

16. The surgical staple cartridge of claim 15, wherein each of the sensors is configured to generate the sensor output corresponding to a tissue parameter associated with tissue clamped between the surgical staple cartridge and an anvil of the surgical stapling instrument.

17. The surgical staple cartridge of claim 16, wherein the series of longitudinally spaced sensors are configured to serially sense the tissue parameter and generate the sensor outputs based on the serially-sensed parameter.

18. A surgical staple cartridge, comprising:

a cartridge body defining:

a plurality of staple holes; and a series of longitudinally-spaced sensor holes interposed with the staple cavities;

a plurality of staples stored in the staple holes; and a plurality of sensors positioned in the sensor holes, wherein each of the sensors is configured to generate a sensor output receivable by a control circuit of a surgical stapling instrument.

* * * * *